(12) United States Patent
Ma et al.

(10) Patent No.: US 12,319,653 B2
(45) Date of Patent: *Jun. 3, 2025

(54) ORGANIC ELECTROLUMINESCENT MATERIALS AND DEVICES

(71) Applicant: Universal Display Corporation, Ewing, NJ (US)

(72) Inventors: Bin Ma, Plainsboro, NJ (US); Ting-Chih Wang, Lawrenceville, NJ (US); Vadim Adamovich, Yardley, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,974

(22) Filed: Feb. 2, 2024

(65) Prior Publication Data

US 2024/0199549 A1  Jun. 20, 2024

Related U.S. Application Data

(63) Continuation of application No. 17/954,841, filed on Sep. 28, 2022, now Pat. No. 11,939,293, which is a
(Continued)

(51) Int. Cl.
*C07D 209/88* (2006.01)
*H10K 50/11* (2023.01)
(Continued)

(52) U.S. Cl.
CPC ........... *C07D 209/88* (2013.01); *H10K 50/11* (2023.02); *H10K 50/14* (2023.02); *H10K 50/81* (2023.02); *H10K 50/82* (2023.02); *H10K 50/18* (2023.02)

(58) Field of Classification Search
None
See application file for complete search history.

(56) References Cited

U.S. PATENT DOCUMENTS

| 4,769,292 A | 9/1988 | Tang et al. |
| 5,061,569 A | 10/1991 | VanSlyke et al. |

(Continued)

FOREIGN PATENT DOCUMENTS

| EP | 0650955 | 5/1995 |
| EP | 1725079 | 11/2006 |

(Continued)

OTHER PUBLICATIONS

Machine translation of WO-2022211594-A1, translation generated May 2024, 33 pages. (Year: 2024).*

(Continued)

*Primary Examiner* — Robert S Loewe
(74) *Attorney, Agent, or Firm* — DUANE MORRIS LLP

(57) ABSTRACT

A composition comprising a first compound and a second compound, wherein the first compound has a formula selected from the group consisting of (Continued)

-continued

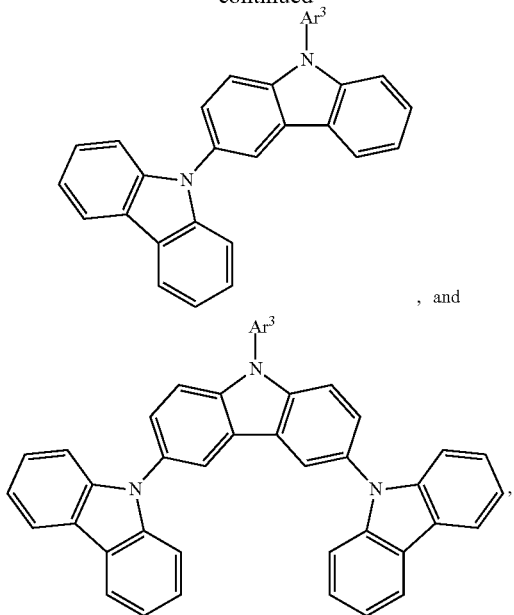

, and wherein the second compound has the formula

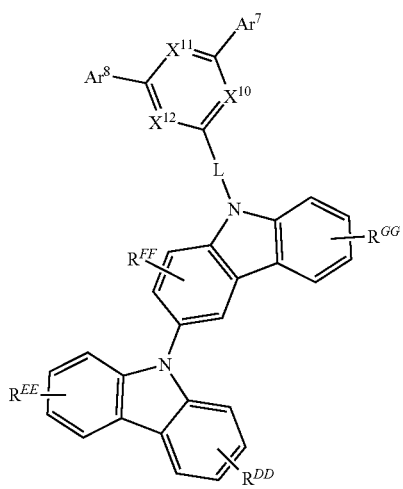

is disclosed.

20 Claims, 2 Drawing Sheets

Related U.S. Application Data continuation of application No. 16/547,789, filed on Aug. 22, 2019, now Pat. No. 11,485,706.

(60) Provisional application No. 62/729,655, filed on Sep. 11, 2018.

(51) Int. Cl.
H10K 50/14 (2023.01)
H10K 50/81 (2023.01)
H10K 50/82 (2023.01)
H10K 50/18 (2023.01)

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,221,905 B2 | 7/2012 | Lin et al. |
| 8,927,118 B2 | 1/2015 | Kato et al. |
| 8,932,734 B2 | 1/2015 | Dyatkin |
| 9,266,865 B2 | 2/2016 | Numata et al. |
| 9,391,288 B2 | 7/2016 | Nagao et al. |
| 9,831,444 B1 | 11/2017 | Yen et al. |
| 9,911,924 B2 | 3/2018 | Kim et al. |
| 10,026,908 B2 | 7/2018 | Park et al. |
| 11,485,706 B2 * | 11/2022 | Ma ........................ H10K 50/11 |
| 11,939,293 B2 * | 3/2024 | Ma ........................ H10K 50/18 |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |

(56) References Cited

U.S. PATENT DOCUMENTS

| | | |
|---|---|---|
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2014/0070204 A1 | 3/2014 | Nagao et al. |
| 2014/0158992 A1 | 6/2014 | Xia et al. |
| 2014/0197386 A1 | 7/2014 | Kim et al. |
| 2015/0126736 A1 | 5/2015 | Cho et al. |
| 2015/0162538 A1 | 6/2015 | Zeng et al. |
| 2015/0357582 A1 | 12/2015 | Hirata et al. |
| 2016/0149139 A1 | 5/2016 | Xia et al. |
| 2016/0293855 A1 | 10/2016 | Zeng |
| 2016/0329502 A1 | 11/2016 | Dyatkin |
| 2017/0005276 A1 | 1/2017 | Kim et al. |
| 2017/0244049 A1 | 8/2017 | Aspuru-Guzik et al. |
| 2017/0346017 A1 | 11/2017 | Nakano et al. |
| 2018/0145262 A1 | 5/2018 | Zeng et al. |
| 2018/0248127 A1 | 8/2018 | Lee et al. |
| 2018/0287072 A1 | 10/2018 | Park et al. |
| 2019/0378991 A1 | 12/2019 | Pan |
| 2024/0121973 A1* | 4/2024 | Nakanotani ............ H10K 50/11 |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2013/165192 | 11/2013 |
| WO | 2012/153725 | 7/2014 |
| WO | 2014/115743 | 7/2014 |
| WO | 2017099490 | 6/2017 |
| WO | 2018016724 | 1/2018 |
| WO | WO-2022211594 A1 * | 10/2022 ............ H10K 50/12 |

OTHER PUBLICATIONS

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1 - 183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "p. 185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

(56) References Cited

OTHER PUBLICATIONS

Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5''-Bis (dimesitylboryl)-2,2'5',2''-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes Of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
Machine translation of WO-2018016724, translation generated Nov. 2021, 41 pages. (Year: 2021).

* cited by examiner

ORGANIC ELECTROLUMINESCENT MATERIALS AND DEVICES

CROSS-REFERENCE TO RELATED APPLICATIONS

This application is a continuation application of co-pending U.S. patent application Ser. No. 17/954,841, filed Sep. 28, 2022, which is a continuation of U.S. patent application Ser. No. 16/547,789, filed Aug. 22, 2019, which claims priority under 35 U.S.C. § 119(e) to U.S. Provisional Application No. 62/729,655, filed Sep. 11, 2018, the entire contents of which are incorporated herein by reference.

FIELD

The present invention relates to compositions for use as hosts and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine) iridium, denoted Ir(ppy)$_3$, which has the following structure:

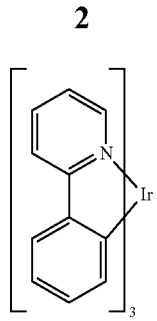

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

A novel composition according to some embodiments is disclosed. The compostion comprises a first compound, wherein the first compound is selected from the group consisting of

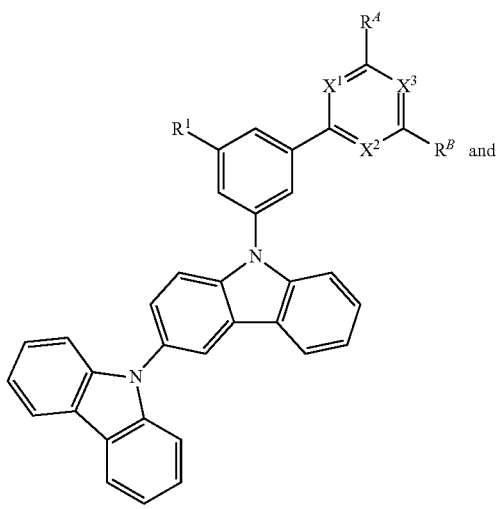

Formula I

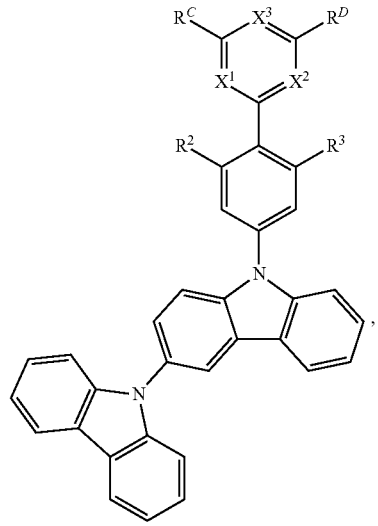

Formula II wherein, $X^1$, $X^2$, and $X^3$ are each independently CH or N; at least two of $X^1$, $X^2$, and $X^3$ are N; $R^A$, $R^B$, $R^C$, and $R^D$ each independently selected from the group consisting of aryl, heteroaryl, substituted aryl, substituted heteroaryl, and combination thereof; each $R^1$, $R^2$ and $R^3$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof;

wherein, in Formula I, $R^1$ is aryl or heteroaryl, or at least one of $R^A$ and $R^B$ comprises two or more aromatic rings; and in Formula II, at least one of $R^C$ and $R^D$ is independently a substituent selected from the group consisting of alkylated aromatic ring, two or more aromatic rings, and $R^C$ and $R^D$ are different.

An OLED comprising the composition of the present disclosure in an organic layer therein is also disclosed.

A consumer product comprising the OLED is also disclosed.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
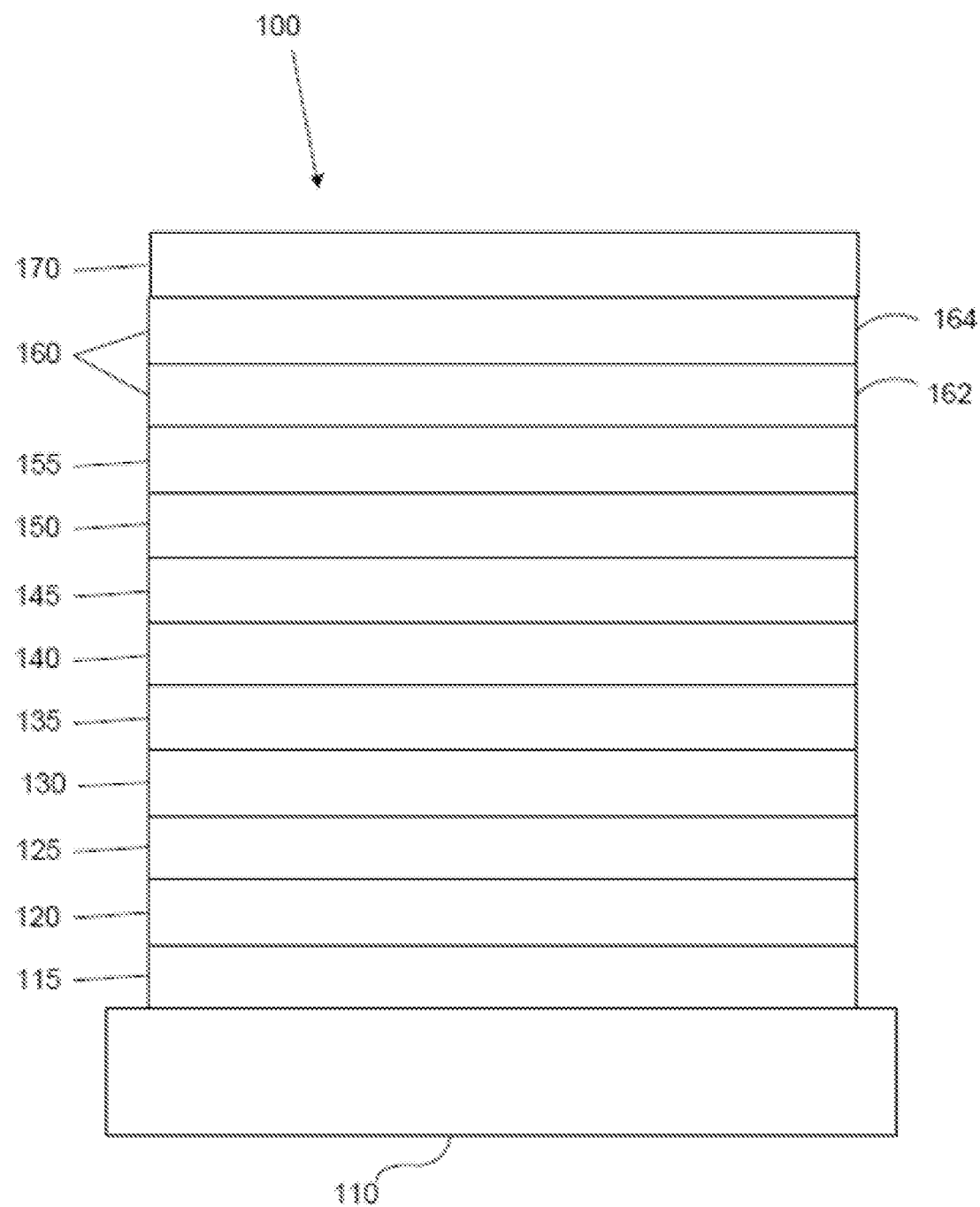
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
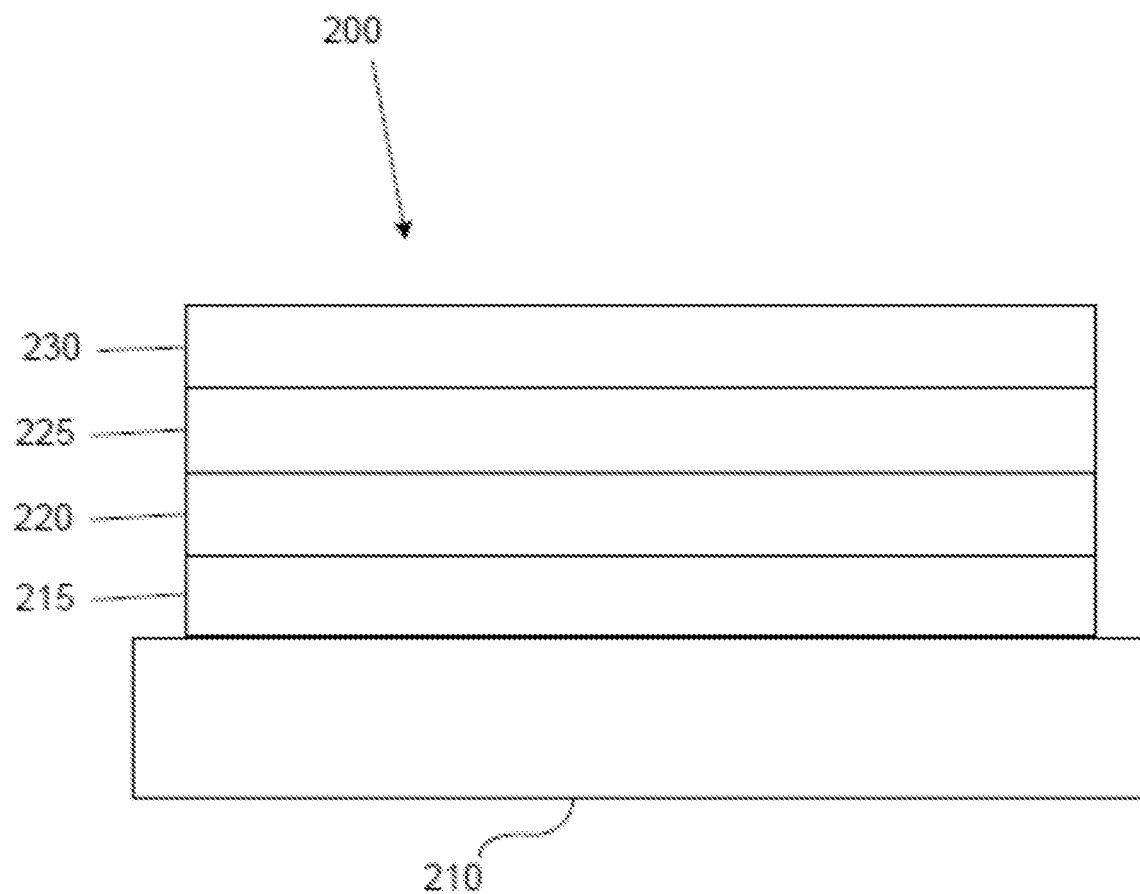
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms "halo," "halogen," and "halide" are used interchangeably and refer to fluorine, chlorine, bromine, and iodine.

The term "acyl" refers to a substituted carbonyl radical (C(O)—$R_s$).

The term "ester" refers to a substituted oxycarbonyl (—O—C(O)—$R_s$ or —C(O)—O—$R_s$) radical.

The term "ether" refers to an —OR radical.

The terms "sulfanyl" or "thio-ether" are used interchangeably and refer to a —$SR_s$ radical.

The term "sulfinyl" refers to a —S(O)—$R_s$ radical.

The term "sulfonyl" refers to a —$SO_2$—$R_s$ radical.

The term "phosphino" refers to a —$P(R_s)_3$ radical, wherein each $R_s$ can be same or different.

The term "silyl" refers to a —$Si(R_s)_3$ radical, wherein each $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group is optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group is optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, O, S or N. Additionally, the heteroalkyl or heterocycloalkyl group is optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N, Preferred alkenyl, cycloalkenyl, or heteroalkenyl groups are those containing two to fifteen carbon atoms. Additionally, the alkenyl, cycloalkenyl, or heteroalkenyl group is optionally substituted.

The term "alkynyl" refers to and includes both straight and branched chain alkyne radicals. Preferred alkynyl groups are those containing two to fifteen carbon atoms. Additionally, the alkynyl group is optionally substituted.

The terms "aralkyl" or "arylalkyl" are used interchangeably and refer to an alkyl group that is substituted with an aryl group. Additionally, the aralkyl group is optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group is optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group is optionally substituted.

Of the aryl and heteroaryl groups listed above, the groups of triphenylene. naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

In some instances, the preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the more preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f.h]quinoxaline and dibenzo[f.h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., Tetrahedron 2015, 71, 1425-30 and Atzrodt et al., Angew. Chem. Int. Ed. (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

A novel composition according to some embodiments is disclosed. The compostion comprises a first compound, wherein the first compound is selected from the group consisting of

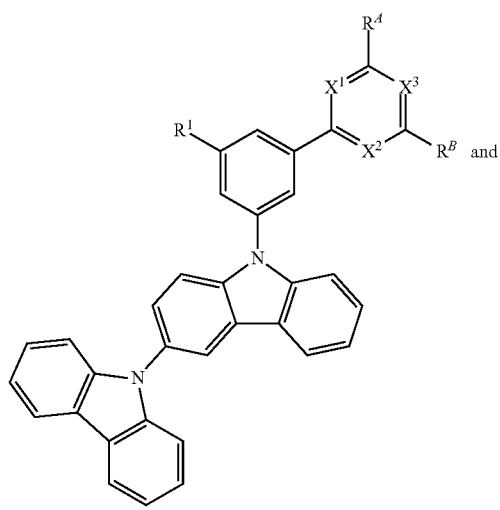

Formula I and

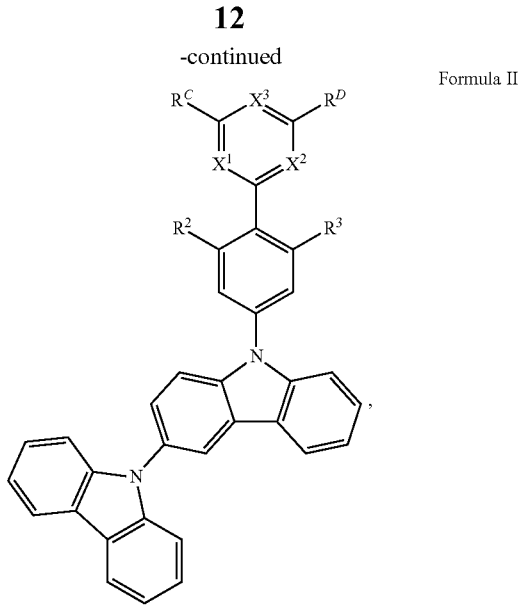

Formula II wherein, $X^1$, $X^2$, and $X^3$ are each independently CH or N; at least two of $X^1$, $X^2$, and $X^3$ are N; $R^A$, $R^B$, $R^C$, and $R^D$ each independently selected from the group consisting of aryl, heteroaryl, substituted aryl, substituted heteroaryl, and combination thereof; each $R^1$, $R^2$ and $R^3$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof;

wherein, in Formula I, $R^1$ is aryl or heteroaryl, or at least one of $R^A$ and $R^B$ comprises two or more aromatic rings; and in Formula II, at least one of $R^C$ and $R^D$ is independently a substituent selected from the group consisting of alkylated aromatic ring, two or more aromatic rings, and $R^C$ and $R^D$ are different.

In some embodiments of the composition, $X^1$, $X^2$, and $X^3$ are N. Where $X^1$, $X^2$, and $X^3$ are N, the first compound can be selected from the group consisting of:

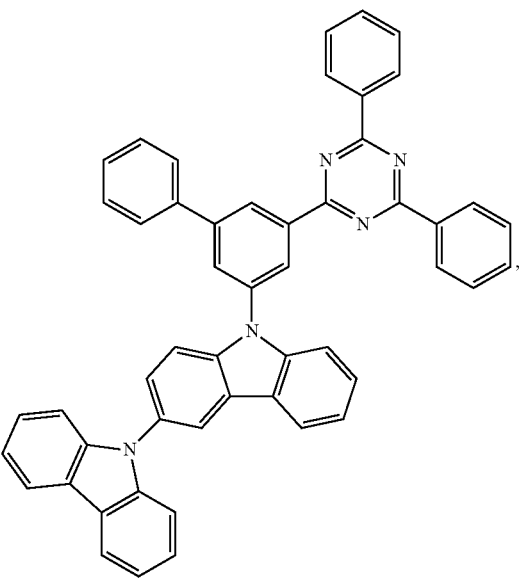

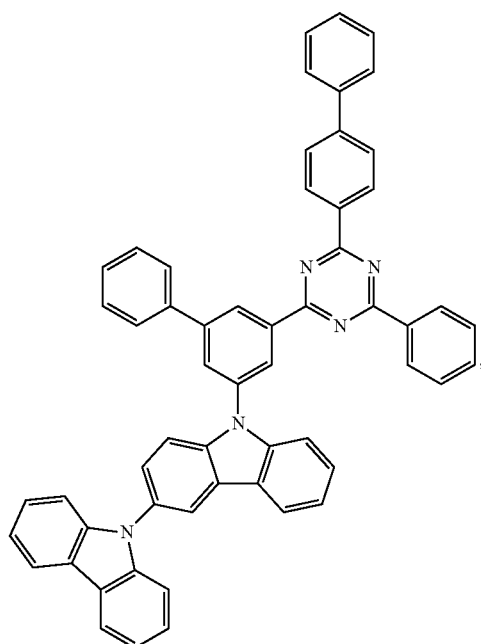
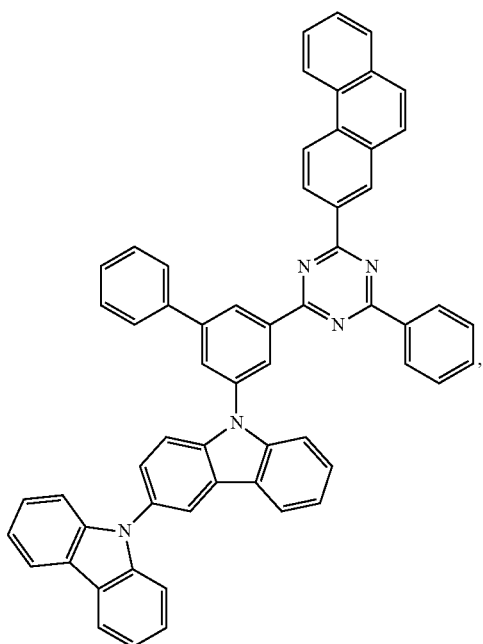
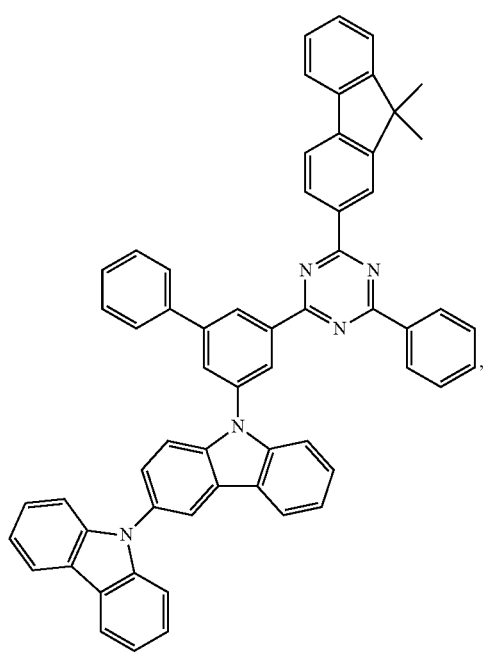
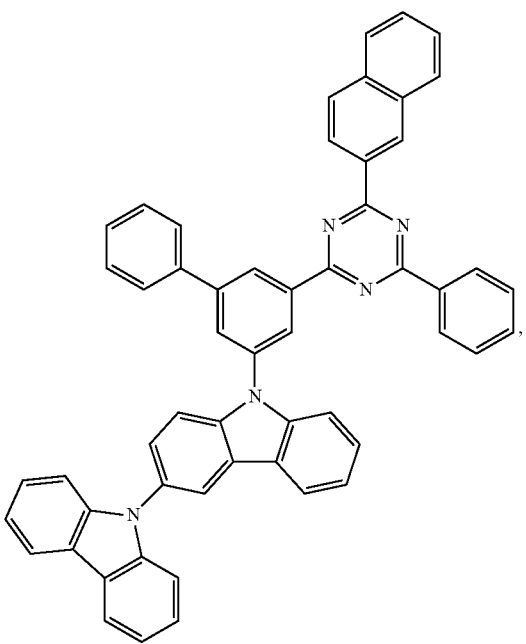

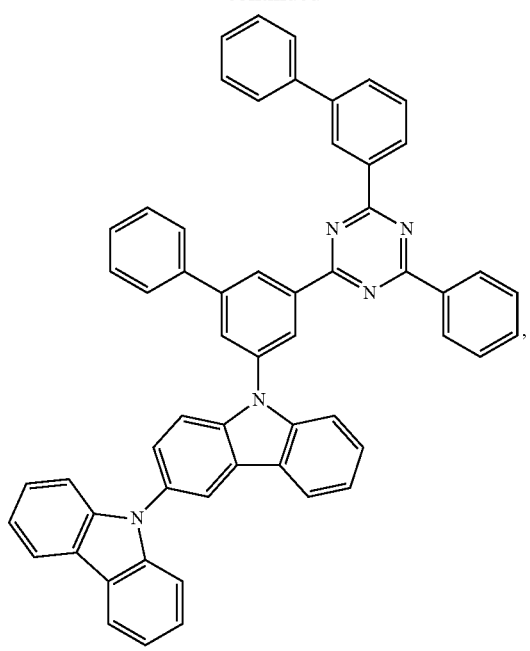
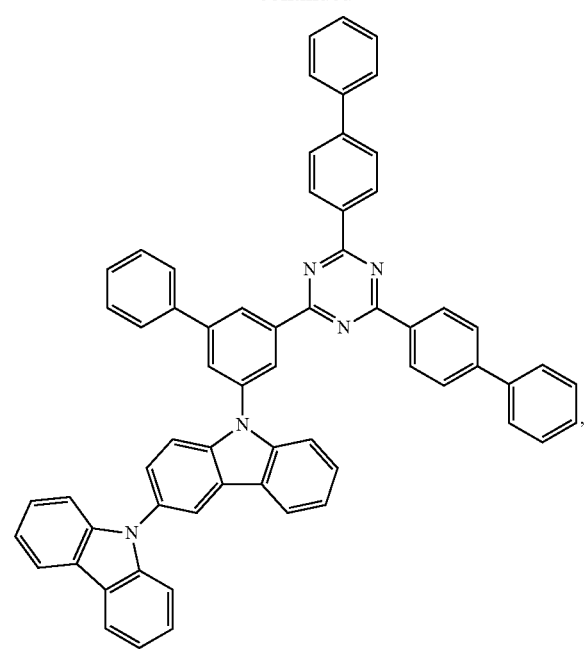
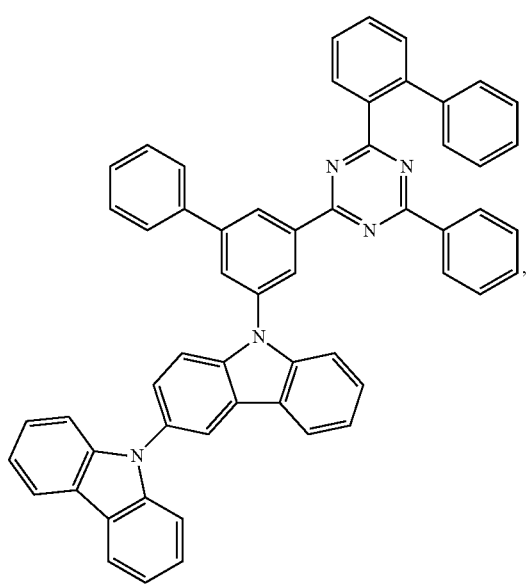
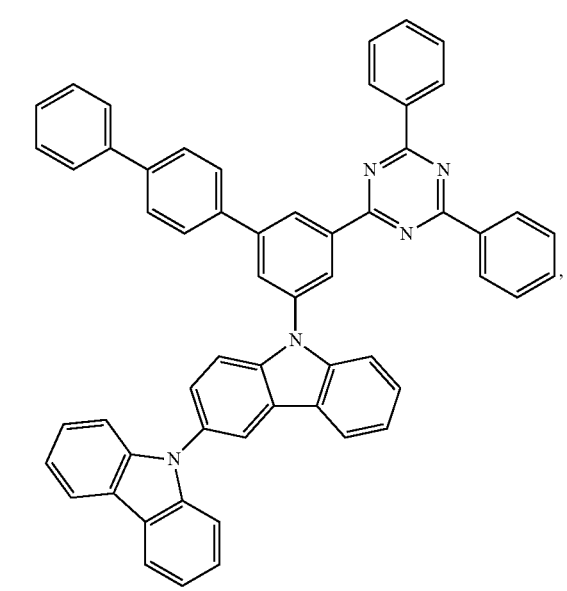

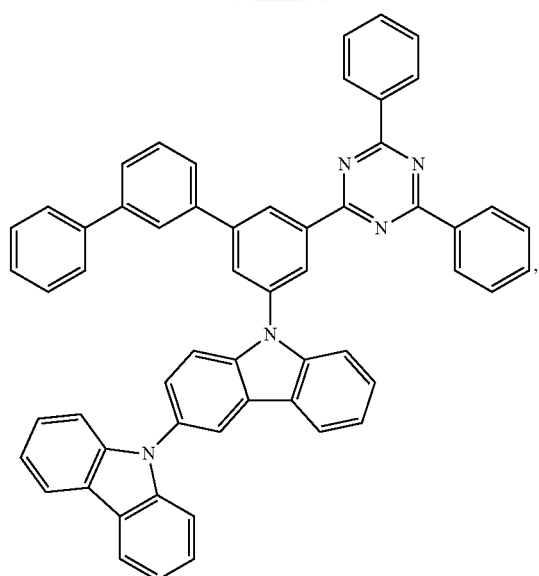
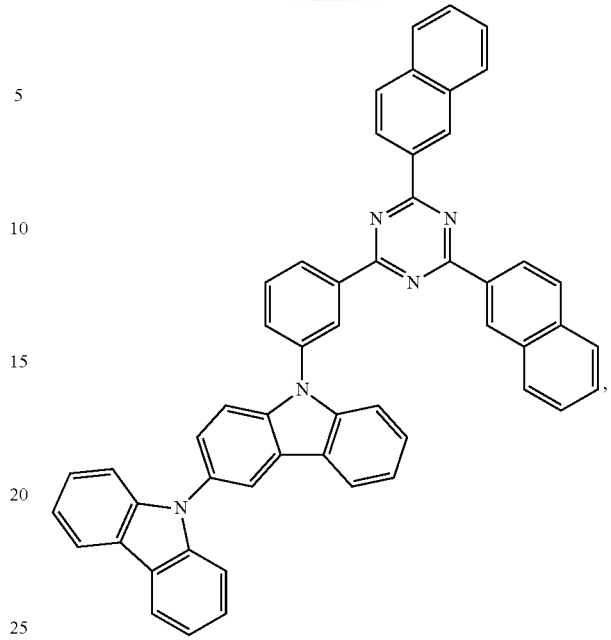
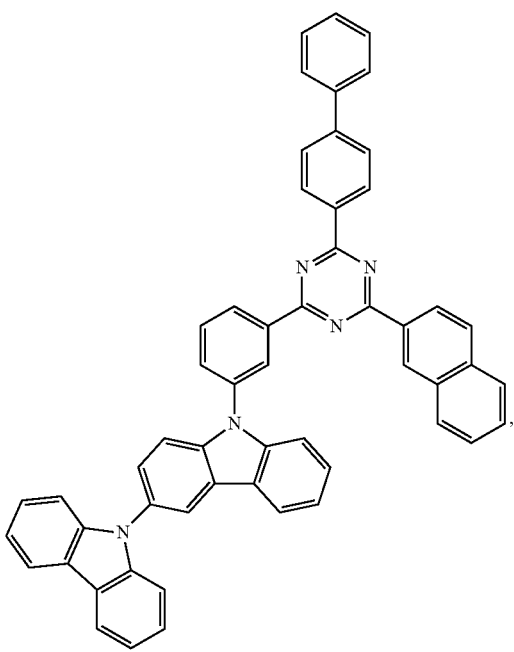

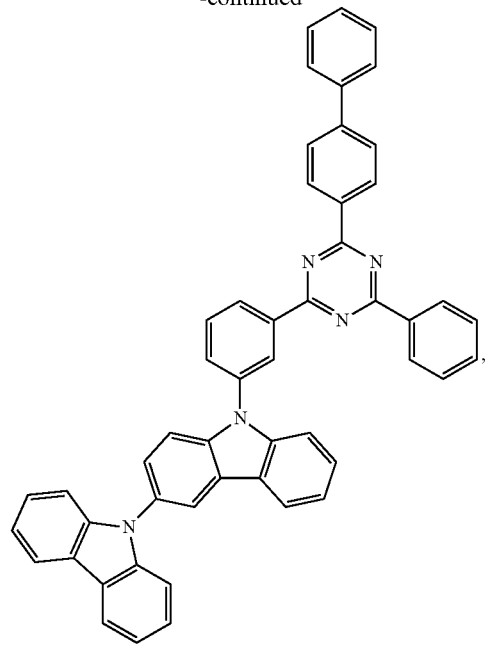
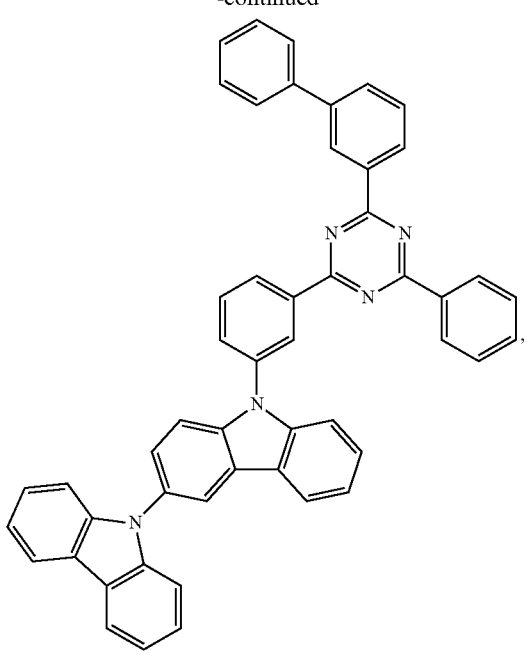
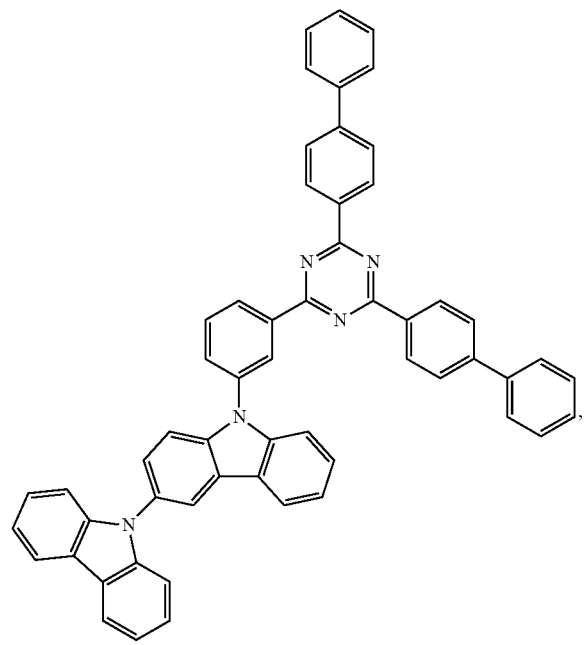
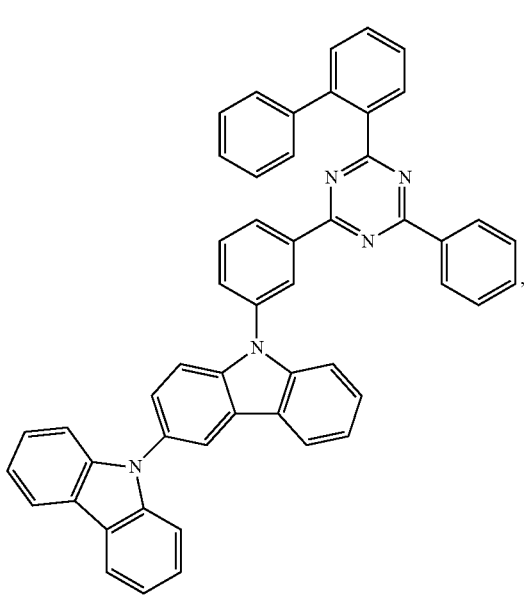

-continued
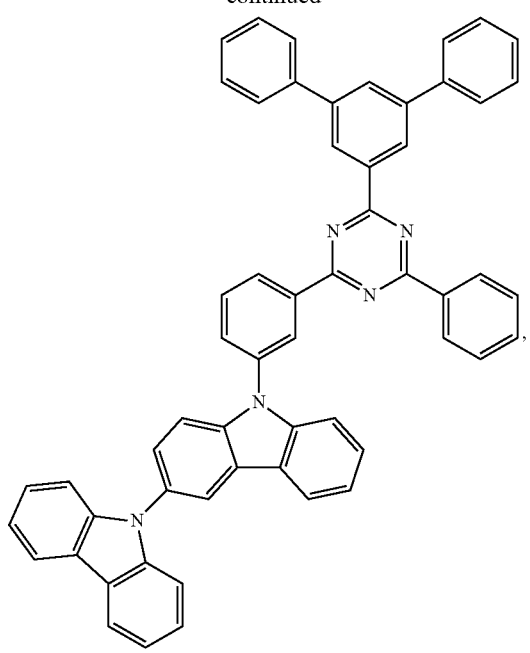
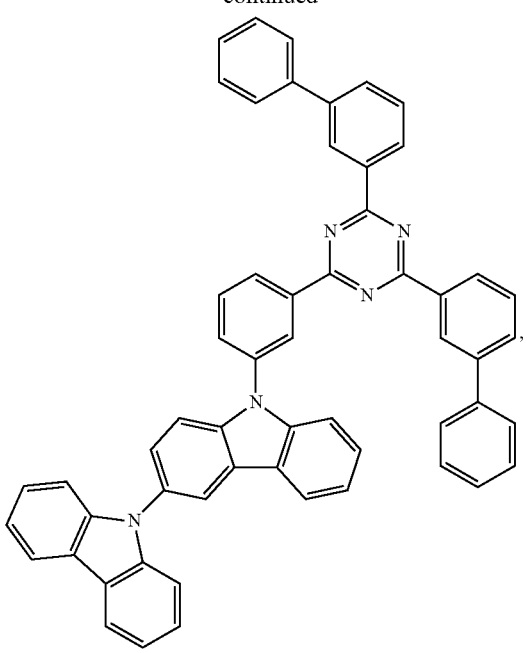
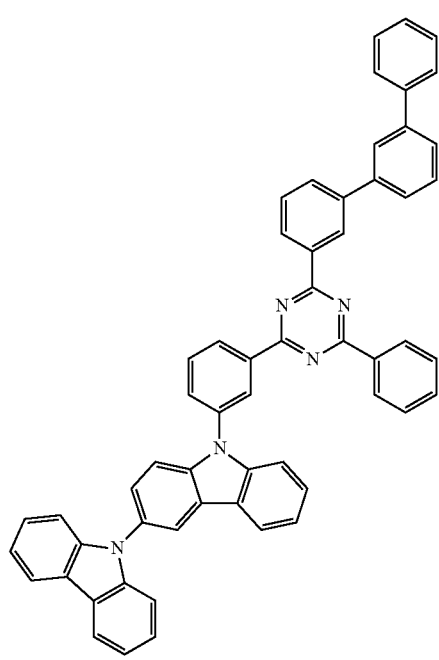
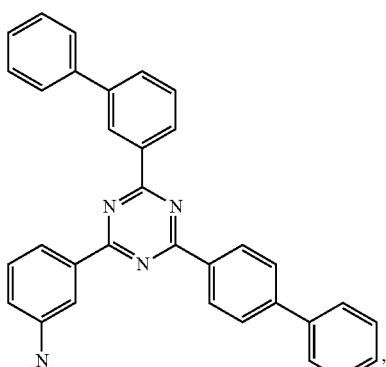

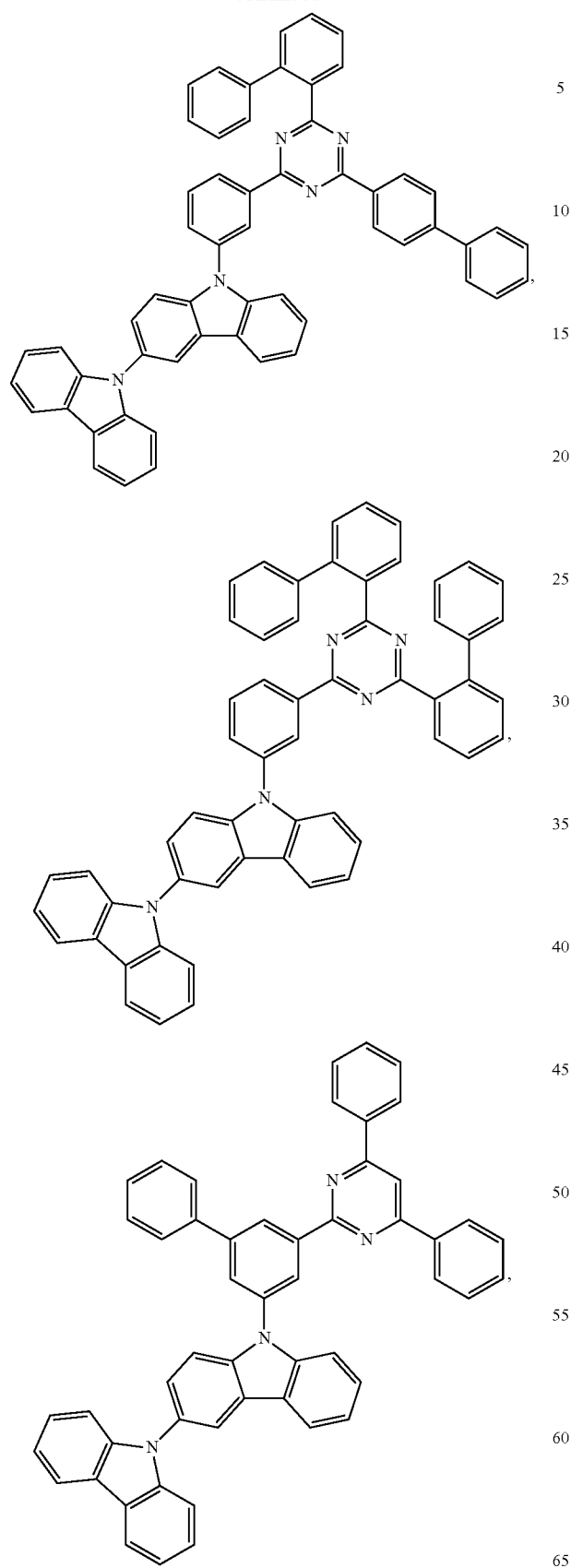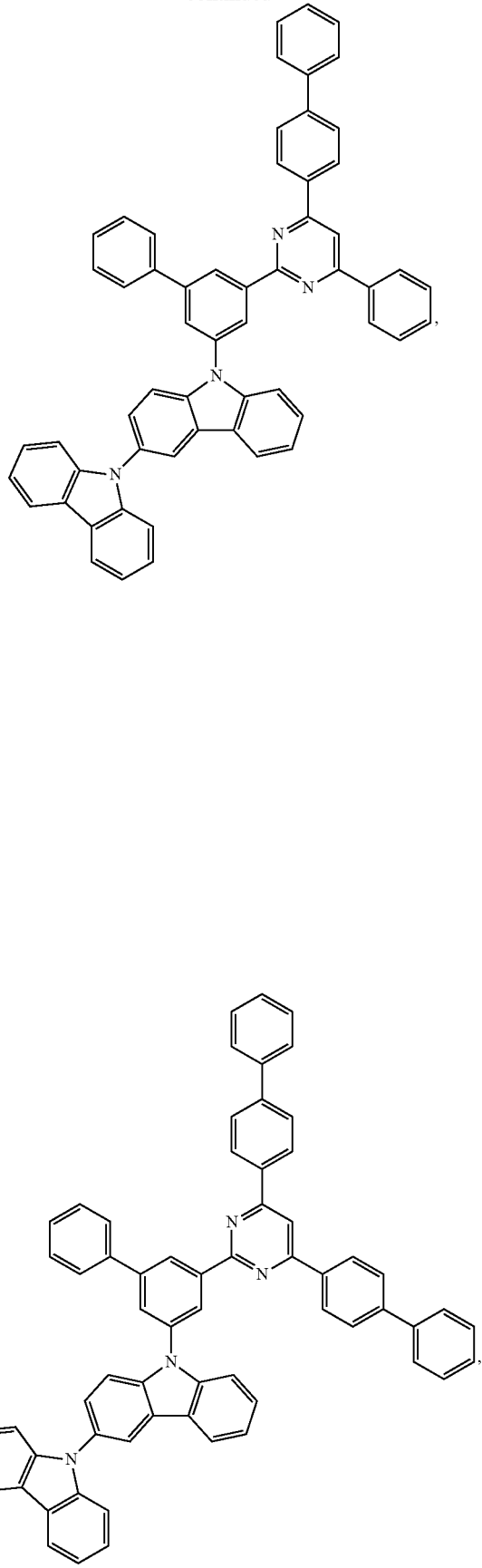

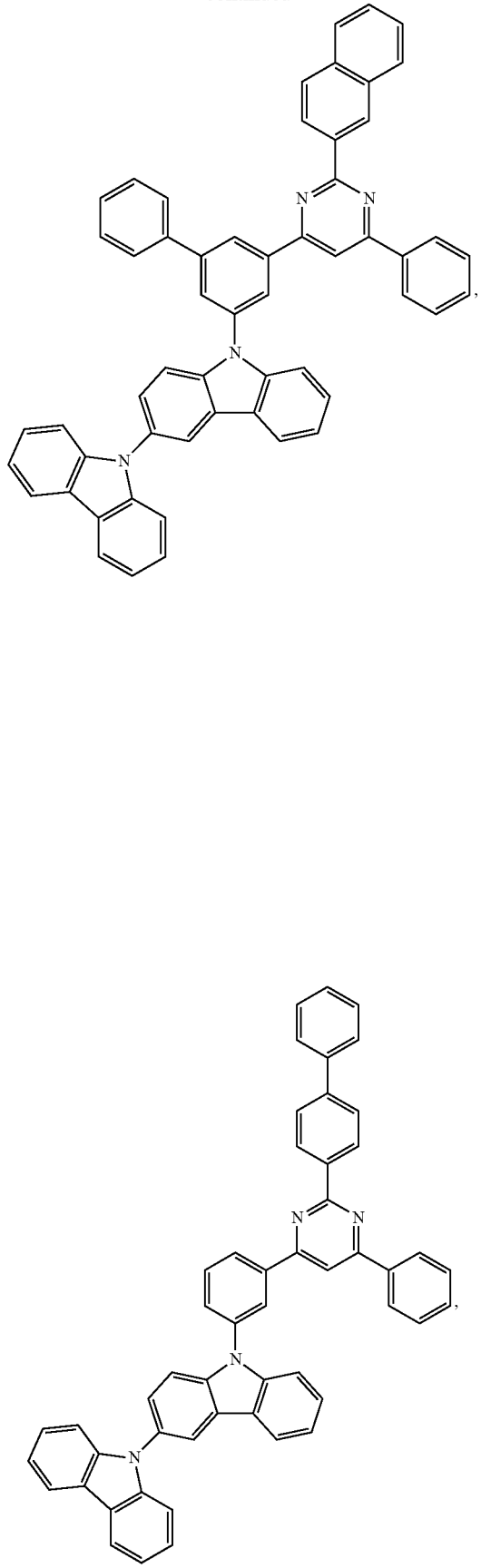

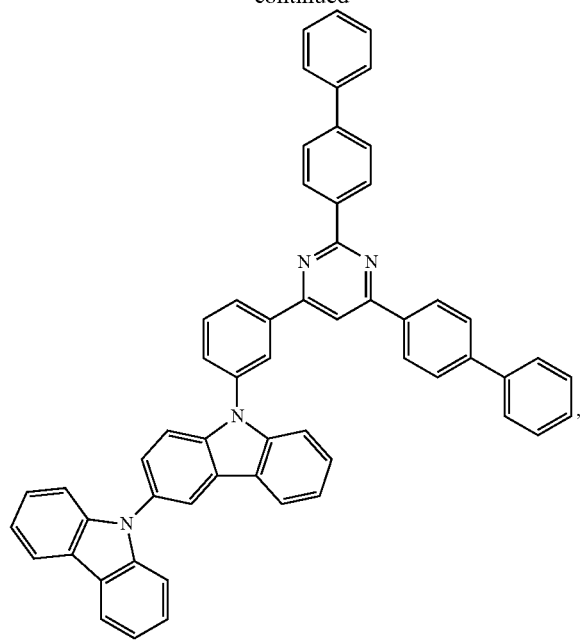
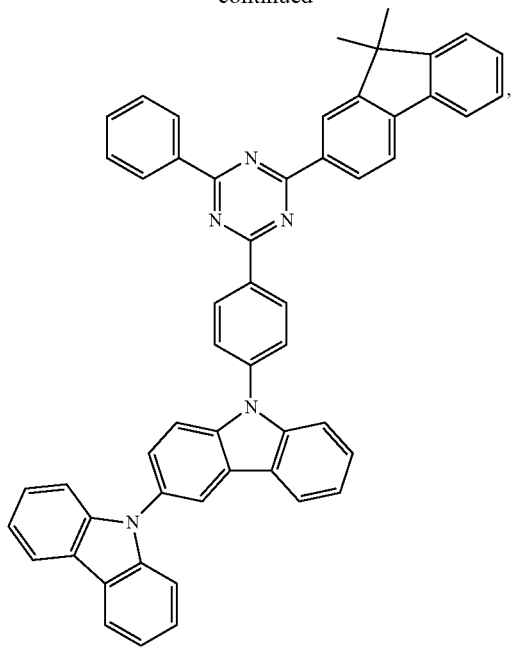
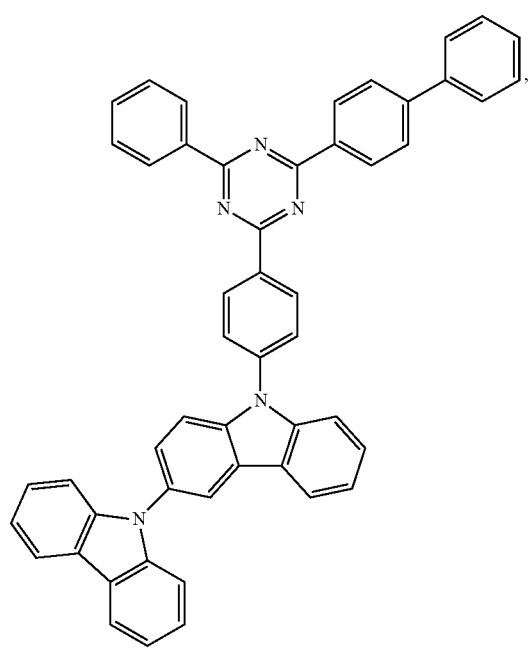
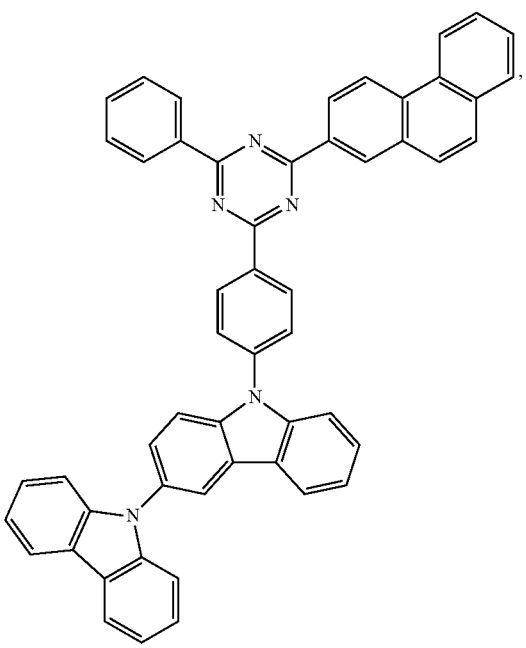

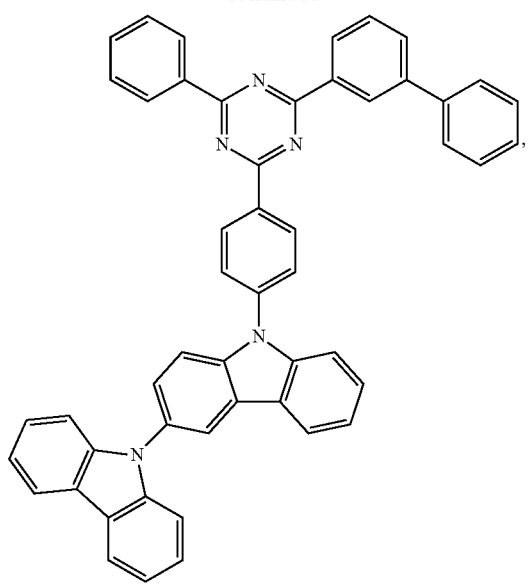
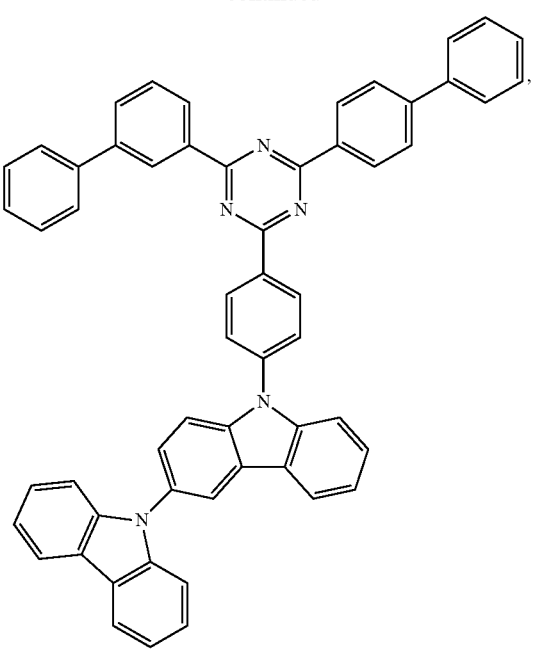
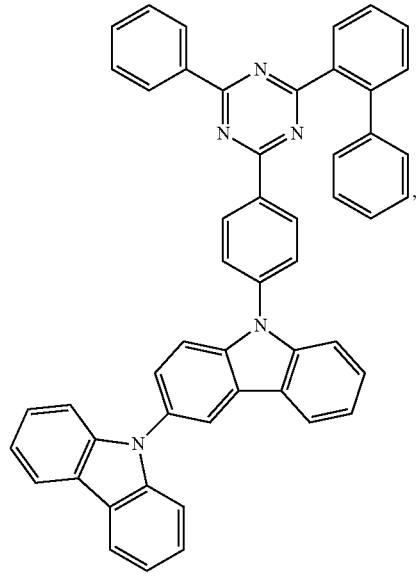
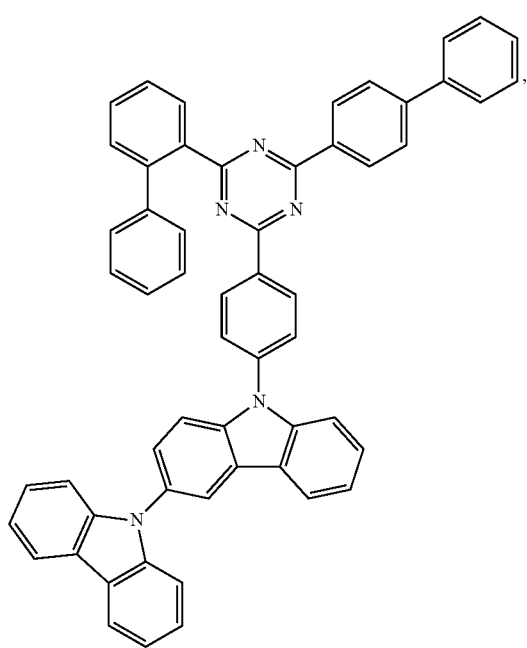

31
-continued
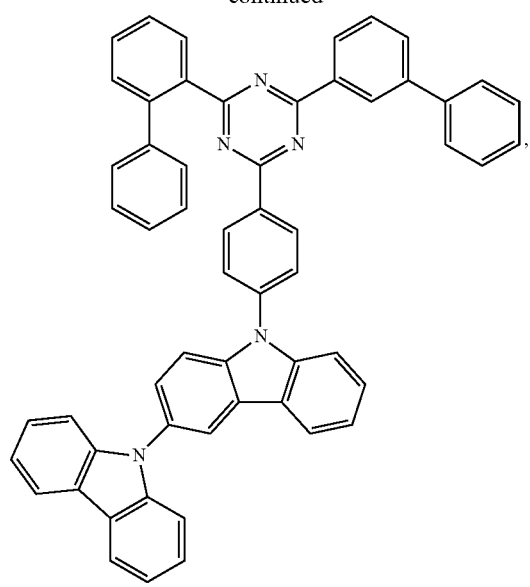
32
-continued
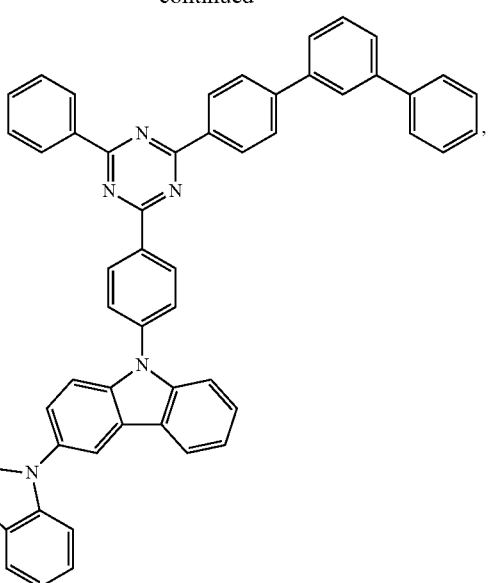
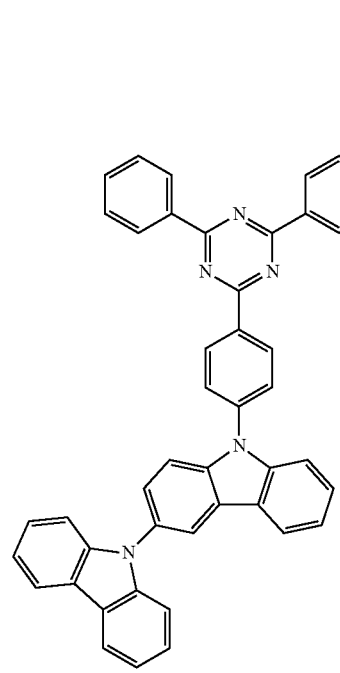
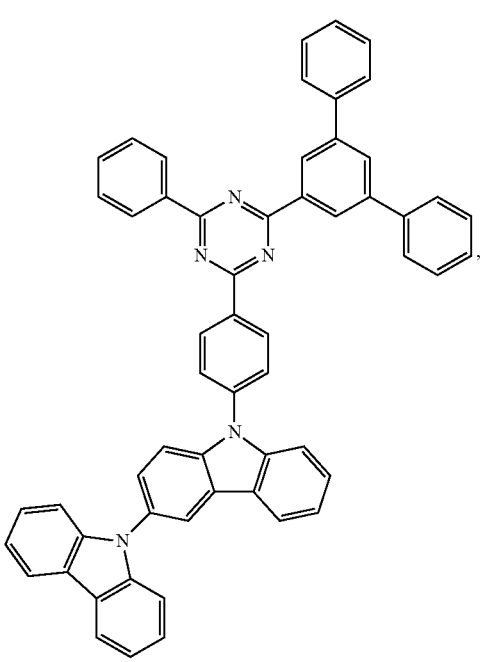

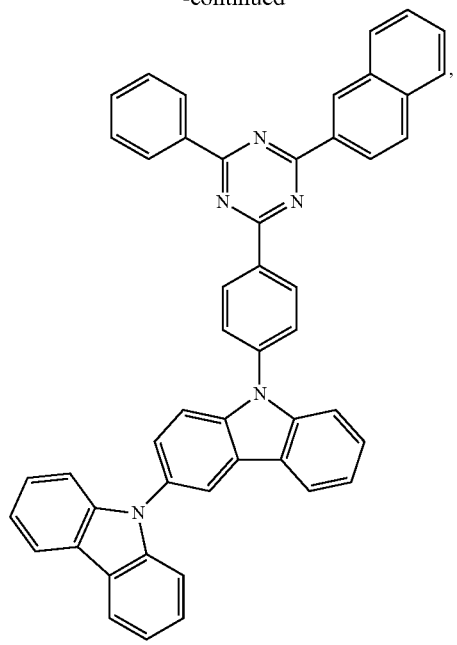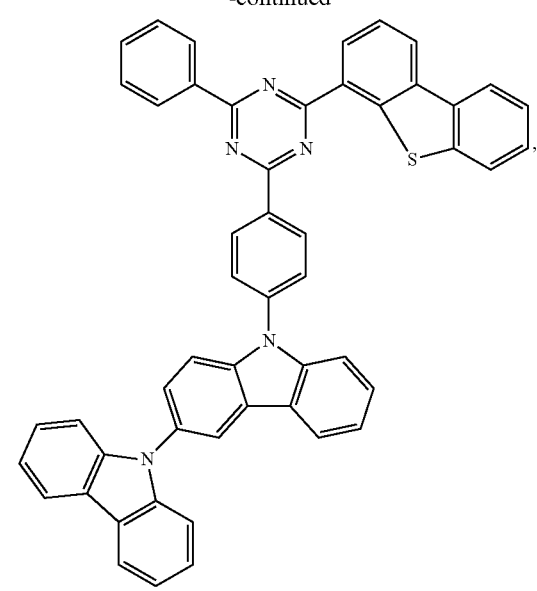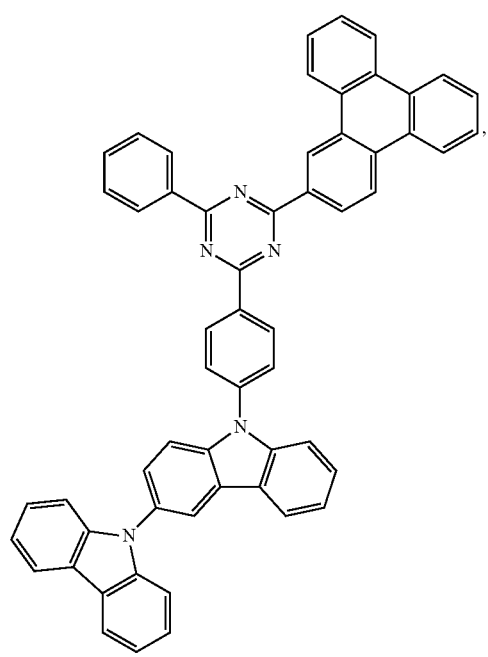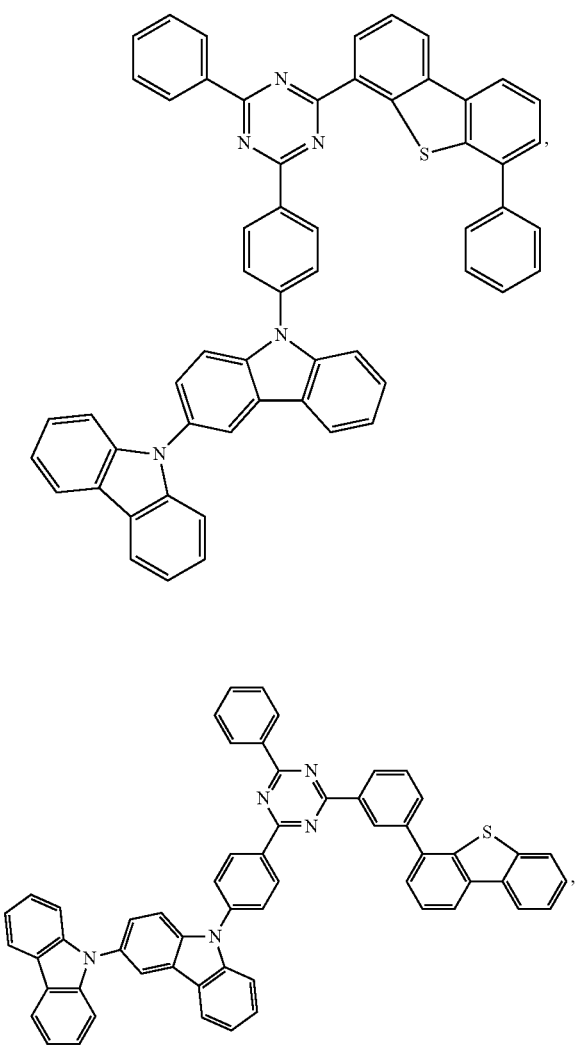

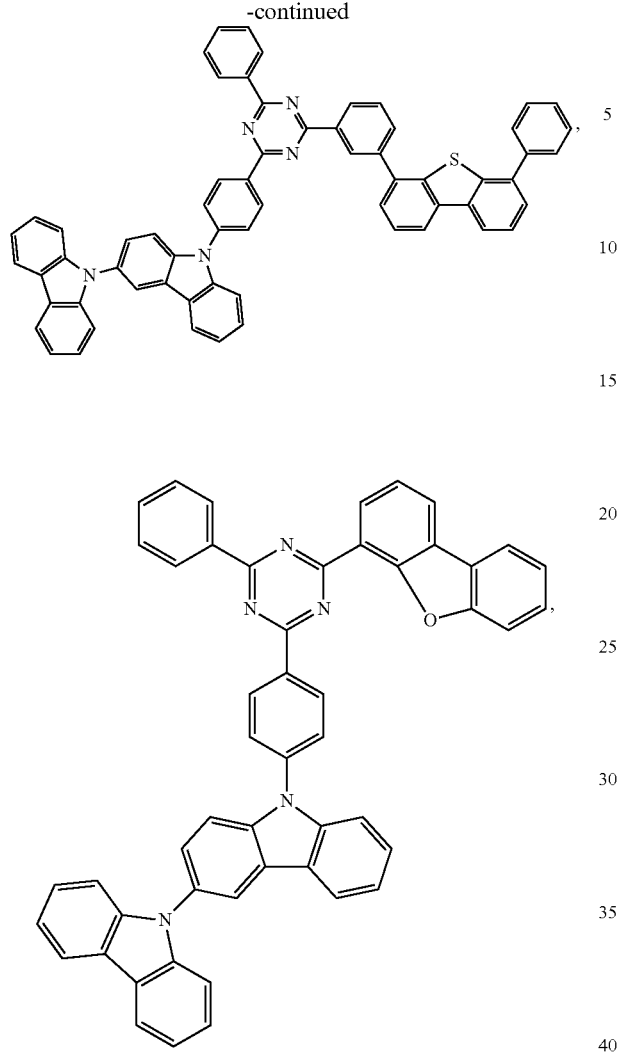
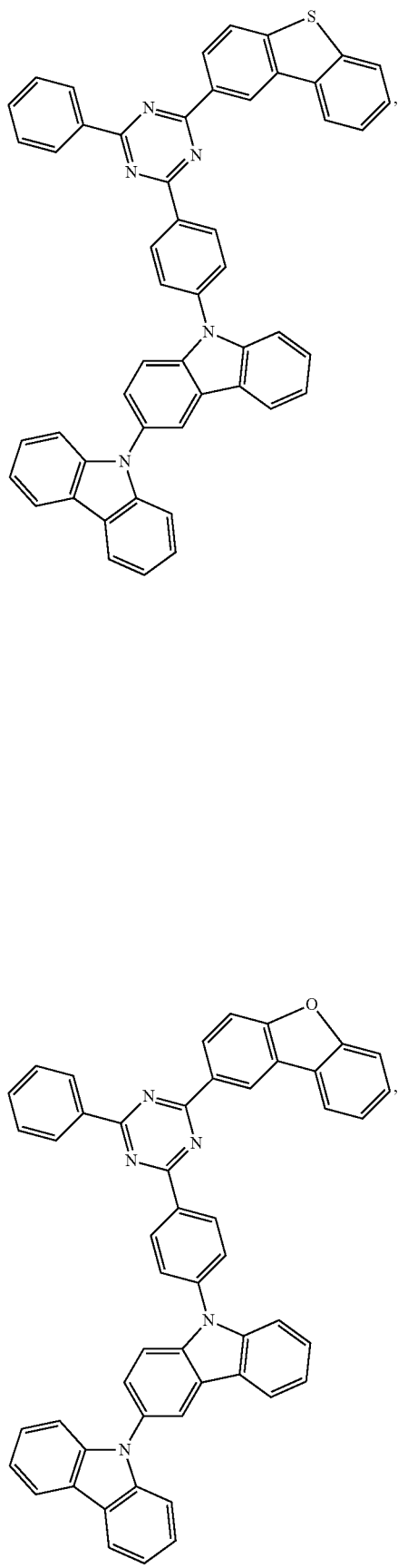

37
-continued
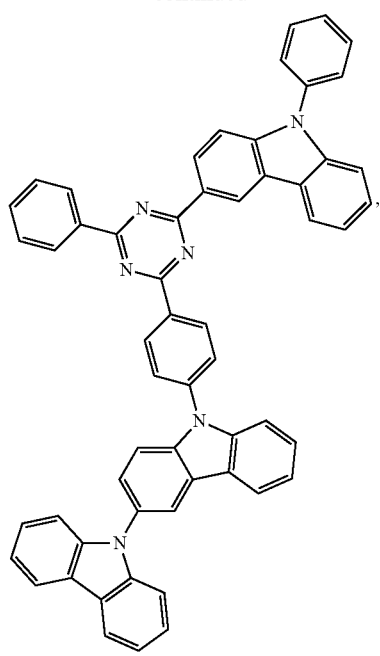
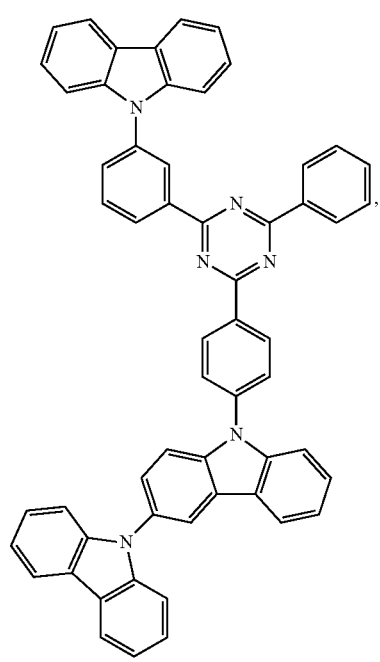
38
-continued
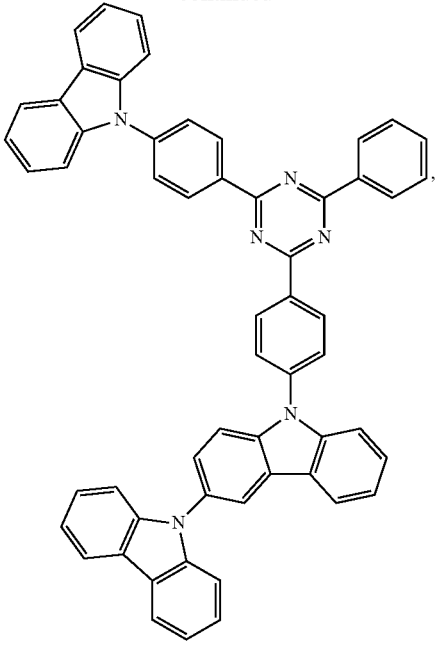
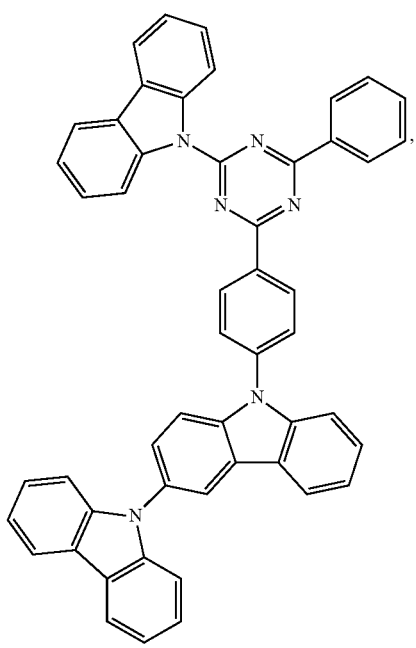

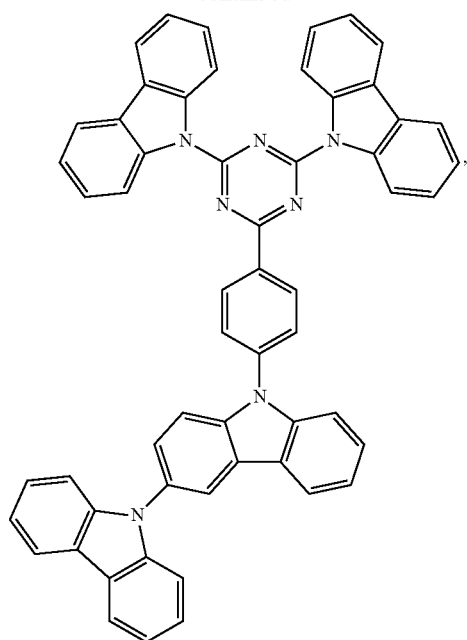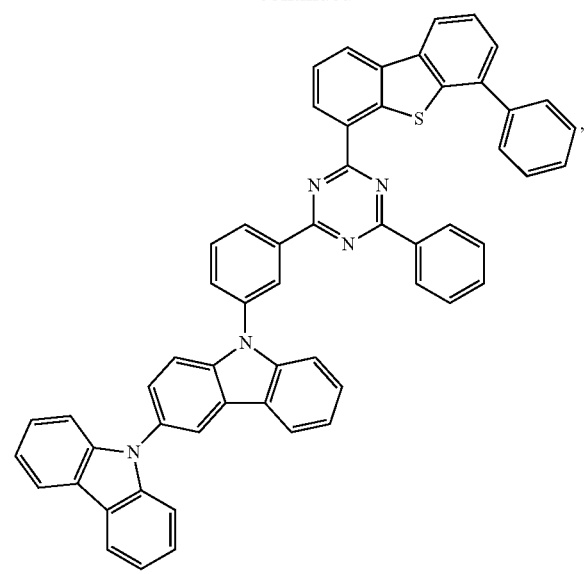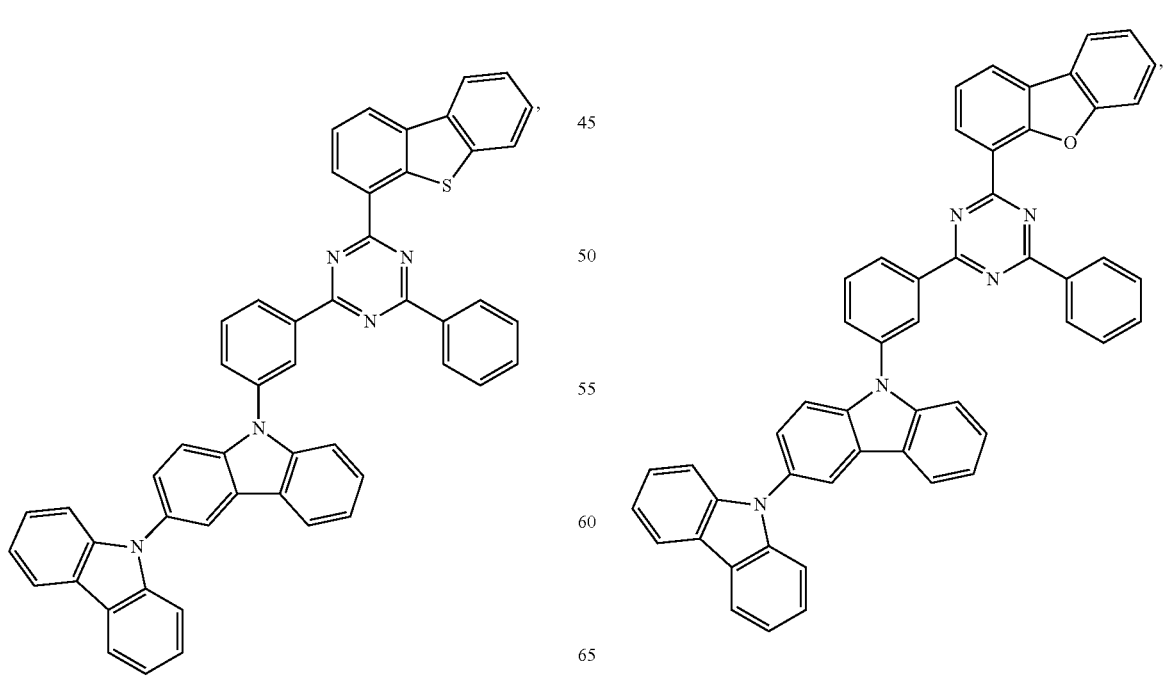

-continued
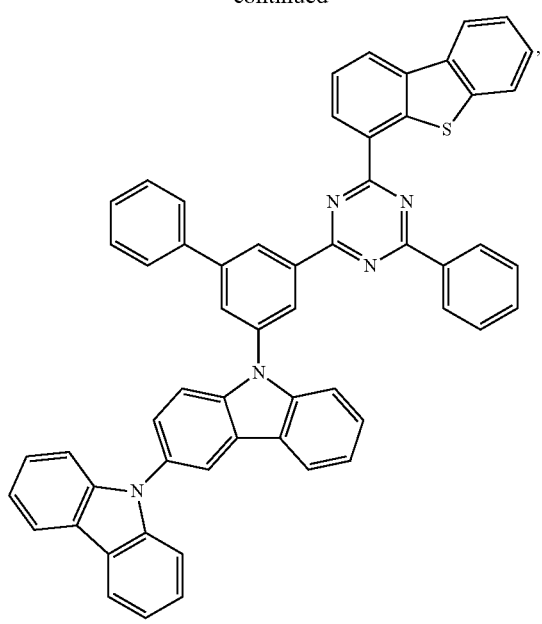
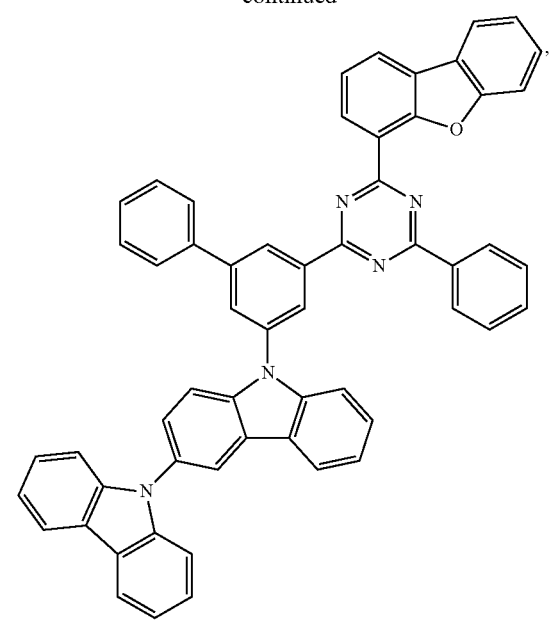

43
-continued
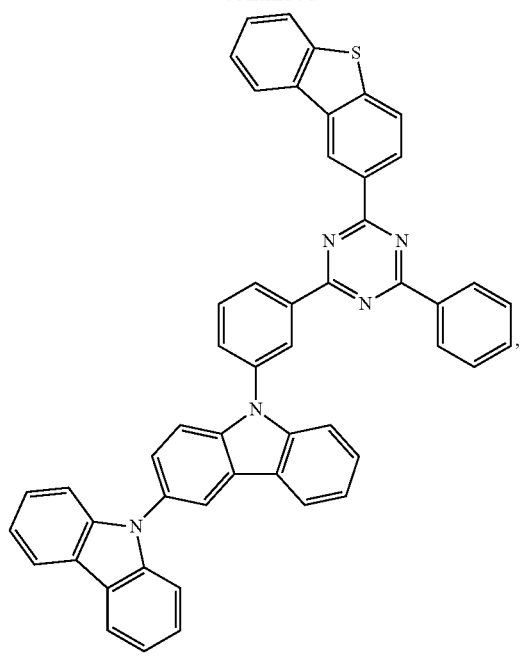
44
-continued
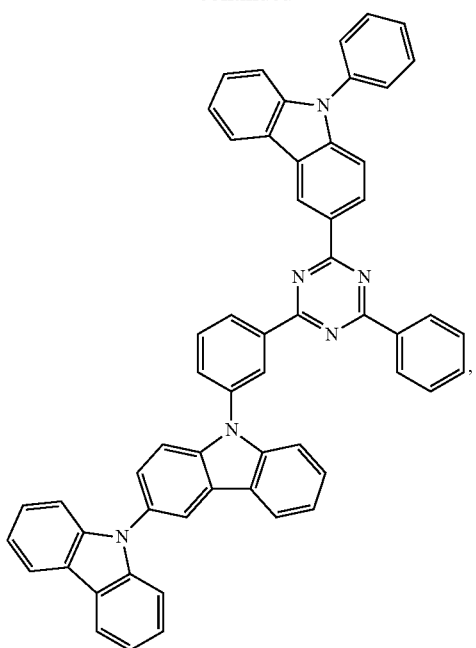

45
-continued
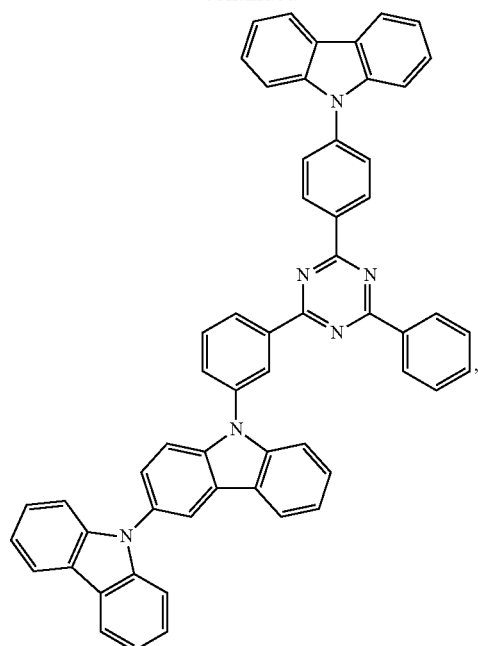
,
46
-continued
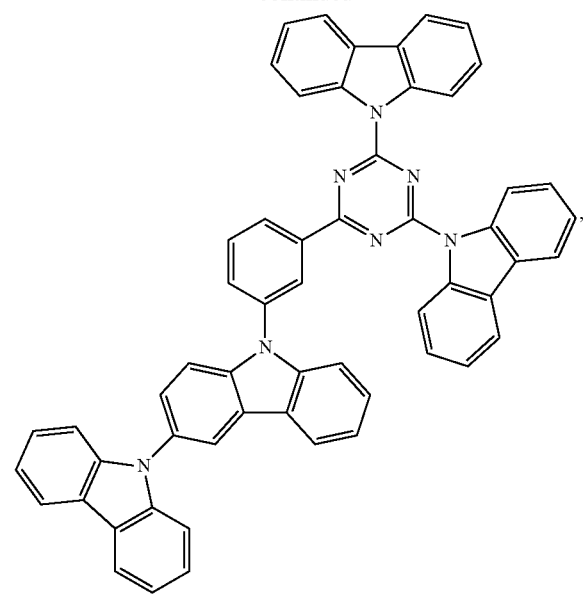
,
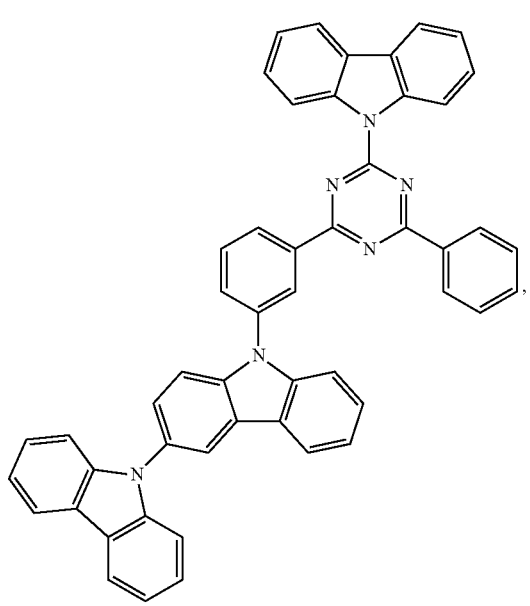
,
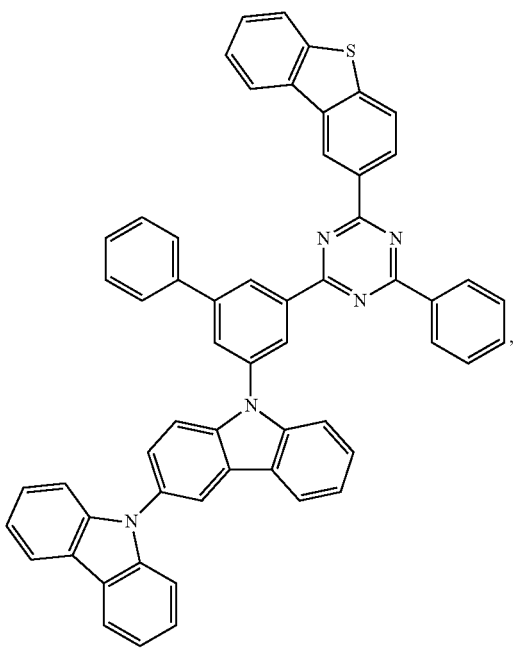
,

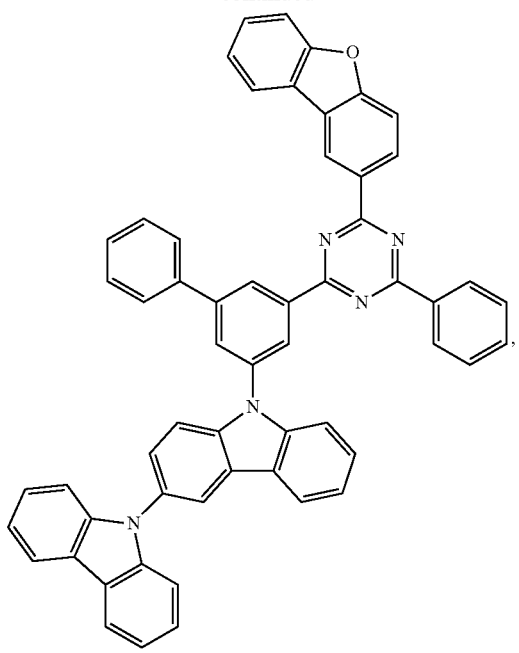
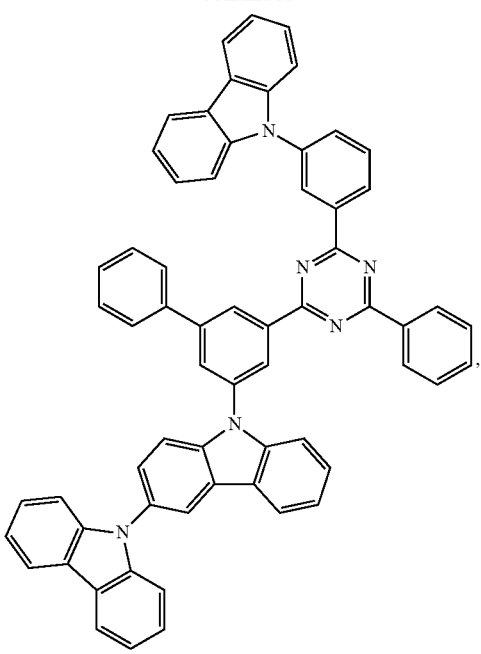
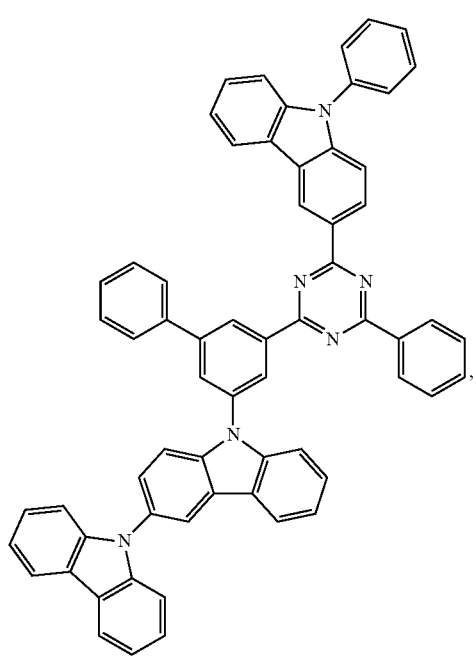
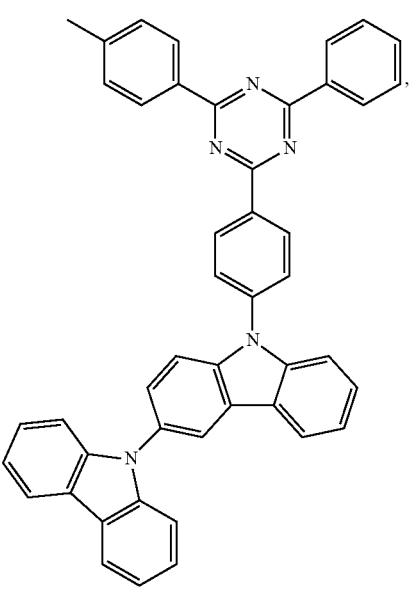

49
-continued
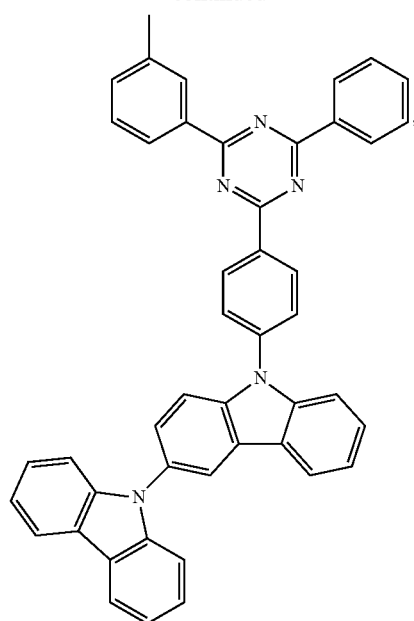
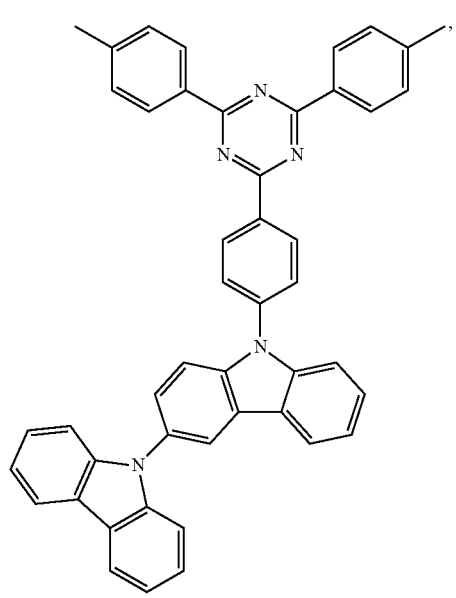
50
-continued
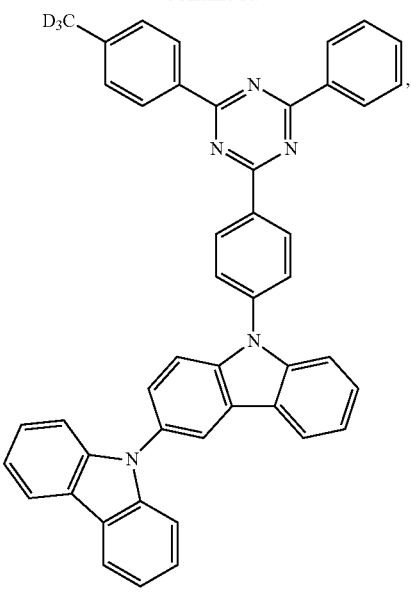
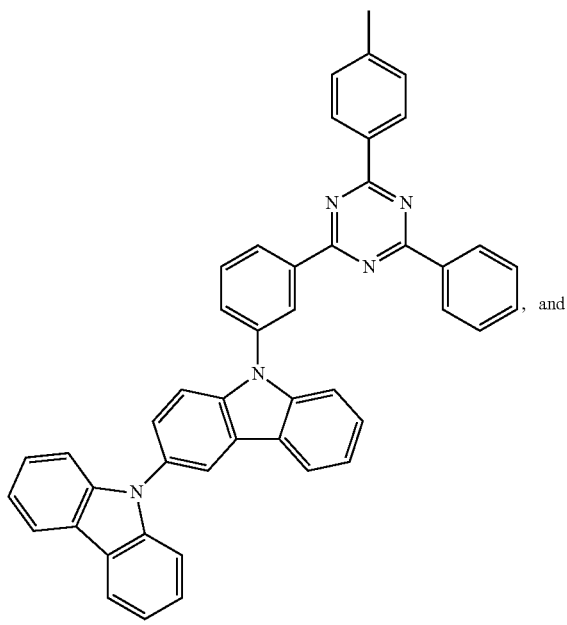, and

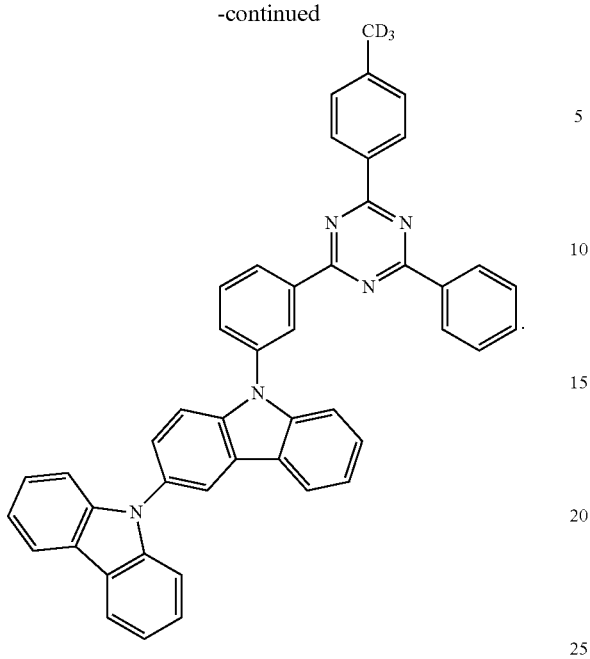

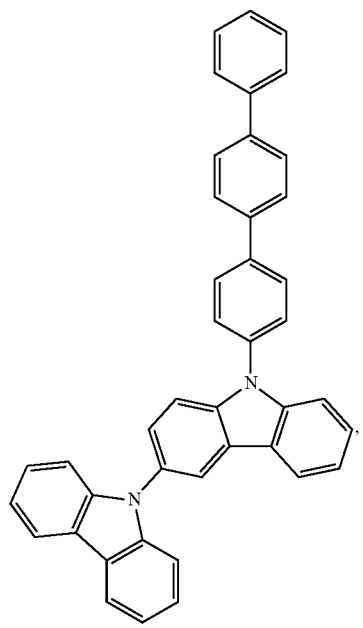

In some embodiments of the composition comprising a first compound, the first compound has the structure Formula III

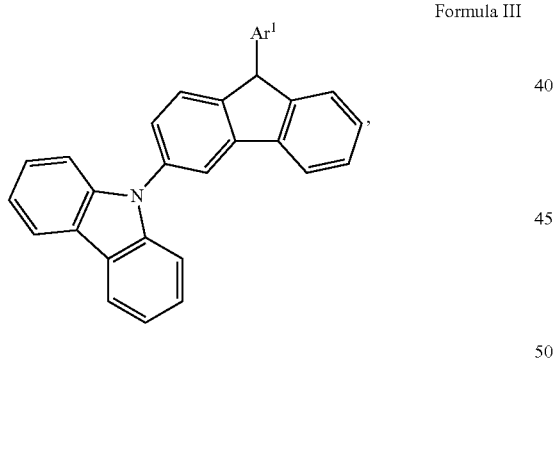

where $Ar^1$ is aryl comprising at least three phenyl rings joined to form a chain, and wherein N is attached to one of the phenyl rings at the end of the chain.

In some embodiments of the composition comprising the first compound that has a structure of Formula II, $Ar^1$ comprises four or more non-fused phenyl rings. In some embodiments of the composition, $Ar^1$ comprises five or more non-fused phenyl rings. In some embodiments of the composition, the first compound is selected from the group consisting of:

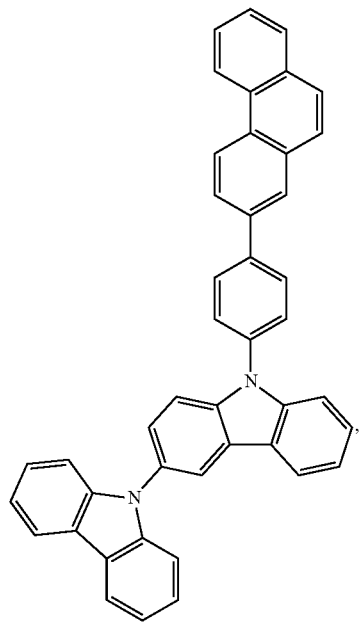

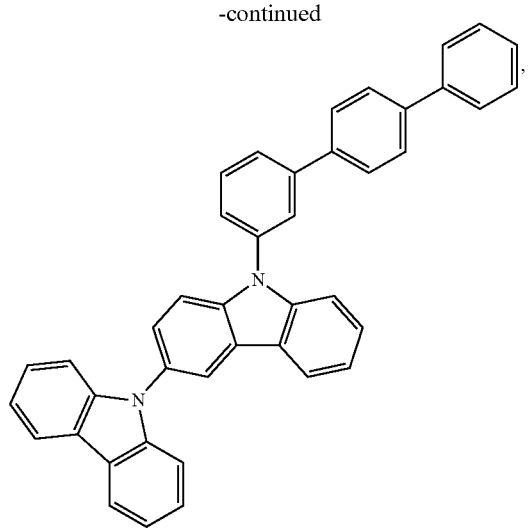
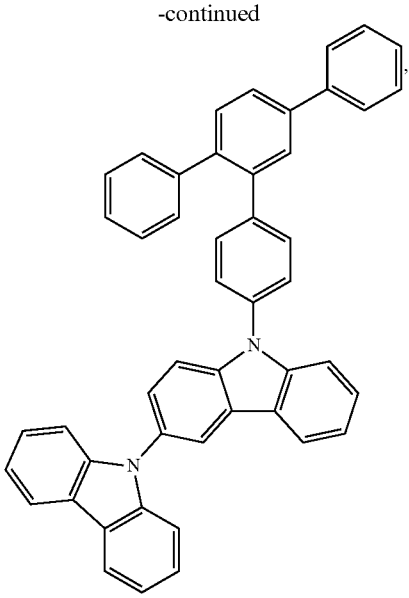
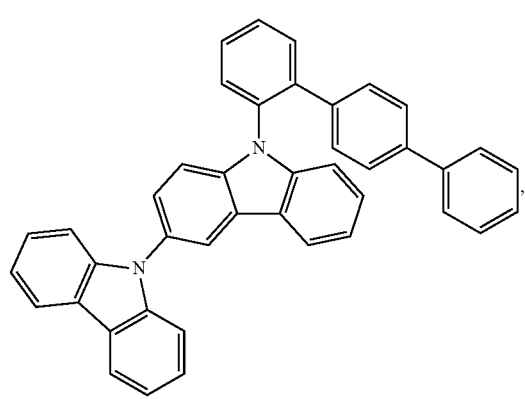
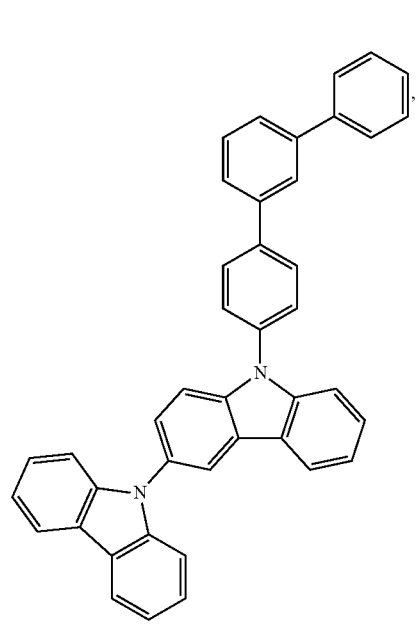
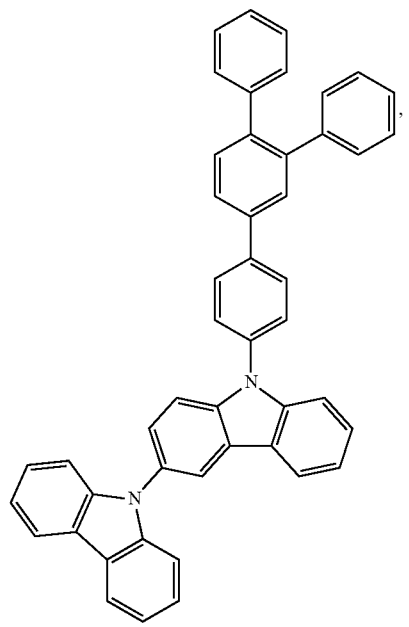

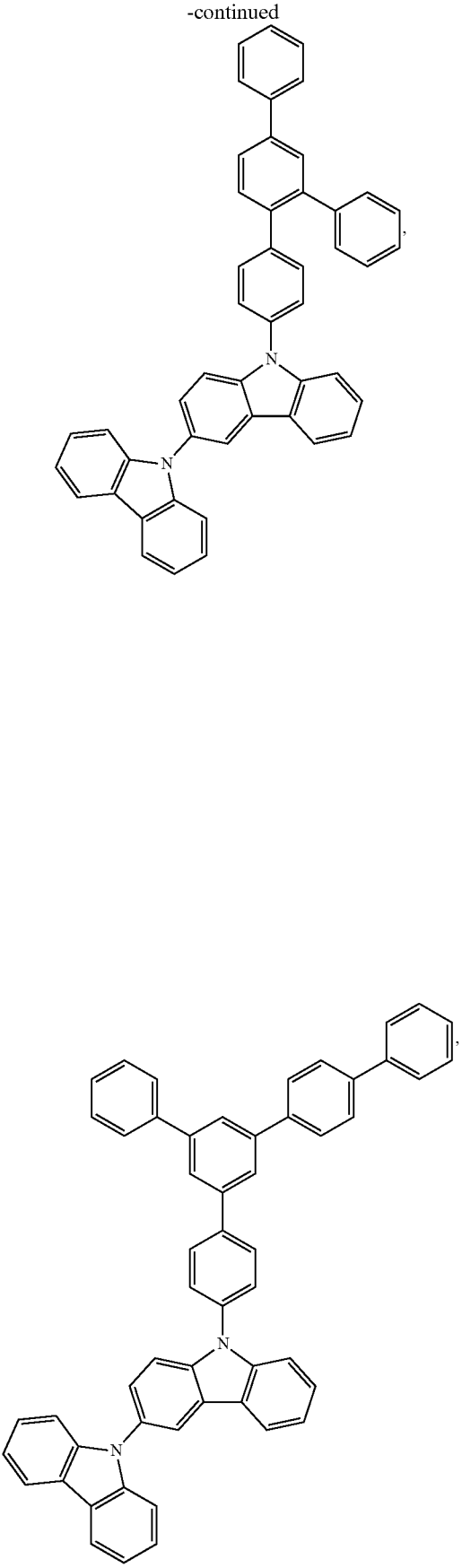
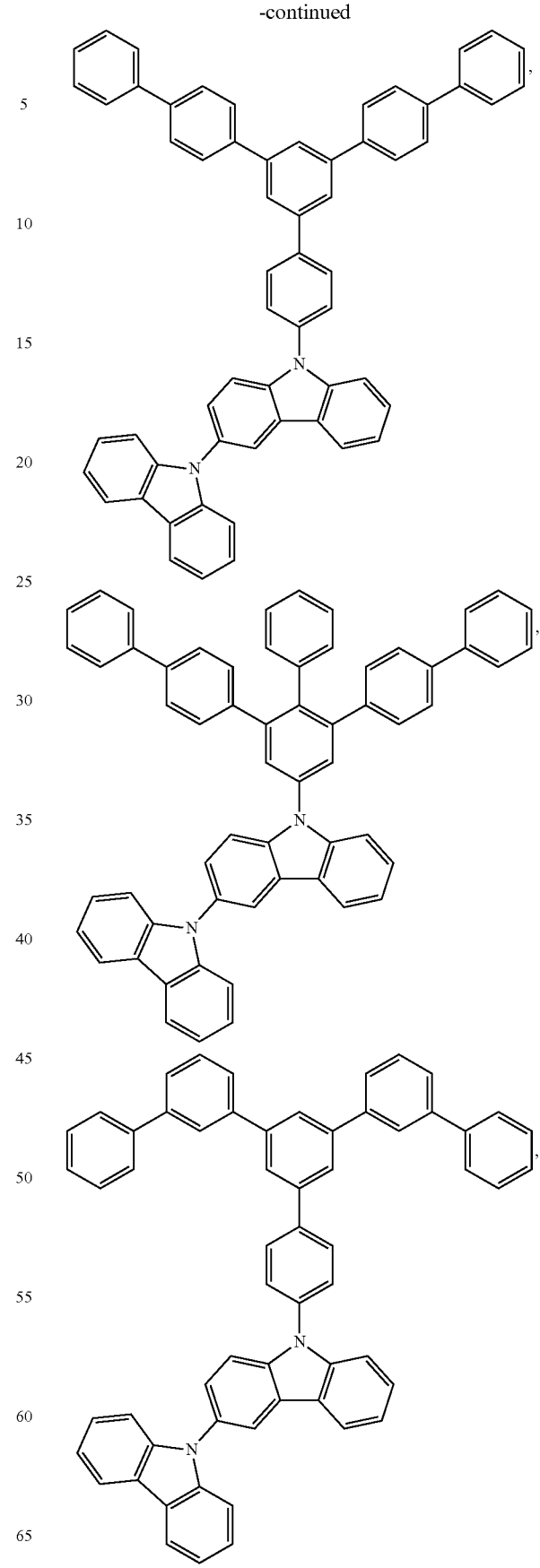

57
-continued
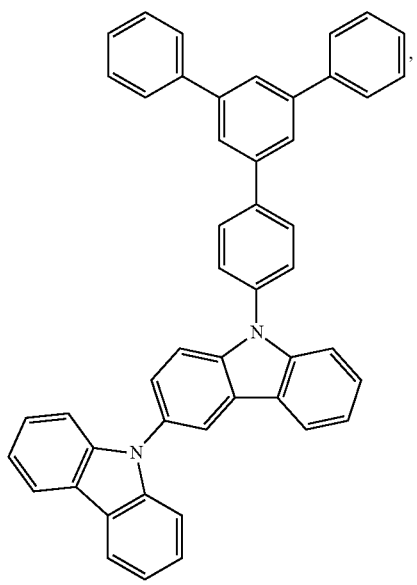
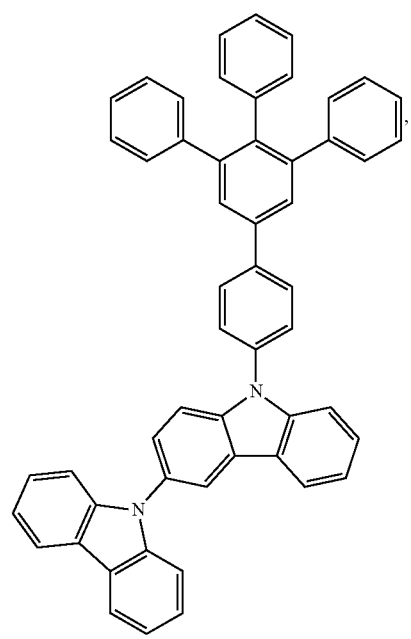
58
-continued
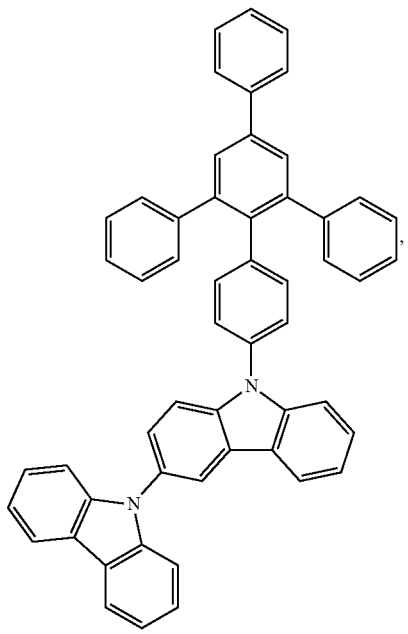
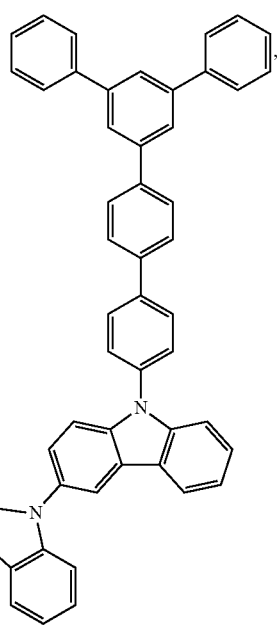

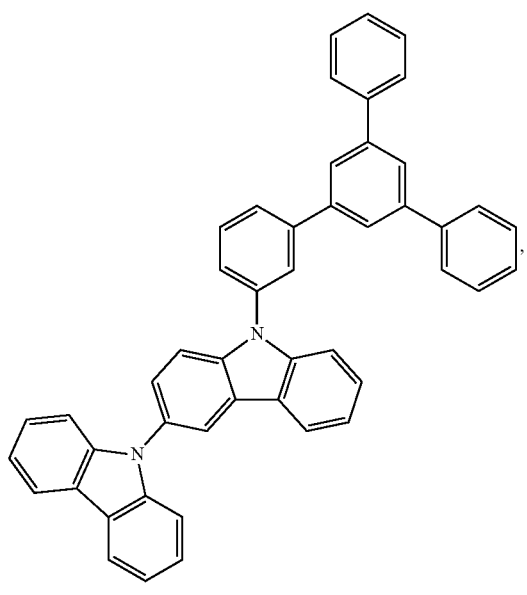
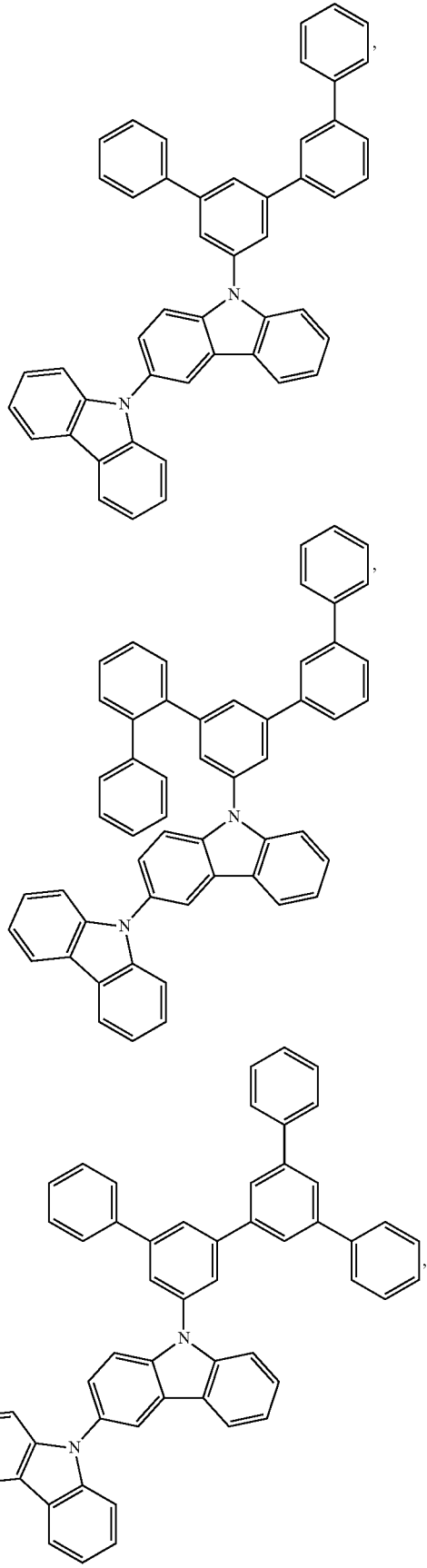

61
-continued
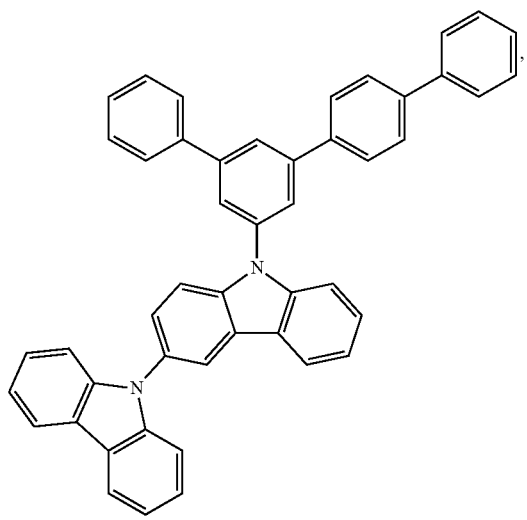
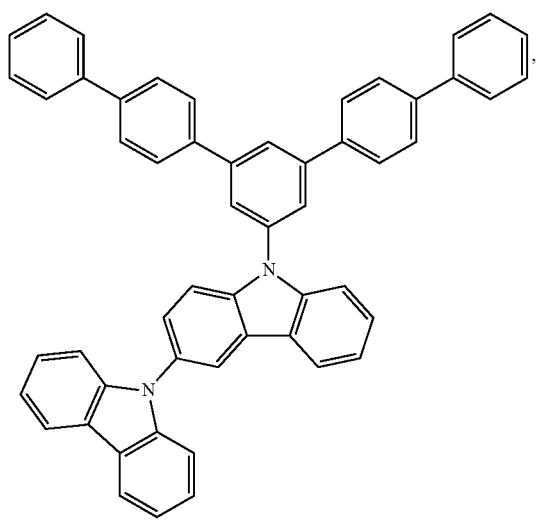
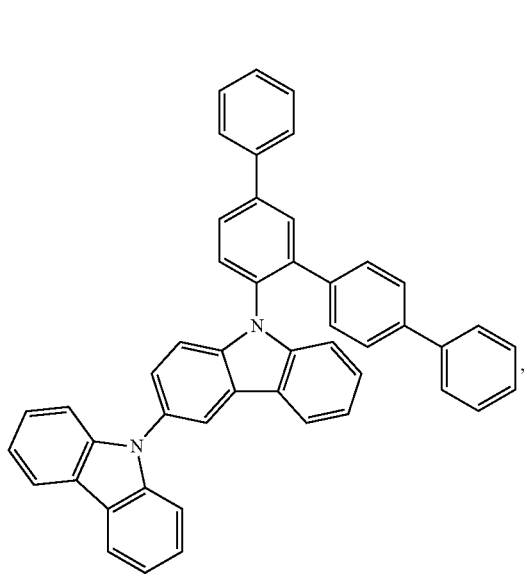
62
-continued
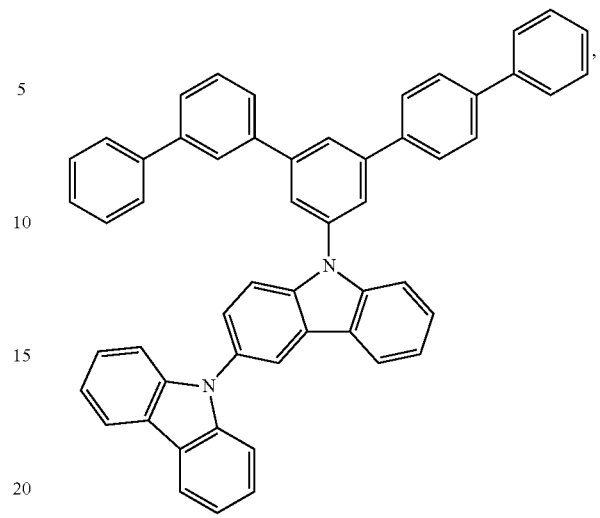
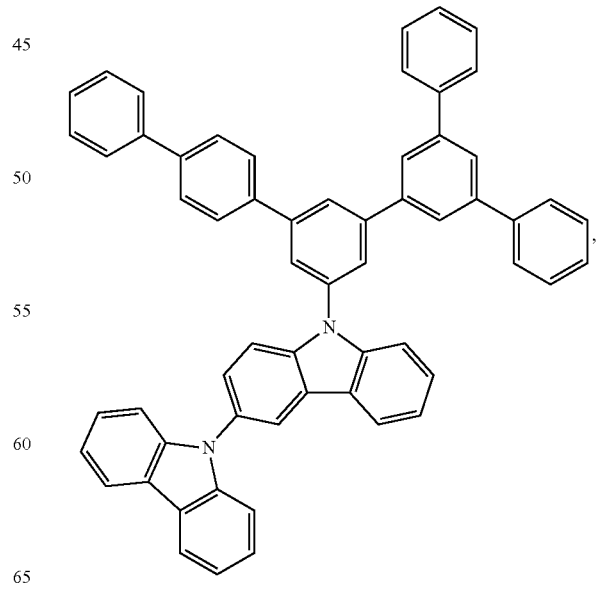

-continued
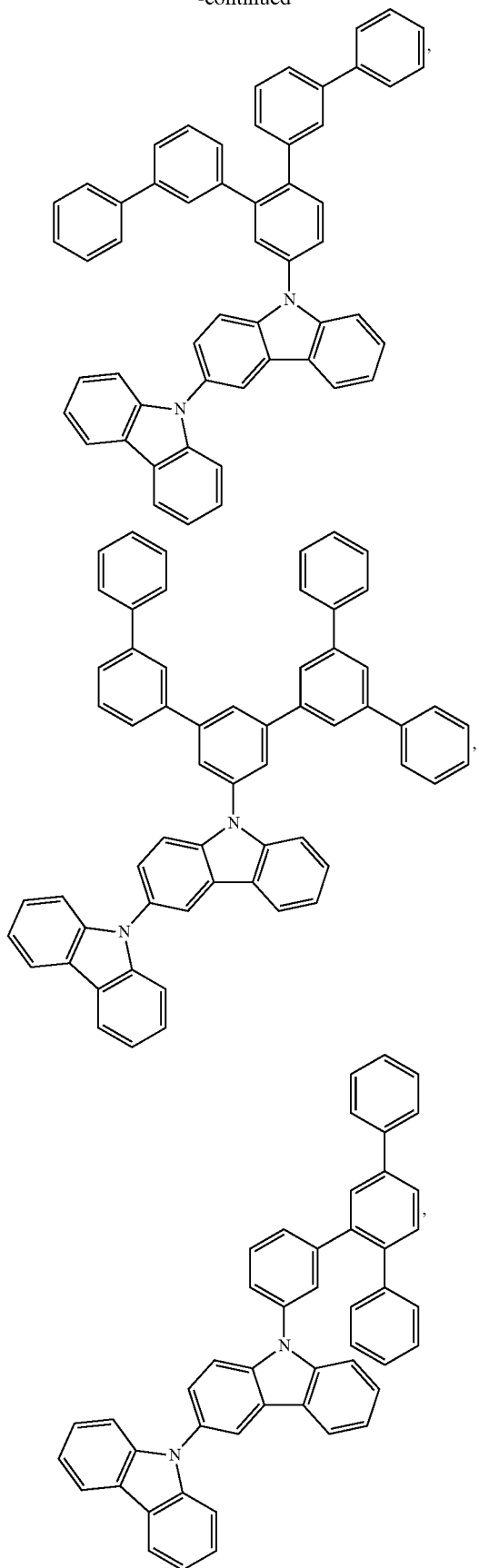
-continued
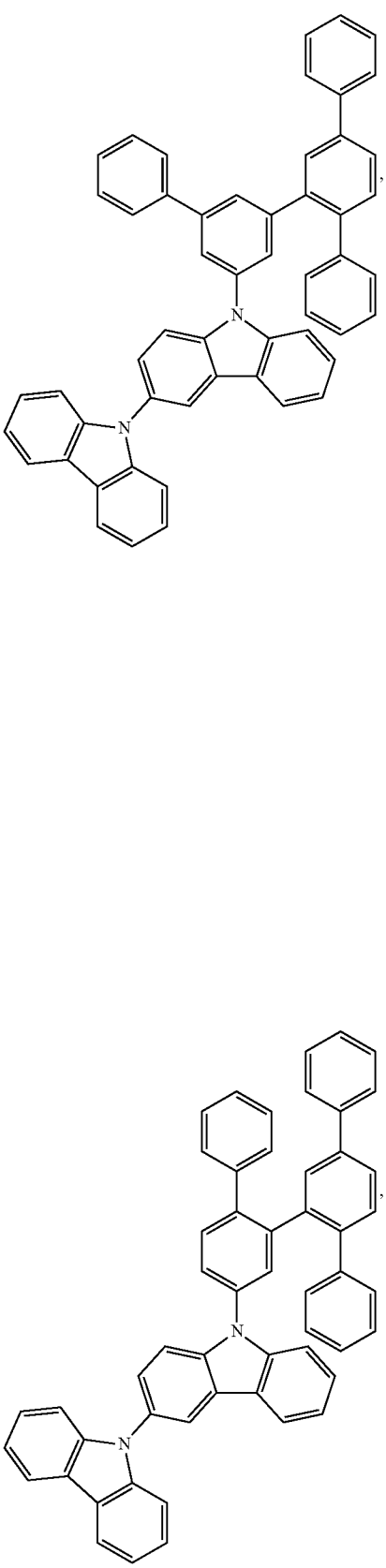

-continued
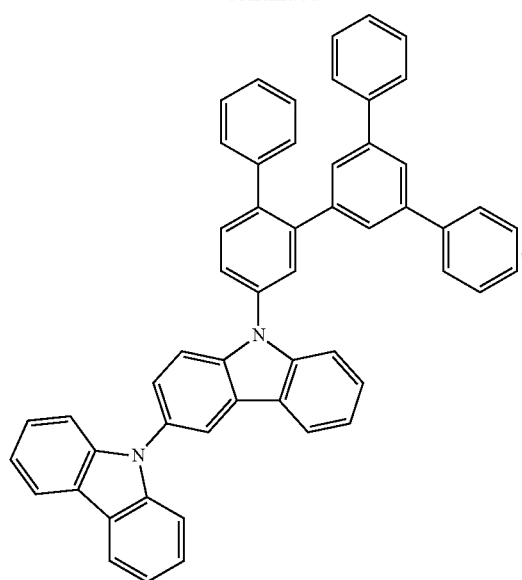
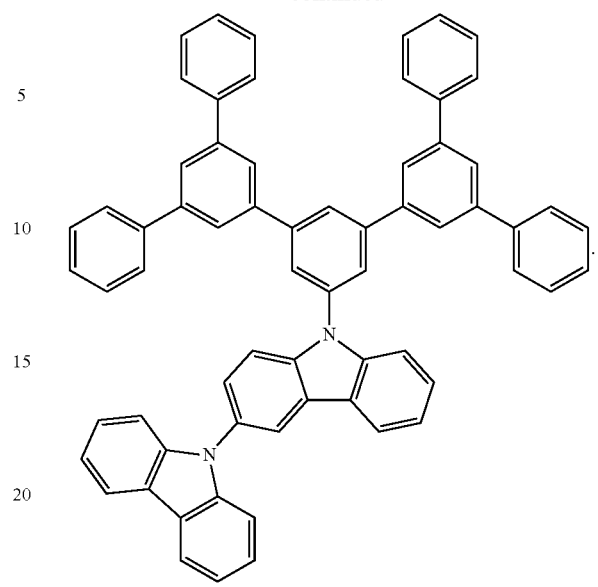
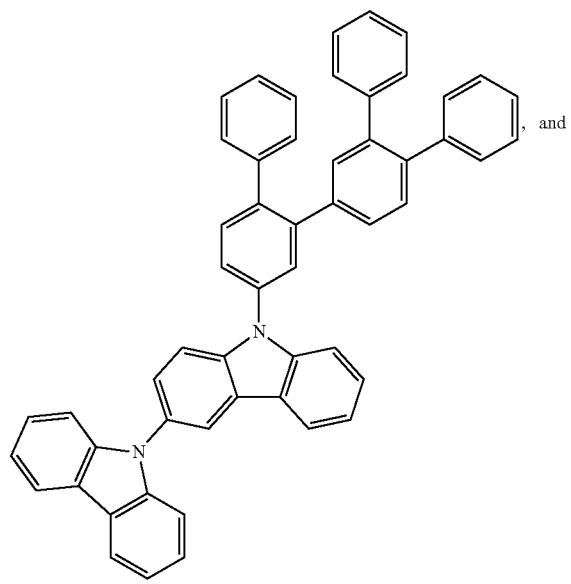
In some embodiments of the composition, the composition further comprises a second compound. The second compound can be selected from the group consisting of:
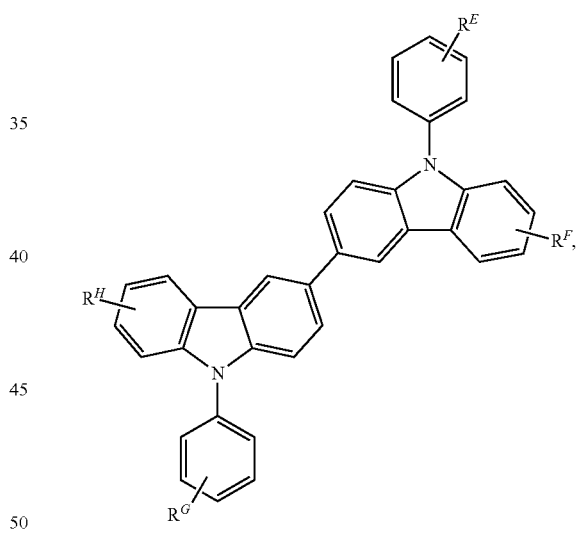
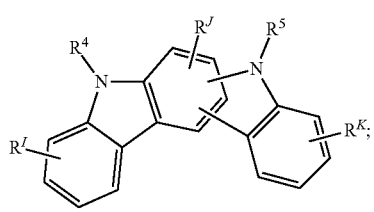

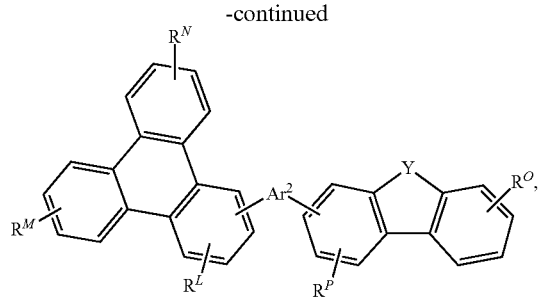

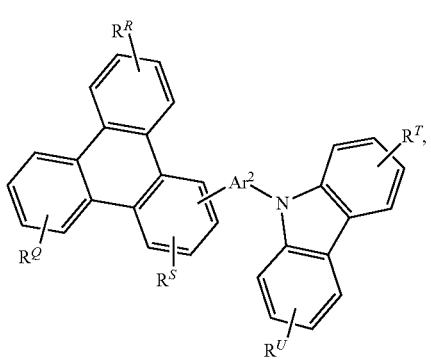

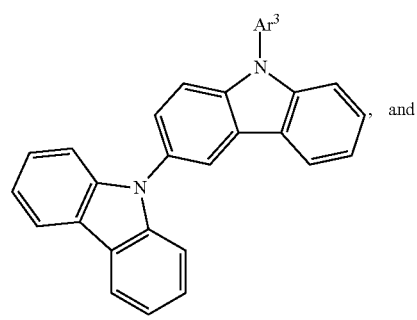

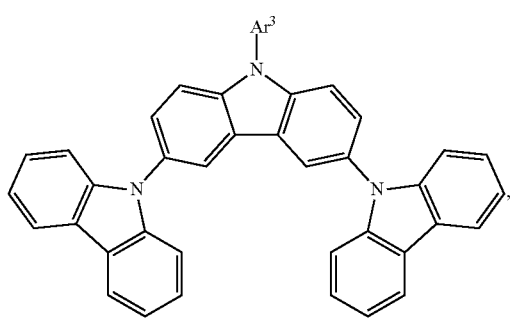

wherein, $R^E$ to $R^U$ each independently represents mono to the maximum allowable substitutions, or no substitution; each $R^4$, $R^5$, and $R^E$ to $R^U$ is independently hydrogen or a substituent selected from the group consisting of the general substituents defined above; any two substituents may be joined or fused together to form a ring; Y is O or S; and $Ar^3$ is a substituted or unsubstituted aryl ring. In some embodiments, each $R^4$, $R^5$, and $R^E$ to $R^U$ is independently hydrogen, or a substituent selected from the group consisting of the preferred general substituents defined above.

In some embodiments of the composition, where the composition comprises a second compound, the second compound can be selected from the group consisting of:

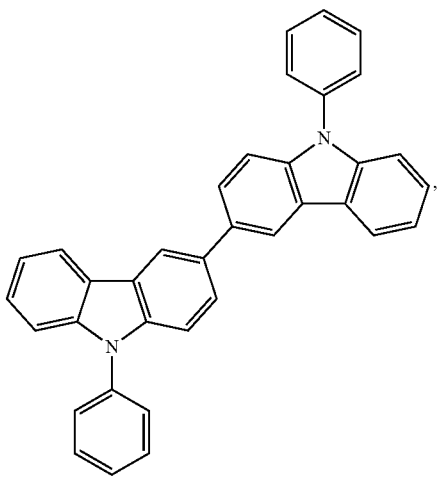

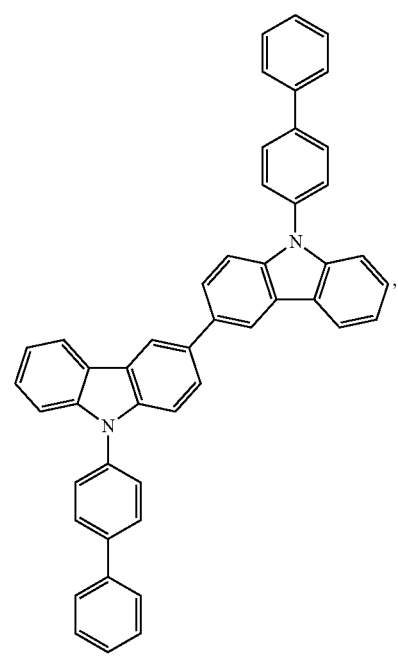

-continued
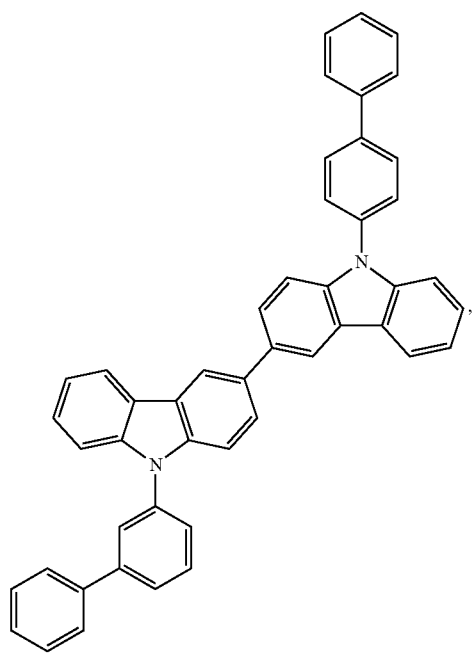
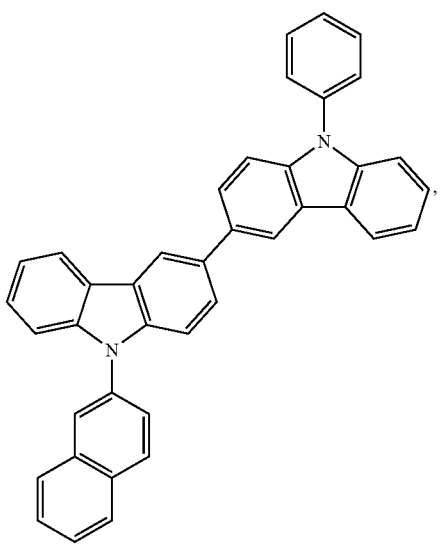
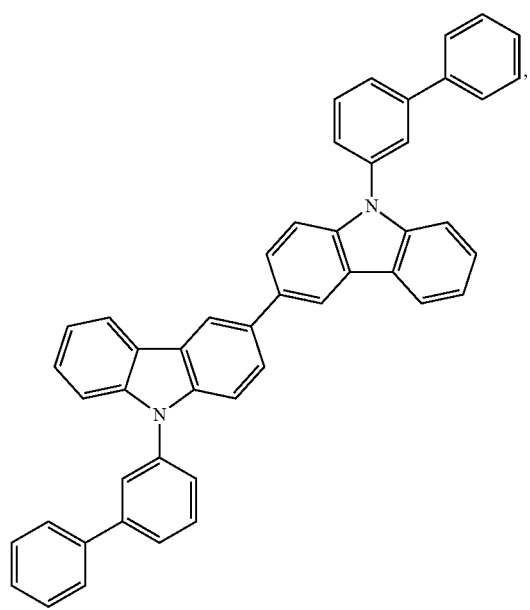
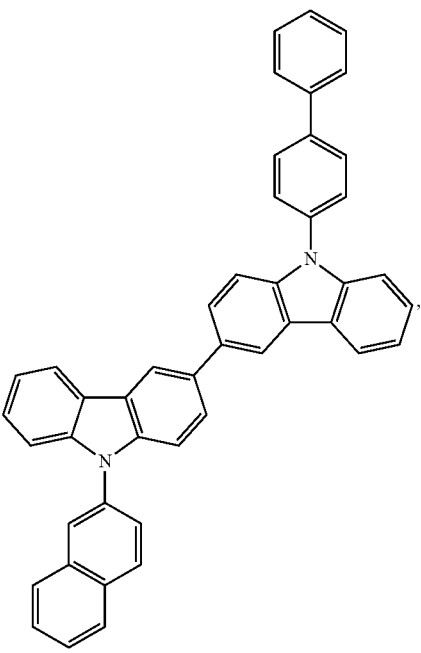

71
-continued
72
-continued
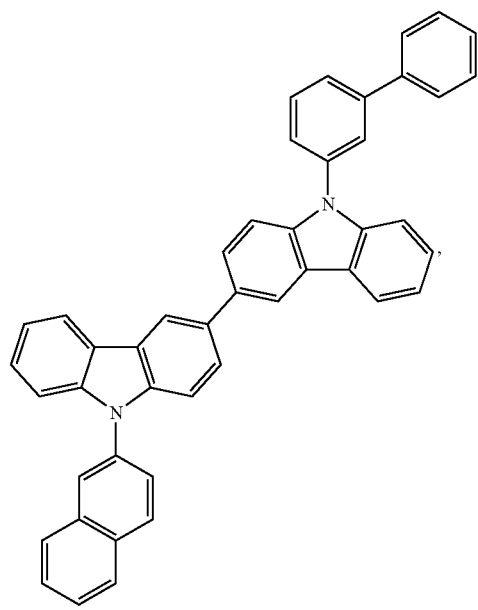
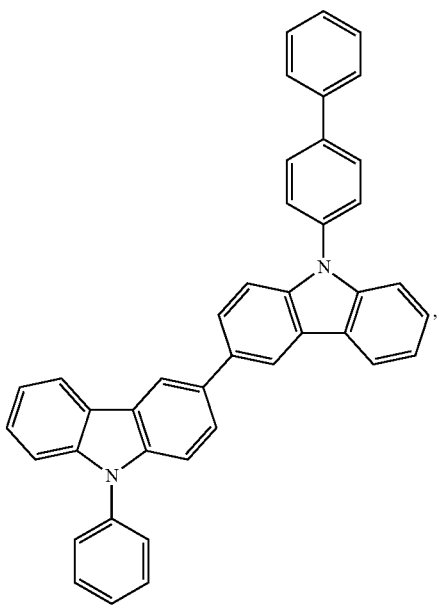

73
-continued
74
-continued
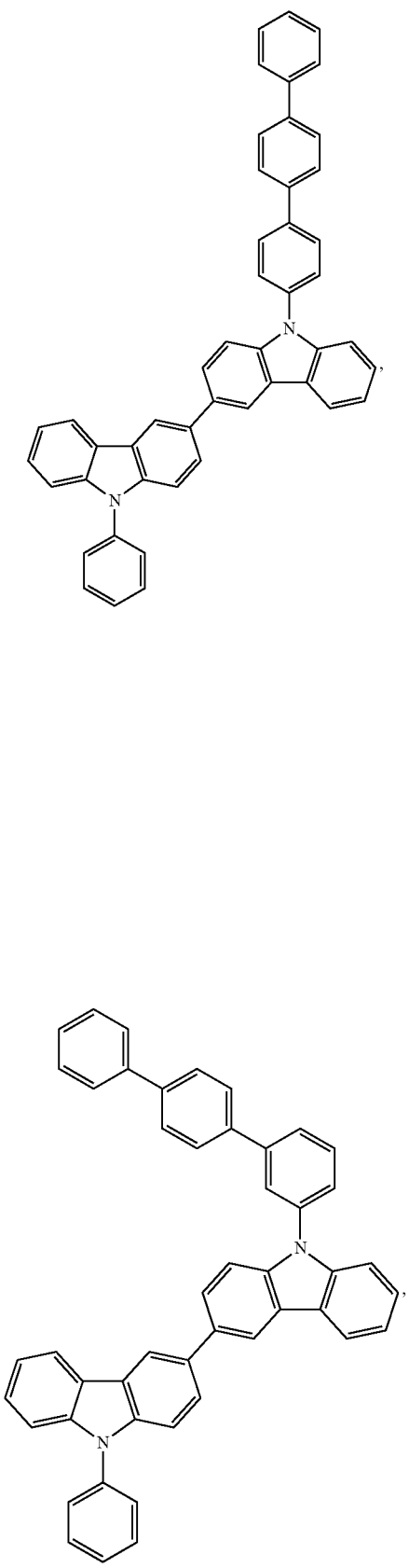
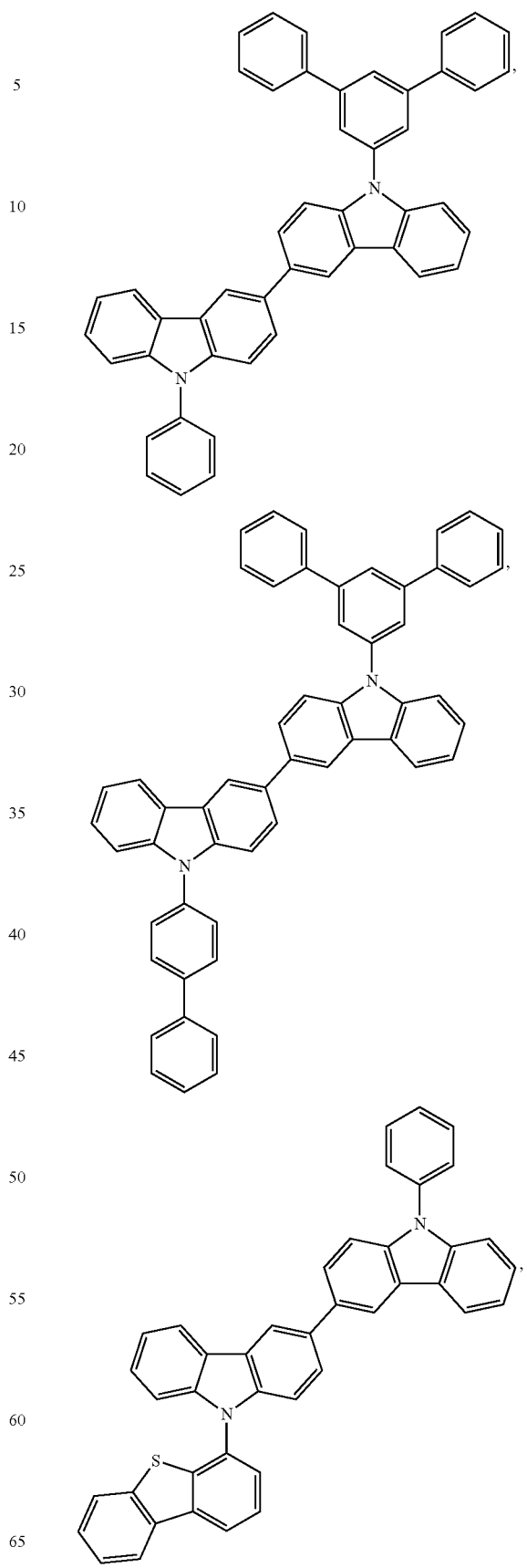

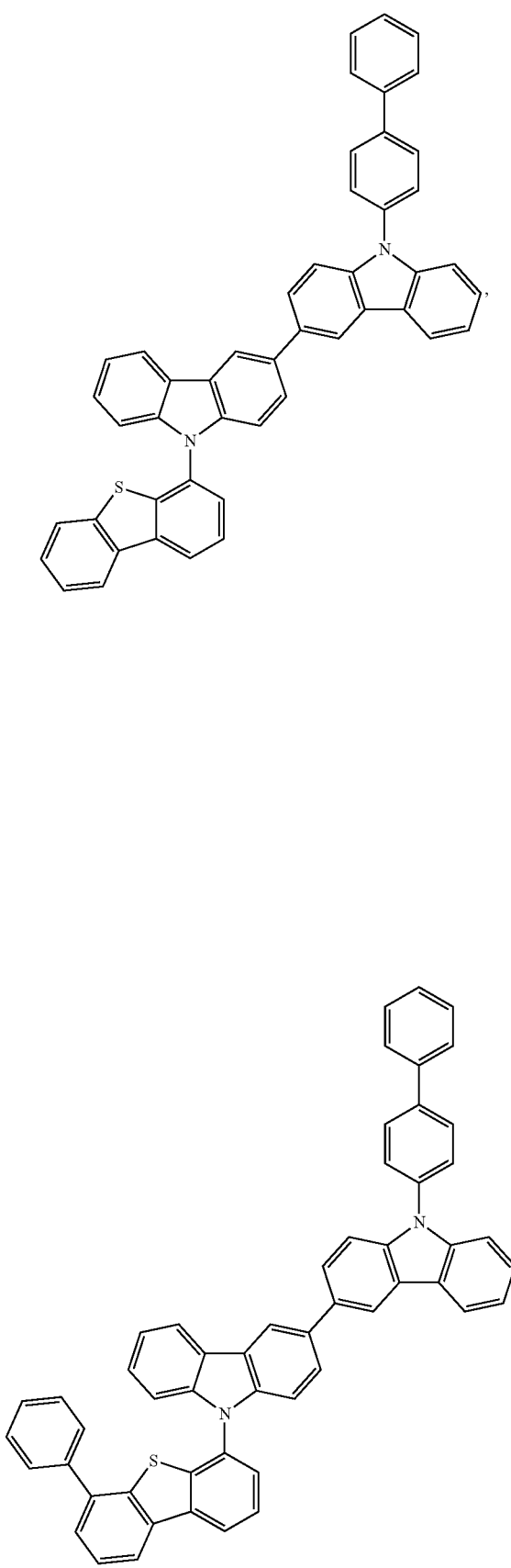
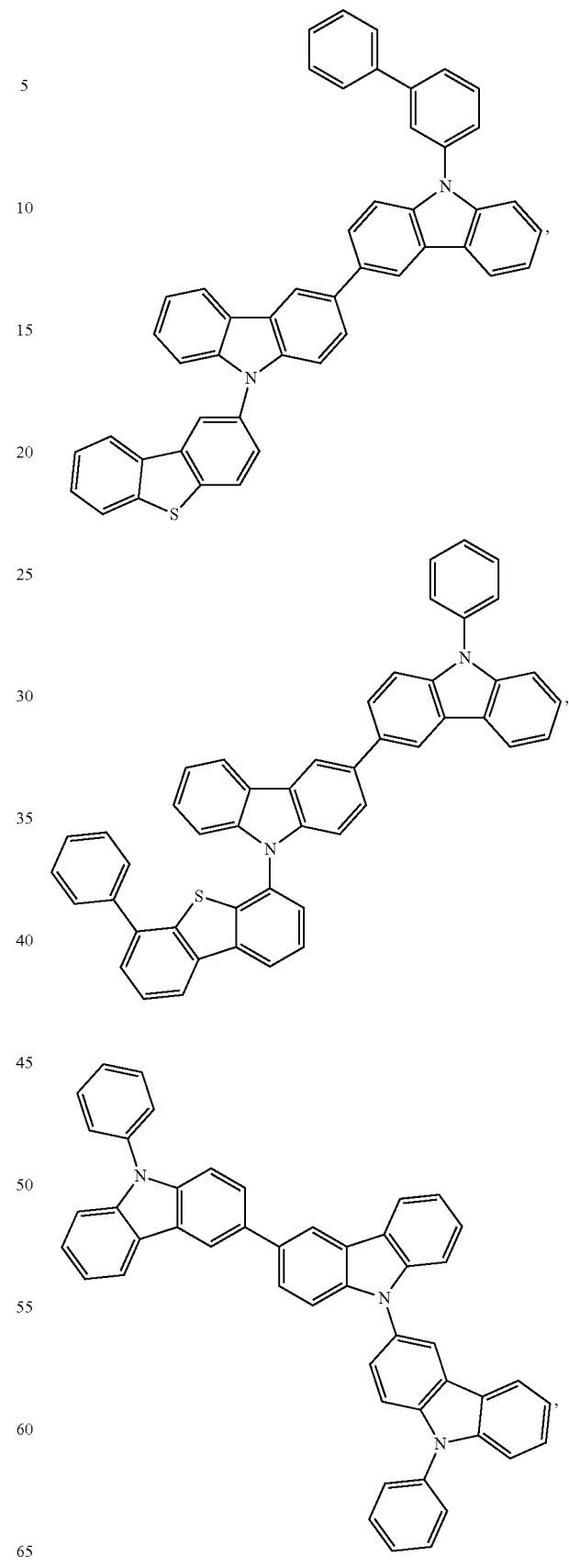

77
-continued
78
-continued
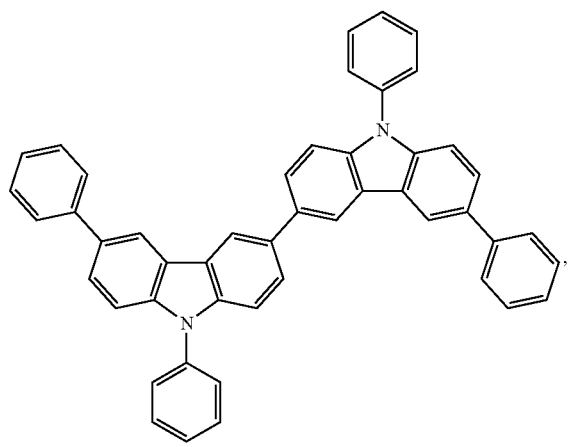
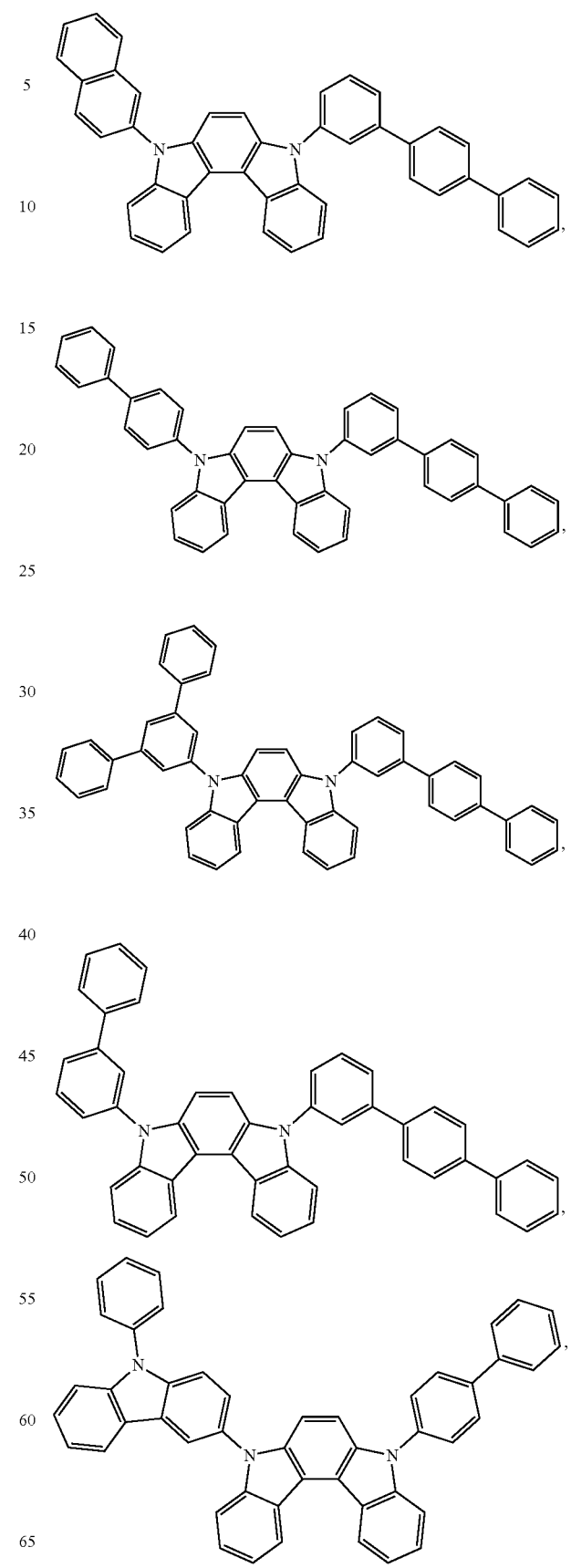

-continued
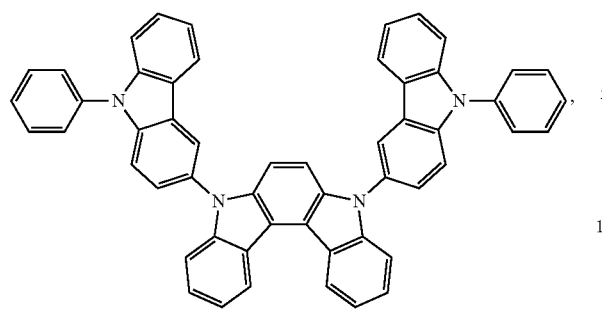
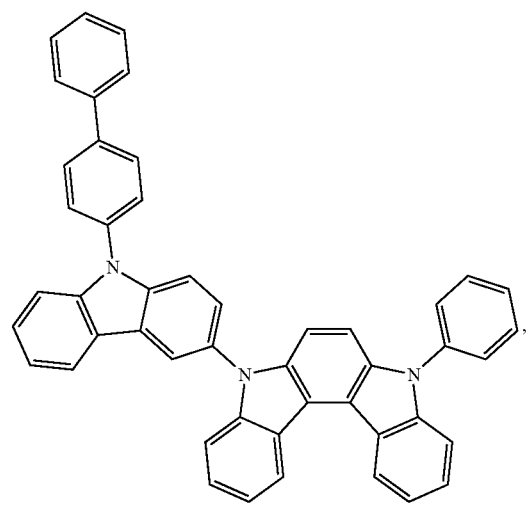
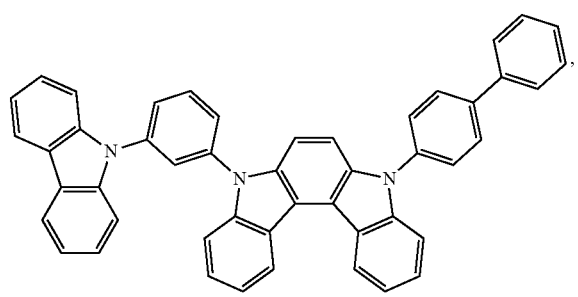
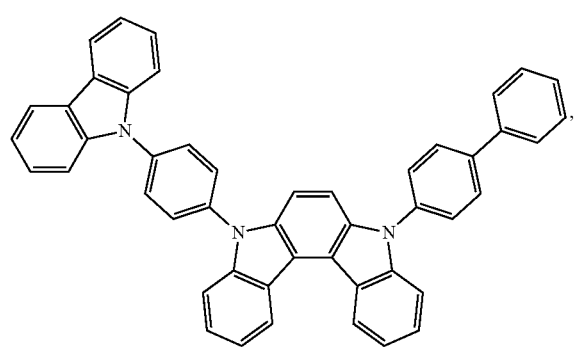
-continued
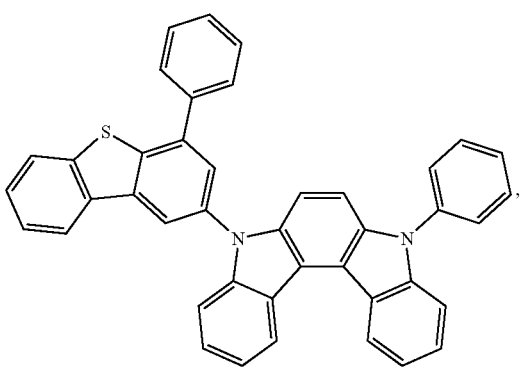
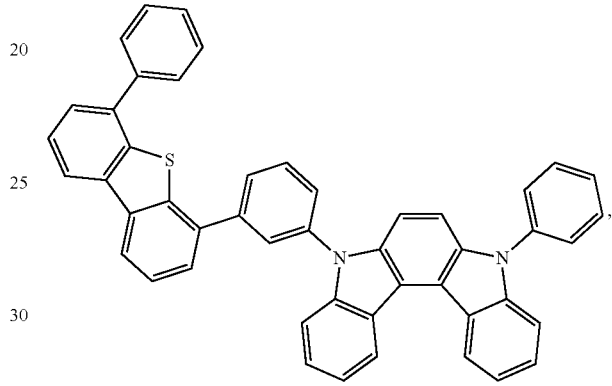
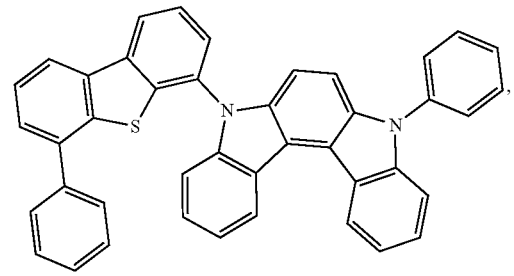
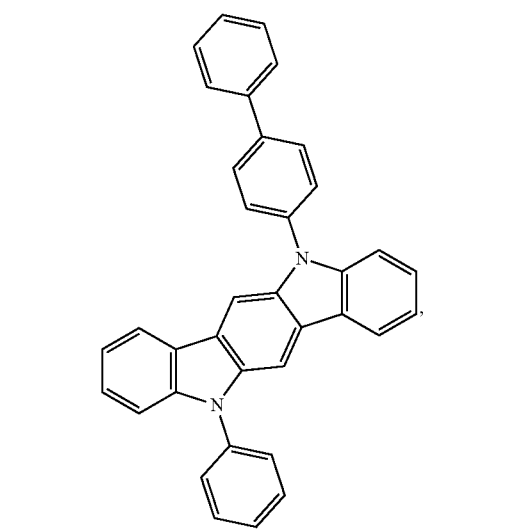

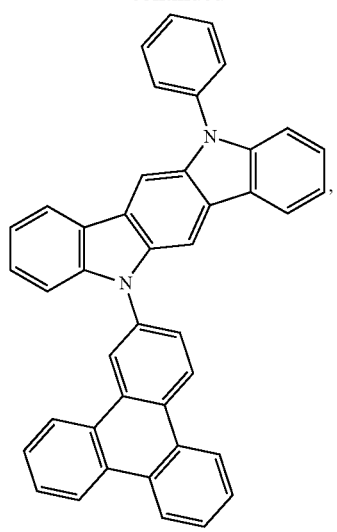
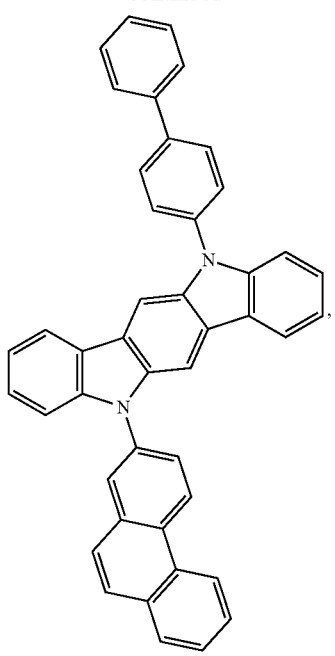
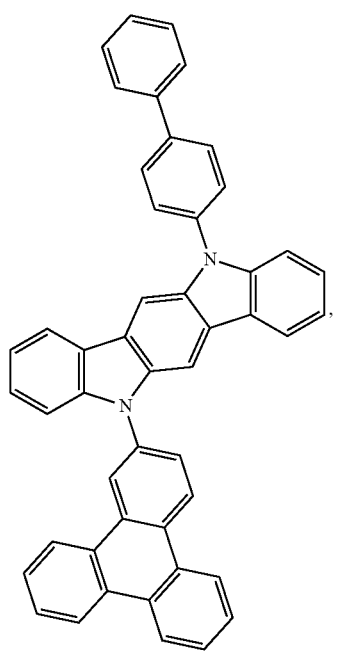
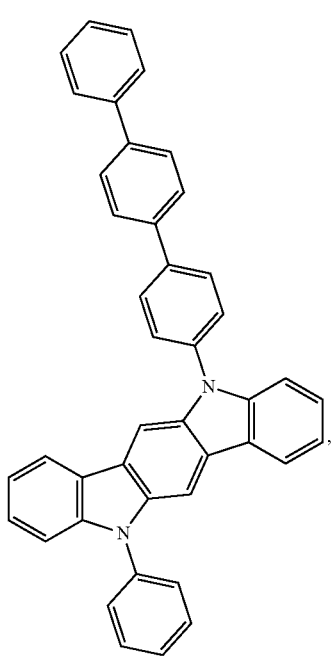

-continued
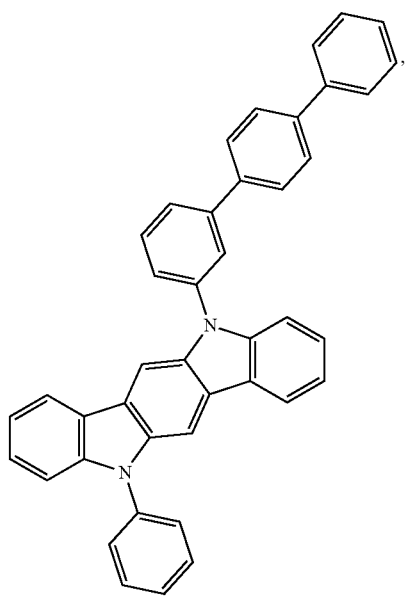
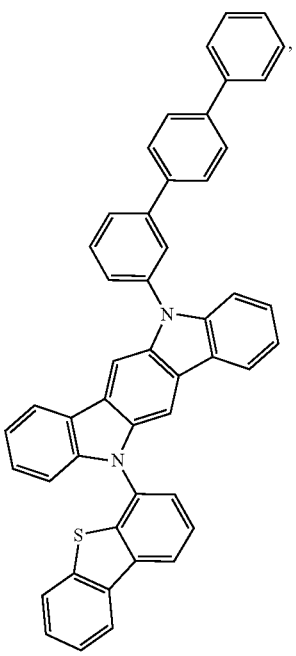
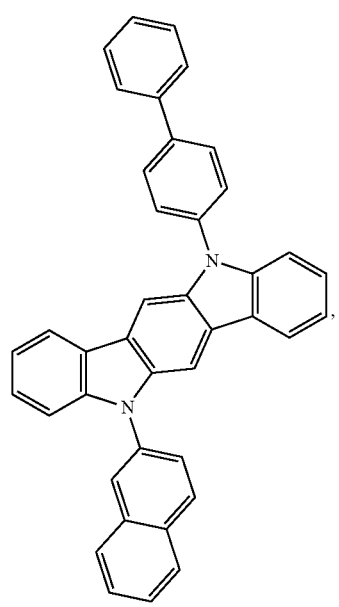
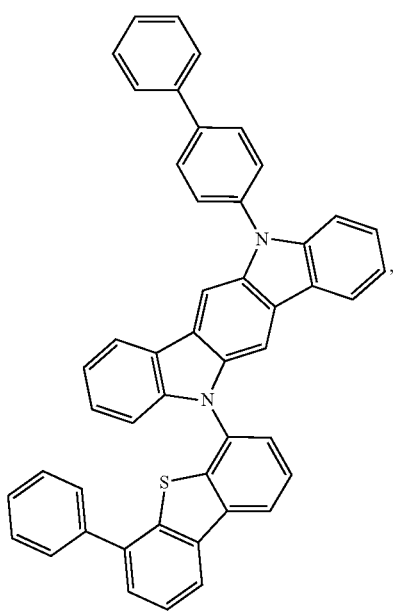

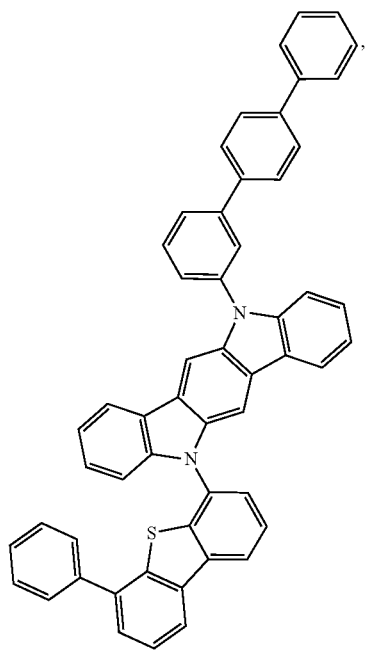
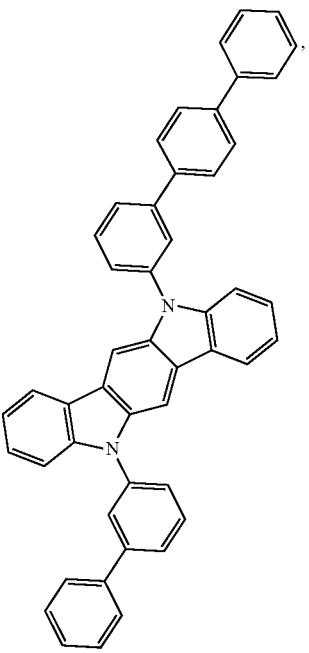
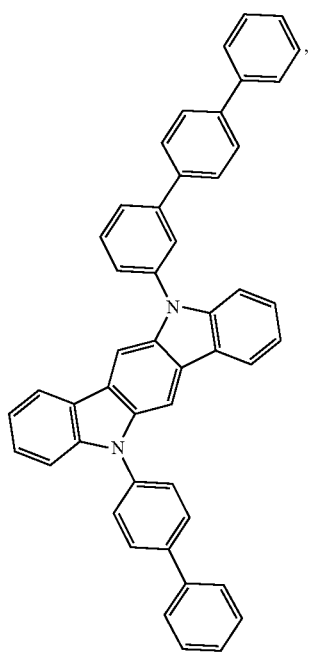
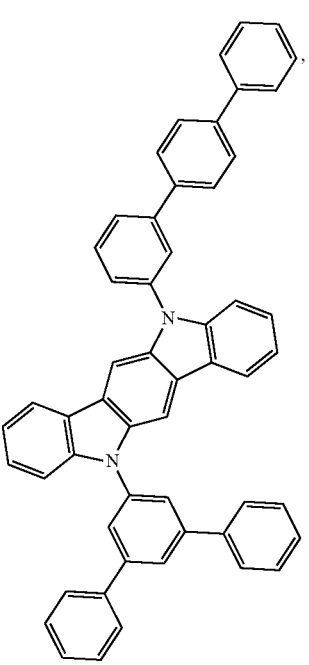

87
-continued
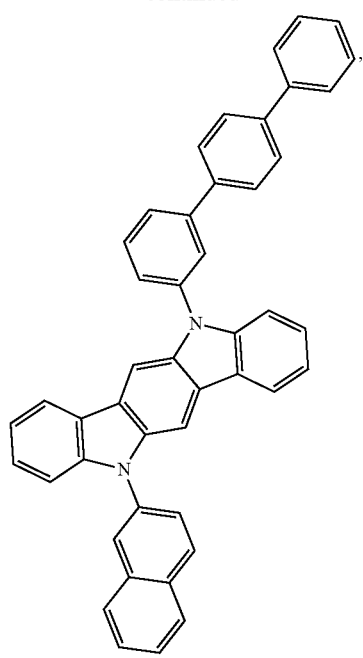
88
-continued
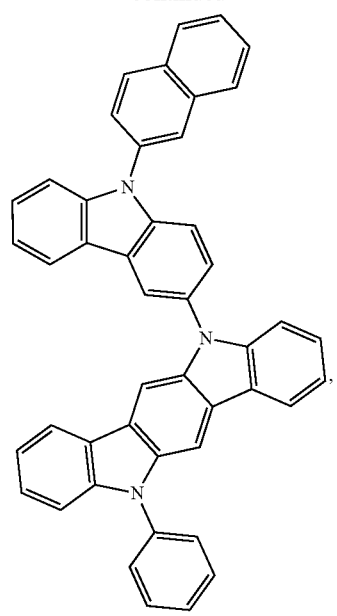

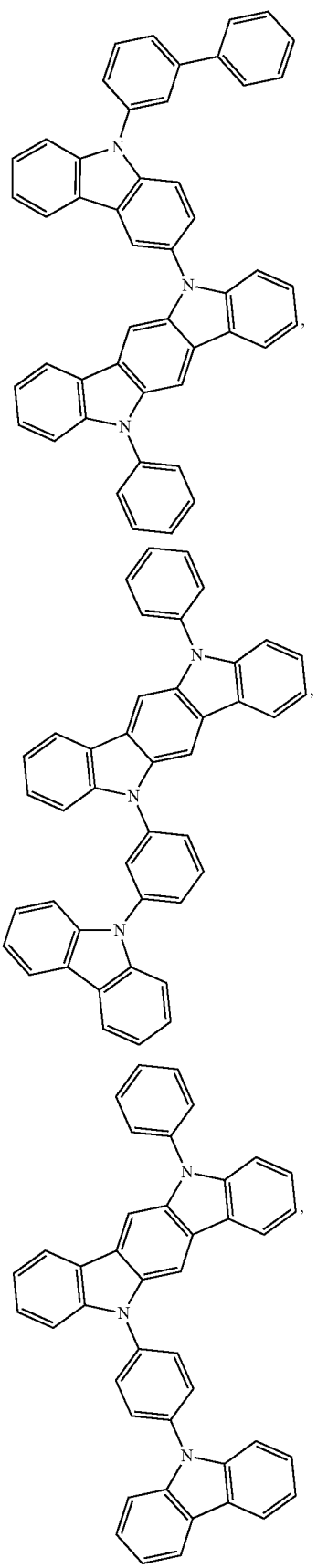
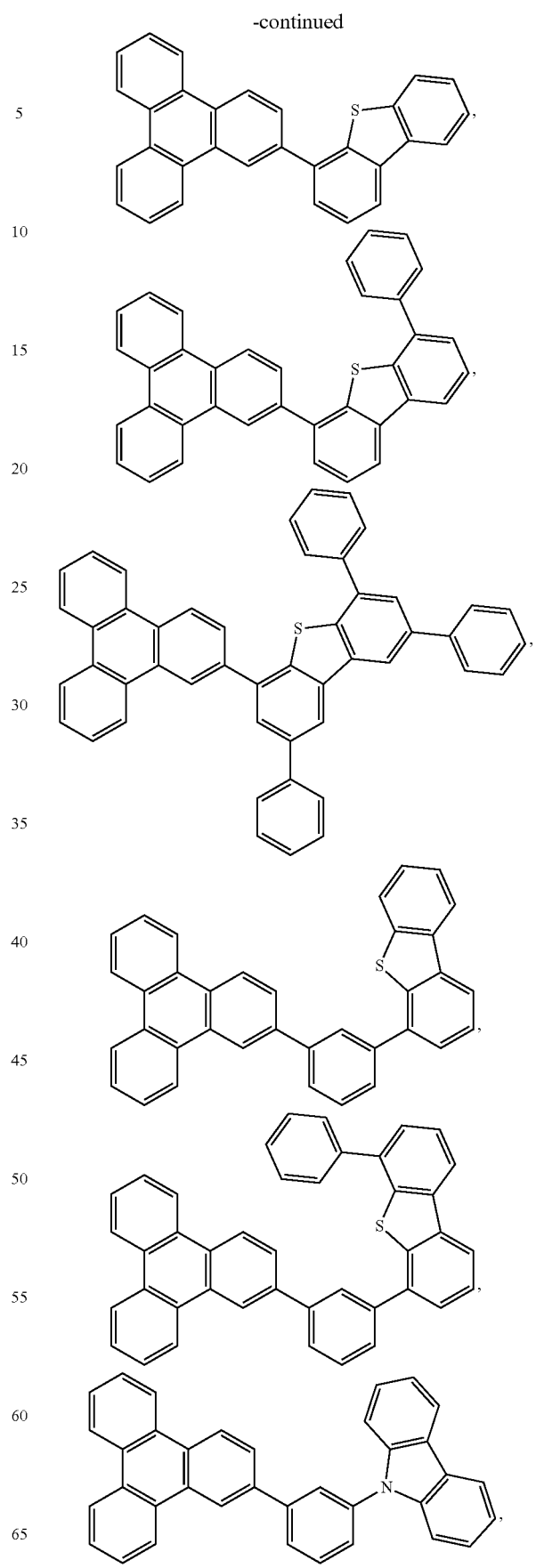

91
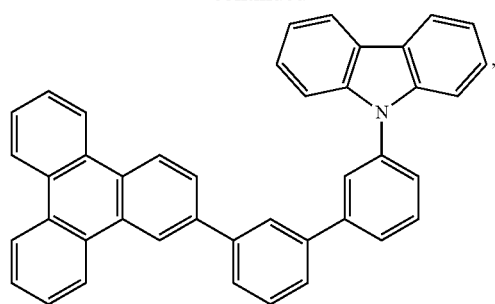
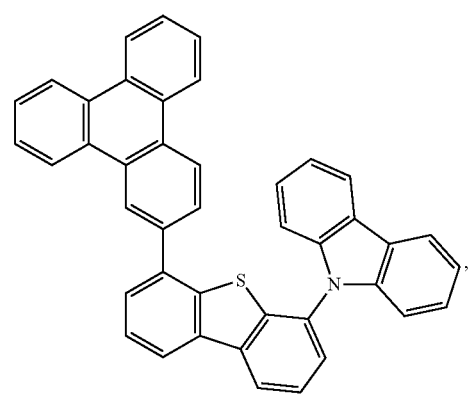
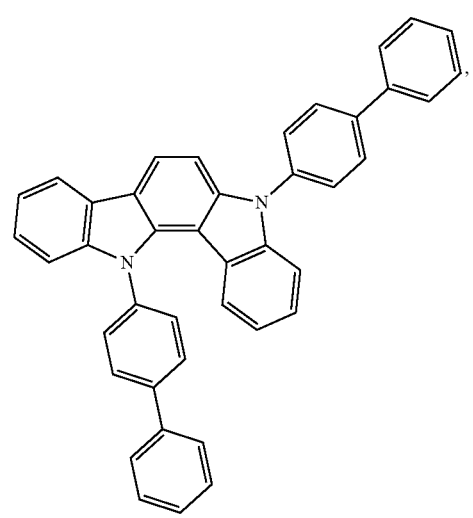
92
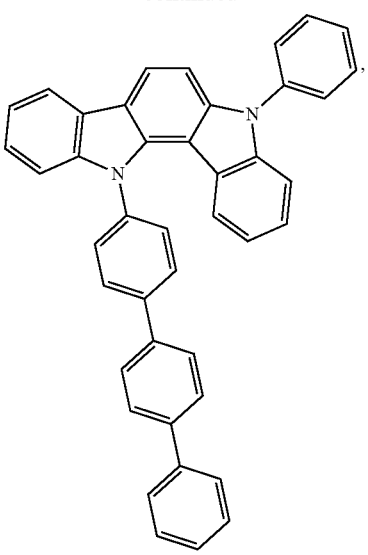
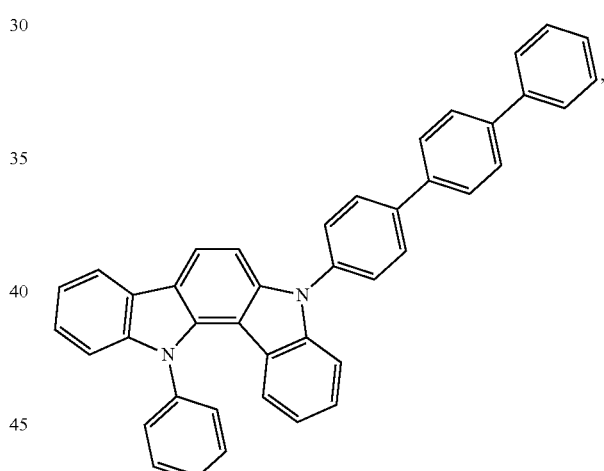
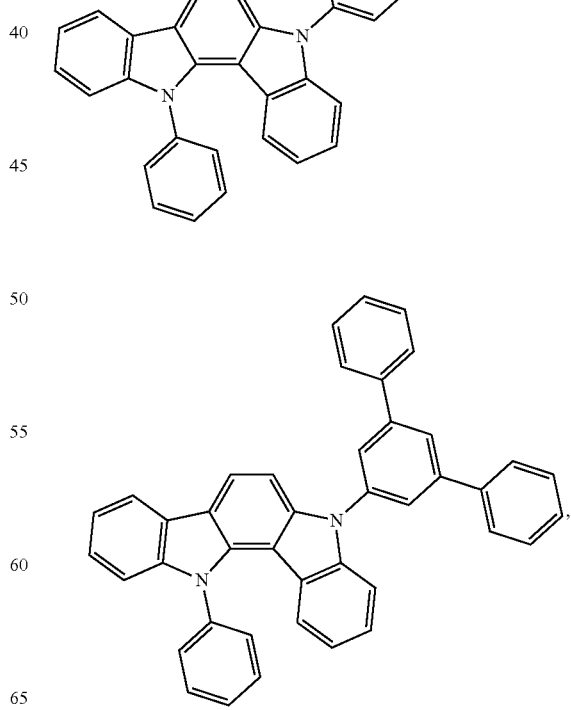

-continued
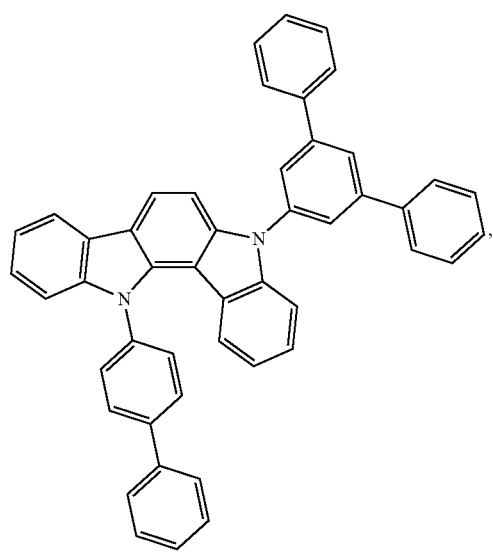
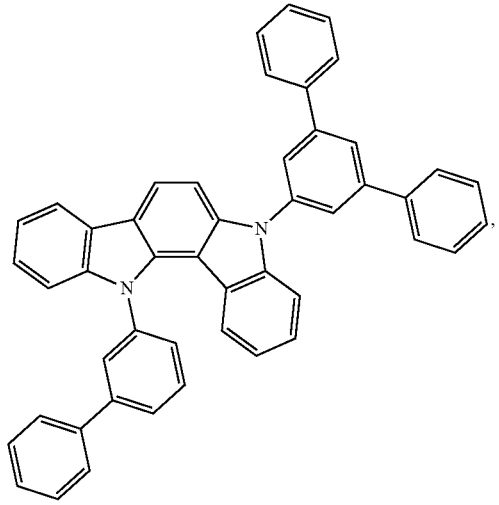
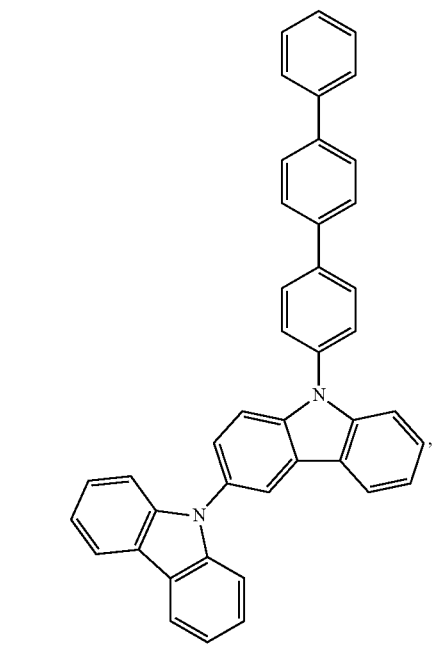
-continued
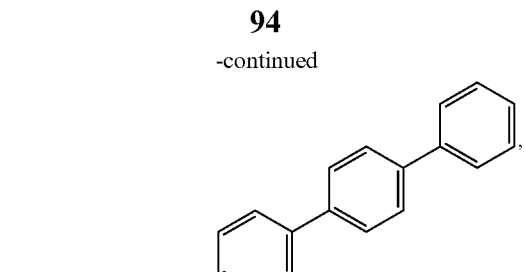
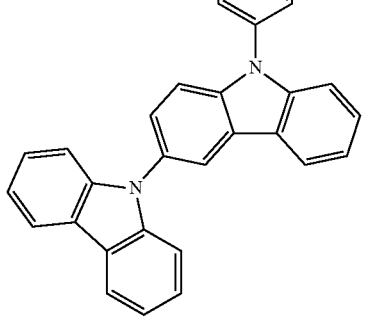
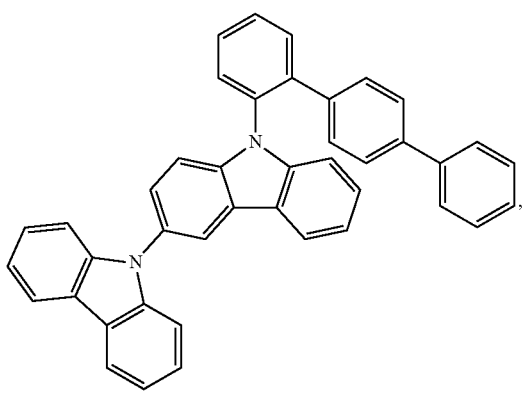
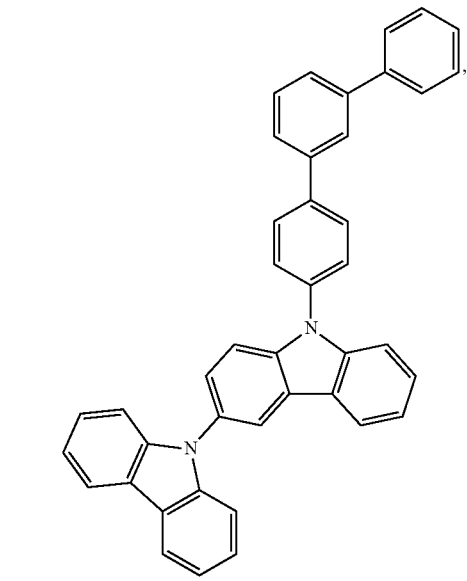

95
-continued
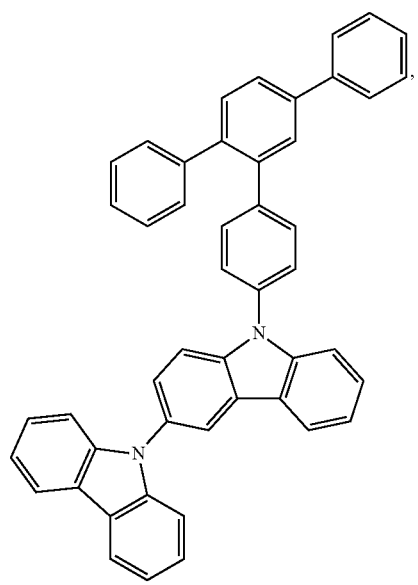
96
-continued
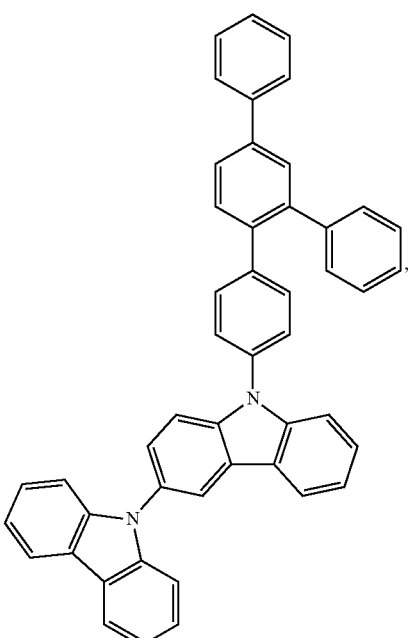
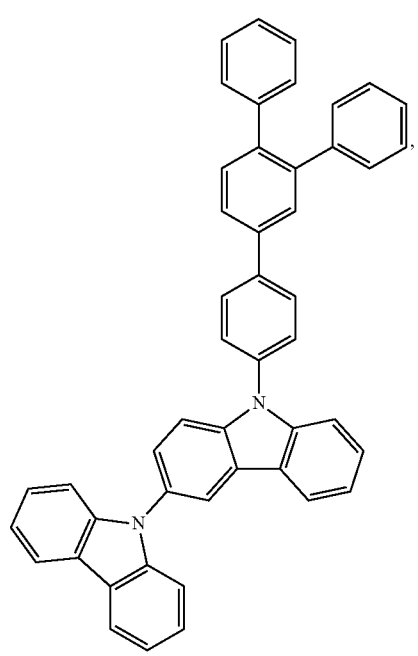
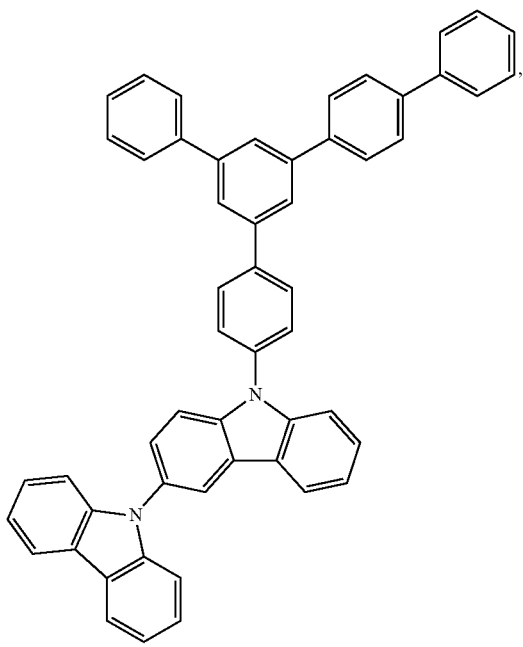

97
-continued
98
-continued
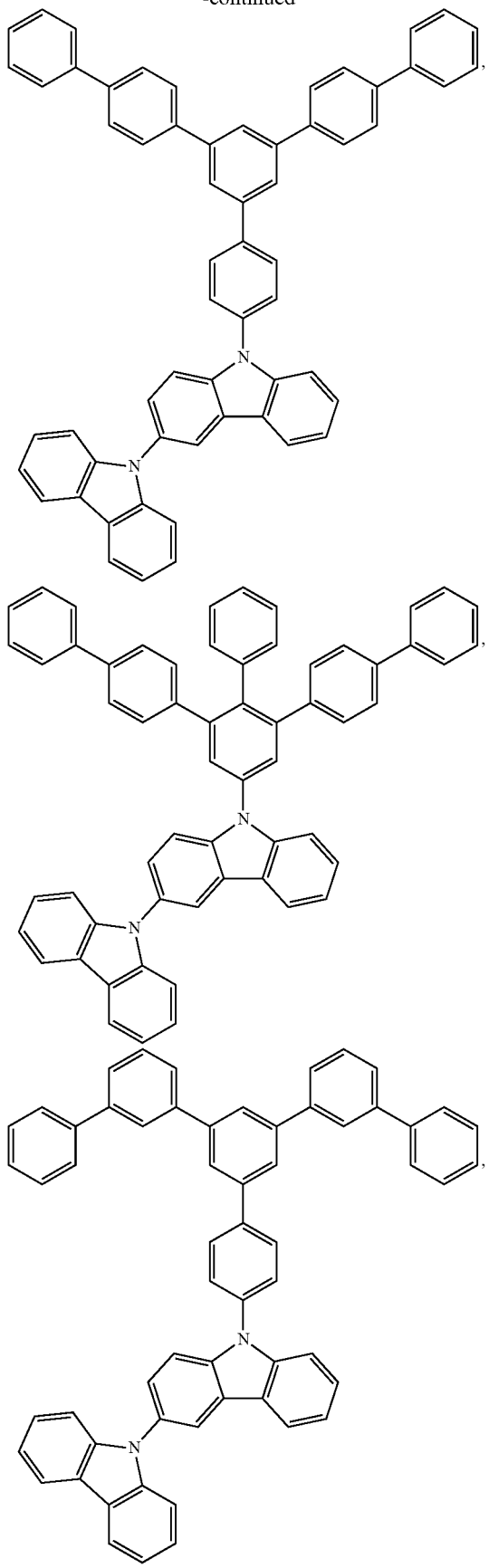

99
-continued
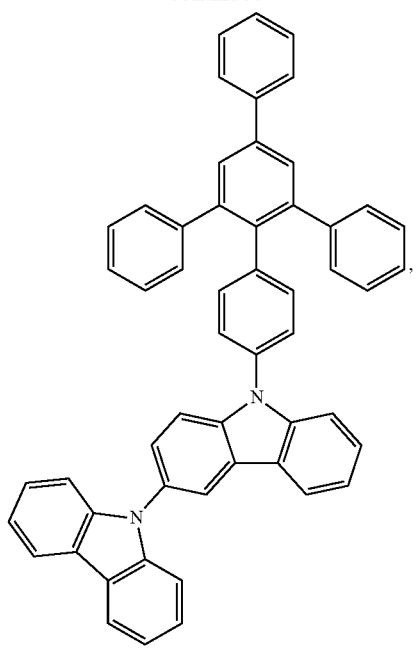
100
-continued
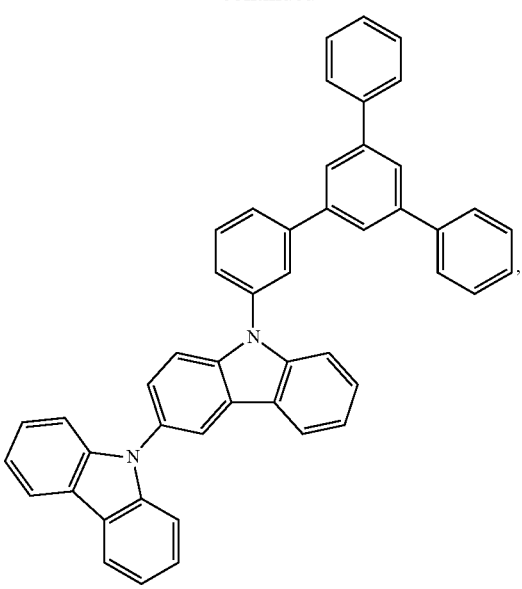

101
-continued
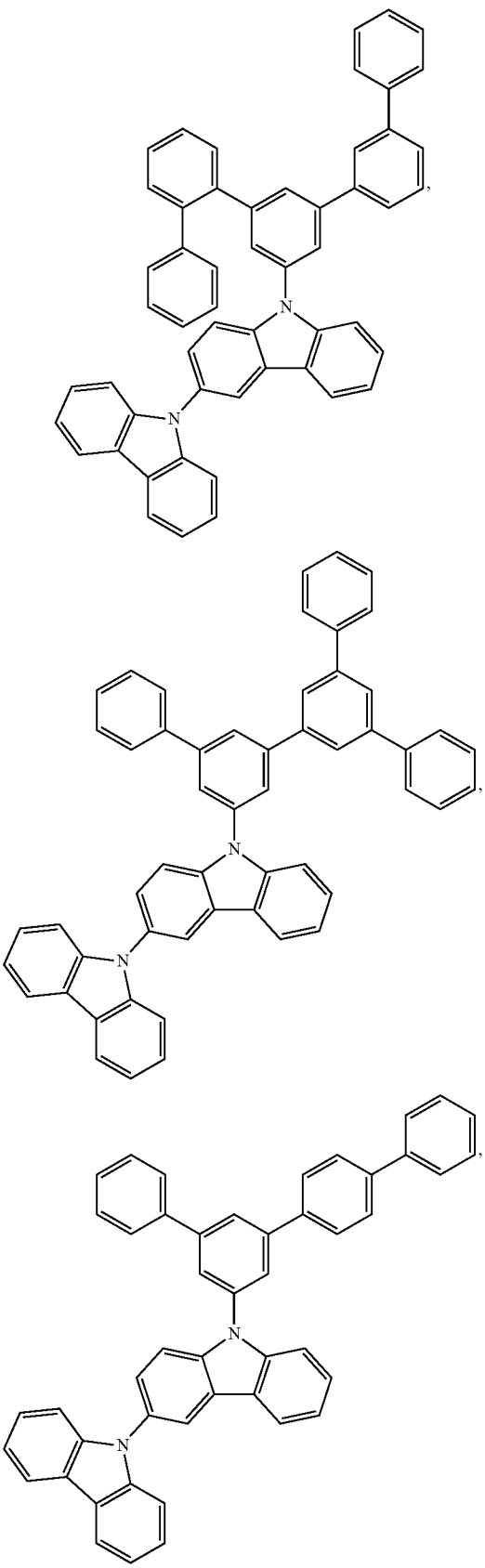
102
-continued
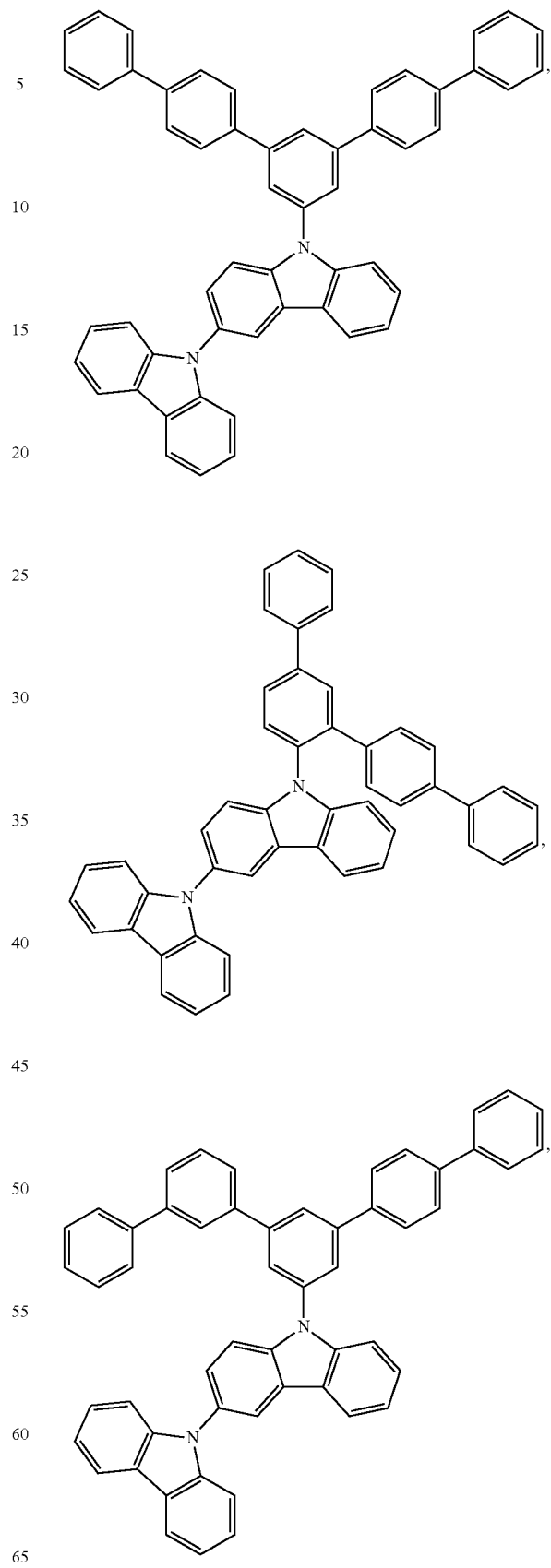

103
-continued
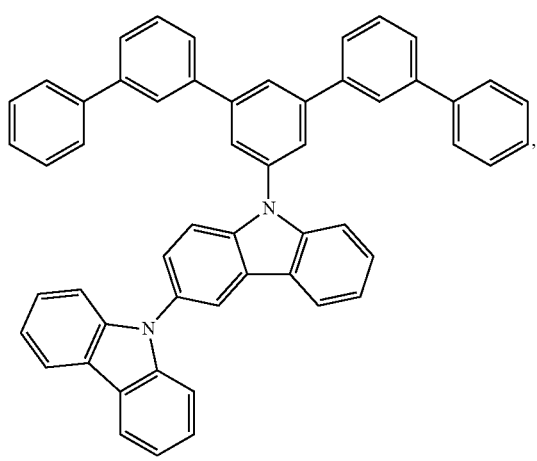
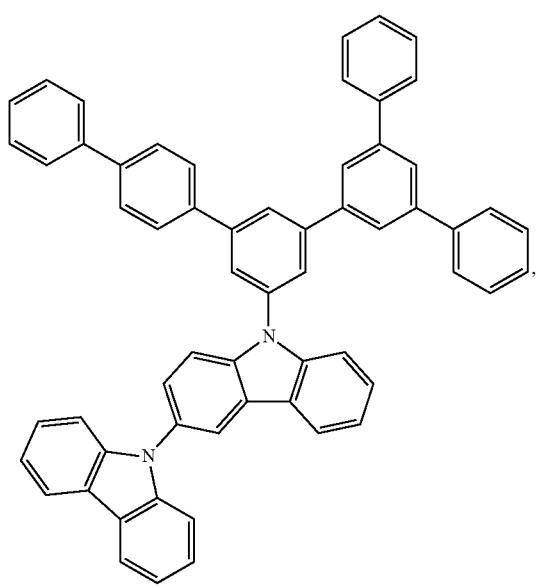
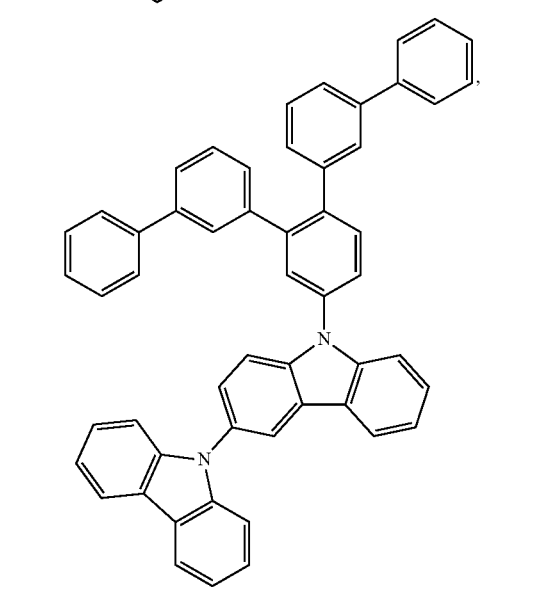
104
-continued
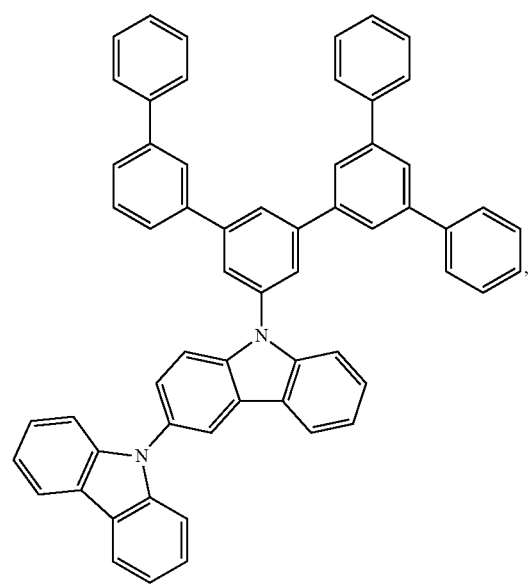
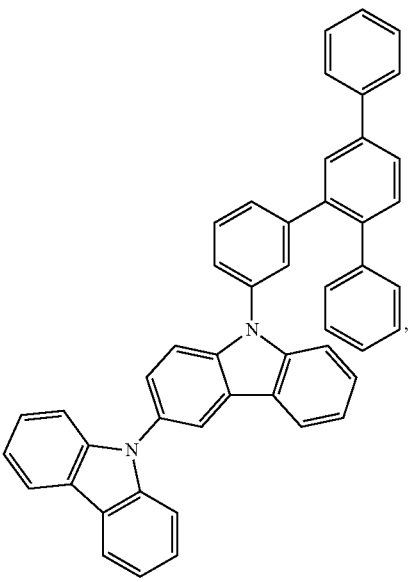

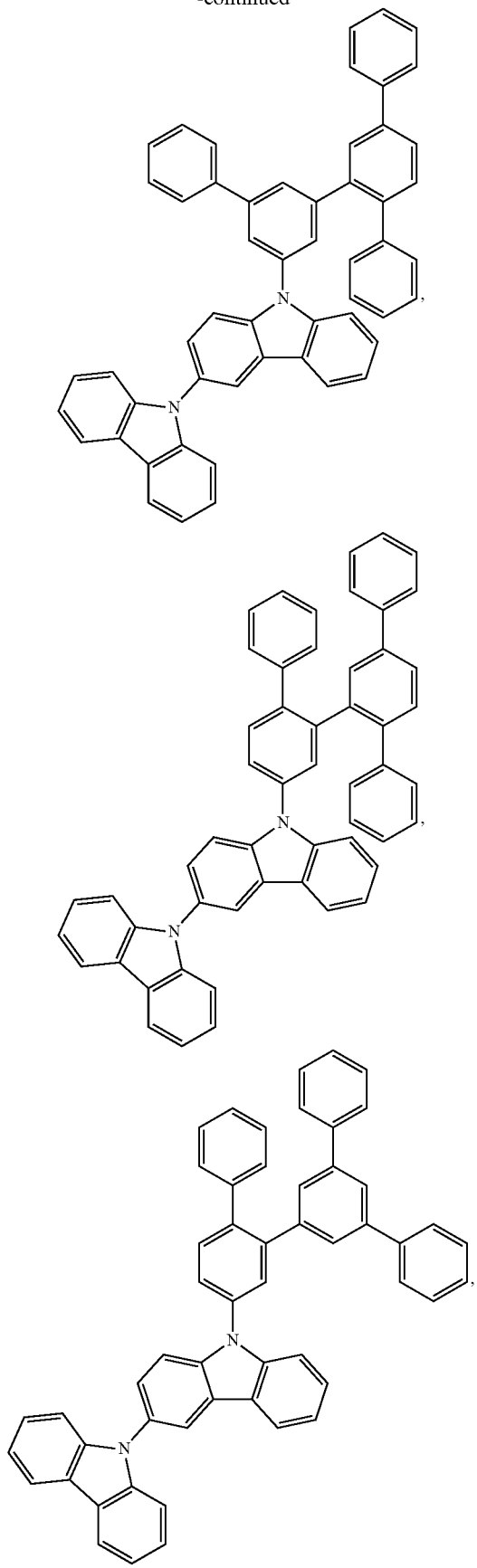
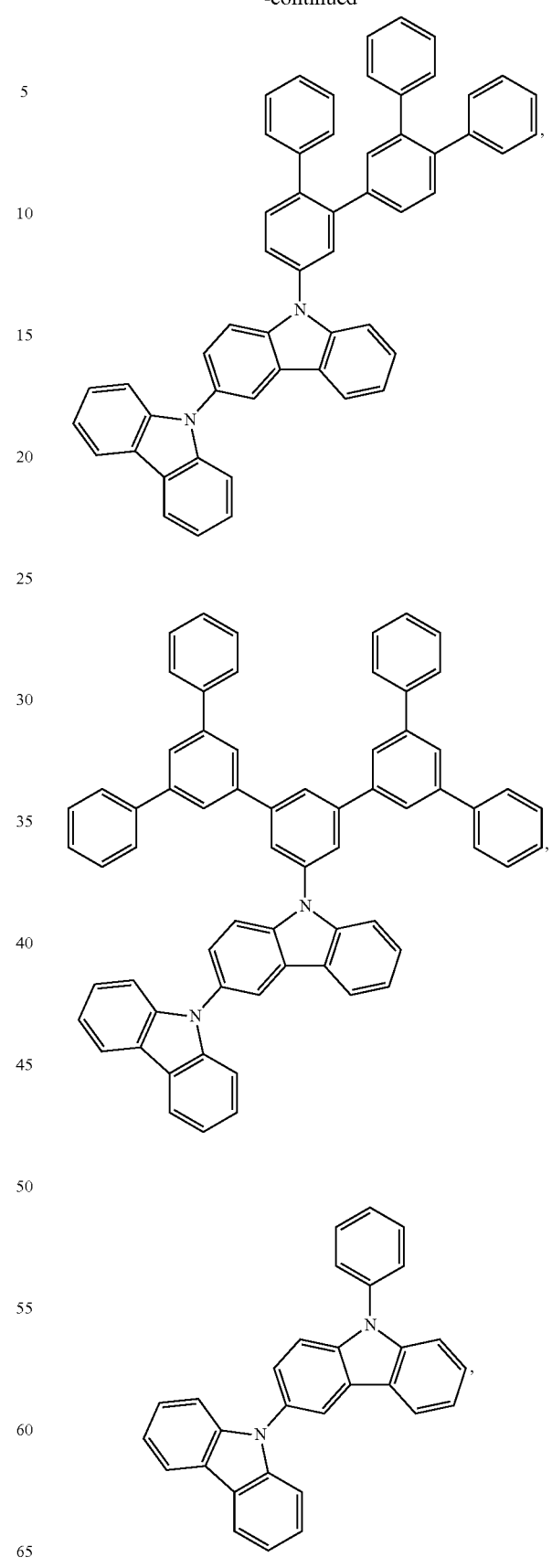

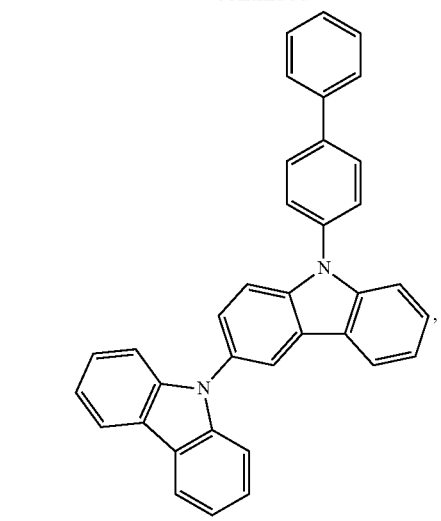
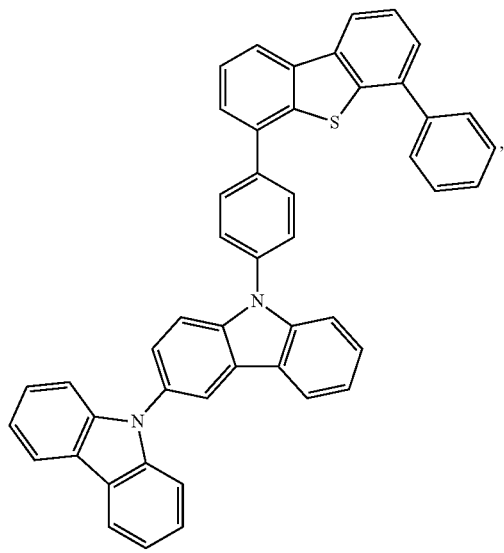
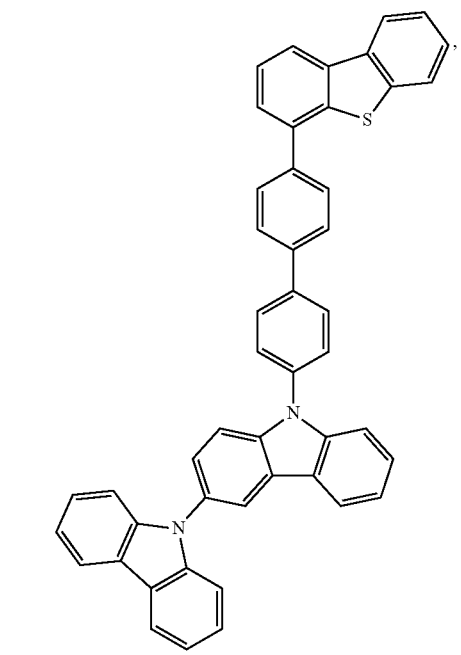
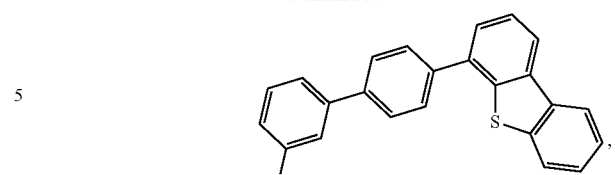
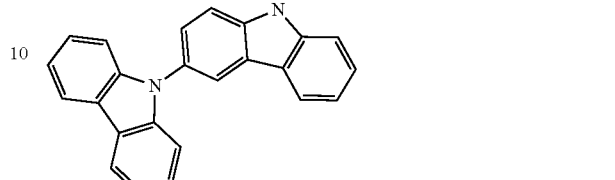
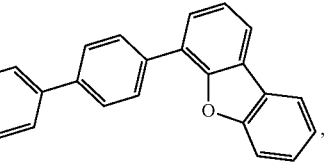
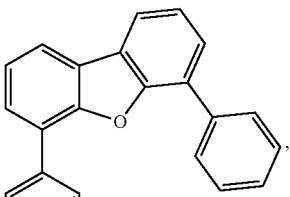
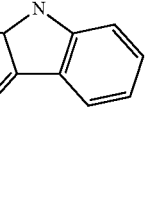

109
-continued
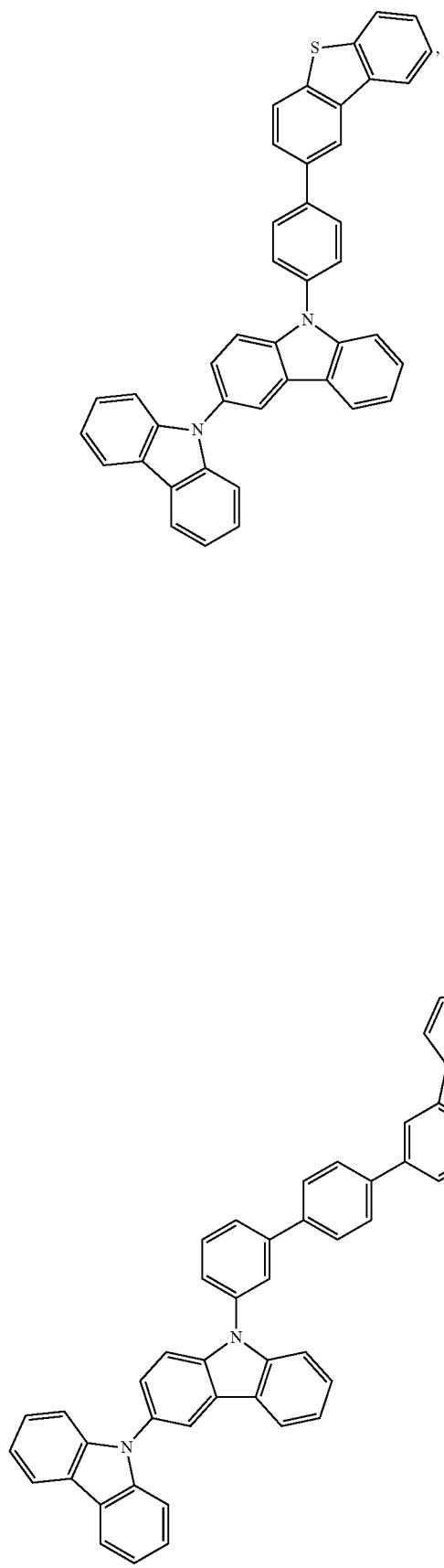
110
-continued
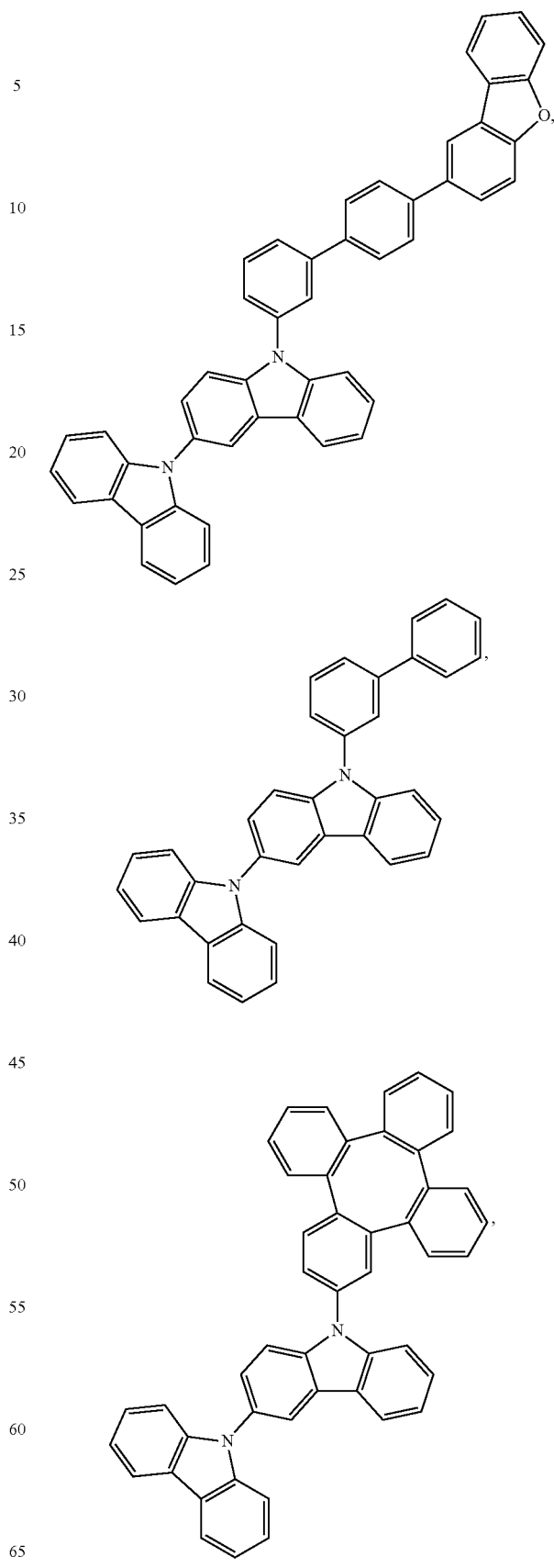

111
-continued
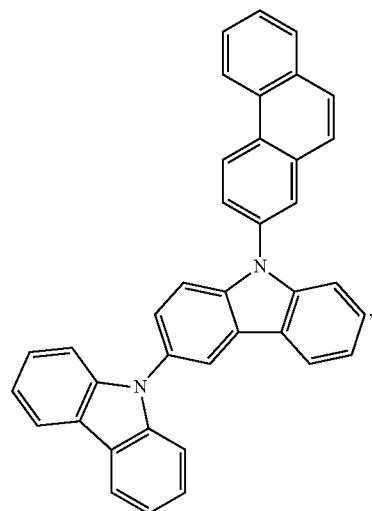
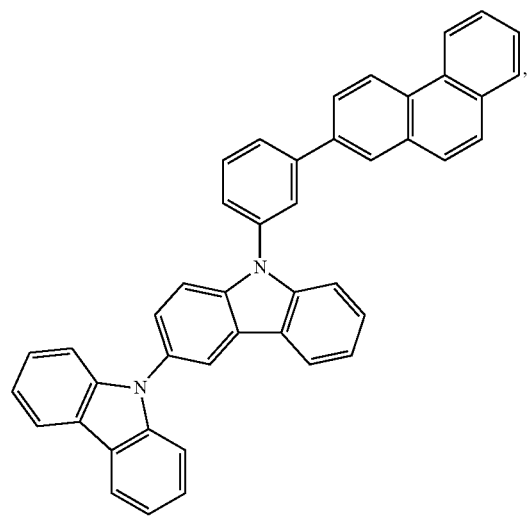
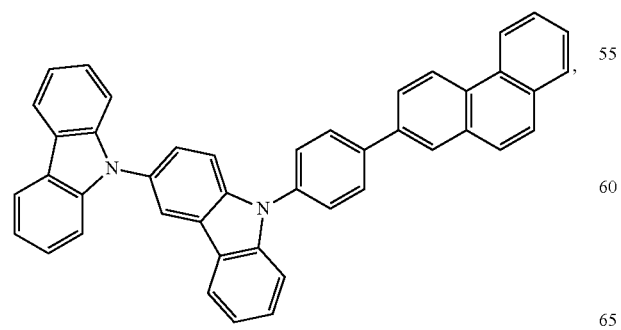
112
-continued
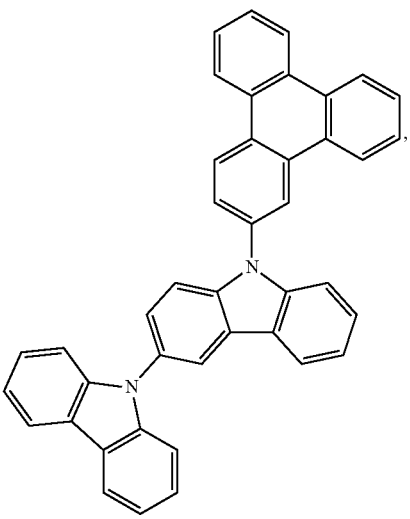
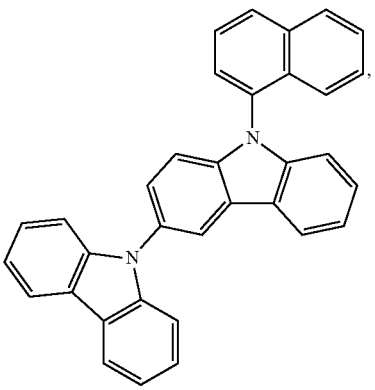
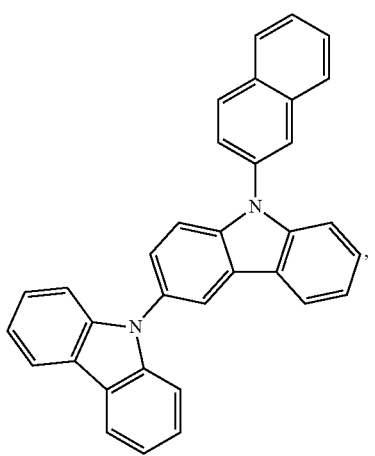

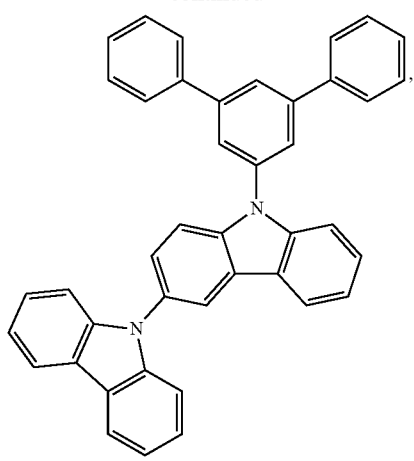
,
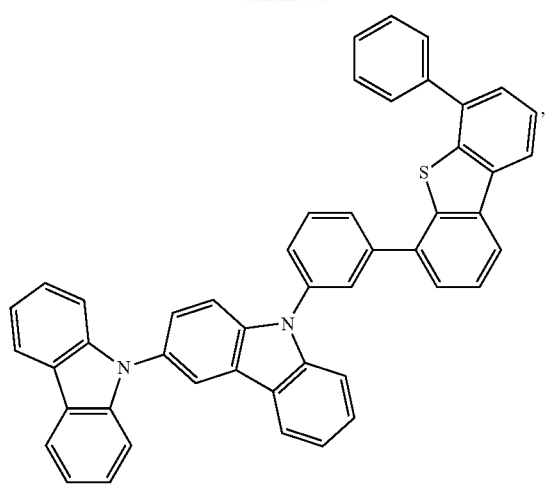
,
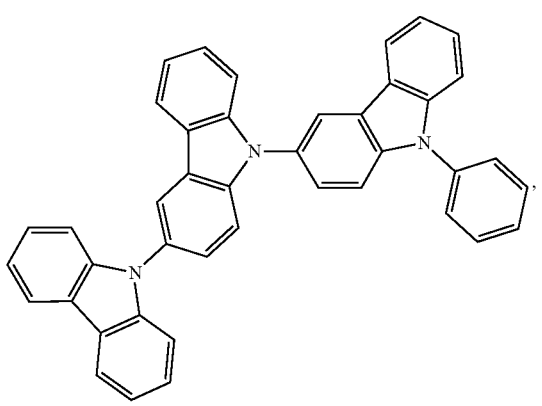
,
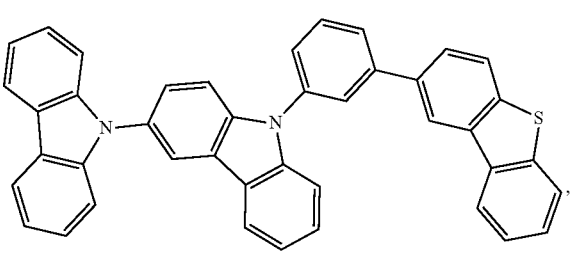
,
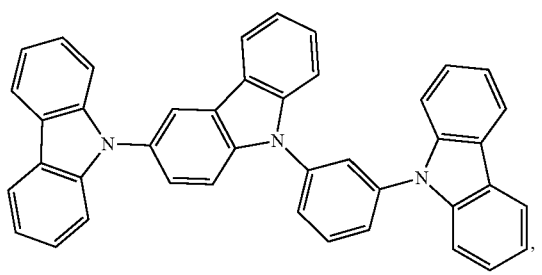
,
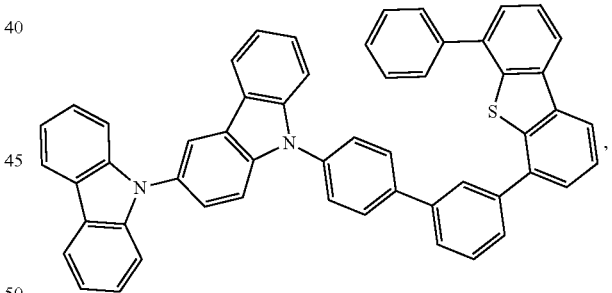
,
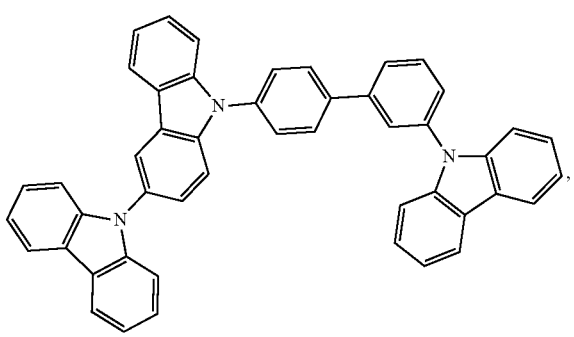
,
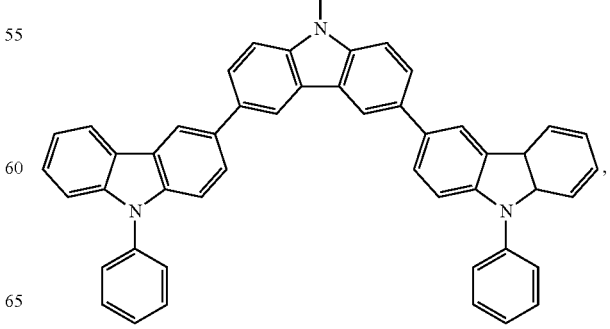
,

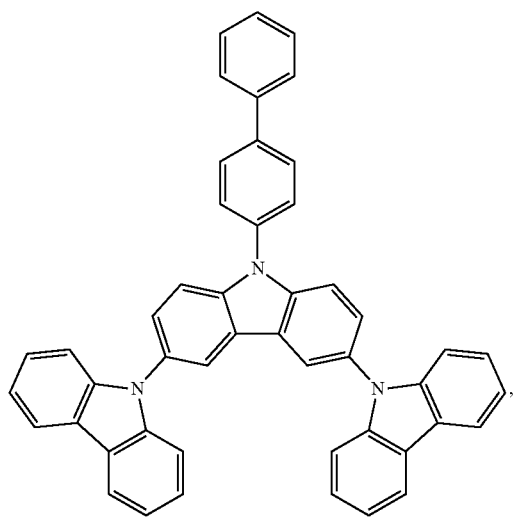
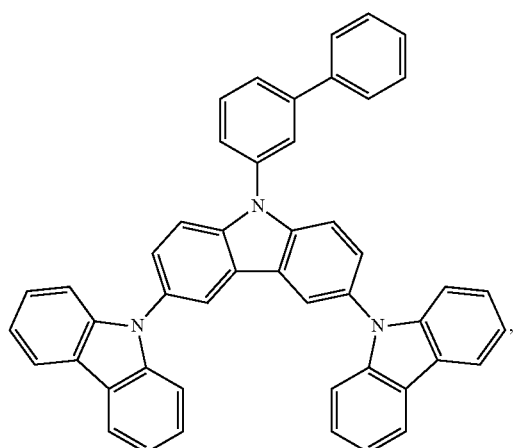
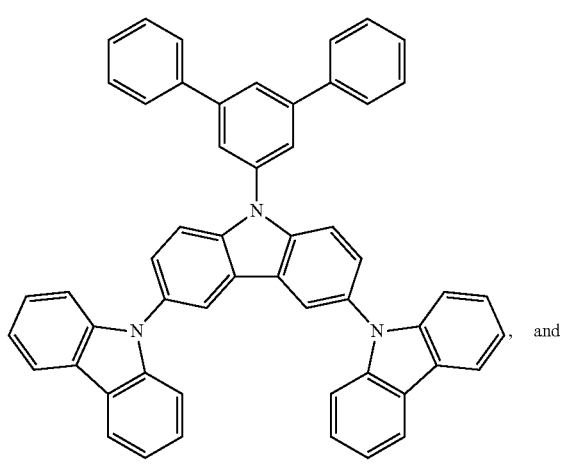
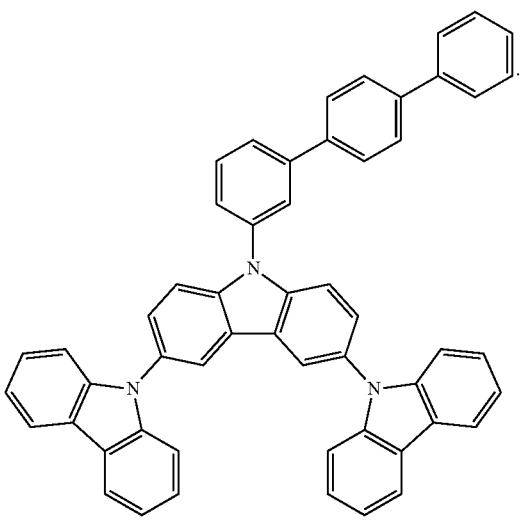 [SMILES: c1ccc(-c2ccc(-c3cccc(-n4c5ccc(-n6c7ccccc7c7ccccc76)cc5c5cc(-n6c7ccccc7c7ccccc76)ccc54)c3)cc2)cc1]
In the embodiments where the composition comprises a first compound having the structure of Formula III defined above, the composition can comprise a second compound. In some embodiments, the second compound can be selected from the group consisting of:
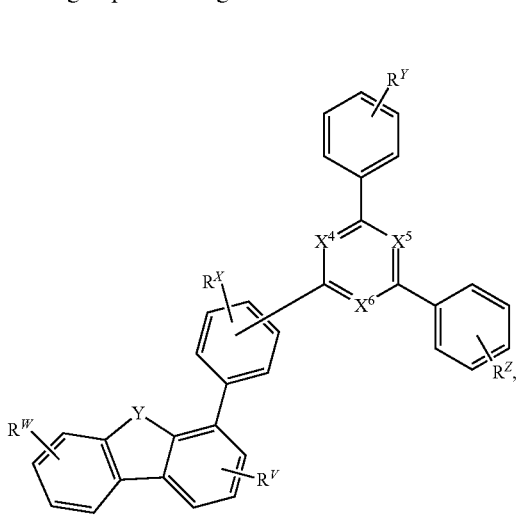
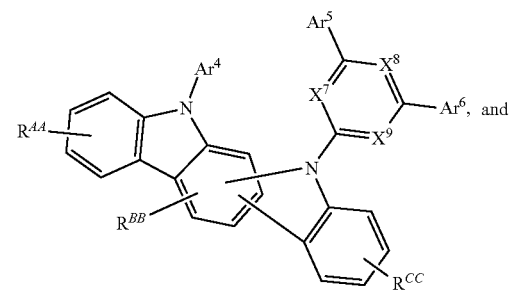

-continued

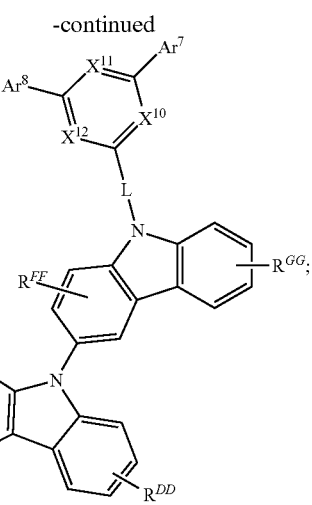

wherein, $R^V$, $R^W$, $R^X$, $R^Y$, $R^Z$, $R^{AA}$, $R^{BB}$, $R^{CC}$, $R^{DD}$, $R^{EE}$, $R^{FF}$, and $R^{GG}$ each independently represent mono to the maximum allowable substitutions, or no substitution; each $R^Y$, $R^W$, $R^X$, $R^Y$, $R^Z$, $R^{AA}$, $R^{BB}$, $R^{CC}$, $R^{DD}$, $R^{EE}$, $R^{FF}$, and $R^{GG}$ is independently hydrogen, or a substituent selected from the group consisting of the general substituents defined above; Y is O or S; $Ar^4$, $Ar^5$, $Ar^6$, $A^7$, and $Ar^8$ are each independently a substituted or unsubstituted aryl ring; $X^4$, $X^5$, $X^6$, $X^7$, $X^8$, $X^9$, $X^{10}$, $X^{11}$, and $X^{12}$ are each independently N or CH; at least two of $X^4$, $X^5$, and $X^6$ are N; at least two of $X^7$, $X^8$, and $X^9$ are N; at least two of $X^{10}$, $X^{11}$, and $X^{12}$ are N; any two substituents may be joined or fused together to form a ring; and L is either an aromatic linker or a direct bond. In some embodiments, each $R^Y$, $R^W$, $R^X$, $R^Y$, $R^Z$, $R^{AA}$, $R^{BB}$, $R^{CC}$, $R^{DD}$, $R^{EE}$, $R^{FF}$, and $R^{GG}$ is independently hydrogen, or a substituent selected from the group consisting of the preferred general substituents defined above. In some embodiments, the second compound can be selected from the group consisting of:

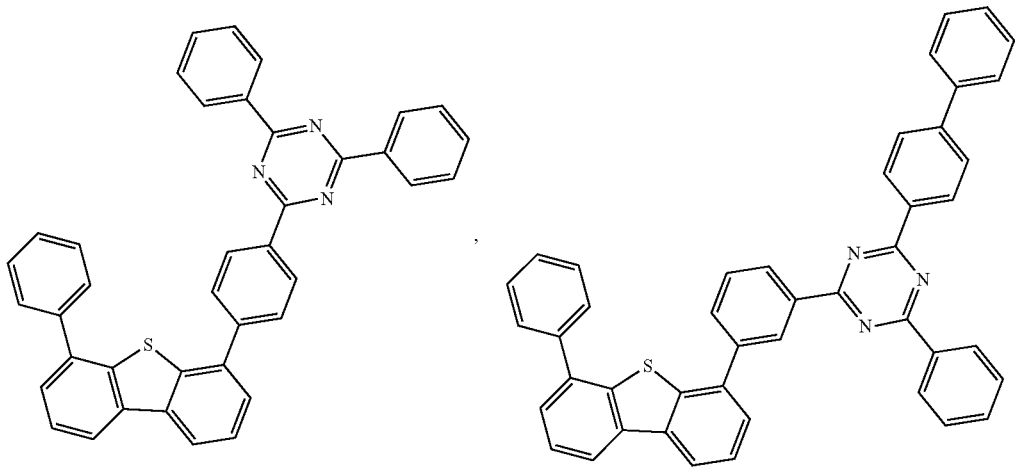

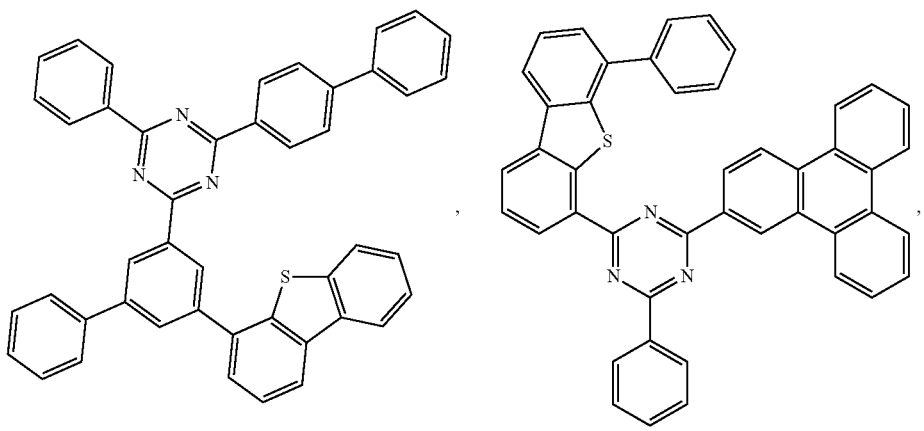

-continued
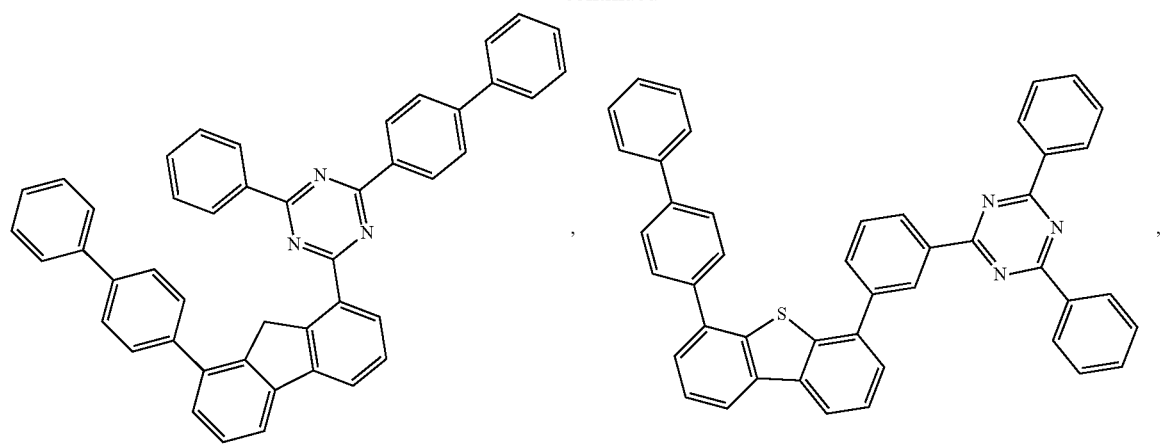
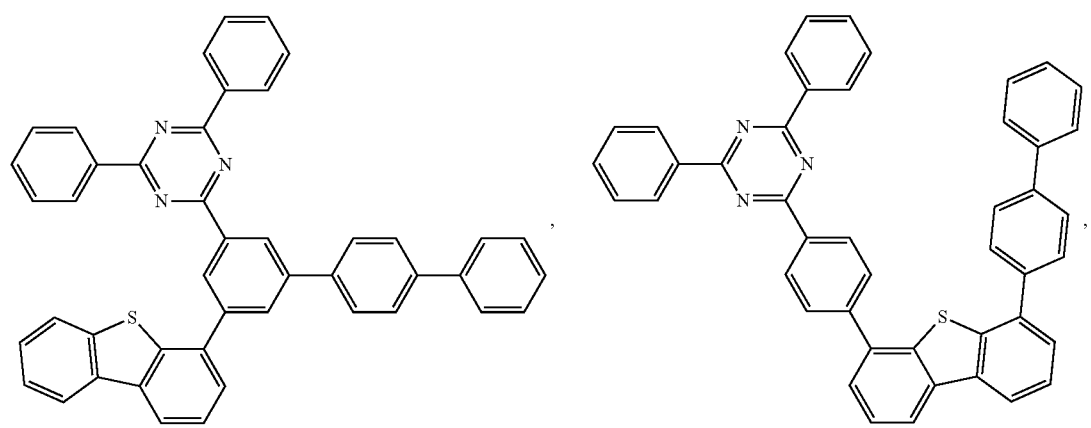
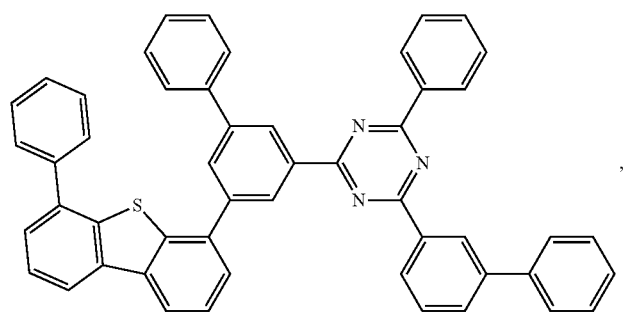
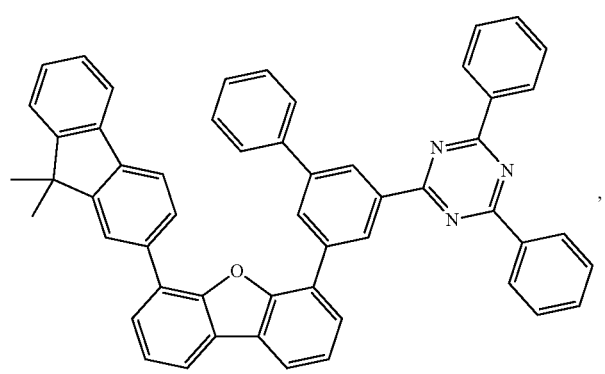

121 122
-continued
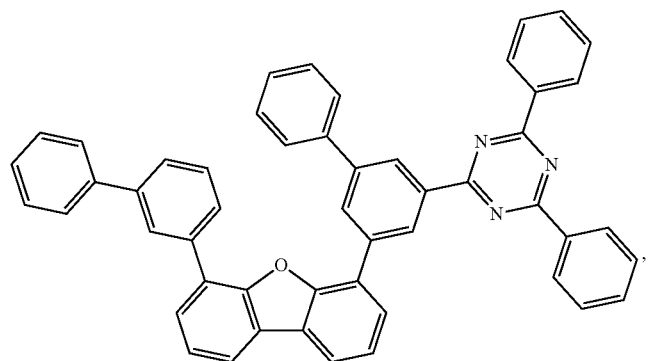
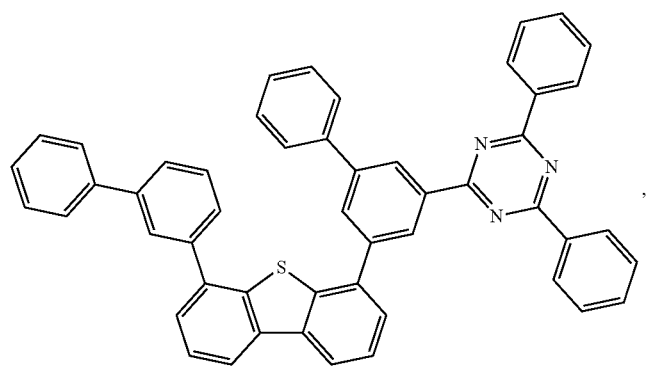
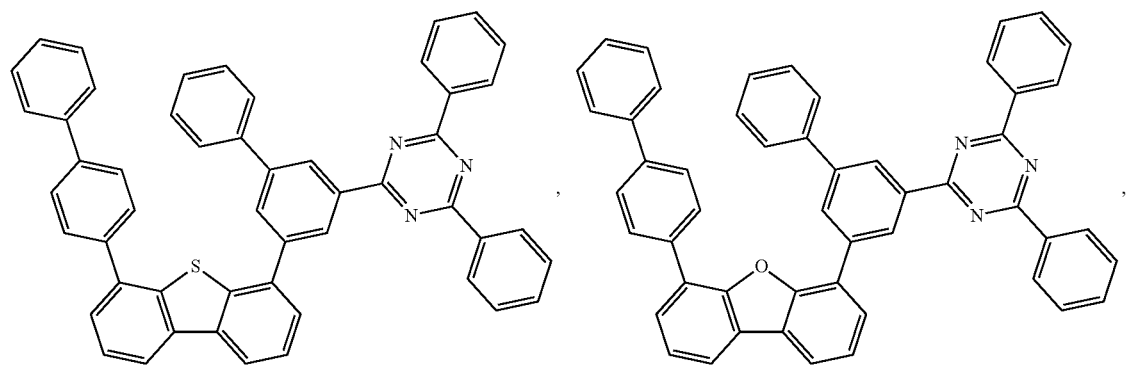
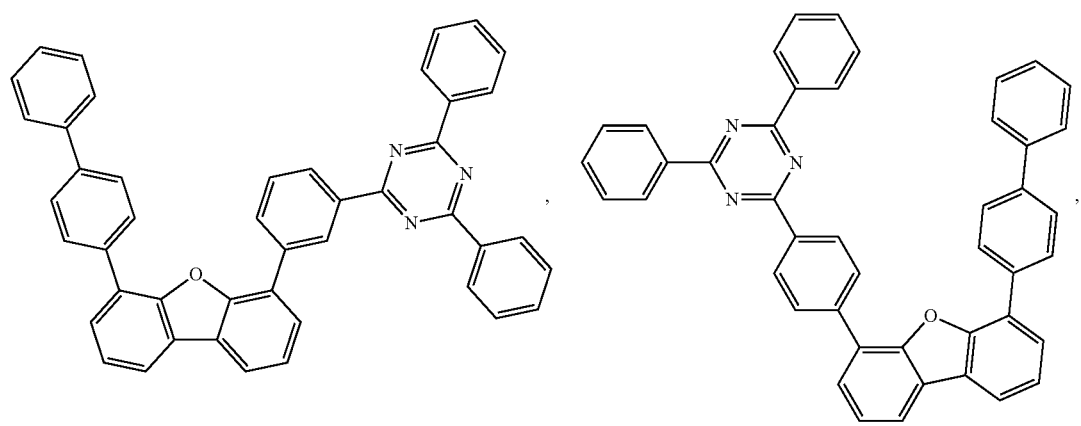

-continued
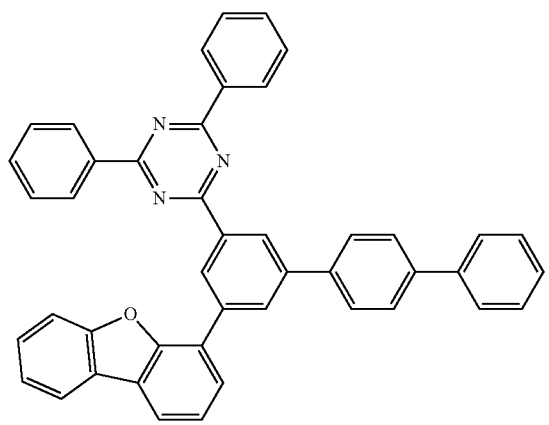
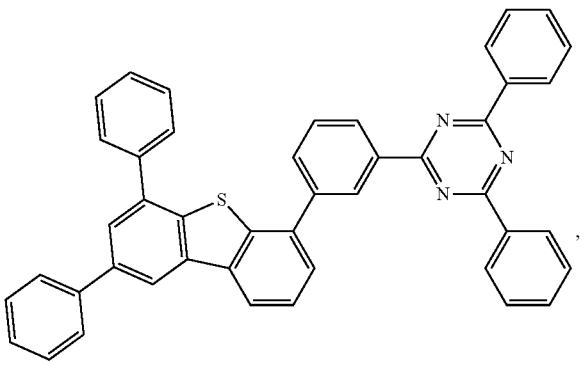
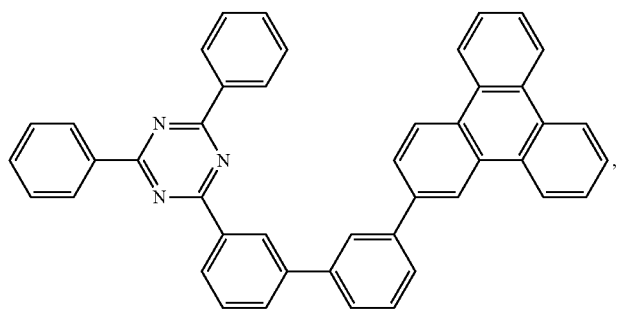
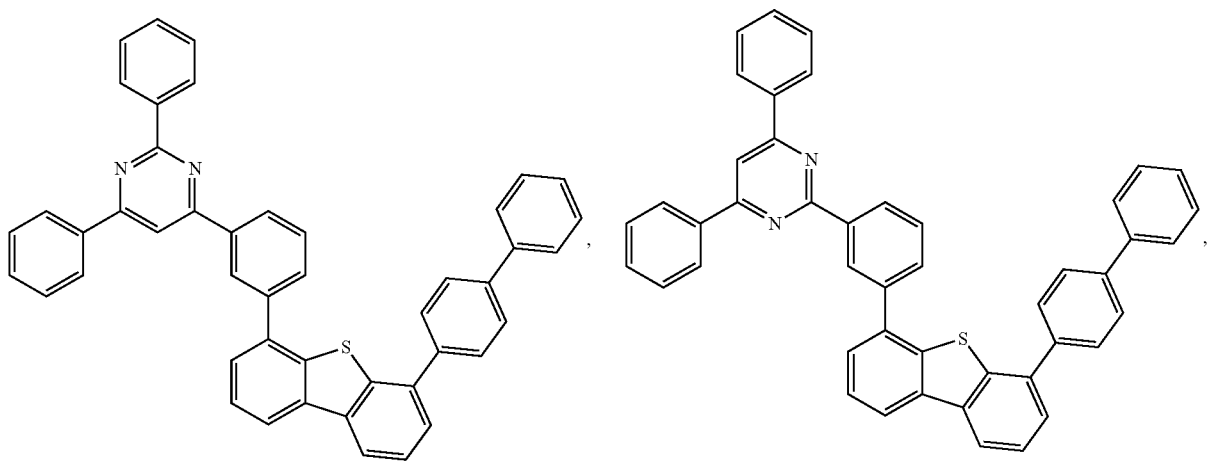
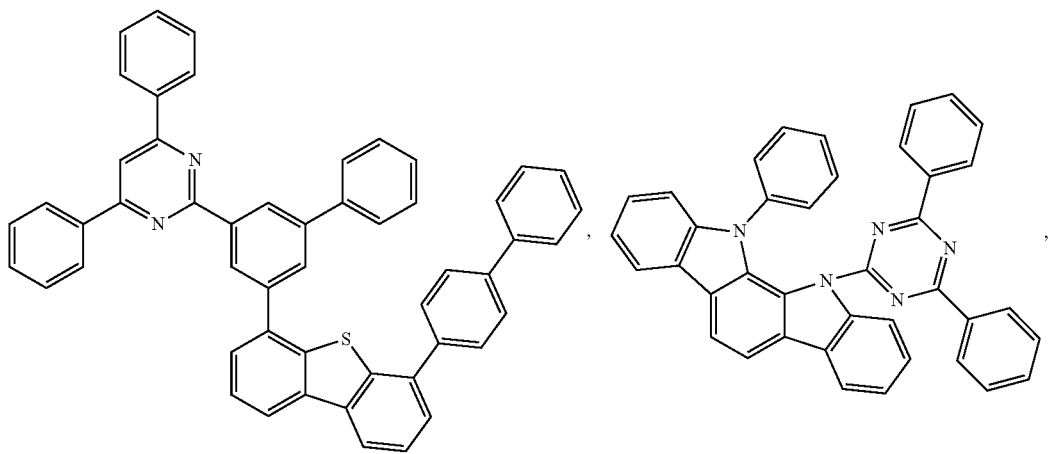

-continued
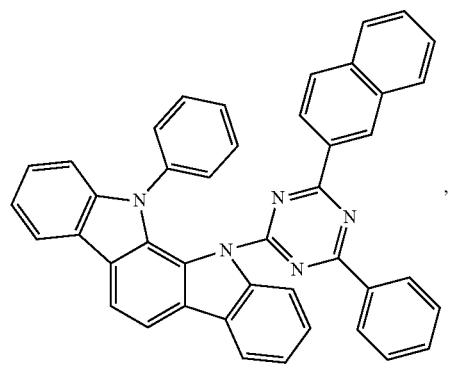
,
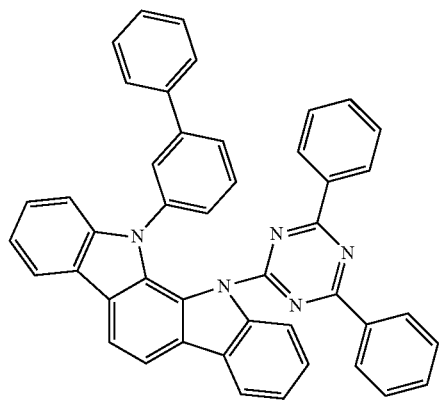
,
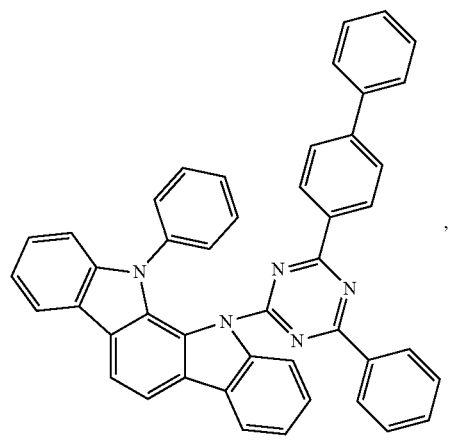
,
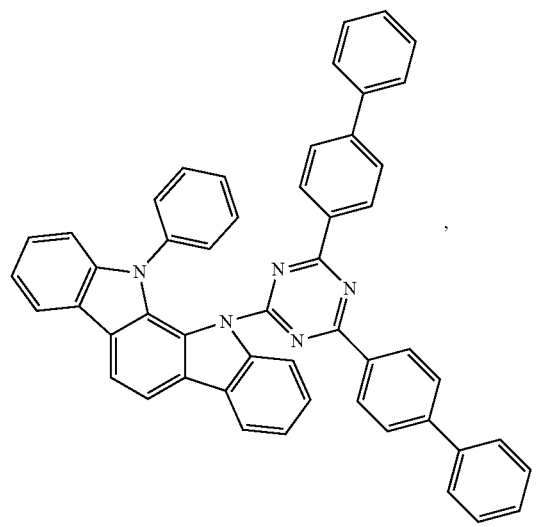
,
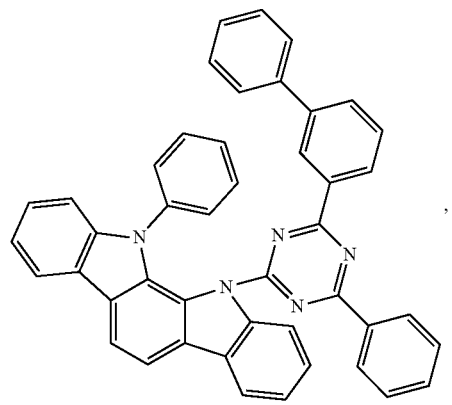
,
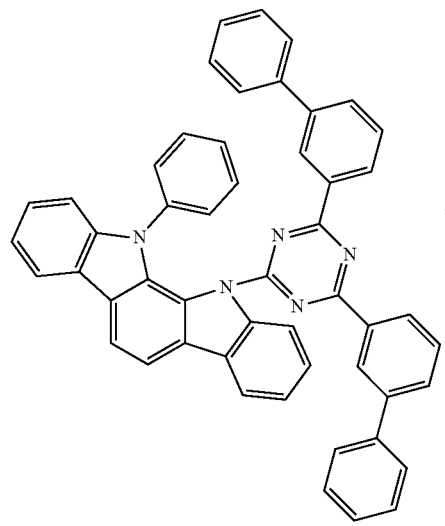
, -continued
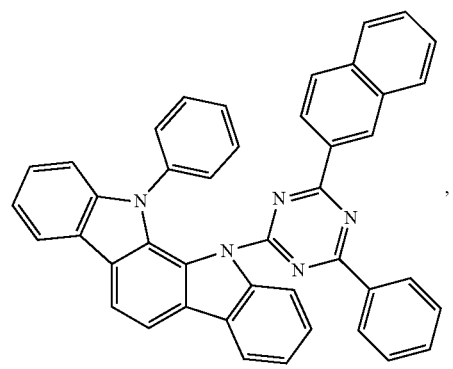
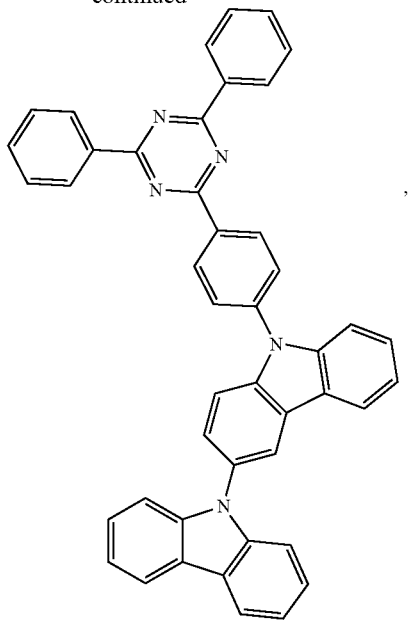
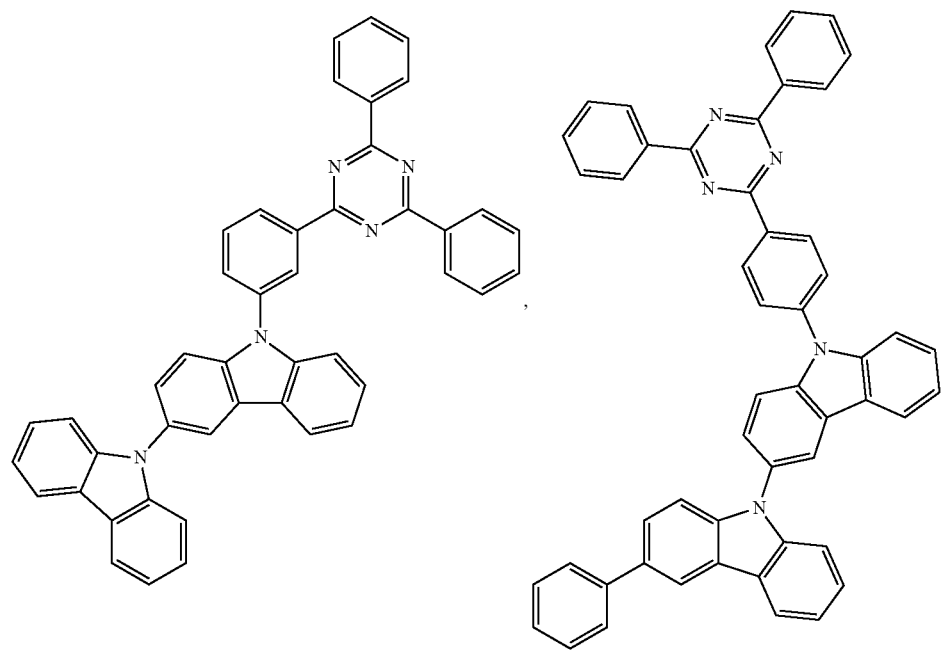

-continued
| 129 | 130 |
|---|---|
| 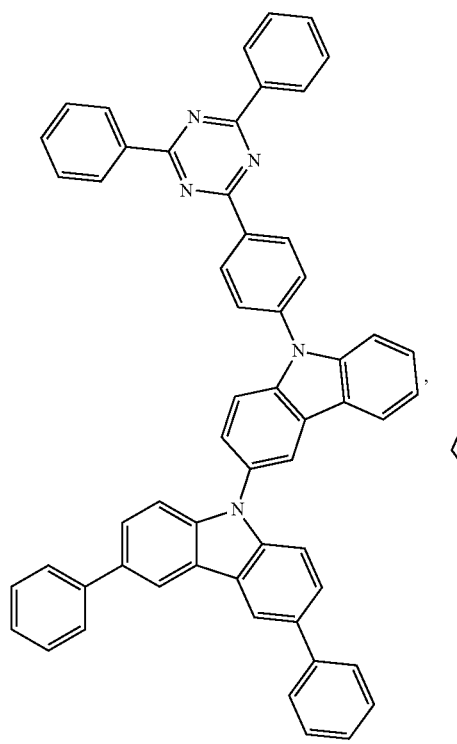 | 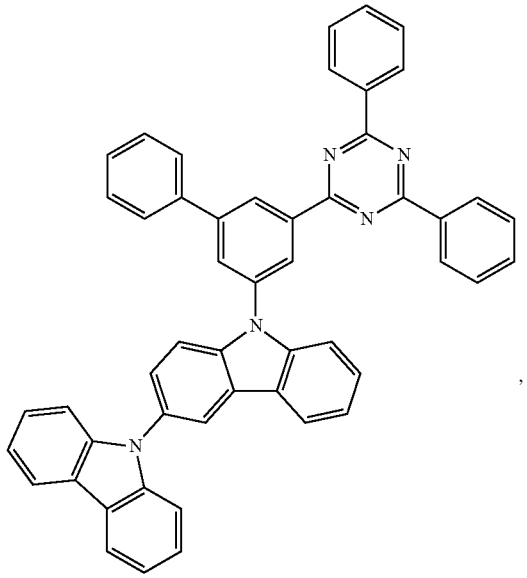 |
| 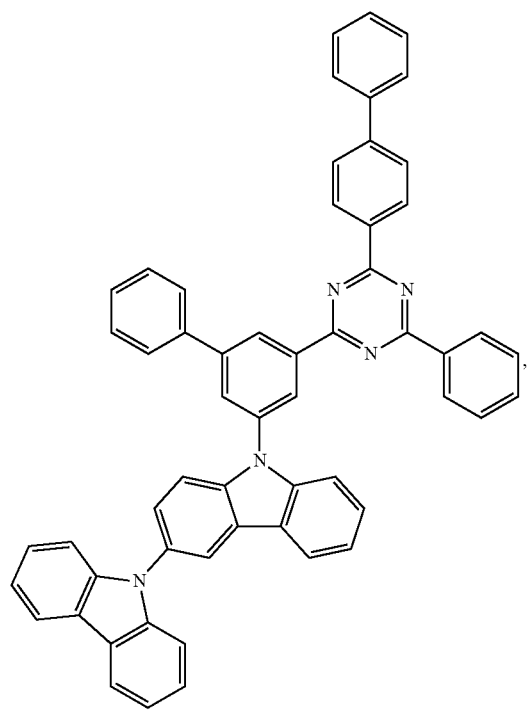 | 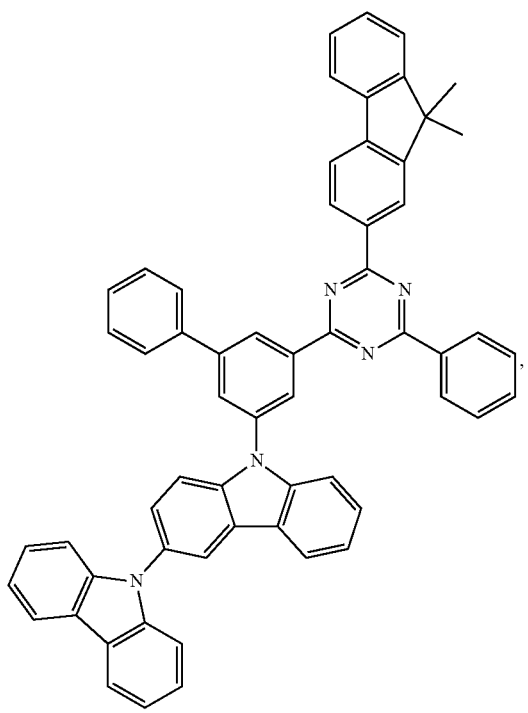 |

-continued
131
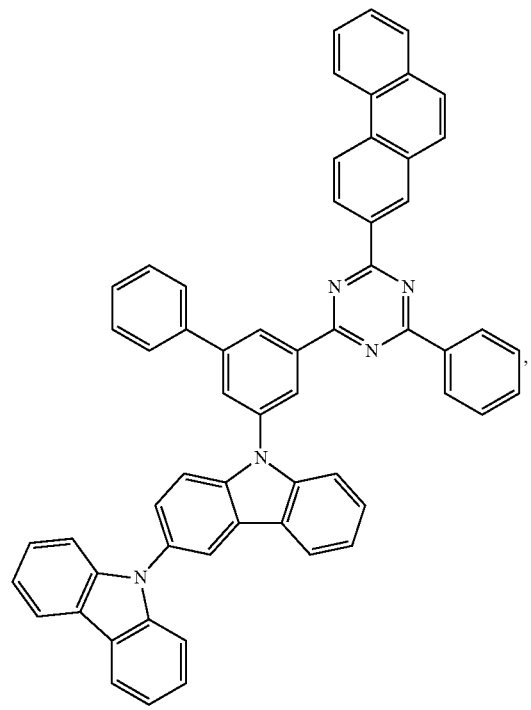
132
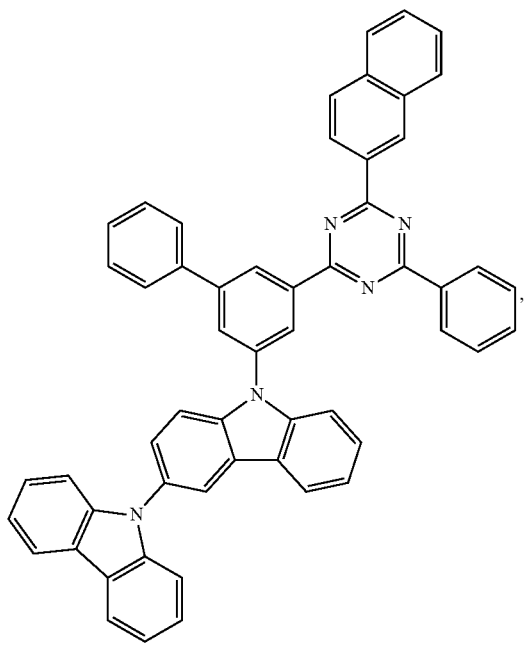
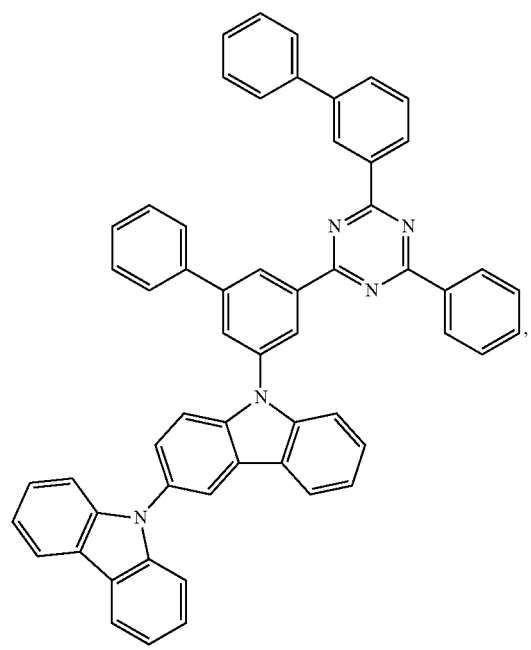
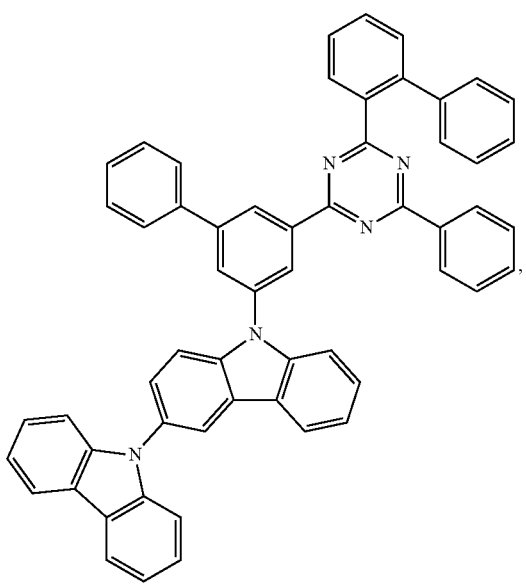

-continued
133
134
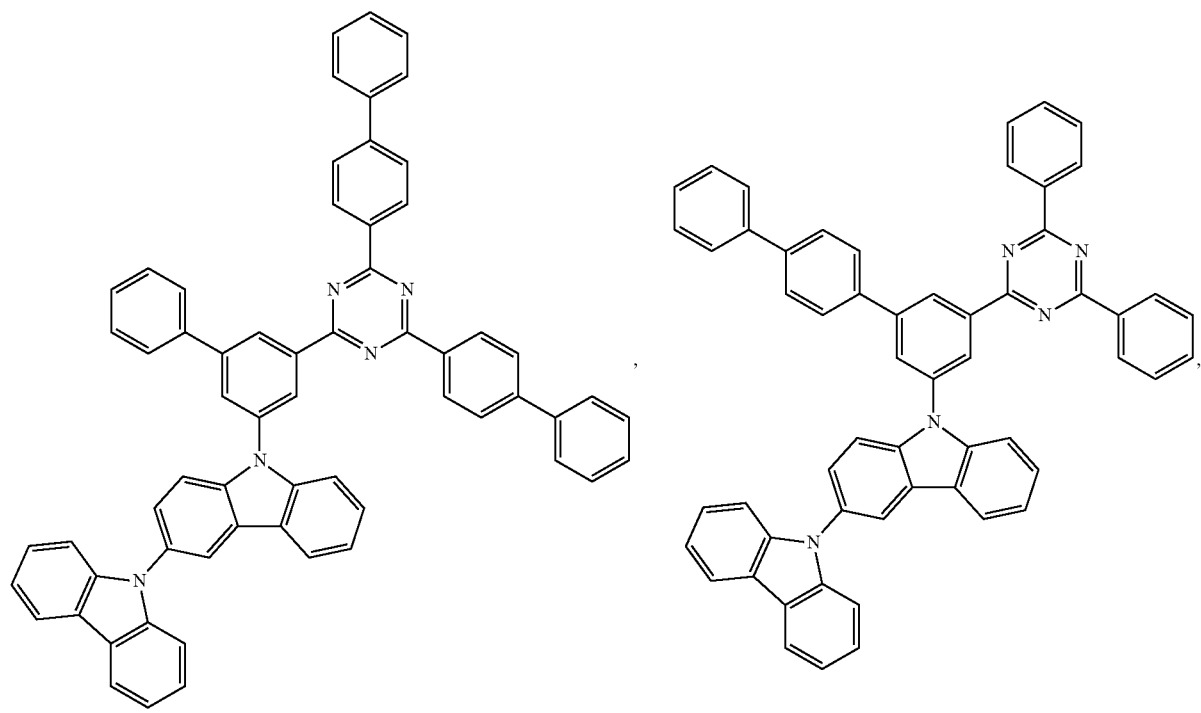
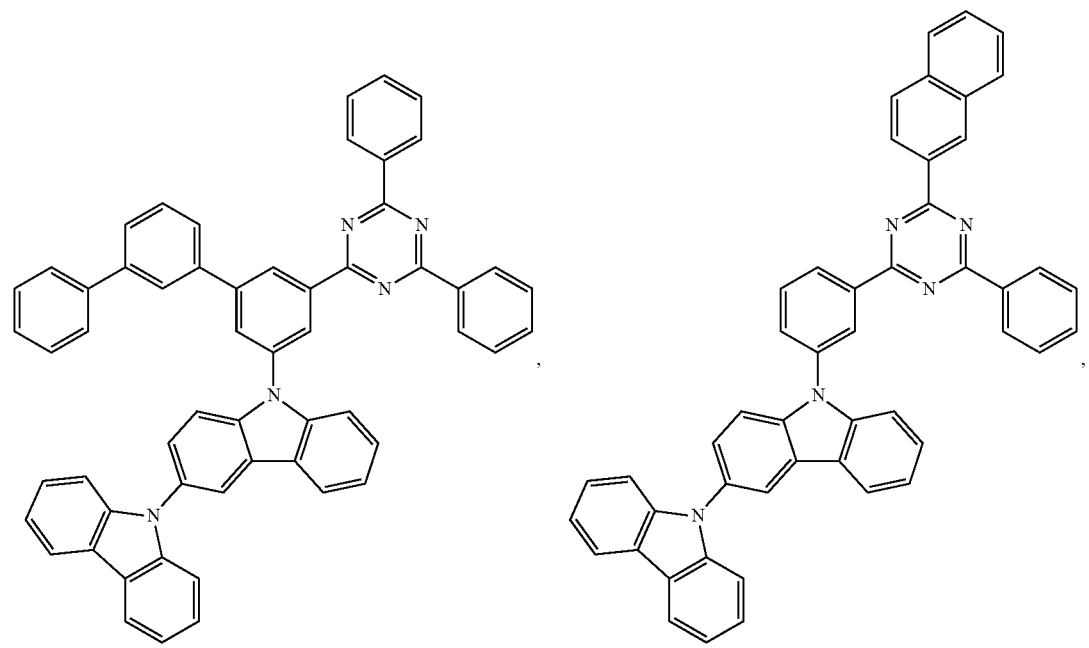

-continued
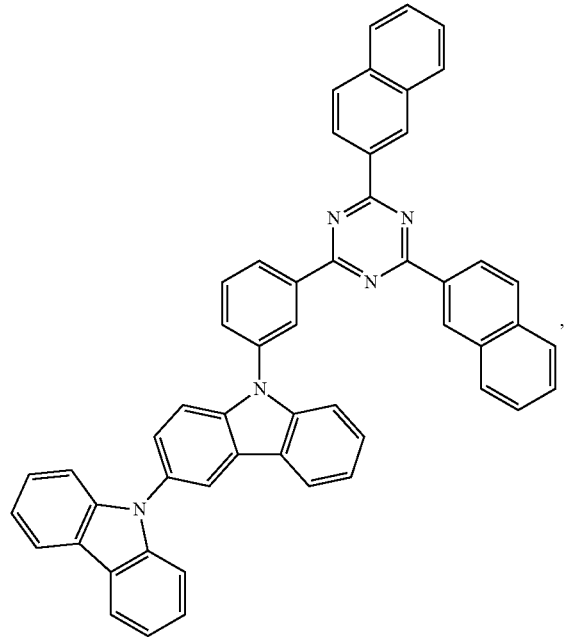
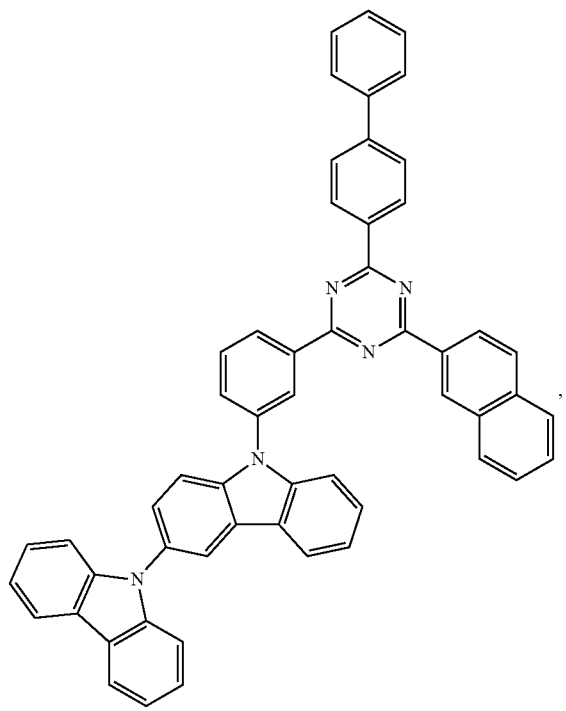
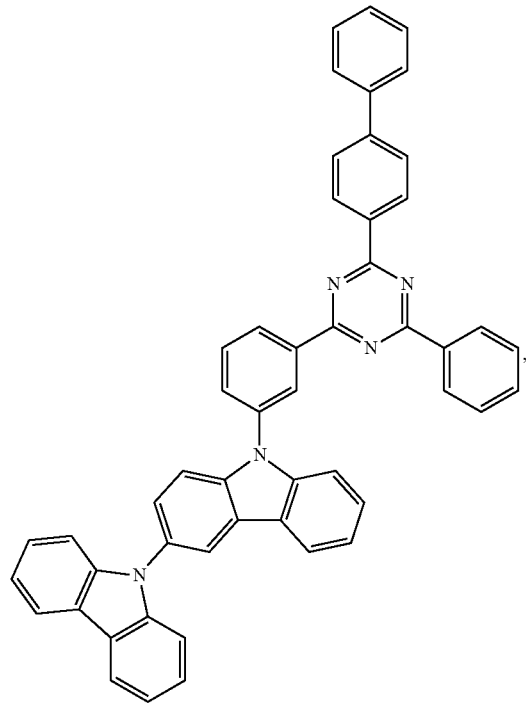
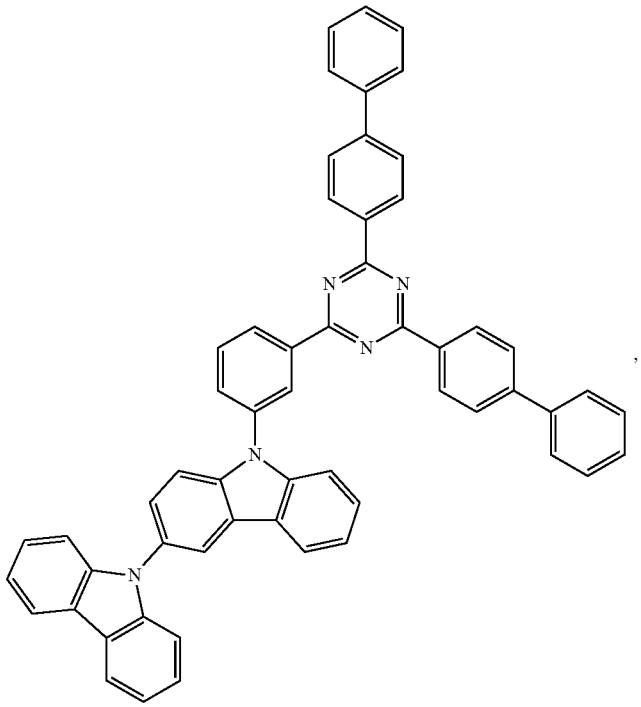

137 138
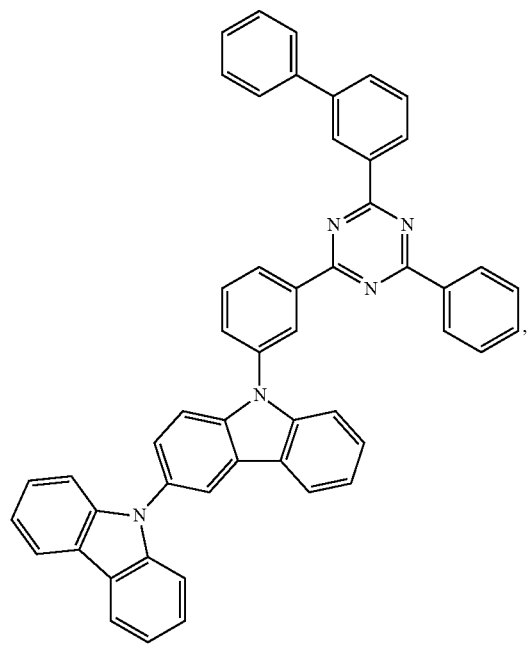
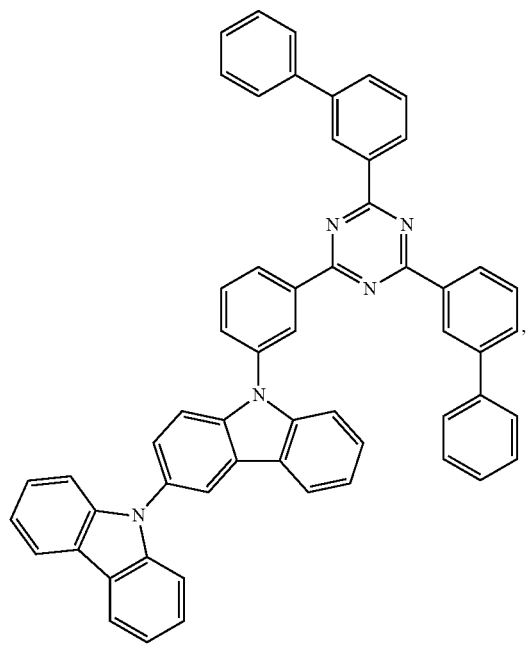
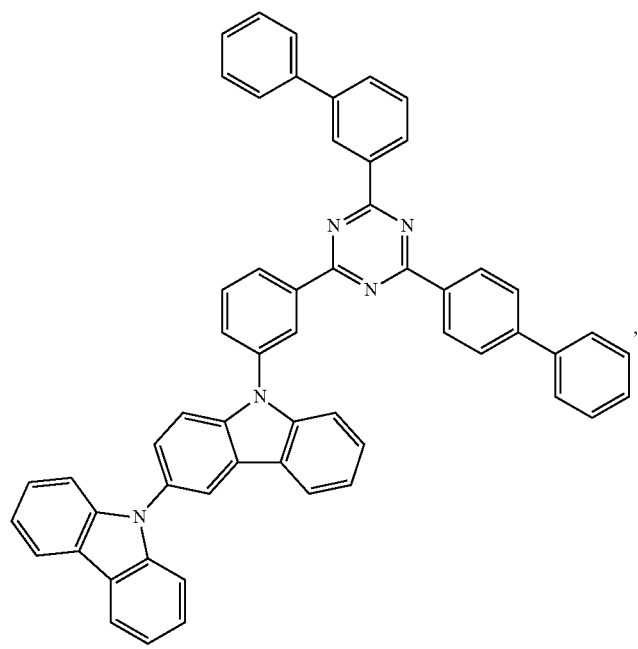

139 140
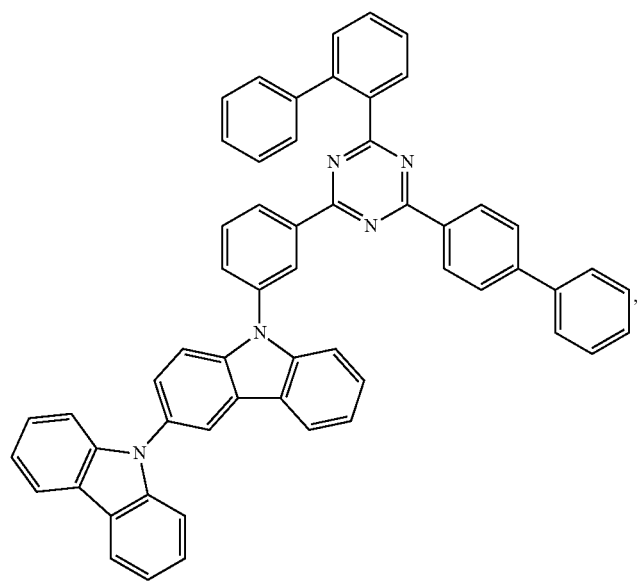 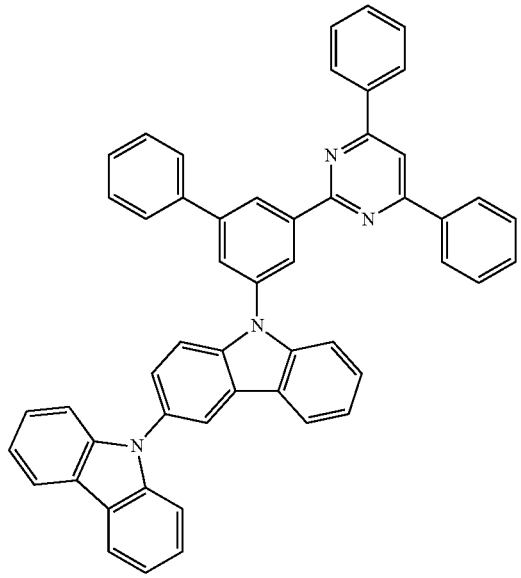
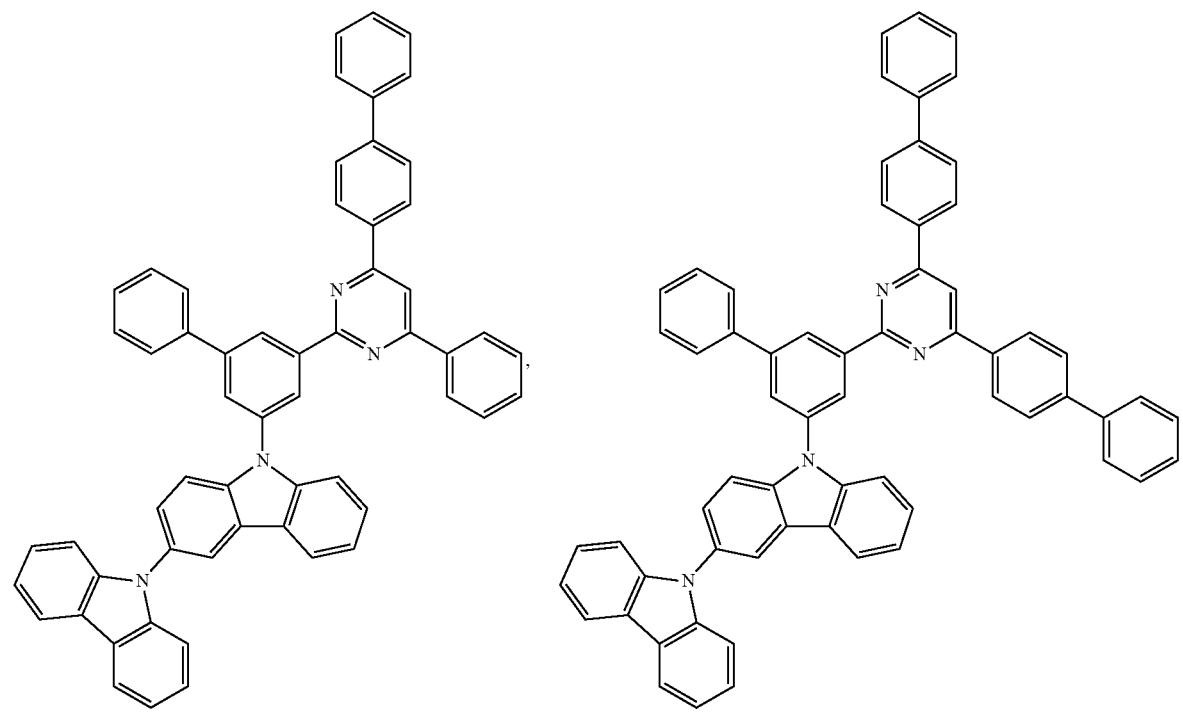

-continued
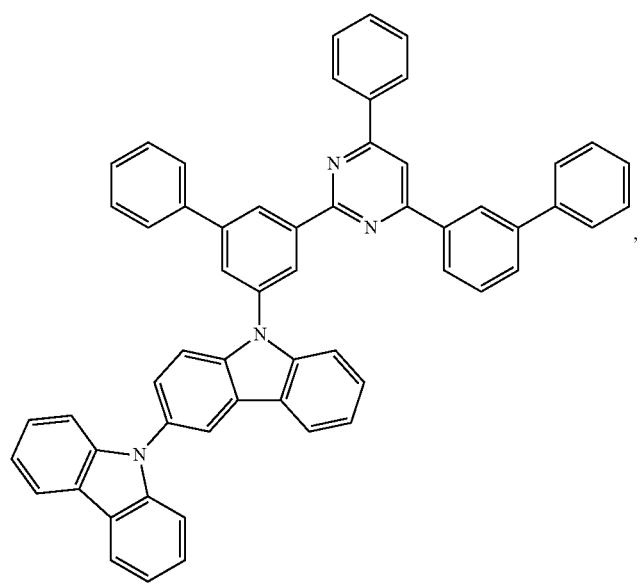
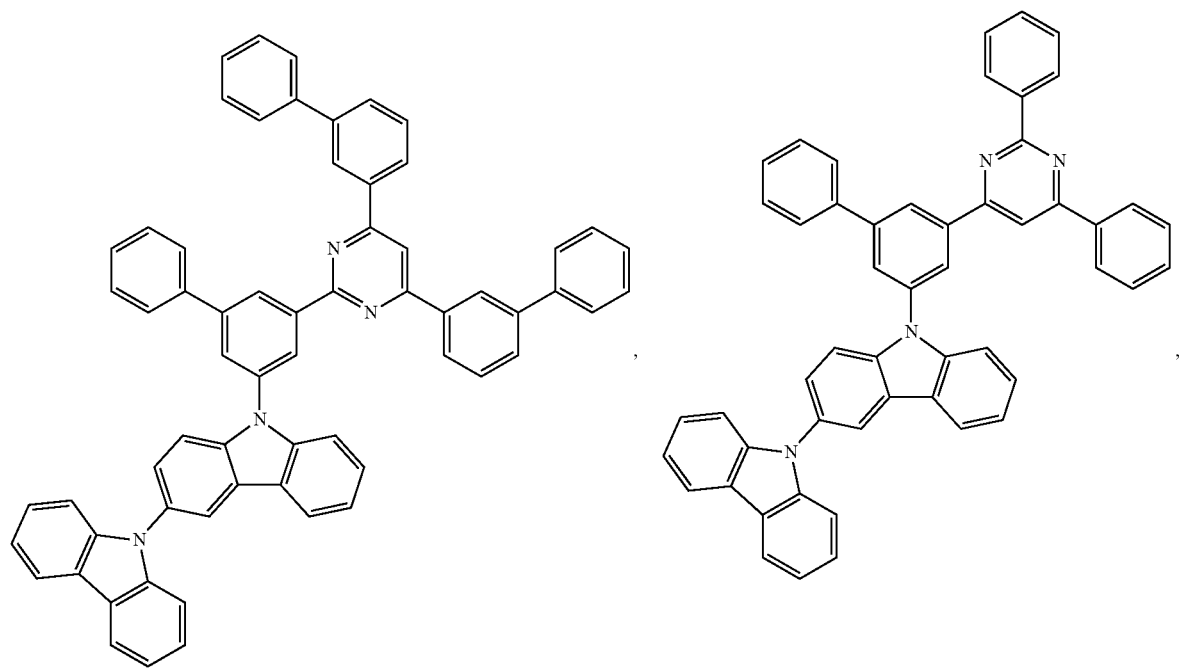

-continued
143
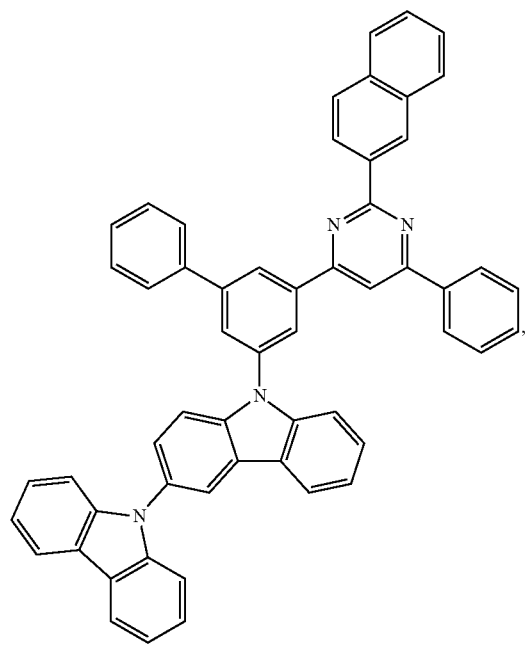
144
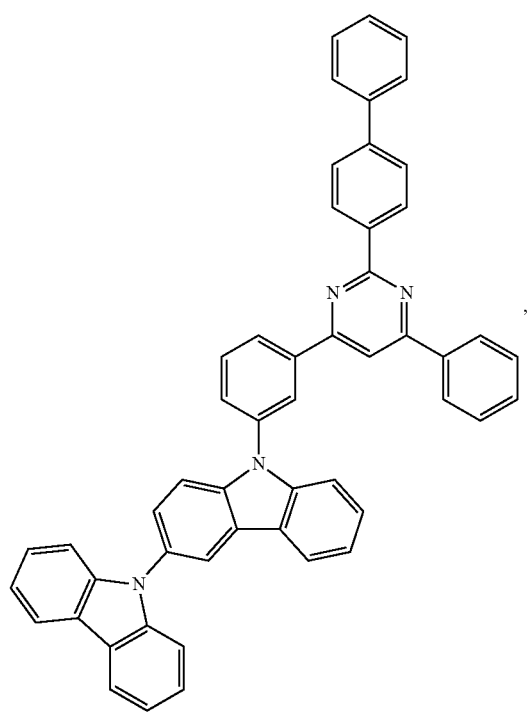
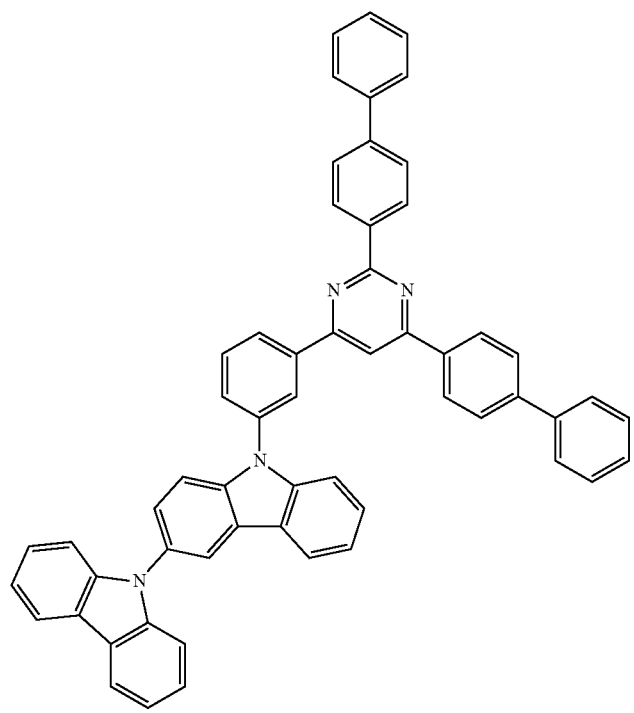
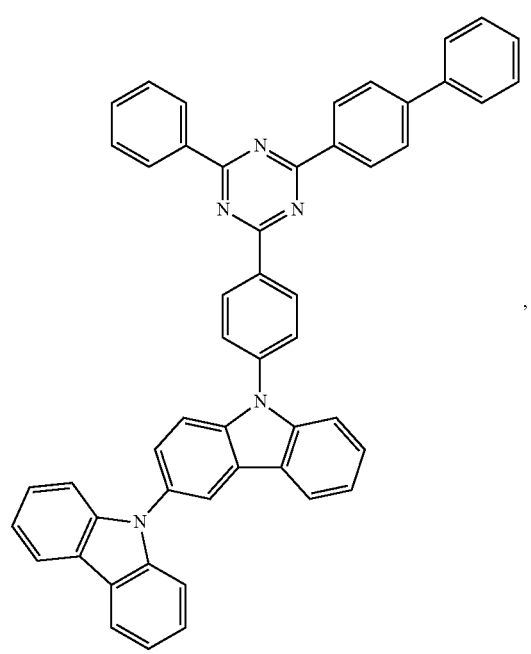

-continued
145
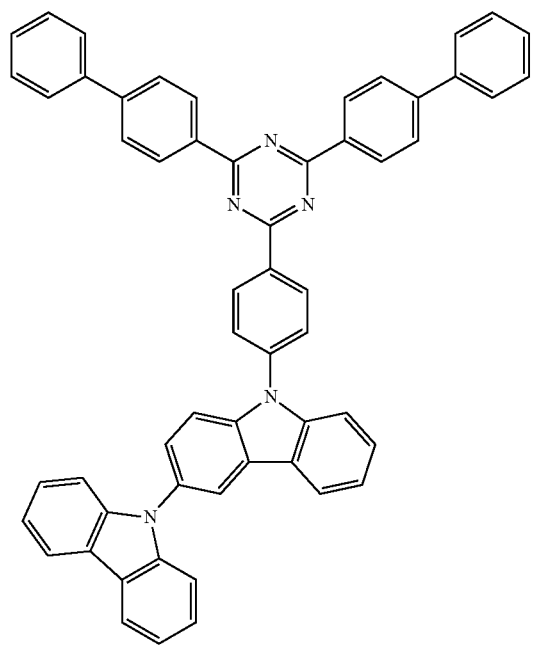
146
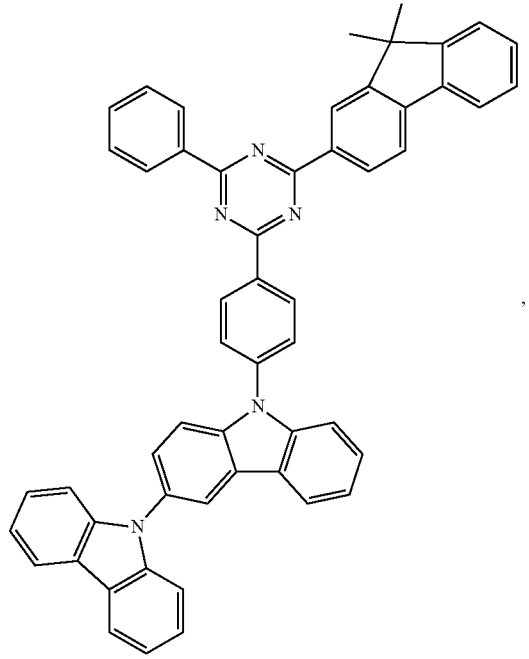
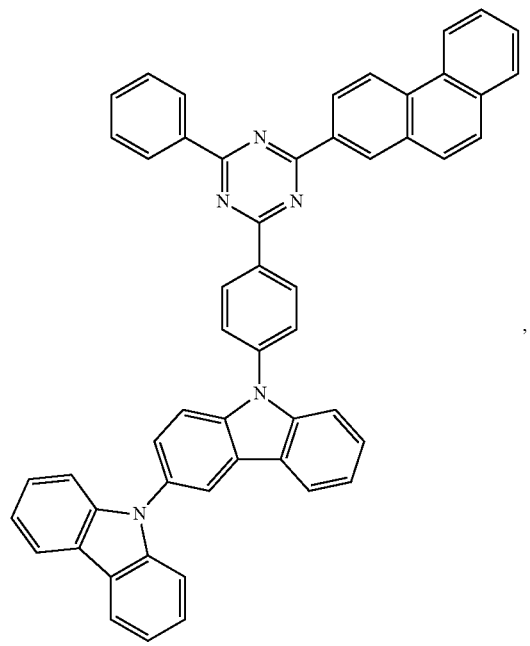
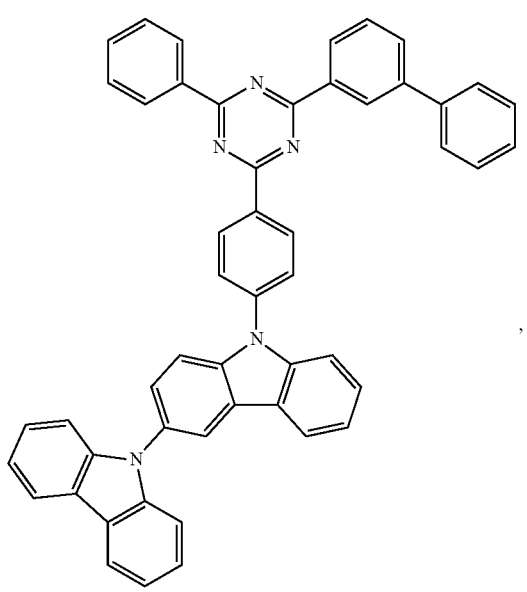

-continued
147
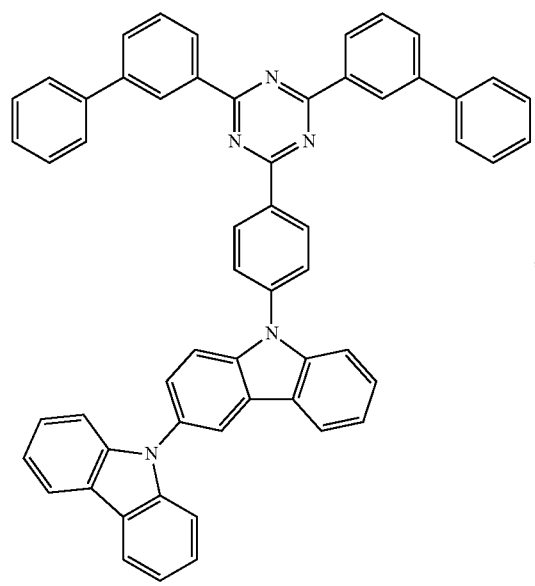
148
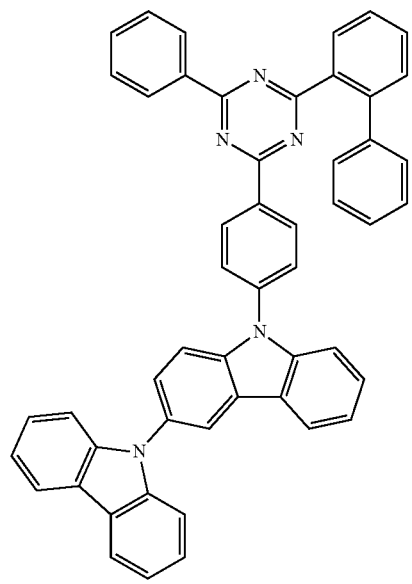
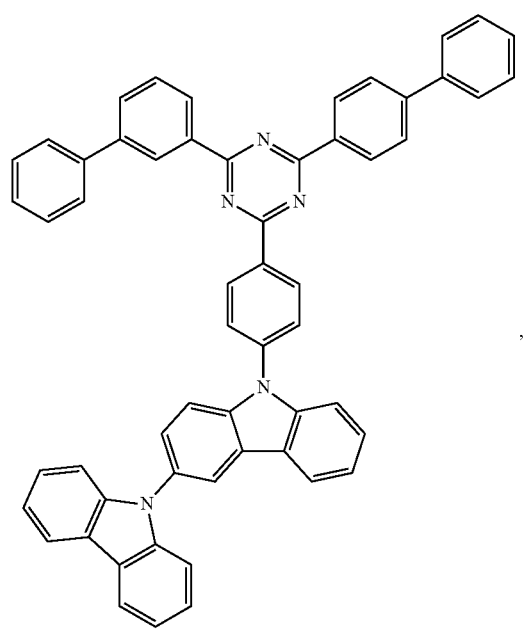
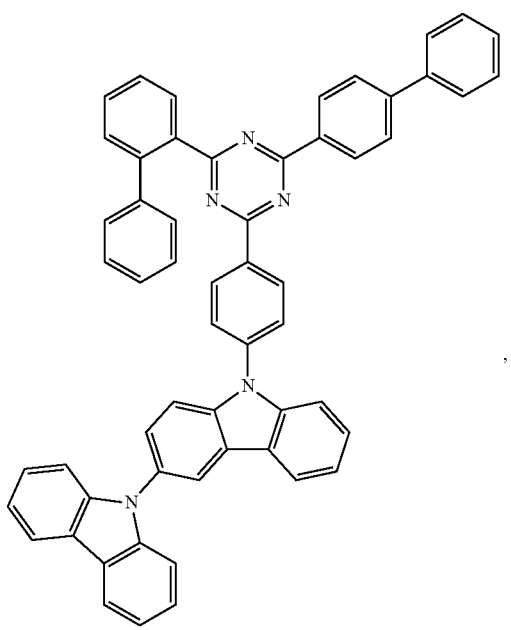

149
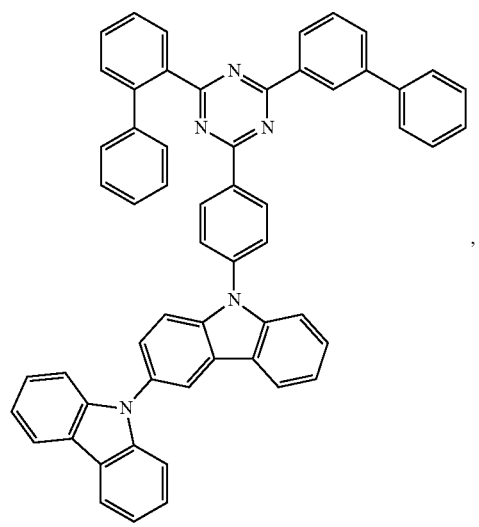
150
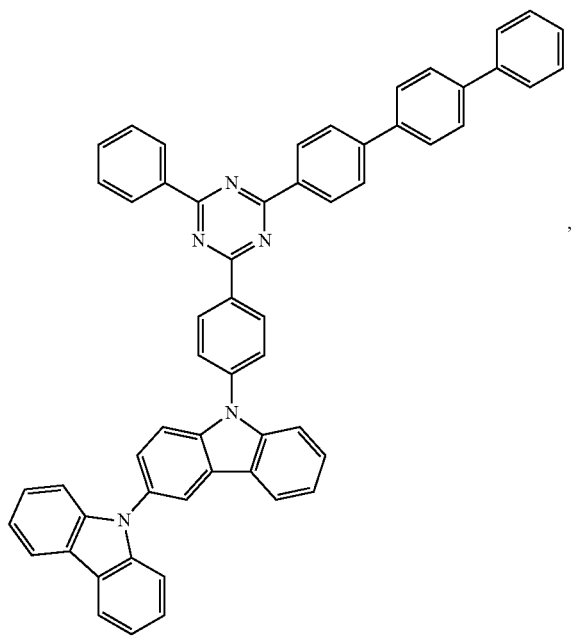
-continued
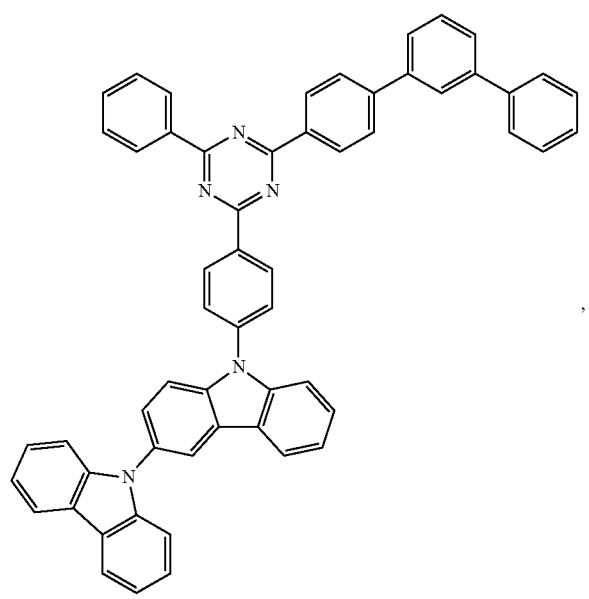
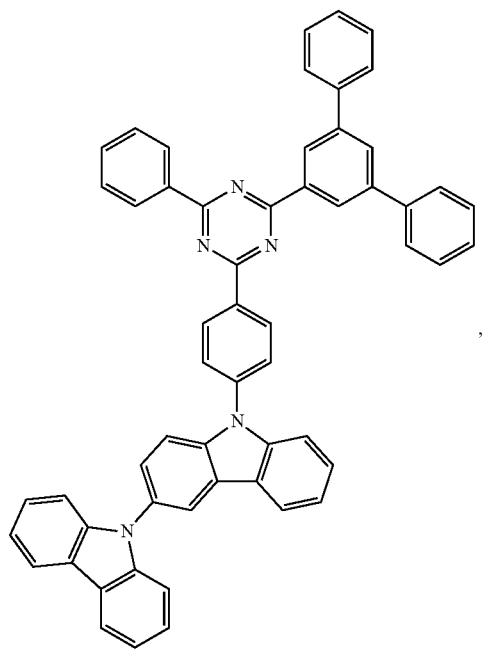

-continued
151
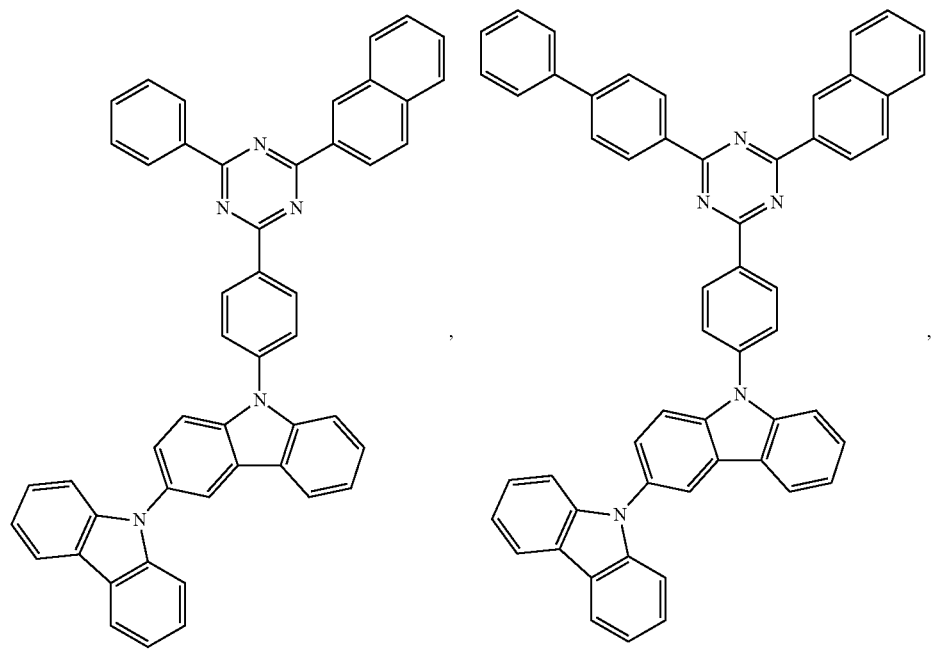
152
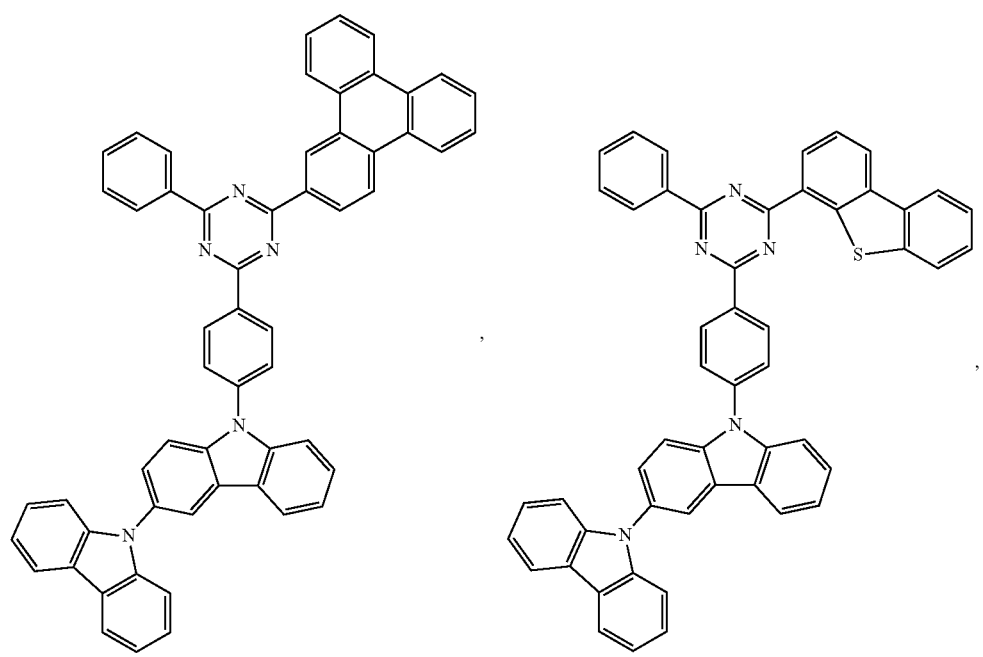

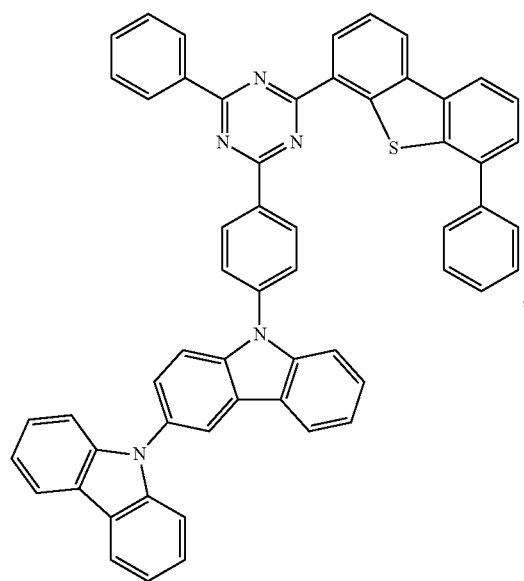,
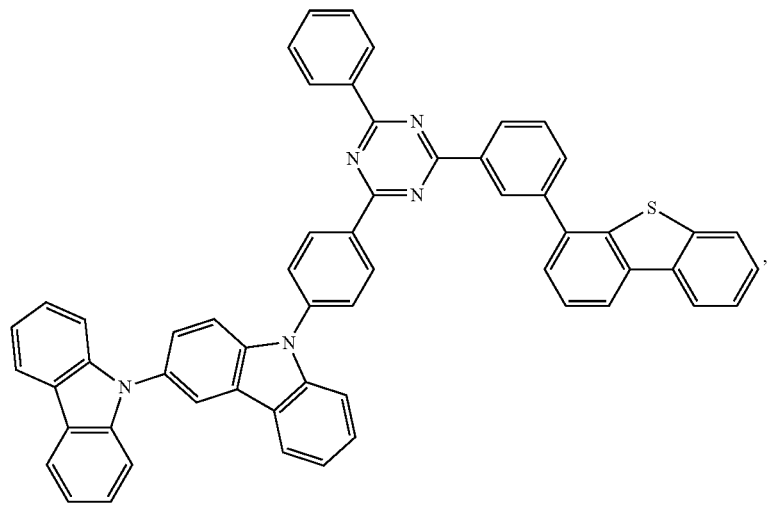,
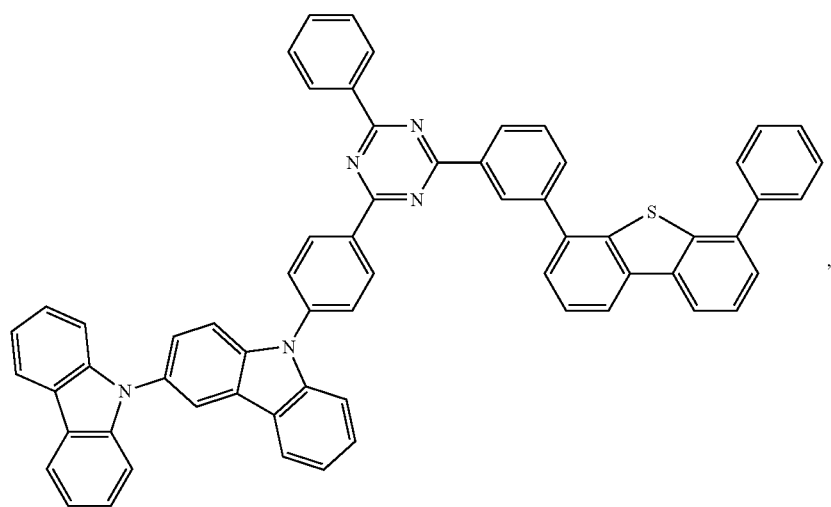, 155 156
-continued
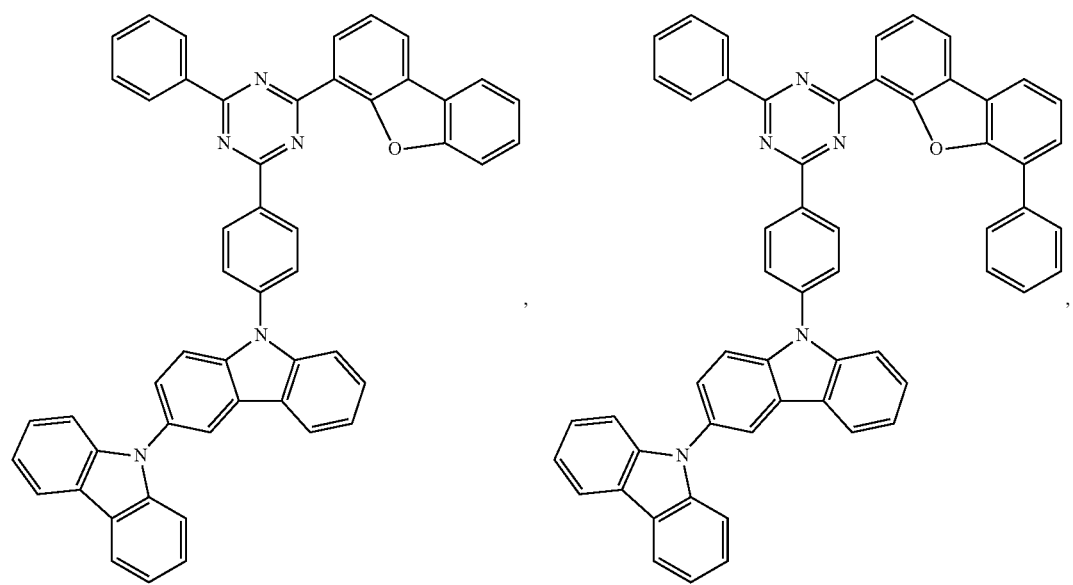
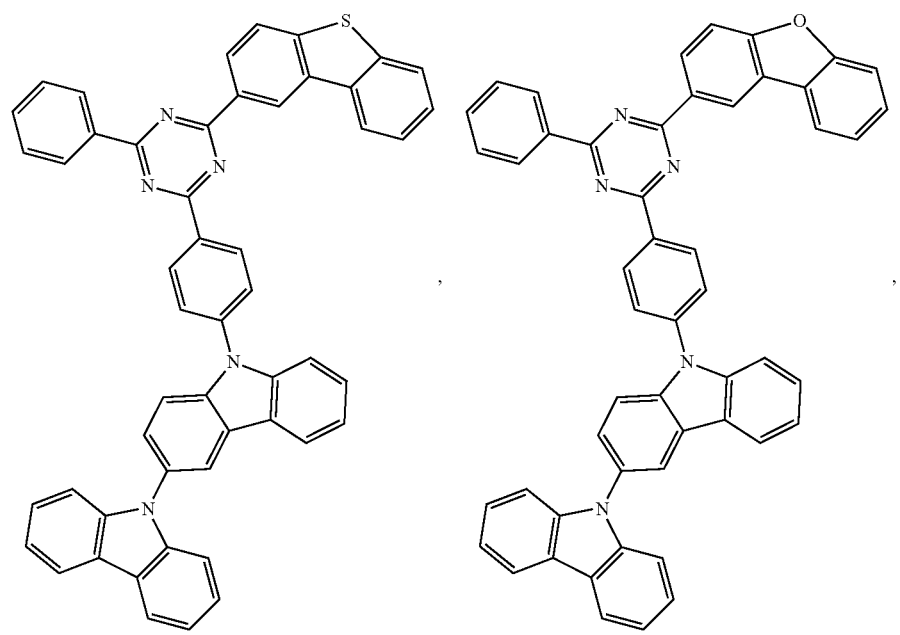

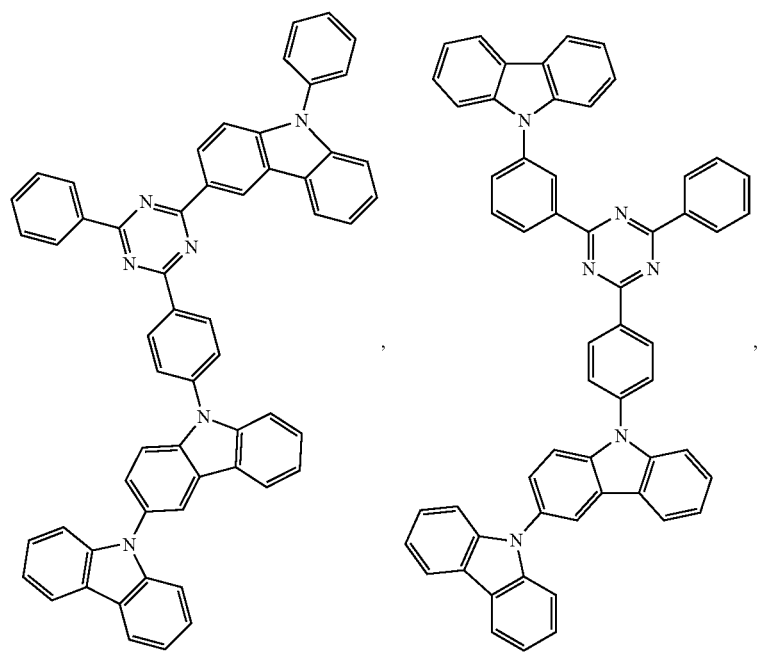
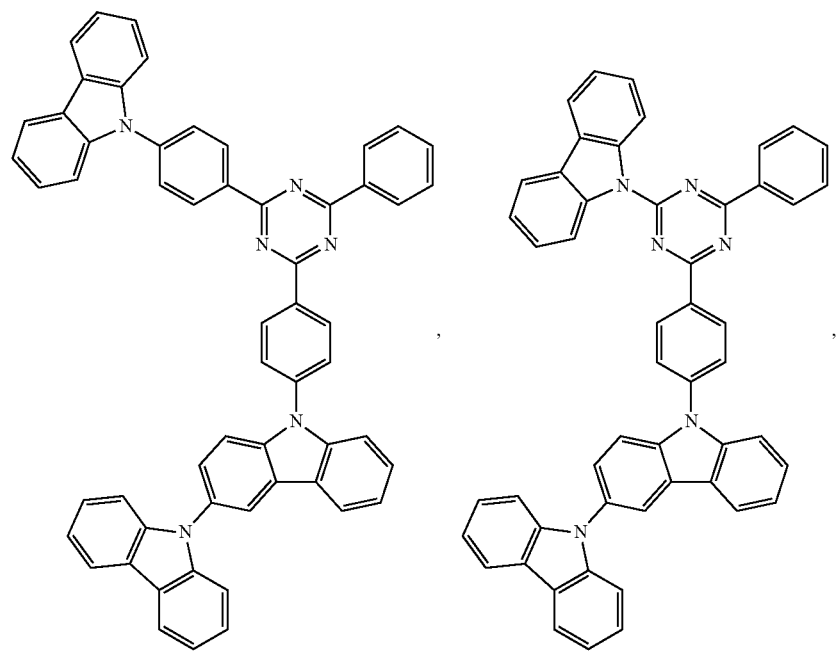

159
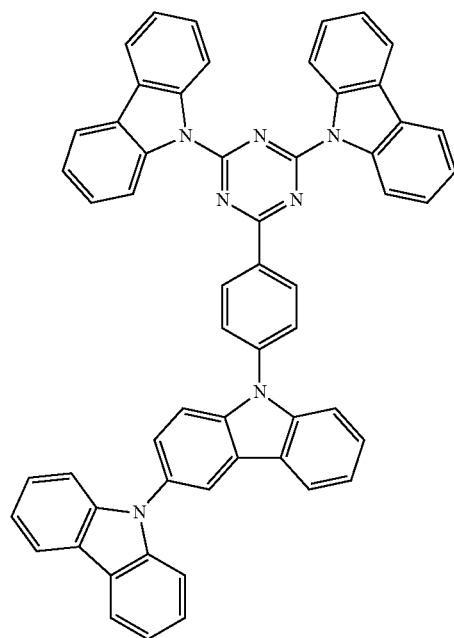
160
-continued
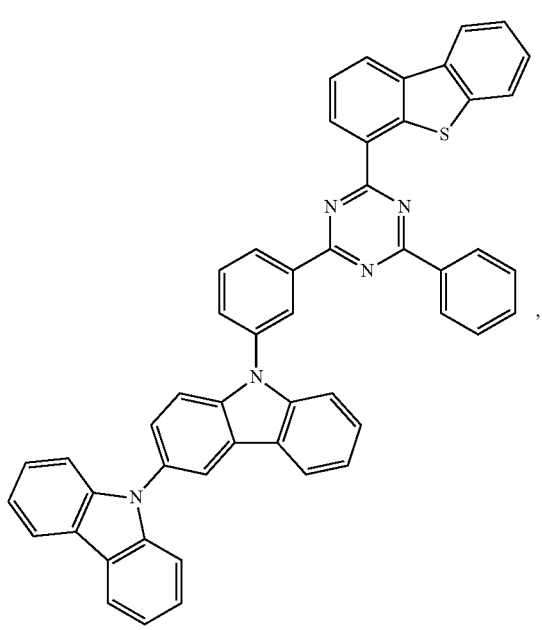
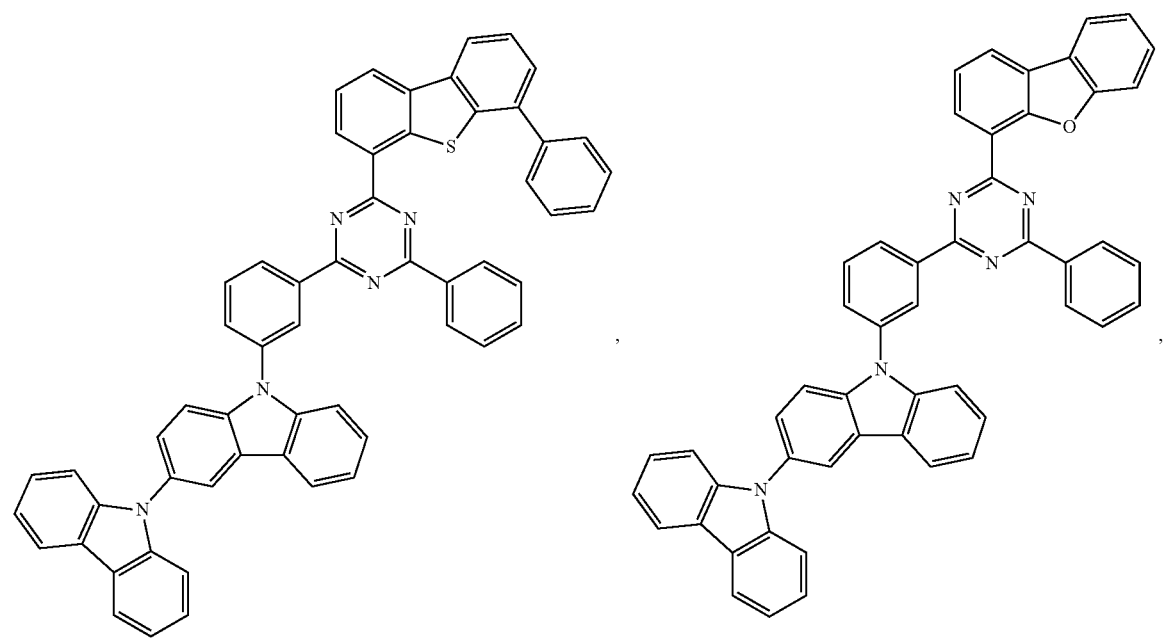

-continued
161 162
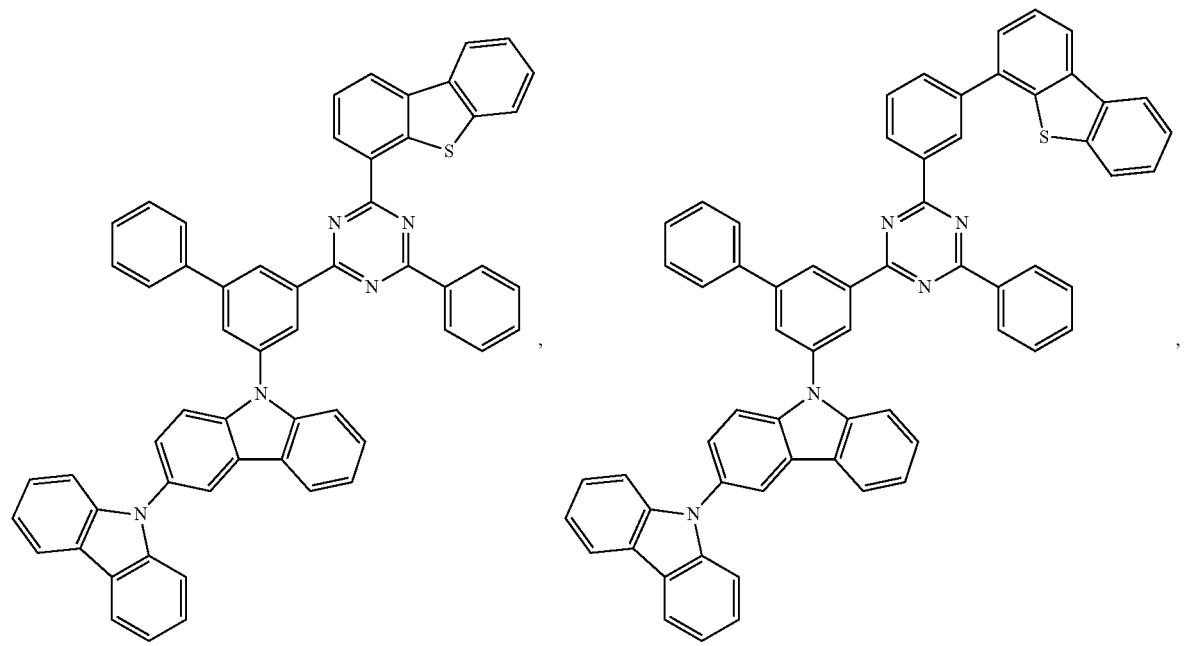
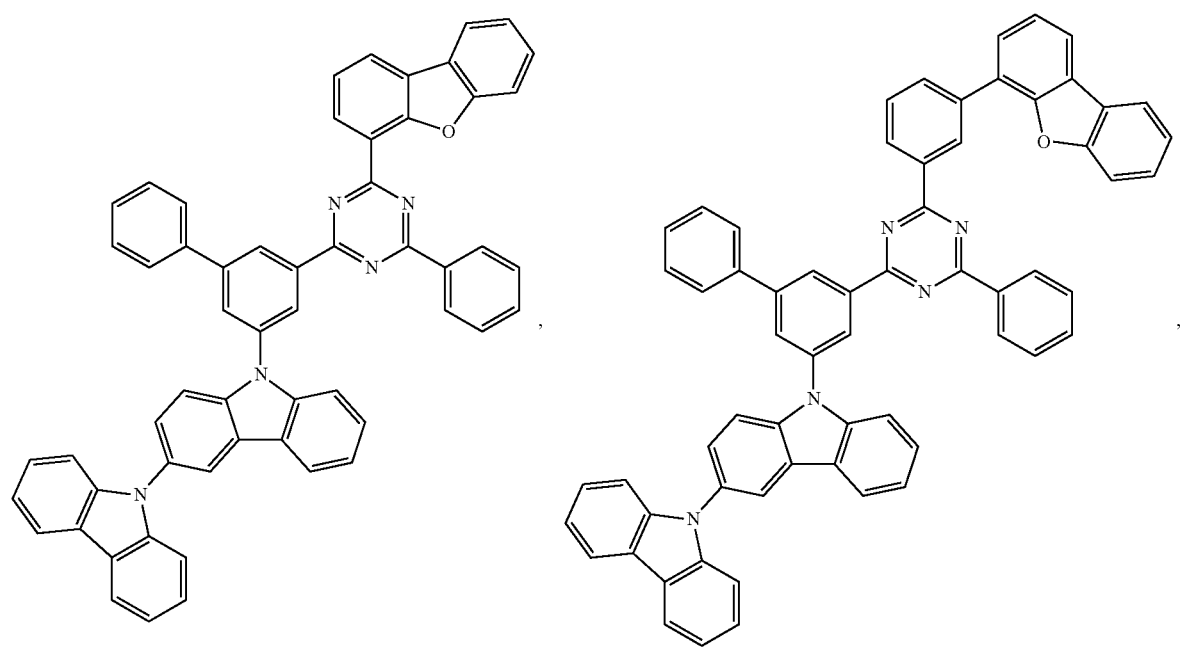

-continued
163
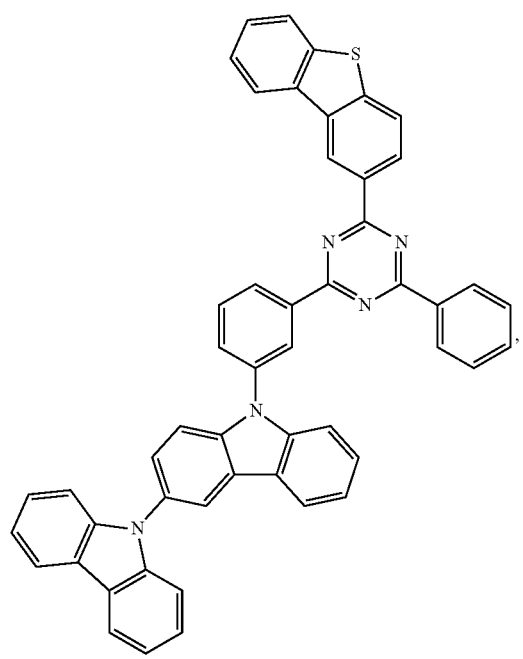
164
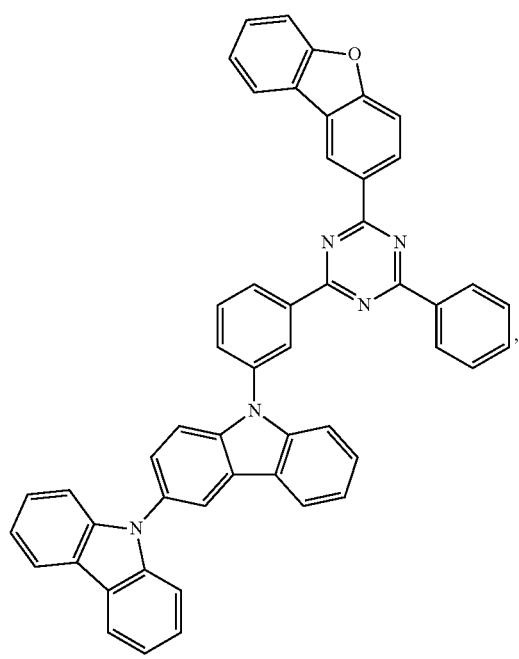
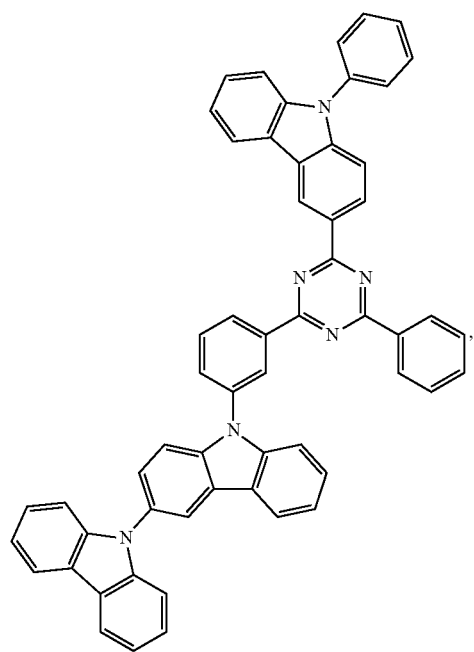
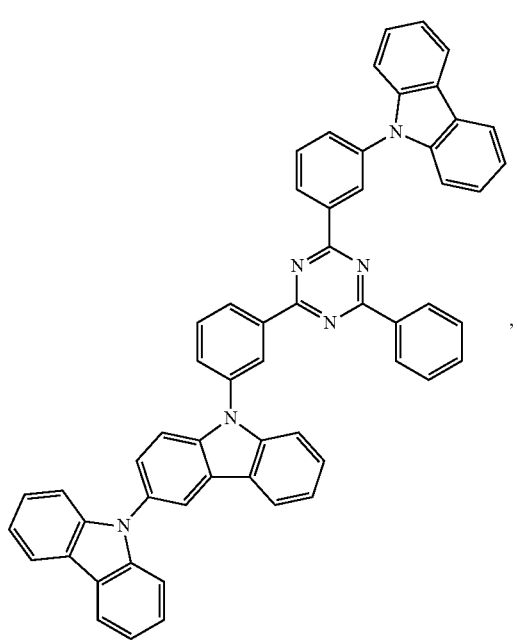

165
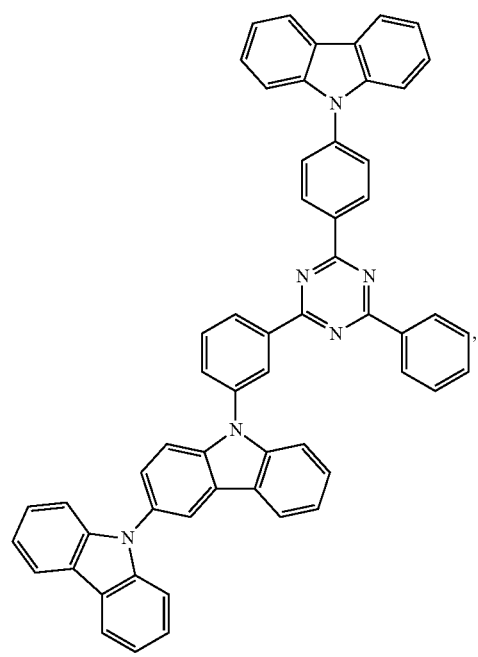
166
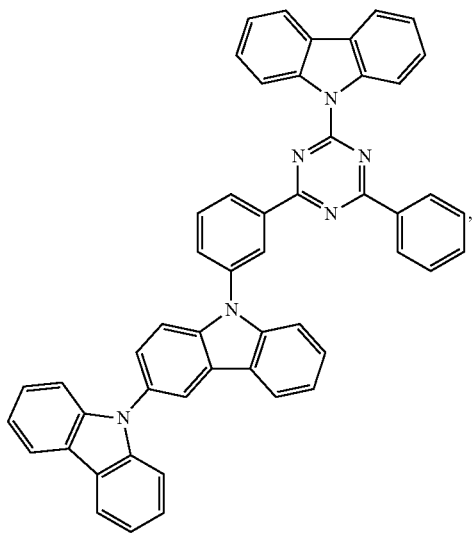
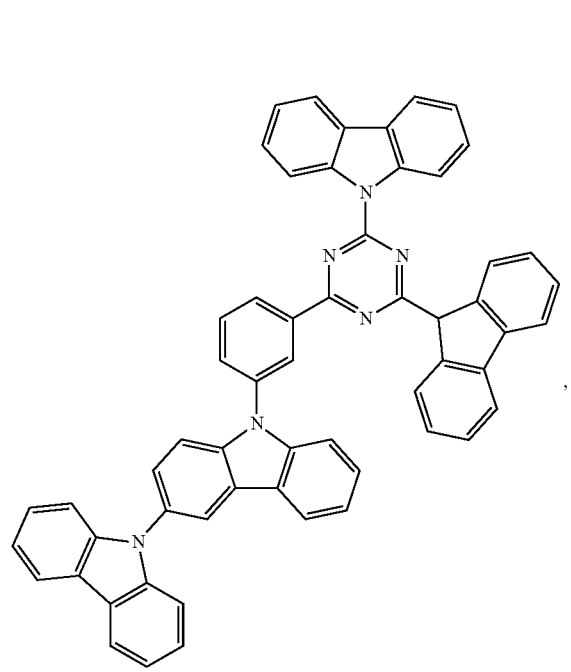
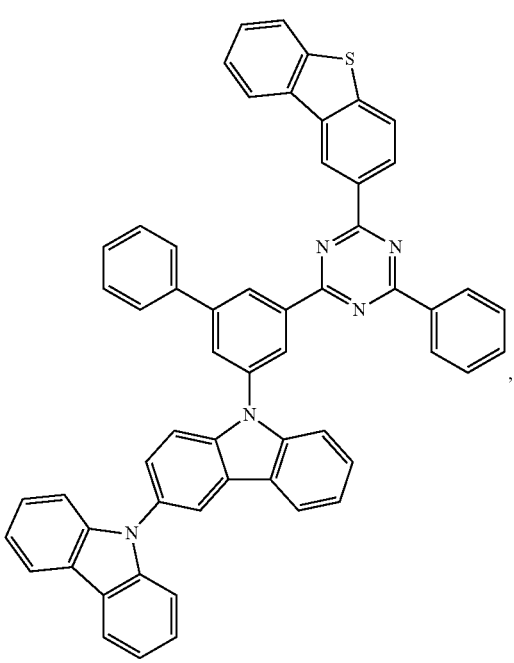

-continued
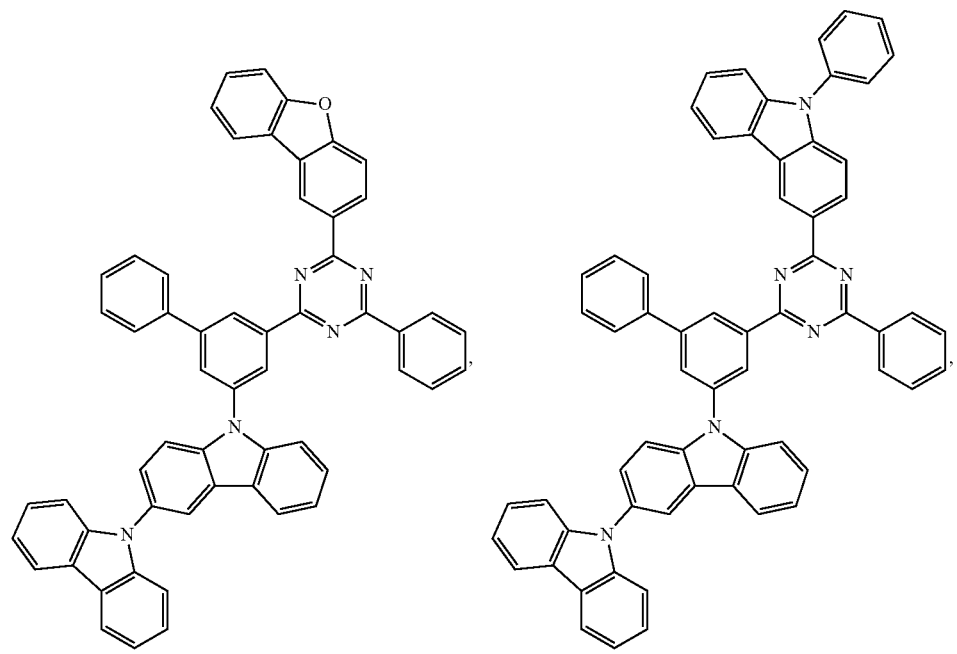
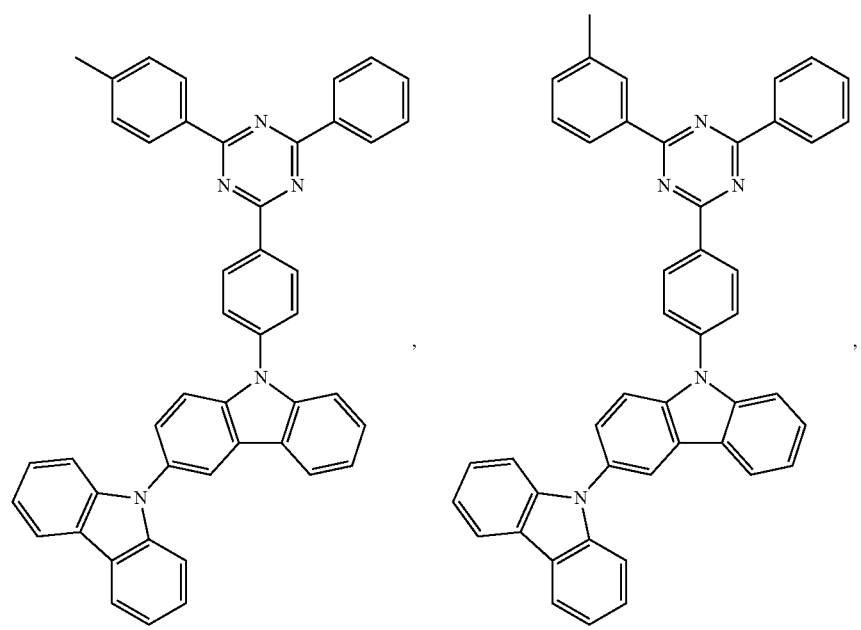

-continued
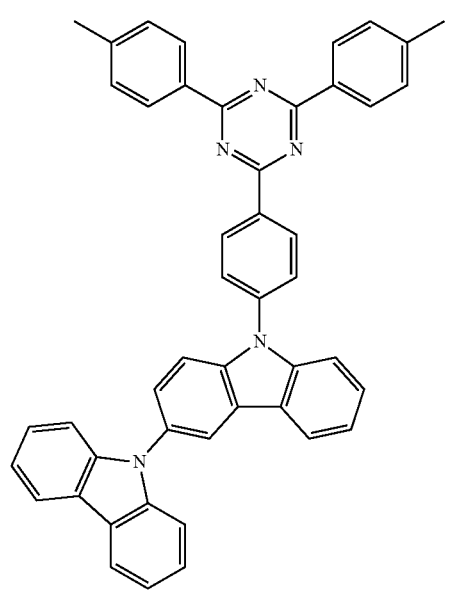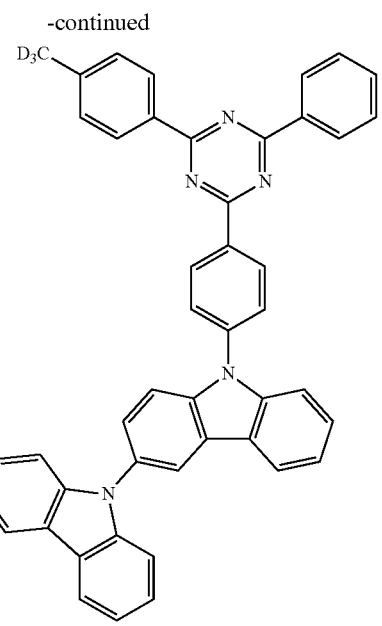
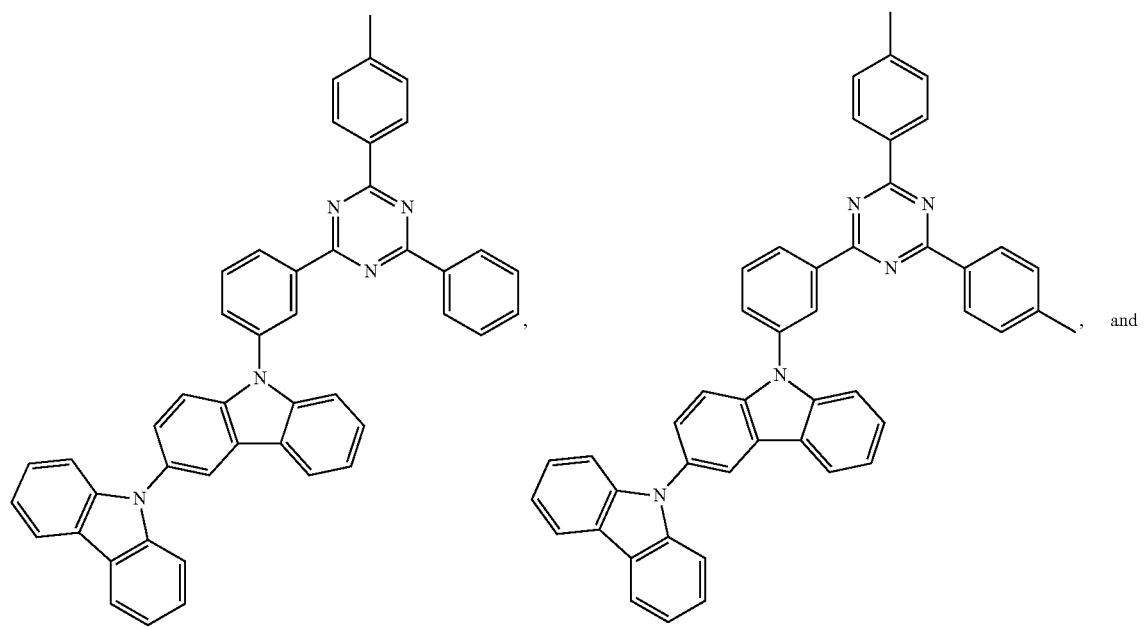

-continued
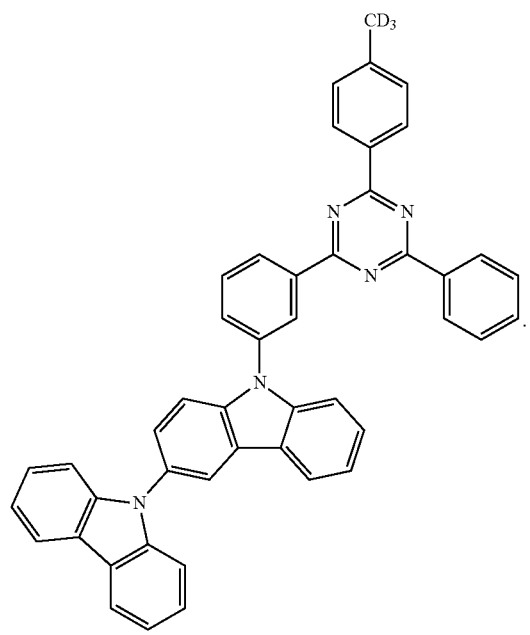
According to some embodiments, a composition comprising a first compound and a second compound is disclosed. The first compound can be selected from the group consisting of:
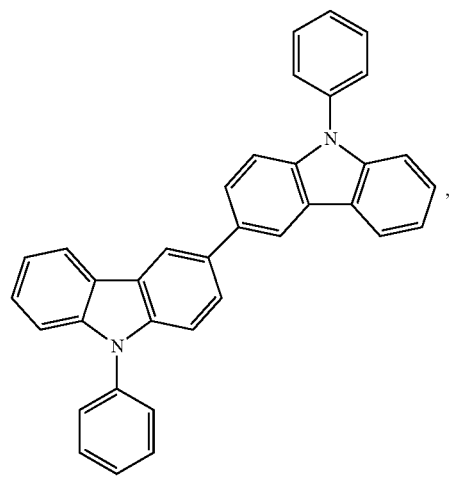
-continued
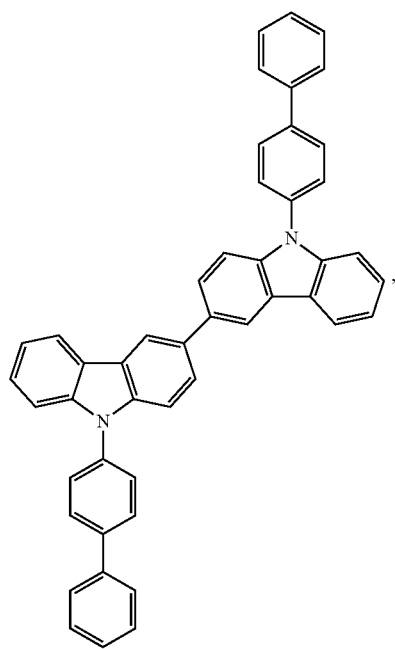

173
174
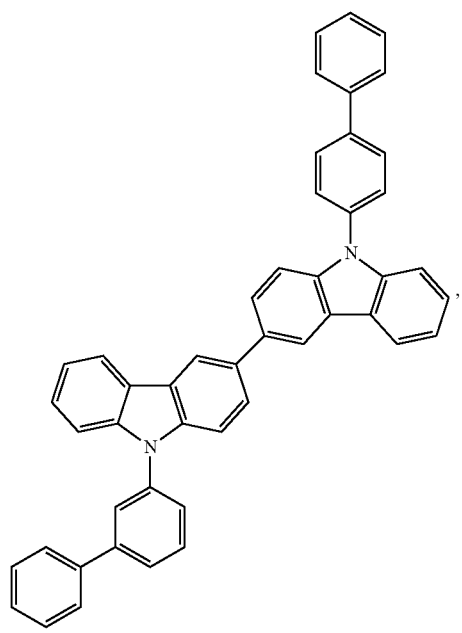
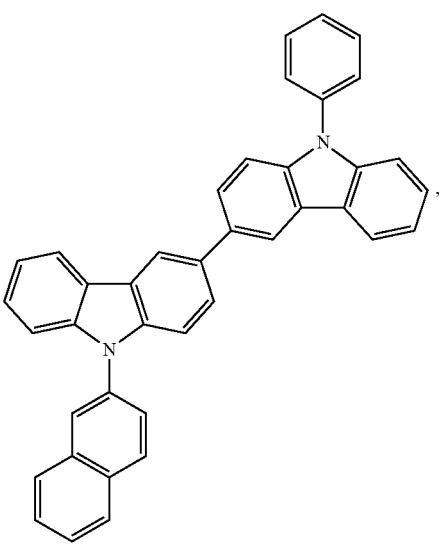
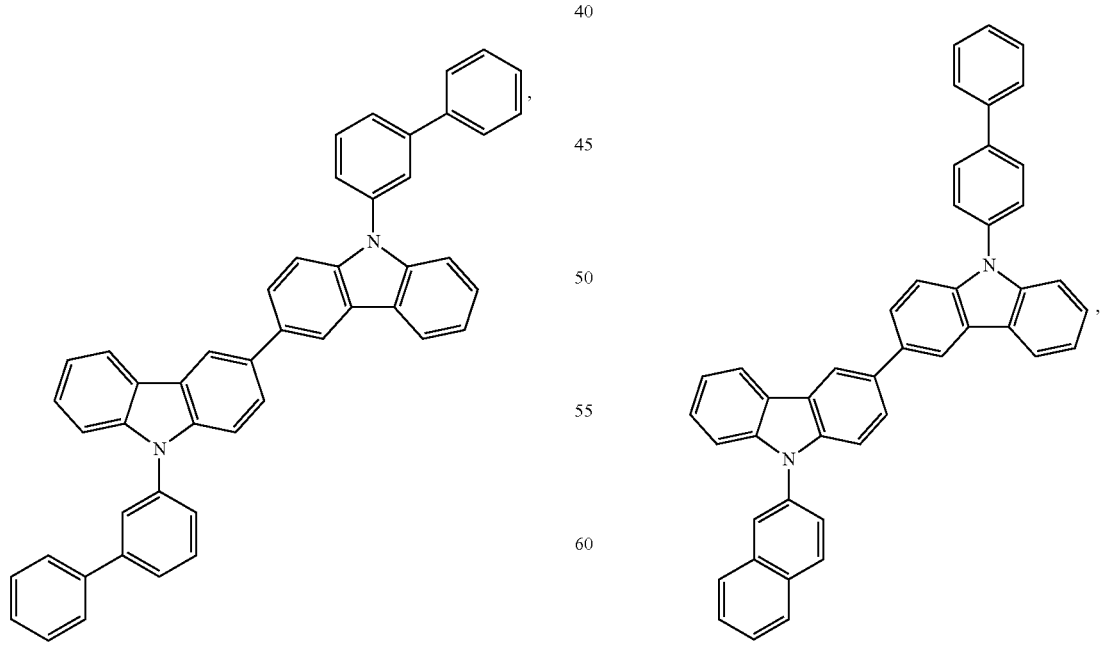

-continued
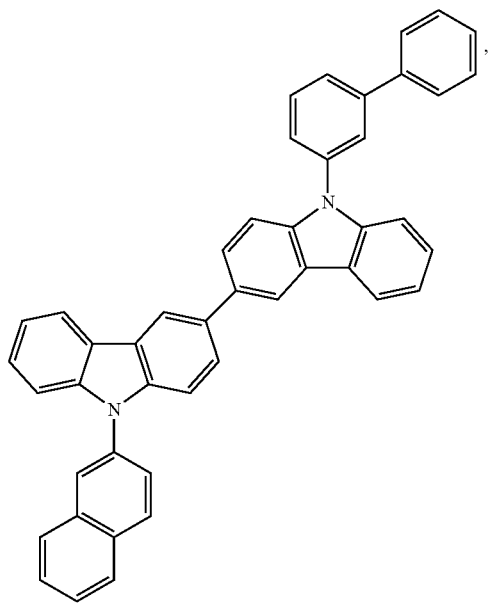
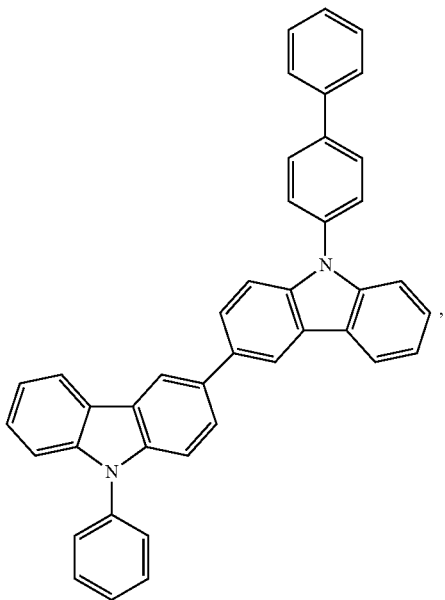
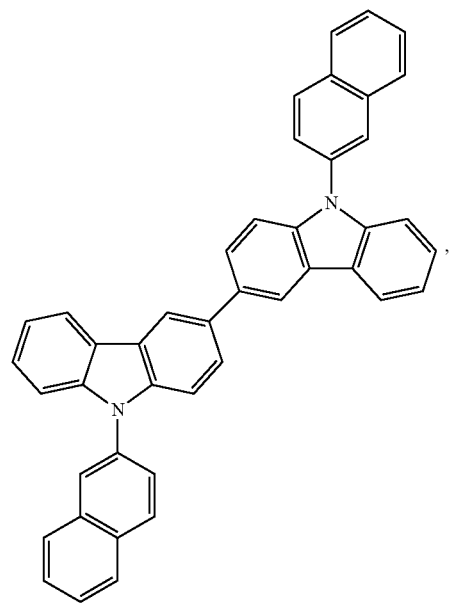
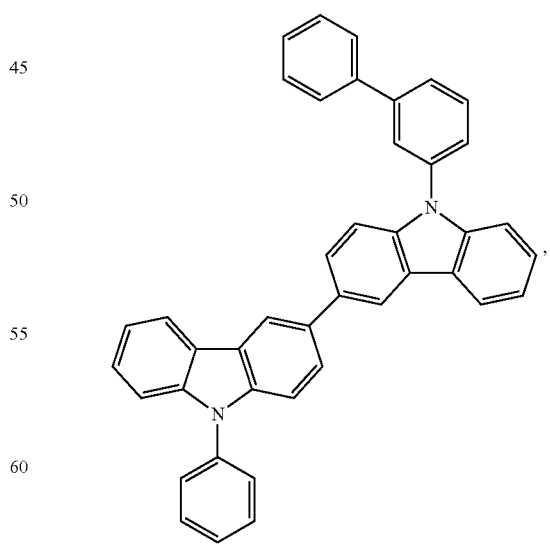

177
-continued
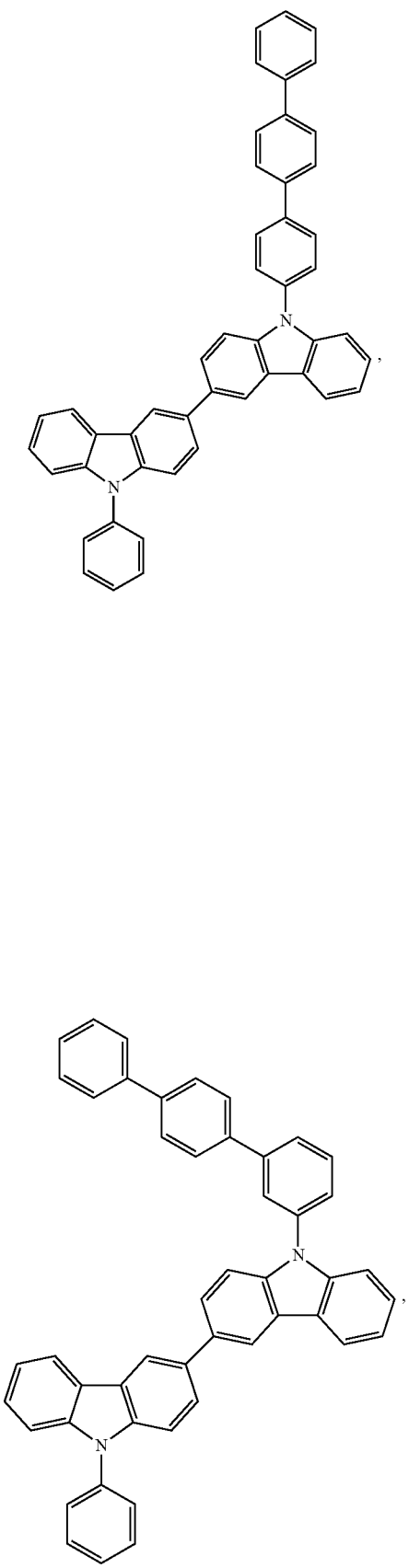
178
-continued
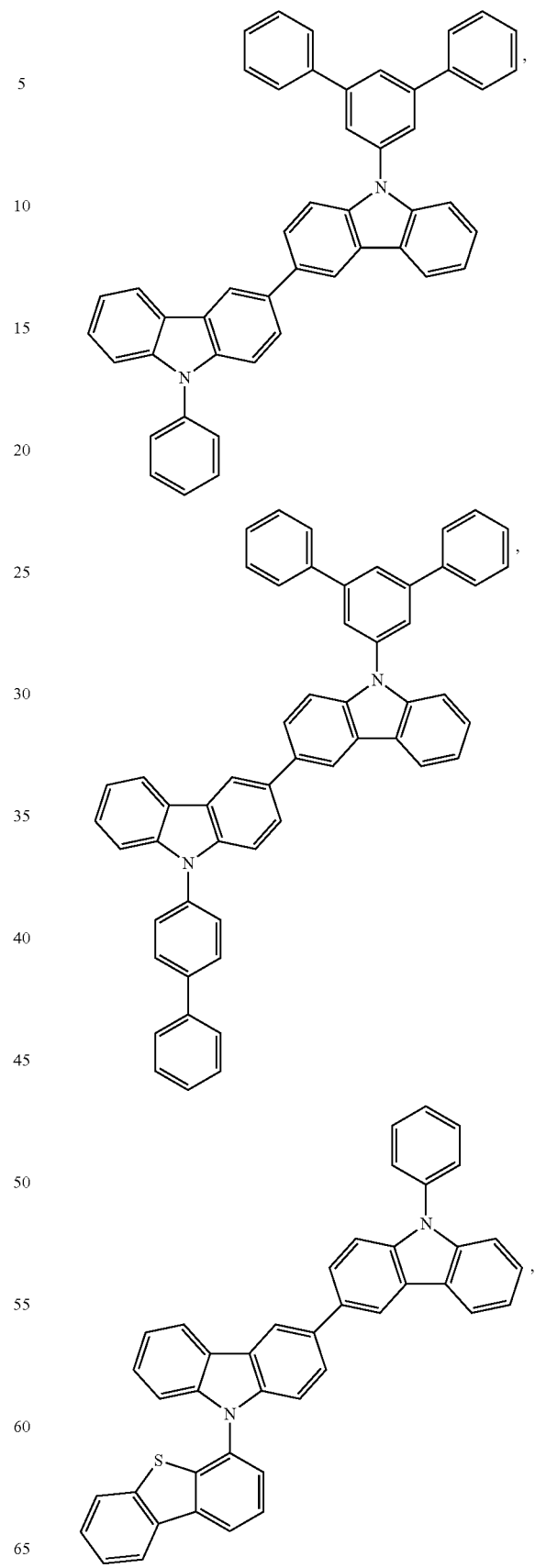

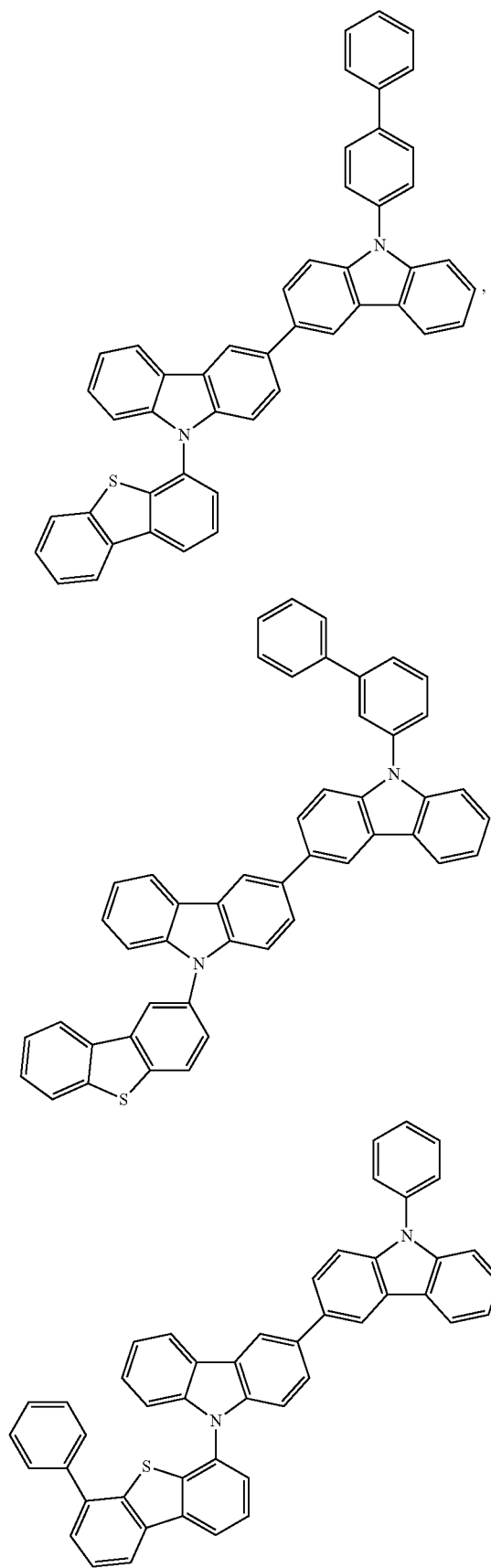
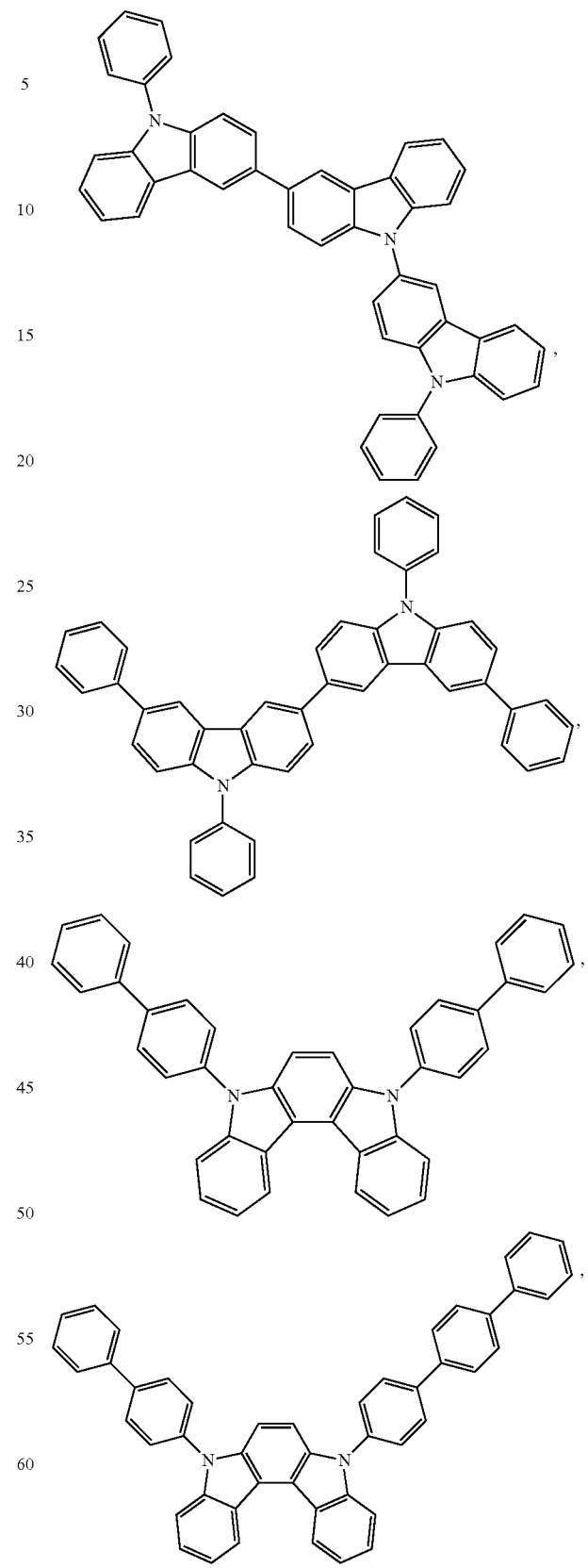

-continued
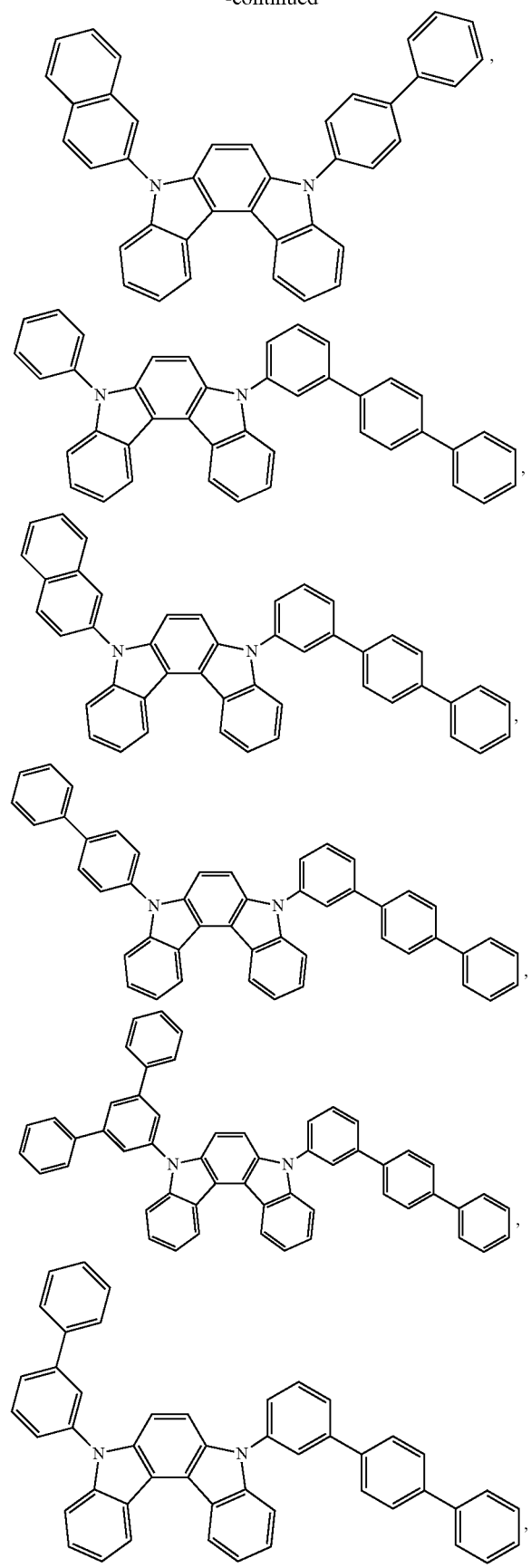
-continued
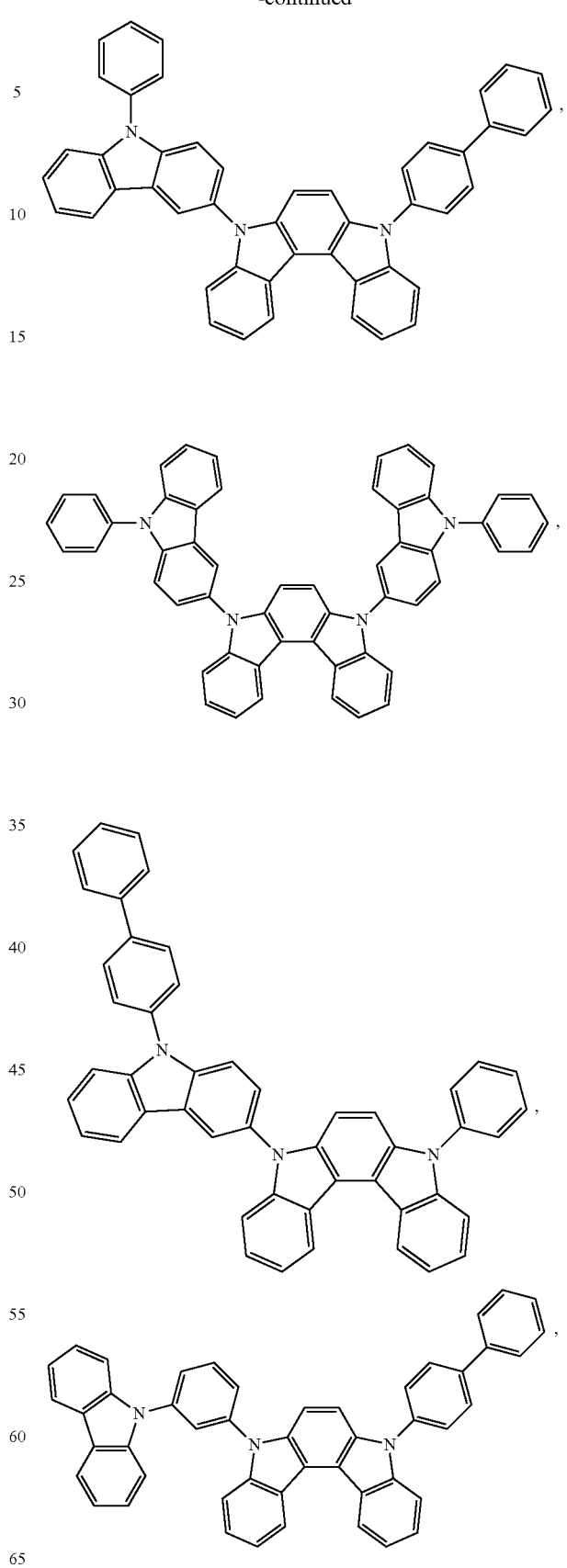

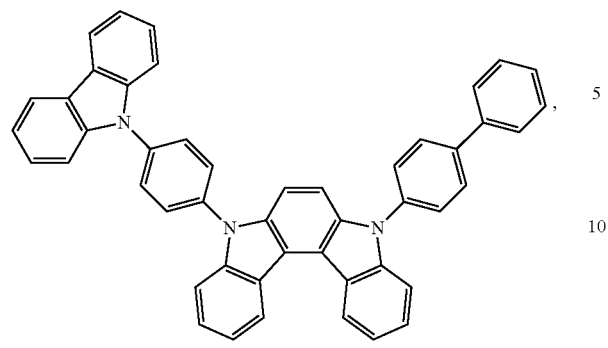
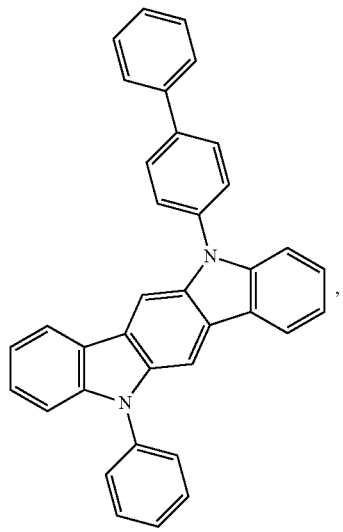
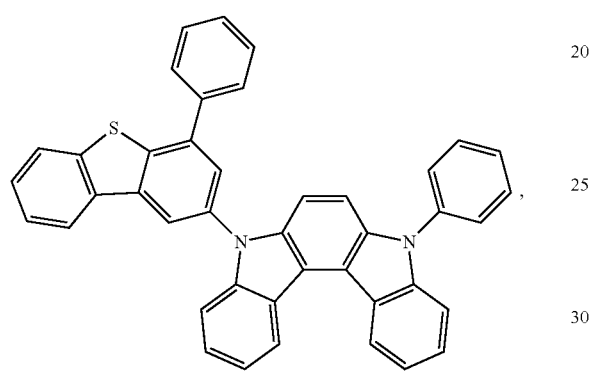
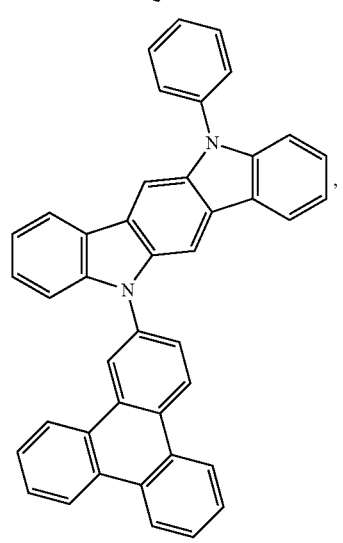
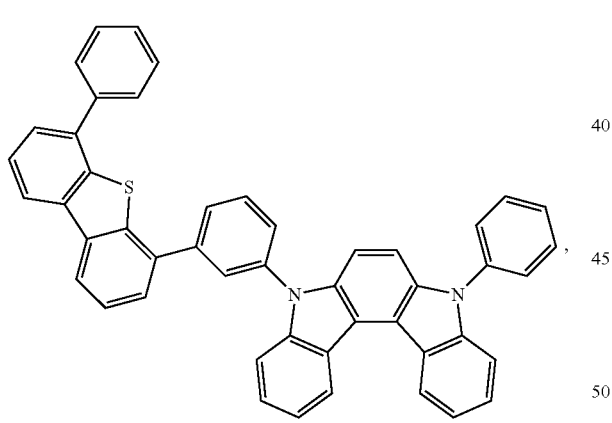
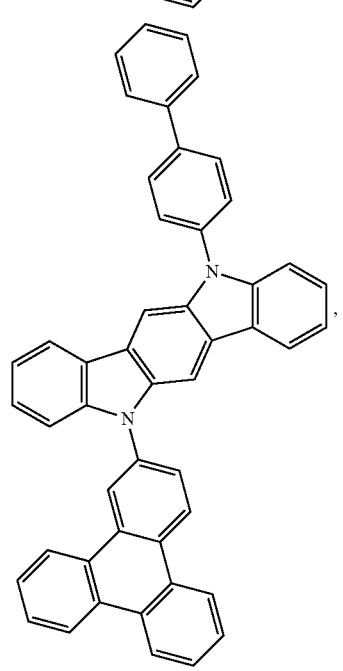
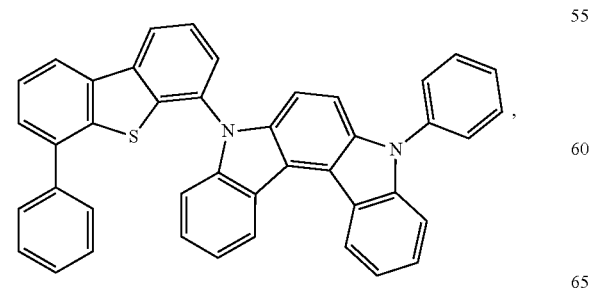

185
-continued
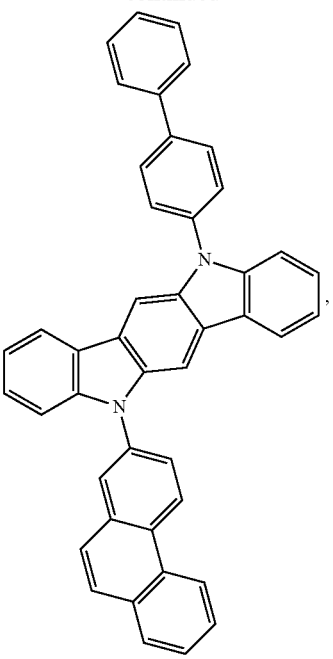
186
-continued
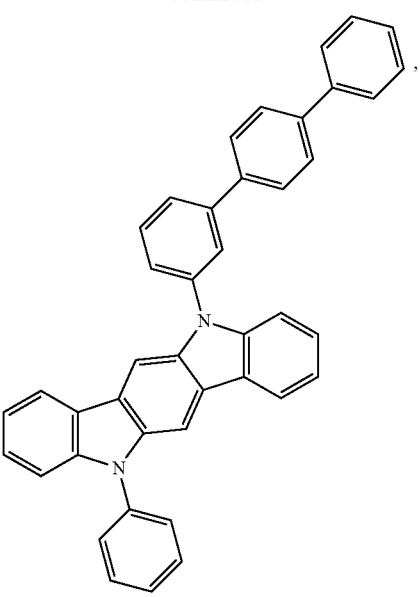
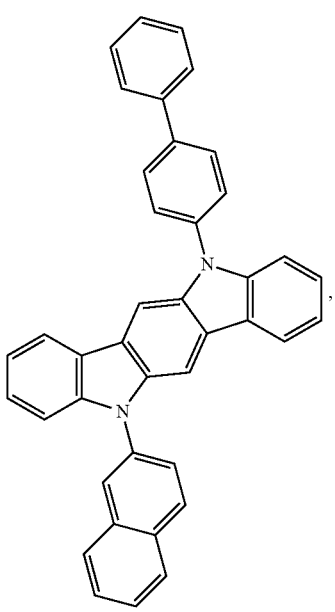

187
-continued
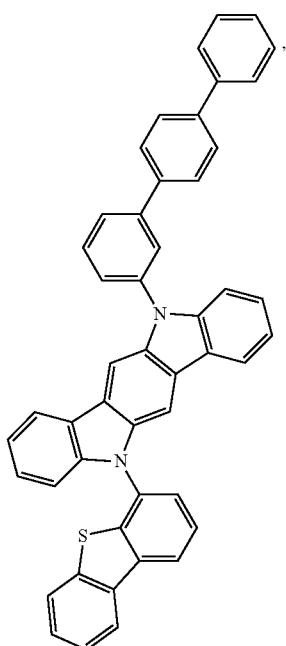
188
-continued
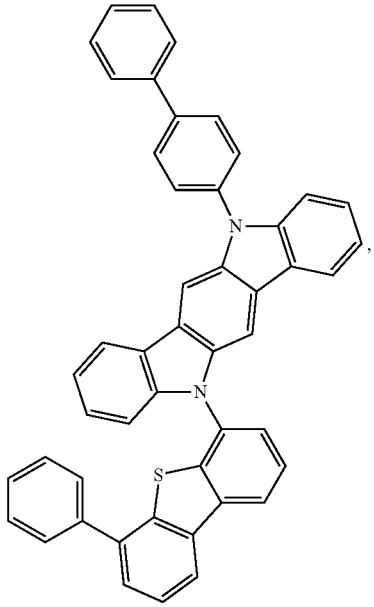
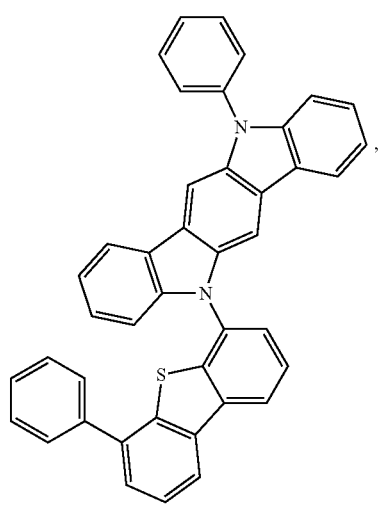
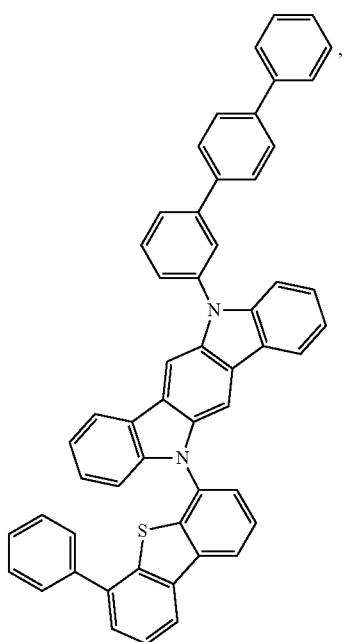

189
-continued
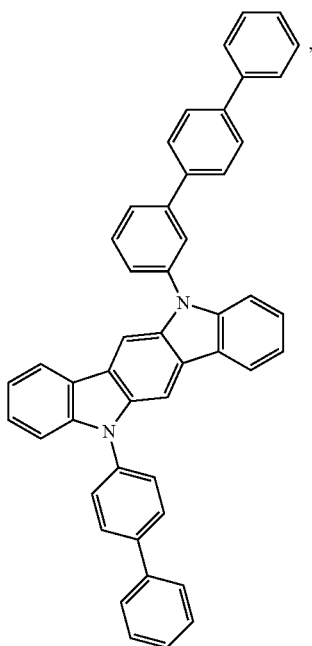
190
-continued
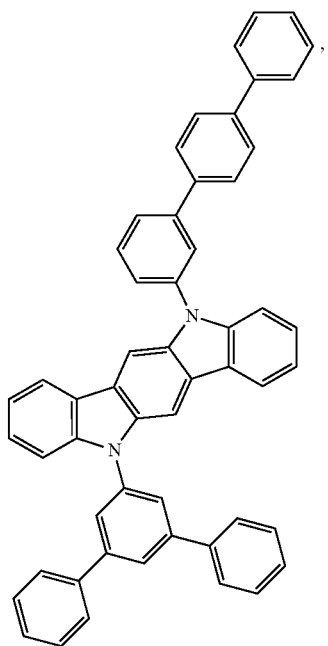
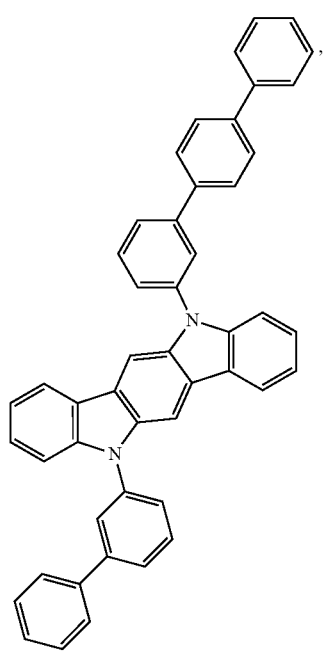

191
-continued
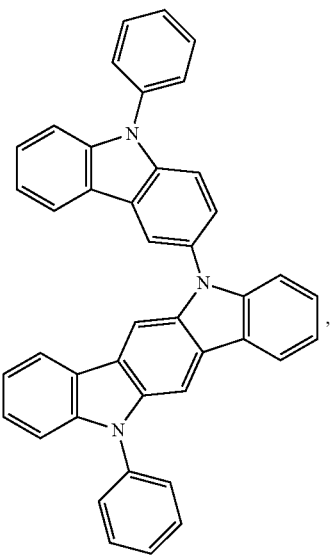
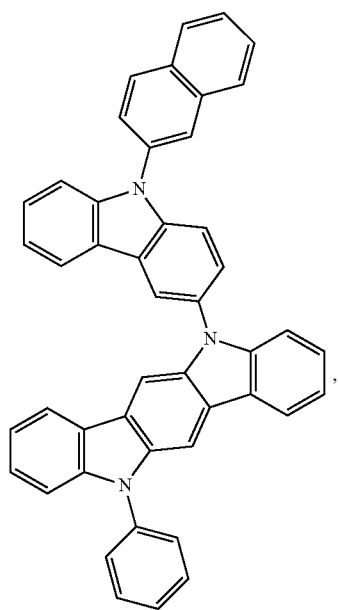
192
-continued
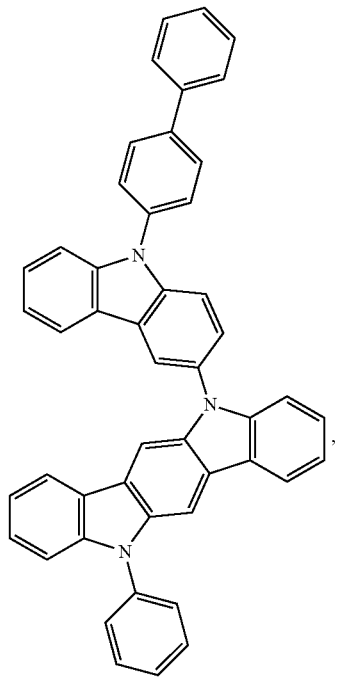
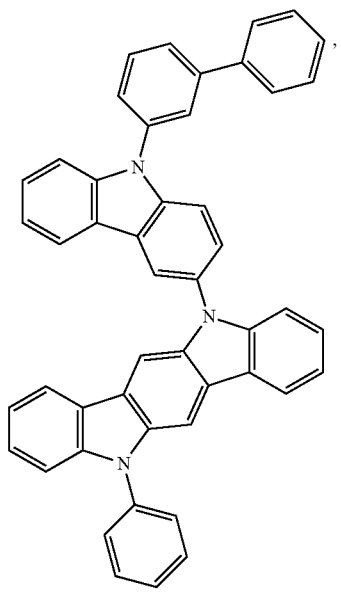

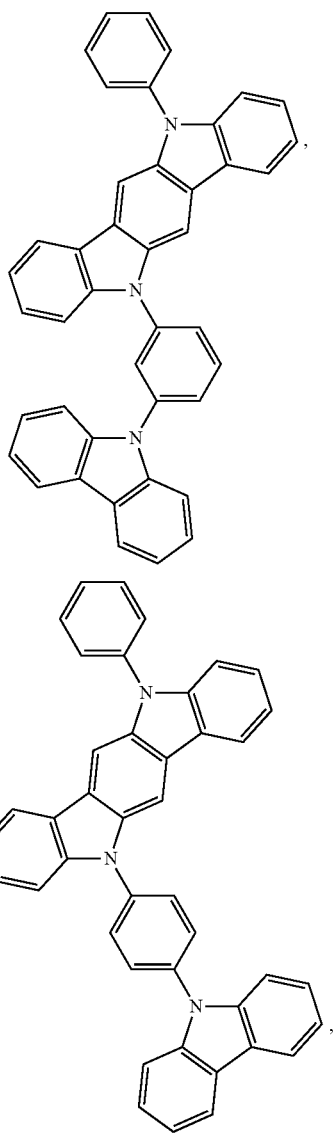
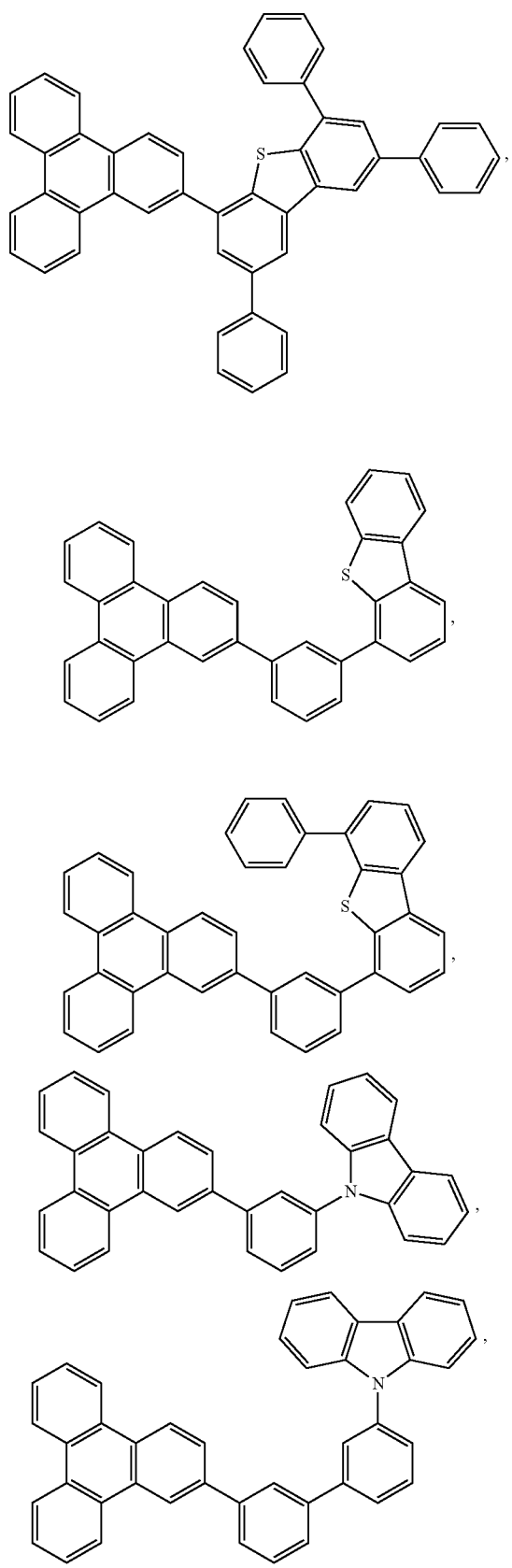

195
-continued
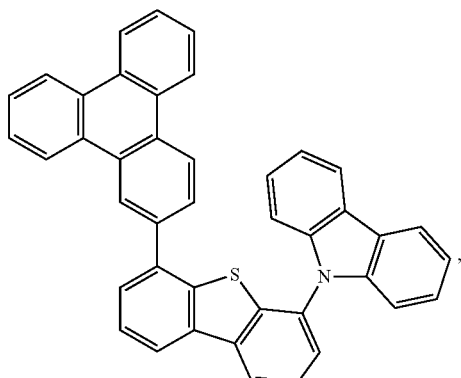
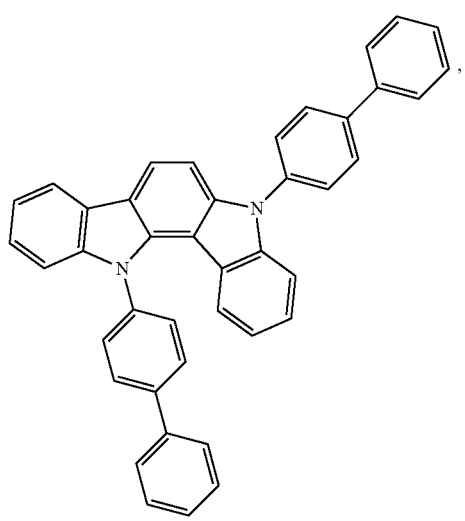
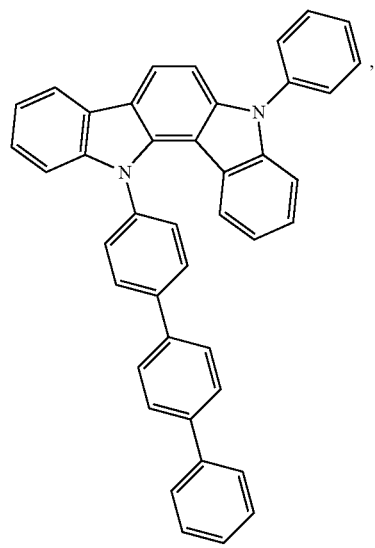
196
-continued
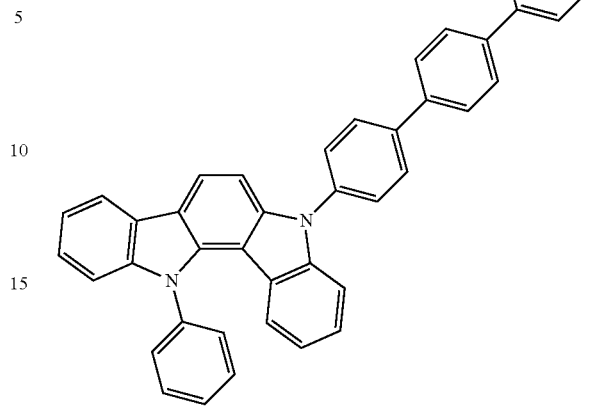
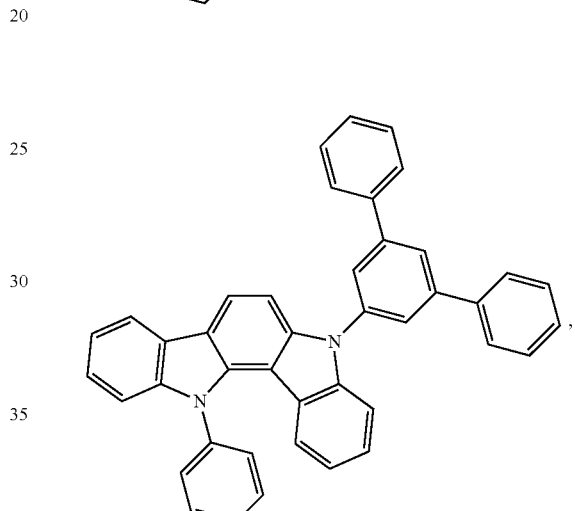
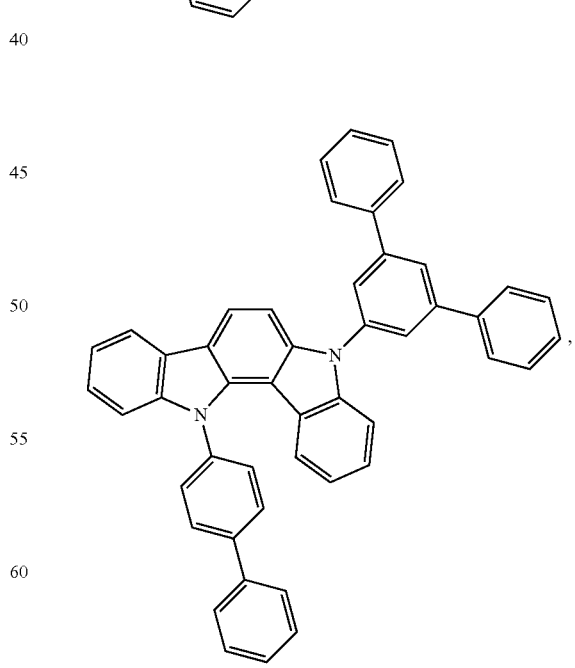

197
-continued
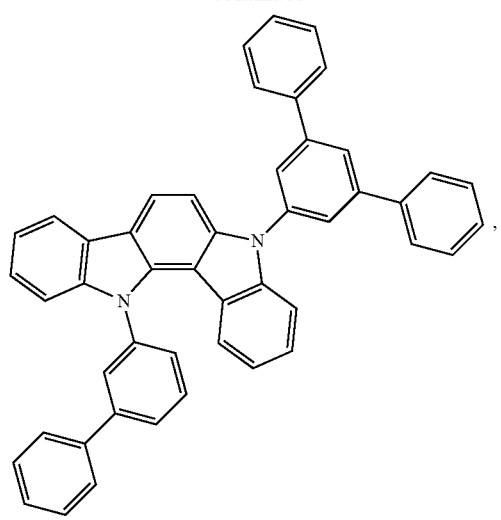
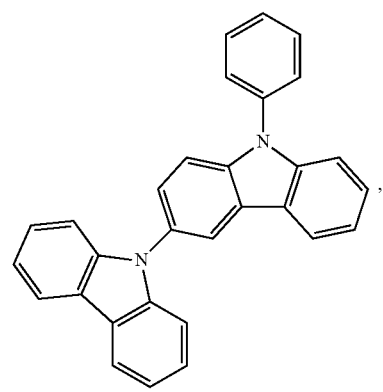
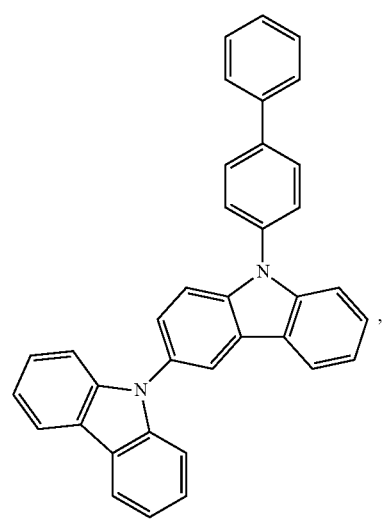
198
-continued
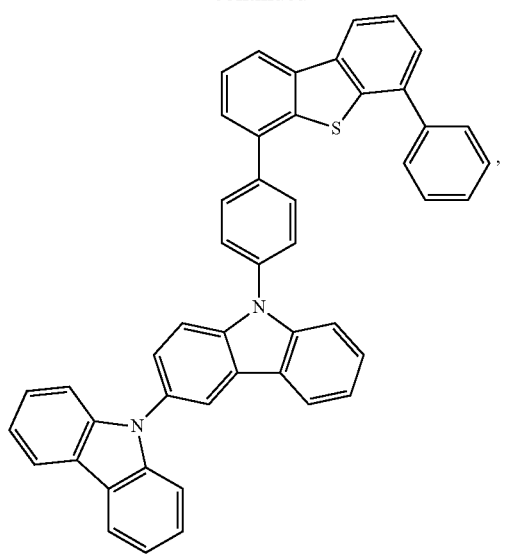
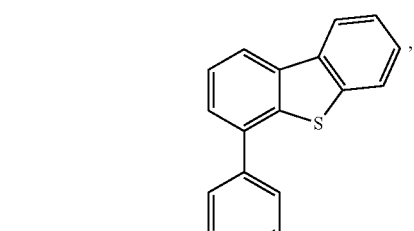
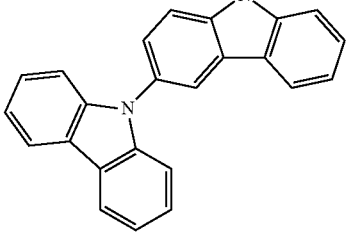
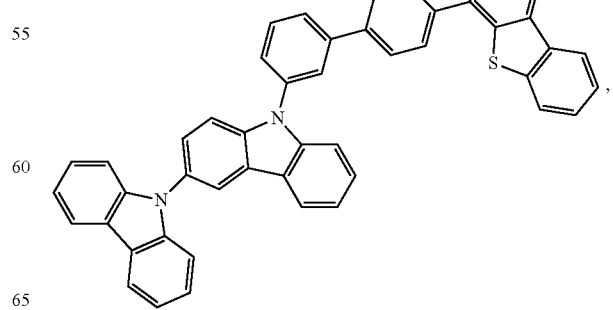

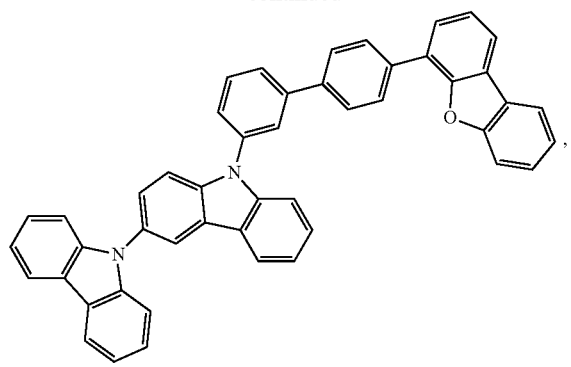
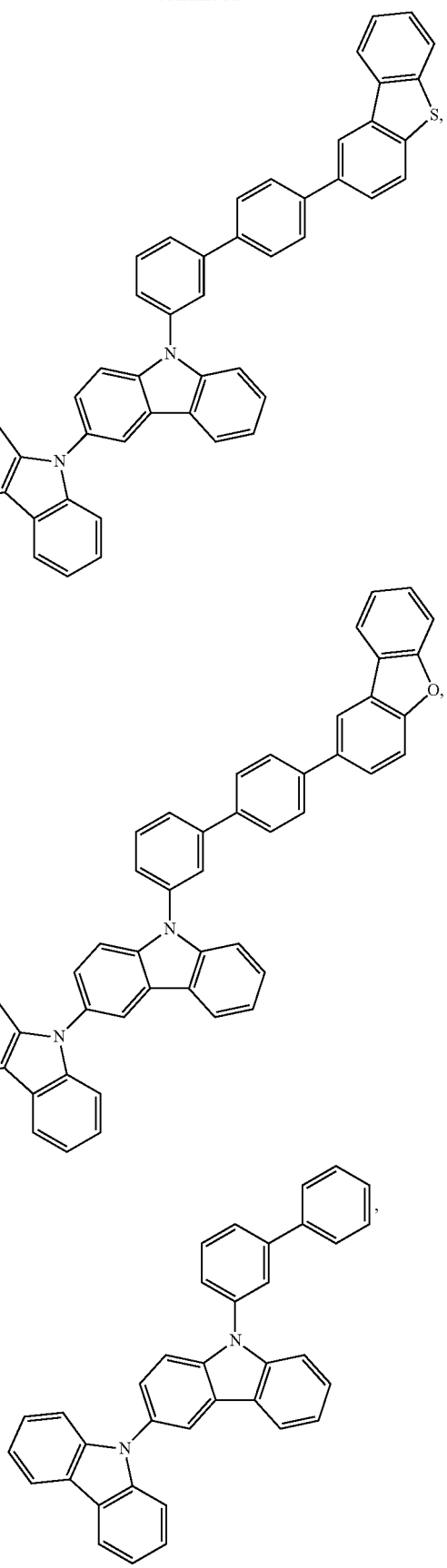

201
-continued
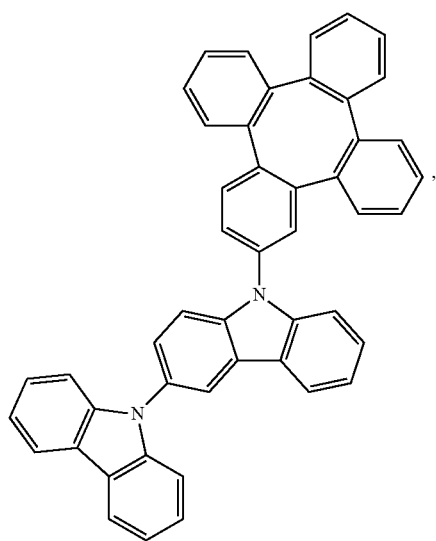
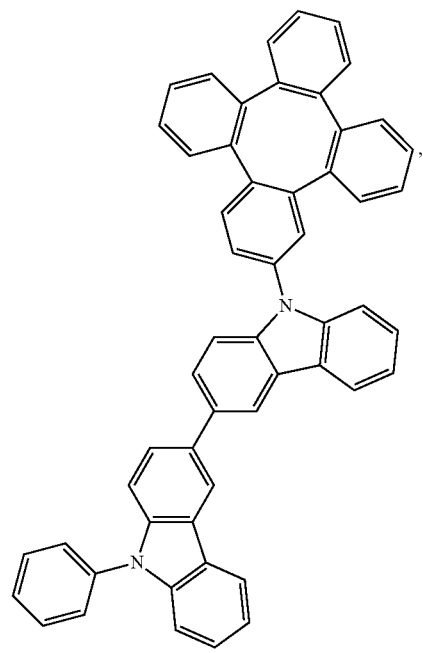
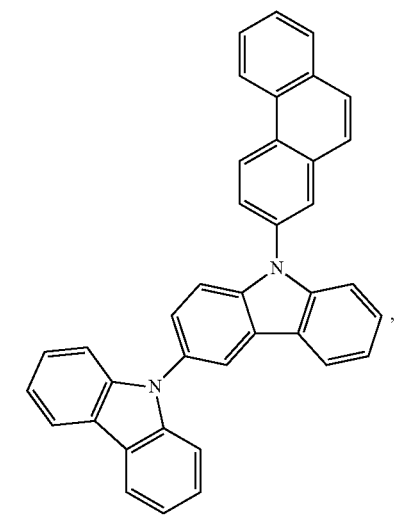
202
-continued
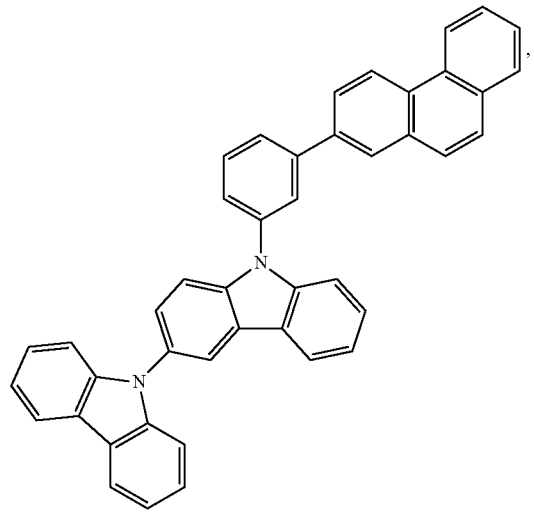
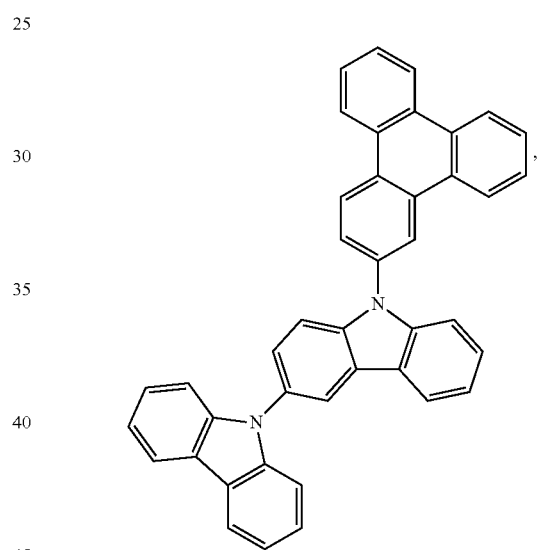
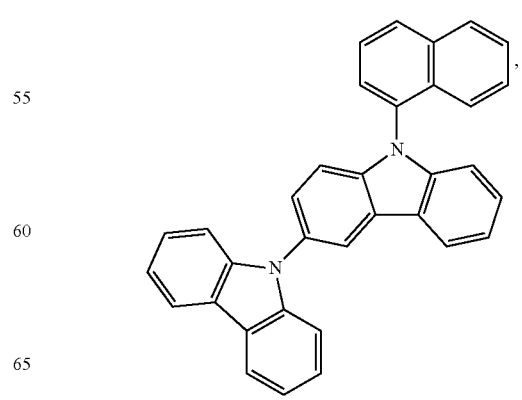

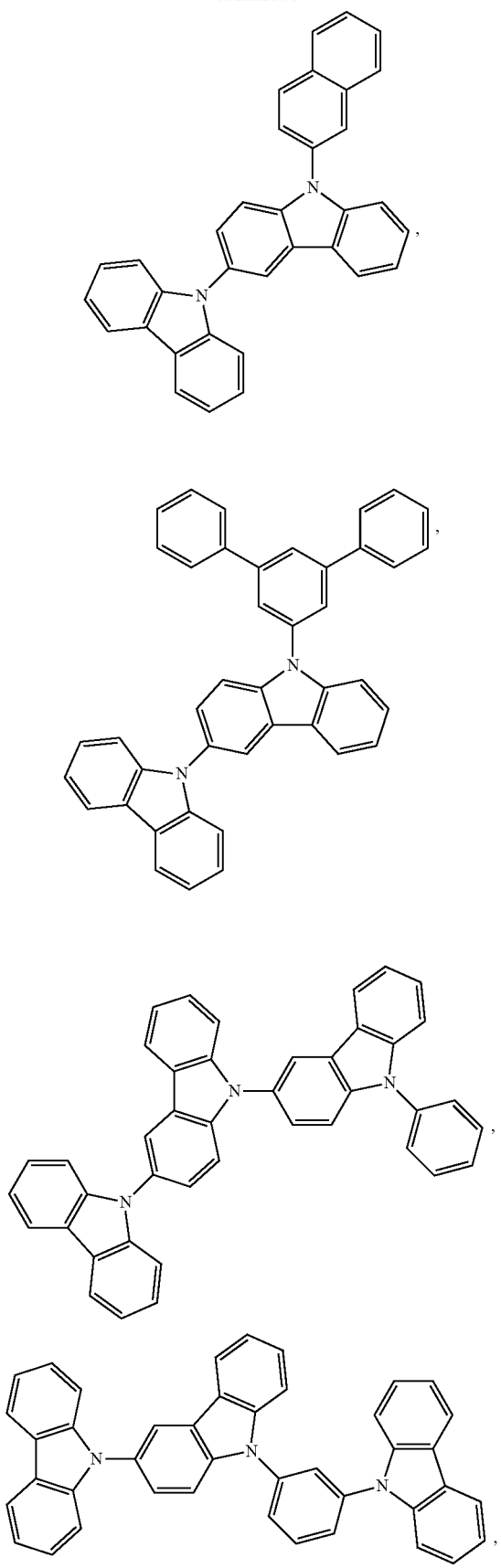

205
-continued
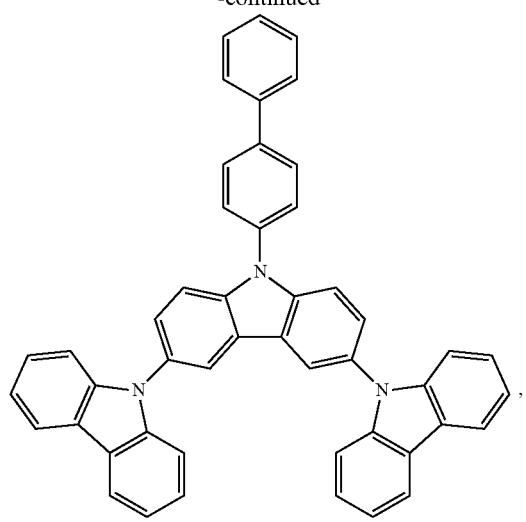
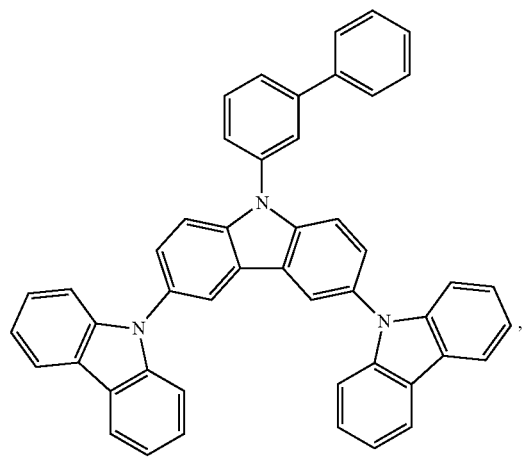
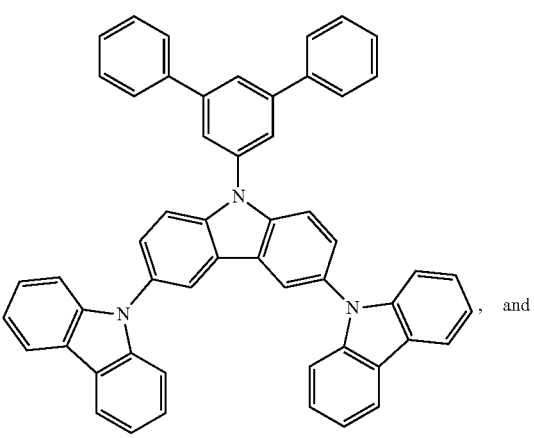
, and
206
-continued
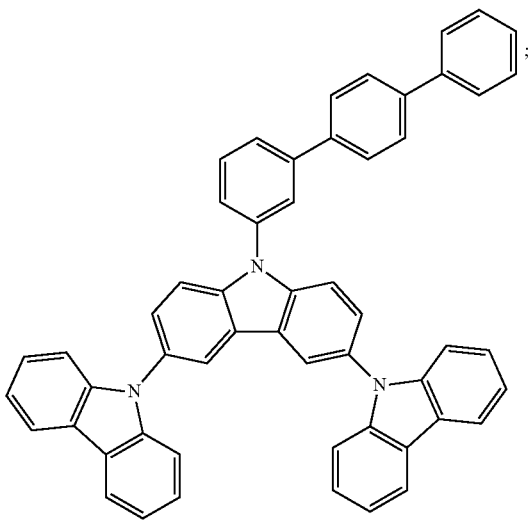
and wherein the second compound can be selected from the group consisting of:
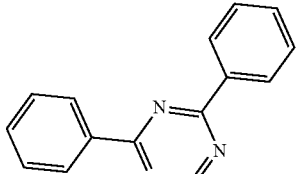

207
-continued
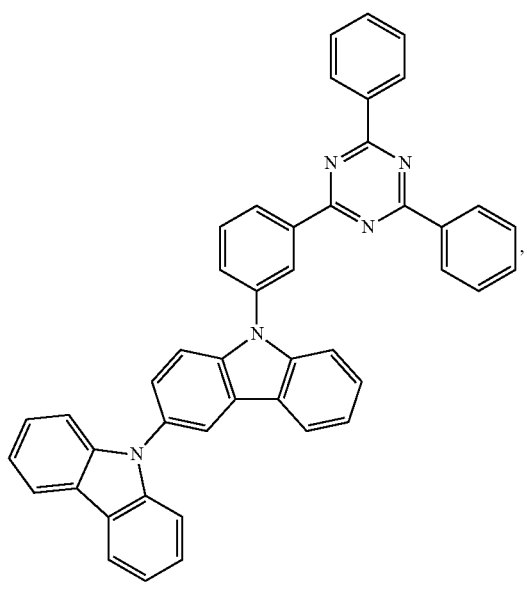
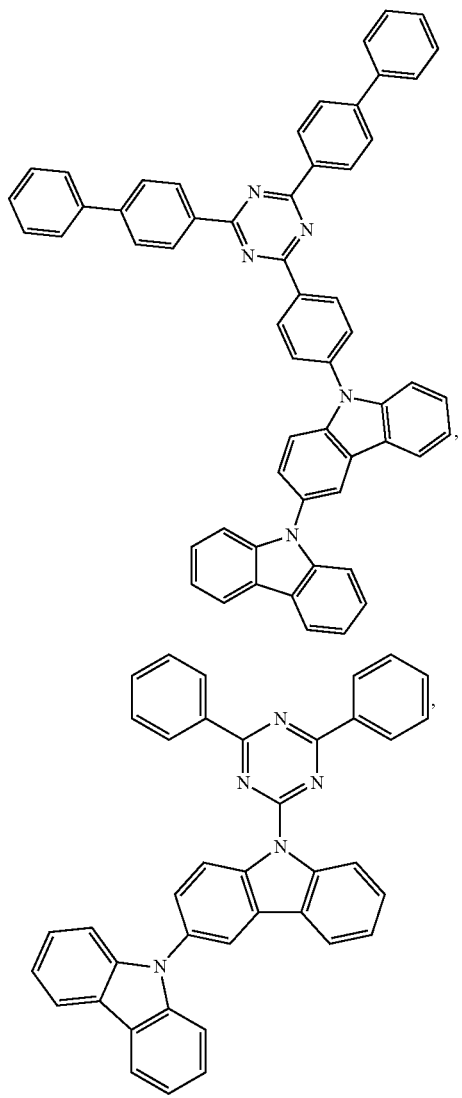
208
-continued
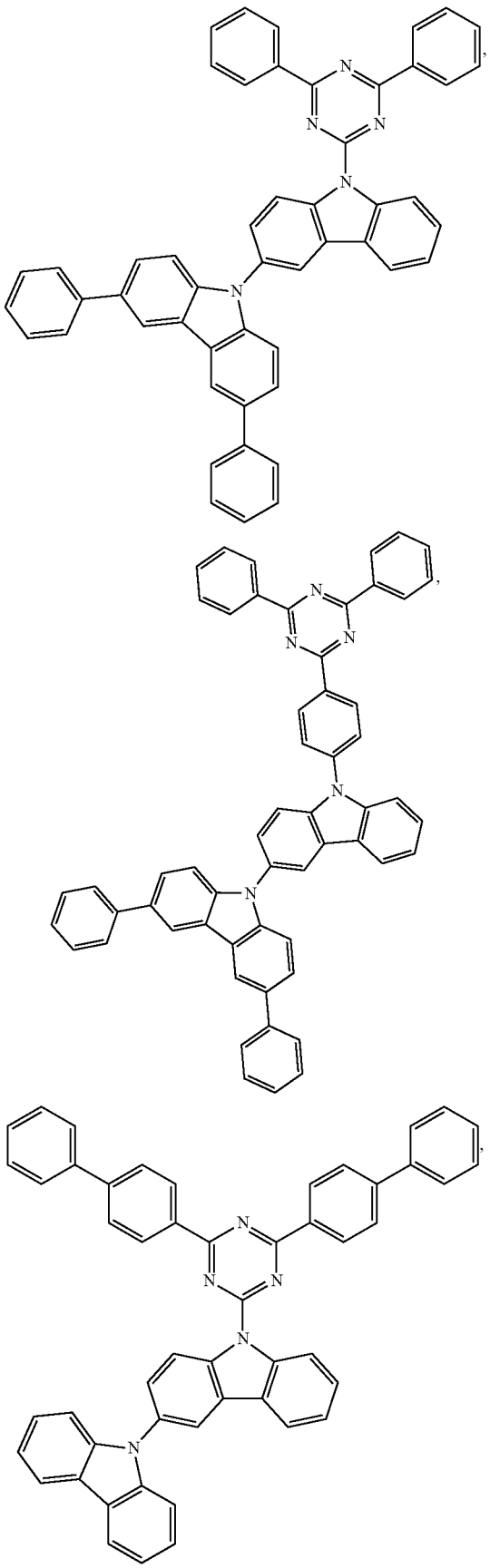

209
-continued
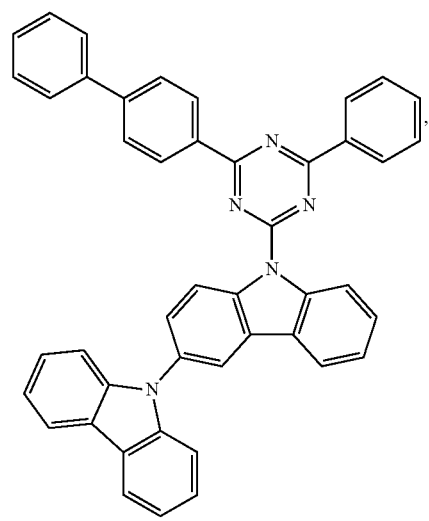
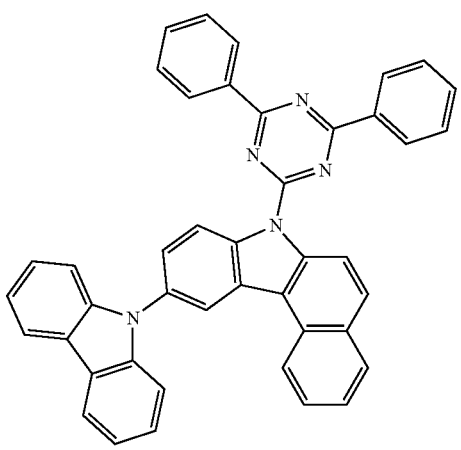
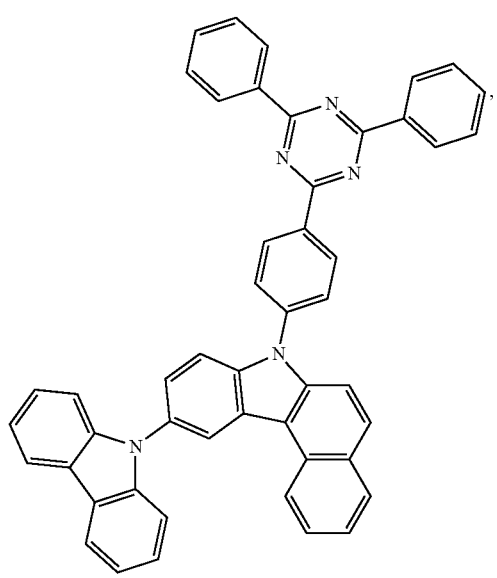
210
-continued
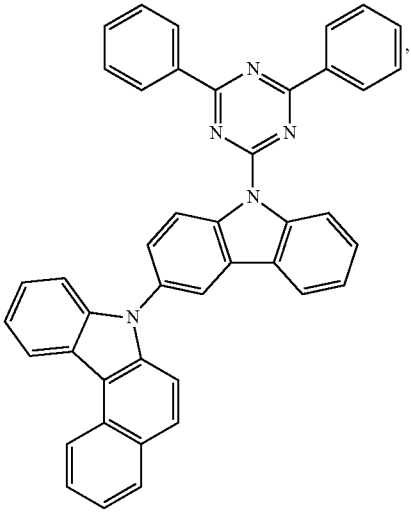
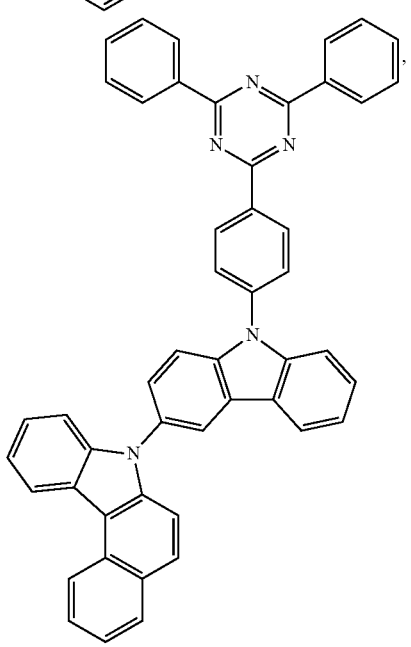
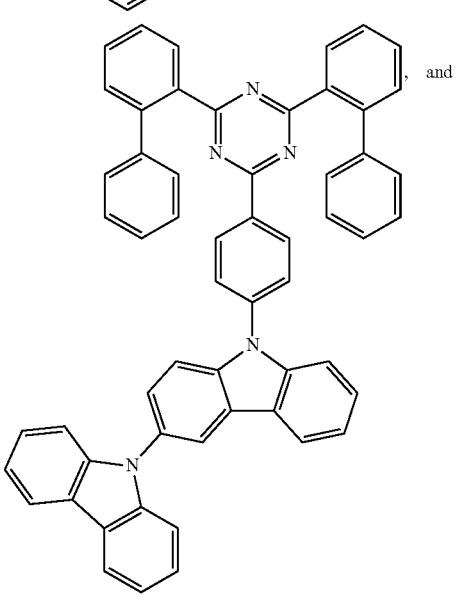, and -continued

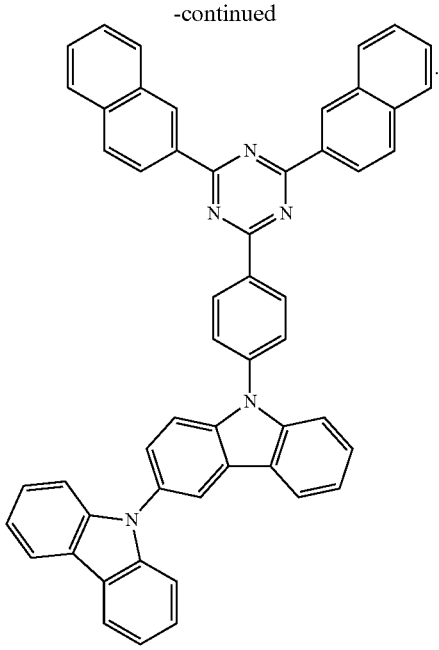

Often, the emissive layer (EML) of OLED devices exhibiting good lifetime and efficiency requires more than two components (e.g. 3 or 4 components). For this purpose, 3 or 4 source materials are required to fabricate such an EML, which is very complicated and costly compared to a standard two-component EML with a single host and an emitter, which requires only two sources. Conventionally, in order to fabricate such EML requiring two or more components, a separate evaporation source for each component is required. Because the relative concentrations of the components of the EML is important for the device performance, the rate of deposition of each component is measured individually during the deposition in order to monitor the relative concentrations. This makes the fabrication process complicated and costly. Thus, it is desirable to premix the materials for the two or more components and evaporate them from a single source in order to reduce the complexity of the fabrication process.

However, the co-evaporation must be stable, i.e. the composition of the evaporated film should remain constant throughout the co-evaporation process. Any composition change may affect the device performance adversely. In order to obtain a stable co-evaporation from a mixture of compounds under vacuum, one would assume that the materials must have the same evaporation temperature under the same condition.

However, this may not be the only parameter one has to consider. When the two compounds are mixed together, they may interact with each other and their evaporation properties may differ from their individual properties. On the other hand, materials with slightly different evaporation temperatures may form a stable co-evaporation mixture. Therefore, it is extremely difficult to achieve a stable co-evaporation mixture. "Evaporation temperature" of a material is measured in a high vacuum deposition tool with a chamber base pressure between $1\times10^6$ Torr to $1\times10^9$ Torr, at a 2 Å/sec deposition rate on a surface positioned at a set distance away from the evaporation source of the material being evaporated, e.g. sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

This disclosure describes a novel composition comprising a mixture of two or more organic compounds that can be used as a stable co-evaporation source in vacuum deposition processes. Many factors other than temperatures can contribute to the evaporation, such as miscibility of different materials, different phase transition. The inventors found that when two or more materials have similar evaporation temperature, and similar mass loss rate or similar vapor pressure, the two or more materials can co-evaporate consistently. Mass loss rate is defined as percentage of mass lost over time (in minutes) and is determined by measuring the time it takes to lose the first 10% of the mass as measured by thermal gravity analysis (TGA) under same experimental condition at a same constant given temperature for each compound after the composition reaches a steady evaporation state. The constant given temperature is one temperature point that is chosen so that the value of mass loss rate is between about 0.05 to 0.50 percent/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

Searching for a high-performance mixture for stable single-source co-evaporation could be a tedious process. A process of searching for a stable mixture would include identifying compounds with similar evaporation temperatures and monitoring the composition of the evaporated mixture. It is often the case that the two materials show slight separation as evaporation goes on. Adjusting the evaporation temperature by changing the chemical structure often, unfortunately, lead to much reduced device performance due to the change in chemical, electrical and/or optical properties. Chemical structure modifications also impact the evaporation temperature much more significantly than needed, resulting in unstable mixtures.

In one embodiment, the stable single-source co-evaporation mixture of two or more components is used for depositing emissive layers by co-evaporation and the single-source co-evaporation mixture can be a mixture of two or more host materials, a mixture of a host material and a dopant material, a mixture of two or more host materials and a dopant material, a mixture of two or more host materials and two or more dopant materials, and a mixture of two or more dopant materials, for example.

In other embodiments, the stable single-source co-evaporation mixture of two or more components is used for depositing charge transport layers or blocking layers by co-evaporation.

According to an embodiment of the present disclosure, a novel two-component composition comprising a mixture of a first compound and a second compound that is a stable co-evaporation mixture is disclosed.

The first compound can have an evaporation temperature T1 of 100 to 400° C. The second compound can have an evaporation temperature T2 of 100 to 400° C. In order to form the inventive composition comprising a mixture of the first compound and the second compound, the absolute value of T1-T2, the difference between T1 and T2, should be less than 20° ° C. Preferably, the absolute value of T1-T2 is less than 10° C. and more preferably less than 5° C.

In order to evaluate the stability of co-evaporation mixtures, the premixed components were thermally co-evaporated at a rate of 2 Å/sec in a vacuum chamber under a pressure between $1\times10^6$ Torr to $1\times10^9$ Torr until depletion, and deposited onto glass substrates. The substrates were replaced continuously after deposition of 400 Å of film without stopping the deposition and cooling the source. The initial amount of the premixed co-evaporation mixture in an evaporation crucible should be enough to grow at least three such substrates. The concentration of each component on each resulting substrate is analyzed. A linear regression was performed by using concentration as y axis, and plate number (1, 2, 3, etc.) as x axis. The obtained slope is referred to herein as a ratio stability. When the ratio stability value is equal to or less than 1, the premixed components are considered to be co-evaporable.

One of ordinary skill in this field should realize that the concentration of each component is expressed as a relative percentage in the mixture. The concentration of each component in the mixture can be measured by a suitable analytical methods such as high pressure liquid chromatography (HPLC) and nuclear magnetic resonance spectroscopy (NMR).

The inventors used HPLC and the percentage was calculated by dividing the integration area under the HPLC trace of each component by the total integration area. HPLC can use different detectors such as UV-vis, photo diode array detector, refractive index detector, fluorescence detector, and light scattering detector. Due to different materials properties, each component in the mixture may respond differently. Therefore, the measured concentration may differ from their real concentration in the mixture. However, the ratio stability value obtained is independent of these variables as long as the experimental condition is kept consistent, for example, all concentrations should be calculated under the exact same HPLC parameters for each component. It is sometimes preferred to select a measurement condition that gives calculated concentration close to the real concentration. However, it is not necessary. It is important to select a detecting condition that accurately detects each component. For example, fluorescence detector should not be used if one of the components does not fluoresce.

In another embodiment of the composition disclosed herein, the first compound has an evaporation temperature T1 of 150 to 350° C. and the second compound has an evaporation temperature T2 of 150 to 350° C. In another embodiment, the first compound has an evaporation temperatrure T1 of 200 to 350° C. and the second compound has an evaporation temperature T2 of 200 to 350° C.

Preferably, the ratio stability is equal to or less than 0.6. More preferably, the ratio stability is equal to or less than 0.3.

In one embodiment of the composition, the first compound has a vapor pressure of P1 at T1 at 1 atm, the second compound has vapor pressure of P2 at T2 at 1 atm, and the ratio of P1/P2 is within the range of 0.90 to 1.10.

In any of the embodiments of the composition, the first compound can have a first mass loss rate and the second compound can have a second mass loss rate, wherein the ratio between the first mass loss rate and the second mass loss rate is within the range of 0.90 to 1.10. In some embodiments of the composition, the ratio between the first mass loss rate and the second mass loss rate is within the range of 0.95 to 1.05. In some embodiments of the composition, the ratio between the first mass loss rate and the second mass loss rate is within the range of 0.97 to 1.03.

In any of the embodiments of the composition, the first compound and the second compound each has a purity in excess of 99% as determined by high pressure liquid chromatography.

In some embodiment of the composition comprising the first and second compounds as defined above, the composition can further comprise a third compound. The third compound can have a different chemical structure than the first and second compounds, where the third compound has an evaporation temperature T3 of 150 to 350° C., and the absolute value of T1-T3 is less than 20° C. In some embodiments, the third compound has a different chemical structure than the first and second compounds, where the third compound has a third mass loss rate and the ratio between the first mass loss rate and third mass loss rate is within the range of 0.90 to 1.10.

An organic light emitting device (OLED) is also disclosed, where the OLED comprises: an anode; a cathode; and an organic layer, disposed between the anode and the cathode, comprising a composition comprising a first compound, where the first compound is selected from the group consisting of

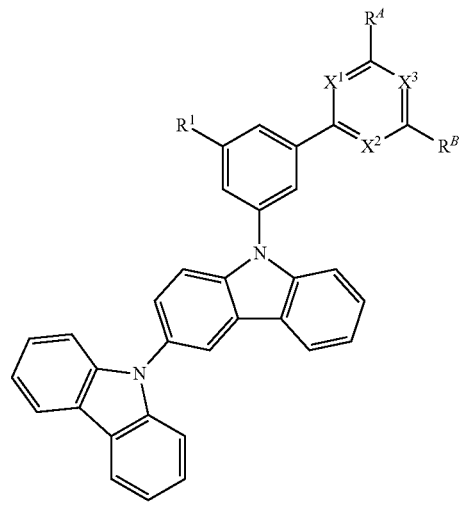

Formula I and

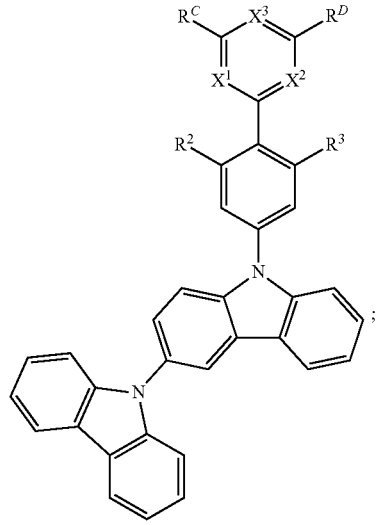

Formula II where $X^1$, $X^2$, and $X^3$ are each independently CH or N; at least two of $X^1$, $X^2$, and $X^3$ are N; $R^A$, $R^B$, $R^C$, and $R^D$ each comprise at least one aromatic ring; each $R^1$, $R^2$ and $R^3$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof; in Formula I, $R^1$ is aryl or heteroaryl, or at least one of $R^A$ and $R^B$ is independently a substituent selected from the group consisting of an alkylated aromatic ring, and two or more aromatic rings; and in Formula II, at least one of $R^C$ and $R^D$ is independently a substituent selected from the group consisting of an alkylated aromatic ring, and two or more aromatic rings, and $R^C$ and $R^D$ are different.

In some embodiments of the OLED, the organic layer is an emissive layer and the composition is a host material.

In some embodiments of the OLED, the organic layer further comprises a phosphorescent emissive dopant; wherein the emissive dopant is a transition metal complex having at least one ligand or part of the ligand, if the ligand is more than bidentate, selected from the group consisting of:

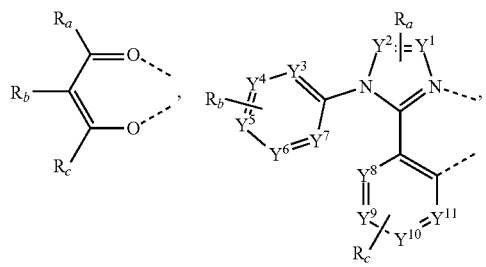

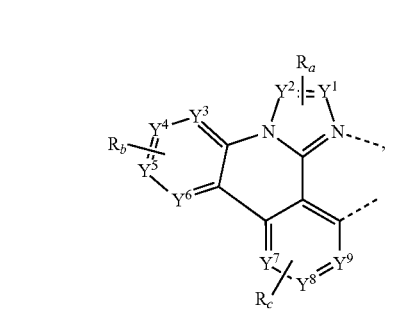

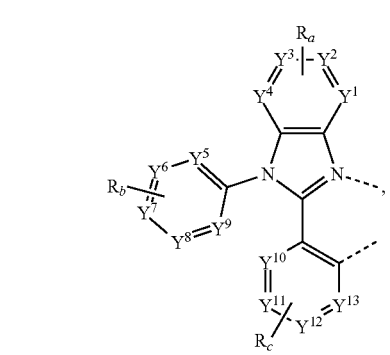

-continued

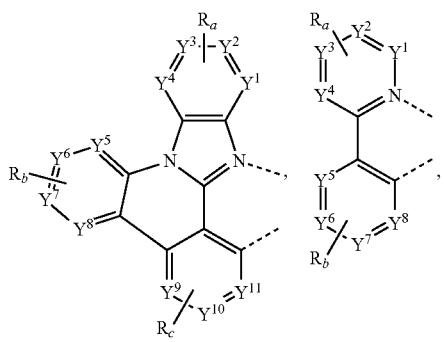

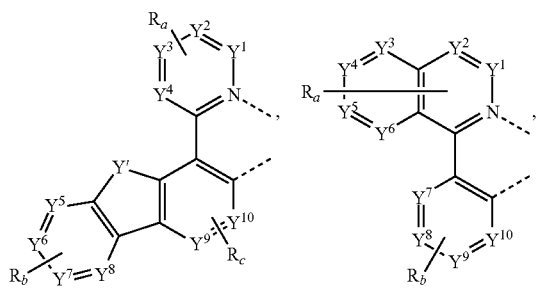

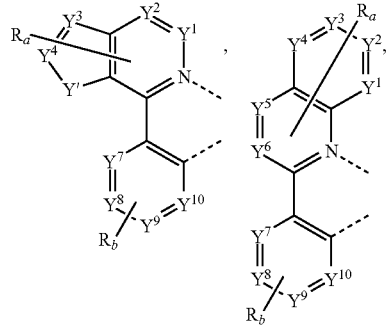

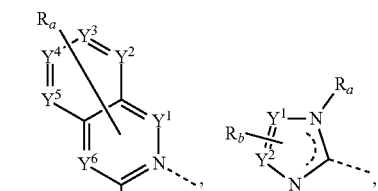

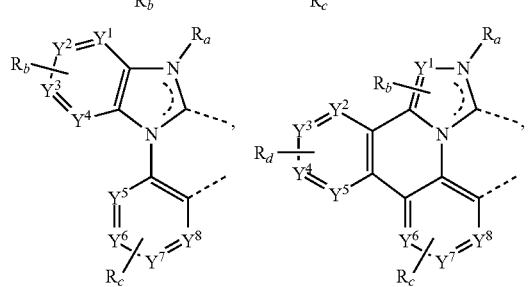

-continued

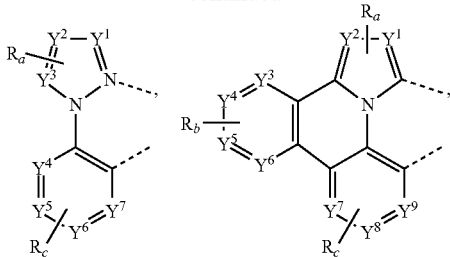

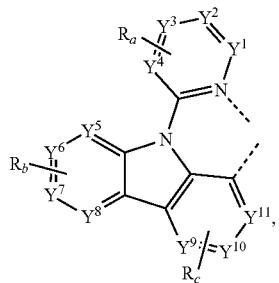

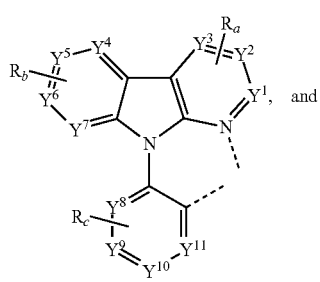

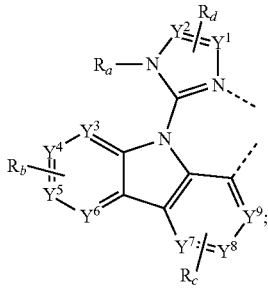

wherein, each $Y^1$ to $Y^{13}$ is independently selected from the group consisting of carbon and nitrogen; Y' is selected from the group consisting of B $R_e$, N $R_e$, P $R_e$, O, S, Se, C=O, S=O, SO$_2$, CR$_e$R$_f$, SiR$_e$R$_f$, and GeR$_e$R$_f$; R$_e$ and R$_f$ are optionally fused or joined to form a ring; each R$_a$, R$_b$, R$_c$, and R$_d$ independently represents from mono substitution to the maximum allowable number of substitutions, or no substitution; each R$_a$, R$_b$, R$_c$, R$_d$, R$_e$ and R$_f$ is independently hydrogen or a substituent selected from the group consisting of the general substituents defined above; and any two adjacent substituents of R$_a$, R$_b$, R$_c$, and R$_d$ can be fused or joined to form a ring or form a multidentate ligand.

In some embodiments of the OLED, the organic layer is a blocking layer and the composition is a blocking material in the organic layer.

In some embodiments of the OLED, the organic layer is a transporting layer and the composition is a transporting material in the organic layer.

A consumer product comprising the OLED defined above is also disclosed.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

The emitter dopants can be phosphorescent dopants and/or fluorescent dopants.

In some embodiments, the composition of the present disclosure is neutrally charged.

According to another aspect, a formulation comprising the compound described herein is also disclosed.

The OLED disclosed herein can be incorporated into one or more of a consumer product, an electronic component module, and a lighting panel.

An emissive region in an OLED incorporating the inventive composition is also disclosed. The emissive region comprises a compostion comprising a first compound, wherein the first compound is selected from the group consisting of Formula I

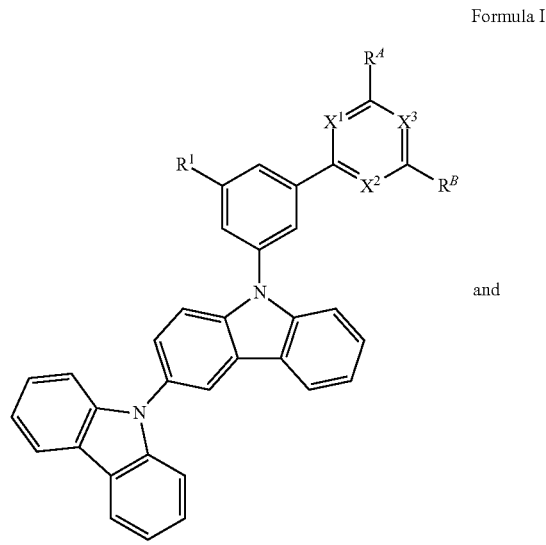

and

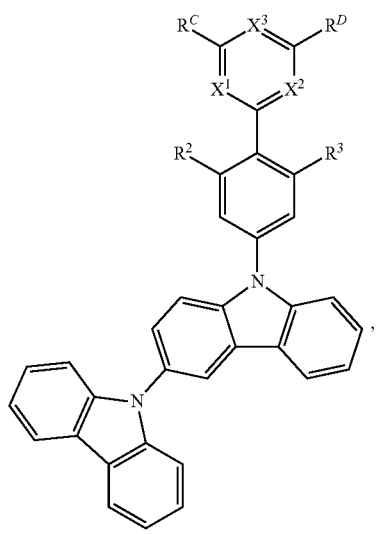

Formula II wherein,

X¹, X², and X³ are each independently CH or N; at least two of X¹, X², and X³ are N; $R^A$, $R^B$, $R^C$, and $R^D$ each independently selected from the group consisting of aryl, heteroaryl, substituted aryl, substituted heteroaryl, and combination thereof; each $R^1$, $R^2$ and $R^3$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof;

wherein, in Formula I, $R^1$ is aryl or heteroaryl, or at least one of $R^A$ and $R^B$ comprises two or more aromatic rings; and in Formula II, at least one of $R^C$ and $R^D$ is independently a substituent selected from the group consisting of alkylated aromatic ring, two or more aromatic rings, and $R^C$ and $R^D$ are different.

In some embodiments of the emissive region, the composition is a host.

In some embodiments of the emissive region, the emissive region further comprises a phosphorescent emissive dopant; wherein the emissive dopant is a transition metal complex having at least one ligand or part of the ligand if the ligand is more than bidentate selected from the group consisting of:

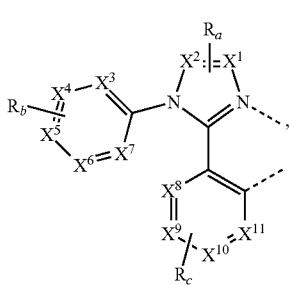

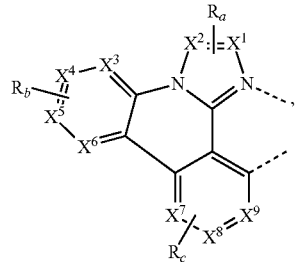

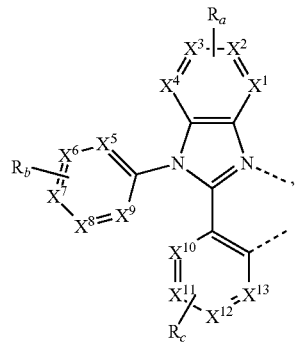

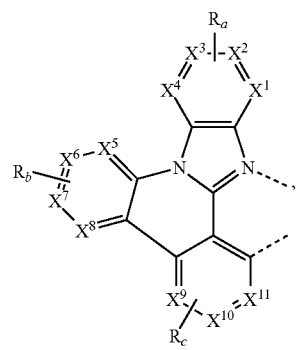 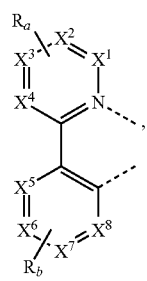

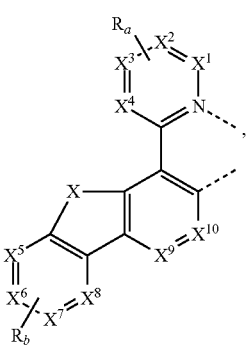 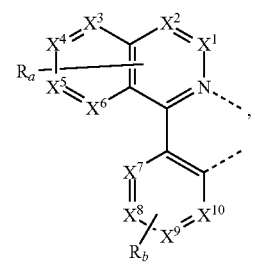

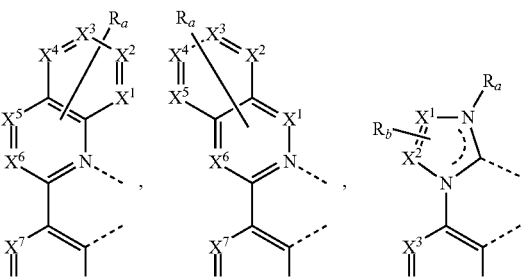

-continued

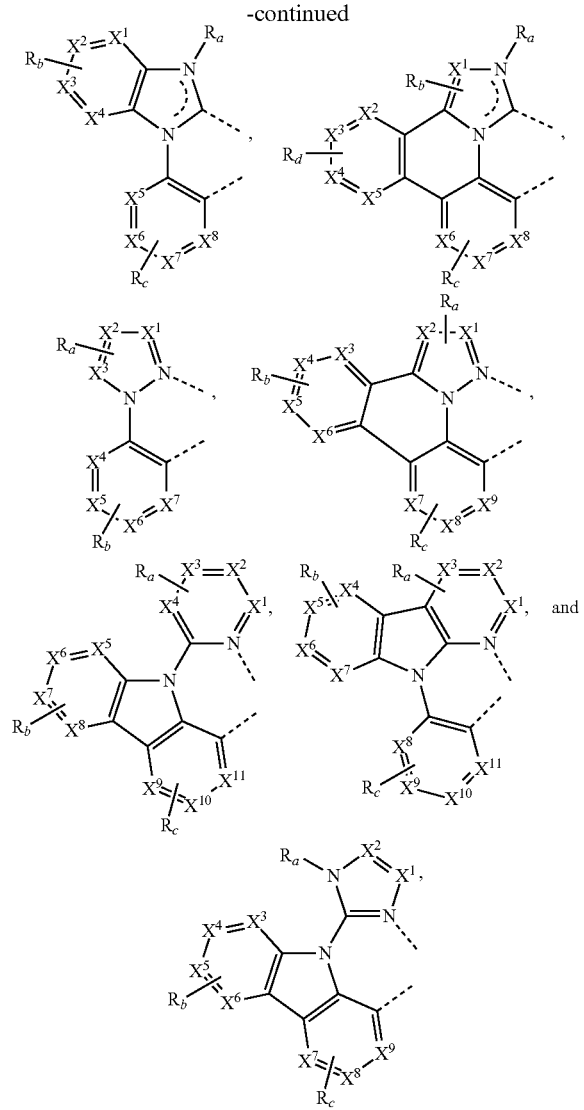

where, each $X^1$ to $X^{13}$ are independently selected from the group consisting of carbon and nitrogen; X is selected from the group consisting of BR', NR', PR', O, S, Se, C=O, S=O, SO$_2$, CR'R", SiR'R", and GeR'R"; R' and R" are optionally fused or joined to form a ring; each $R_a$, $R_b$, $R_c$, and $R_d$ may represent from mono substitution to the possible maximum number of substitution, or no substitution; R', R", $R_a$, $R_b$, $R_c$, and $R_d$ are each independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof; and any two substituents of $R_a$, $R_b$, $R_e$, and $R_a$ are optionally fused or joined to form a ring or form a multidentate ligand.

In yet another aspect of the present disclosure, a formulation that comprises the novel compound disclosed herein is described. The formulation can include one or more components selected from the group consisting of a solvent, a host, a hole injection material, hole transport material, electron blocking material, hole blocking material, and an electron transport material, disclosed herein.

The present disclosure encompasses any chemical structure comprising the novel compound of the present disclosure, or a monovalent or polyvalent variant thereof. In other words, the inventive compound, or a monovalent or polyvalent variant thereof, can be a part of a larger chemical structure. Such chemical structure can be selected from the group consisting of a monomer, a polymer, a macromolecule, and a supramolecule (also known as supermolecule). As used herein, a "monovalent variant of a compound" refers to a moiety that is identical to the compound except that one hydrogen has been removed and replaced with a bond to the rest of the chemical structure. As used herein, a "polyvalent variant of a compound" refers to a moiety that is identical to the compound except that more than one hydrogen has been removed and replaced with a bond or bonds to the rest of the chemical structure. In the instance of a supramolecule, the inventive compound is can also be incorporated into the supramolecule complex without covalent bonds.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

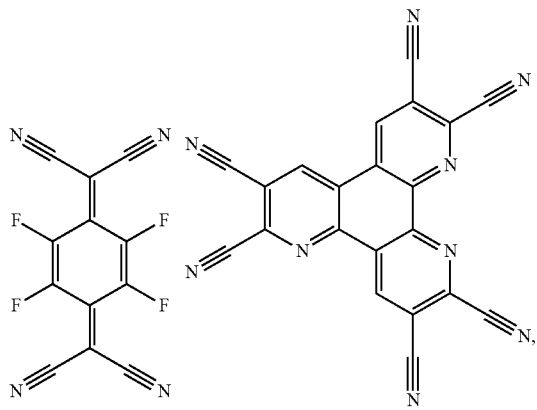

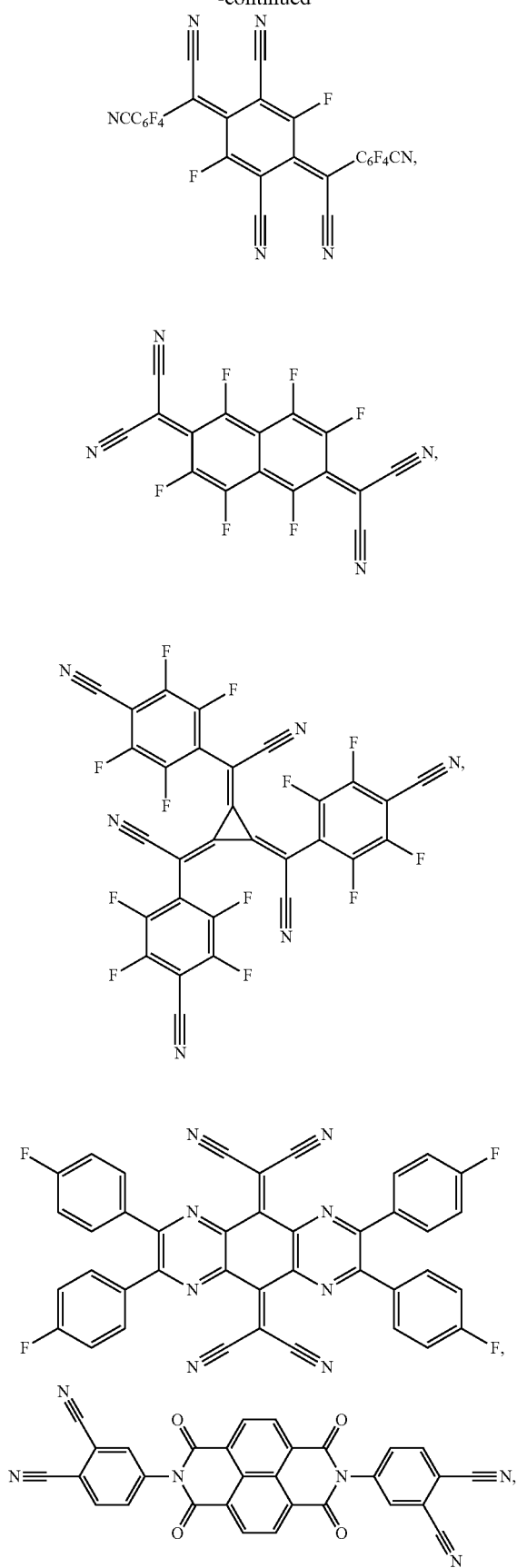

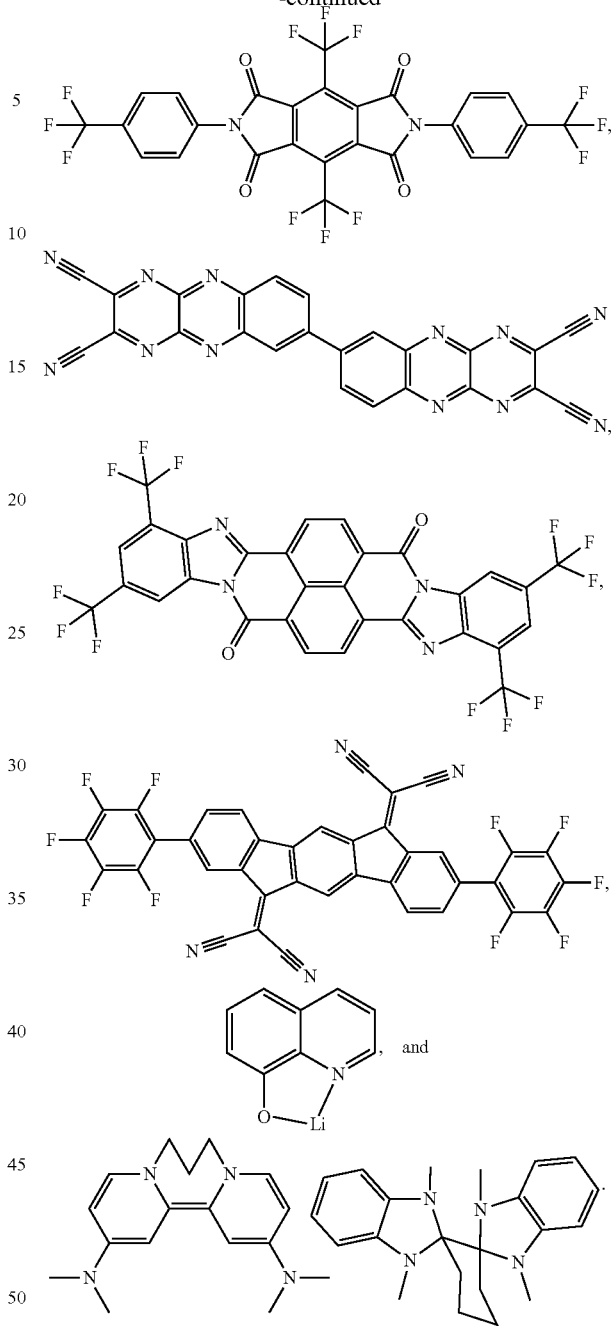

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as MoOx; a p-type semiconducting organic compound, such as 1,4,5, 8,9,12-Hexaazatriphenylenehexacarbonitrile; a metal complex, and a cross-linkable compounds.

Examples of aromatic amine derivatives used in HIL or HTL include, but are not limited to the following general structures:

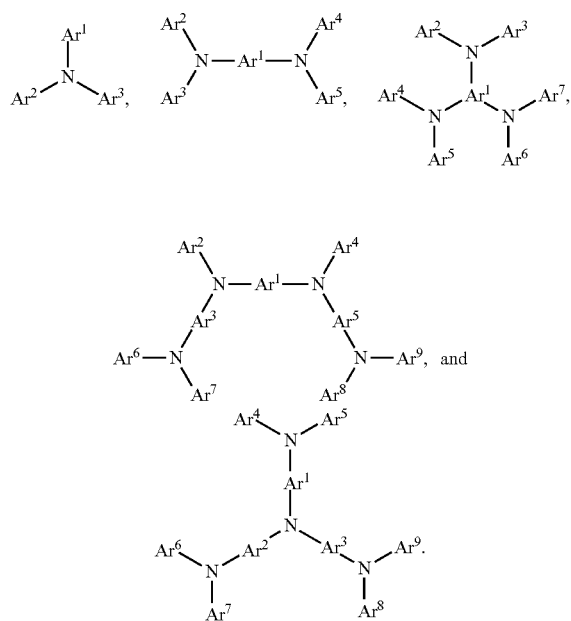

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

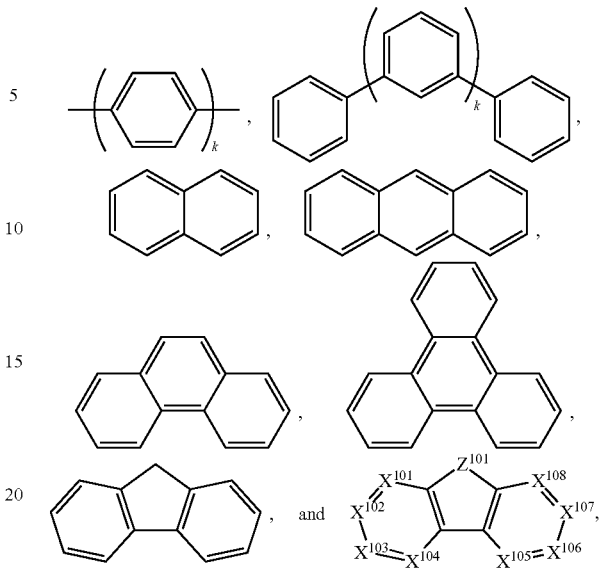

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

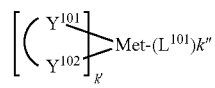

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642,

| 227 | 228 |
|---|---|
| US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, | WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018, |
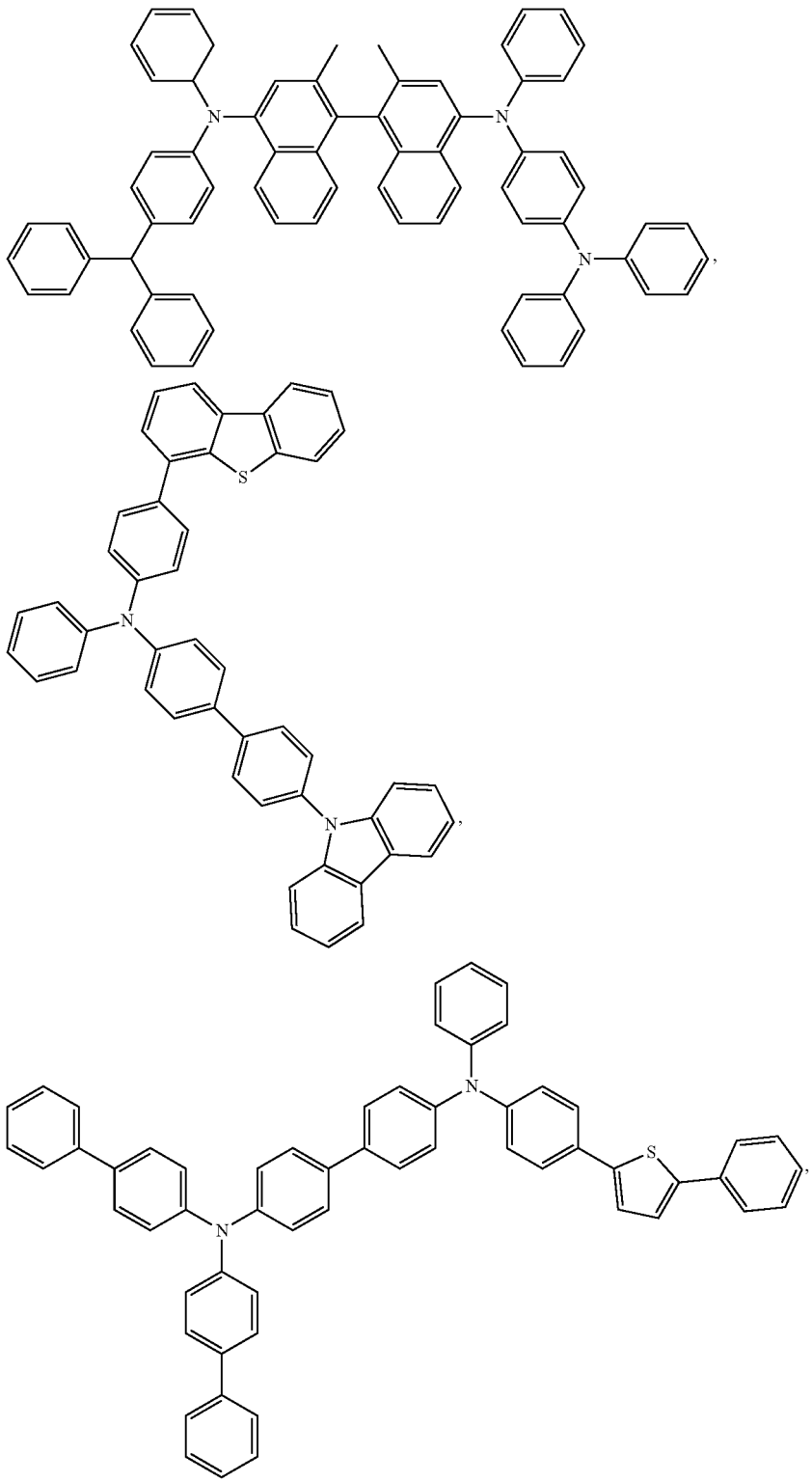

-continued
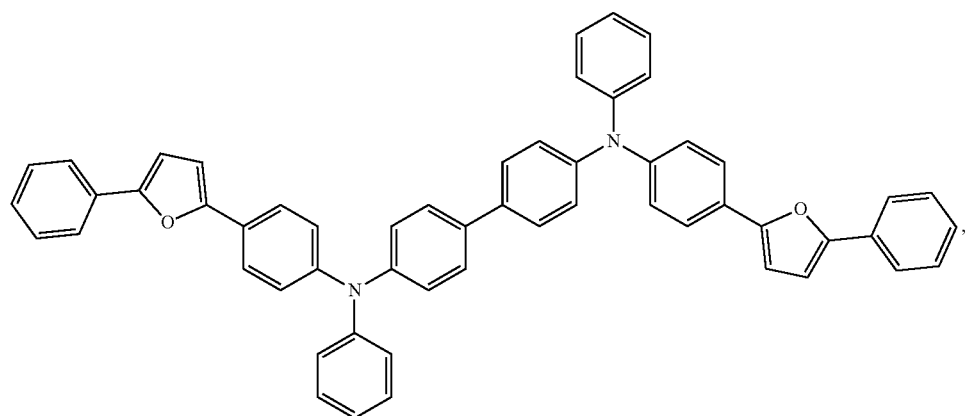 [SMILES: c1ccc(-c2ccc(-c3ccc(N(c4ccccc4)c4ccc(-c5ccc(N(c6ccccc6)c6ccc(-c7ccc(-c8ccccc8)o7)cc6)cc5)cc4)cc3)o2)cc1]
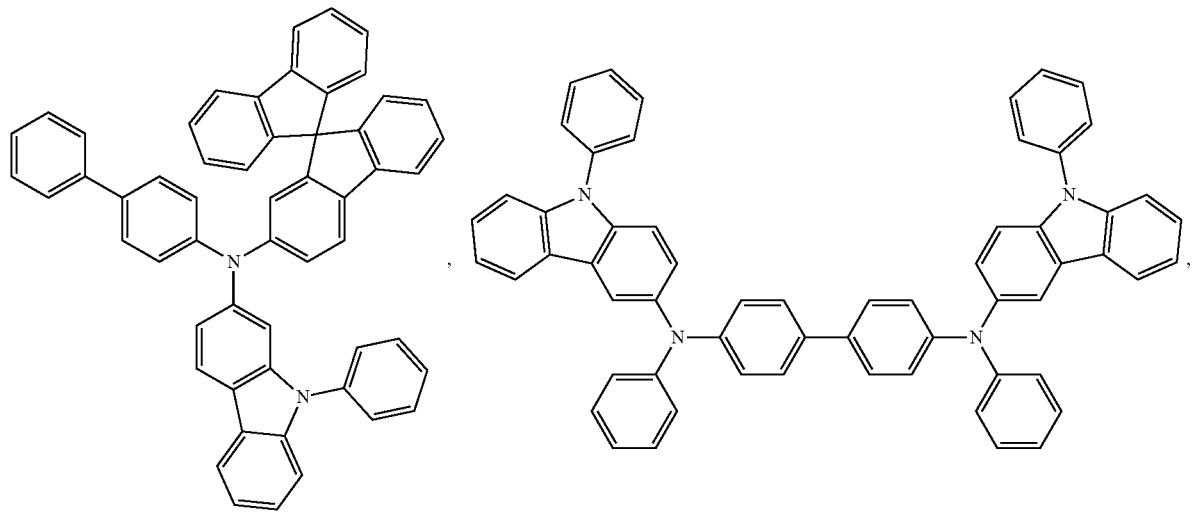
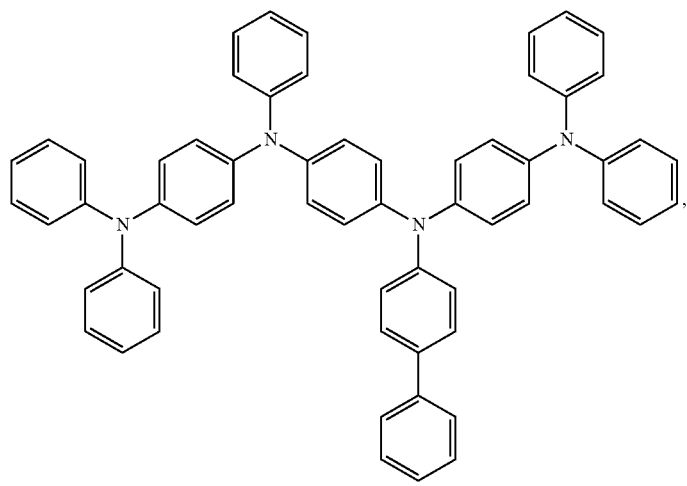

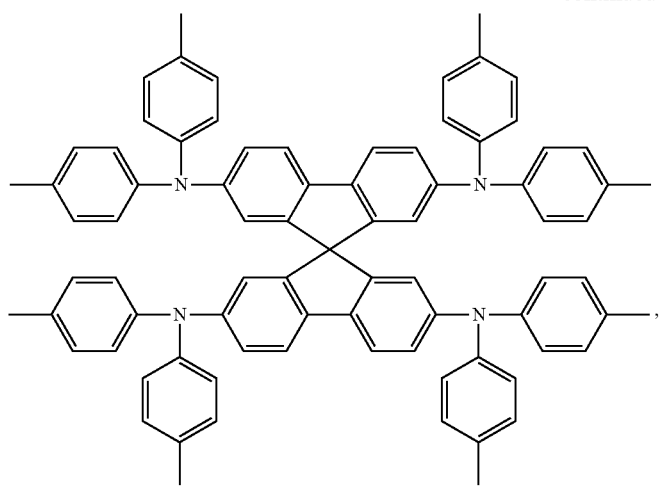
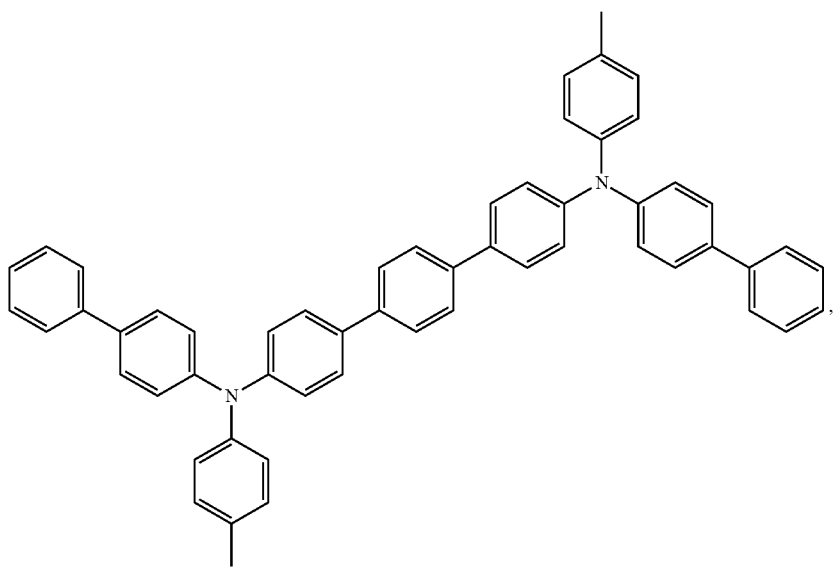
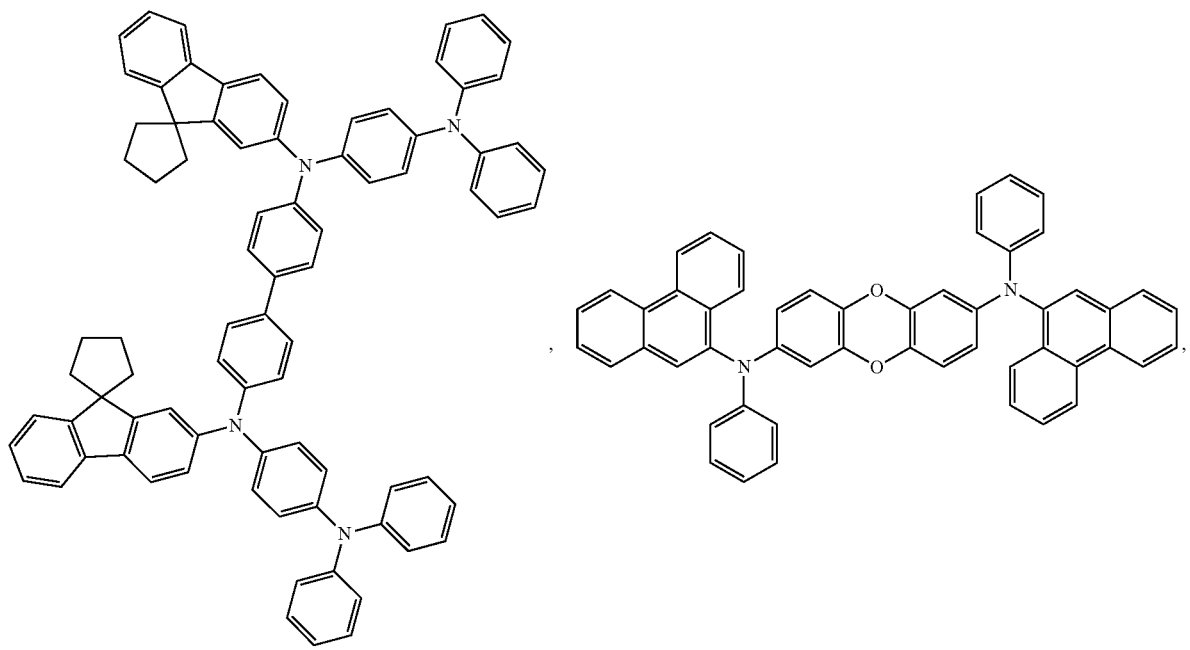

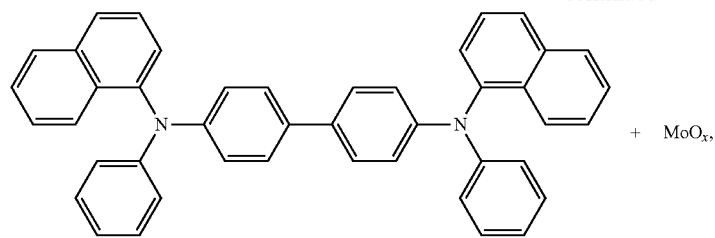
+ MoOx,
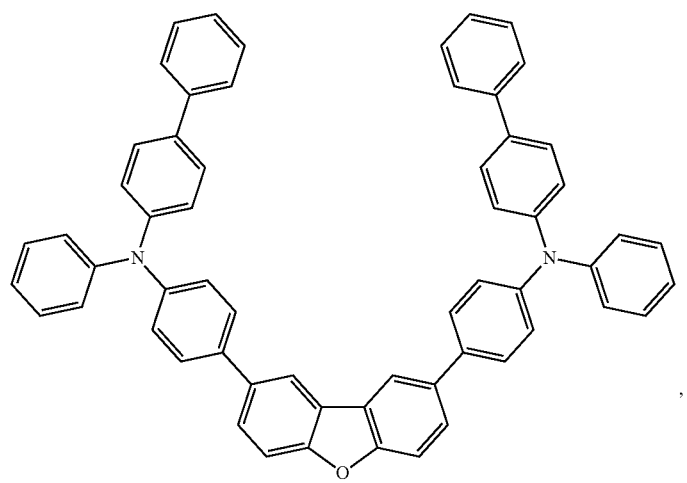
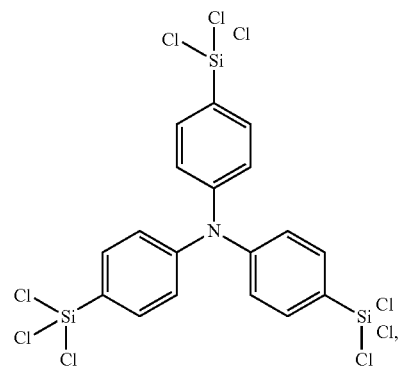
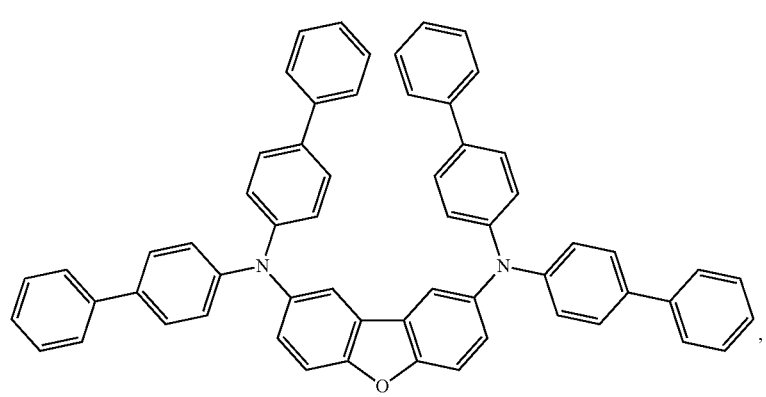
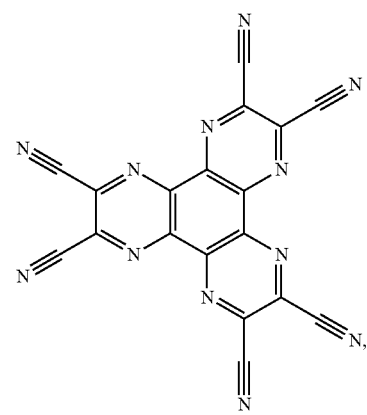
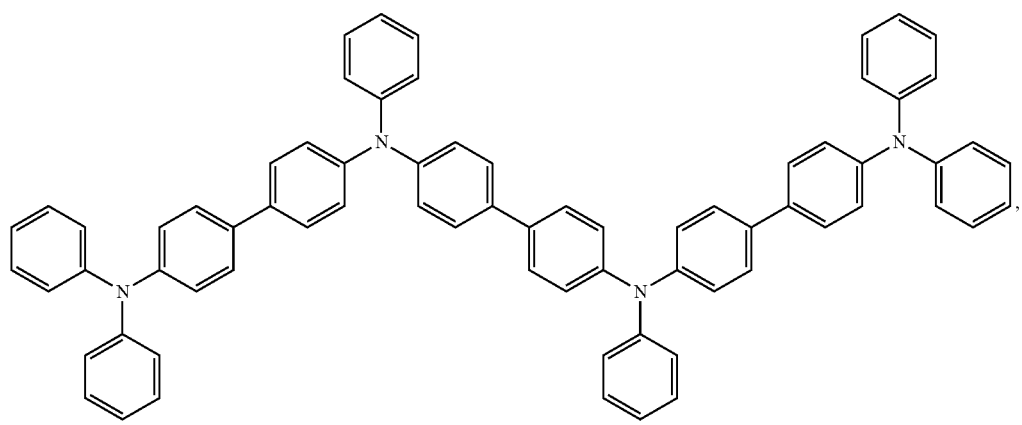

-continued
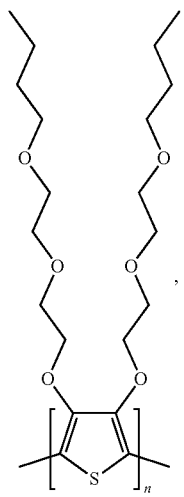
,
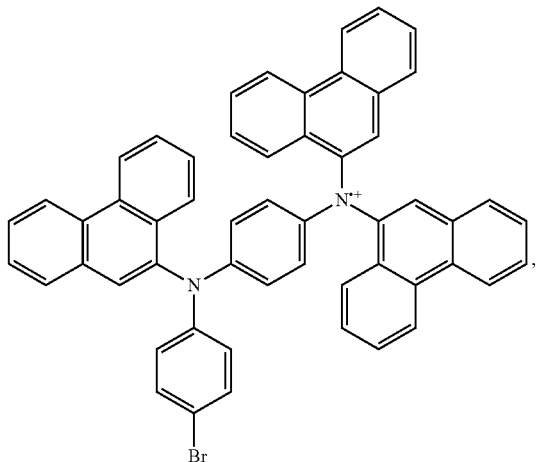
,
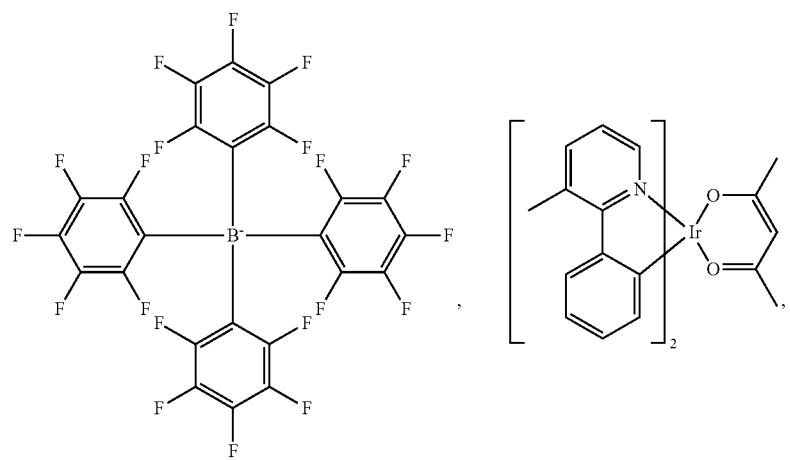
,
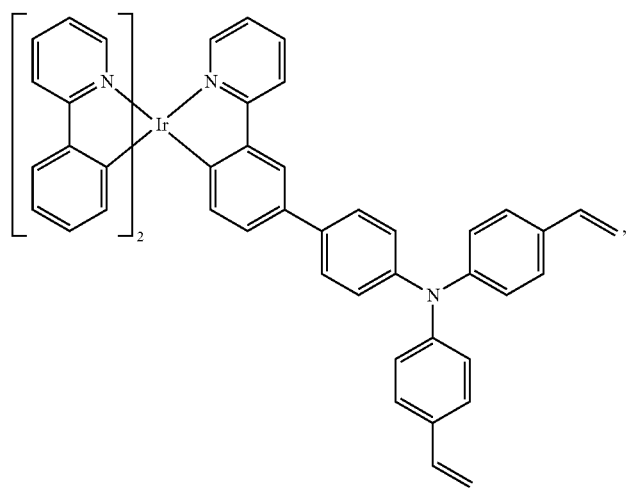
,

-continued
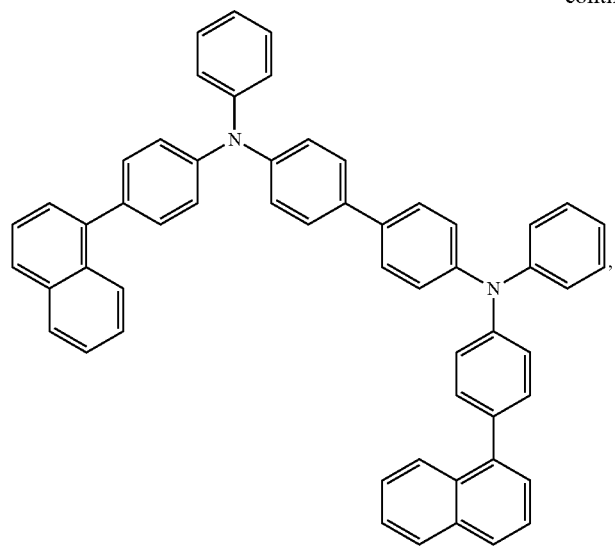
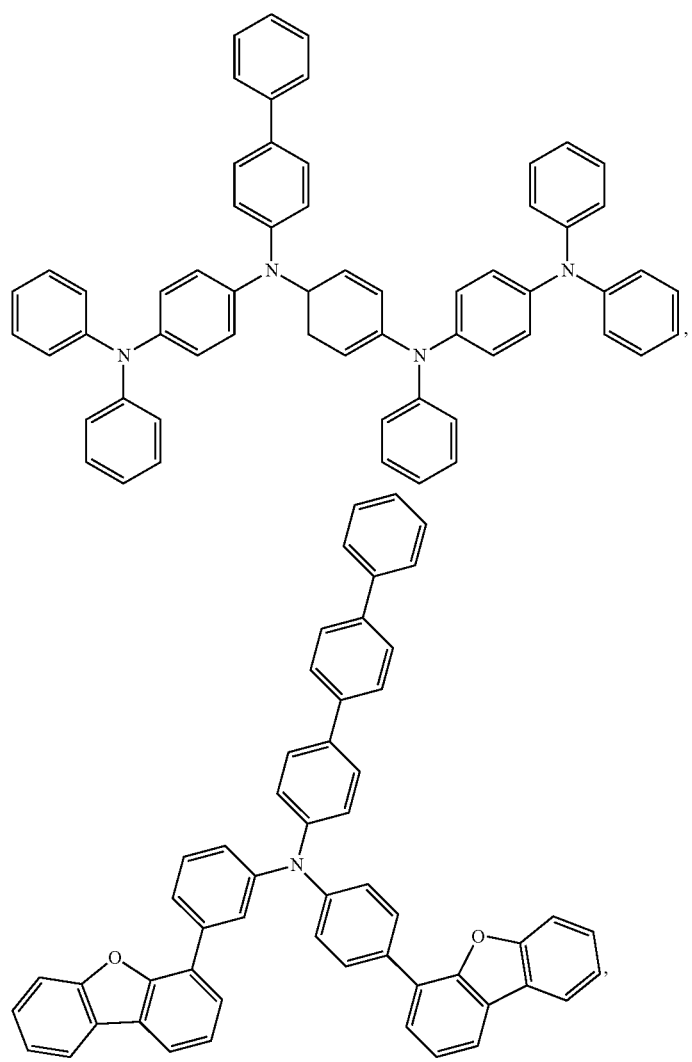

-continued
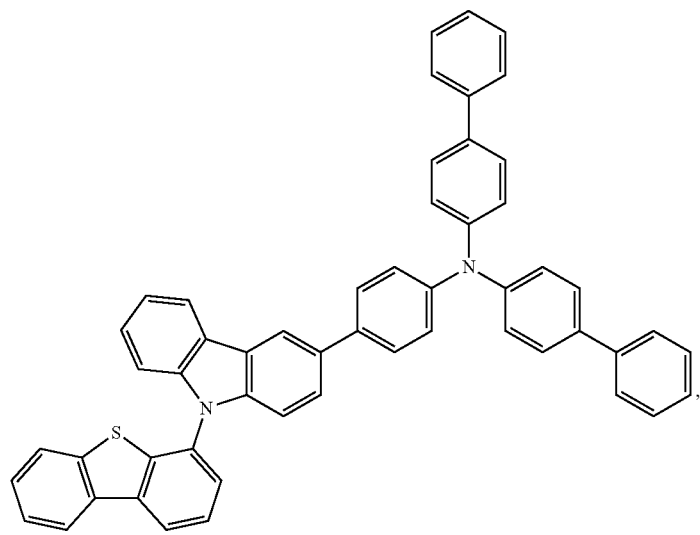
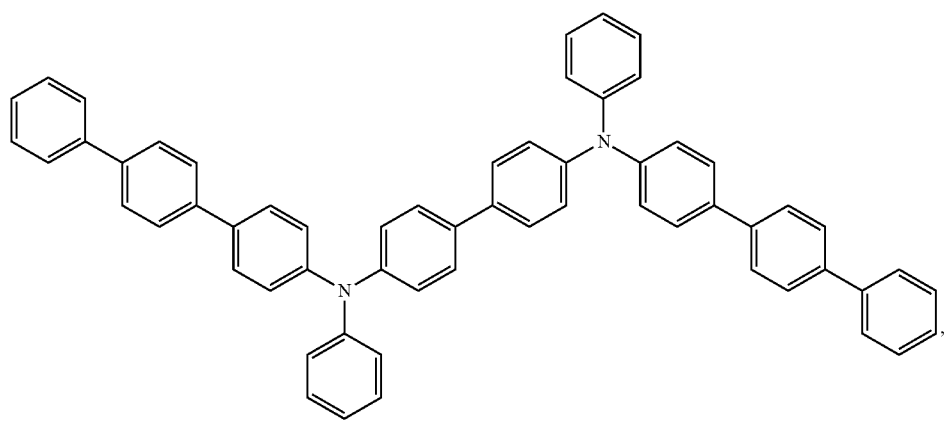
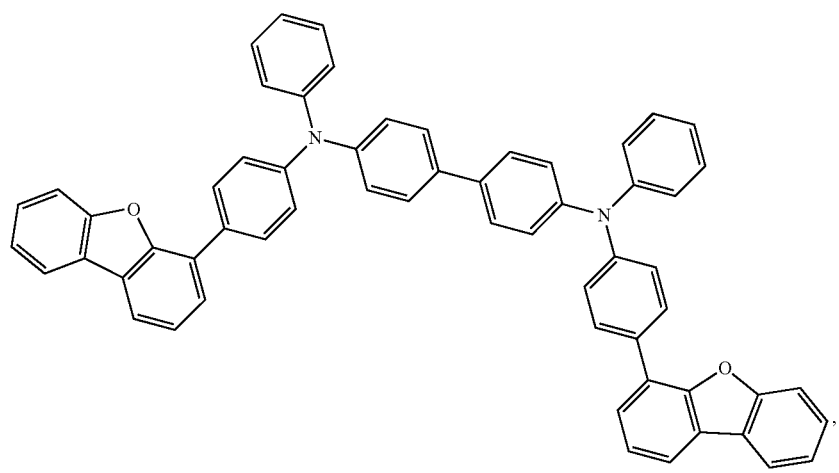

241
-continued
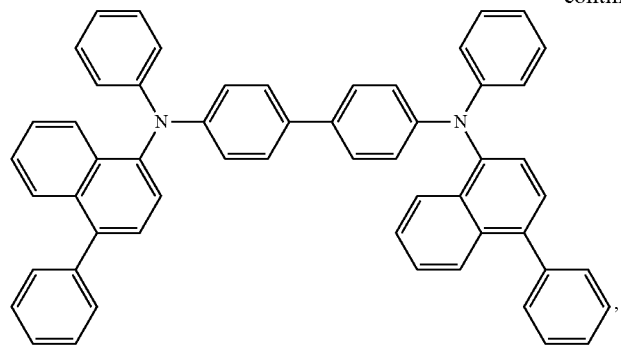
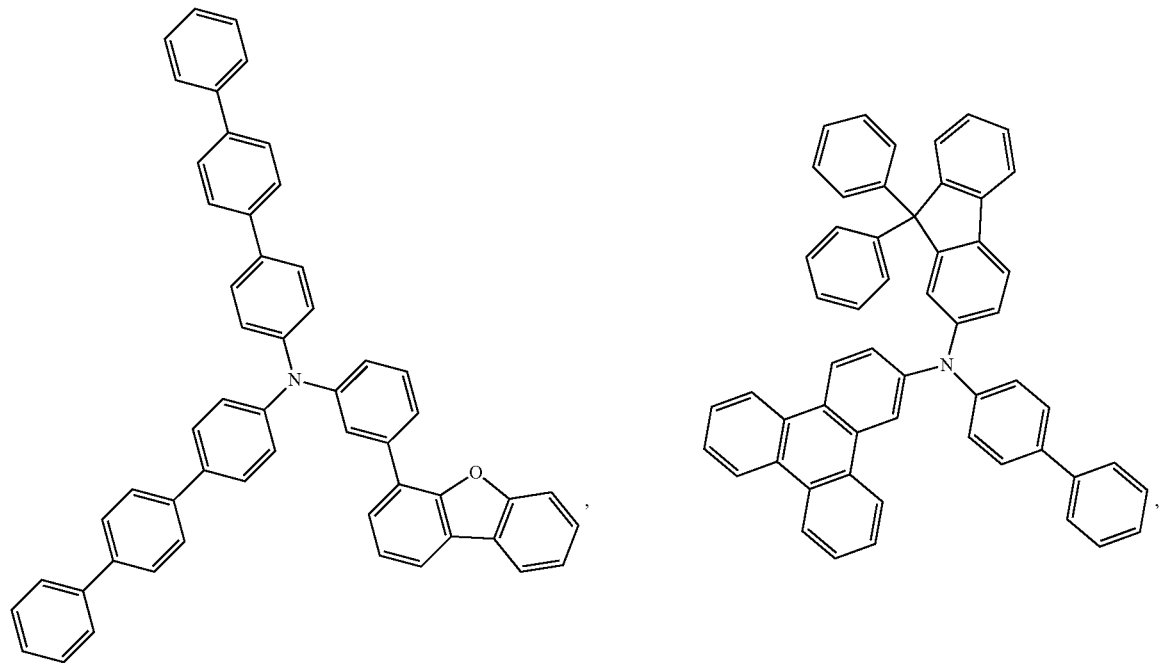
242
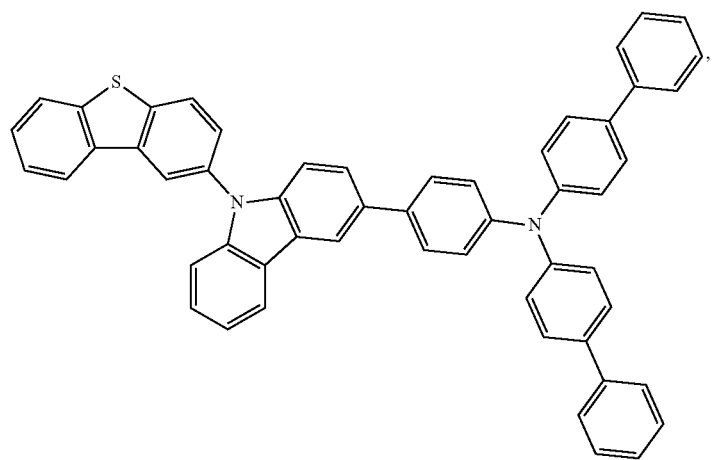

243
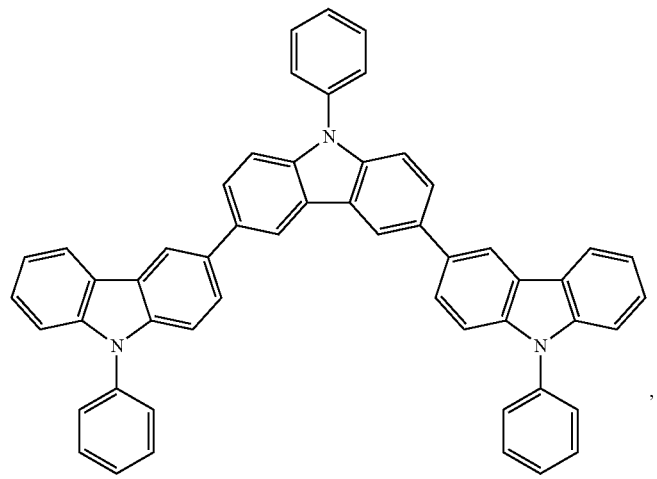
244
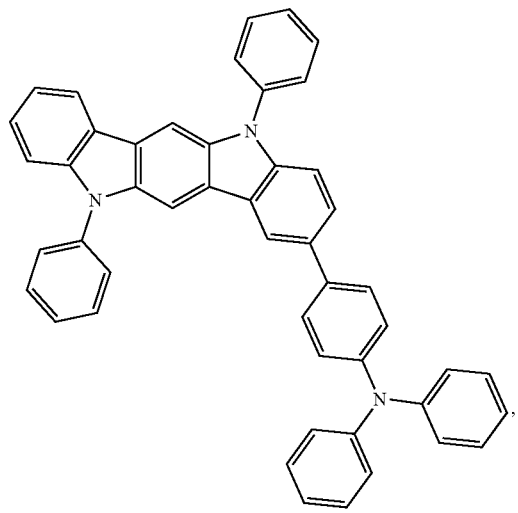
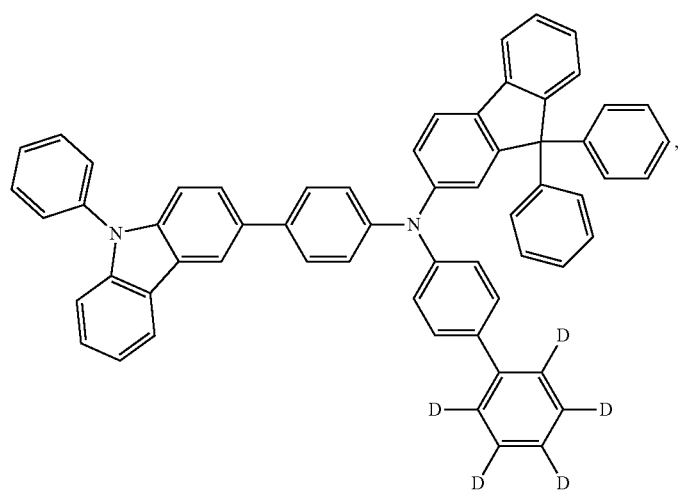
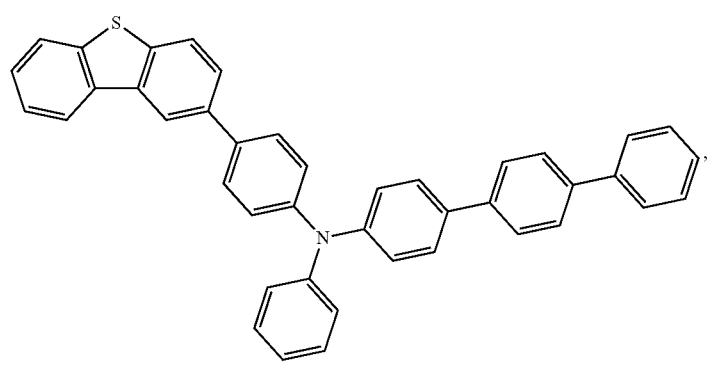

245
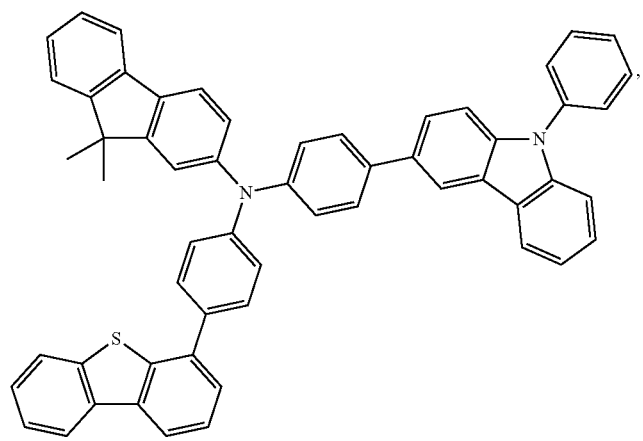
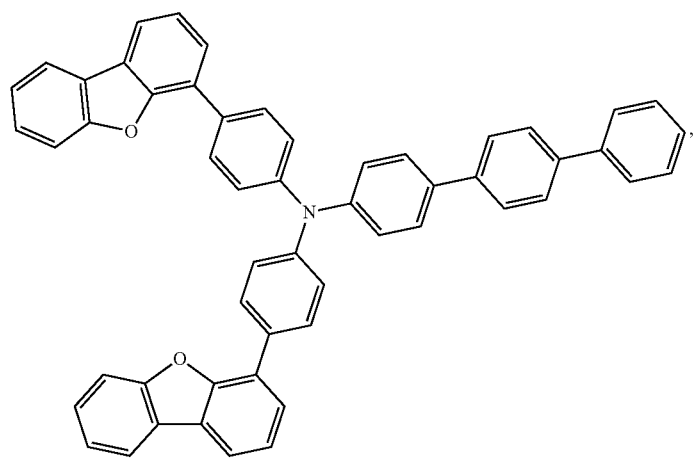
246
-continued
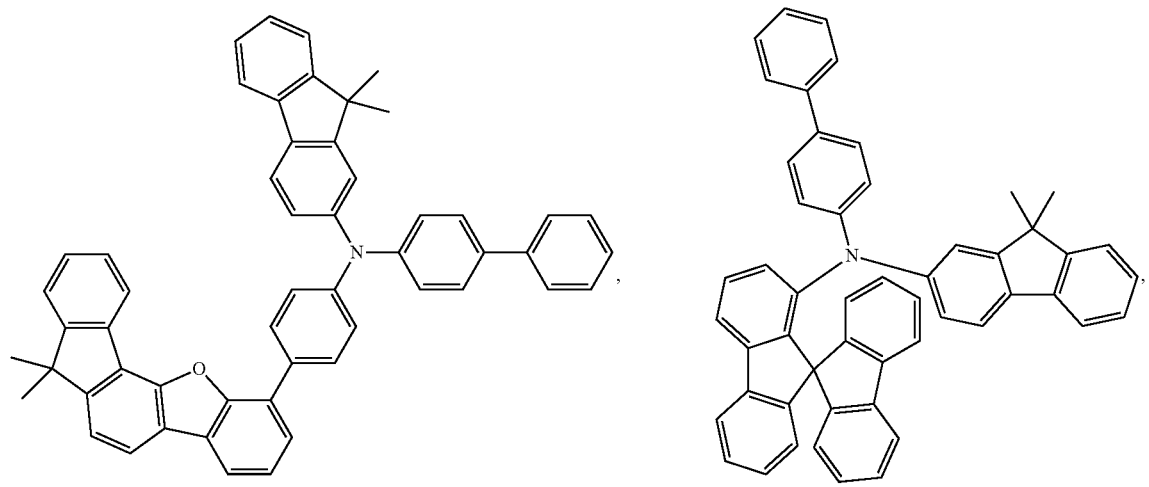

-continued
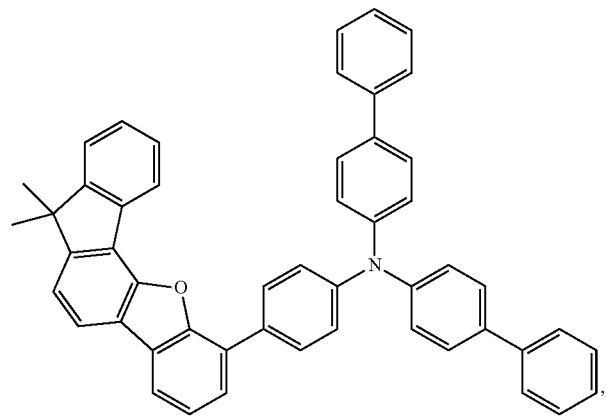
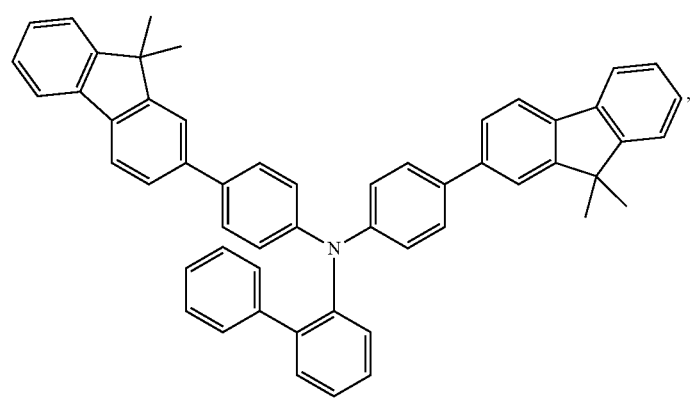
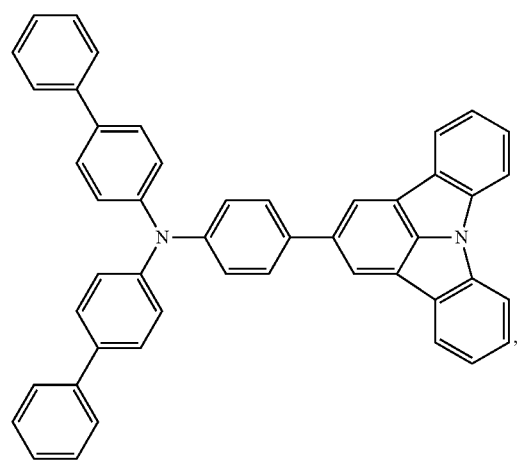

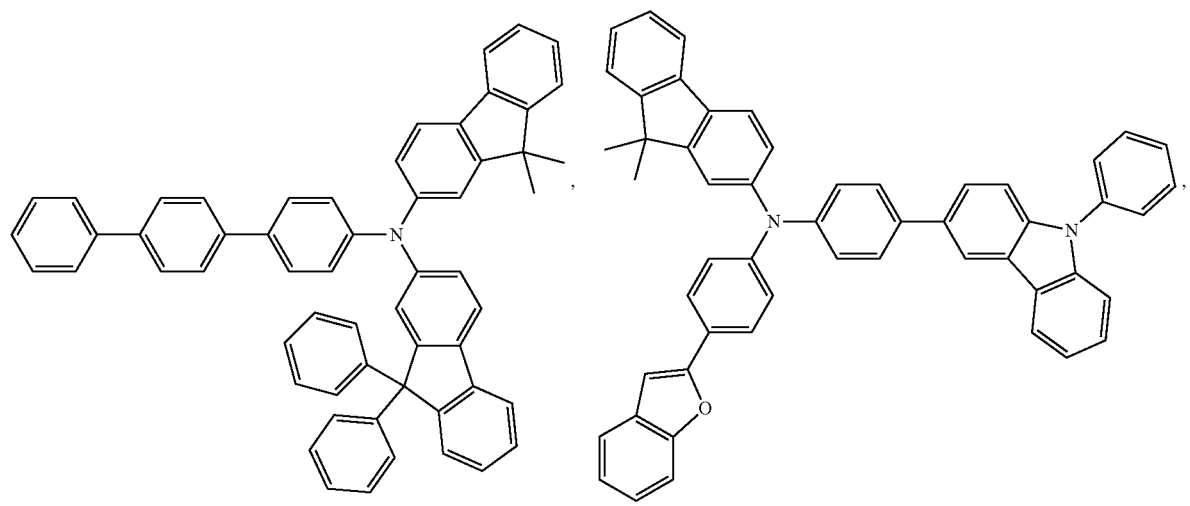
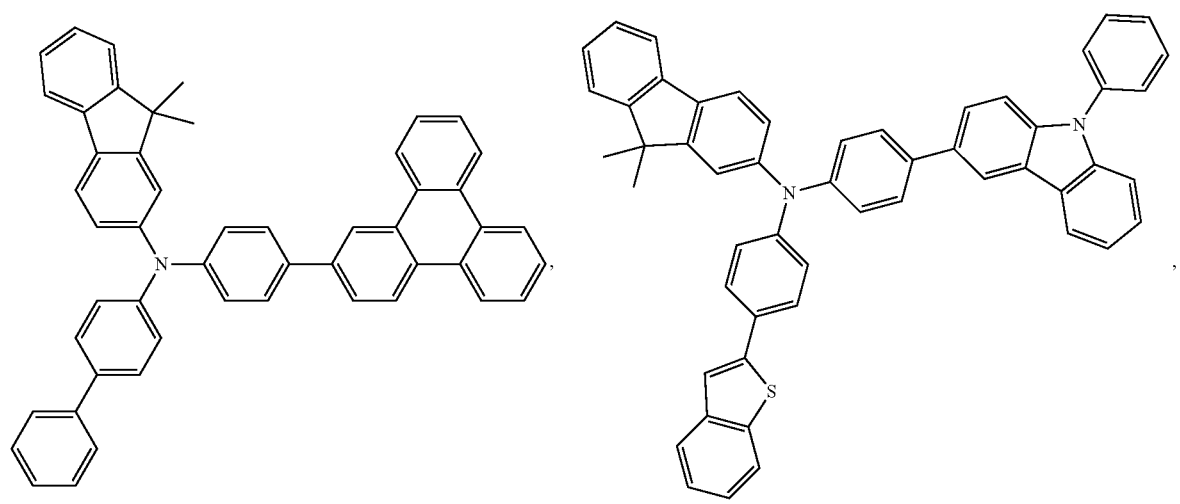
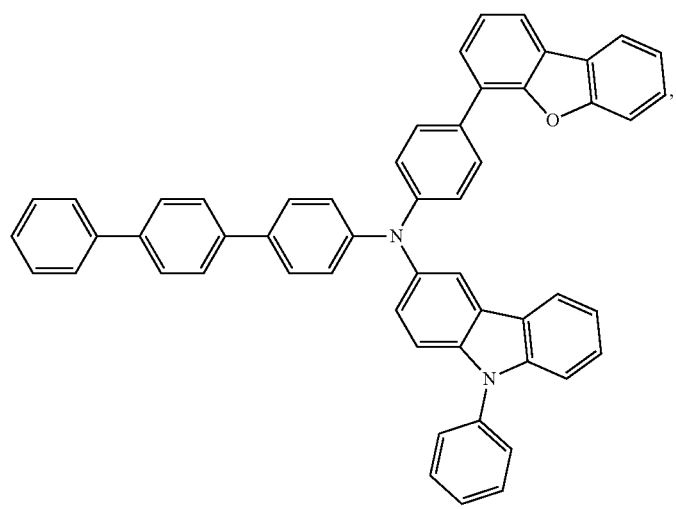

-continued
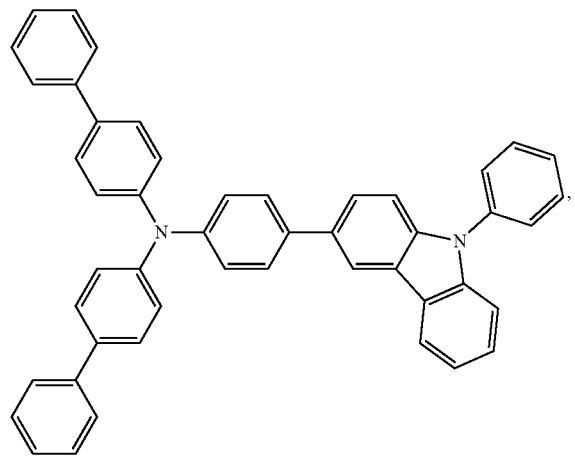
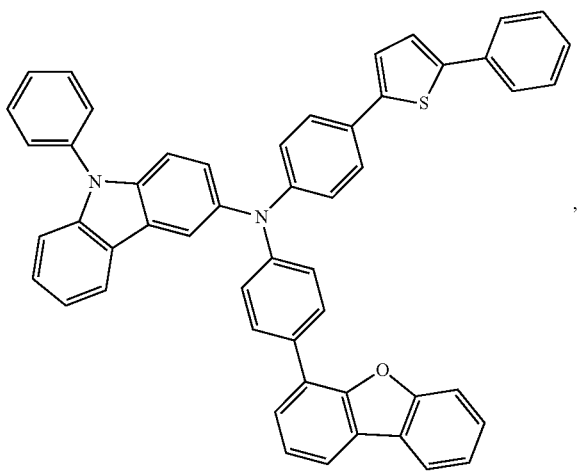
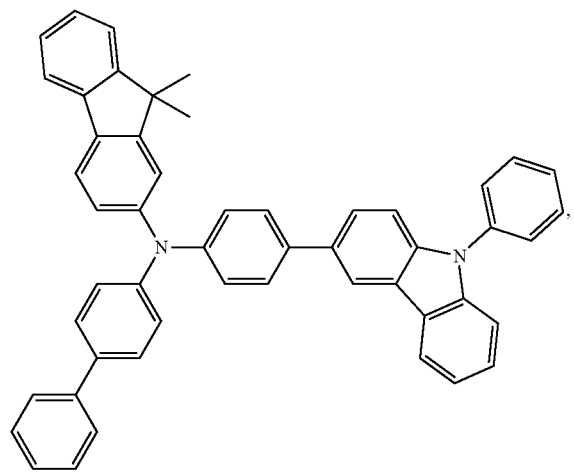
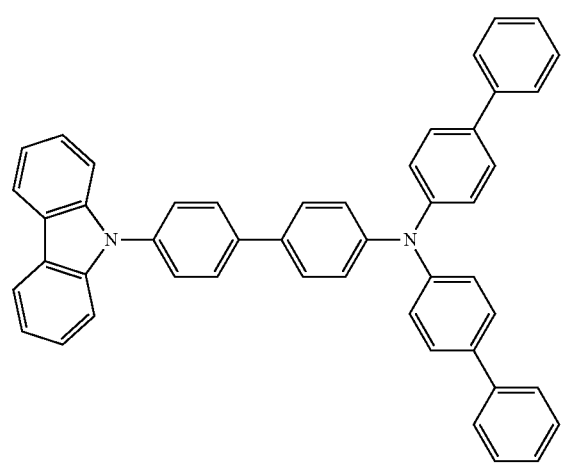
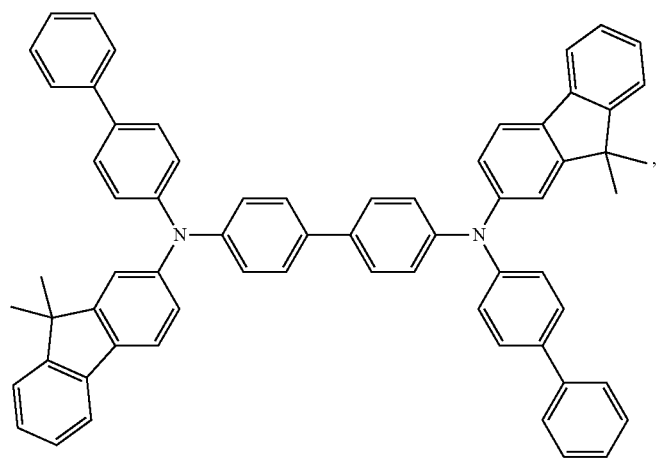

-continued
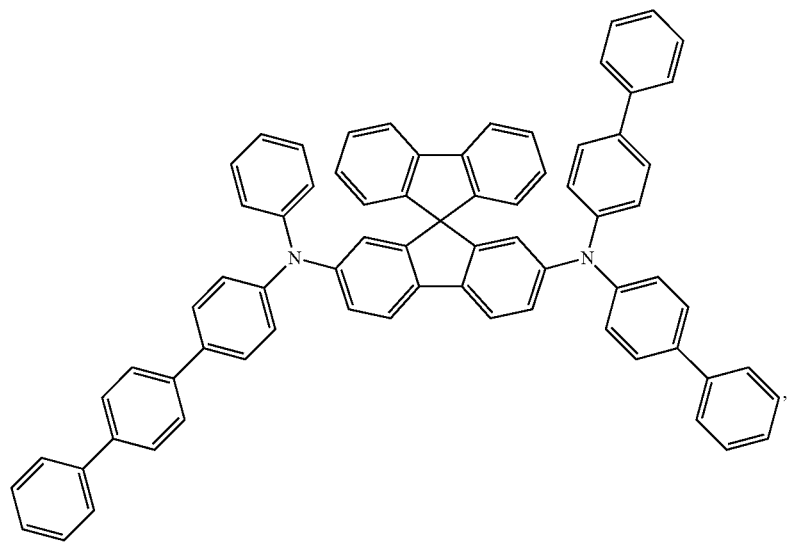
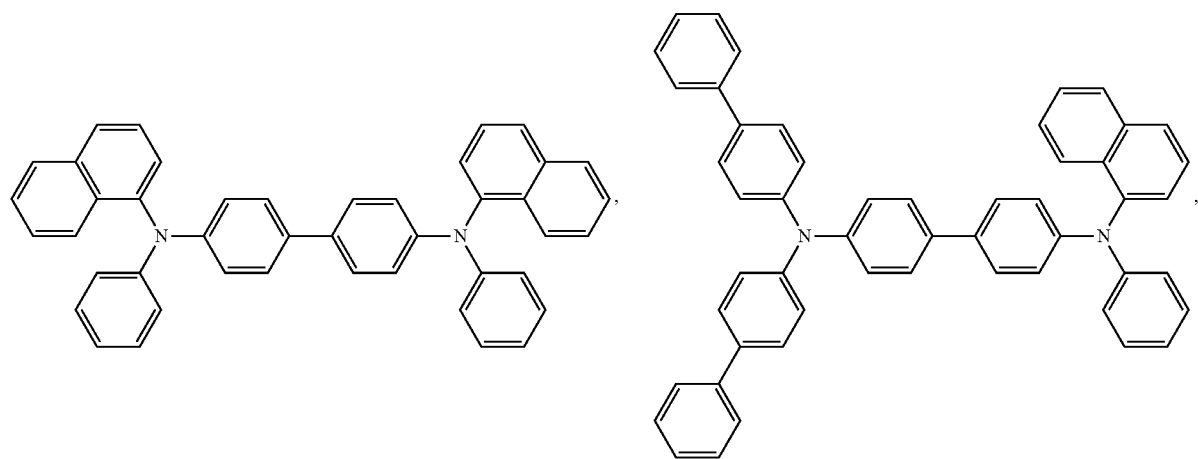
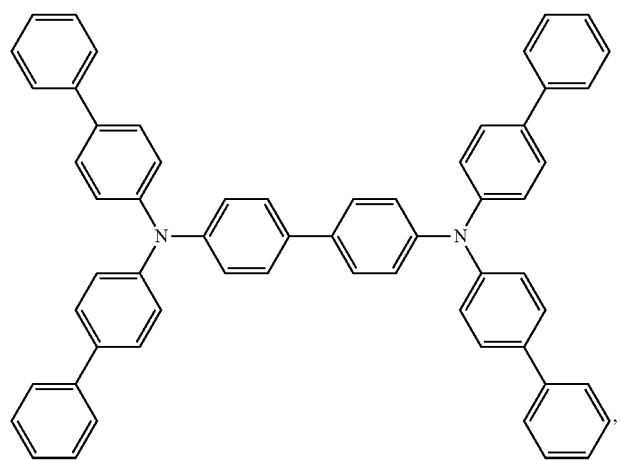

-continued
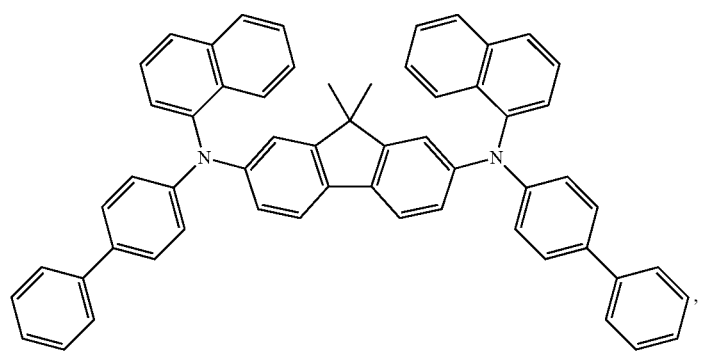
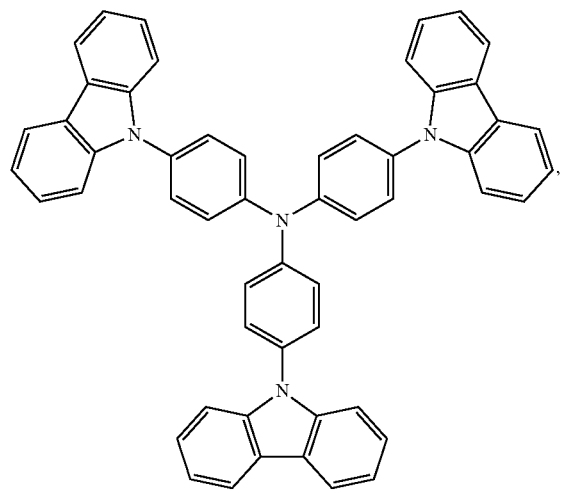
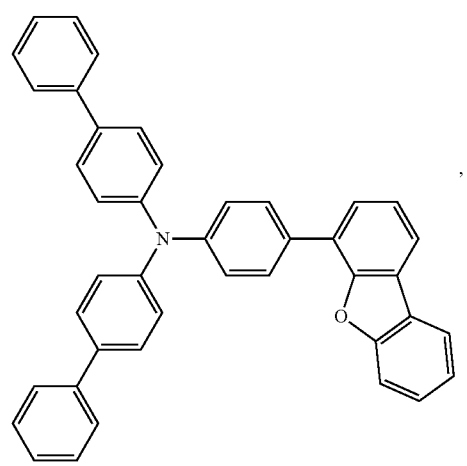
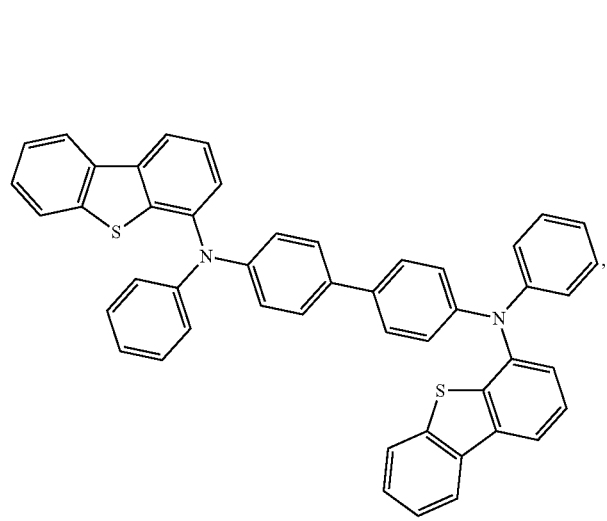
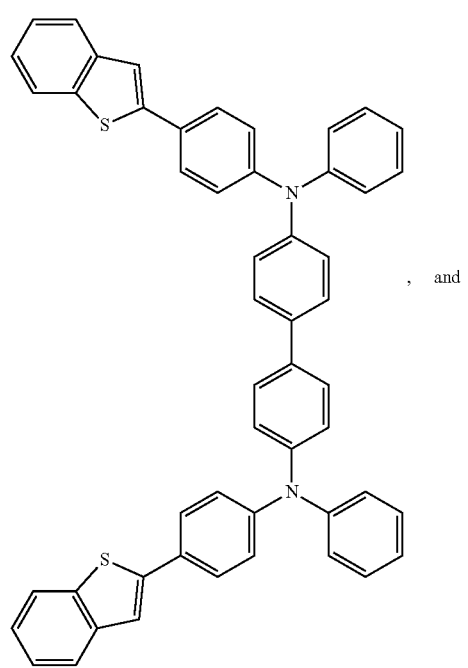

-continued

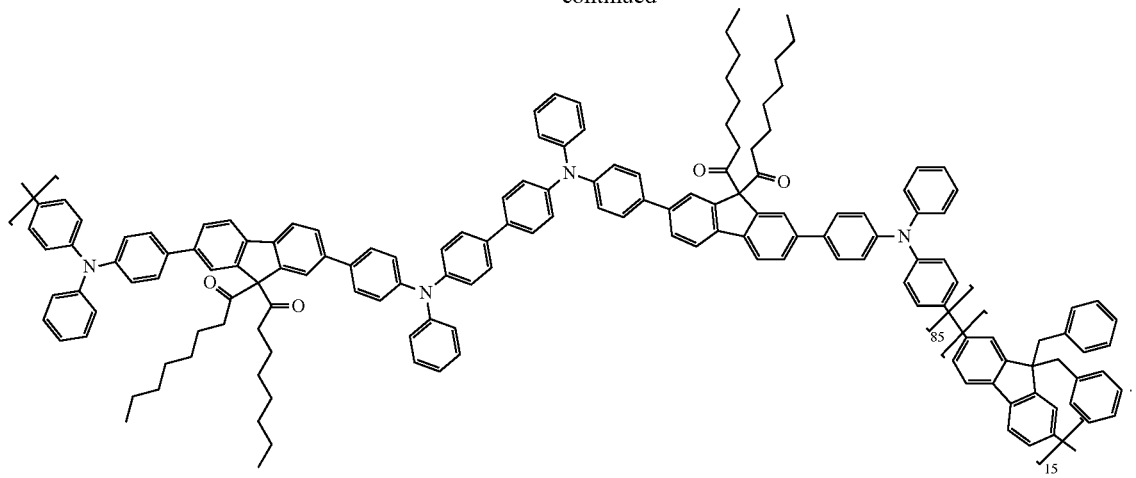

EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

Additional Hosts:

The light emitting layer of the organic EL device of the present invention preferably contains at least a metal complex as light emitting dopant material, and may contain one or more additional host materials using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

Examples of metal complexes used as host are preferred to have the following general formula:

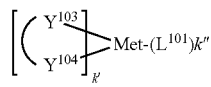

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

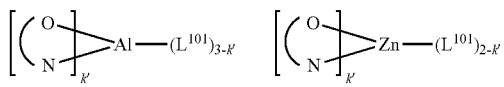

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

In one aspect, the host compound contains at least one of the following groups selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, host compound contains at least one of the following groups in the molecule:

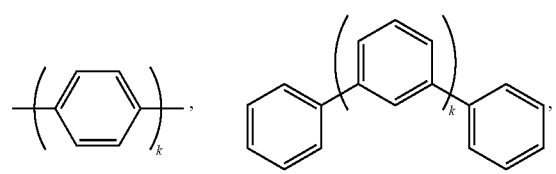
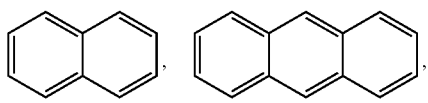
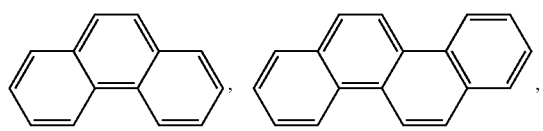
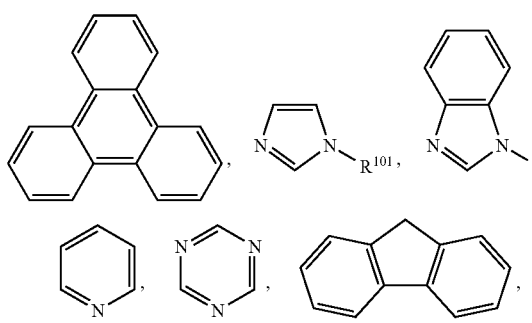
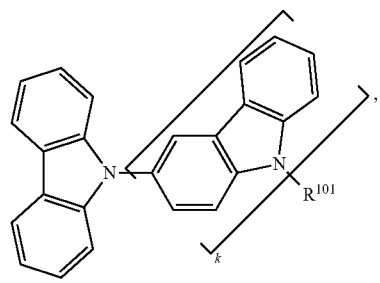
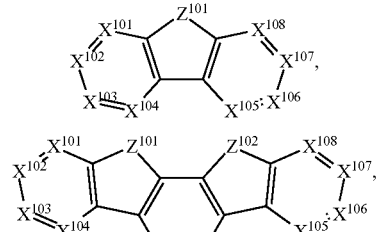

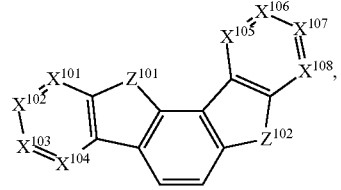
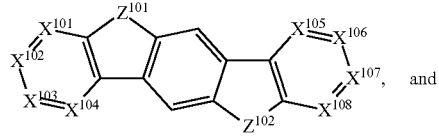
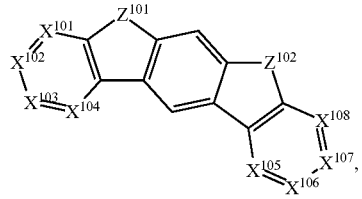

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20. $X^{101}$ to $X^{108}$ are independently selected from C (including CH) or N. $Z^{101}$ and $Z^{102}$ are independently selected from $NR^{101}$, O, or S.

Non-limiting examples of the additional host materials that may be used in an OLED in combination with the host compound disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472, US20170263869, US20160163995, U.S. Pat. No. 9,466,803.

261 262
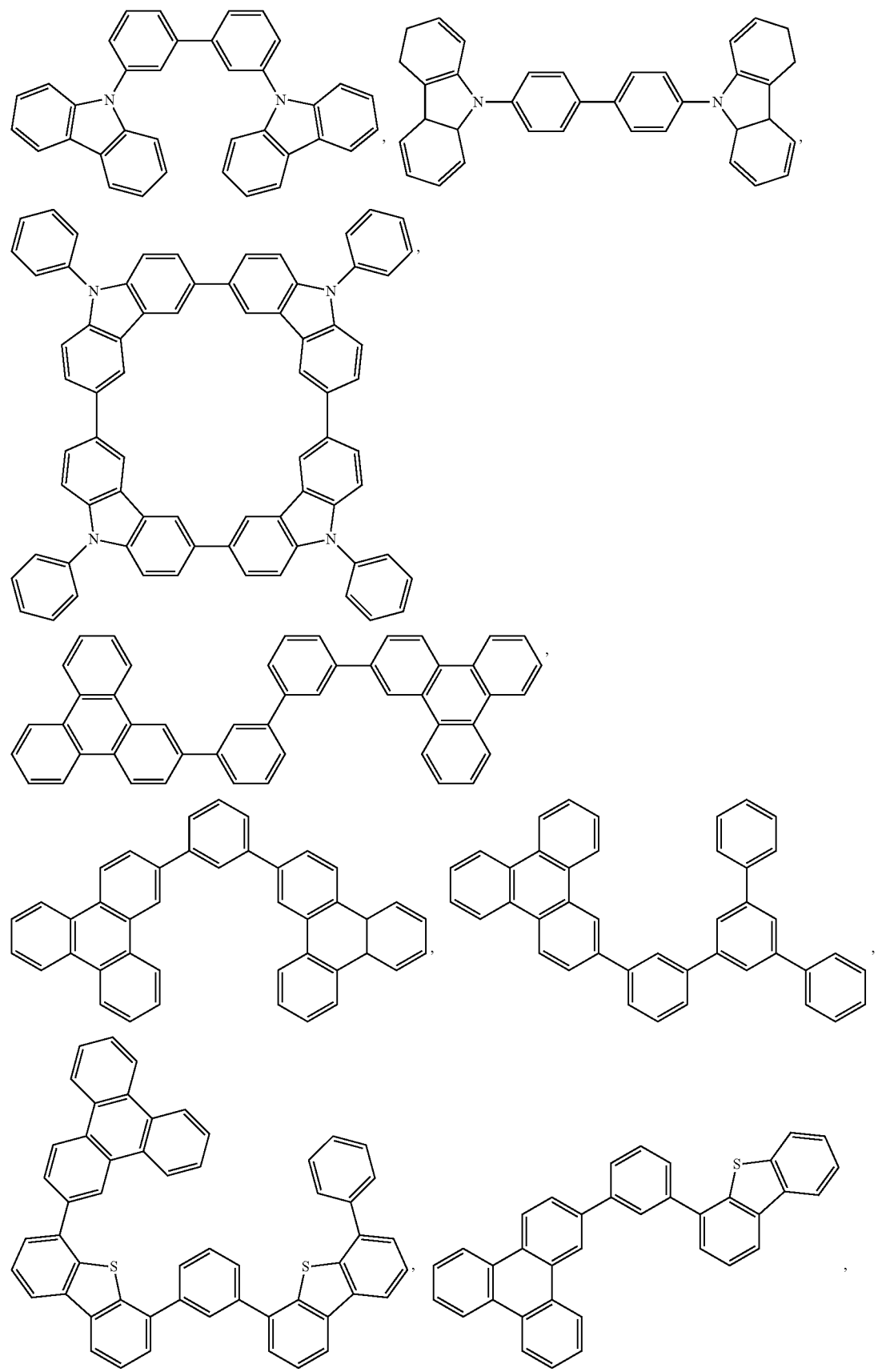

-continued
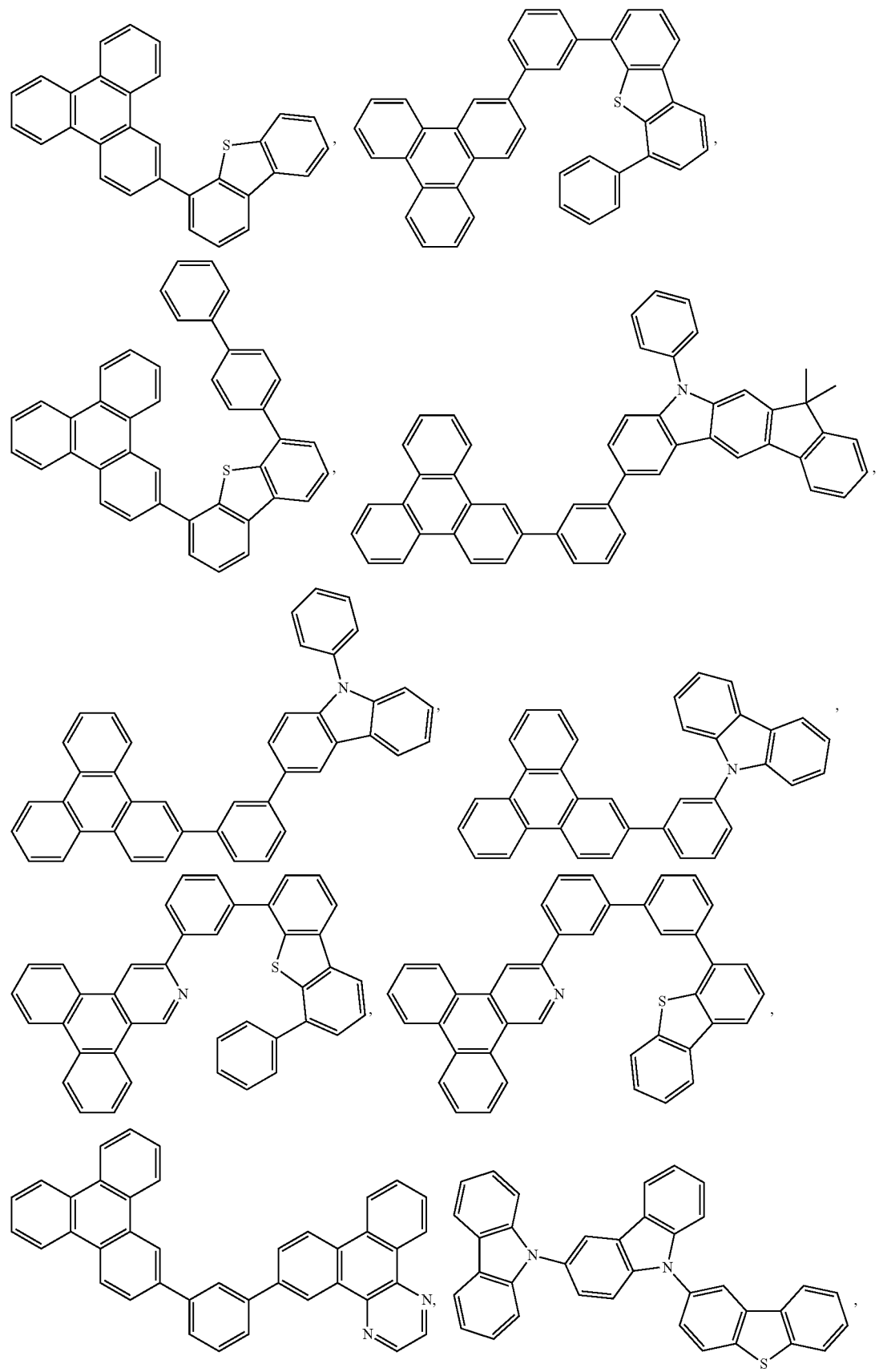

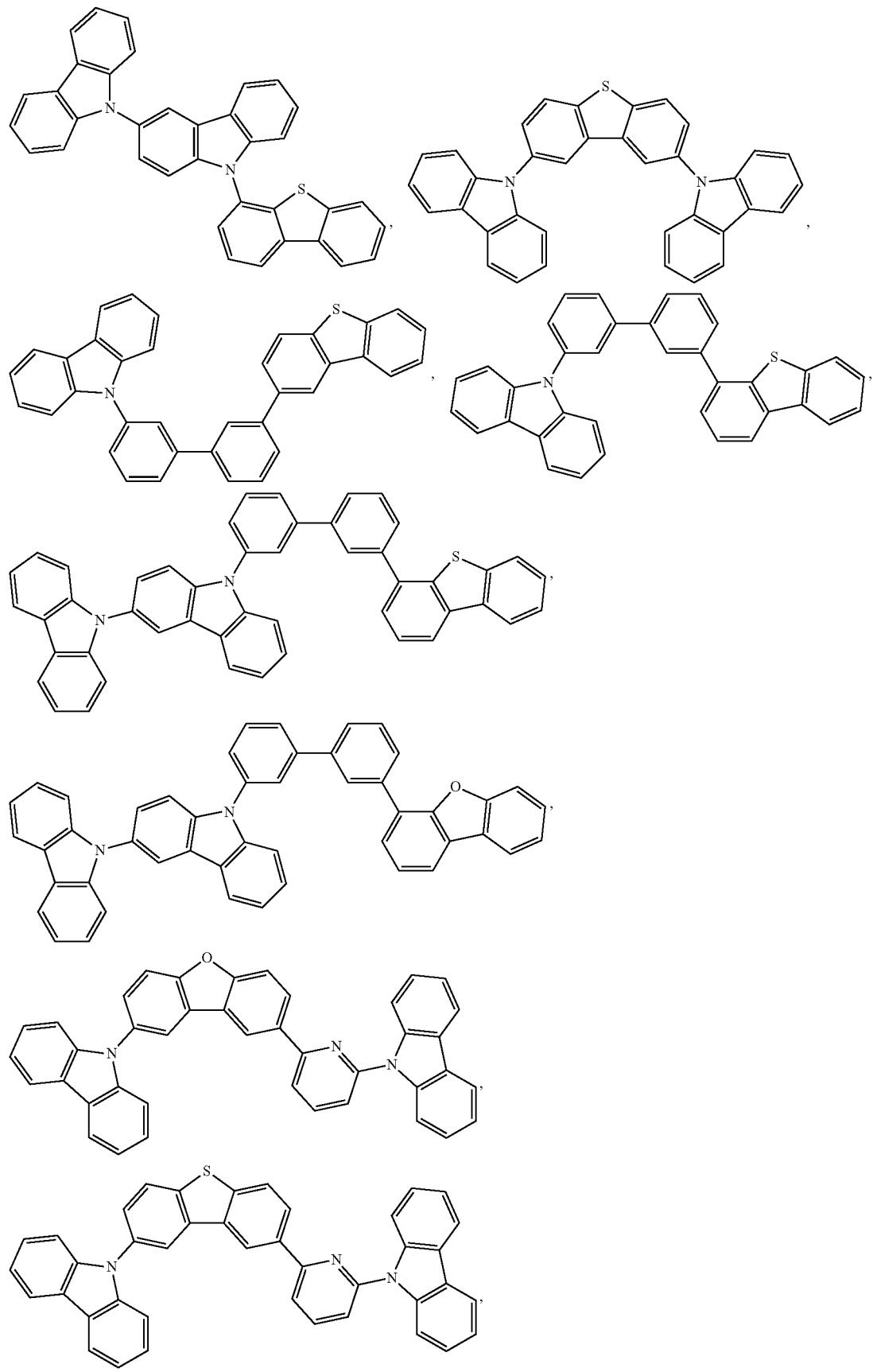

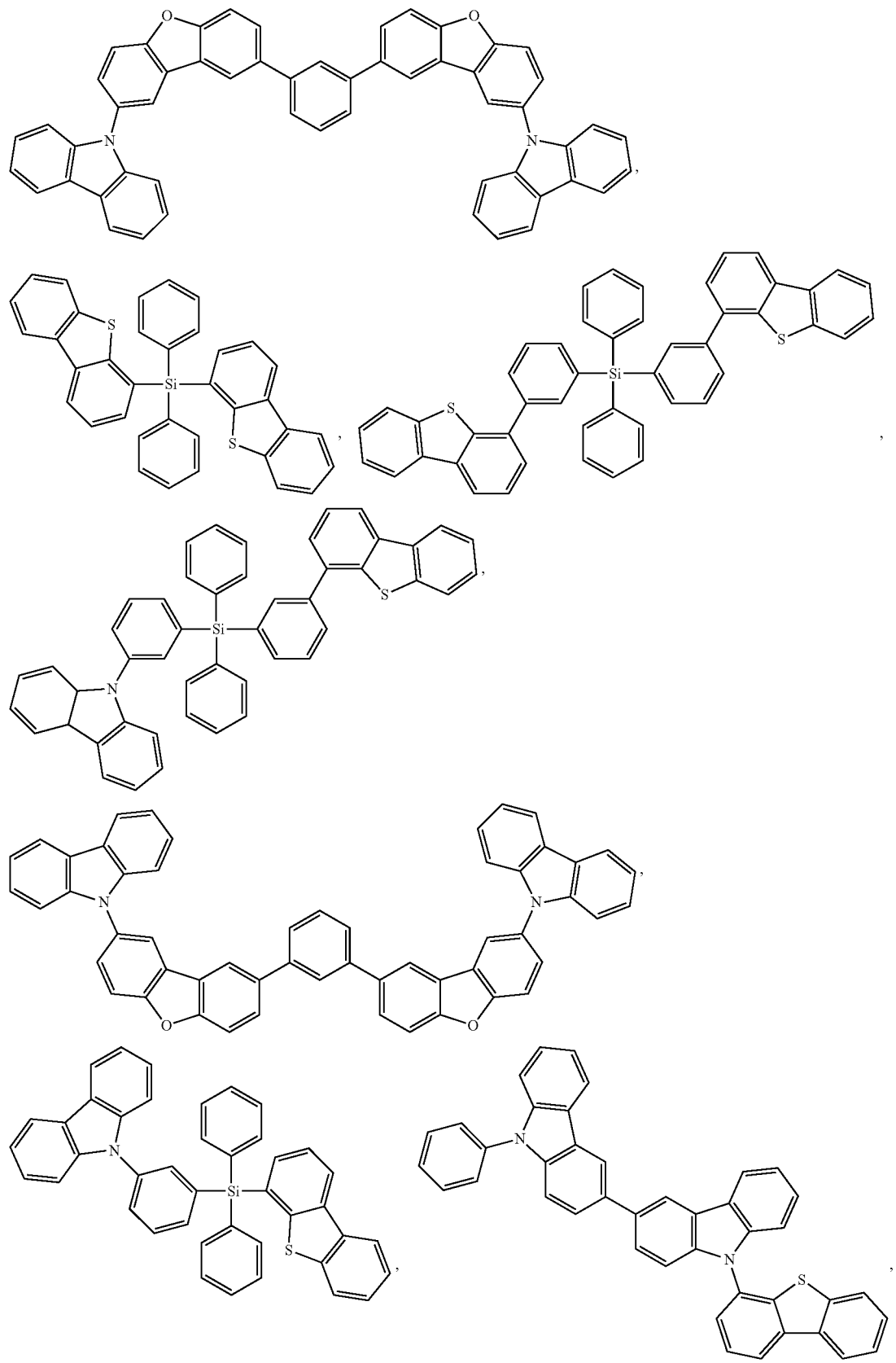

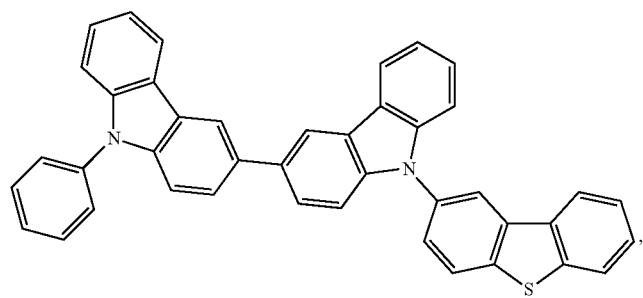
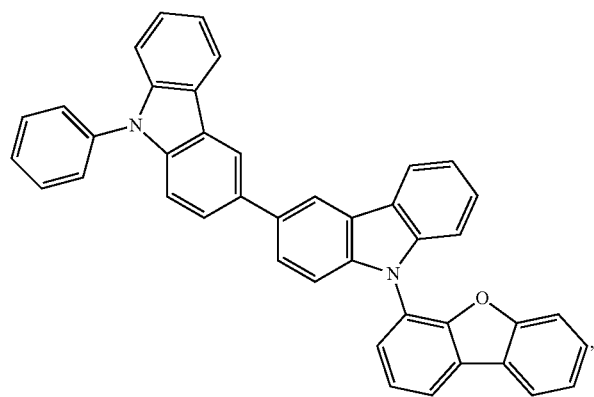
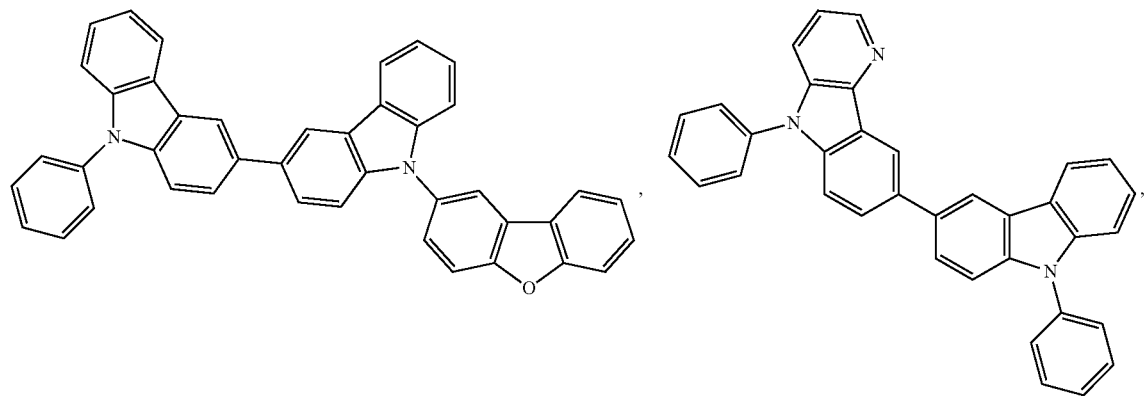
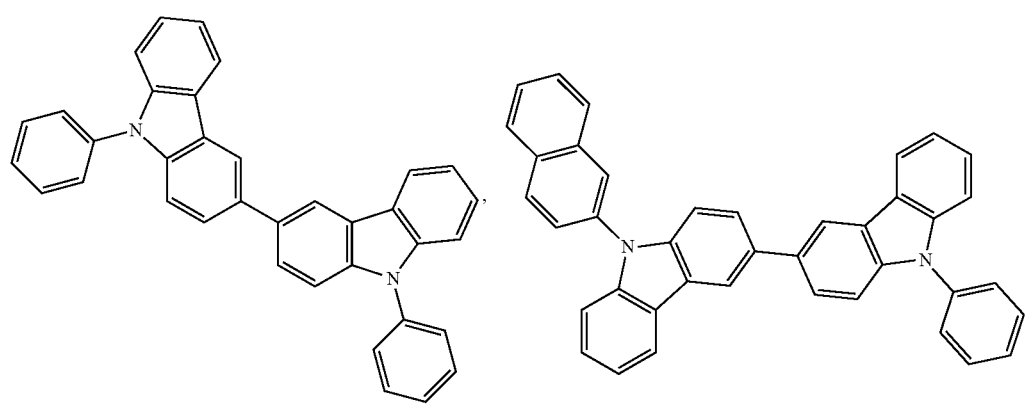

271
272
-continued
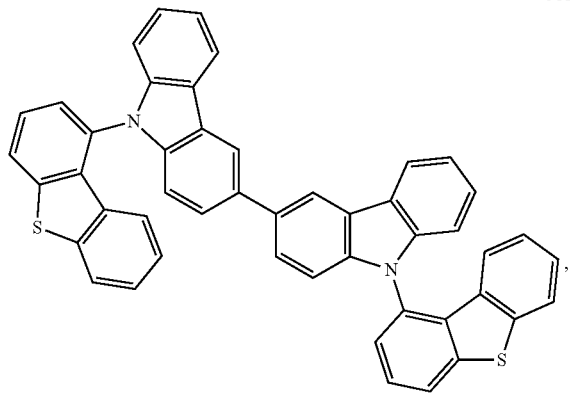
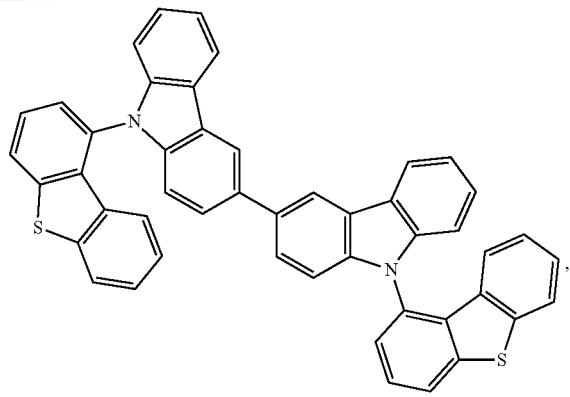
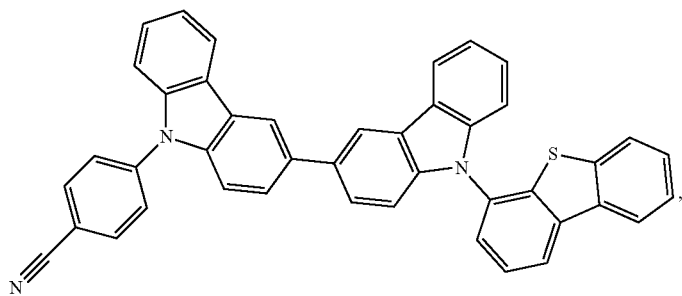
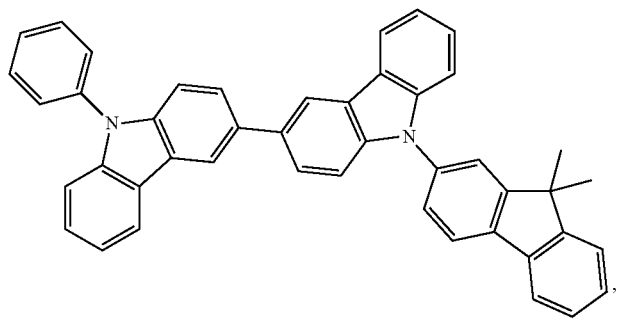
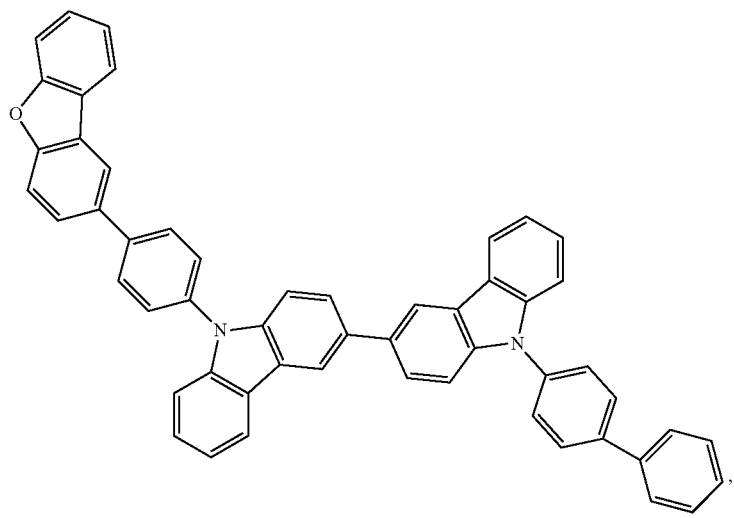

-continued
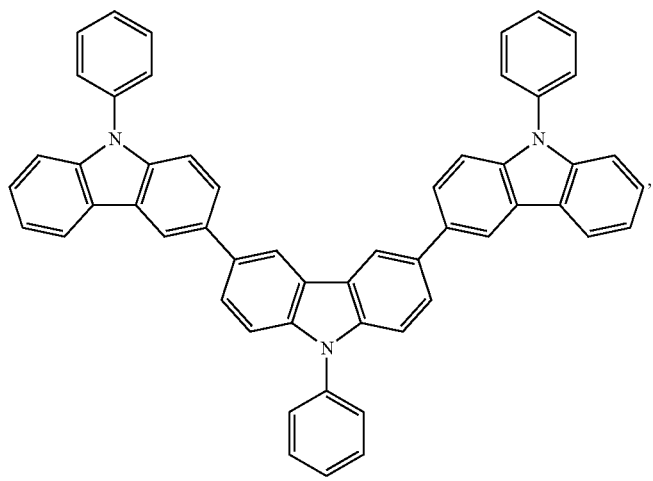
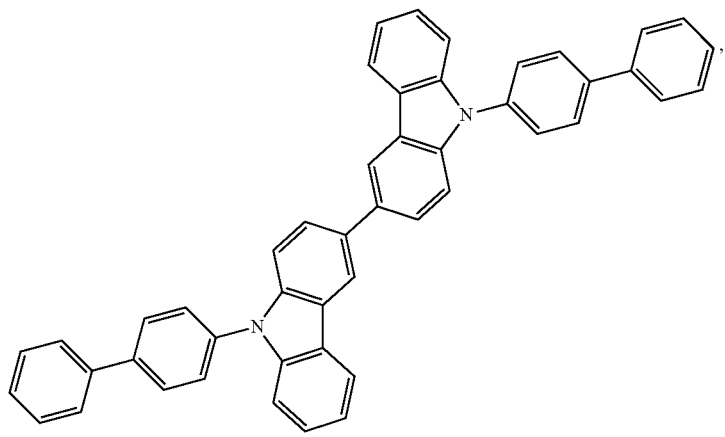
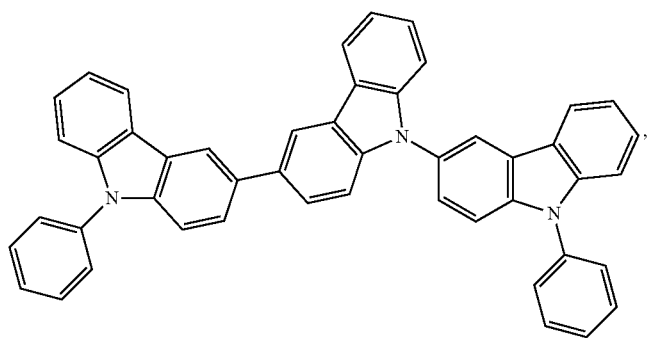
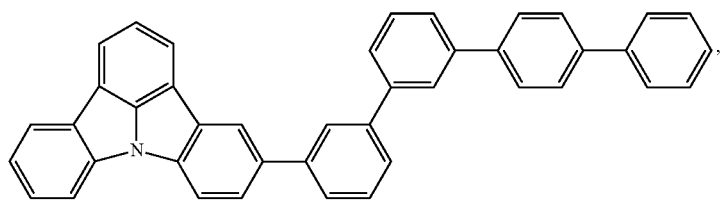

-continued
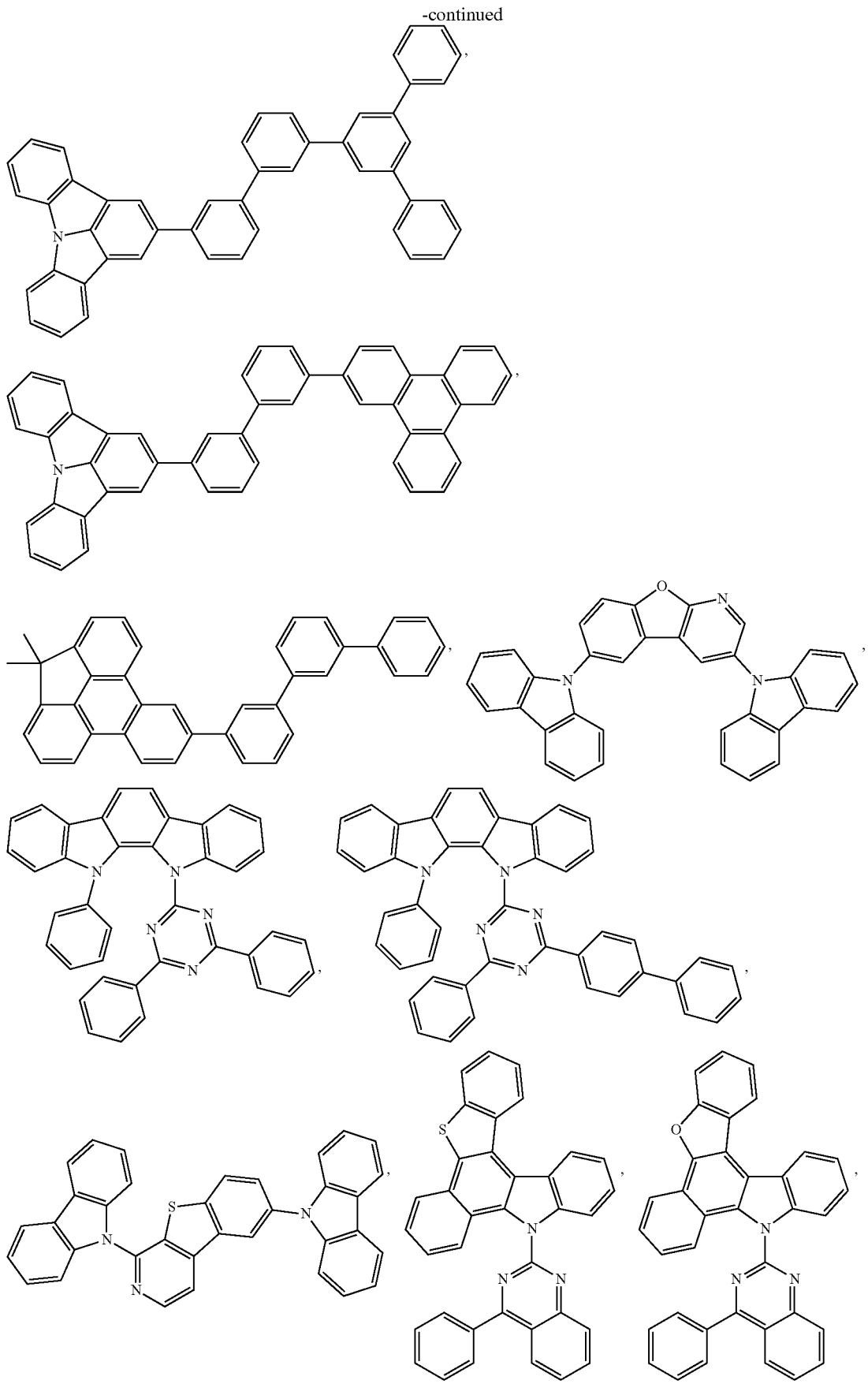

-continued
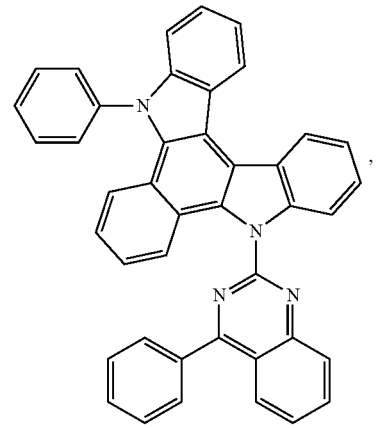
,
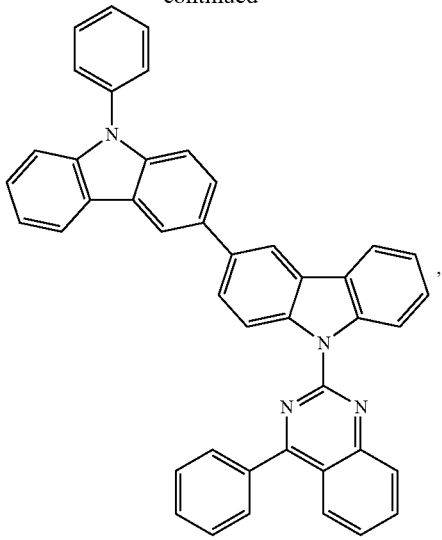
,
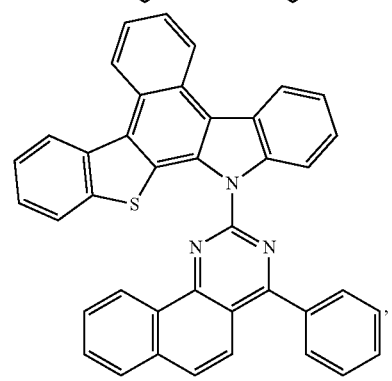
,
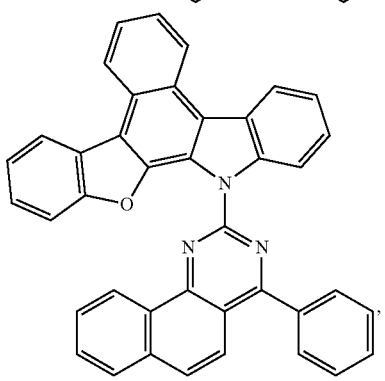
,
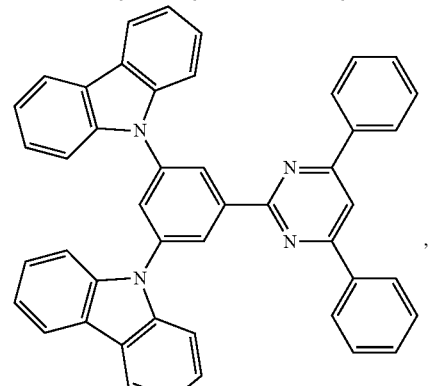
,
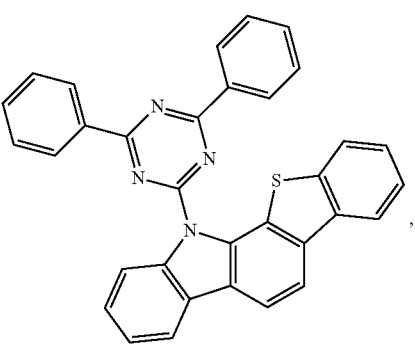
,
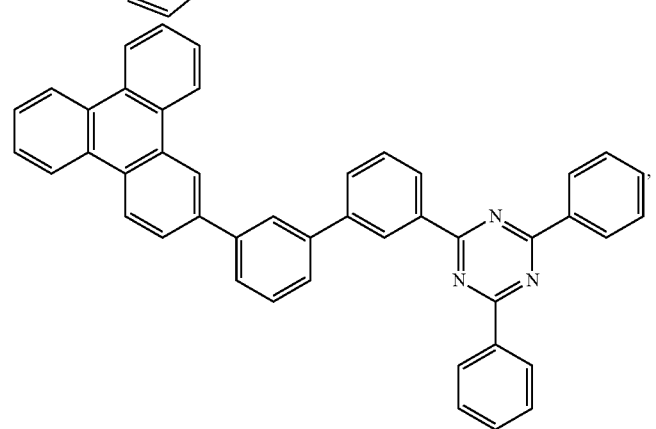
, -continued
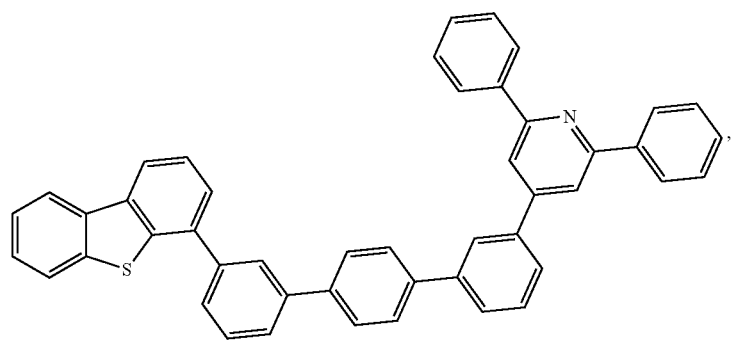
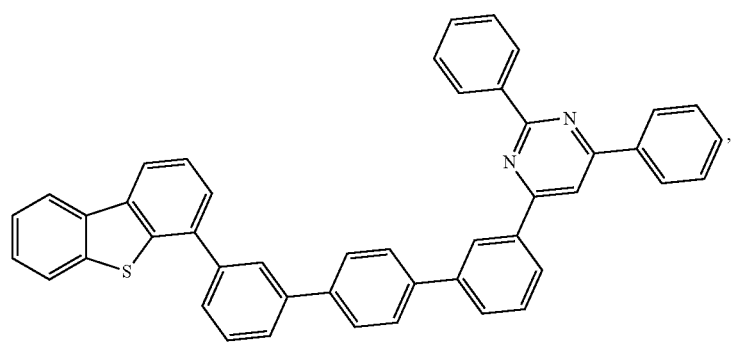
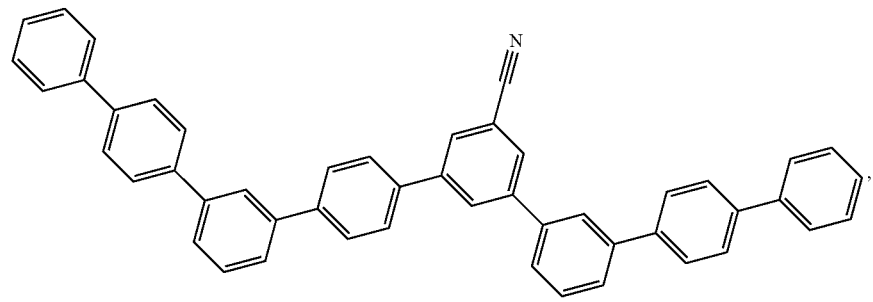
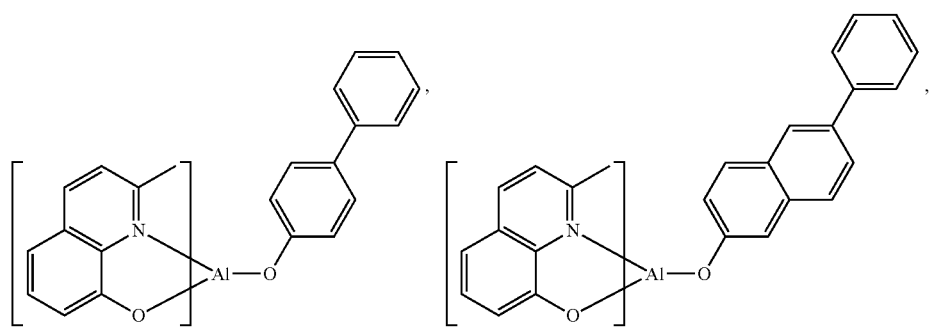
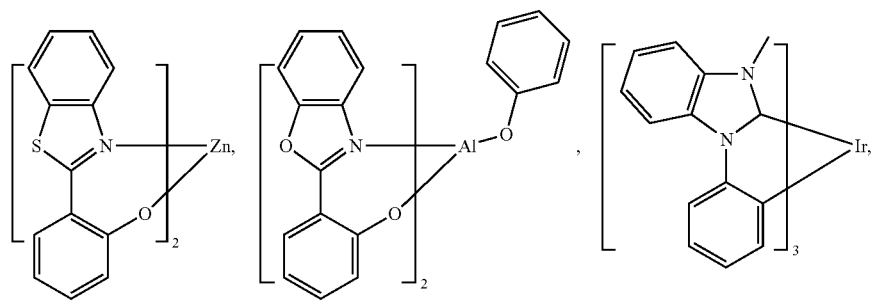

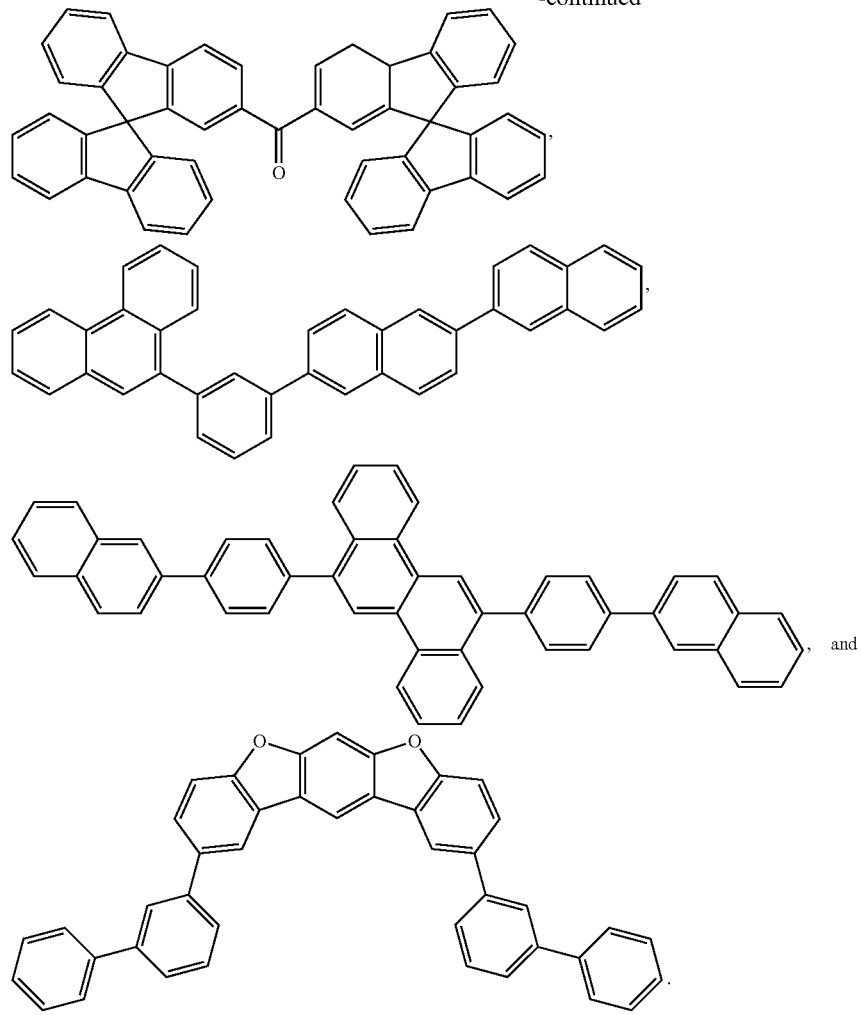

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence; see, e.g., U.S. application Ser. No. 15/700,352, which is hereby incorporated by reference in its entirety), triplet-triplet annihilation, or combinations of these processes. In some embodiments, the emissive dopant can be a racemic mixture, or can be enriched in one enantiomer.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. No. 06/699,599, U.S. Ser. No. 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004. US2010270916, US20110057559, US20110108822, US20110204333, US2011215710. US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257,
WO2005019373, WO2006056418, WO2008054584,
WO2008078800, WO2008096609, WO2008101842,
WO2009000673, WO2009050281, WO2009100991,
WO2010028151, WO2010054731. WO2010086089,
WO2010118029, WO2011044988, WO2011051404,
WO2011107491, WO2012020327, WO2012163471,
WO2013094620, WO2013107487, WO2013174471.
WO2014007565, WO2014008982, WO2014023377,
WO2014024131, WO2014031977, WO2014038456,
WO2014112450.
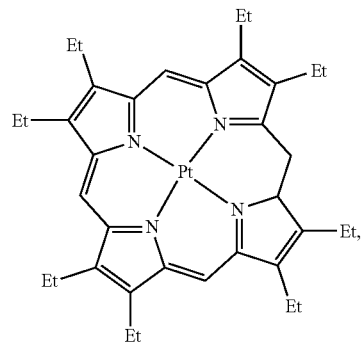
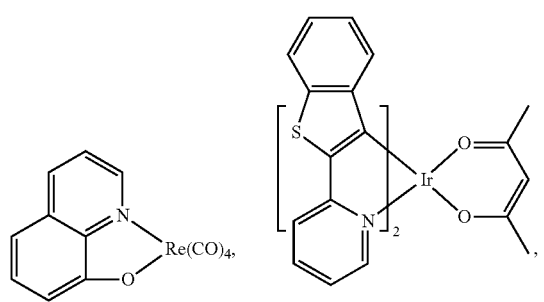
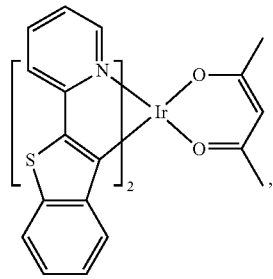
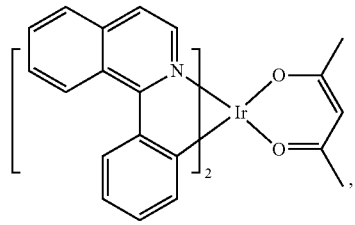
-continued
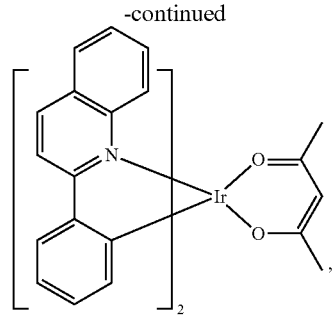
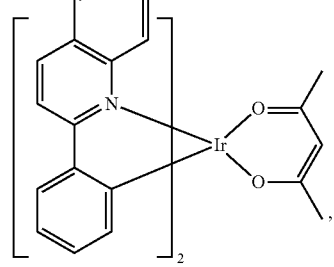
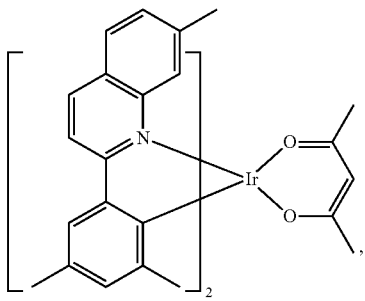
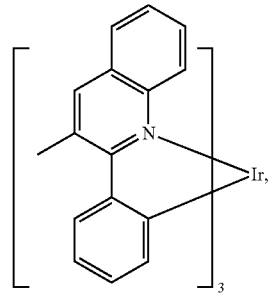
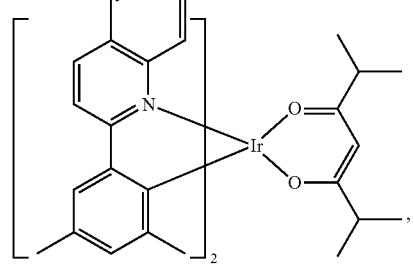
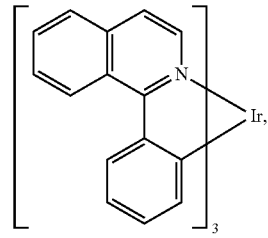

-continued
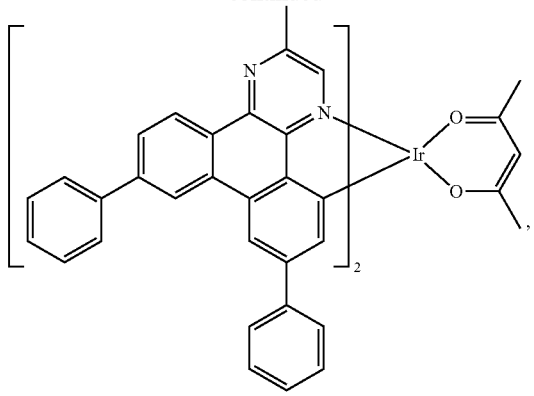
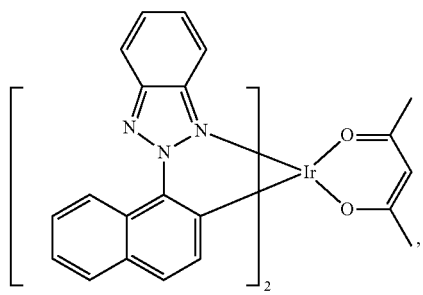
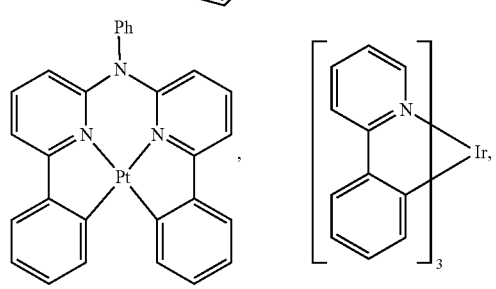
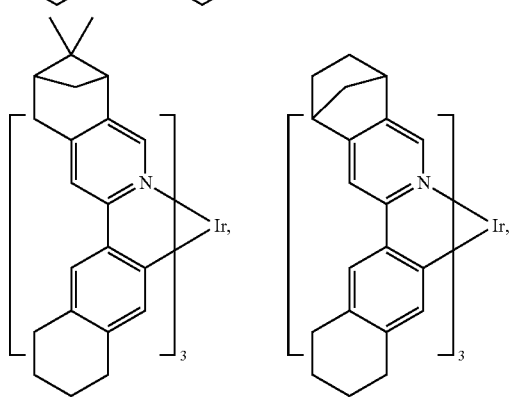
-continued
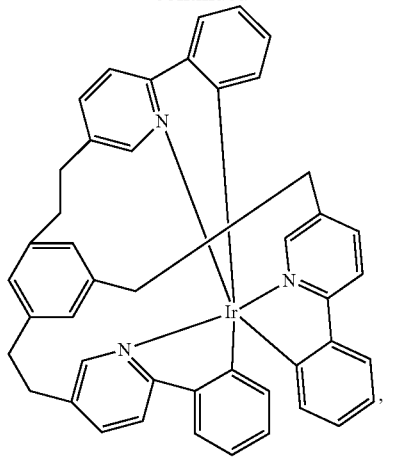
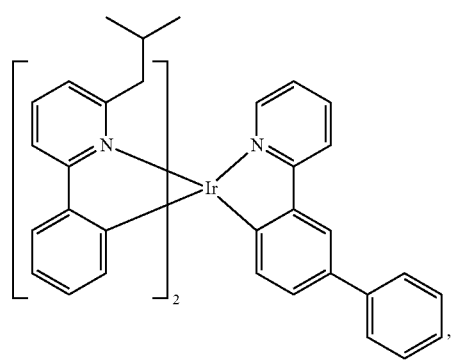
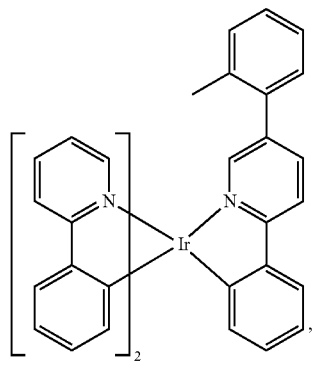
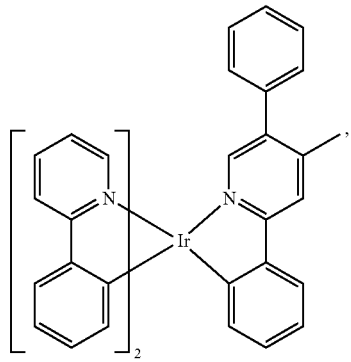

-continued
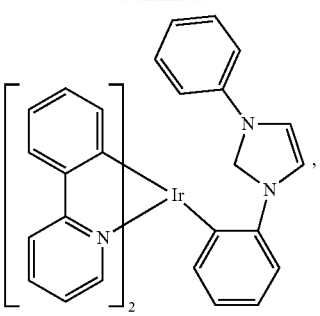
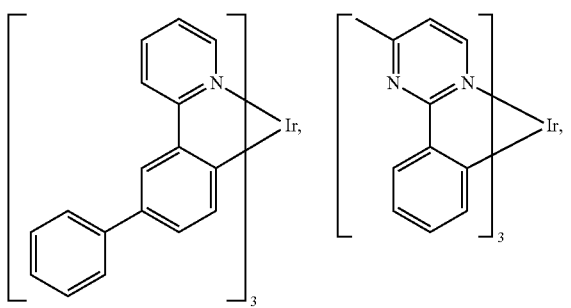
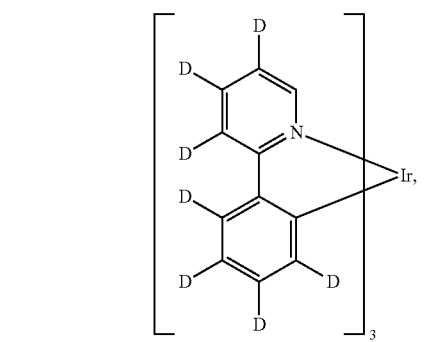
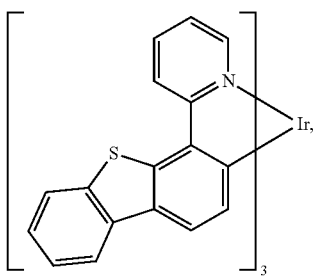
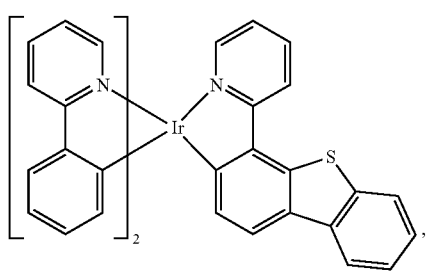
-continued
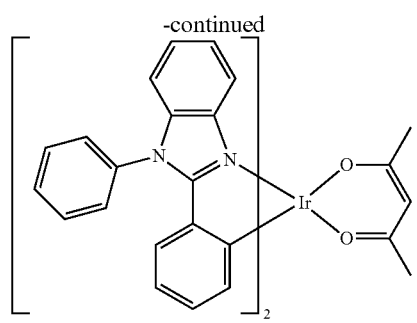
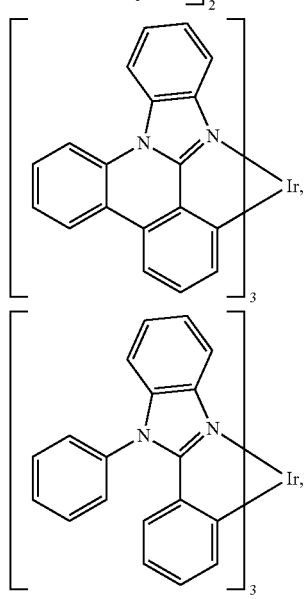
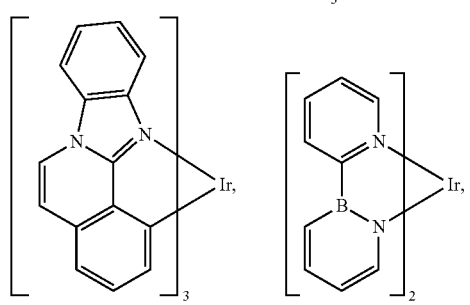
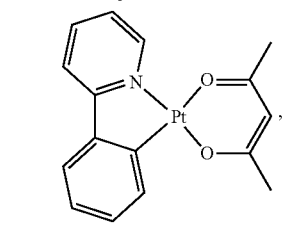
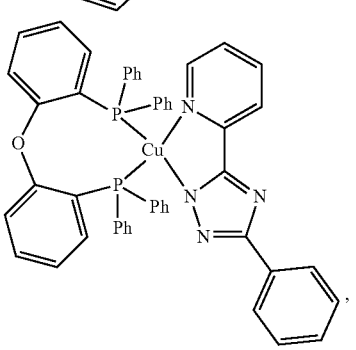

-continued
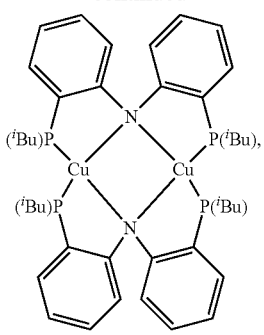
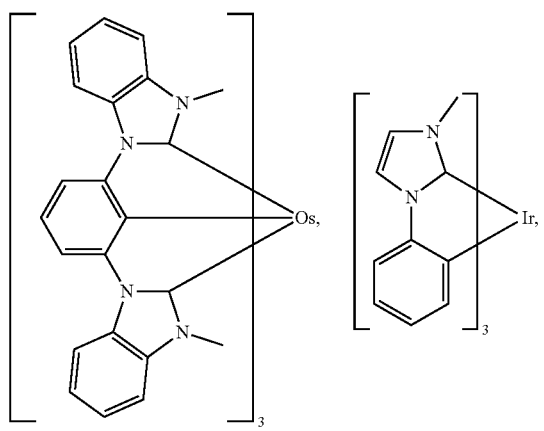
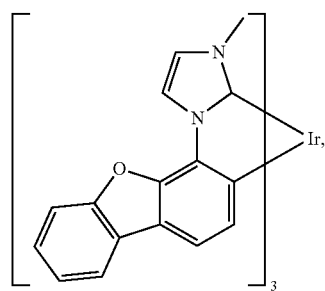
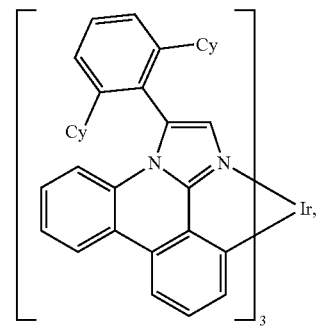
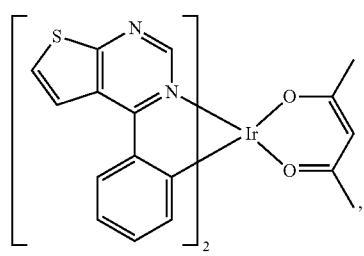
-continued
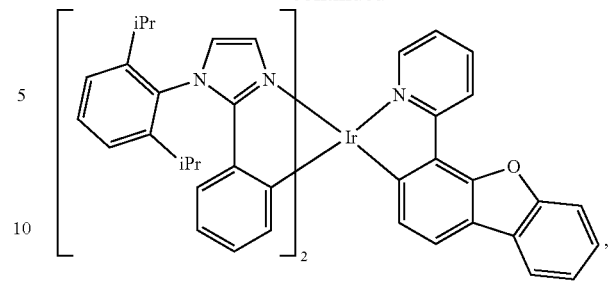
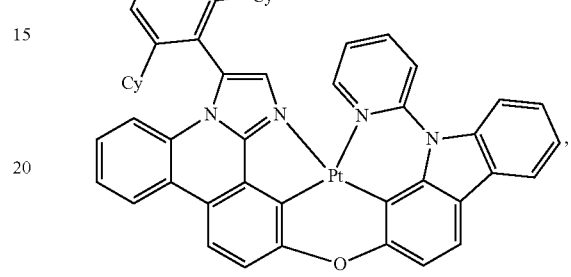
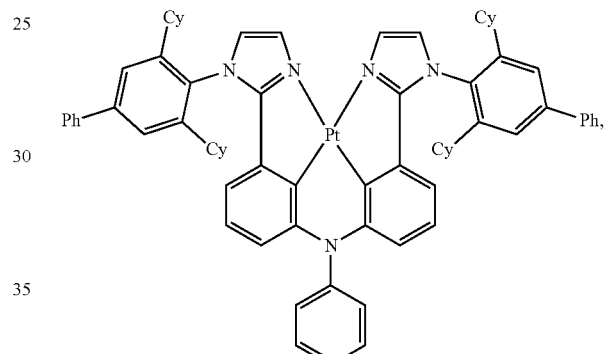
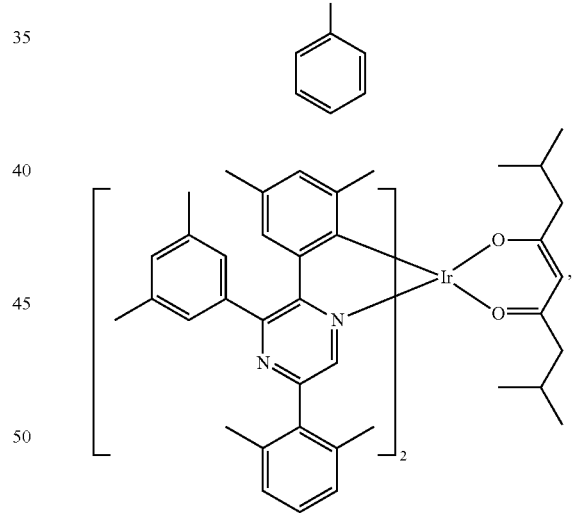
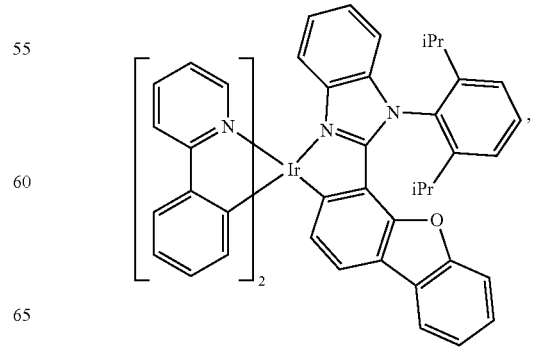

291
-continued
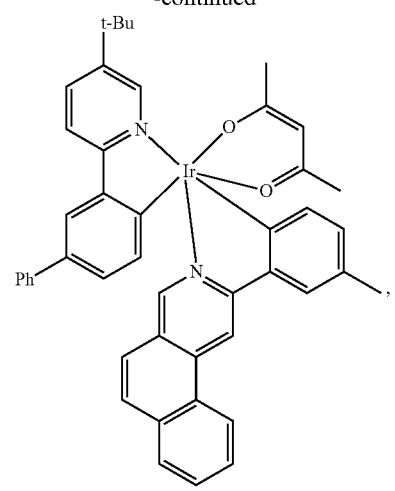
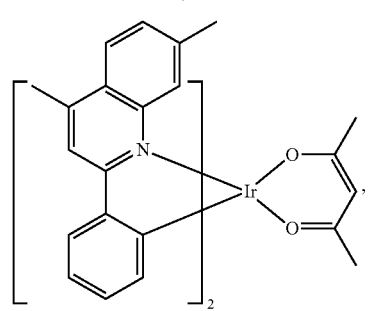
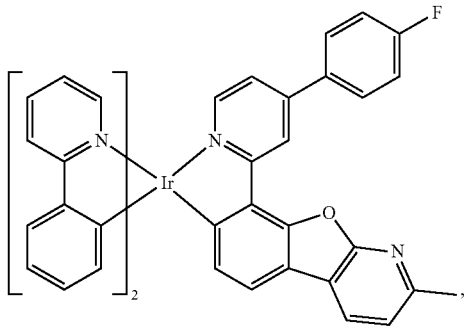
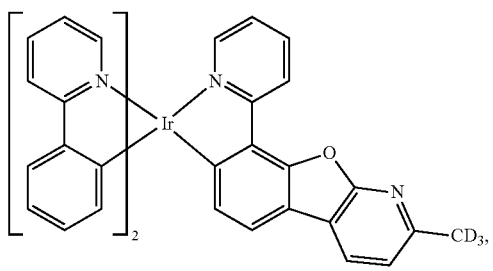
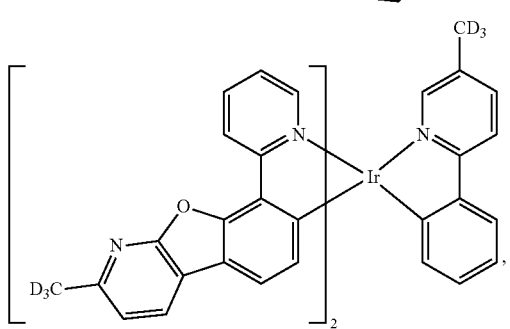
292
-continued
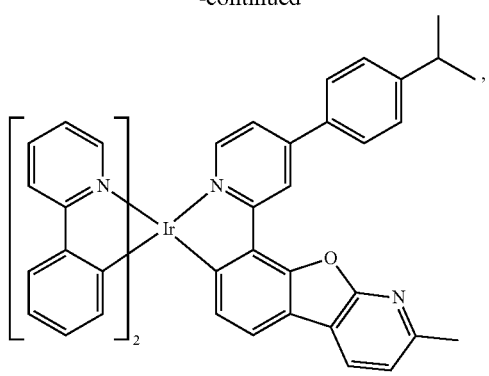
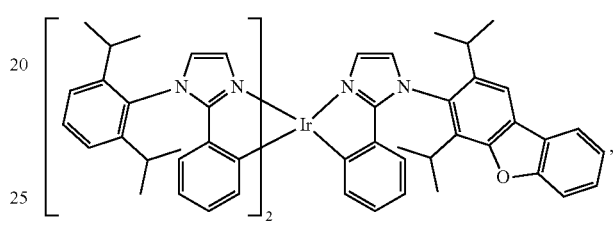
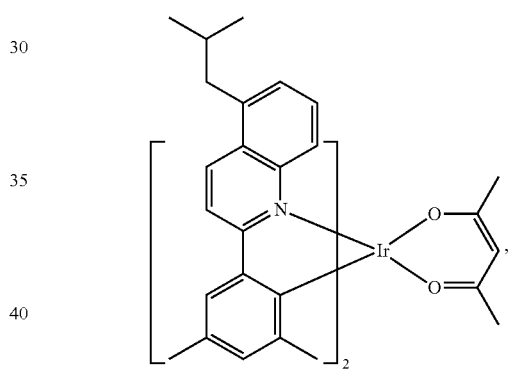
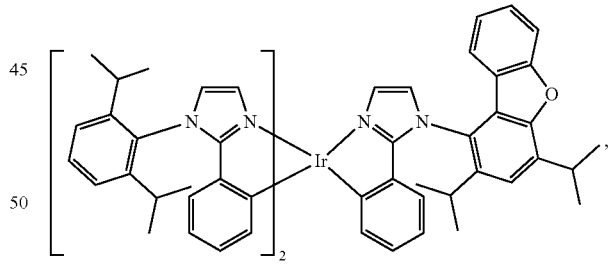
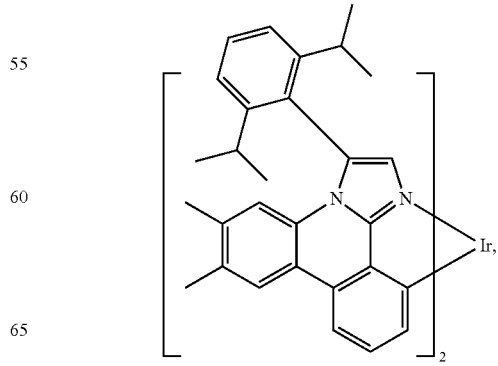

-continued
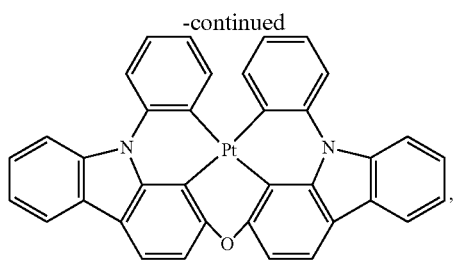
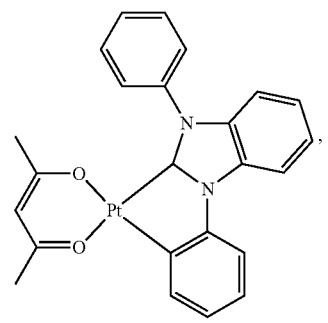
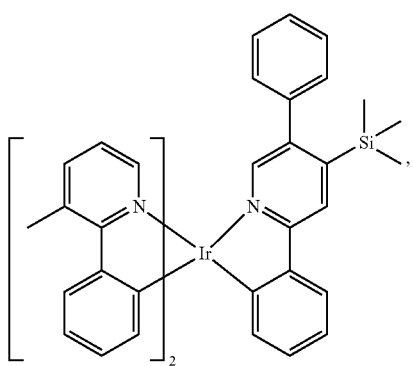
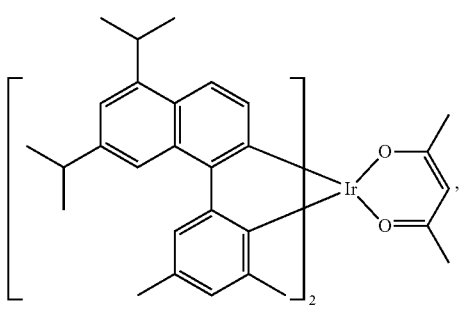
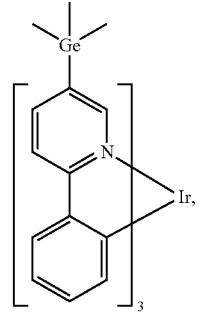
-continued
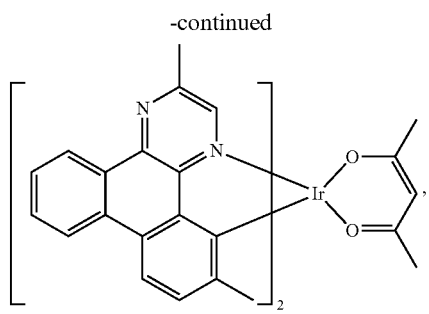
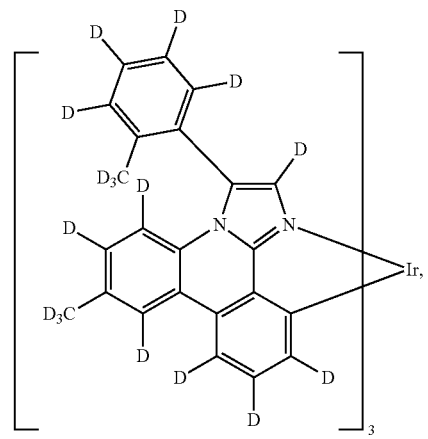
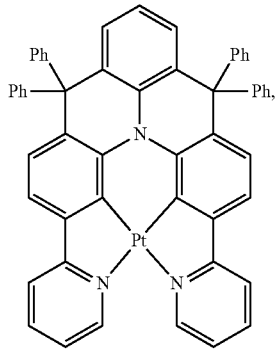
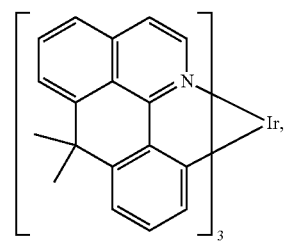
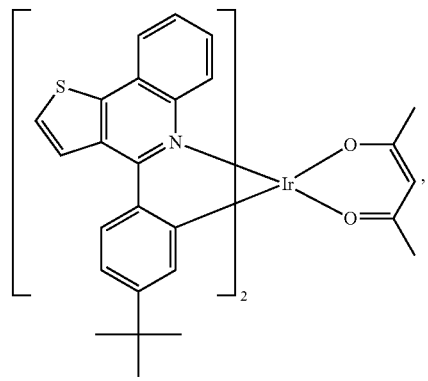

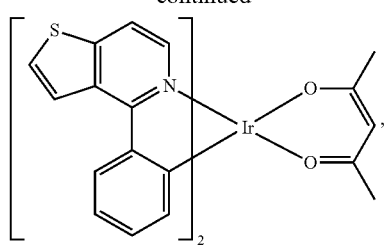
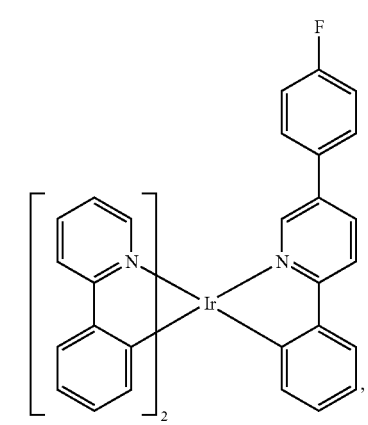
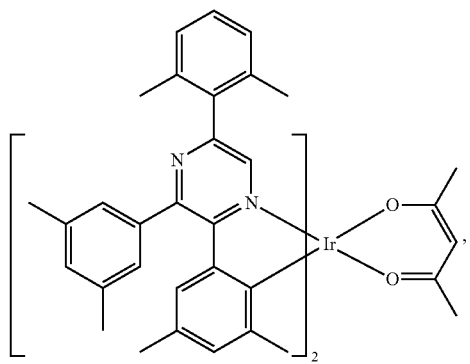
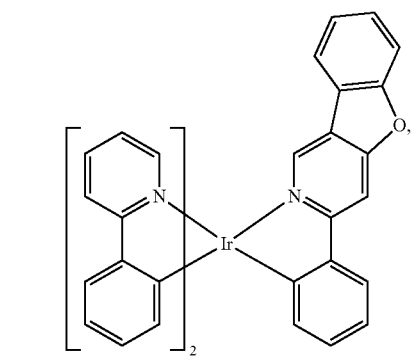
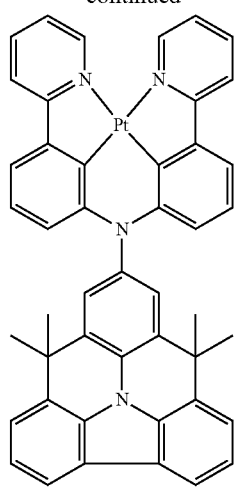
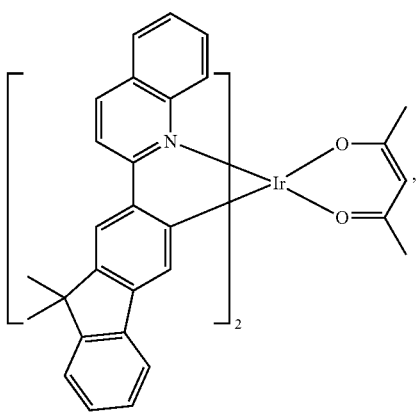
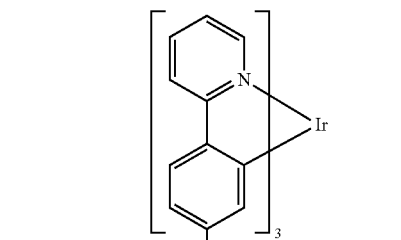
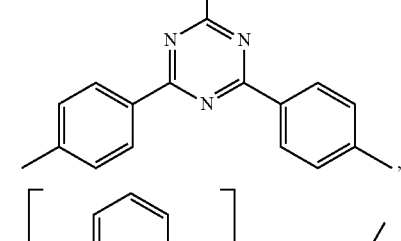
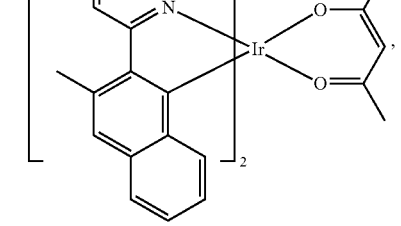

297
-continued
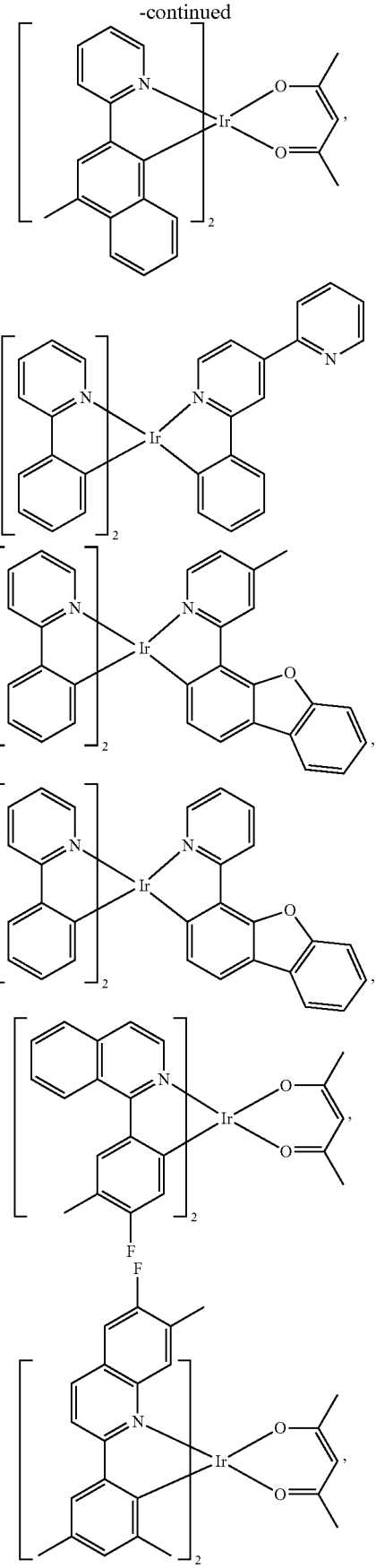
298
-continued
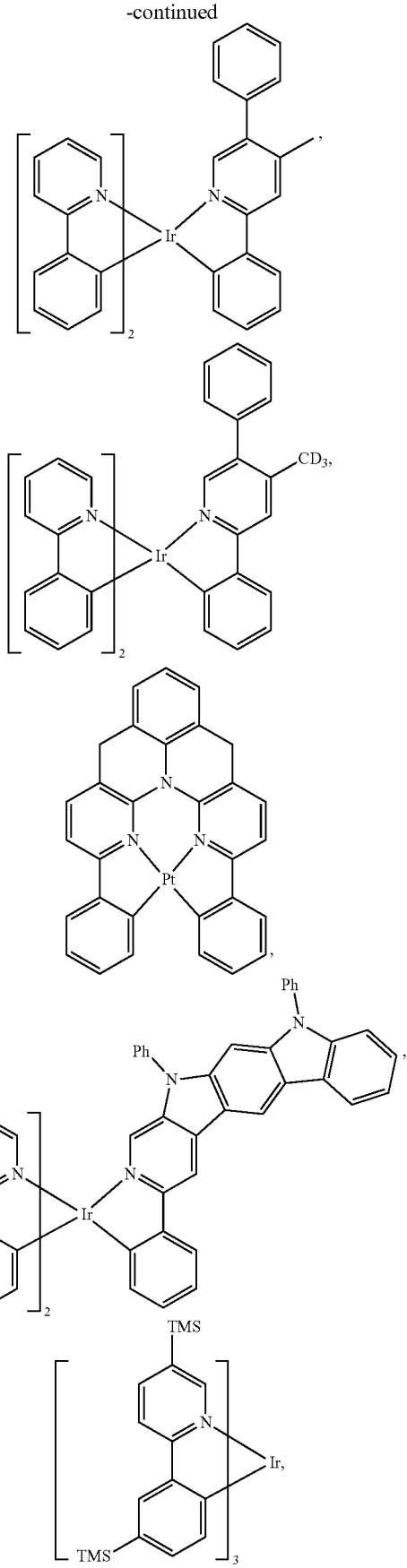

299
-continued
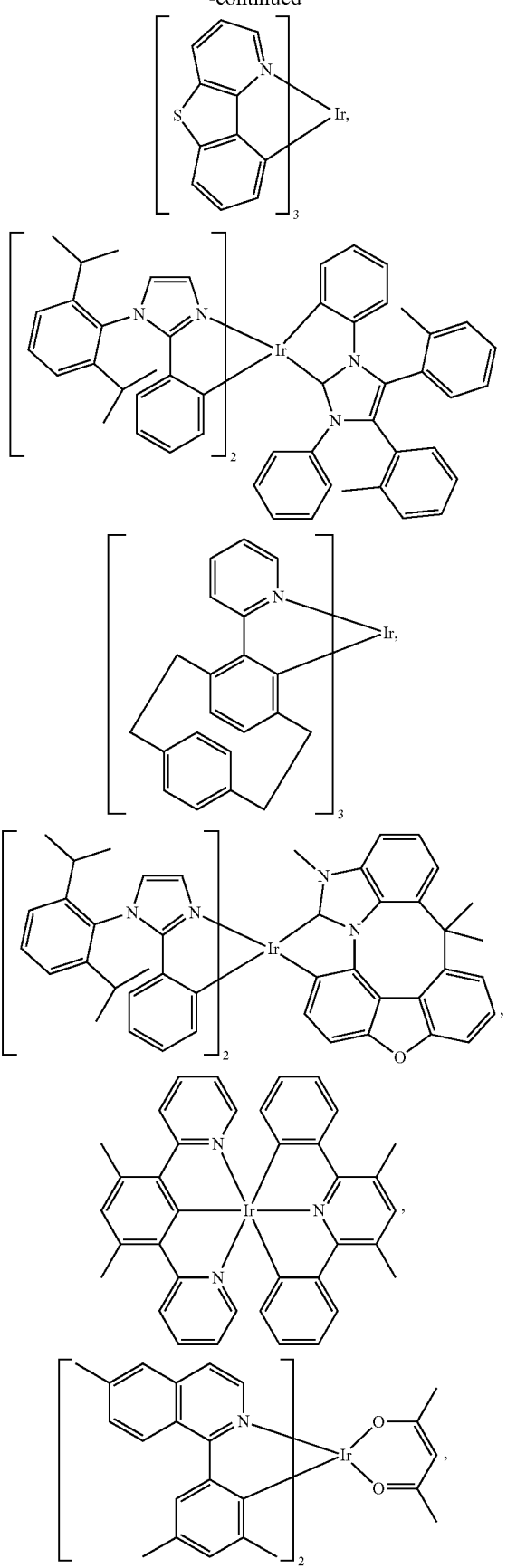
300
-continued
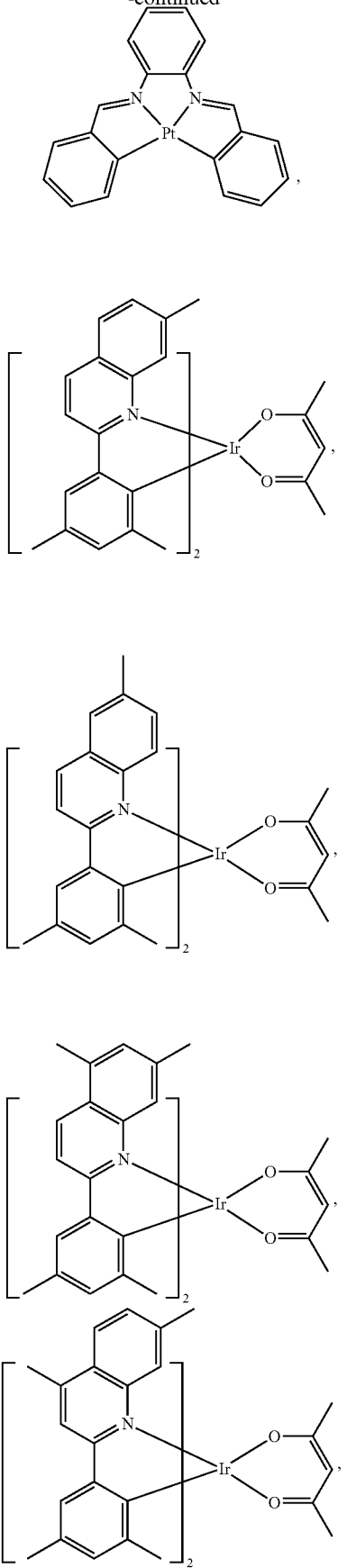

301
-continued
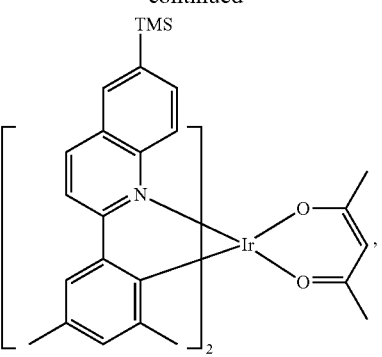
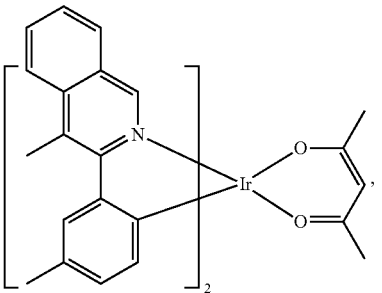
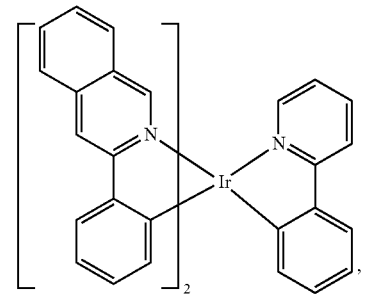
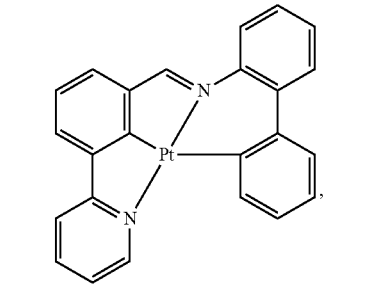
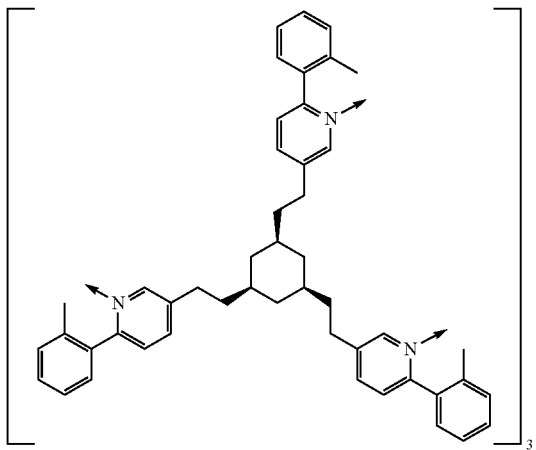
302
-continued
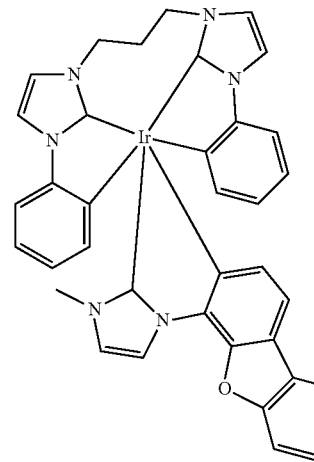
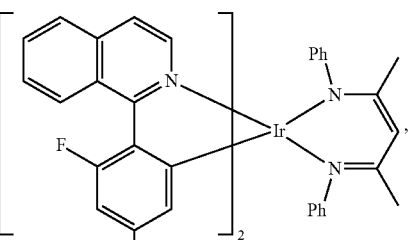
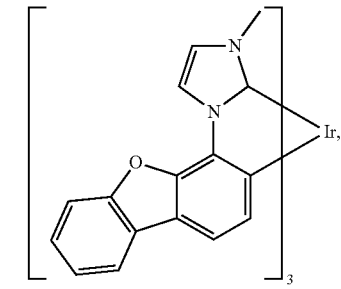
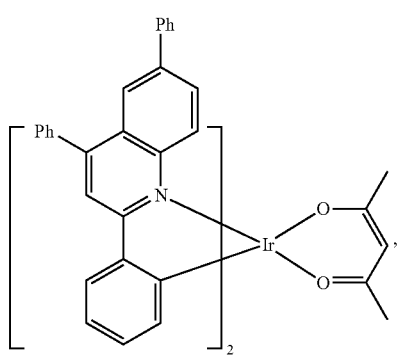
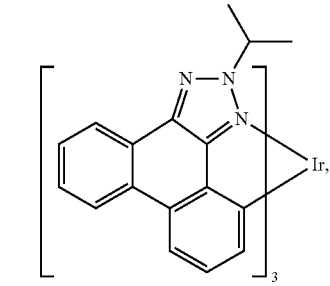

-continued
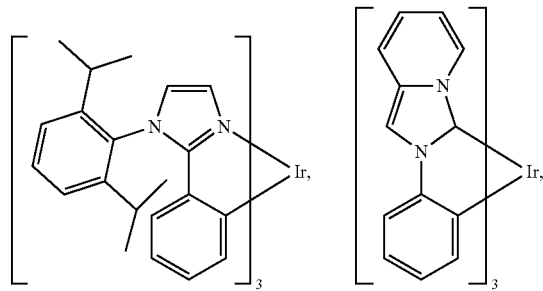
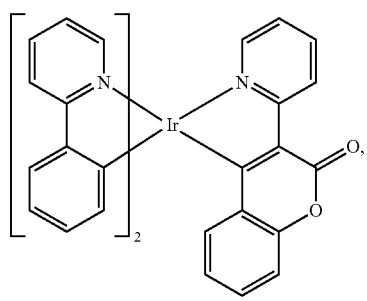
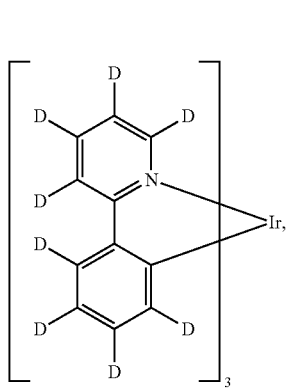
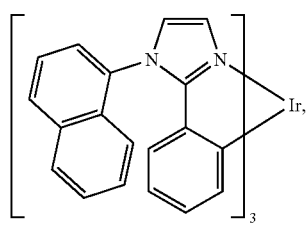
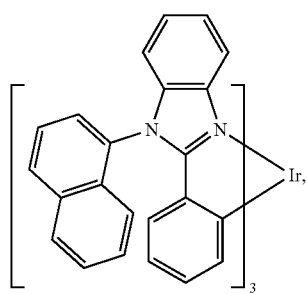
-continued
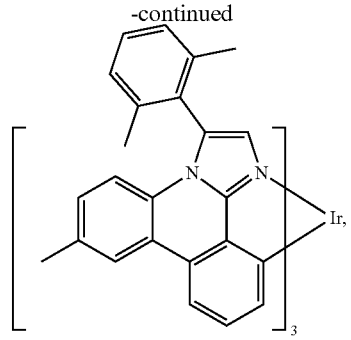
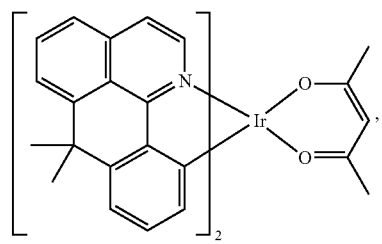
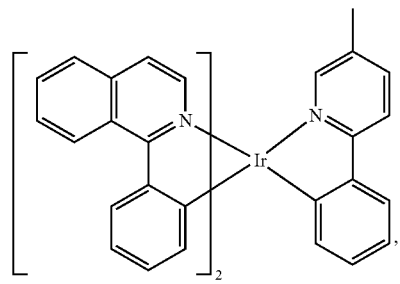
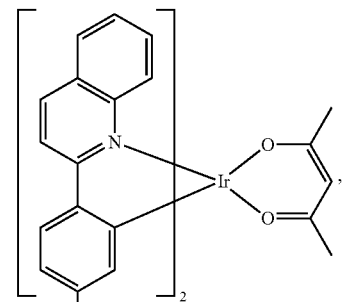
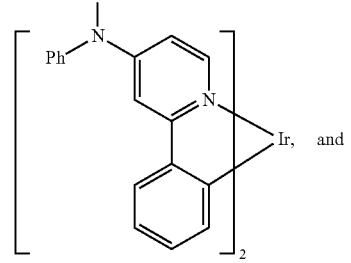
and

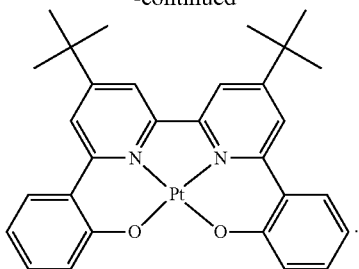

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

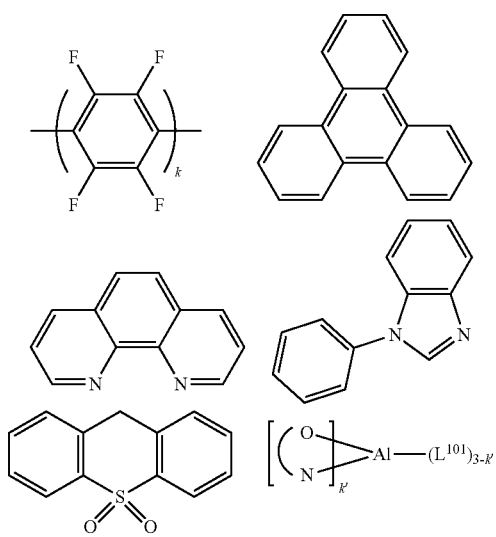

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

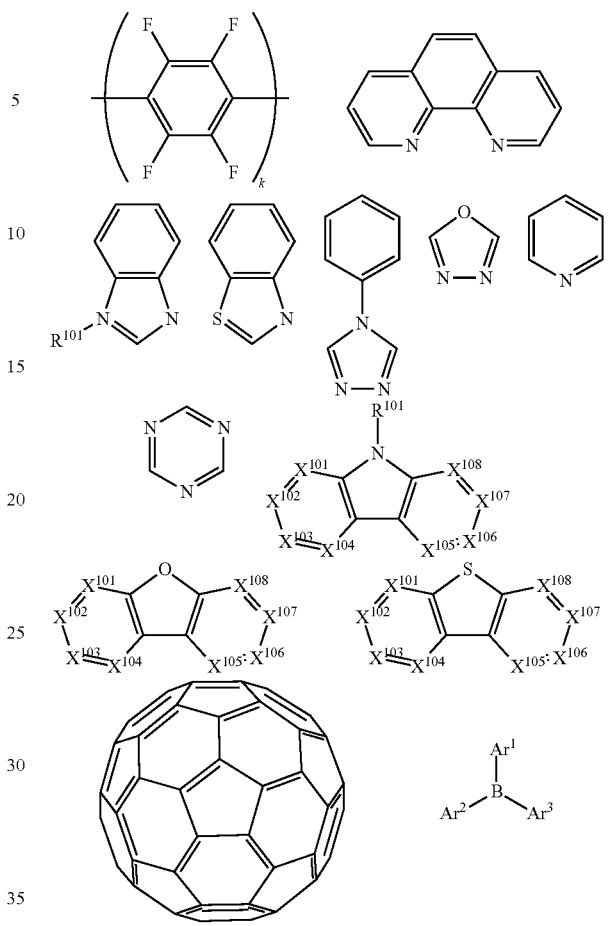

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

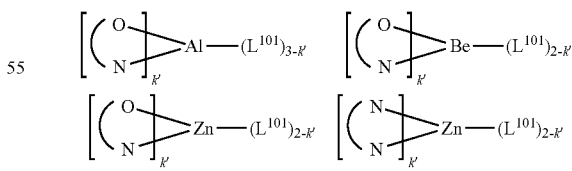

wherein (O—N) or (N—N) is a bidentate ligand, having metal coordinated to atoms O, N or N, N; $L^{101}$ is another ligand: k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535.
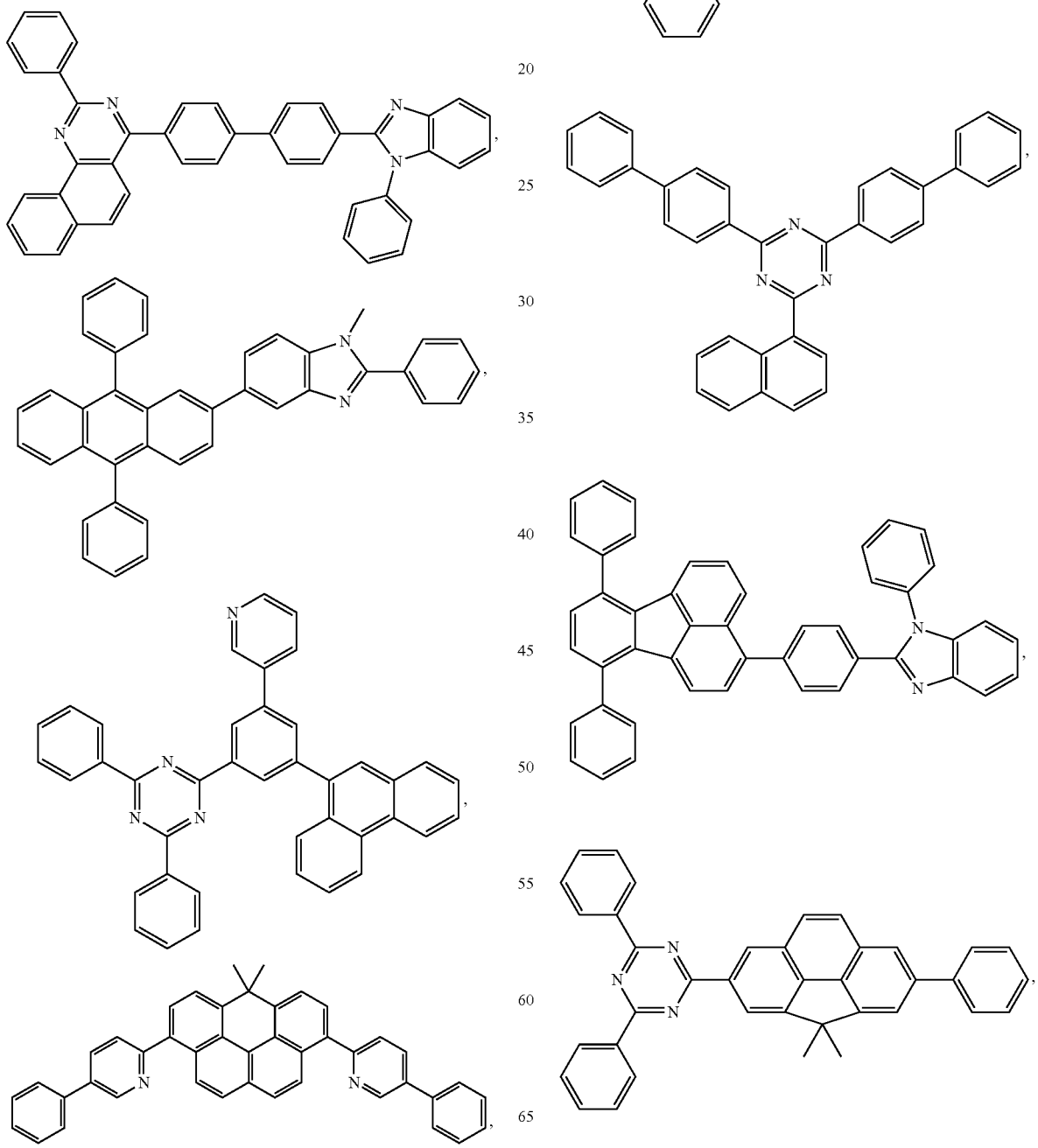

309
-continued
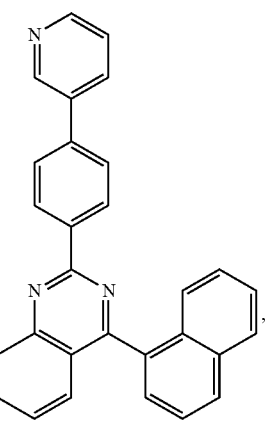
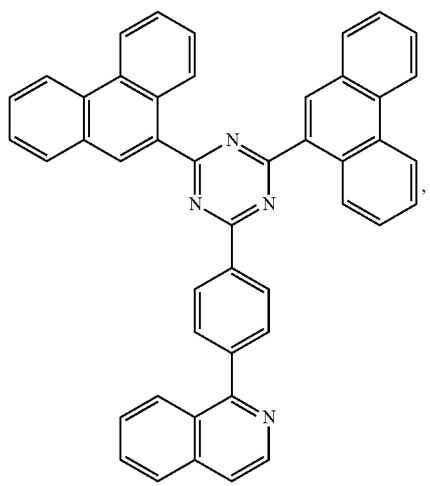
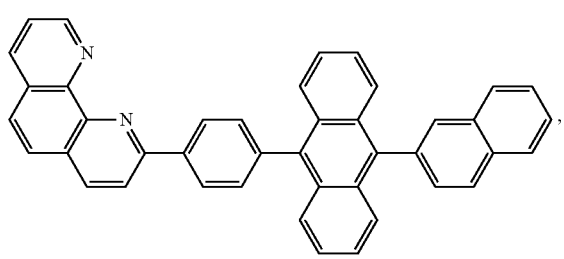
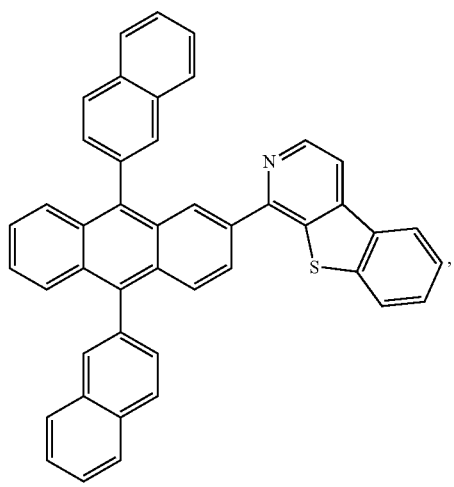
310
-continued
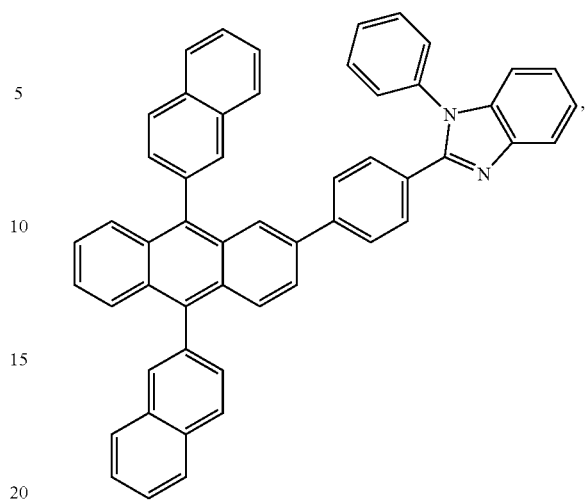
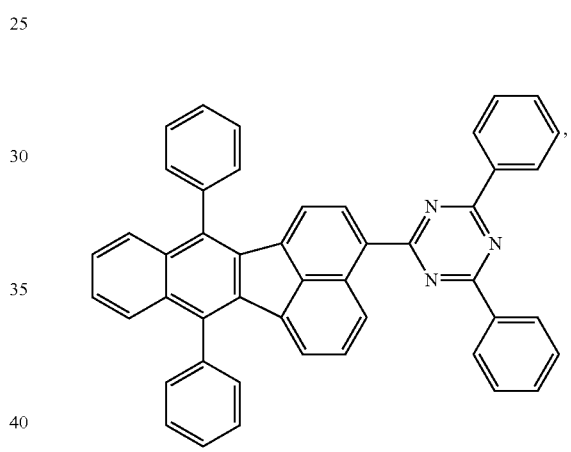
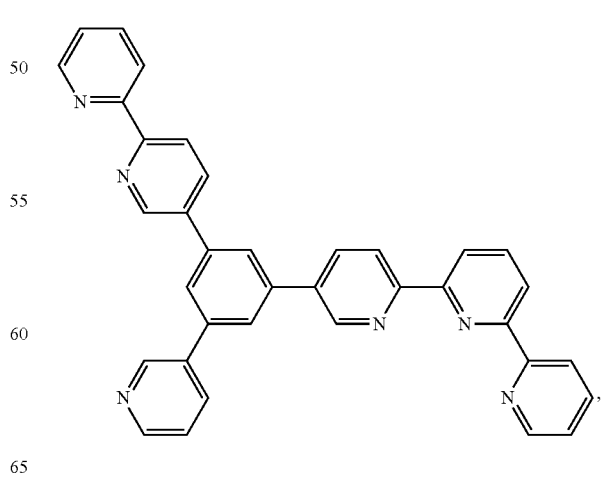

311
-continued
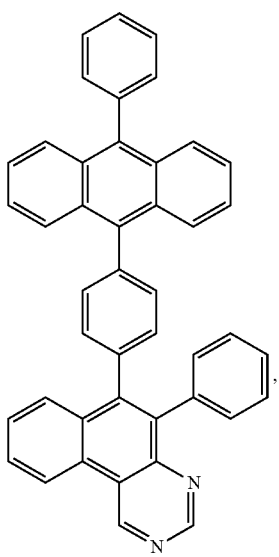
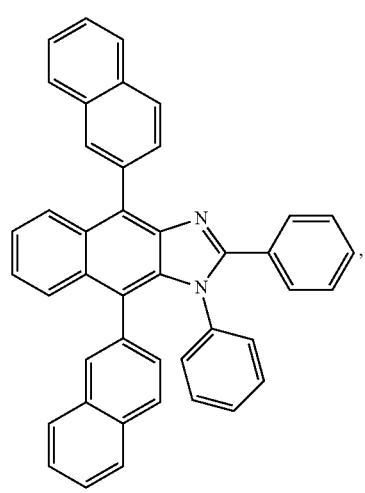
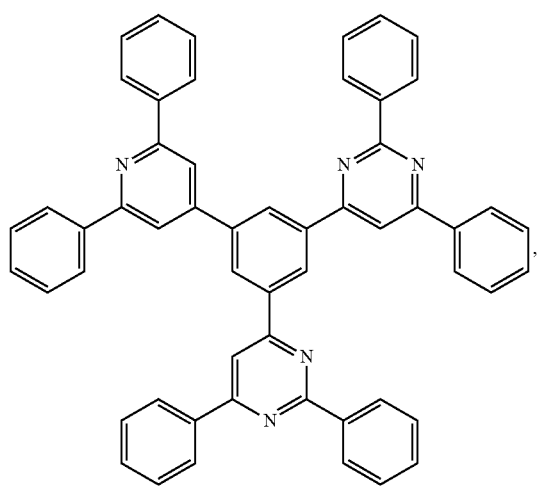
312
-continued
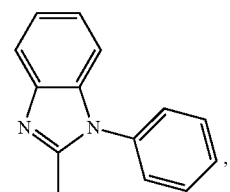
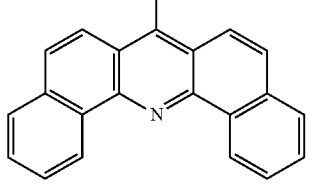
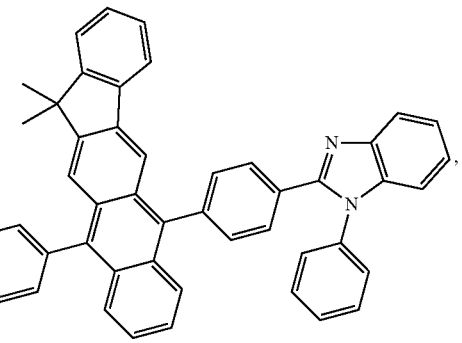
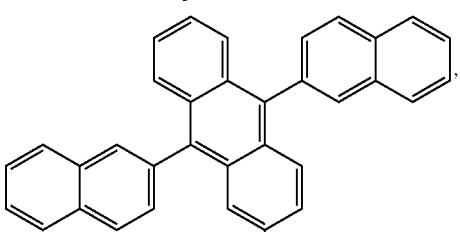
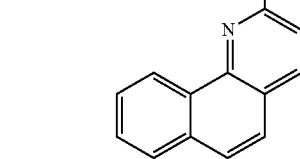
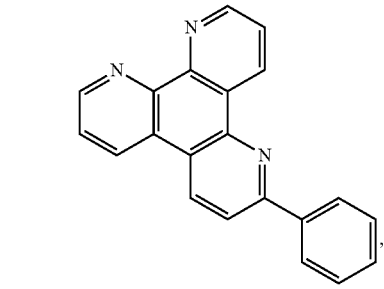

313
-continued
314
-continued
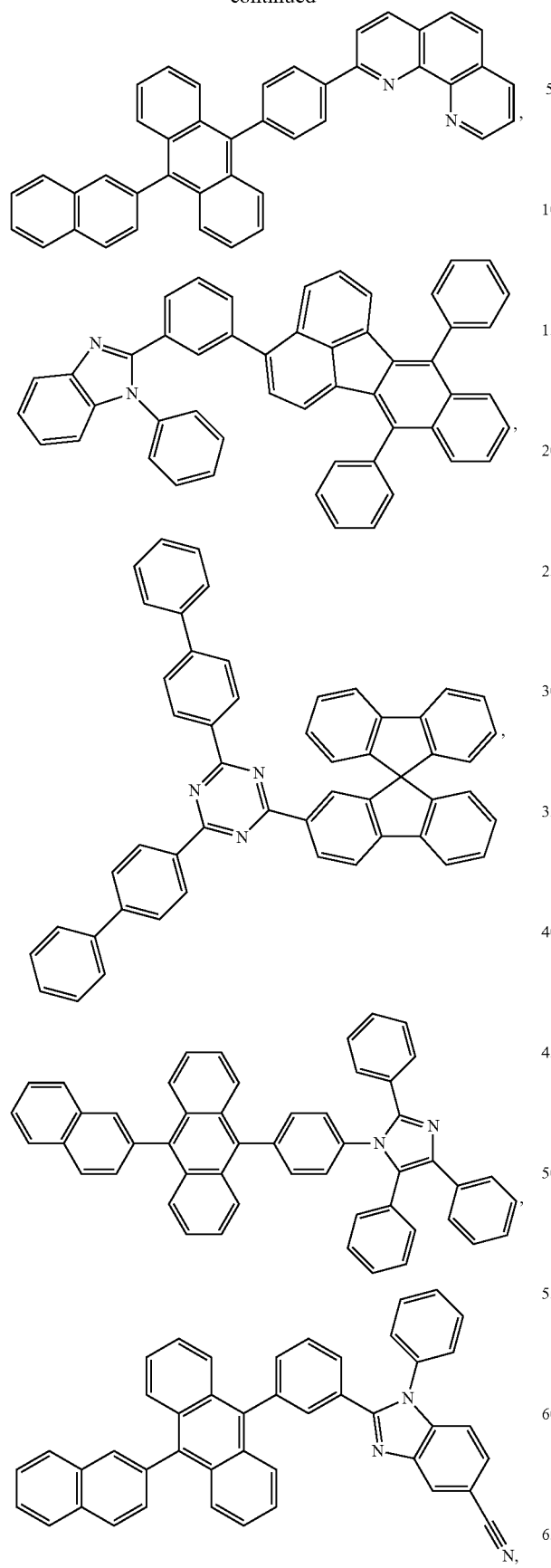
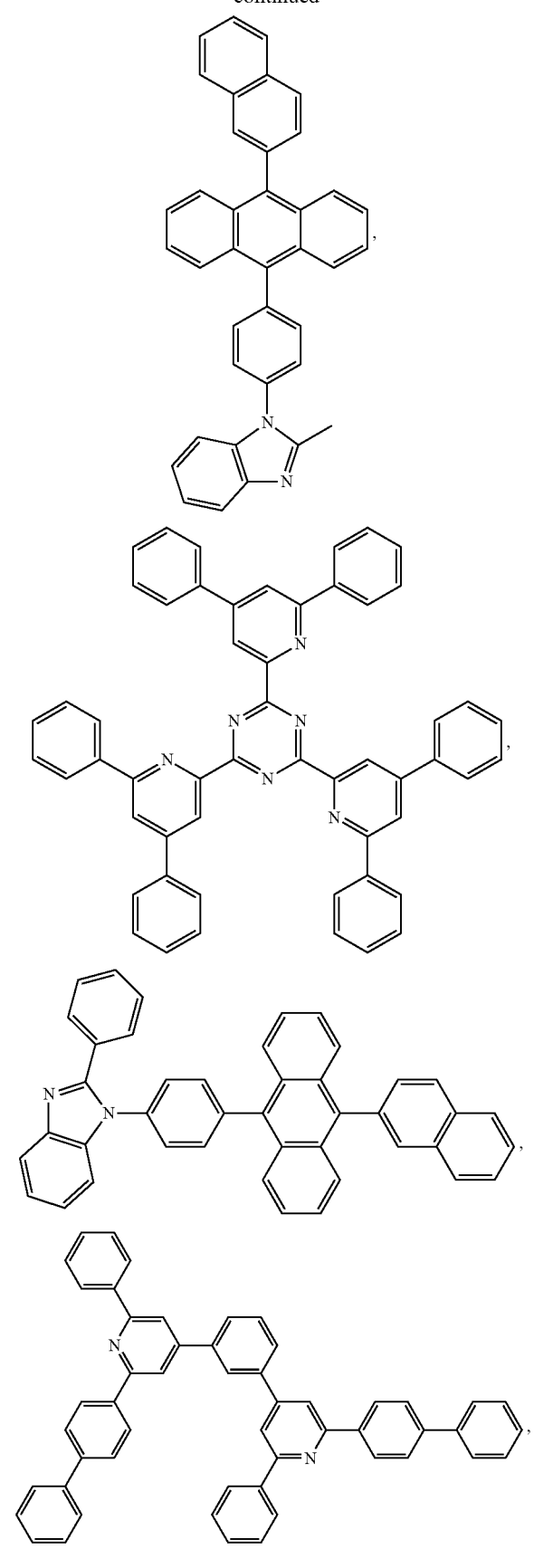

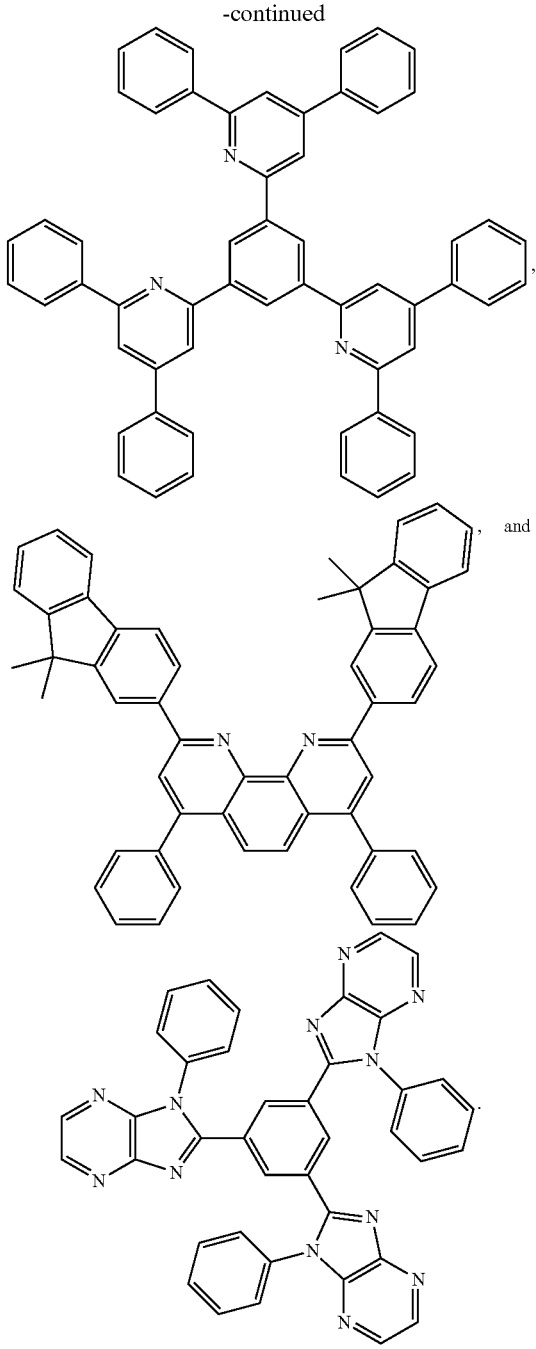
, and

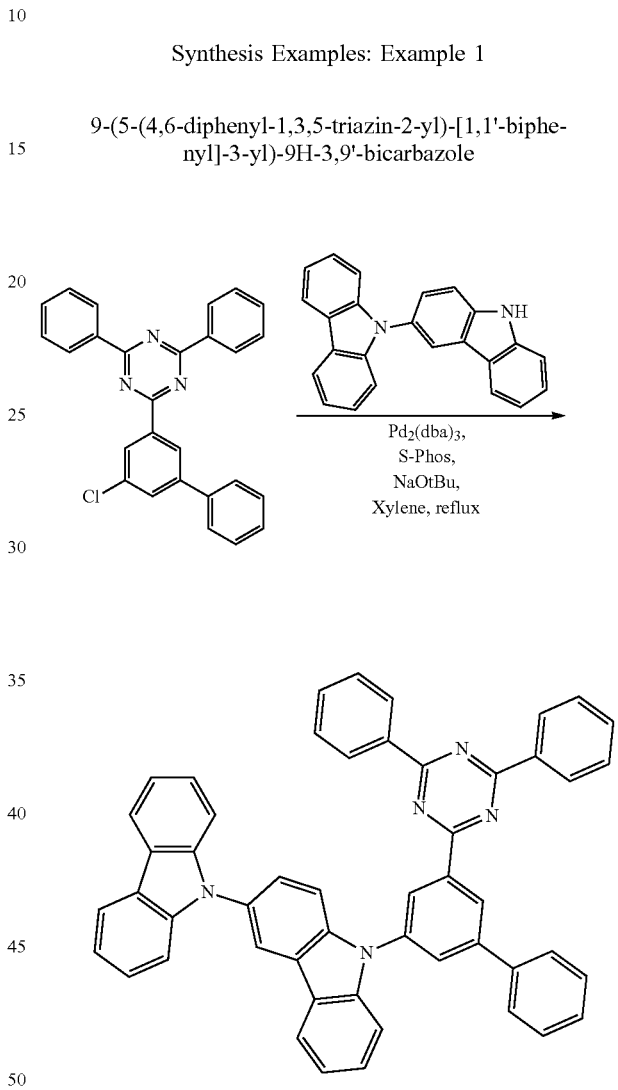

such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

EXPERIMENTAL

Synthesis Examples: Example 1

9-(5-(4,6-diphenyl-1,3,5-triazin-2-yl)-[1,1'-biphenyl]-3-yl)-9H-3,9'-bicarbazole To a 500 mL flask was added 9H-3,9'-bicarbazole (10.0 g, 30.1 mmol), 2-(5-chloro-[1,1'-biphenyl]-3-yl)-4,6-diphenyl-1,3,5-triazine (13.90 g, 33.1 mmol), sodium tert-butoxide (7.23 g, 75 mmol), dicyclohexyl(2',6'-dimethoxy-[1,1'-biphenyl]-2-yl)phosphane (1.235 g, 3.01 mmol), Pd$_2$(dba)$_3$ (1.377 g, 1.504 mmol), and freshly degassed xylenes (150 mL) under nitrogen. Resulting mixture was stirred and heated to reflux for 22 hours. The reaction mixture was cooled to room temperature, diluted with toluene (500 mL) and heated. The resulting solution was filtered through a plug of silica gel and eluted with hot toluene. After concentration of the filtrate under reduced pressure the solid was recrystallized from EtOAc to give 9-(5-(4,6-diphenyl-1,3,5-triazin-2-yl)-[1,1'-biphenyl]-3-yl)-9H-3,9'-bicarbazole (18.8 g; 86% yield) as a yellow solid.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent,

Synthesis Examples: Example 2

9-(3-(4-([1,1'-biphenyl]-3-yl)-6-phenyl-1,3,5-triazin-2-yl)phenyl)-9H-3,9'-bicarbazole

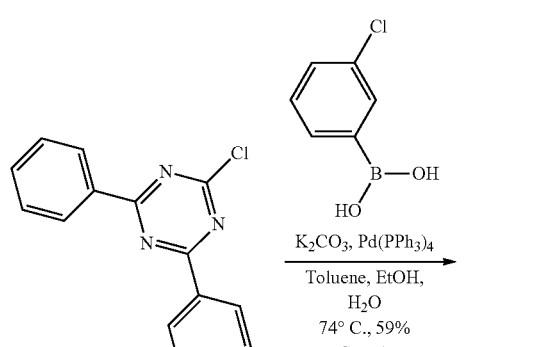

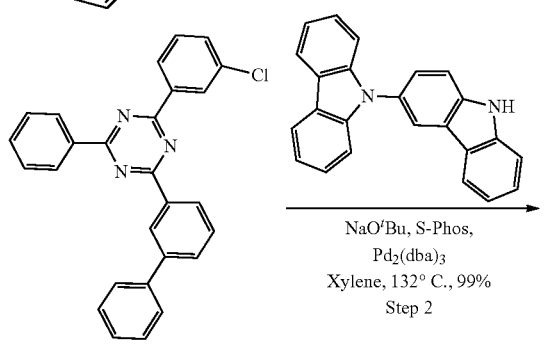

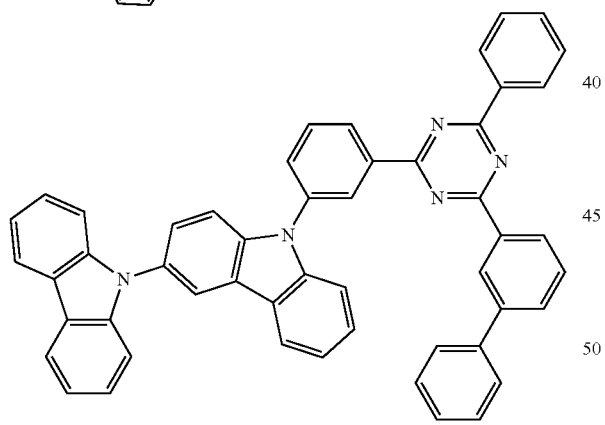

Step 1. 500 mL flask was charged with 2-([1,1'-biphenyl]-3-yl)-4-chloro-6-phenyl-1,3,5-triazine (14 g, 40.7 mmol), (3-chlorophenyl)boronic acid (7.00 g, 44.8 mmol), $K_2CO_3$ (16.88 g, 122 mmol), toluene (86 ml), ethanol (42.8 ml), and water (42.8 ml). The resulting mixture was stirred, degassed and then Pd(PPh$_3$)$_4$ (2.353 g, 2.036 mmol) was added. After overnight reflux, the reaction mixture cooled to room temperature. Precipitated solid was filtered and washed with water, methanol, and acetone. The solid was further dissolved in DCM, washed with water and brine. The organic layer was dried with $Na_2SO_4$, filtered through a plug of silica, and then concentrated to dryness. Resulting solid was triturated with DCM and MeOH to afford 2-([1,1'-biphenyl]-3-yl)-4-(3-chlorophenyl)-6-phenyl-1,3,5-triazine (14.18 g, 33.4 mmol, 82% yield) as a white solid.

Step 2. To a 500 mL flask under nitrogen was added 9H-3,9'-bicarbazole (9.000 g, 27.1 mmol), 2-([1,1'-biphenyl]-3-yl)-4-(3-chlorophenyl)-6-phenyl-1,3,5-triazine (13.64 g, 32.5 mmol), sodium tert-butoxide (6.51 g, 67.7 mmol), dicyclohexyl(2',6'-dimethoxy-[1,1'-biphenyl]-2-yl)phosphine (1.112 g, 2.71 mmol), Pd$_2$(dba)$_3$ (1.240 g, 1.354 mmol) and xylene (136 ml). The resulting mixture was stirred, degassed and then heated to reflux overnight. The reaction mixture was cooled, diluted with toluene, heated and then resulting solution was passed through a plug of silica gel. The plug was eluted with hot toluene, fractions containing product were combined and concentrated. The resulting residue was triturated with Toluene/MeOH followed by DCM/MeOH to obtain 9-(3-(4-([1,1'-biphenyl]-3-yl)-6-phenyl-1,3,5-triazin-2-yl)phenyl)-9H-3,9'-bicarbazole (18.64 g, 26.0 mmol, 96% yield) as a yellow solid.

Synthesis Examples: Example 3

9-(3-(4-([1,1'-biphenyl]-2-yl)-6-phenyl-1,3,5-triazin-2-yl)phenyl)-9H-3,9'-bicarbazole

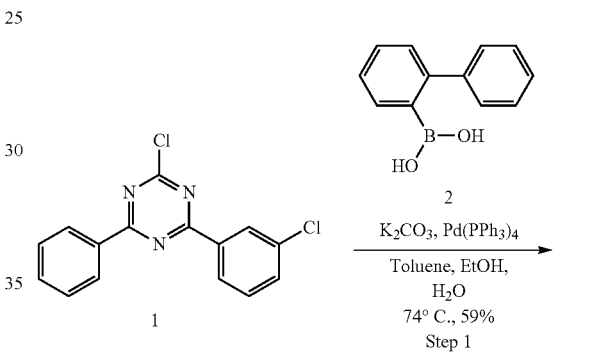

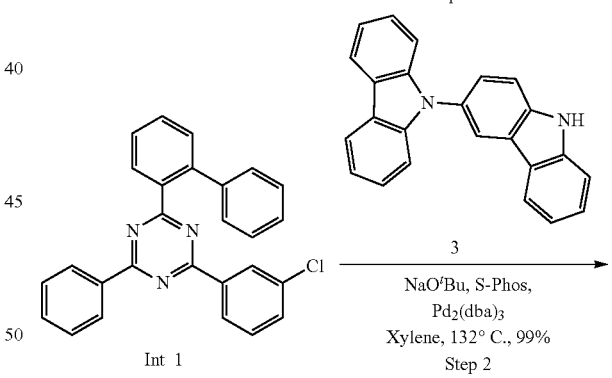

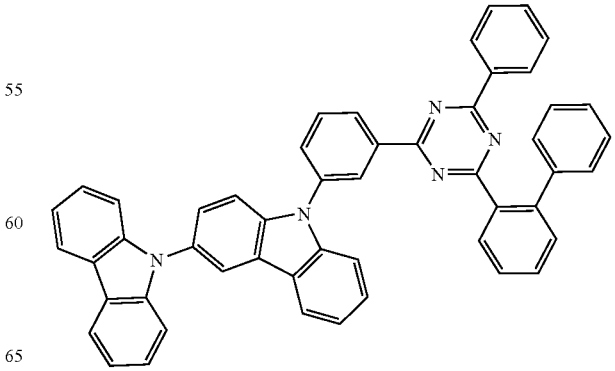

Step 1. A 1 L flask equipped with stir bar, condenser, and thermowell was charged with 2-chloro-4-(3-chlorophenyl)-6-phenyl-1,3,5-triazine (15 g, 49.6 mmol), [1,1'-biphenyl]-2-ylboronic acid (10.03 g, 50.6 mmol), potassium carbonate (20.58 g, 149 mmol), toluene (100 ml), ethanol (50.0 ml) and water (50.0 ml). The resultant mixture was degassed (vacuum and nitrogen backfill for 3 times). Pd(PPh$_3$)$_4$ (2.87 g, 2.482 mmol) was then added, and the reaction mixture was heated to reflux for overnight. The reaction mixture was cooled, organic layer was separated, and aqueous layer was extracted with toluene. The combined organic layer was washed with water and filtered through the silica plug, plug was eluted with hot toluene and fractions containing product were concentrated. Resulting solid was triturated with Toluene/MeOH followed by MeOH to obtain 2-([1, 1'-biphenyl]-2-yl)-4-(3-chlorophenyl)-6-phenyl-1,3,5-triazine (12.44 g, 59% yield).

Step 2. To a 1L Round Bottom flask equipped with stir bar, condenser, and thermowell was added 2-([1, 1'-biphenyl]-2-yl)-4-(3-chlorophenyl)-6-phenyl-1,3,5-triazine (12.4 g, 29.5 mmol), 9H-3,9'-bicarbazole (8.92 g, 26.8 mmol), dicyclohexyl(2',6'-dimethoxy-[1,1'-biphenyl]-2-yl)phosphane (1.322 g, 3.22 mmol), sodium tert-butoxide (5.16 g, 53.7 mmol), Xylene (224 ml). The resultant mixture was degassed (vacuum and nitrogen refill for 3 times), and Pd$_2$(dba)$_3$ (1.474 g, 1.610 mmol) was added. The resulting mixture was stirred and heated and refluxed overnight. The reaction mixture was then cooled to room temperature, filtered through the silica plug, and plug was eluted with toluene. Fractions containing product were combined and concentrated. Trituration of the resulting solid with Toluene/MeOH gave 19 g (99% yield) of 9-(3-(4-([1,1'-biphenyl]-2-yl)-6-phenyl-1,3,5-triazin-2-yl)phenyl)-9H-3,9'-bicarbazole as a yellow solid.

Synthesis Examples: Example 4

9-(3-(4-([1,1'-biphenyl]-4-yl)-6-phenyl-1,3,5-triazin-2-yl)phenyl)-9H-3,9'-bicarbazole

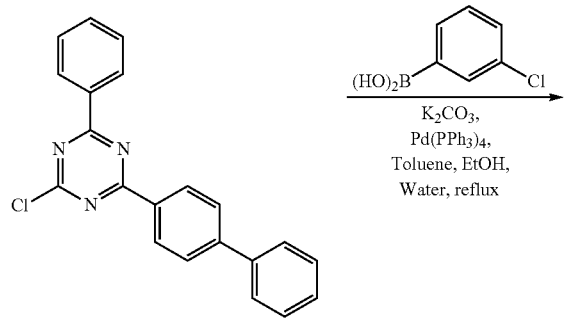

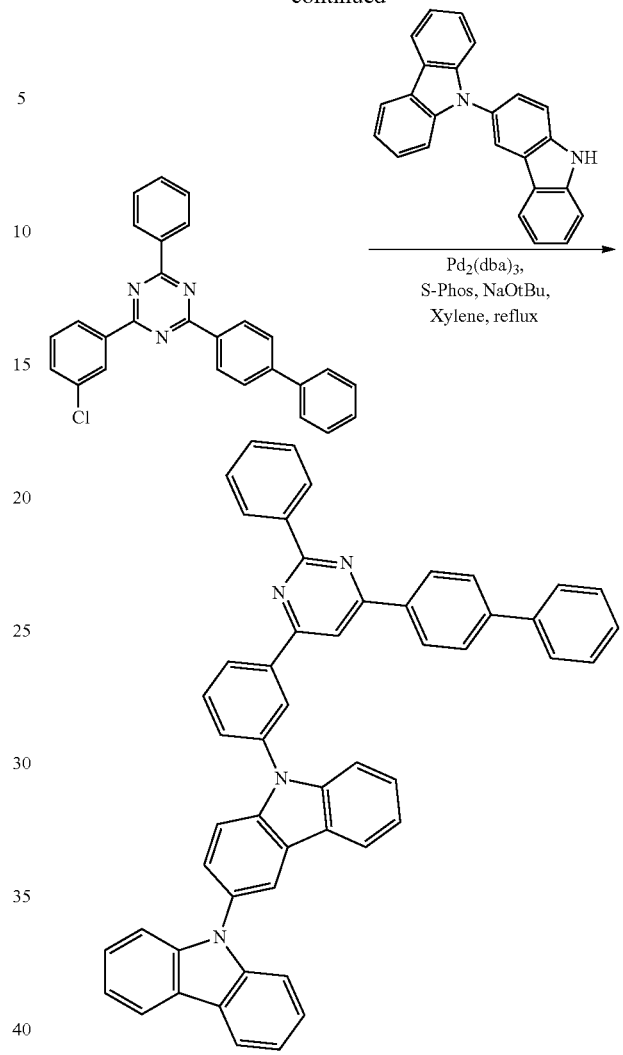

Step 1. To a 1 L, 3-neck flask under nitrogen, equipped with a water condenser, magnetic stirrer and thermowell, 2-([1,1'-biphenyl]-4-yl)-4-chloro-6-phenyl-1,3,5-triazine (20 g, 58.2 mmol), (3-chlorophenyl)boronic acid (10.01 g, 64.0 mmol), potassium carbonate (24.12 g, 175 mmol), toluene (120 mL), ethanol (60 mL) and water (60 mL) were added and the mixture was degassed (vacuum-nitrogen backfill for 3 times). Pd(PPh$_3$)$_4$ (3.36 g, 2.91 mmol) was added and the resulting mixture was further degassed (vacuum-nitrogen backfill for 3 times). The reaction mixture was heated to reflux. After 16 hours, the reaction mixture was cooled to room temperature. The precipitated solid was filtered, washed with water, methanol and acetone. The solid was dried, suspended in acetone and stirred for 2 h. The suspension was filtered to obtain 2-([1, 1'-biphenyl]-4-yl)-4-(3-chlorophenyl)-6-phenyl-1,3,5-triazine (24 g, 98%) as a white solid.

Step 2. To a dry 1 L 3-neck flask under nitrogen, equipped with a water condenser, magnetic stirrer and thermowell, 2-([1,1'-biphenyl]-4-yl)-4-(3-chlorophenyl)-6-phenyl-1,3,5-triazine (10.75 g, 25.6 mmol), 9H-3,9'-bicarbazole (8.51 g, 25.6 mmol), sodium 2-methylpropan-2-olate (4.92 g, 51.2 mmol) and Xylene (213 ml) were added and the mixture was degassed (vacuum-nitrogen backfill for 3 times). Dicyclohexyl(2',6'-dimethoxy-[1,1'-biphenyl]-2-yl)phosphane (1.261 g, 3.07 mmol) and Pd$_2$dba$_3$ (1.407 g, 1.536 mmol) were added and the resulting mixture was further degassed (vacuum-nitrogen backfill for 3 times). The reaction mixture was heated to reflux. After 18 hours, the hot mixture was passed over a thick pad of silica saturated with hot toluene. The compound was eluted with hot toluene and TLC pure fractions were combined, concentrated and triturated with methanol to obtain 9-(3-(4-([1,1'-biphenyl]-4-yl)-6-phenyl-1,3,5-triazin-2-yl)phenyl)-9H-3,9'-bicarbazole as a yellow solid (16.66 g, 91%).

Synthesis Examples: Example 5

Synthesis of 9-(4-(4-([1,1'-biphenyl]-3-yl)-6-phenyl-1,3,5-triazin-2-yl)phenyl)-9H-3,9'-bicarbazole

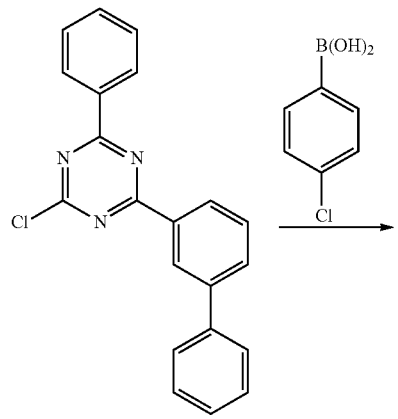

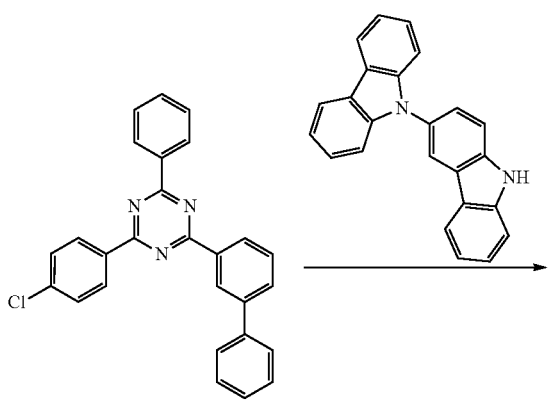

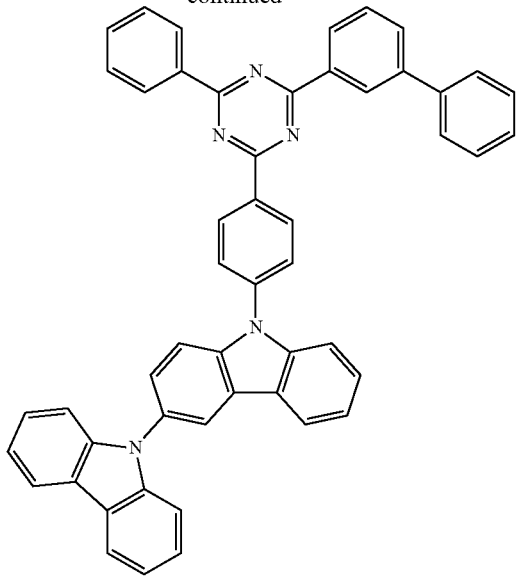

Step 1. To a mixture of 2-([1,1'-biphenyl]-3-yl)-4-chloro-6-phenyl-1,3,5-triazine (8.60 g, 25.0 mmol) and (4-chlorophenyl)boronic acid (4.30 g, 27.5 mmol) in 1,4-dioxane (200 mL) was added a solution of sodium carbonate (5.83 g, 55.0 mmol) in water (40 mL) and the mixture was degassed with bubbling N$_2$ for 30 min. Tetrakis(triphenylphosphine)palladium (1.45 g, 1.25 mmol) was added and the mixture was stirred at 80° C. for 17 hours. The reaction mixture was cooled to room temperature (RT), diluted with water (200 mL) and the solid was collected by filtration. Purification by flash column chromatography (silica gel, 220 g column, 0-100% DCM/hexane) provided a solid, which was suspended in MeOH (200 mL) and heated at reflux for 16 hours, then cooled to RT. The solid was collected by filtration, washed with MeOH (50 mL) and isohexane (100 mL) and dried in vacuo to give 2-([1,1'-biphenyl]-3-yl)-4-(4-chlorophenyl)-6-phenyl-1,3,5-triazine (6.57 g, 15.5 mmol, 62% yield, 99% purity) as a pale yellow solid.

Step 2. A mixture of 9H-3,9'-bicarbazole (5.20 g, 15.7 mmol), 2-([1,1'-biphenyl]-3-yl)-4-(4-chlorophenyl)-6-phenyl-1,3,5-triazine (1) (6.57 g, 15.7 mmol) and sodium tert-butoxide (4.51 g, 46.9 mmol) in toluene (150 mL) was degassed with bubbling N$_2$ for 20 min. Di-tert-butyl(1-methyl-2,2-diphenylcyclopropyl)phosphane (cBRIDP) (0.662 g, 1.88 mmol) and allylpalladium chloride dimer (0.172 g, 0.469 mmol) were added and the mixture stirred at reflux for 19.5 hours. The reaction mixture was cooled to RT and diluted with MeOH (200 mL). The solid was collected by filtration, washed with MeOH (50 mL) and isohexane (100 mL) and dried in vacuo to afford 9-(4-(4-([1,1'-biphenyl]-3-yl)-6-phenyl-1,3,5-triazin-2-yl)phenyl)-9H-3,9'-bicarbazole (2) (10.1 g, 13.4 mmol, 86% yield, >95% purity) as a grey/green solid. The solide was further purified by silica column and gave an off white solide (6.07 g, 60% yield, 99.89% HPLC purity).

Example 6

9-(4-(4-([1,1'-biphenyl]-4-yl)-6-phenyl-1,3,5-triazin-2-yl)phenyl)-9H-3,9'-bicarbazole

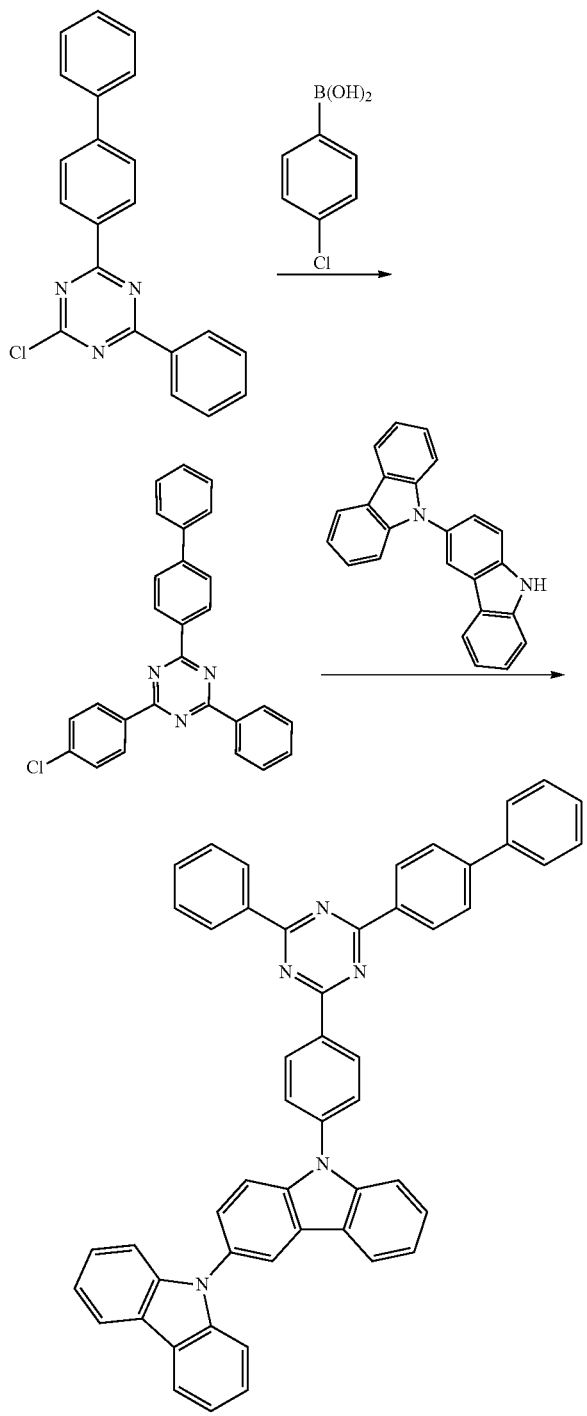

Step 1. A suspension of 2-([1,1'-biphenyl]-4-yl)-4-chloro-6-phenyl-1,3,5-triazine (10 g, 29 mmol), (4-chlorophenyl)boronic acid (5.00 g, 32.0 mmol) and sodium carbonate (6.78 g, 64.0 mmol) in 1,4-dioxane (100 mL) and water (25.00 ml) was degassed with nitrogen bubbling for 15 min. Pd(Ph$_3$P)$_4$ (1.68 g, 1.45 mmol) was added and the mixture was stirred at 80° C. overnight. The reaction mixture was diluted with water (200 mL) and the precipitate was collected by filtration and dried in a vacuum desiccator at 50° C. for 5 hours. The crude solid was purified by flash column chromatography (silica gel, 120 g column, dry load on silica gel, 0-30% DCM/isohexane) to provide 2-([1,1'-biphenyl]-4-yl)-4-(4-chlorophenyl)-6-phenyl-1,3,5-triazine (9.5 g, 21 mmol, 72% yield, 93% purity) as a white solid.

Step 2. A suspension of 9H-3,9'-bicarbazole (7.52 g, 22.6 mmol), sodium tert-butoxide (6.52 g, 67.9 mmol), 2-([1,1'-biphenyl]-4-yl)-4-(4-chlorophenyl)-6-phenyl-1,3,5-triazine (9.5 g, 23 mmol) and di-tert-butyl(1-methyl-2,2-diphenyl-cyclopropyl)-phosphane (cBRIDP) (0.957 g, 2.71 mmol) in anhydrous 1,4-dioxane (300 mL) degassed with nitrogen bubbling for 15 min. Allylpalladium chloride dimer (0.248 g, 0.679 mmol) was added and the reaction mixture was stirred at 100° ° C. for 24 hours. The reaction mixture was cooled to RT, diluted with MeOH (800 mL) and the precipitate was collected by filtration and washed with MeOH (150 mL). The green wet solid was dried in the desiccator at 50° C. for 4 hours to give the crude product as a green solid (22.3 g), which was dissolved in refluxing toluene (500 mL), then cooled to RT. The precipitate was collected by filtration, washed with toluene (100 mL) and dried in a vacuum desiccator at 50° C. overnight to give 9-(4-(4-([1,1'-biphenyl]-4-yl)-6-phenyl-1,3,5-triazin-2-yl)phenyl)-9H-3,9'-bicarbazole (12.7 g, 16.9 mmol, 75% yield, 95% purity) as a green solid which was further purified to give product (9.25 g, 77% yield, 99.81% HPLC purity) as a cream solid.

Device Examples

All example devices were fabricated by high vacuum (<10$^7$ Torr) thermal evaporation. The anode electrode was 750 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of H$_2$O and O$_2$) immediately after fabrication with a moisture getter incorporated inside the package. The organic stack of the device examples consisted of sequentially, from the ITO Surface: 100 Å of HAT-CN as the hole injection layer (HIL); 450 Å of HTM as a hole transporting layer (HTL); emissive layer (EML) with thickness 400 Å. Emissive layer containing H-host (HH): E-host 40 weight % and 10 weight % of green emitter GD1. EML was followed by 350 Å of Liq (8-hydroxyquinoline lithium) doped with 40% of ETM as the electron transporting layer (ETL). E-host EH1 was used as inventive Example 1, E-host EH2 was used as inventive Example 2, E-host EH3 used as a comparative example CE1. Device structure is shown in the table 1.

The chemical structures of the device materials are shown below

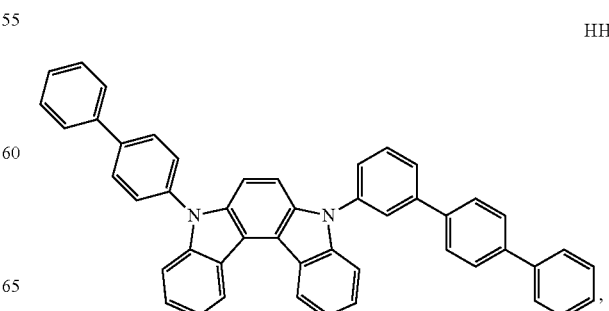

HH

HH2
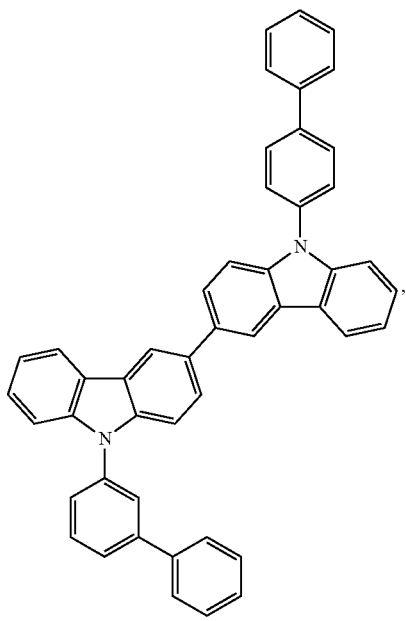
HH3
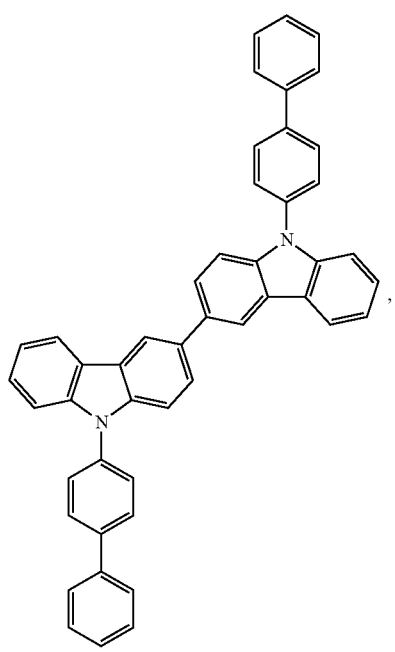
HH4
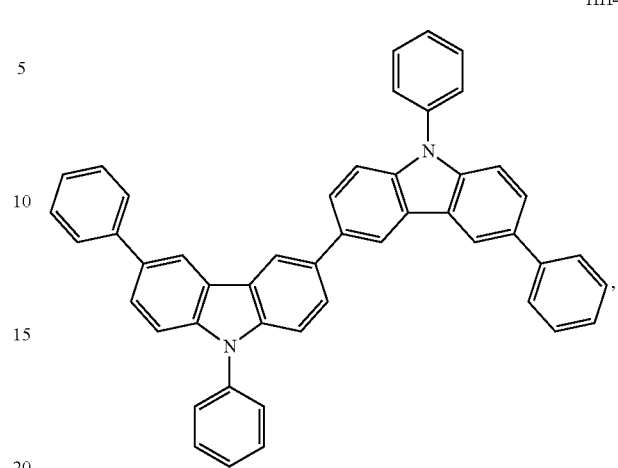
HH5
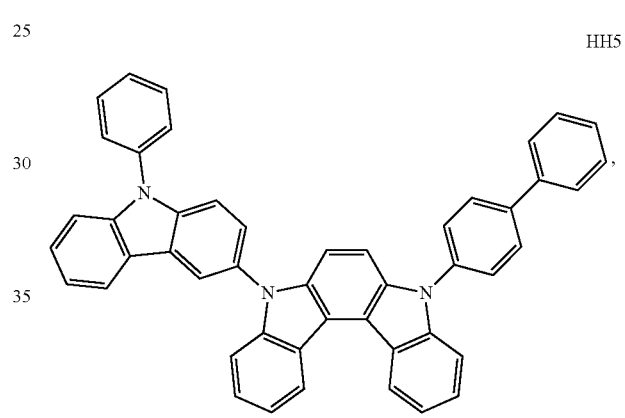
EH1
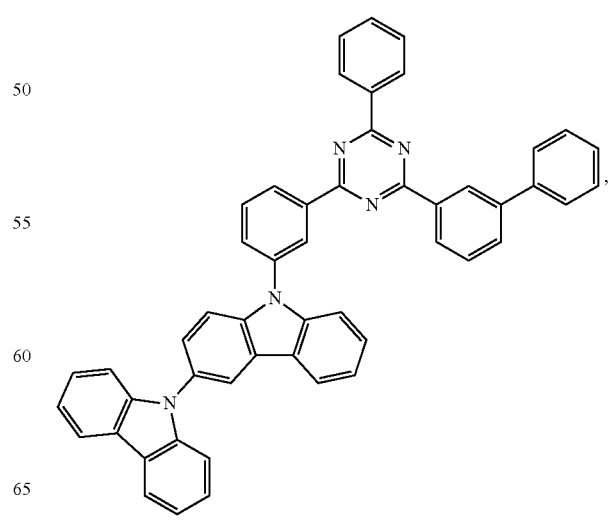

EH2
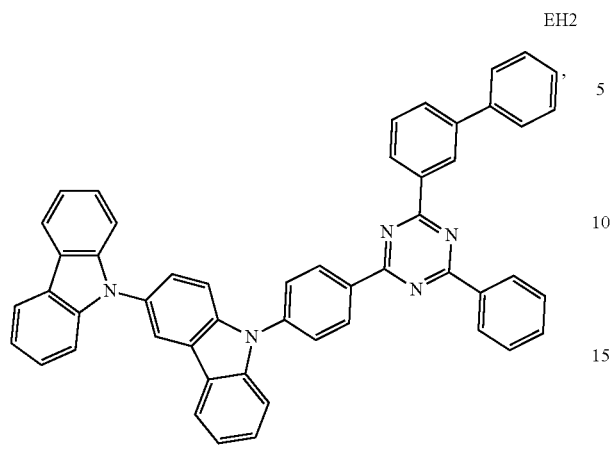
EH3
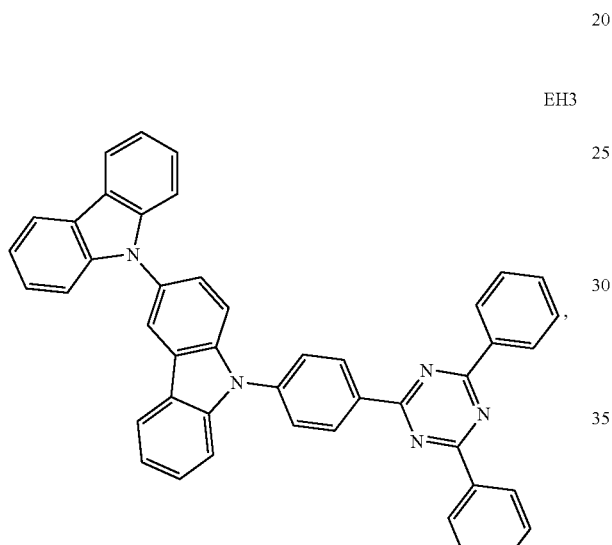
EH4
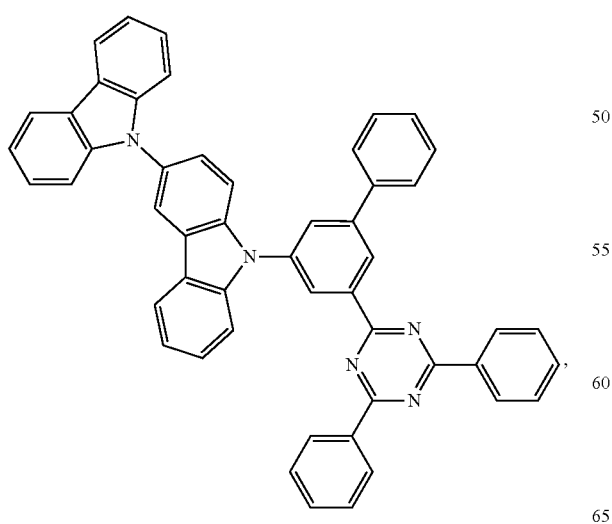
GD1
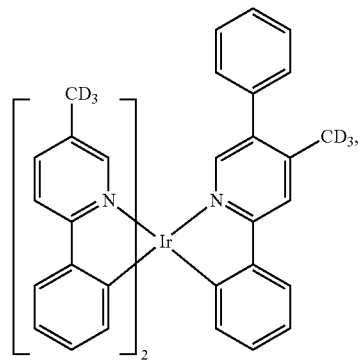
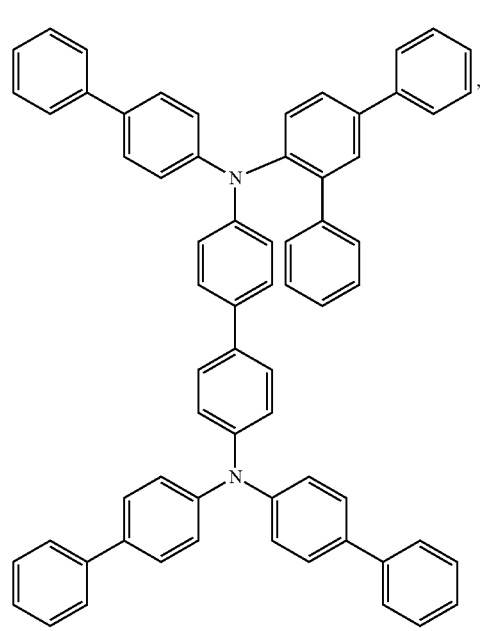
HTM
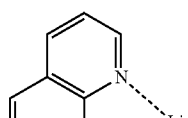
Liq
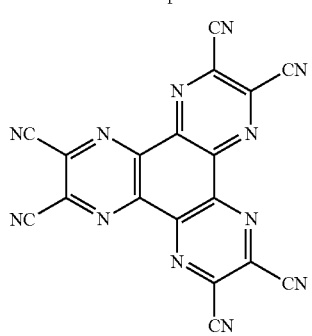
HATCN

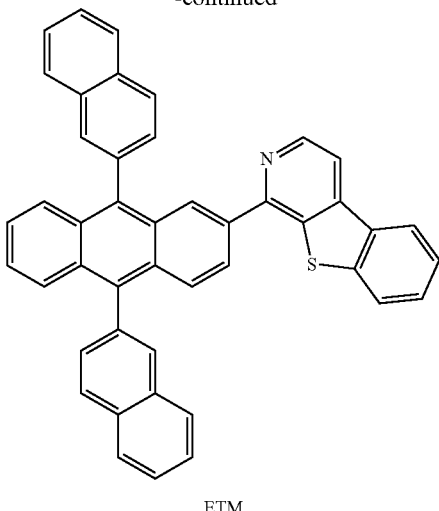

ETM

Upon fabrication the devices EL and JVL performance have been measured. All device examples emitted green emission with maximum wavelength 529 nm defined by green emitter GD1. The devices stability (lifetime) was tested at very high luminance accelerated conditions at DC current density of 80 mA/cm2. The lifetime value at 1,000 nits was calculated assuming acceleration factor 1.8 from accelerated lifetime data. Device performance is shown in the Table 2.

TABLE 1

Device example layer structure

| Layer | Material | Thickness [Å] |
|---|---|---|
| Anode | ITO | 750 |
| HIL | HAT-CN | 100 |
| HTL | HTM | 450 |
| Green EML | HH:EH 40%:GD1 10% | 400 |
| ETL | Liq:ETM 35% | 350 |

TABLE 1-continued

Device example layer structure

| Layer | Material | Thickness [Å] |
|---|---|---|
| EIL | Liq | 10 |
| Cathode | Al | 1,000 |

TABLE 2

Device Performance of Examples 1, 2 and CE1

| | | | | At 1,000 nits | | |
|---|---|---|---|---|---|---|
| Example | E-Host | Color | Maximum emission wavelength [nm] | Voltage [V] | Normalized LE [%] | Normalized $LT_{95\%}$ [%] |
| Example 1 | EH1 | green | 529 | 3.0 | 107% | 109% |
| Example 2 | EH2 | green | 529 | 2.9 | 100% | 123% |
| CE 1 | EH3 | green | 529 | 2.9 | 100% | 100% |

It is obvious from the device data that inventive compound EH1 (Example 1) has 7% higher luminance efficacy (LE) and 9% longer LT vs. comparative compound EH3. Inventive compound EH2 (Example 2) has similar luminance efficacy and 23% longer LT95 vs. comparative compound EH3.

Premixtures PM-1, PM-2, PM-3, PM-4, and PM-5:

Each pair of premixable h-host and e-host at a weight ratio of 3:1 or 1:1 was physically mixed, grinded, and loaded into an evaporation source. The total weight of the mixture was 0.4 g. The premixed components were thermally co-evaporated at a rate of 2 Å/s in a vacuum chamber under a pressure less than 10-7 Torr until depletion, and deposited onto glass substrates. The substrates were replaced continuously after deposition of 400 Å of film without stopping the deposition and cooling the source. The compositions of the films were analyzed by high-performance liquid chromatography (HPLC) and the results are shown in Table 1. A linear regression was performed by using concentration as y axis, and plate number (1, 2, 3, etc.) as x axis. The obtained slope is the ratio stability.

TABLE 3

Experimental HPLC data on Premixability for Premixtures PM-1, PM-2, PM-3, PM-4, and PM-5

| Premixture | | | Ratio Stability | H-Host/E-host ratio in deposited films [%] | | | | | |
|---|---|---|---|---|---|---|---|---|---|
| | | | | 1 | 2 | 3 | 4 | 5 | 6 |
| PM-1 | H-Host | HH3 | 0.65 | 74.1 | 73.6 | 73.8 | 76.2 | | |
| | E-host | EH3 | | 25.9 | 26.4 | 26.2 | 23.8 | | |
| PM-2 | H-Host | HH4 | 0.64 | 74.2 | 72.5 | 71.5 | 72.4 | | |
| | E-host | EH3 | | 25.8 | 27.5 | 28.5 | 27.6 | | |
| PM-3 | H-Host | HH | 0.11 | 70.3 | 69.1 | 68.0 | 68.8 | 71.0 | |
| | E-host | EH3 | | 29.7 | 30.9 | 32.0 | 31.2 | 29.0 | |
| PM-4 | H-Host | HH2 | 0.20 | 74.6 | 73.5 | 73.7 | 74.8 | 75.0 | 74.9 |
| | E-host | EH3 | | 25.4 | 26.5 | 26.3 | 25.2 | 25.0 | 25.1 |
| PM-5 | H-Host | HH5 | 0.54 | 44.8 | 45.1 | 44.6 | 43.9 | 42.7 | |
| | E-host | EH4 | | 55.2 | 54.9 | 55.4 | 56.1 | 57.3 | |

The data in Table 3 shows that the ratio of the two components in premixtures PM-1, PM-2, PM-3, PM-4, and PM-5 does not change significantly over a continuous single-source coevaporation. The minor fluctuations in the concentrations do not reveal any trend and can be explained by the accuracy of HPLC analysis. Normally, the ratio stability within 1.0 is considered to be good and useful for commercial OLED application. These experiments conclude that PM-1, PM-2, PM-3, PM-4, and PM-5 are stable premixtures for coevaporation. The coevaporation stability of these premixtures is believed to tracable to the unique chemical structures associated with these two classes of materials.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

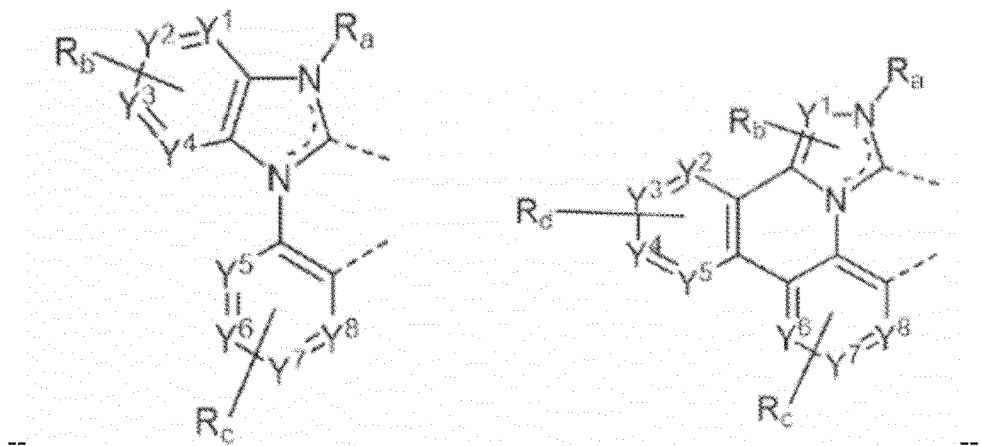

We claim:

1. A composition comprising a first compound and a second compound;

wherein the first compound has a formula selected from the group consisting of:

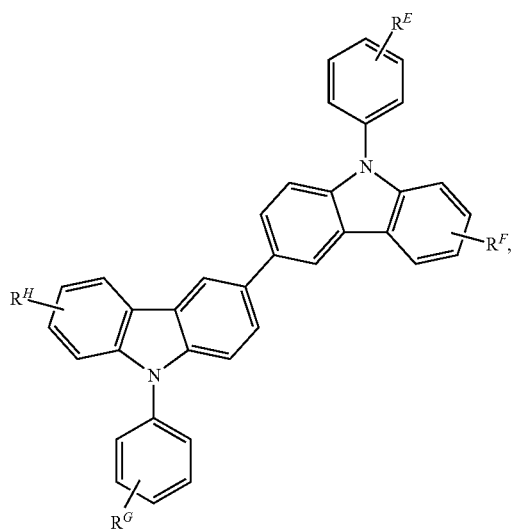

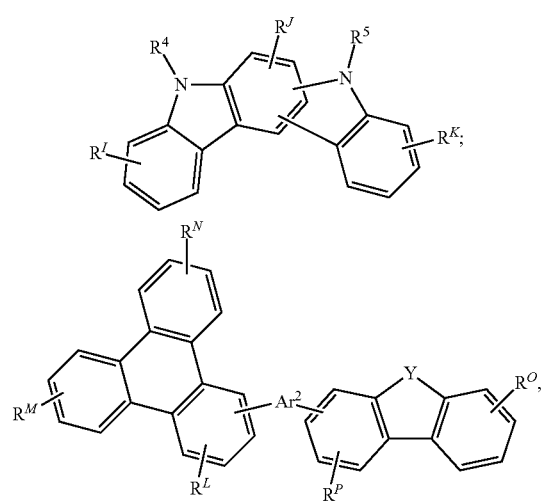

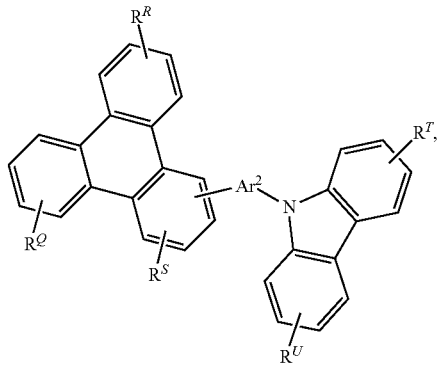

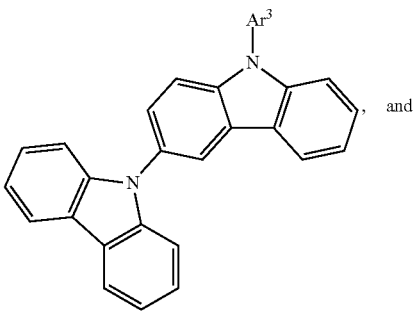, and

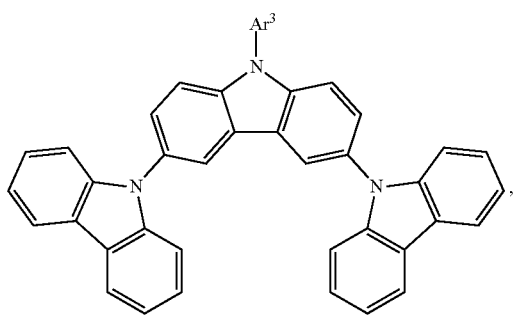, wherein, $R^E$ to $R^U$ each independently represents mono to the maximum allowable substitutions, or no substitution;

each $R^4$, $R^5$, and $R^E$ to $R^U$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

any two substituents may be joined or fused together to form a ring;

Y is O or S; and $Ar^3$ is a substituted or unsubstituted aryl ring;

wherein the second compound has a formula having the structure:

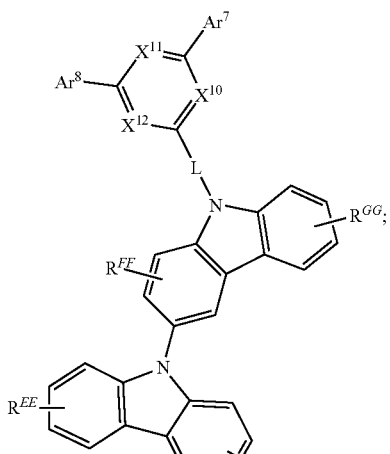

wherein,

R$^{DD}$, R$^{EE}$, R$^{FF}$, and R$^{GG}$ each independently represent mono to the maximum allowable substitutions, or no substitution;

each R$^{DD}$, R$^{EE}$, R$^{FF}$, and R$^{GG}$ is independently hydrogen, or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;

Ar$^7$ and Ar$^8$ are each independently a substituted or unsubstituted aryl ring;

X$^{10}$, X$^{11}$, and X$^{12}$ are each independently N or CH;

at least two of X$^{10}$, X$^{11}$, and X$^{12}$ are N;

any two substituents may be joined or fused together to form a ring; and

L is either an aromatic linker or a direct bond.

2. The composition of claim 1, wherein each R$^4$, R$^5$, and R$^E$ to R$^U$ is independently hydrogen or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

3. The composition of claim 1, wherein each R$^{DD}$, R$^{EE}$, R$^{FF}$, and R$^{GG}$ is independently hydrogen, or a substituent selected from the group consisting of deuterium, fluorine, alkyl, cycloalkyl, heteroalkyl, alkoxy, aryloxy, amino, silyl, alkenyl, cycloalkenyl, heteroalkenyl, aryl, heteroaryl, nitrile, isonitrile, sulfanyl, and combinations thereof.

4. The composition of claim 1, wherein the first compound has the structure of

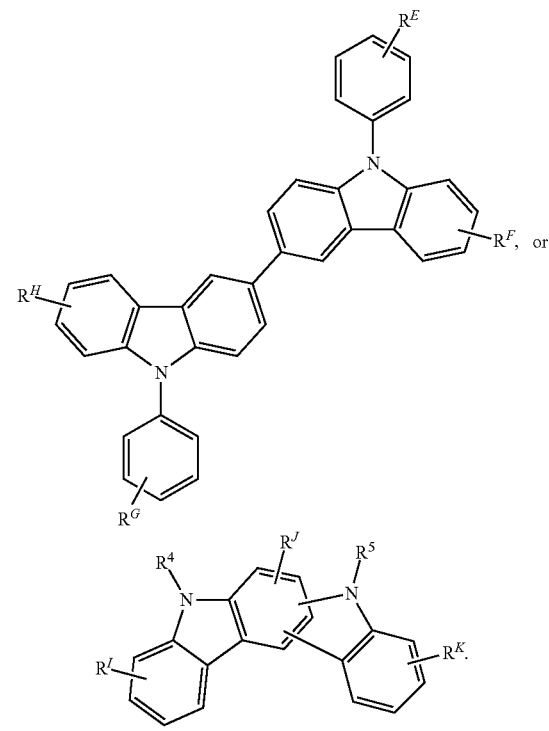

5. The composition of claim 4 wherein the first compound has the structure of:

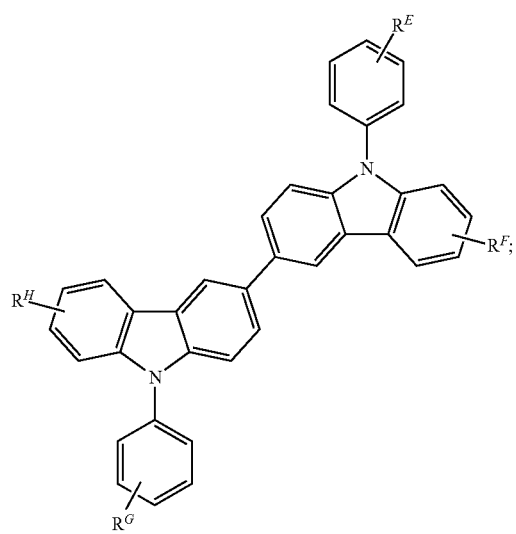

and the first compound comprises at least two or more non-fused phenyl rings, wherein said at least two or more non-fused phenyl rings is inclusive of the phenyl ring containing R$^E$ and/or the phenyl ring containing R$^G$.

6. The compound of claim 4 wherein the first compound has the structure of:

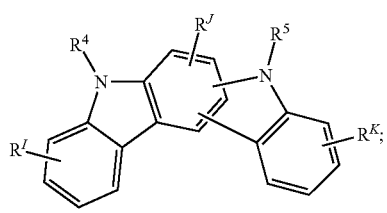
and
at least one of $R^4$ and $R^5$ comprise at least two or more non-fused phenyl rings.
7. The compound of claim 1, wherein the first compound is selected from the group consisting of:
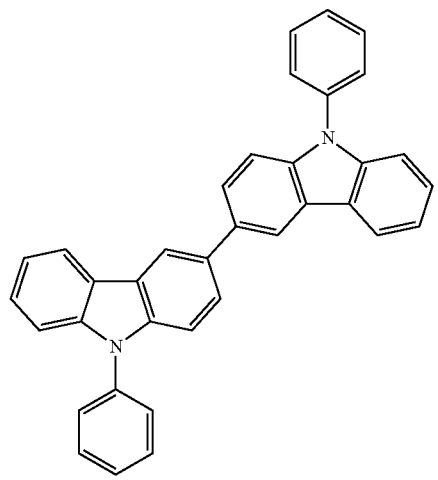
,
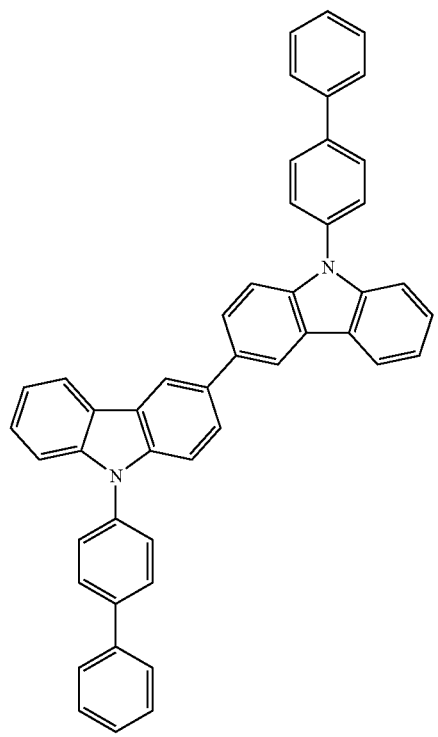
,
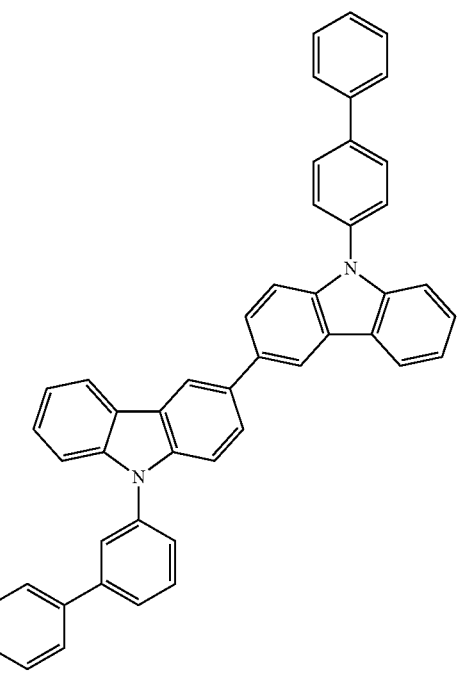
, 337
-continued
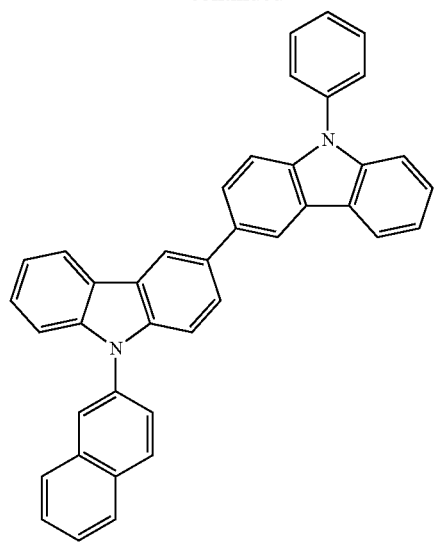
,
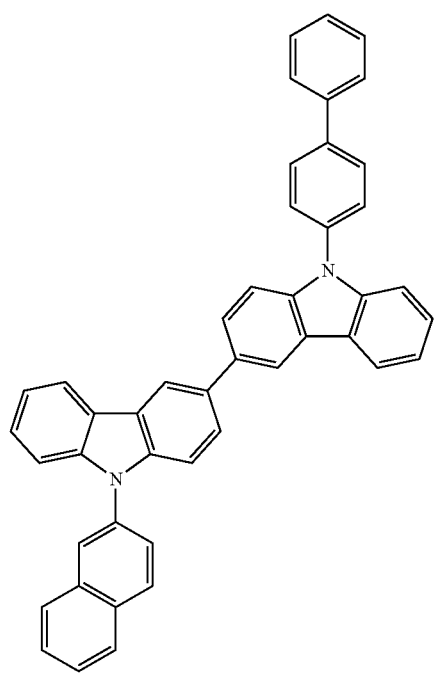
,
338
-continued
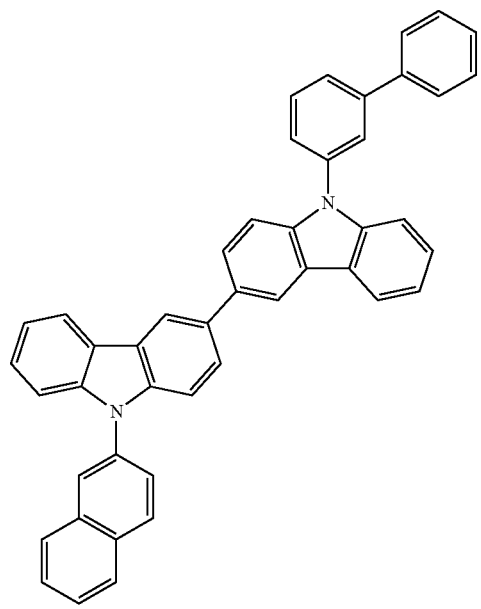
,
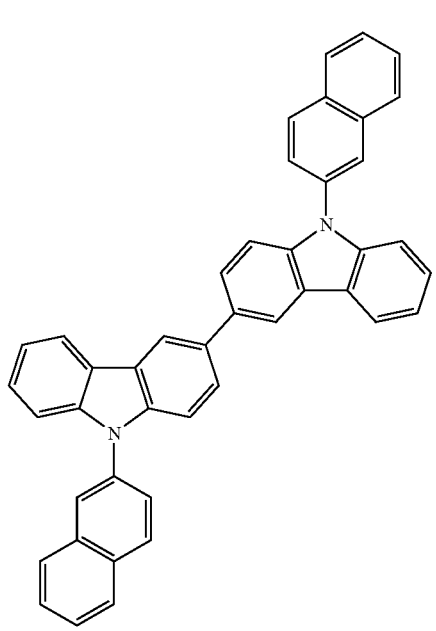
, 339
-continued
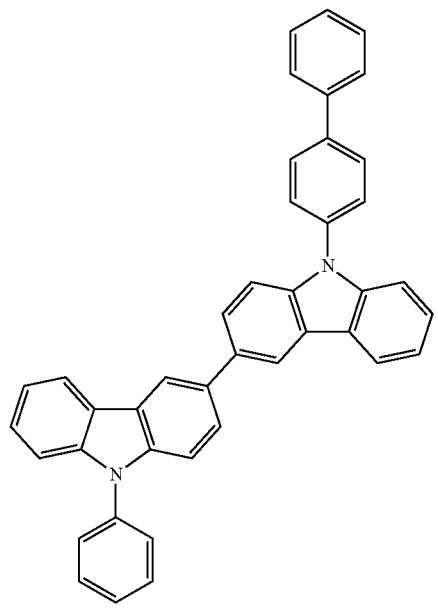
,
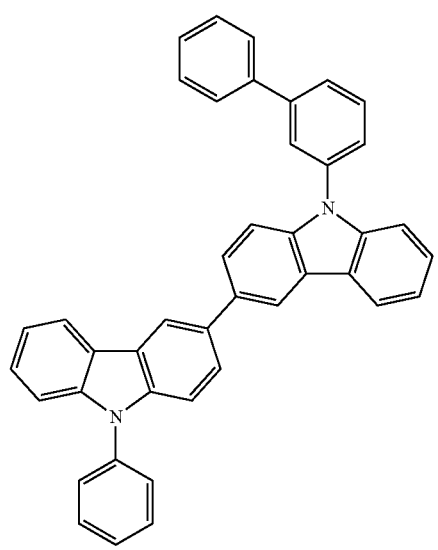
,
340
-continued
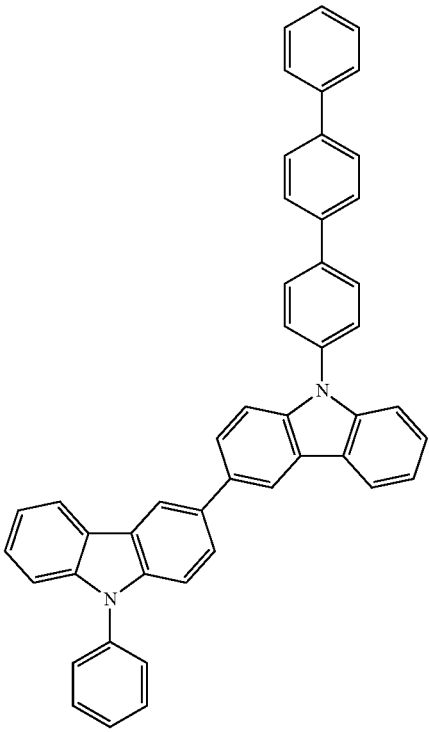
,
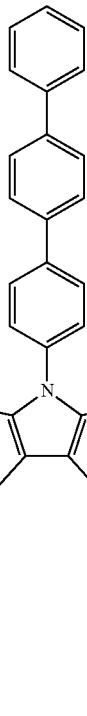
, 341
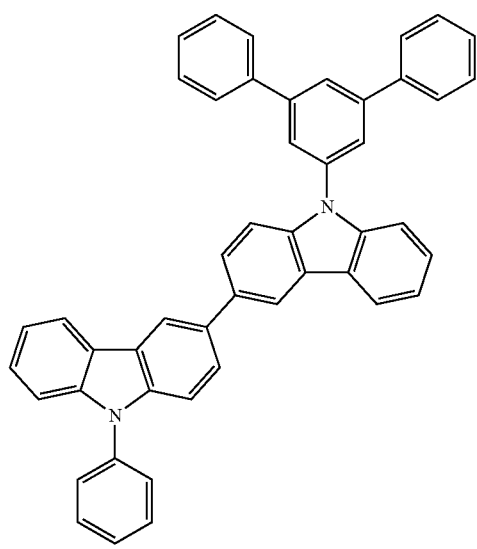
342
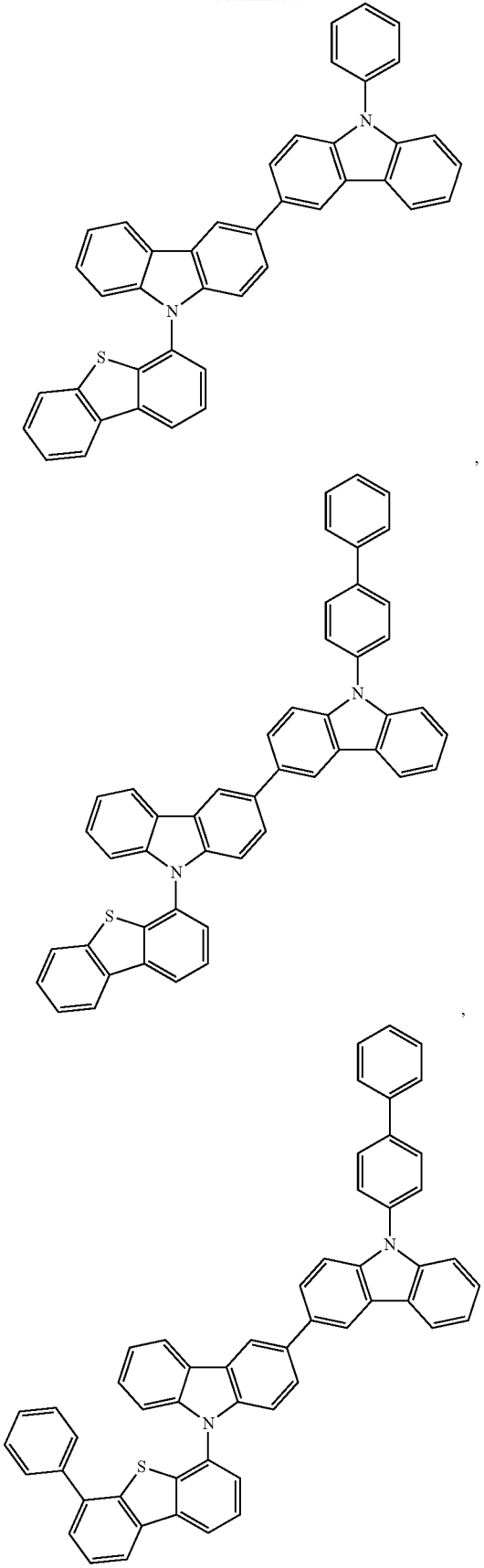

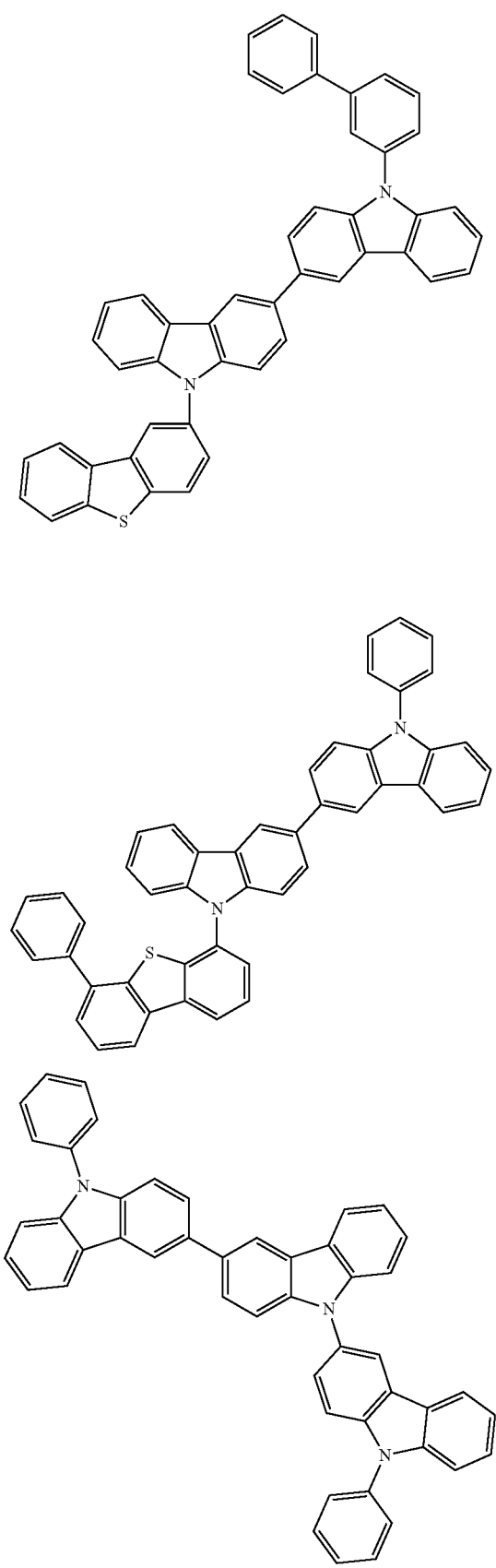
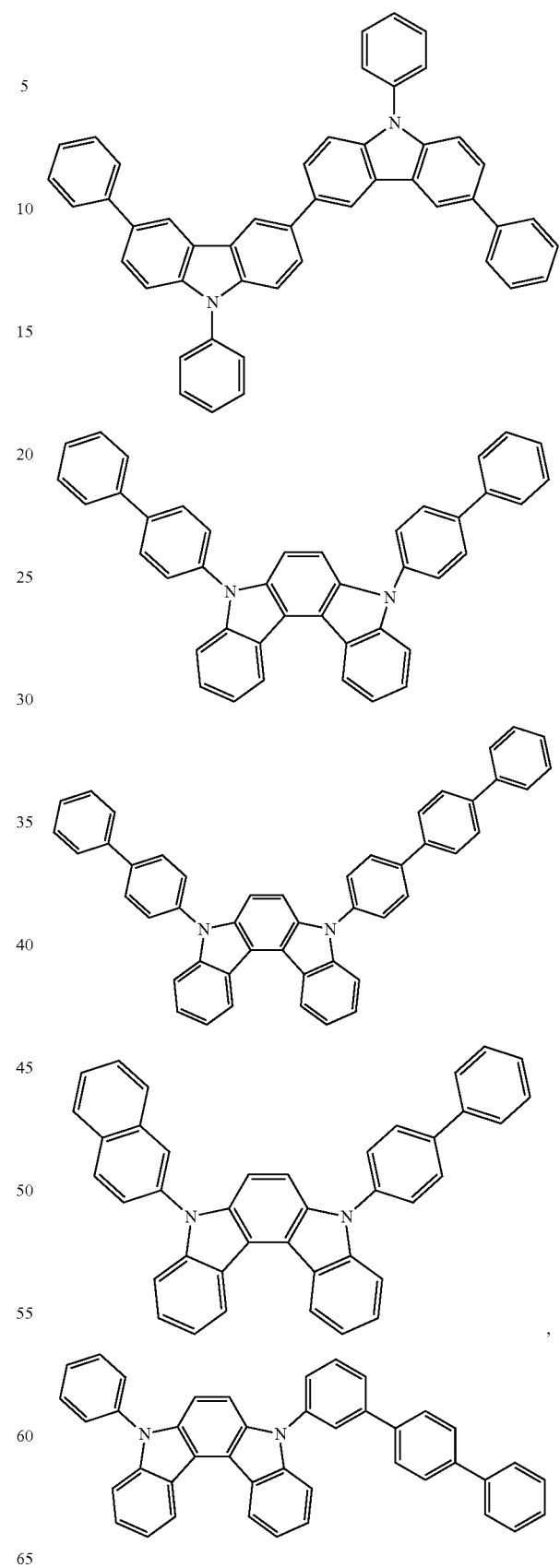

345
-continued
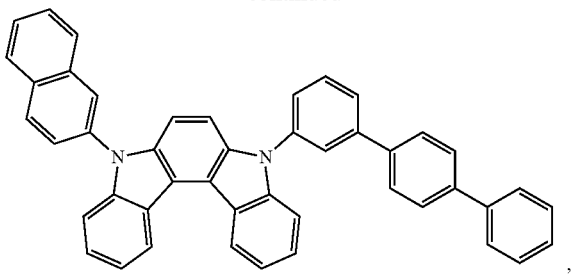
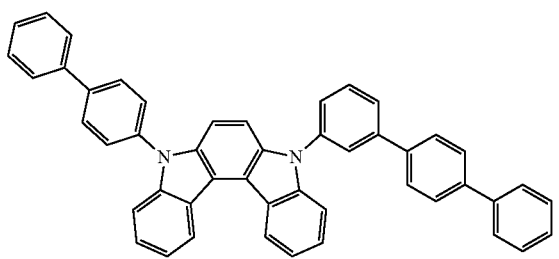
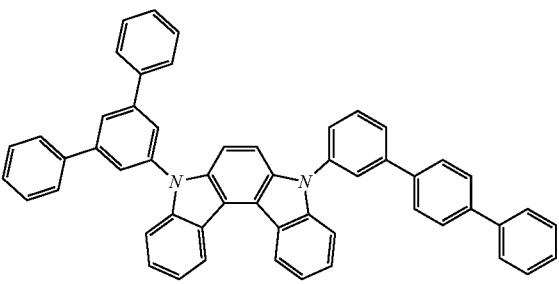
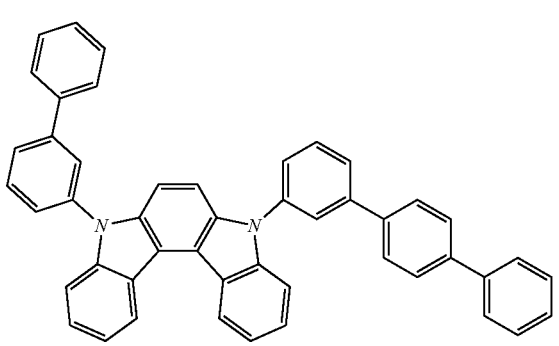
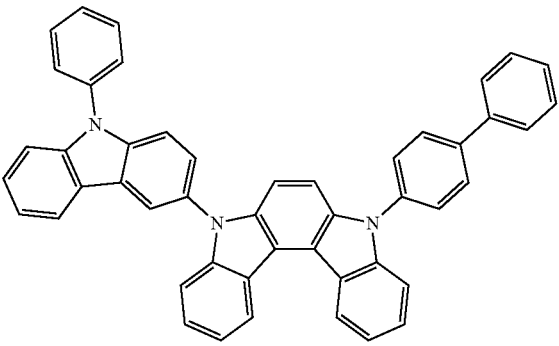
346
-continued
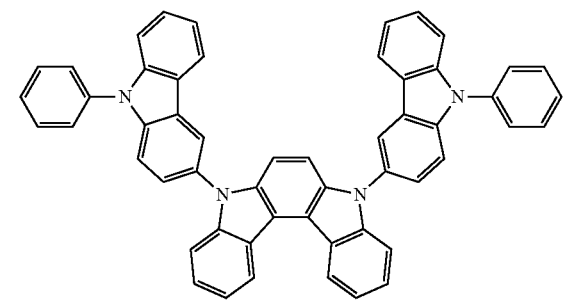
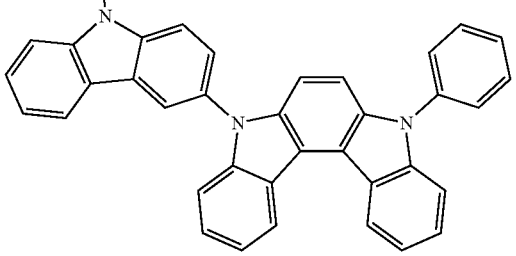
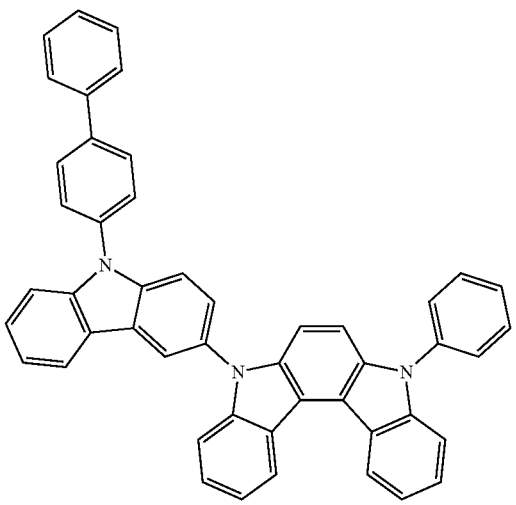
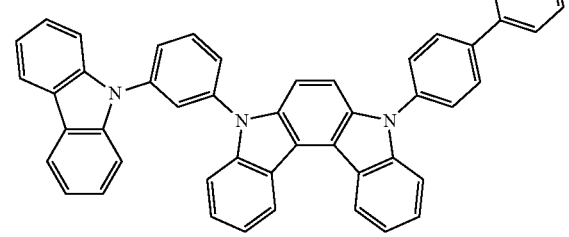
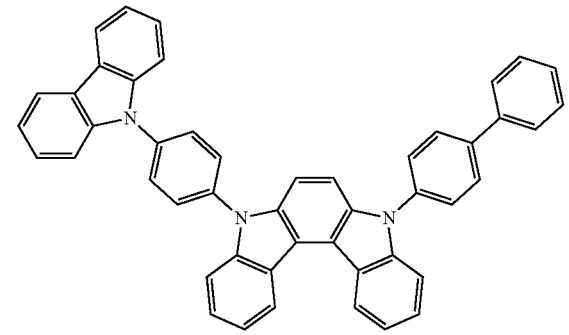

347
-continued
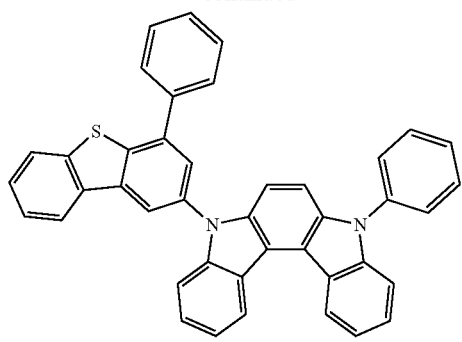
,
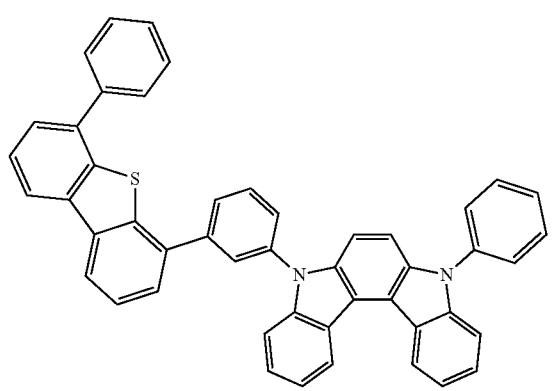
,
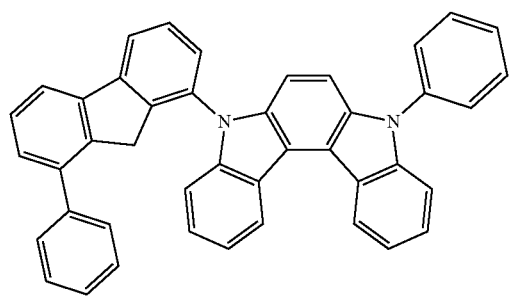
,
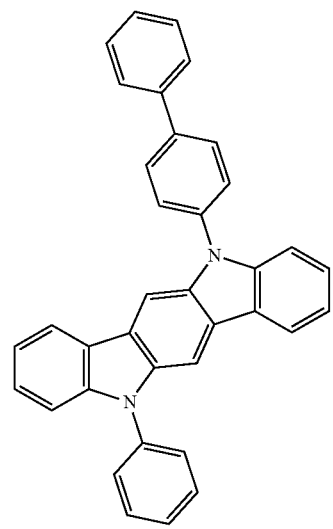
,
348
-continued
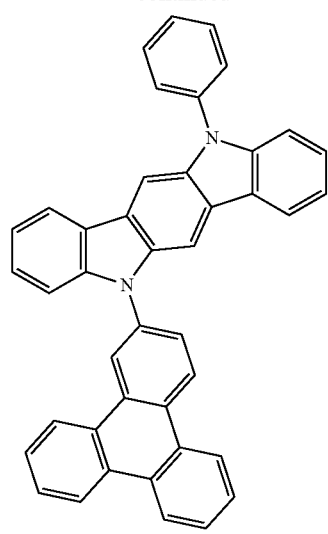
,
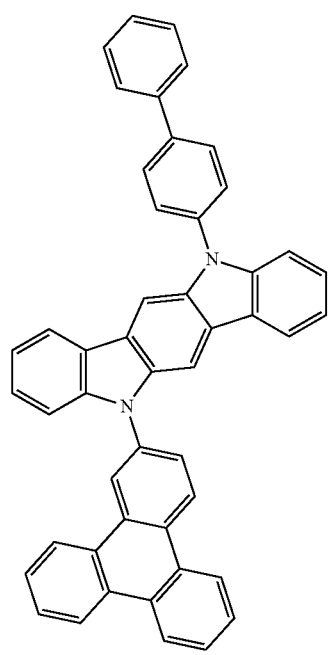
, 349
-continued
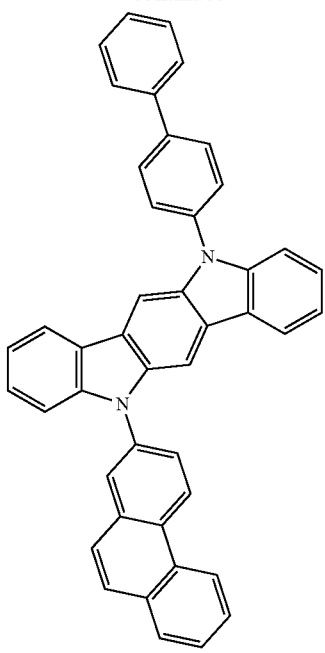
350
-continued
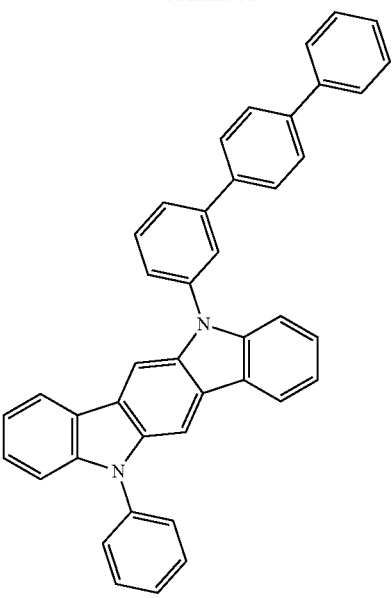
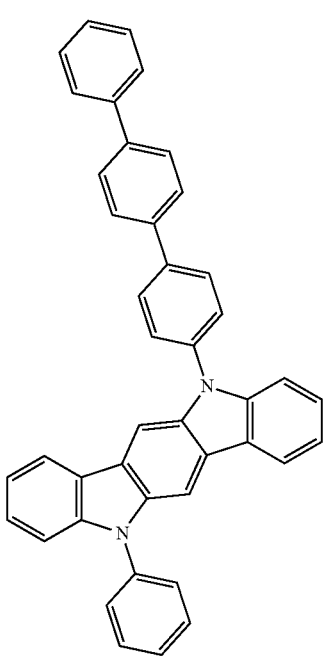
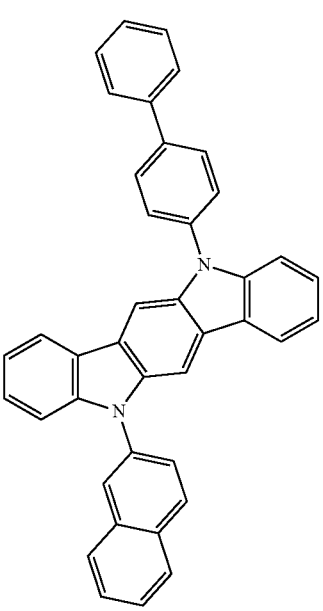

351
-continued
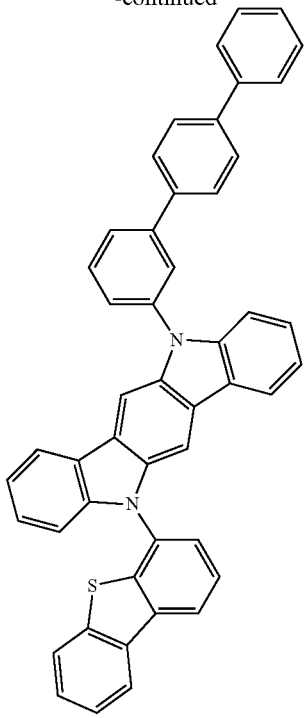
352
-continued
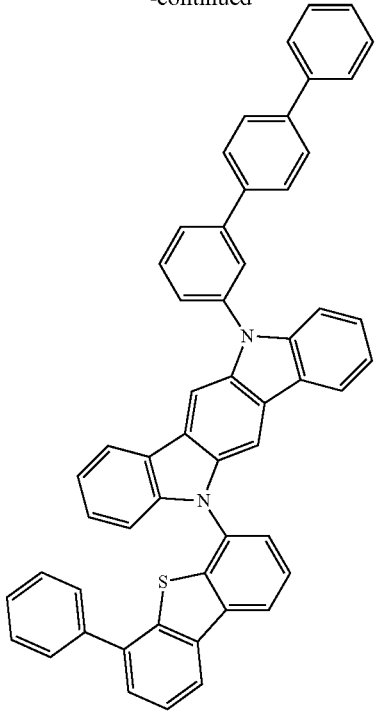
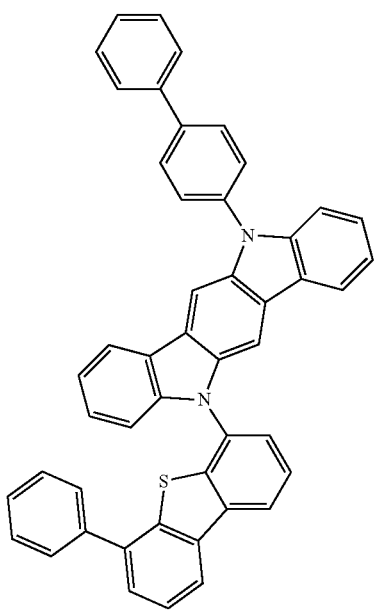
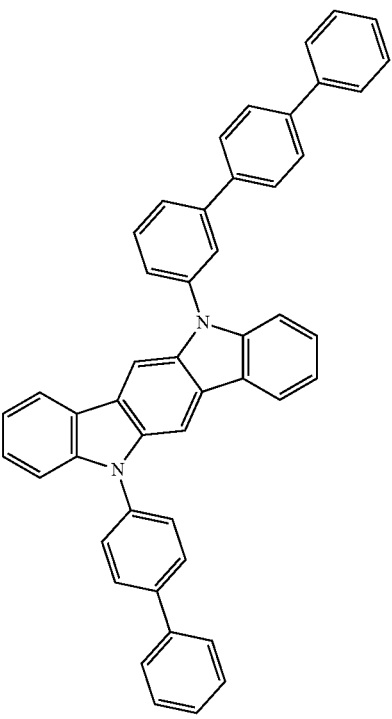

353
-continued
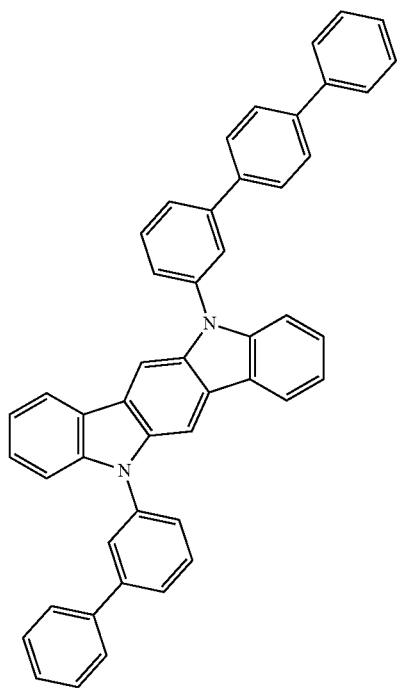
,
354
-continued
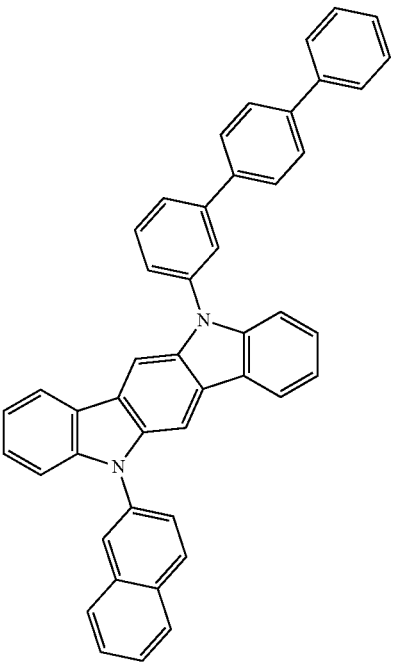
,
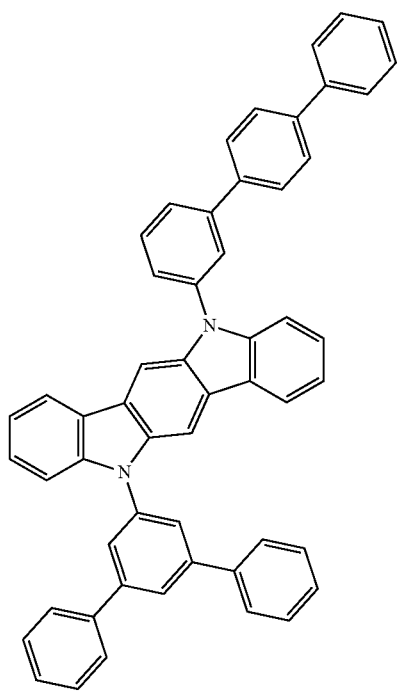
,
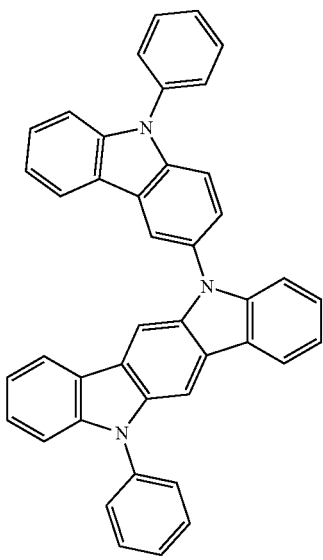
, 355
-continued
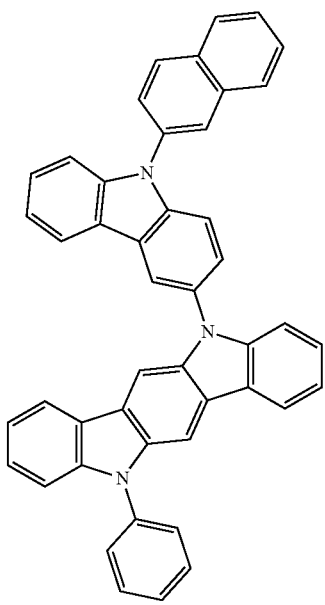
356
-continued
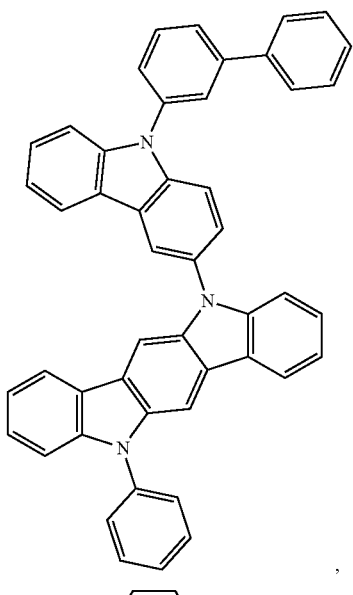
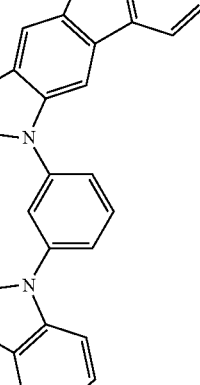
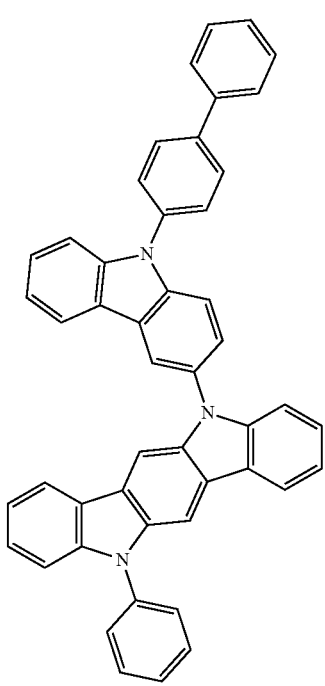
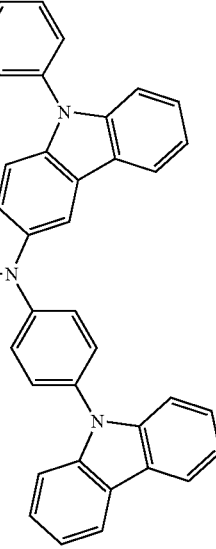

357
-continued
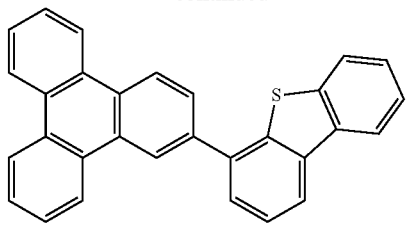
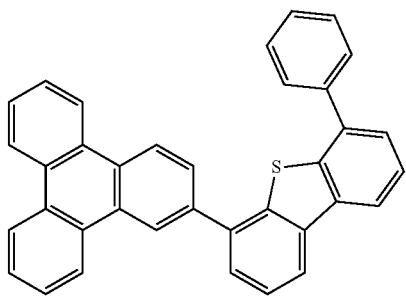
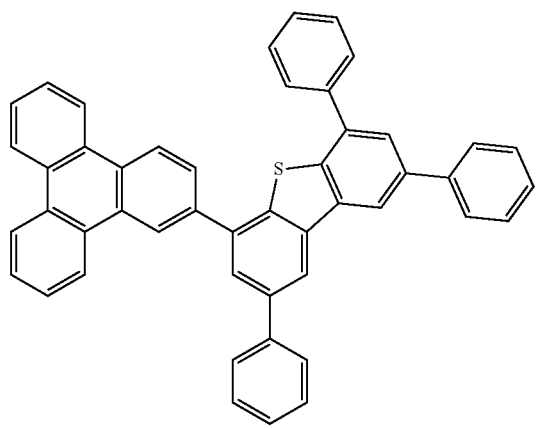
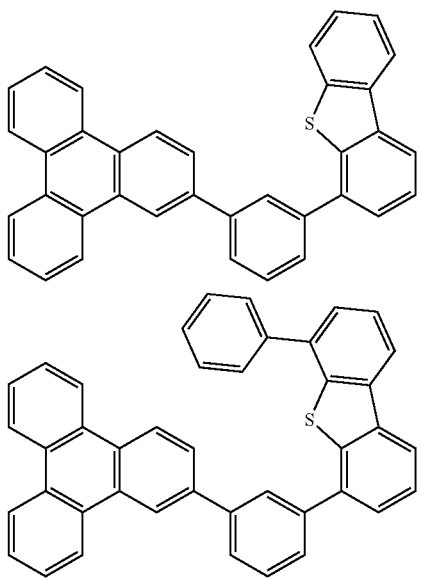
358
-continued
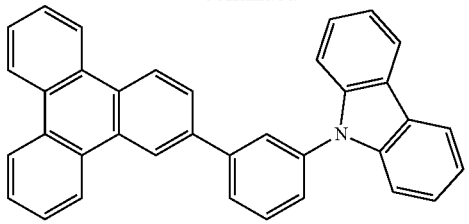
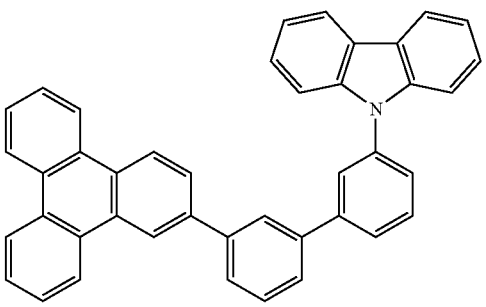
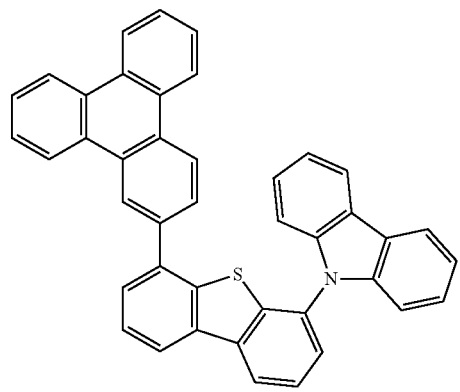
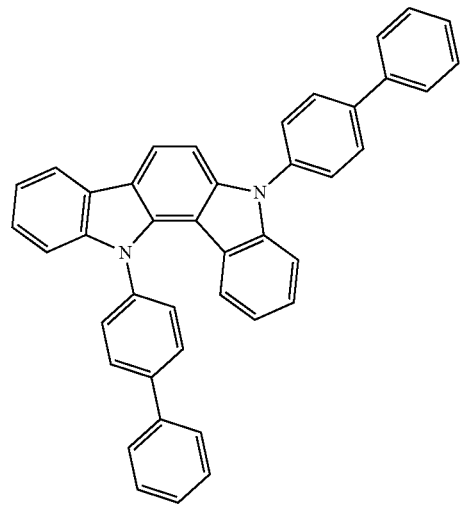

359
-continued
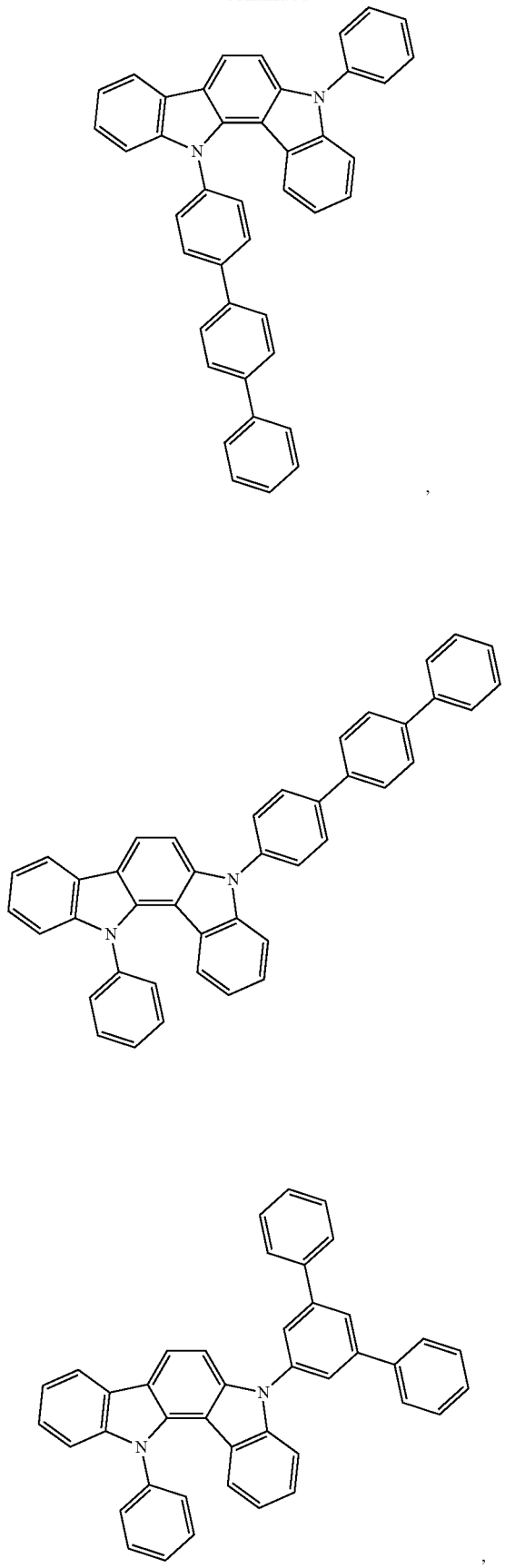
360
-continued
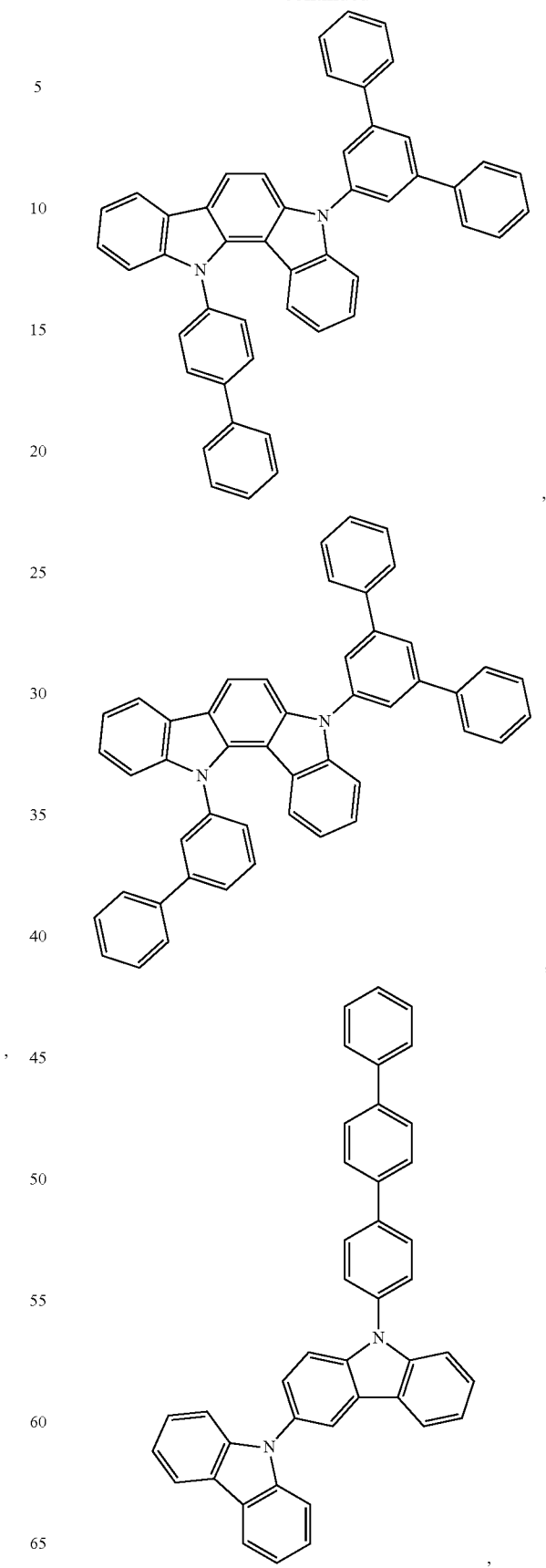

361
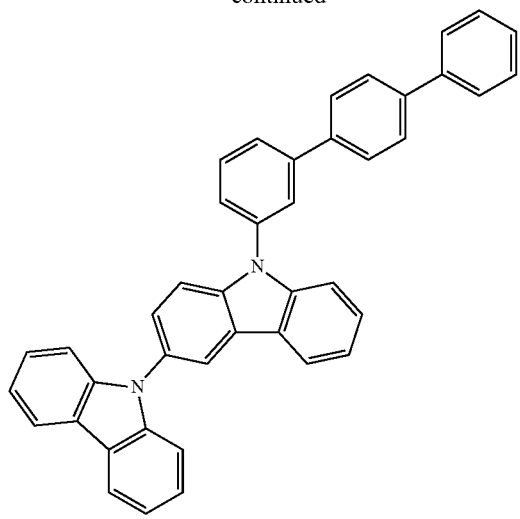
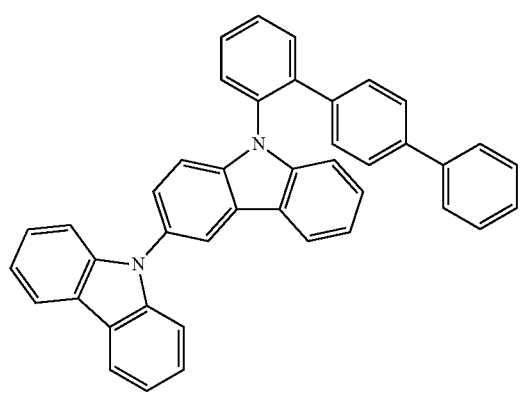
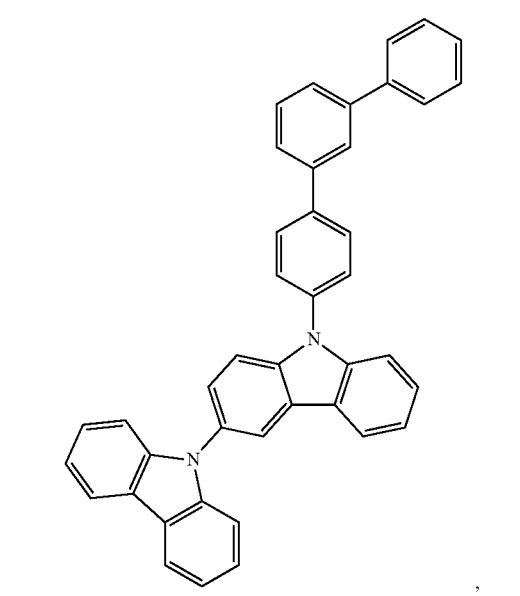
362
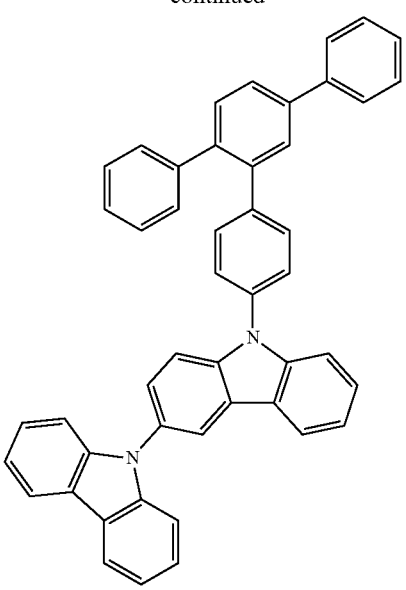
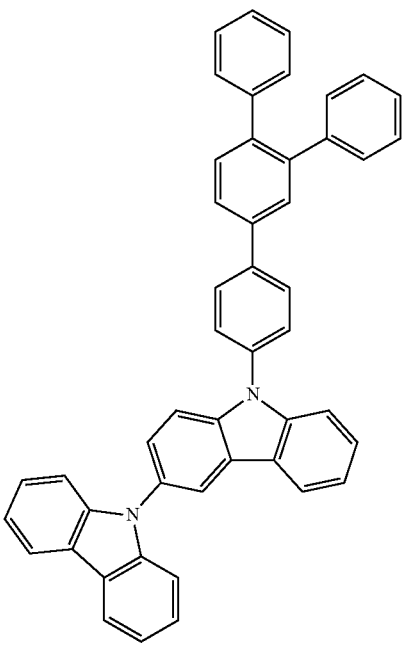

363
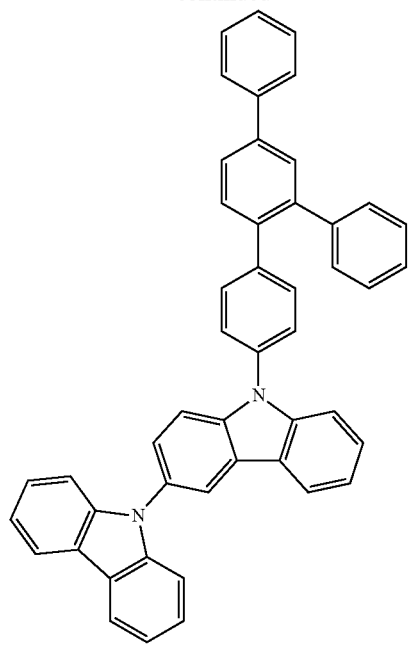
364
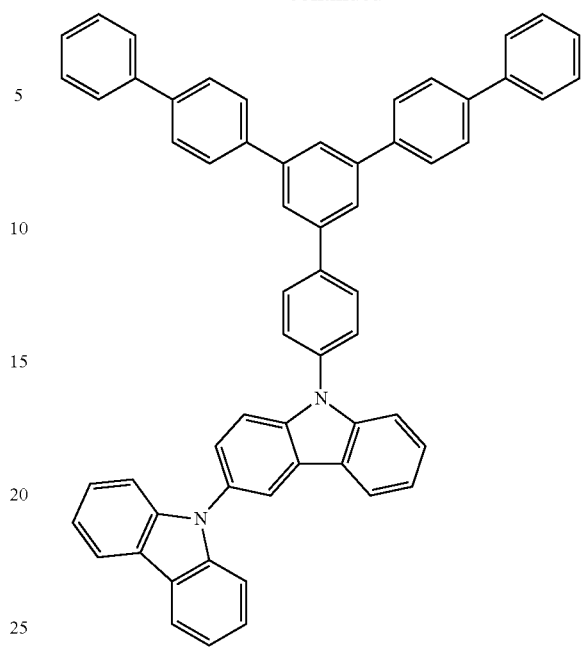
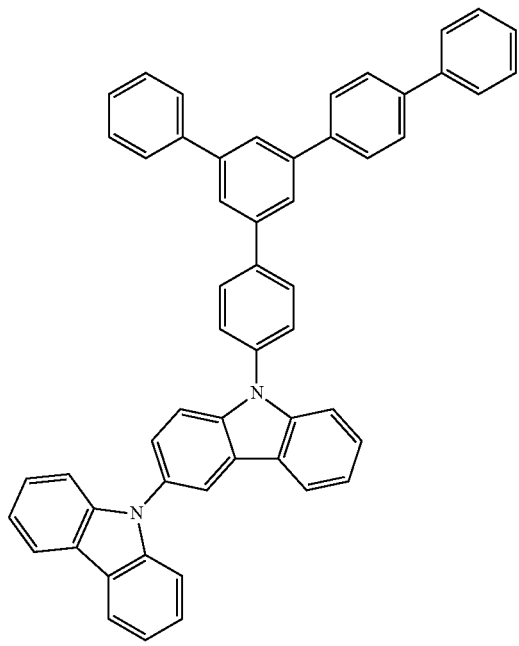
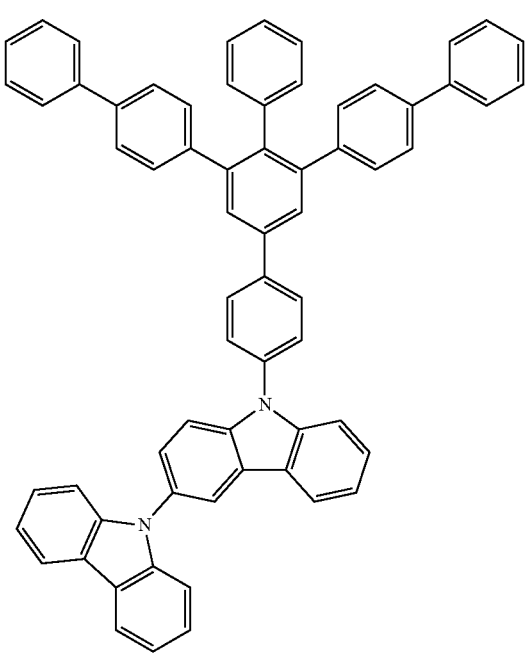

365
-continued
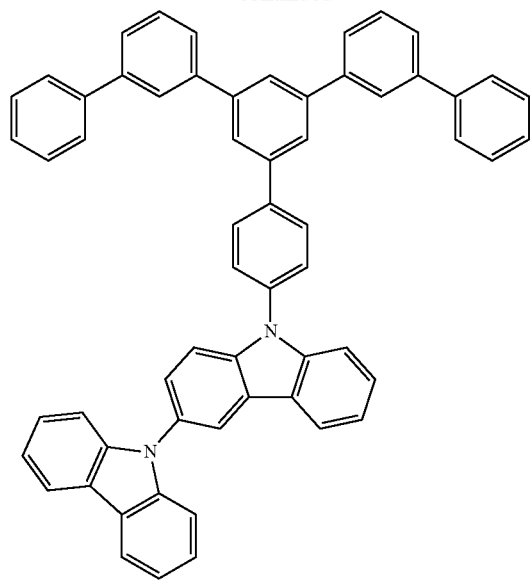
,
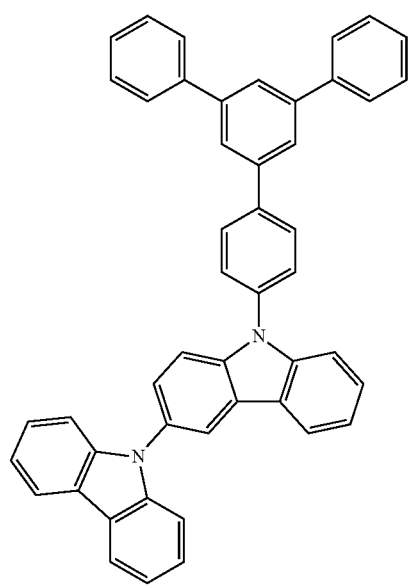
,
366
-continued
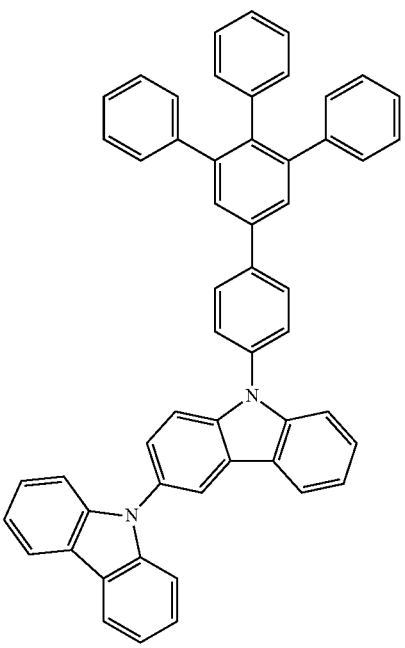
,
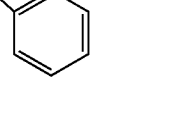
, 367
-continued
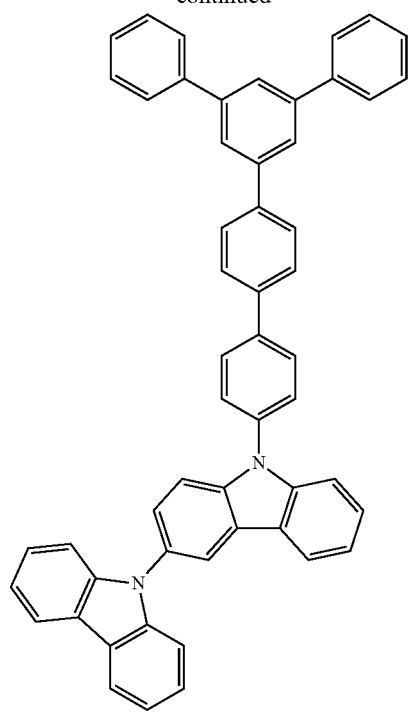
368
-continued
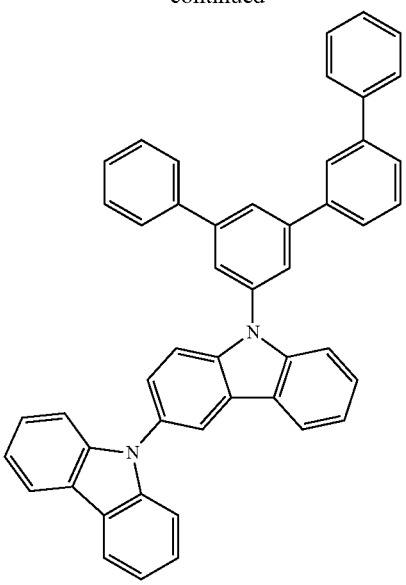
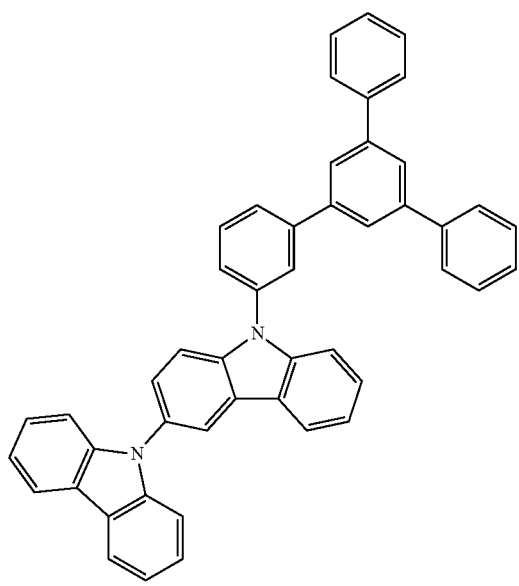
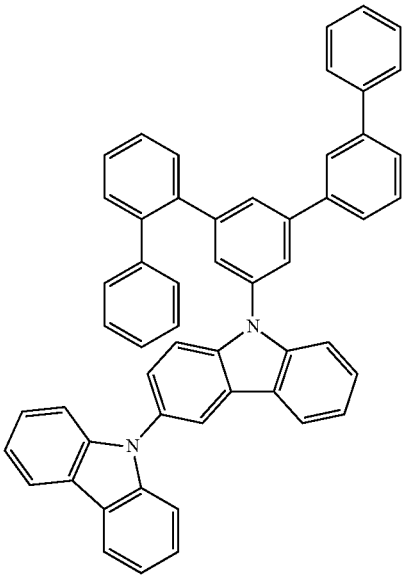

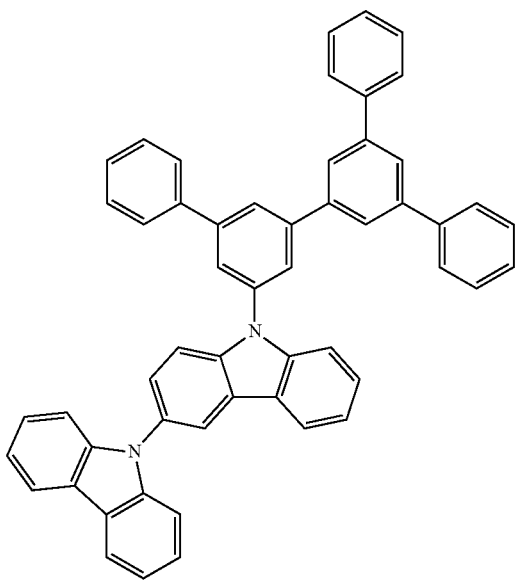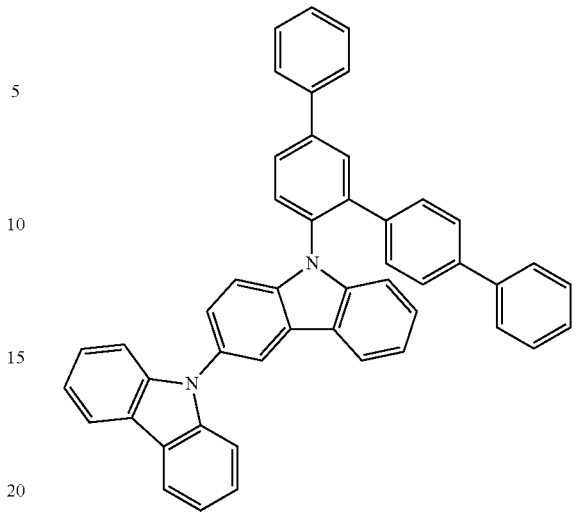

371
-continued
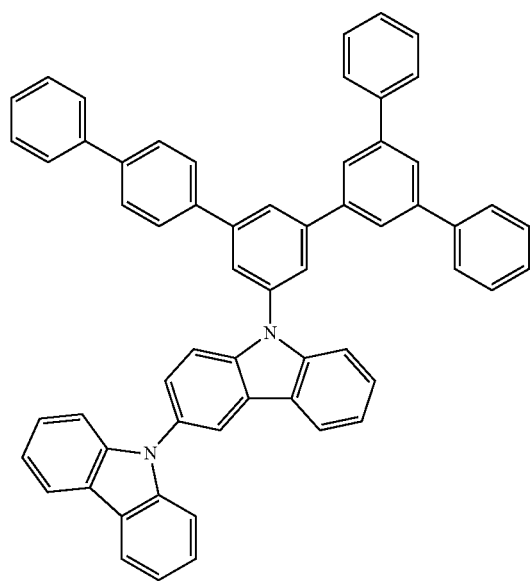
372
-continued
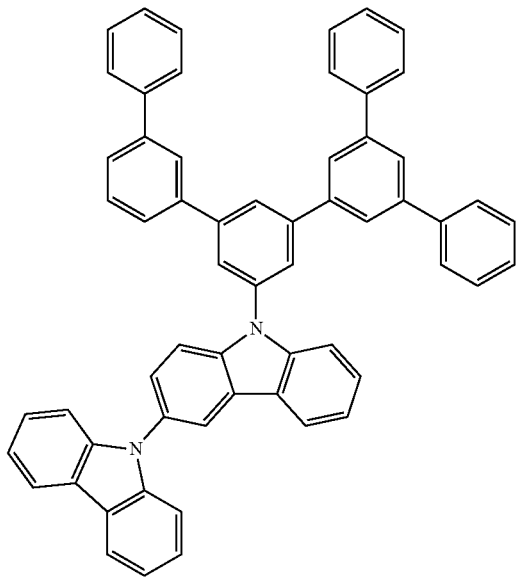
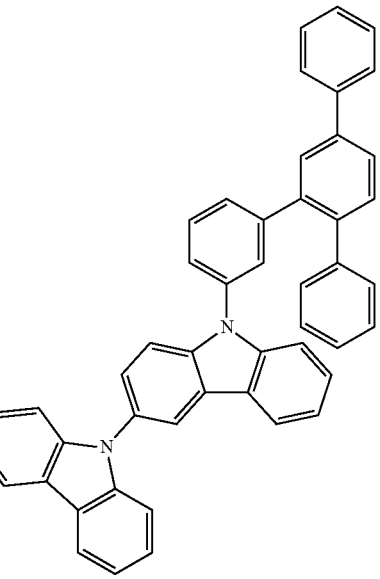

373
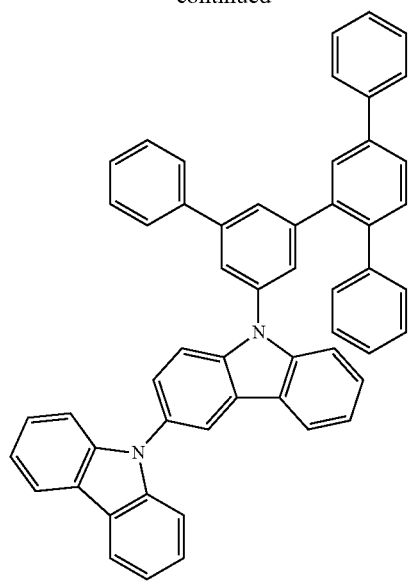
,
374
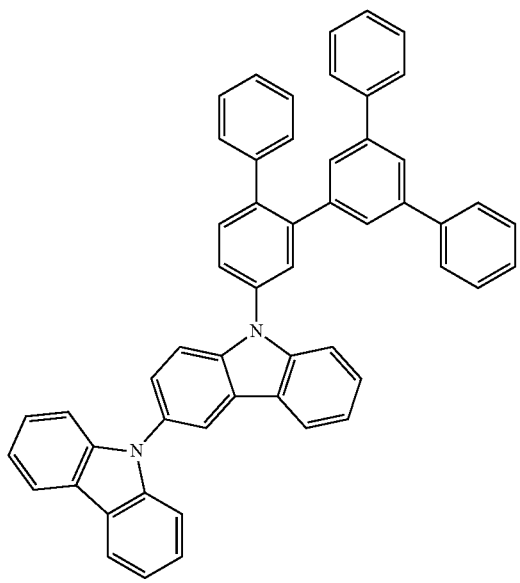
,
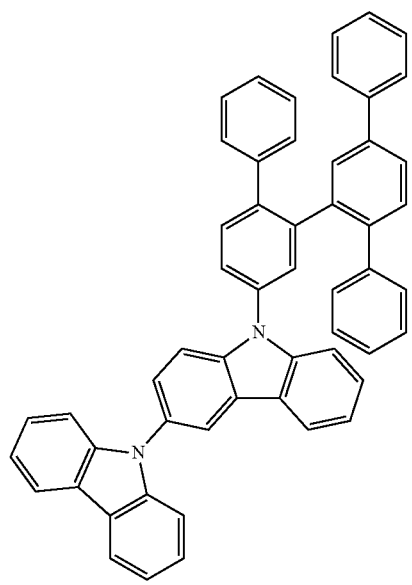
,
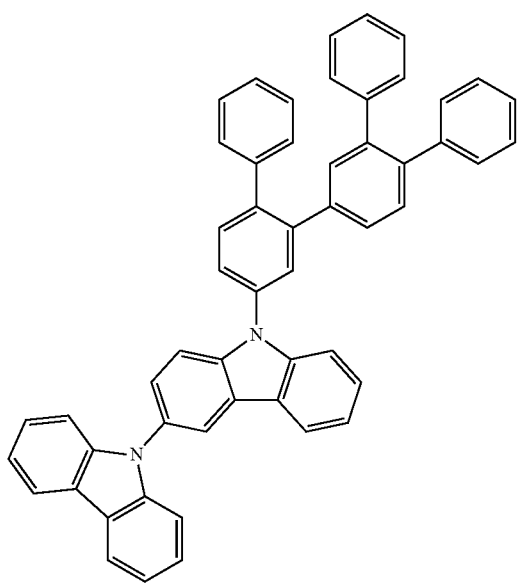
,

375
-continued
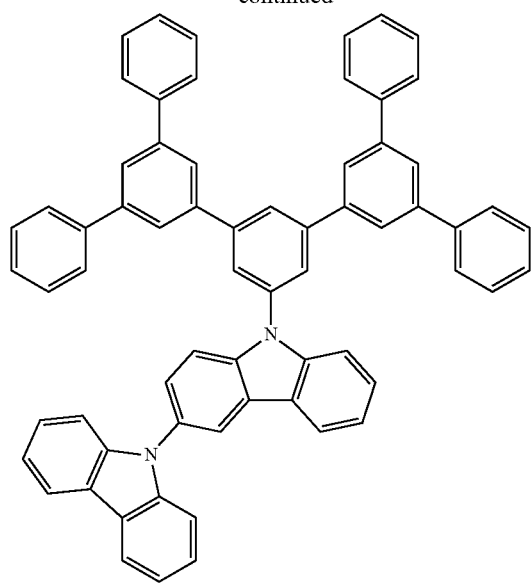
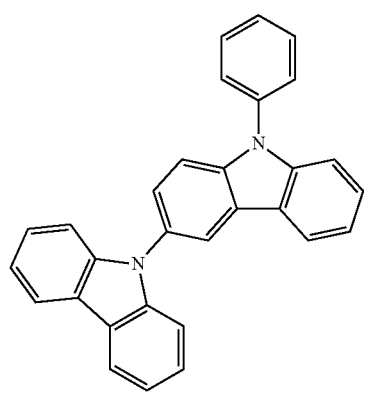
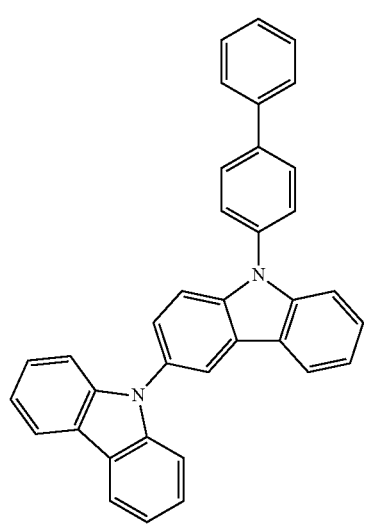
376
-continued
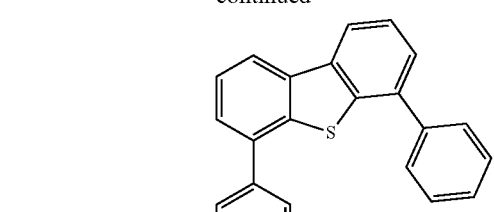
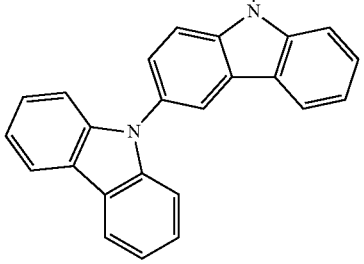
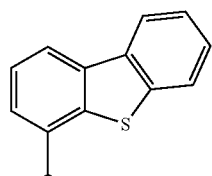
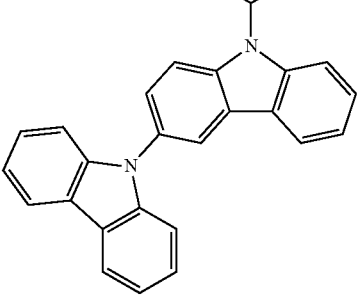
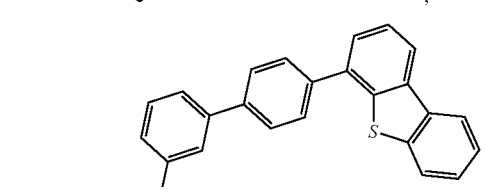
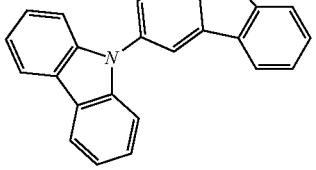

377
-continued
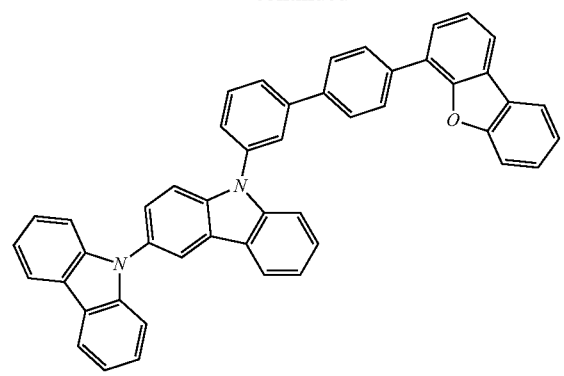
,
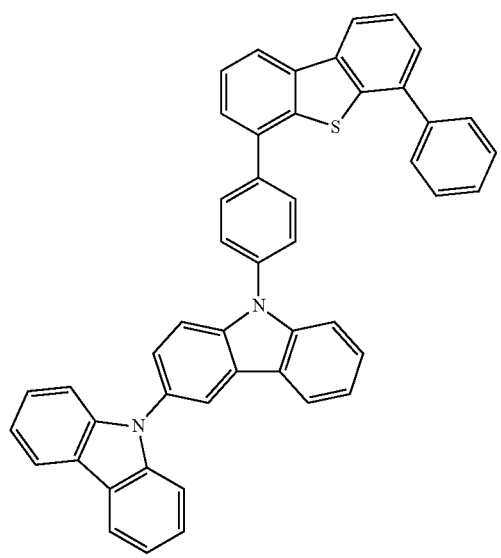
,
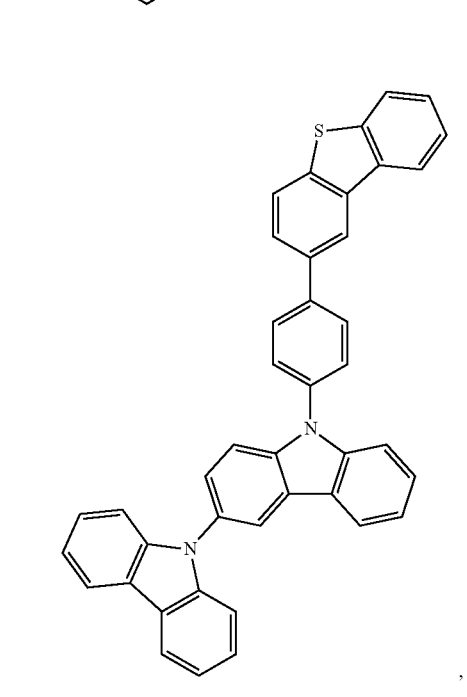
,
378
-continued
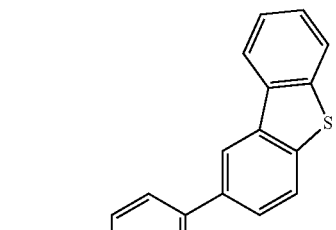
,
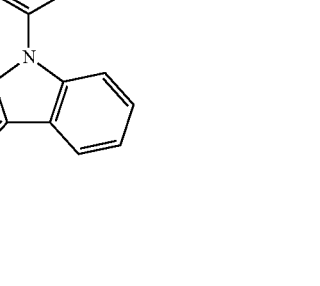
,
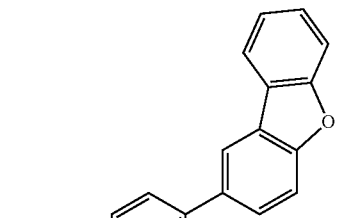
,
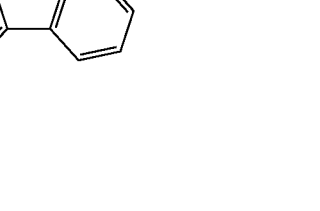
, -continued
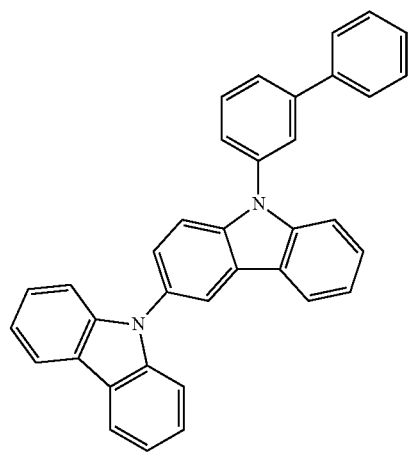
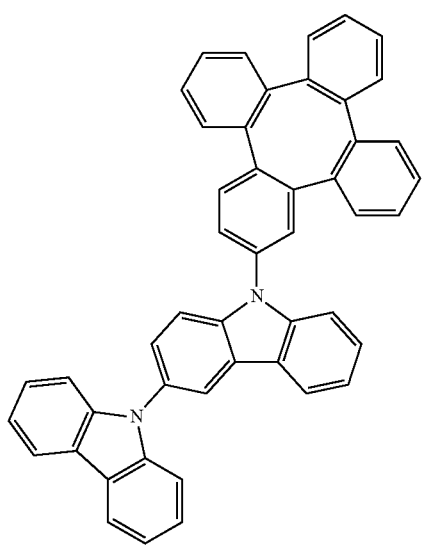
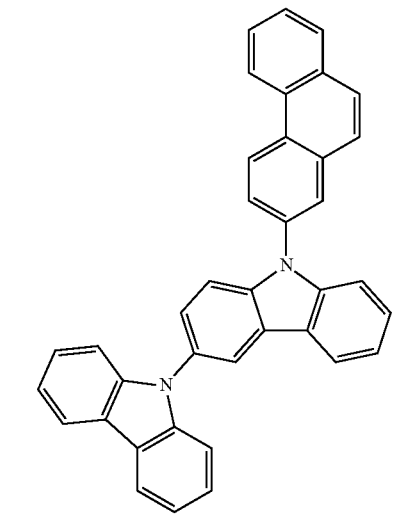
-continued
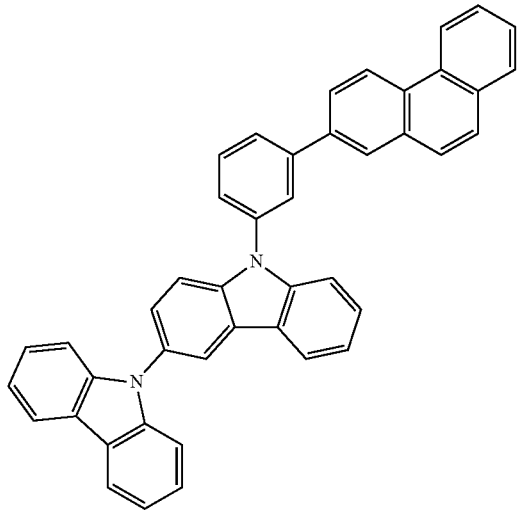
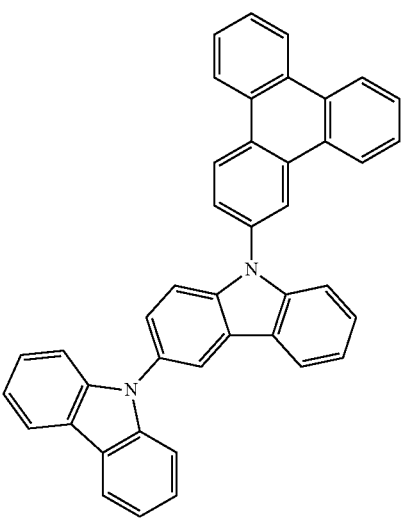
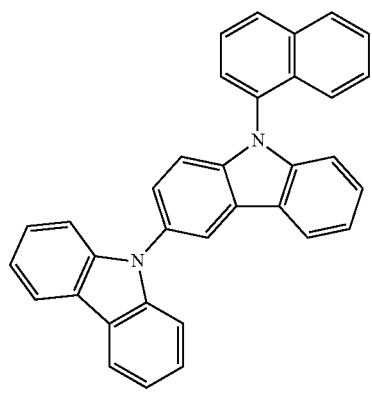

381
-continued
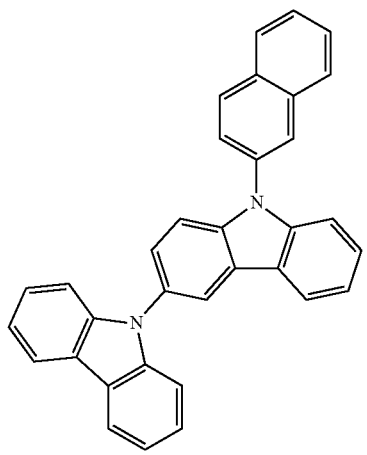
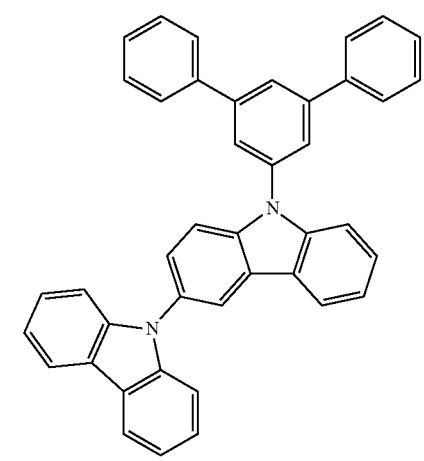
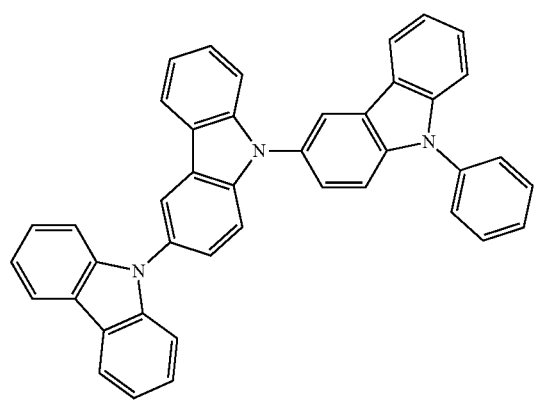
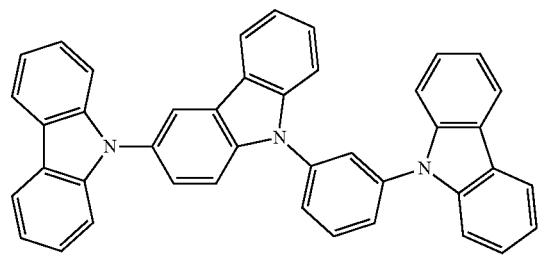
382
-continued
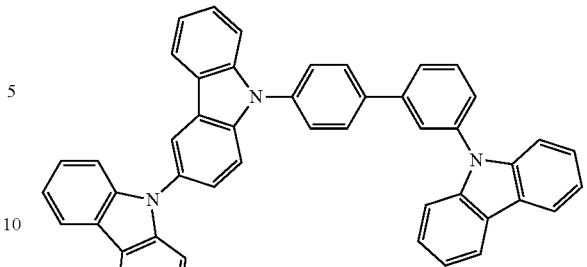
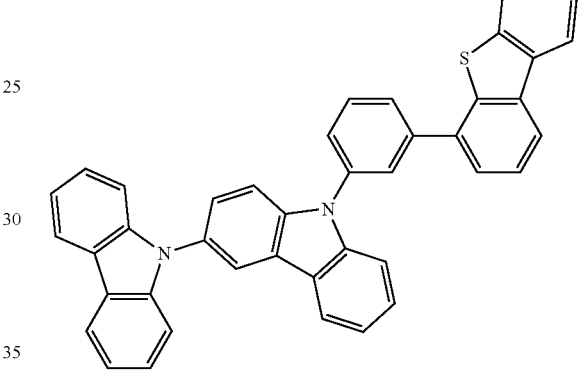
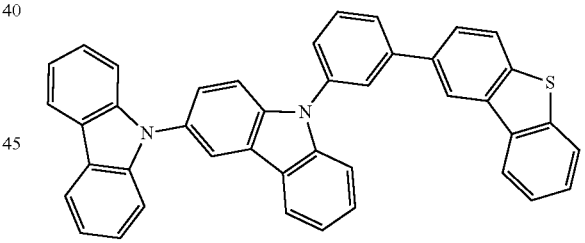
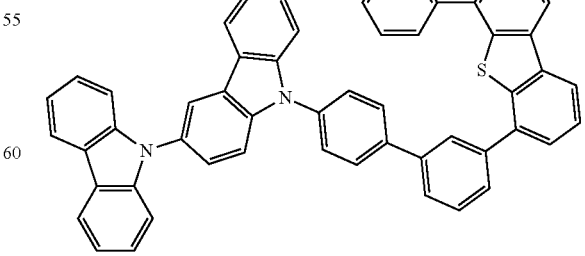

383
-continued

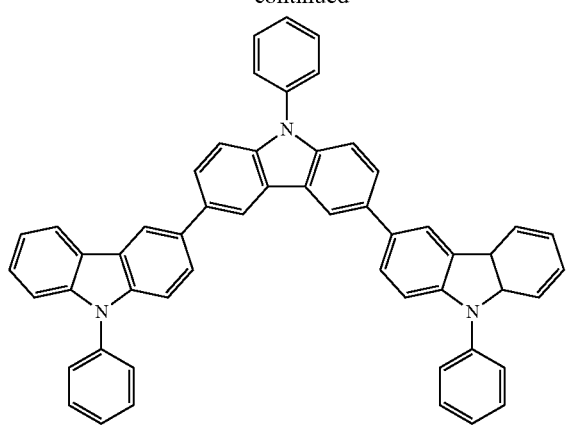

,

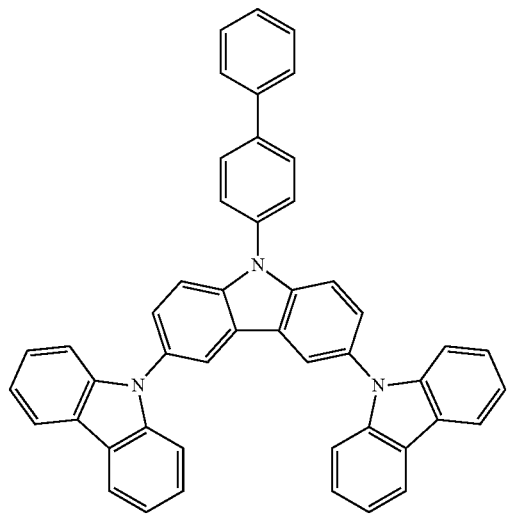

,

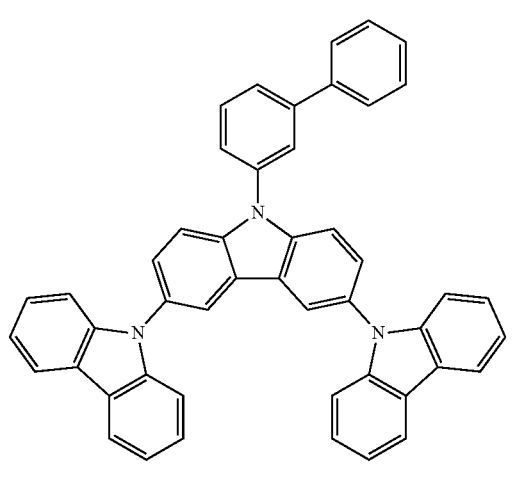

,

384
-continued

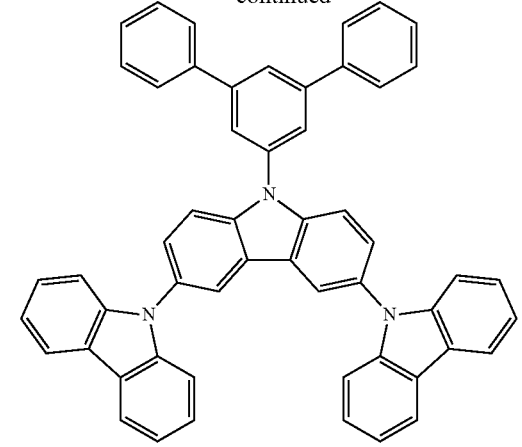

, and partially or fully deuterated variants thereof.

8. The compound of claim 1, wherein $X^{10}$, $X^{11}$, and $X^{12}$ are N.

9. The composition of claim 1, wherein L is a direct bond.

10. The composition of claim 1, wherein L is an aromatic linker.

11. The composition of claim 10, wherein the aromatic linker is phenyl.

12. The composition of claim 11, wherein the phenyl linker bonds to the ring containing $Ar^7$ and $Ar^8$ at a para position relative to the bond to the nitrogen atom of the N-carbazolyl-carbazole.

13. The composition of claim 1, wherein at least one of $Ar^7$ and $Ar^8$ comprises at least two phenyl rings.

14. The composition of claim 1, wherein the second compound is selected from the group consisting of:

385
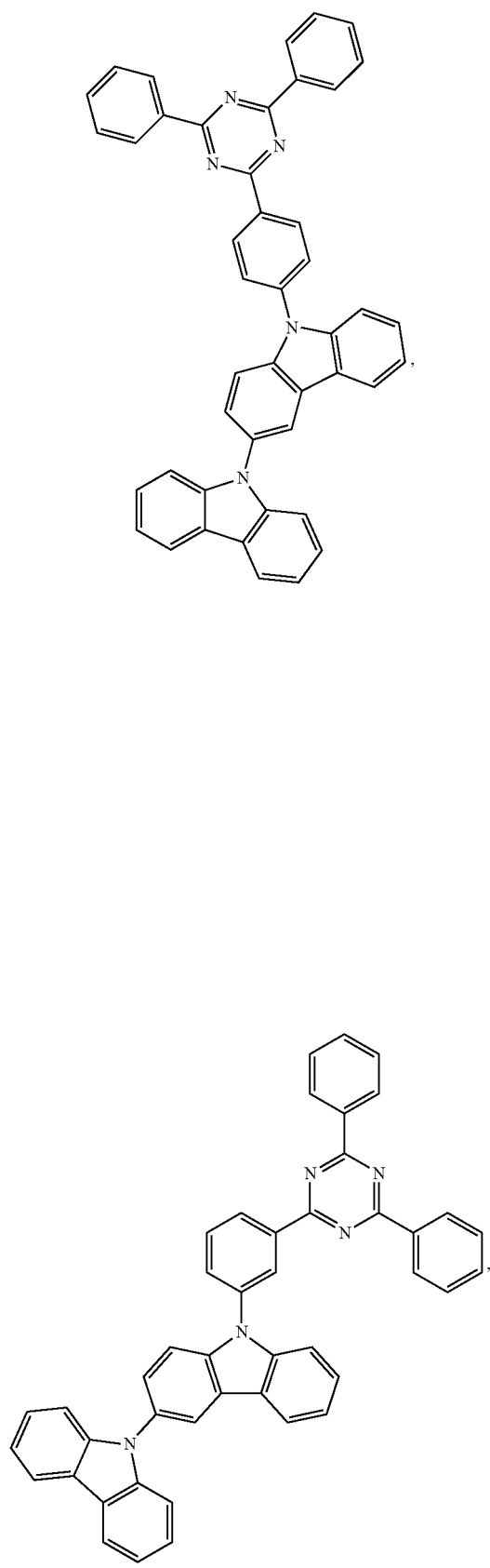
386
-continued
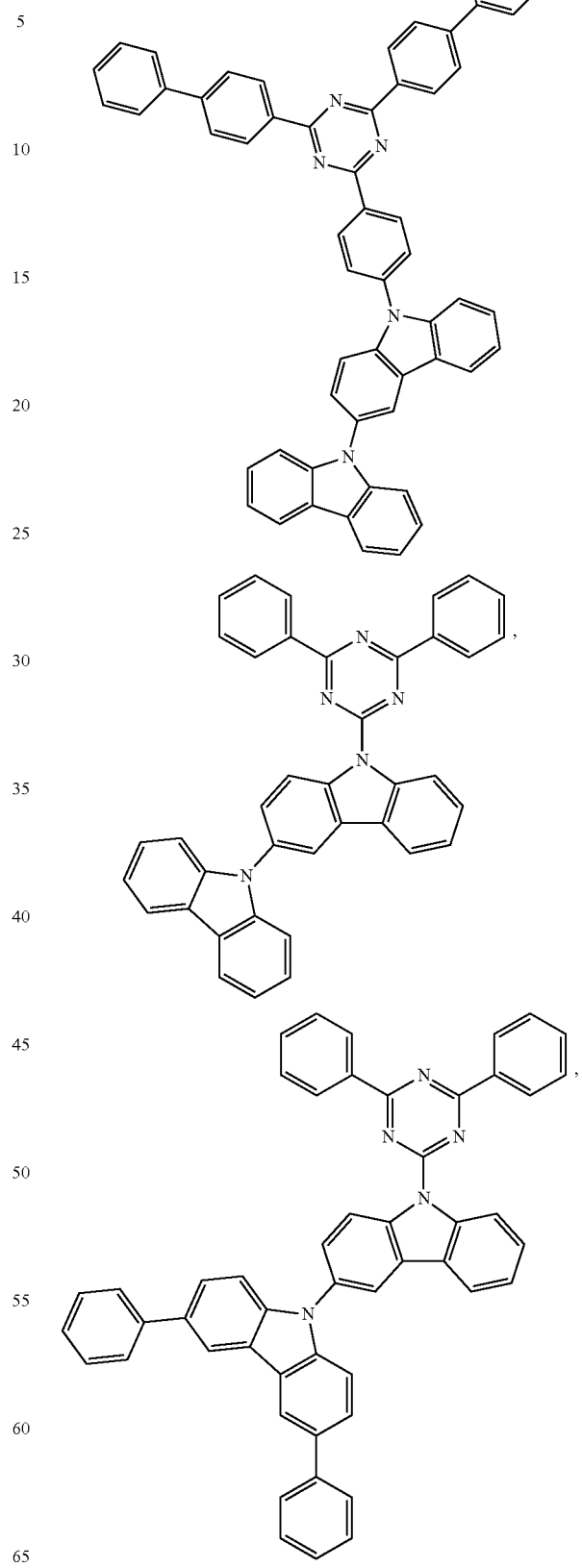

387
-continued
388
-continued
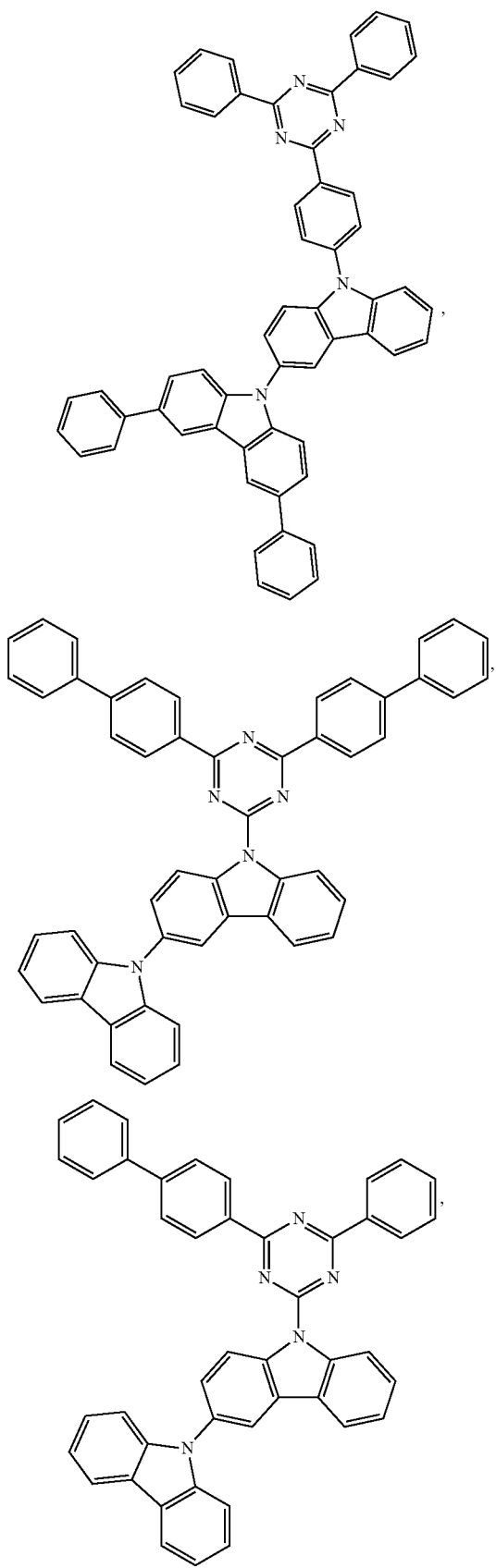
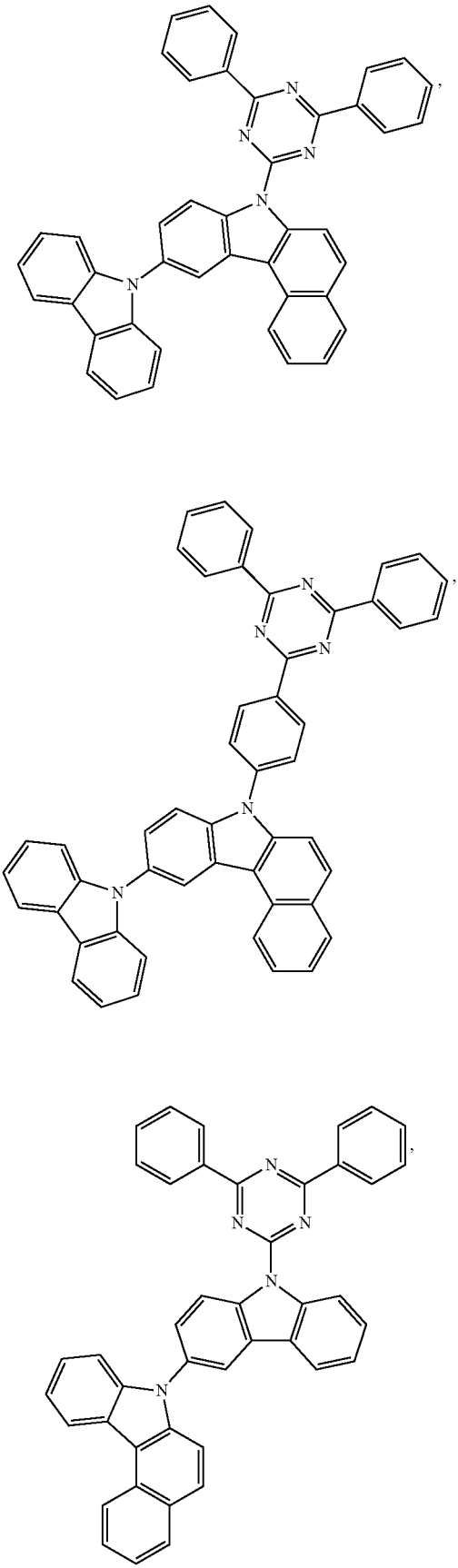

389
-continued
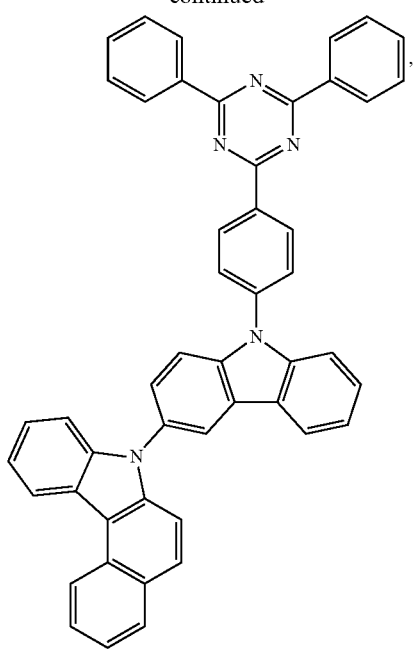
390
-continued
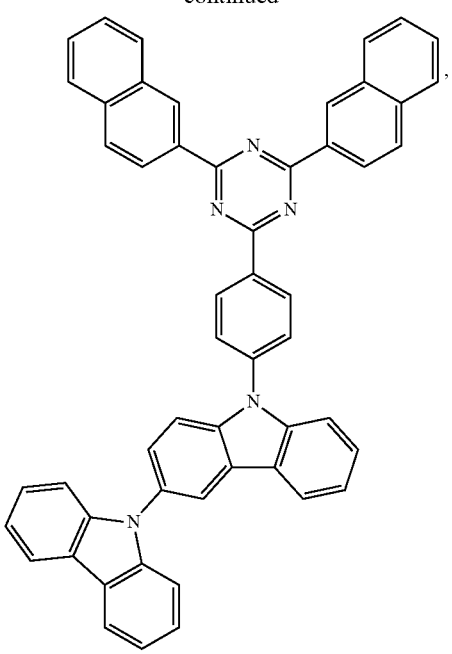
and partially or fully deuterated variants thereof.
15. The composition of claim 1, wherein the first compound is selected from the group consisting of:
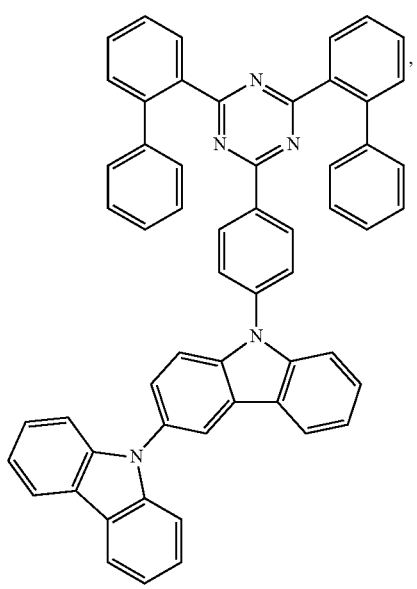
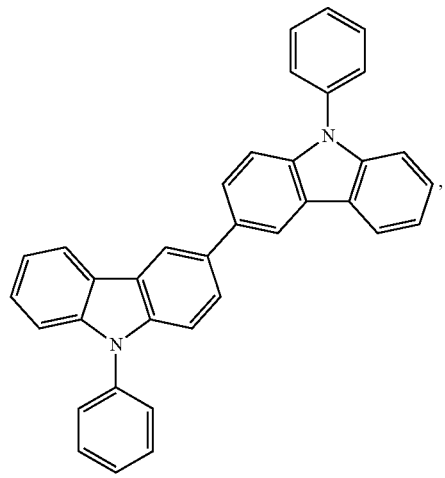

391
-continued
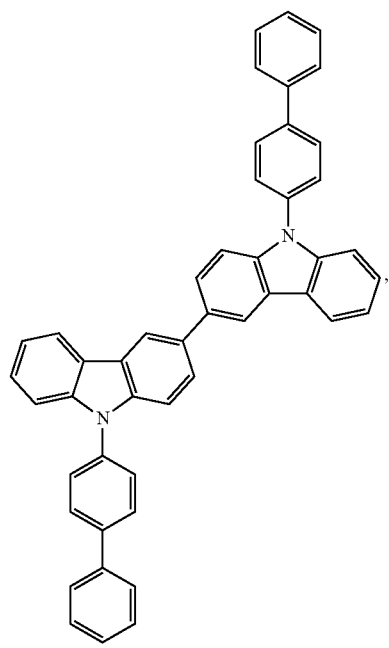
392
-continued
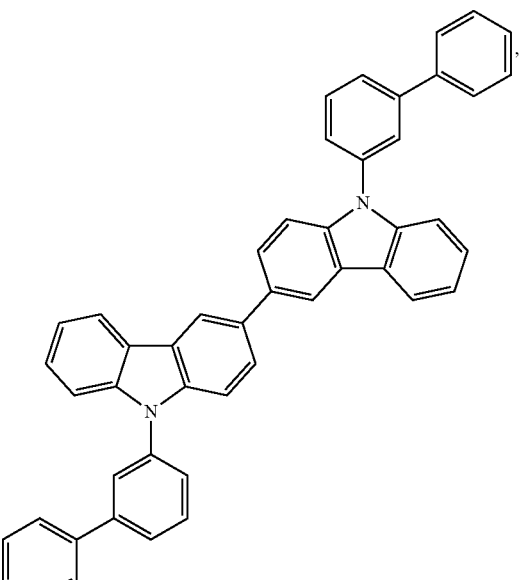
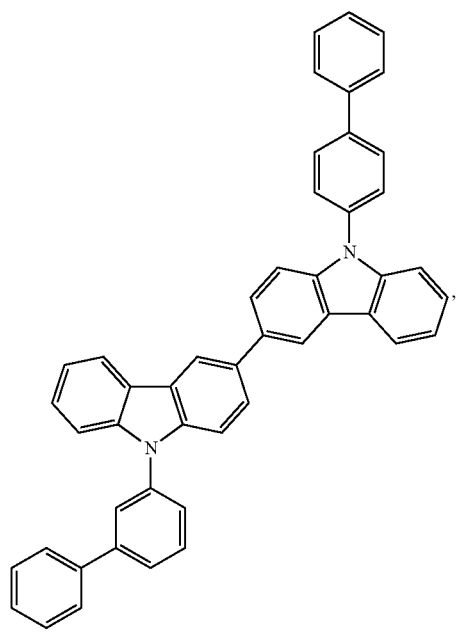
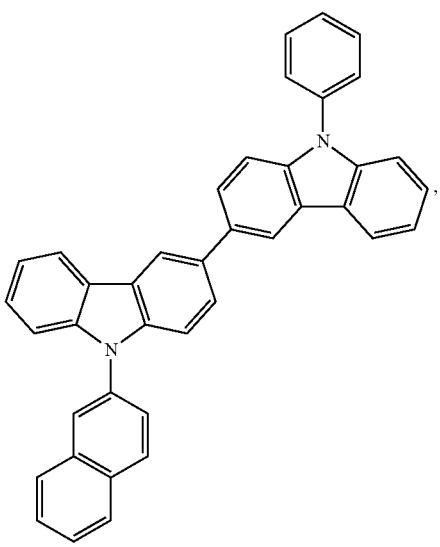

393
-continued
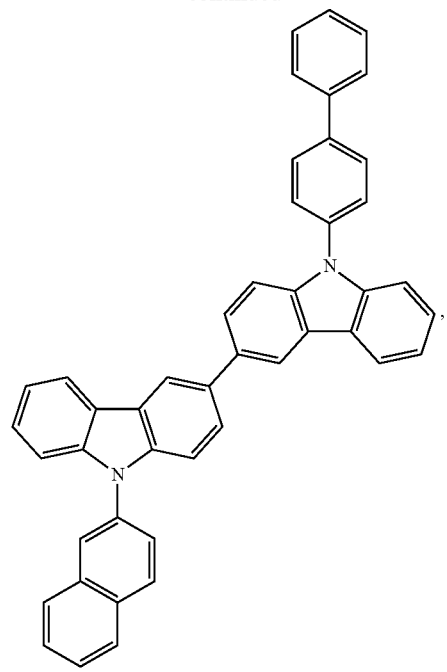
394
-continued
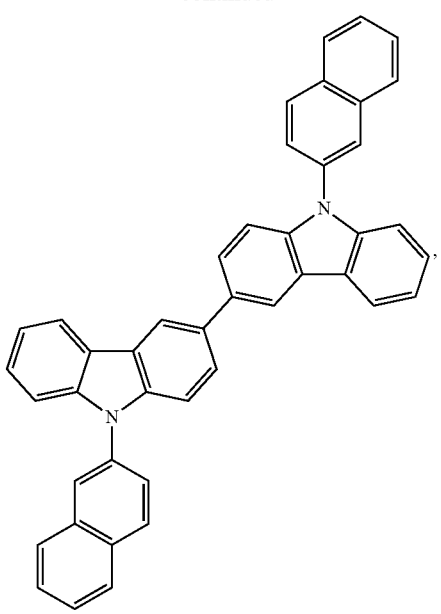
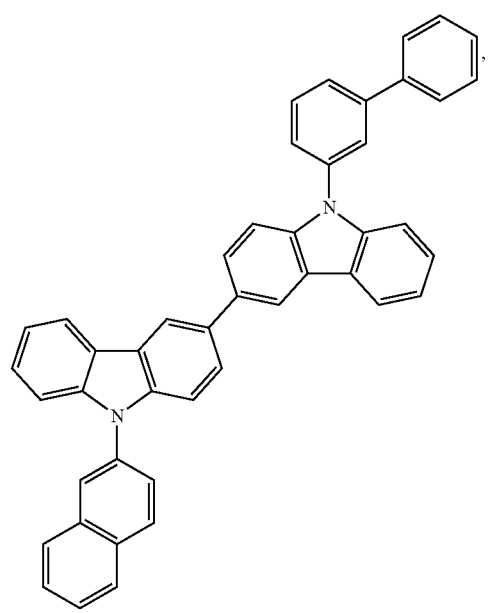
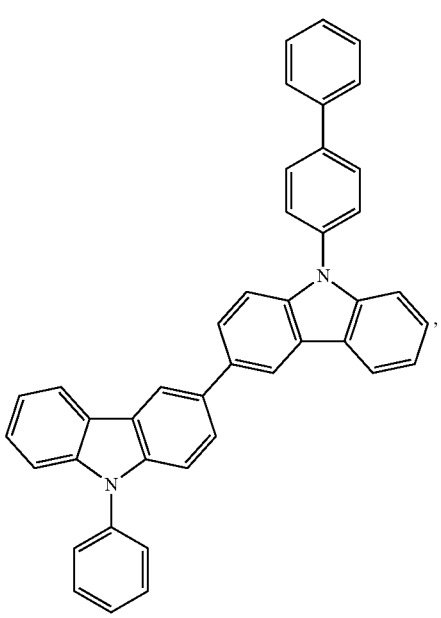

395
-continued
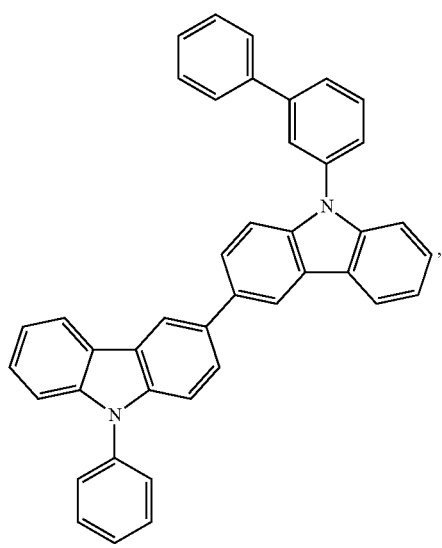
396
-continued
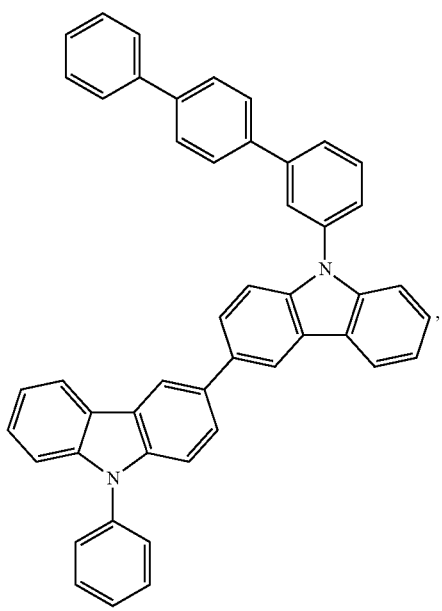
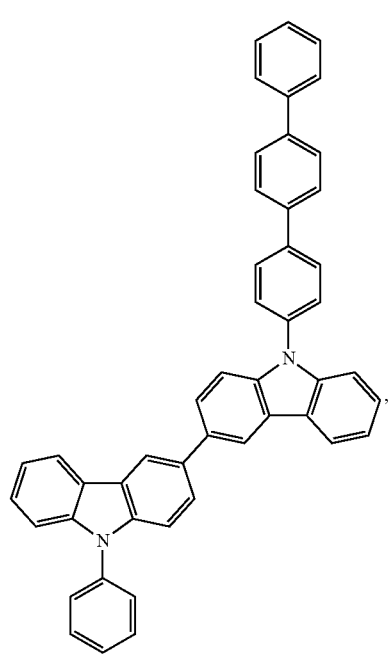
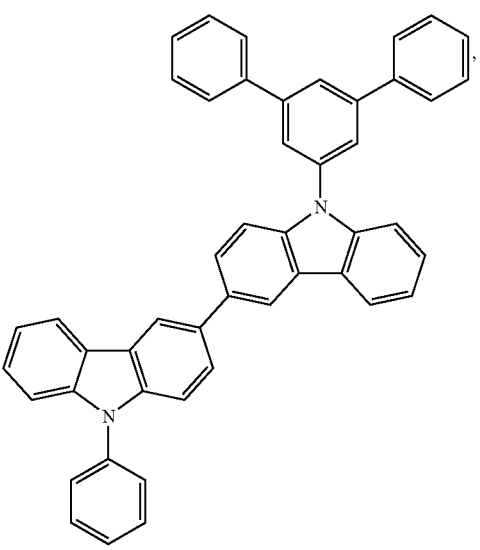

397
-continued
398
-continued
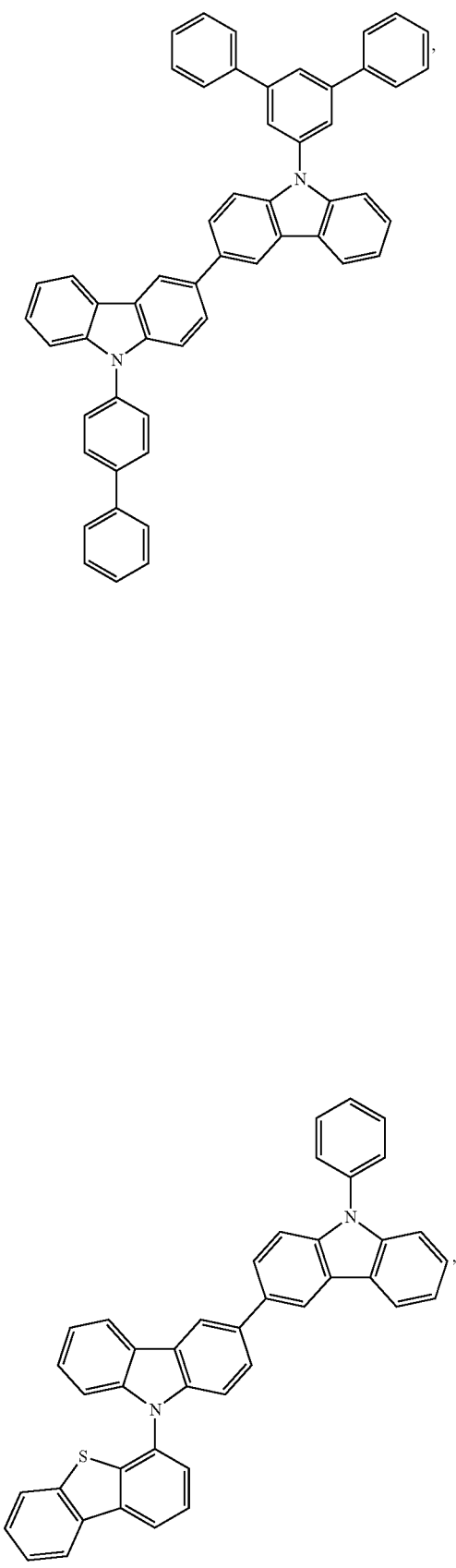
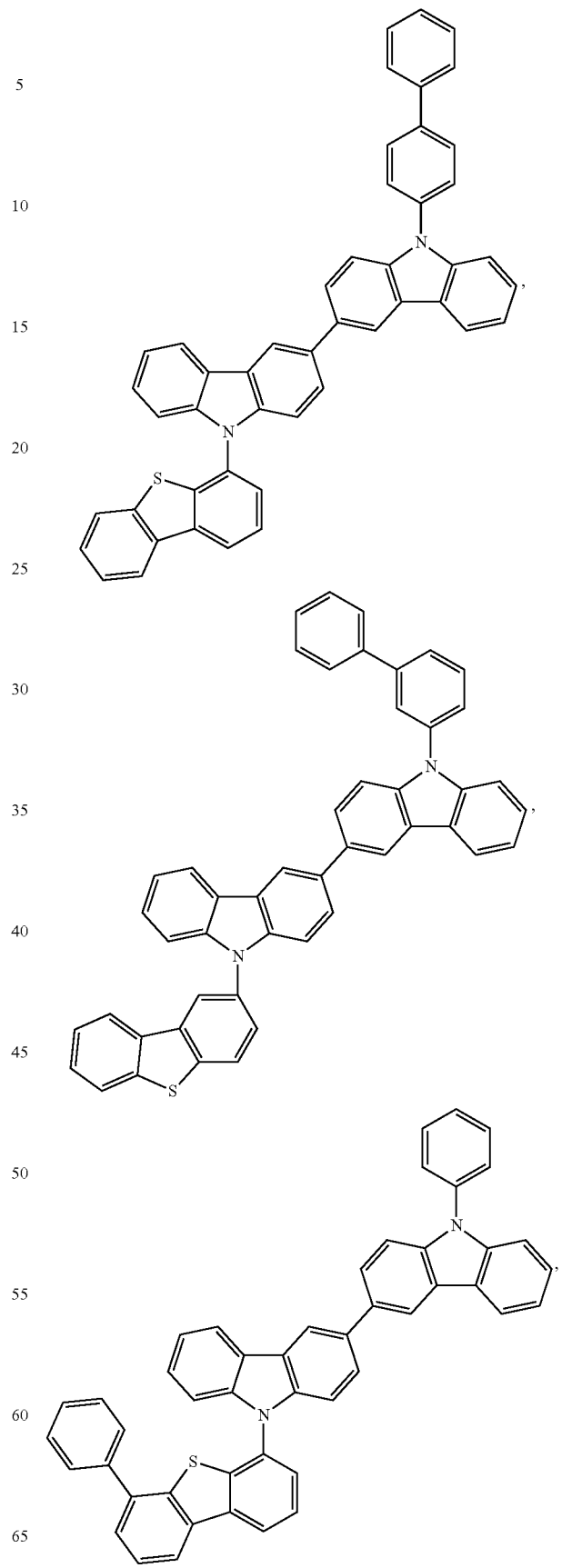

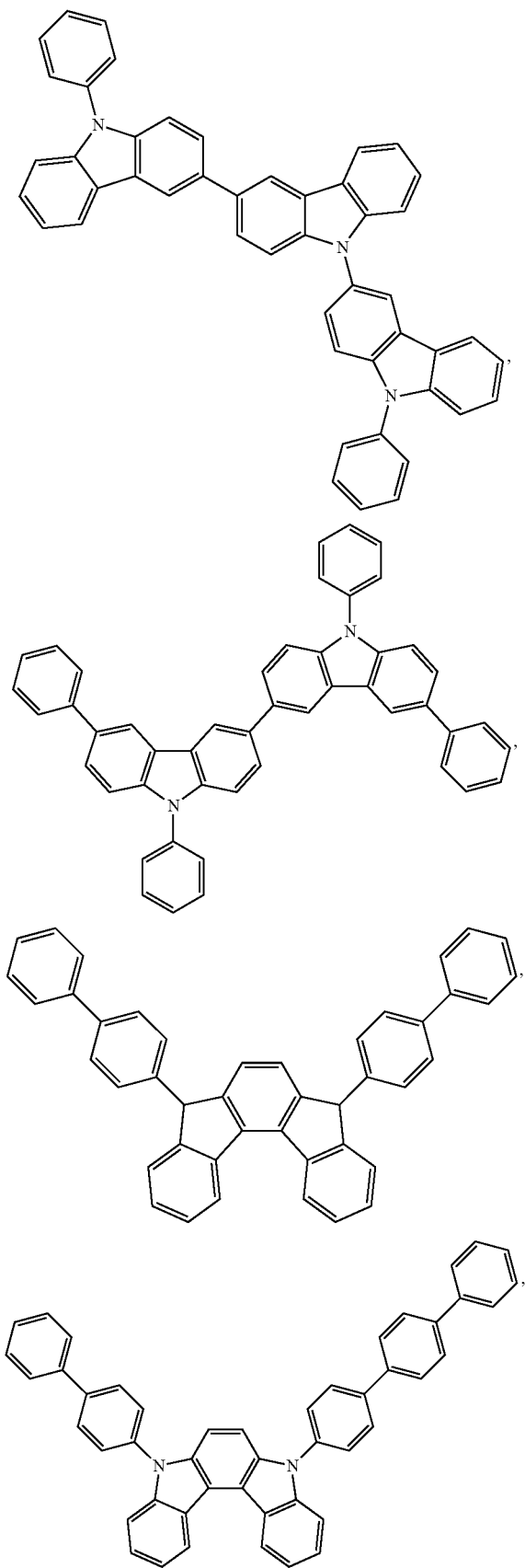
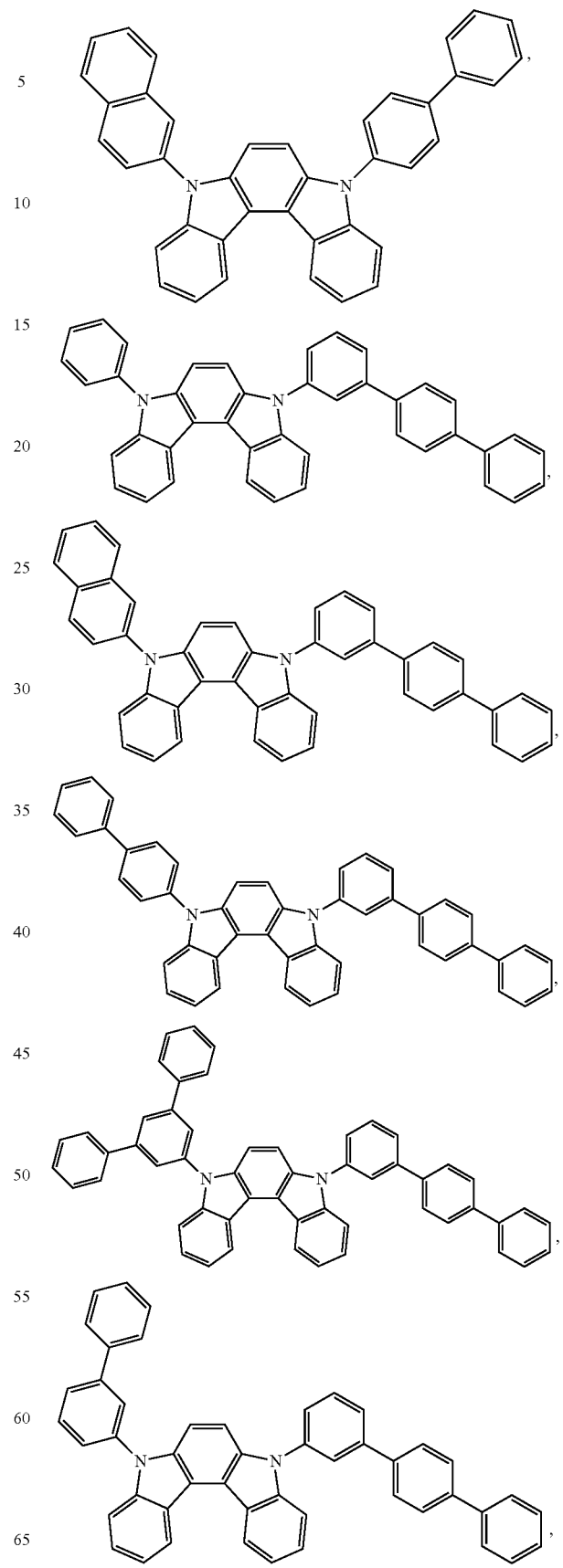

401
-continued
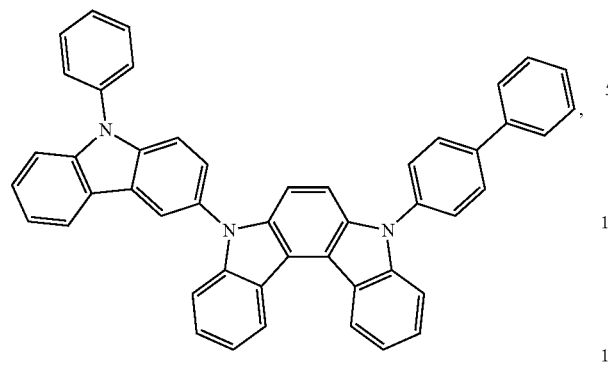
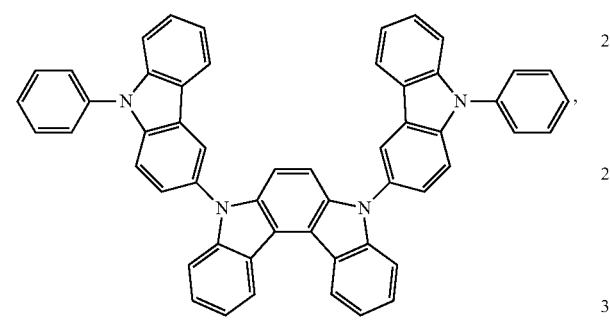
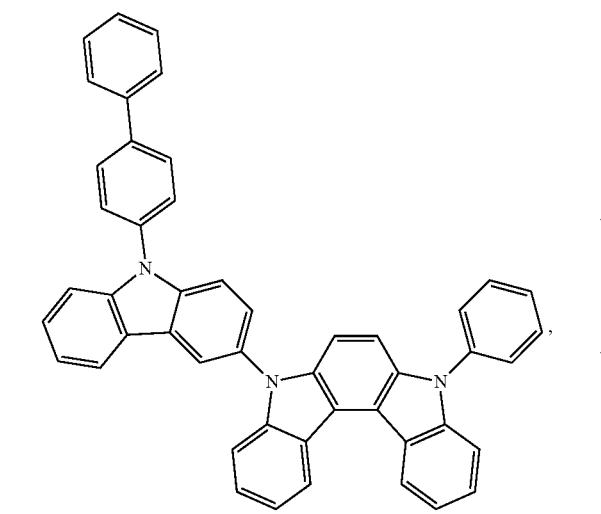
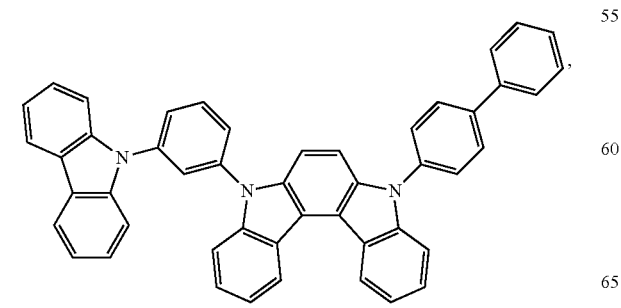
402
-continued
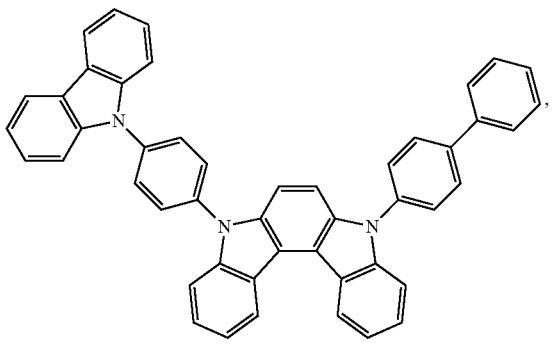
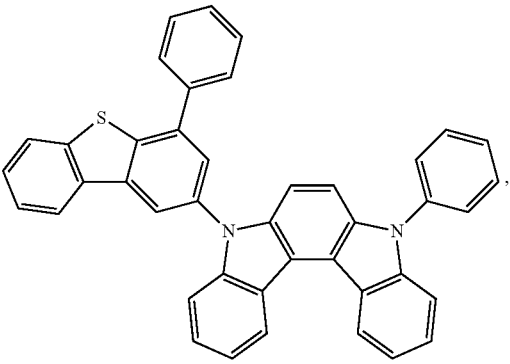
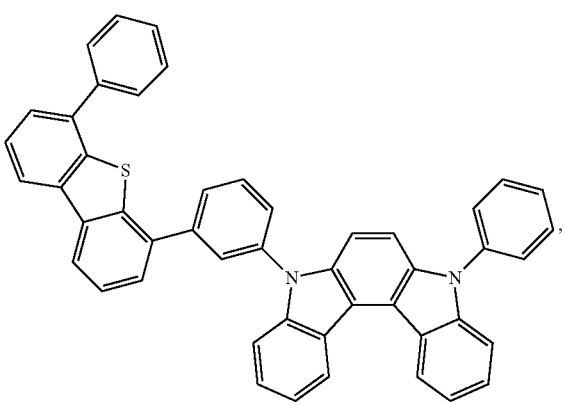
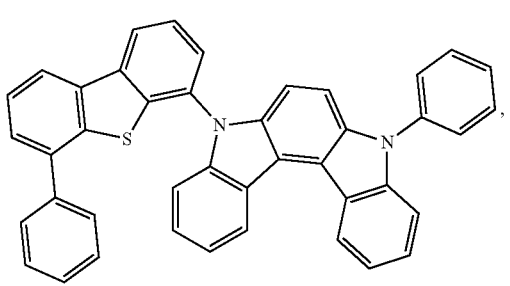

403
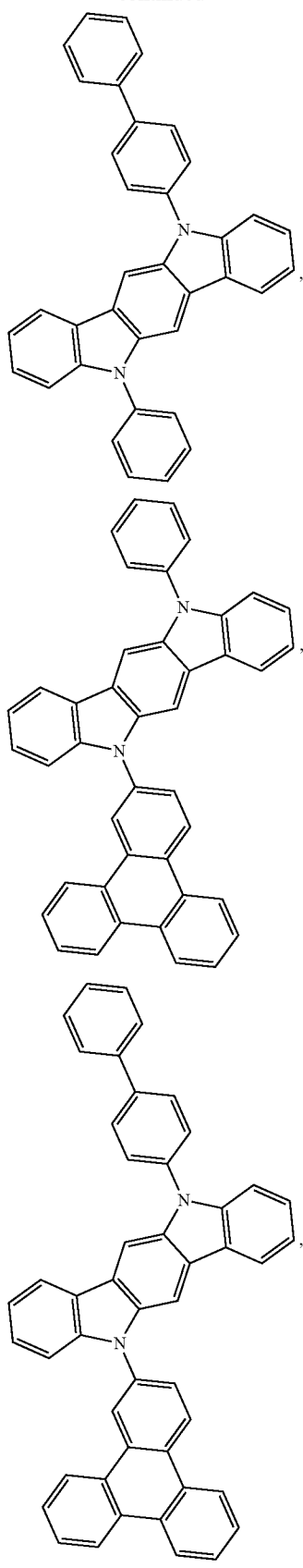
404

405
-continued
406
-continued
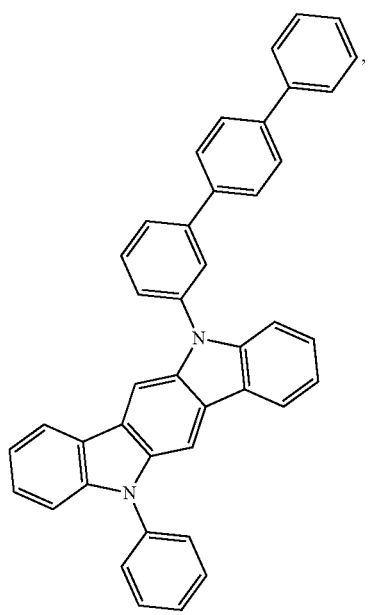
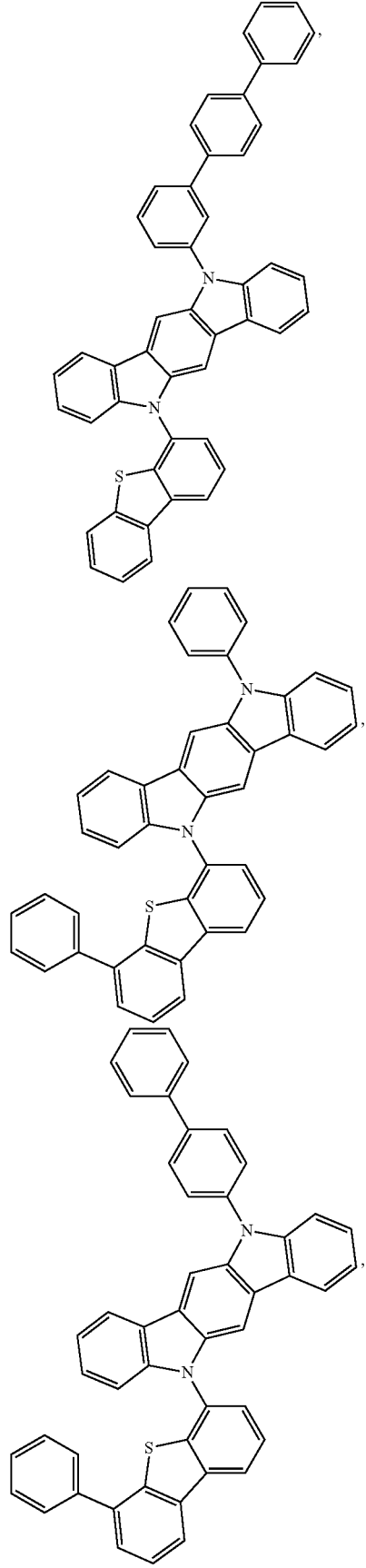

407
-continued
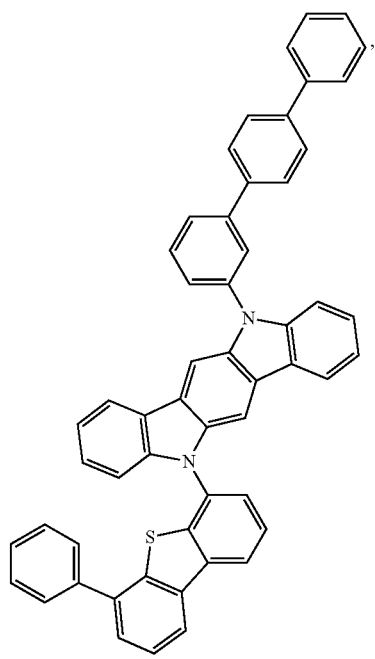
408
-continued
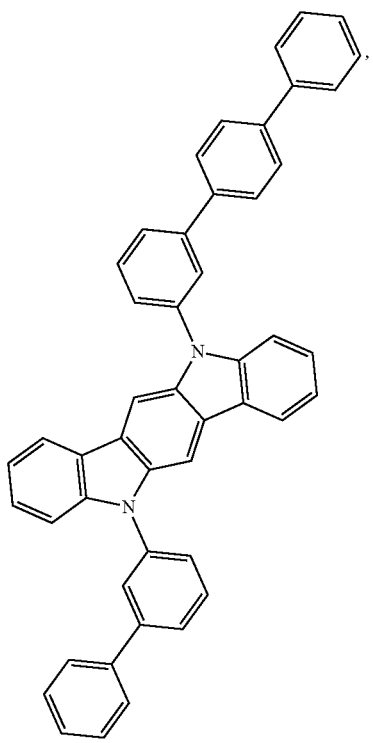
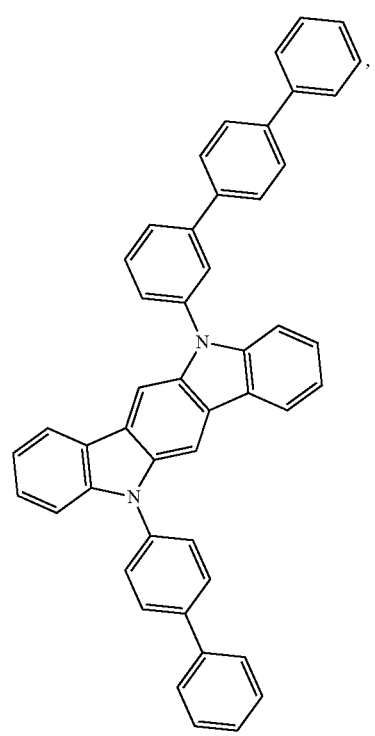
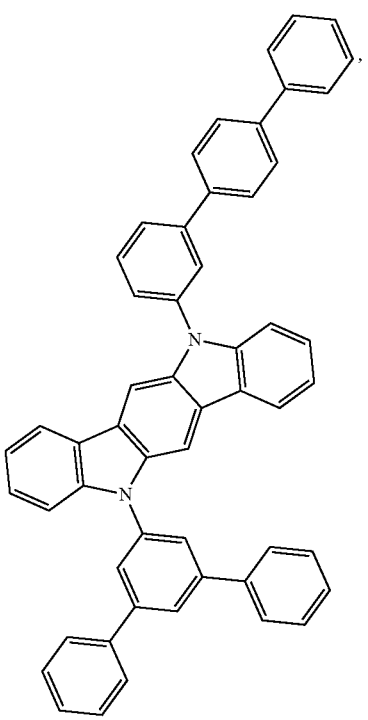

409
-continued
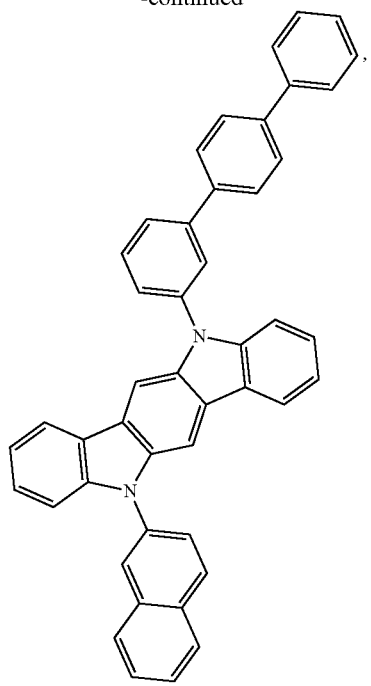
410
-continued
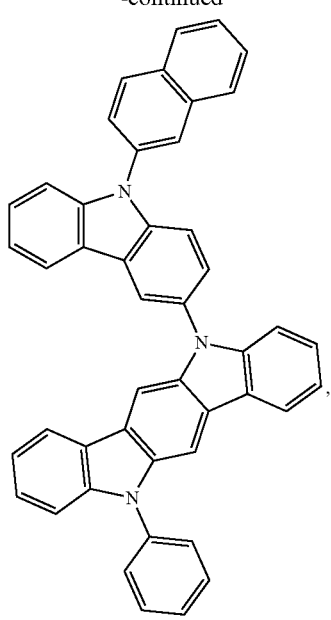

411
-continued
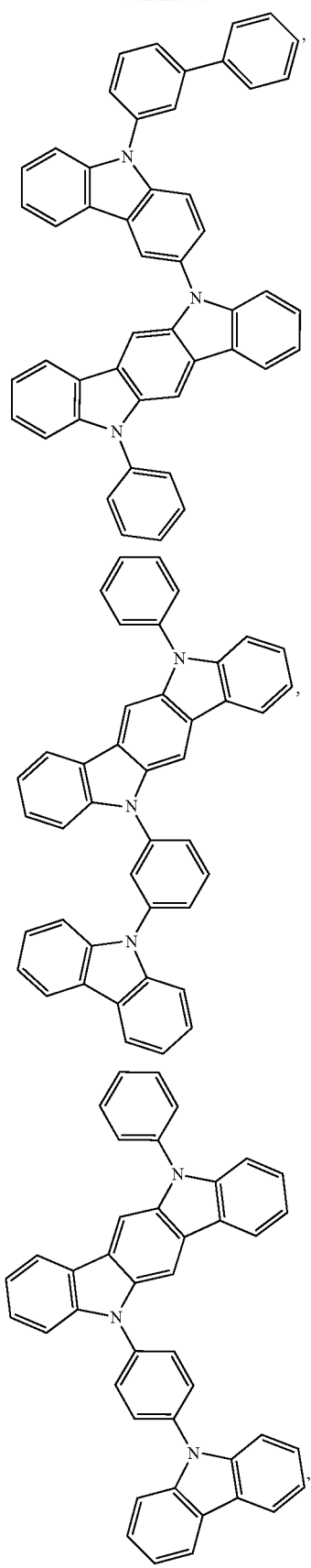
412
-continued
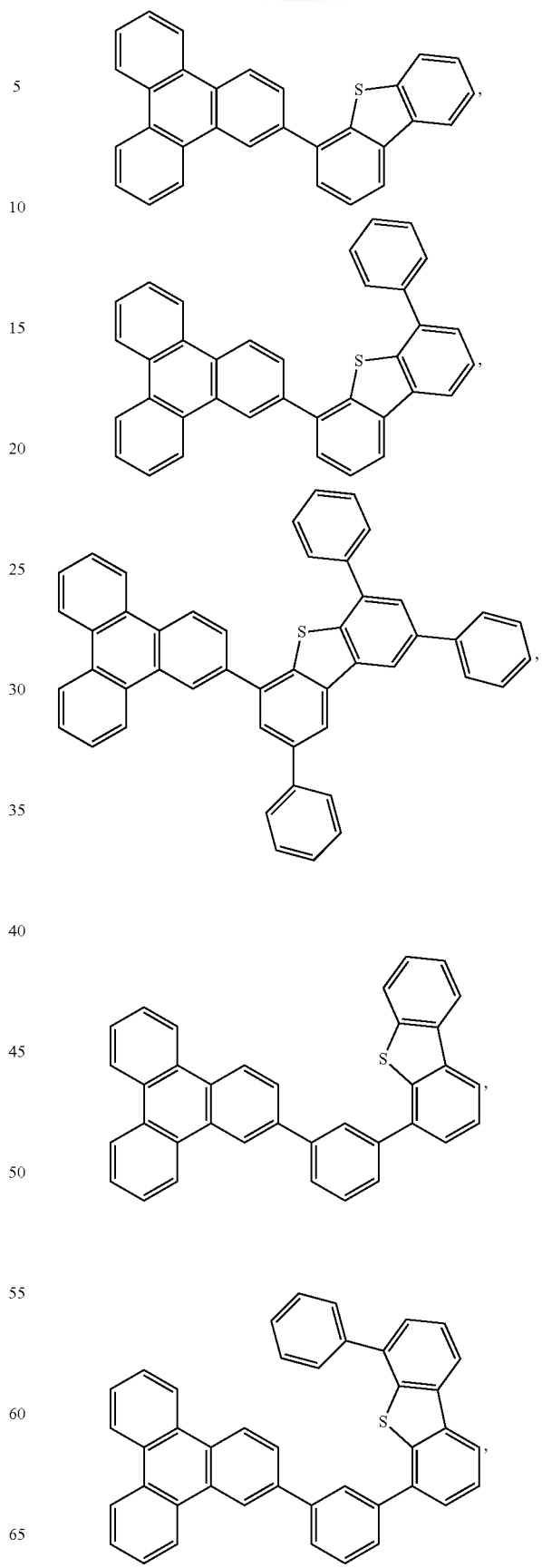

413
-continued
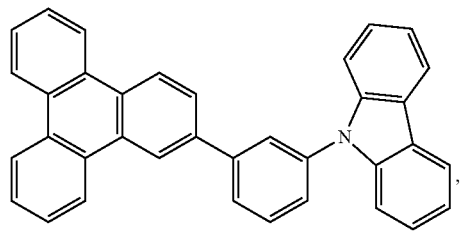
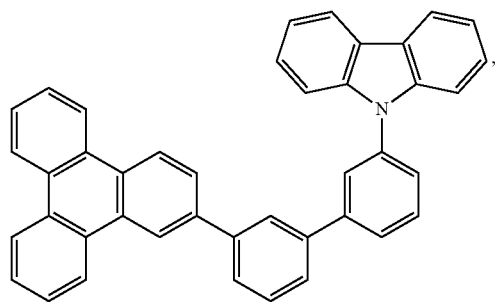
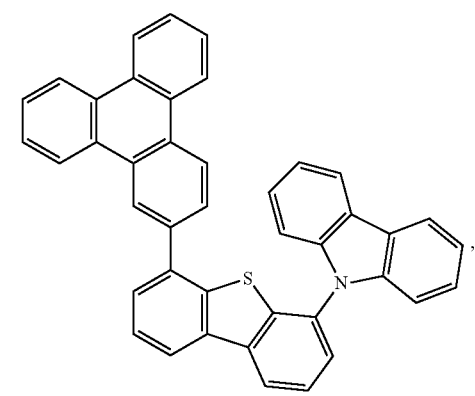
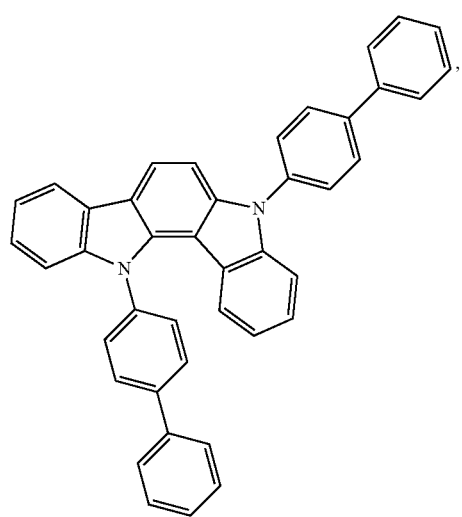
414
-continued
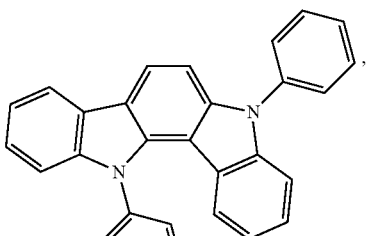
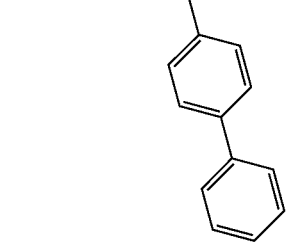
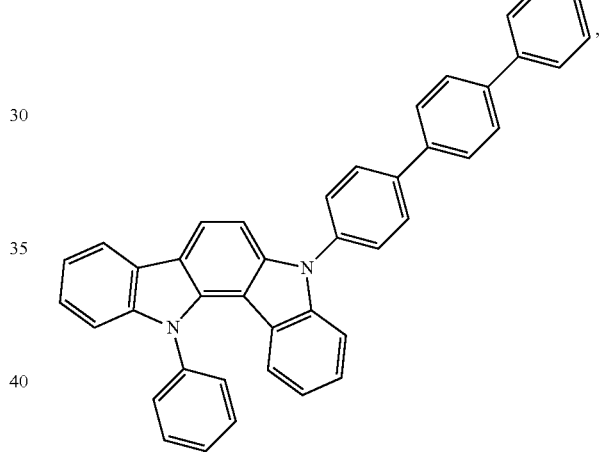
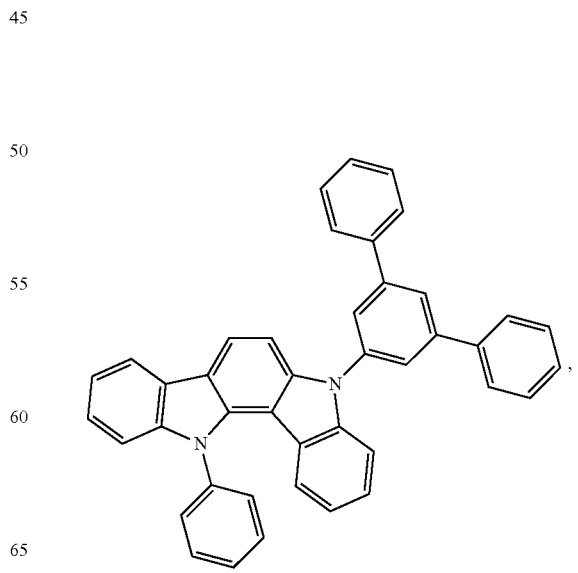

415
-continued
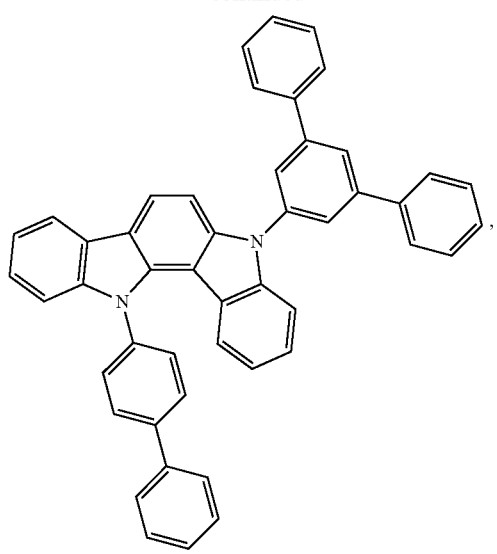,
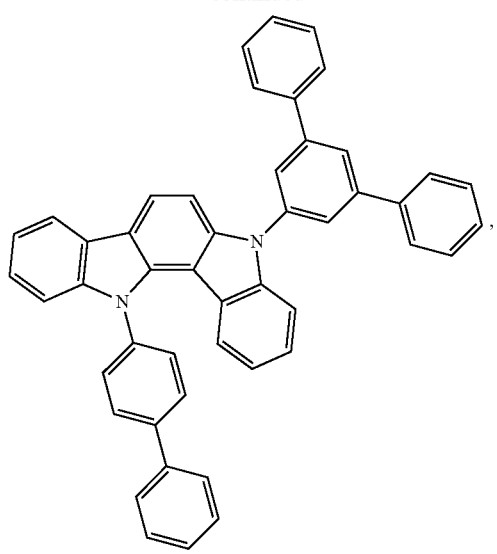,
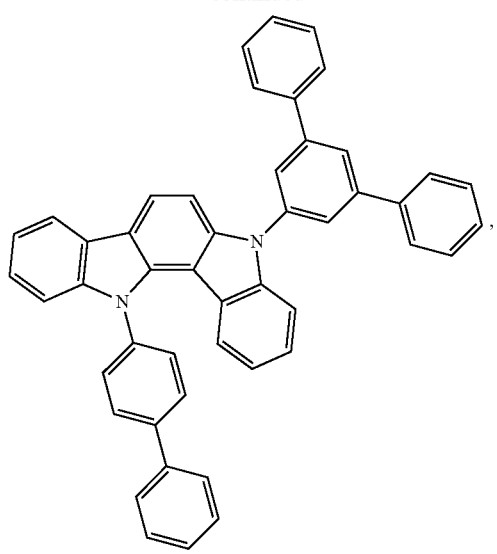,
416
-continued
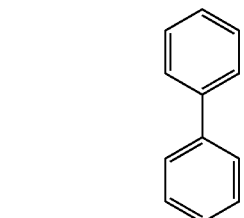
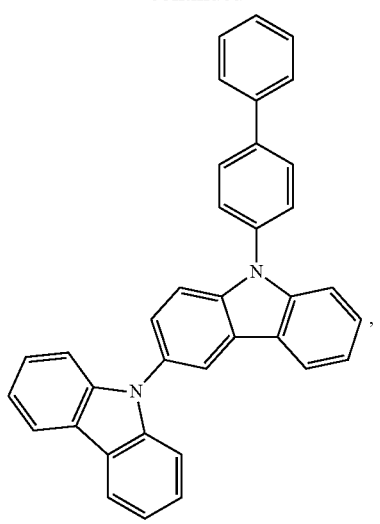,
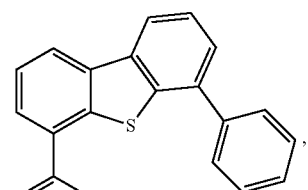
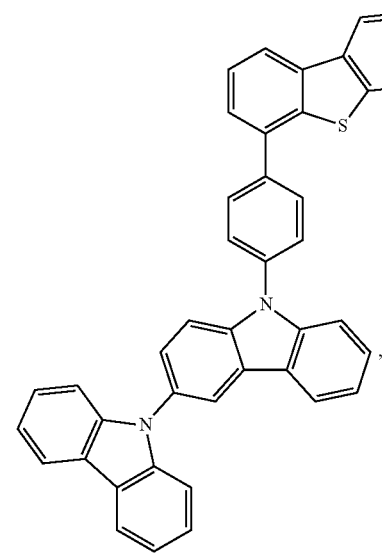,
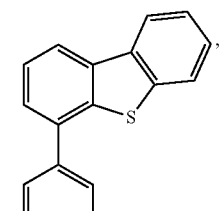
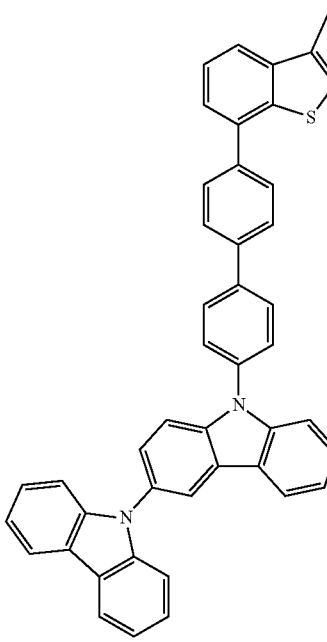, 417
-continued
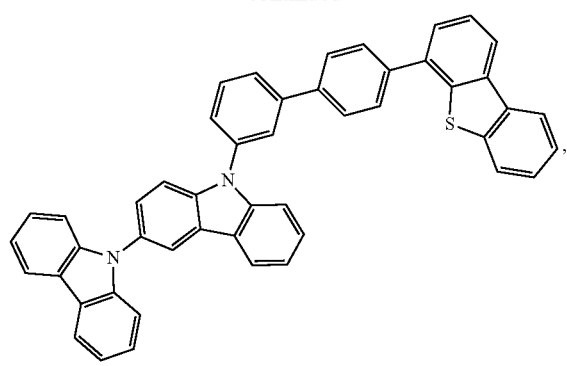
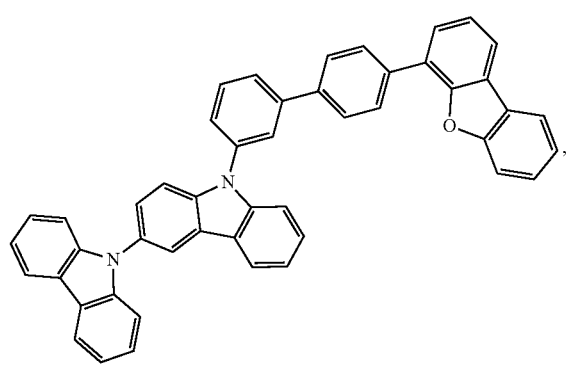
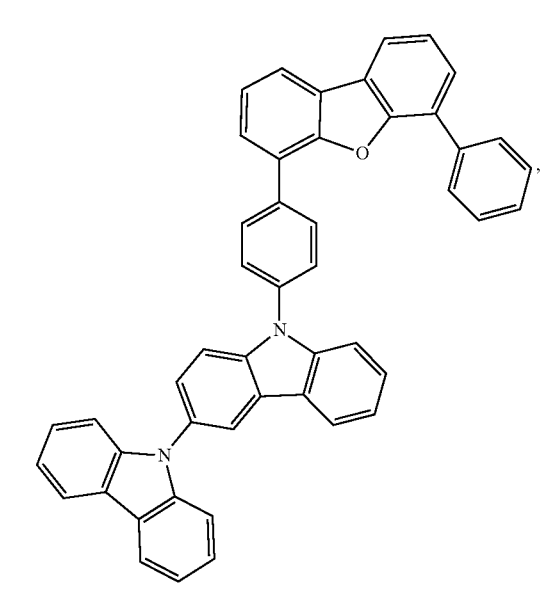
418
-continued
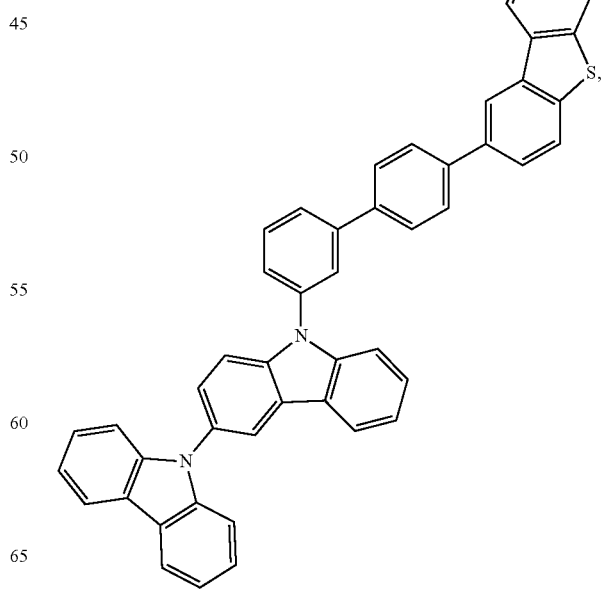

419
-continued
420
-continued
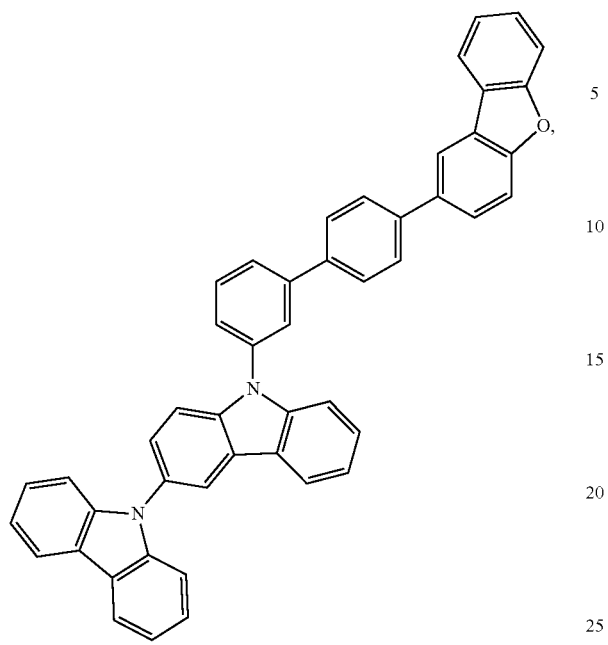
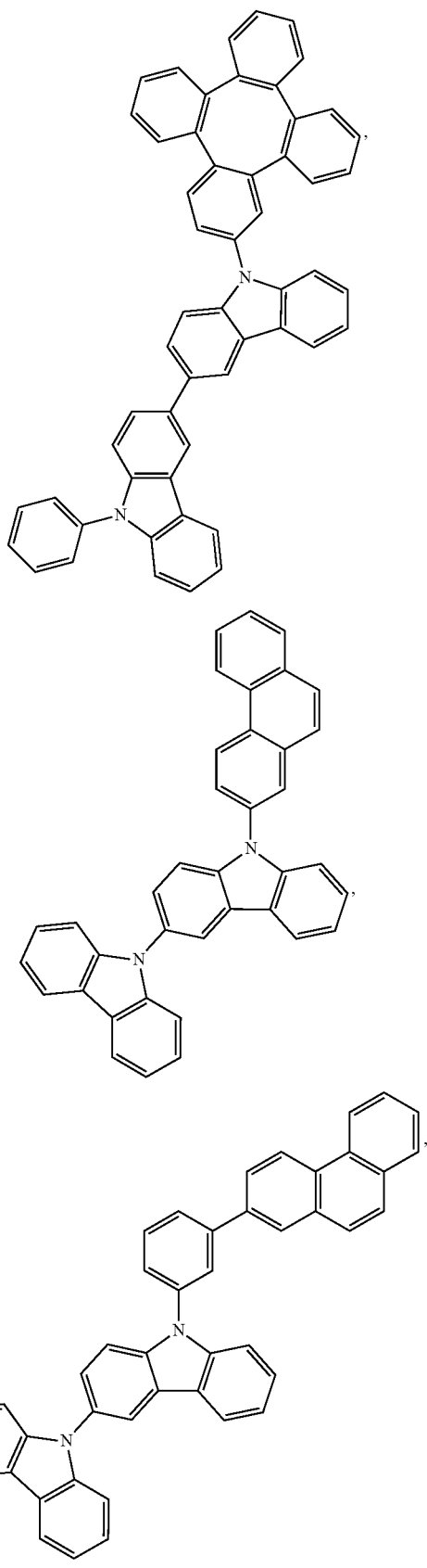

421
-continued
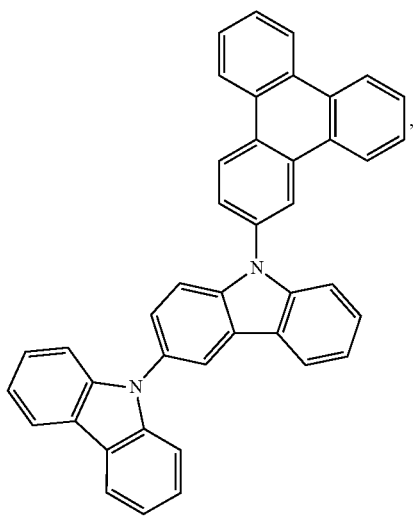
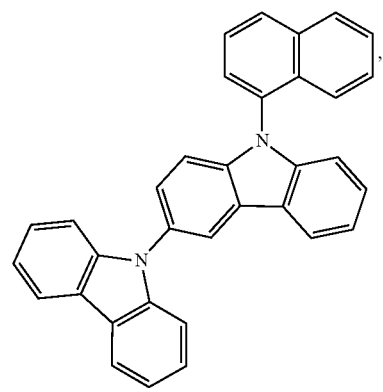
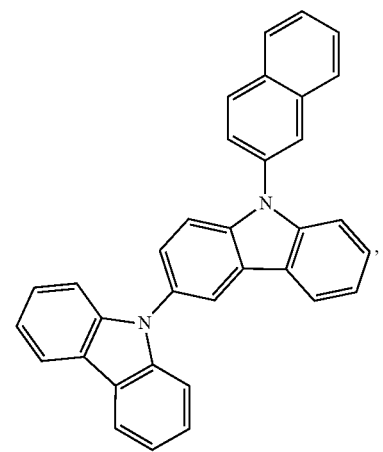
422
-continued
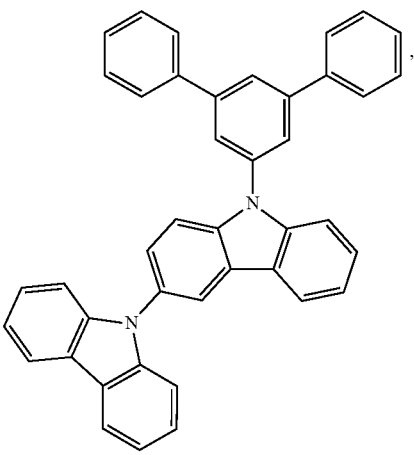
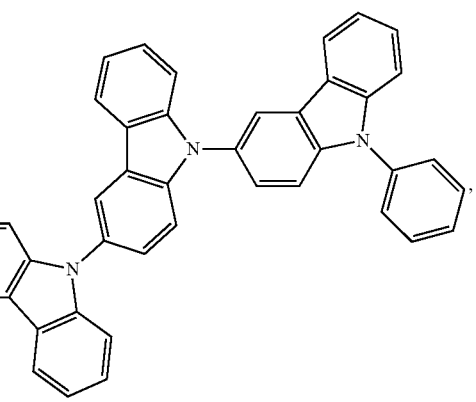
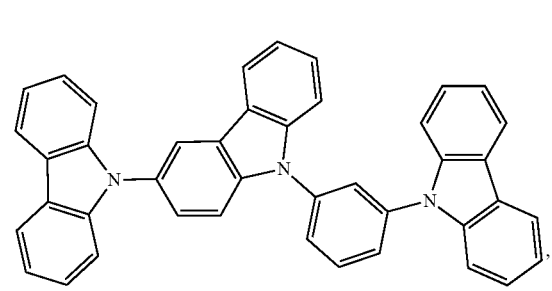
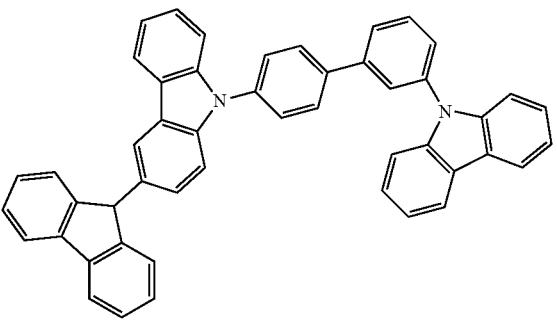

423
-continued
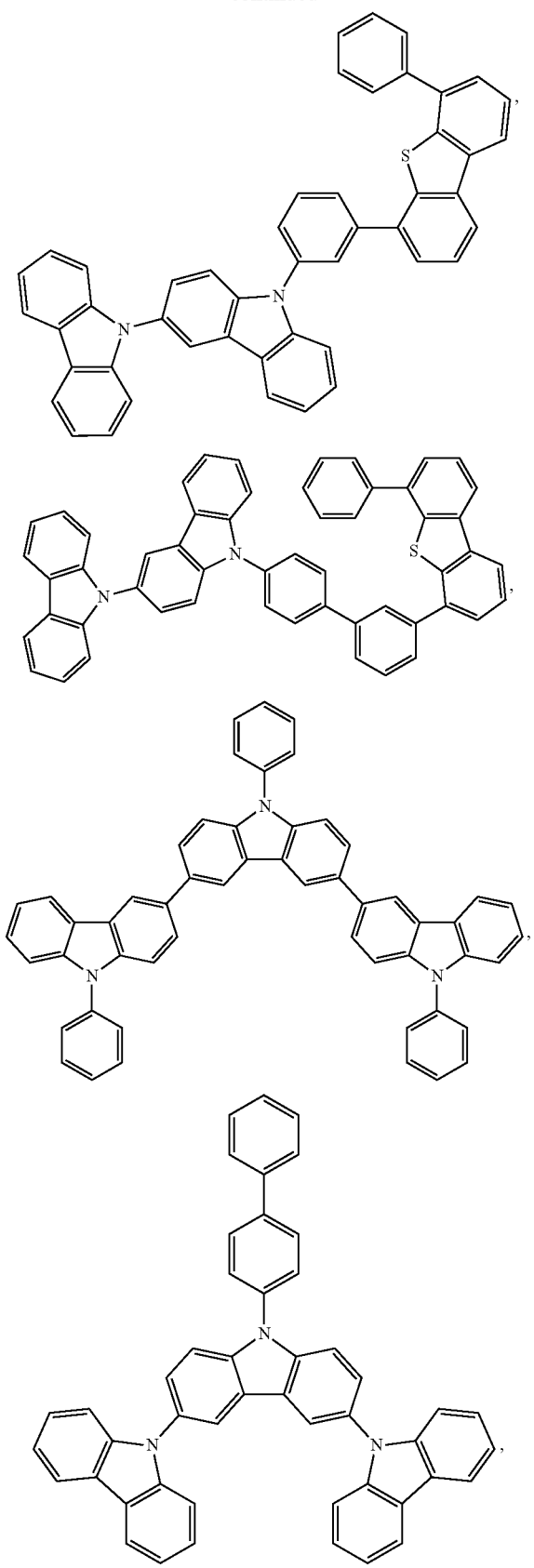
424
-continued
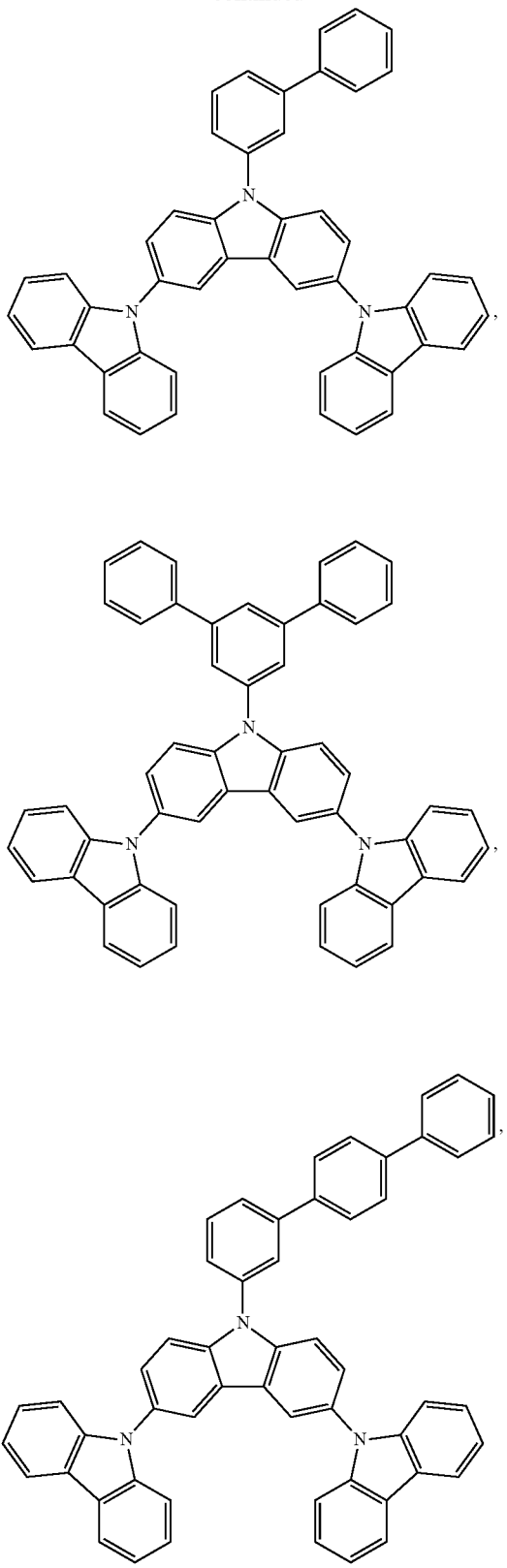
and partially or fully deuterated variants thereof; and
wherein the second compound is selected from the group consisting of:

425
426
-continued
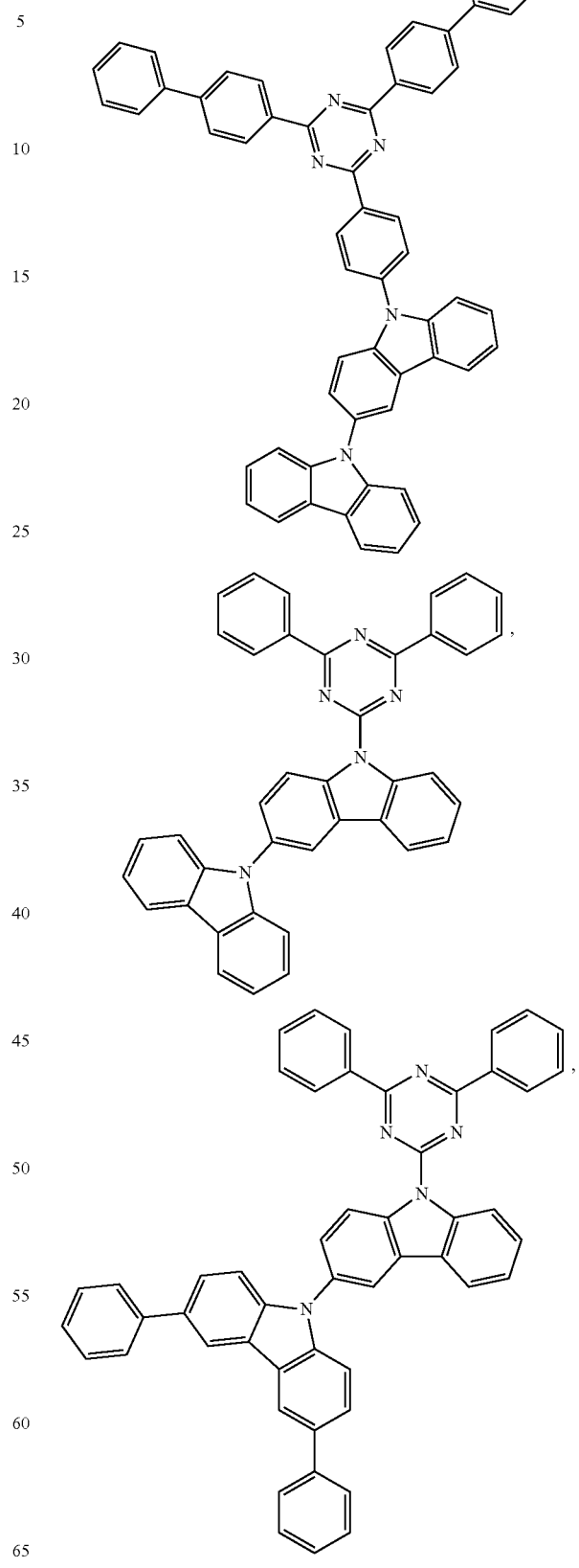

427
-continued
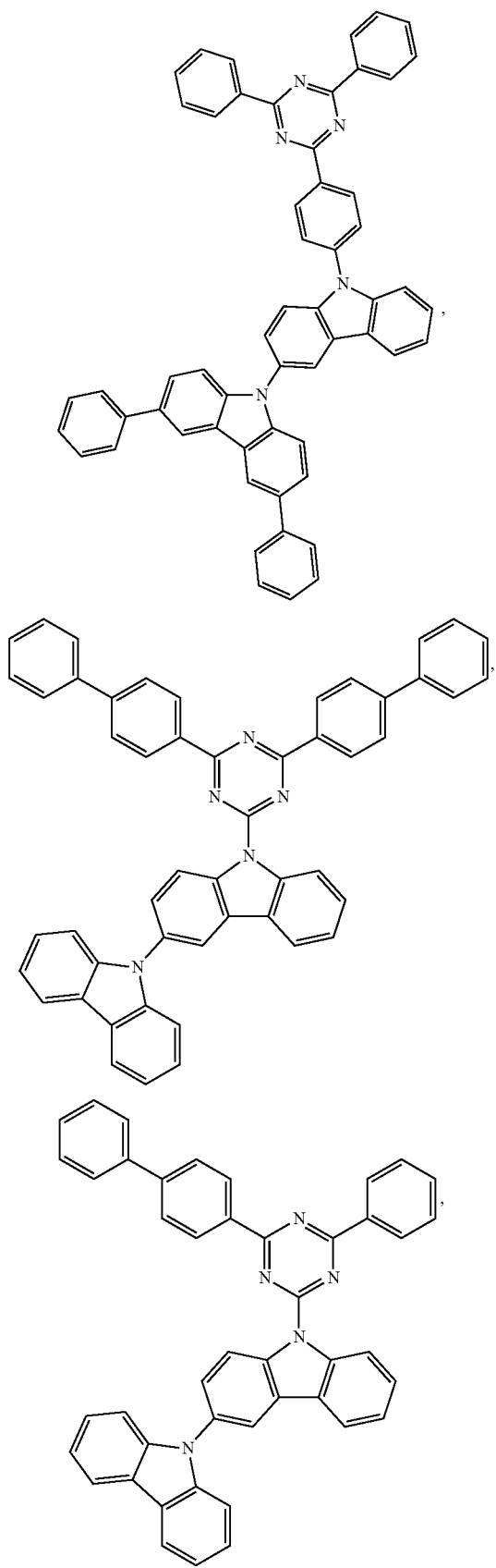
428
-continued
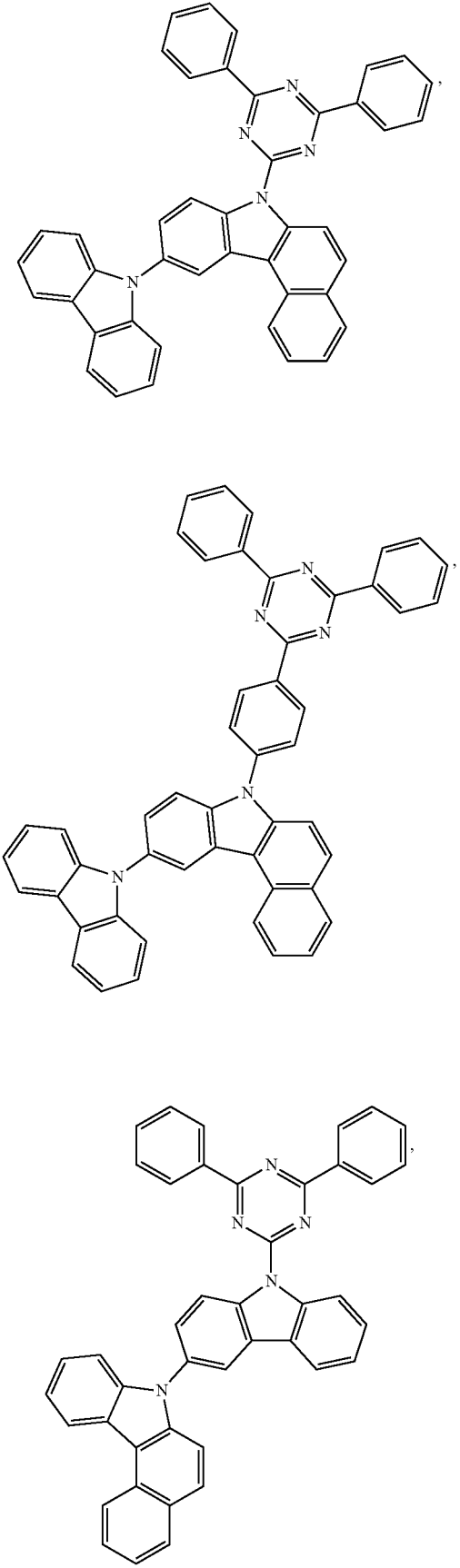

429
-continued

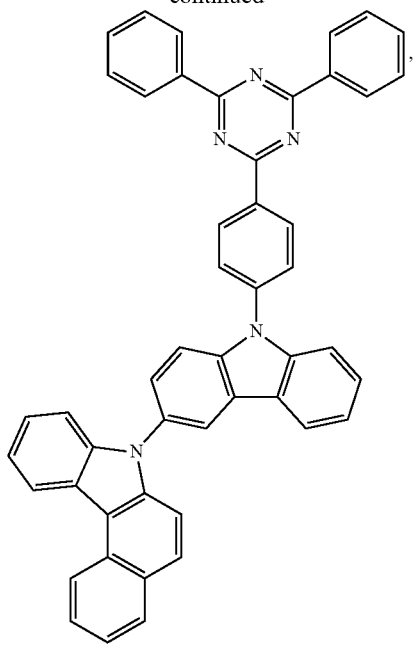

430
-continued

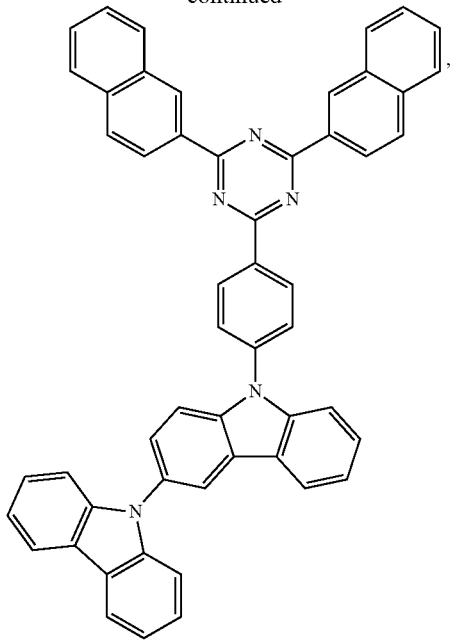

and partially deuterated or fully deuterated variants thereof.

16. An organic light emitting device (OLED) comprising:
an anode;
a cathode; and
an organic layer, disposed between the anode and the cathode, comprising a composition, the composition comprising a first compound and a second compound,
wherein the first compound has a formula selected from the group consisting of:

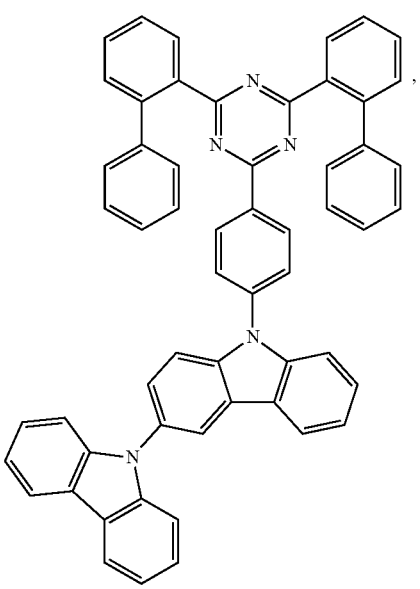

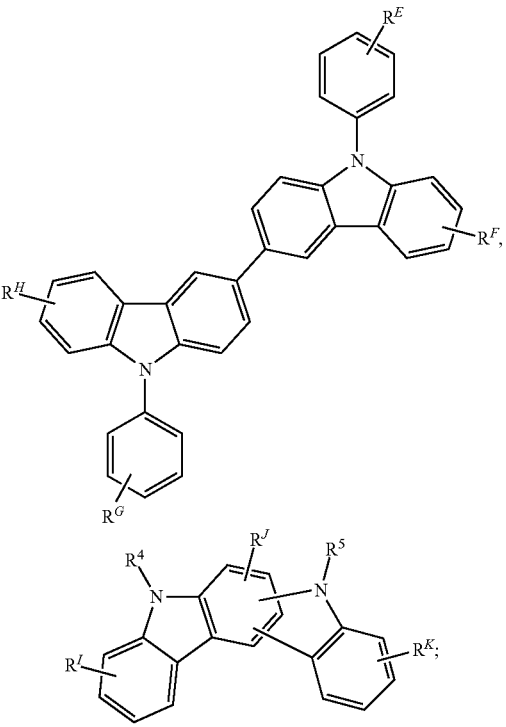

-continued

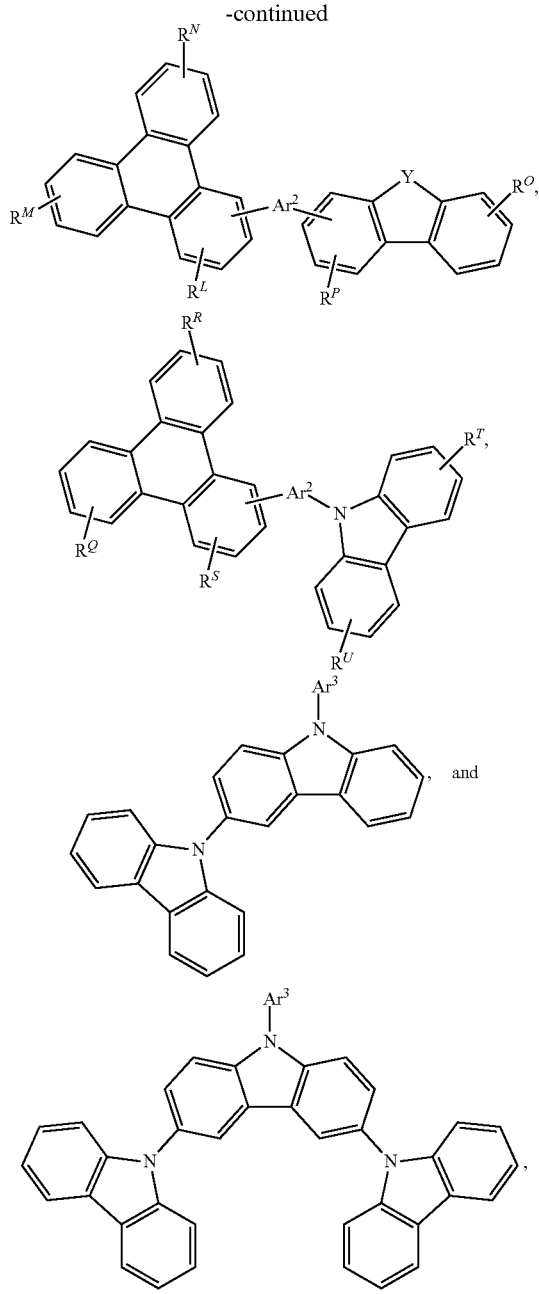

wherein,
R$^E$ to R$^U$ each independently represents mono to the maximum allowable substitutions, or no substitution;
each R$^4$, R$^5$, and R$^E$ to R$^U$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
any two substituents may be joined or fused together to form a ring;
Y is O or S; and
Ar$^3$ is a substituted or unsubstituted aryl ring;
wherein the second compound has a formula having the structure:

wherein,
R$^{DD}$, R$^{EE}$, R$^{FF}$, and R$^{GG}$ each independently represent mono to the maximum allowable substitutions, or no substitution;
each R$^{DD}$, R$^{EE}$, R$^{FF}$, and R$^{GG}$ is independently hydrogen, or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
Ar$^7$ and Ar$^8$ are each independently a substituted or unsubstituted aryl ring;
X$^{10}$, X$^{11}$, and X$^{12}$ are each independently N or CH;
at least two of X$^{10}$, X$^{11}$, and X$^{12}$ are N;
any two substituents may be joined or fused together to form a ring; and
L is either an aromatic linker or a direct bond.

17. The OLED of claim 16, wherein the organic layer is an emissive layer and the composition is a host material.

18. The OLED of claim 16, wherein the organic layer further comprises a phosphorescent emissive dopant; wherein the emissive dopant is a transition metal complex having at least one ligand or part of the ligand if the ligand is more than bidentate selected from the group consisting of:

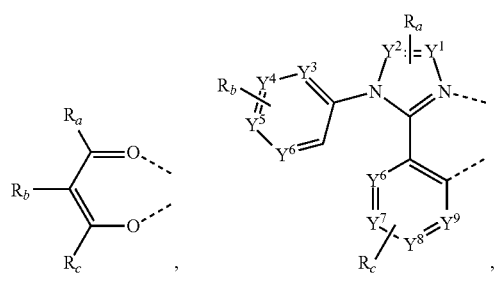

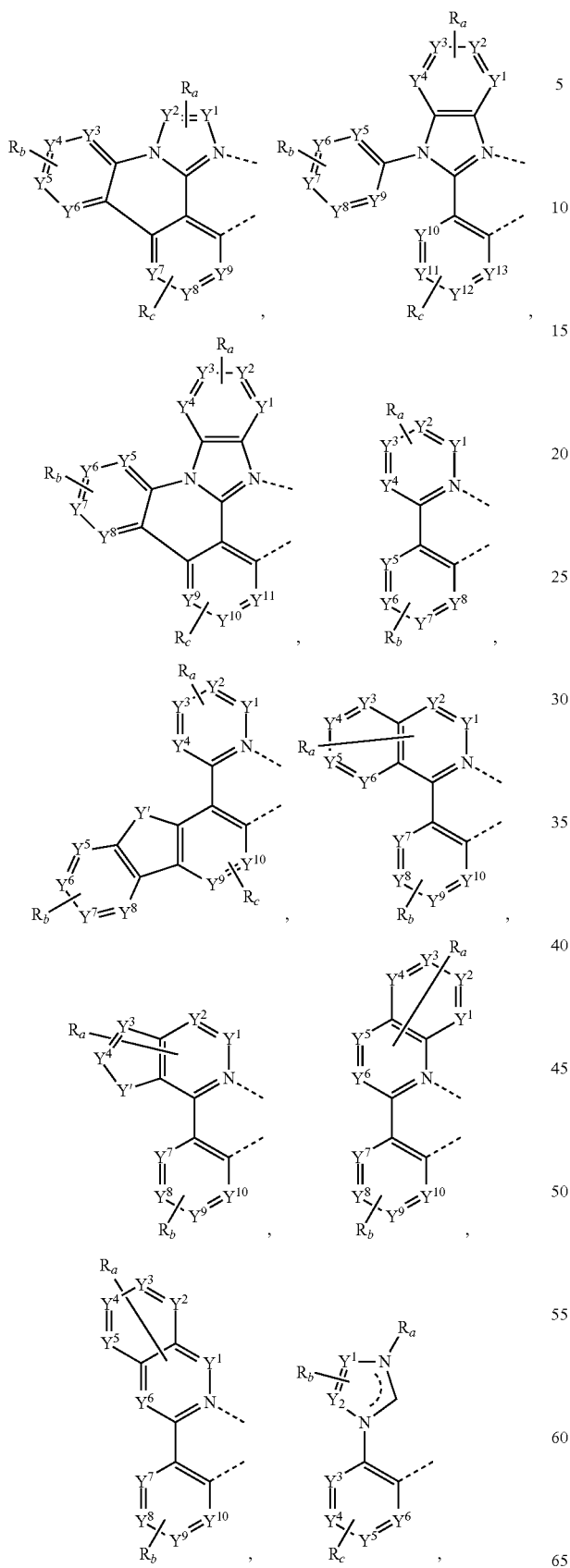

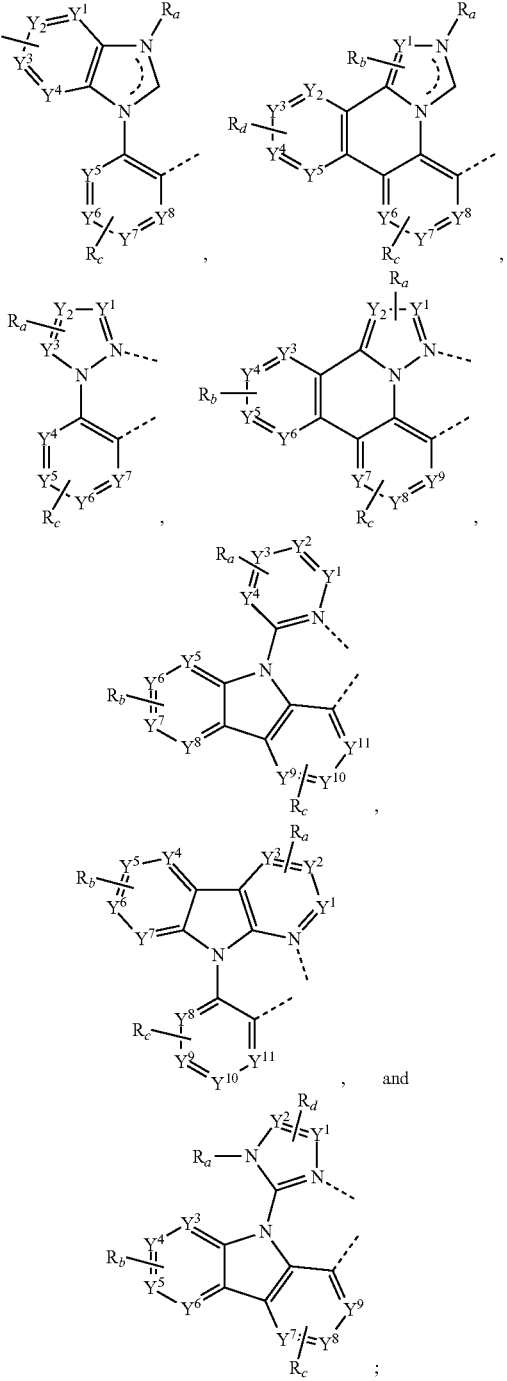

wherein,
each $Y^1$ to $Y^{13}$ is independently selected from the group consisting of carbon and nitrogen;
Y' is selected from the group consisting of B $R_e$, N $R_e$, P $R_e$, O, S, $S_e$, C=O, S=O, $SO_2$, $CR_eR_f$, $SiR_eR_f$, and $GeR_eR_f$;
$R_e$ and $R_f$ are optionally fused or joined to form a ring;
each $R_a$, $R_b$, $R_c$, and $R_d$ independently represents from mono substitution to the maximum allowable substitutions, or no substitution;
each $R_a$, $R_b$, $R_c$, $R_d$, $R_e$ and $R_f$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof; and any two adjacent substituents of $R_a$, $R_b$, $R_c$, and $R_d$ can be fused or joined to form a ring or form a multidentate ligand.

19. The OLED of claim 16, wherein the organic layer is a blocking layer and the composition is a blocking material in the organic layer; or the organic layer is a transporting layer and the composition is a transporting material in the organic layer.

20. A consumer product comprising an organic light-emitting device comprising:
    an anode;
    a cathode; and
    an organic layer, disposed between the anode and the cathode, comprising a composition, the composition comprising a first compound and a second compound,
    wherein the first compound has a formula selected from the group consisting of:

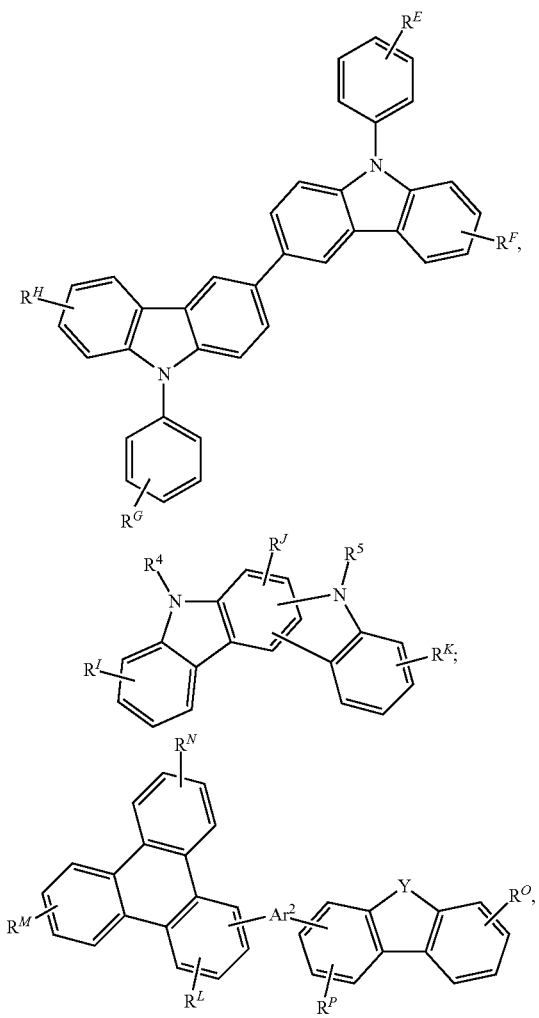

-continued

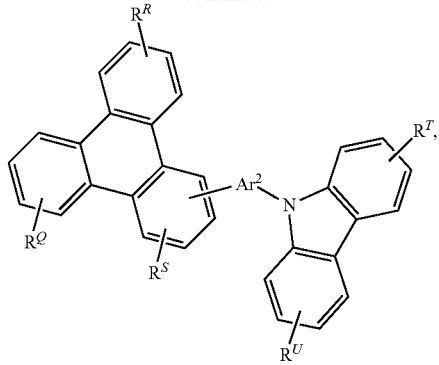

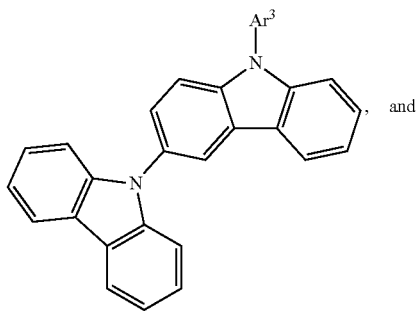

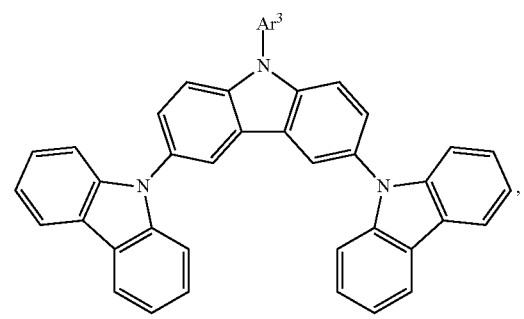

wherein,
$R^E$ to $R^U$ each independently represents mono to the maximum allowable substitutions, or no substitution;
each $R^4$, $R^5$, and $R^E$ to $R^U$ is independently hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
any two substituents may be joined or fused together to form a ring;
Y is O or S; and
$Ar^3$ is a substituted or unsubstituted aryl ring;
wherein the second compound has a formula having the structure:

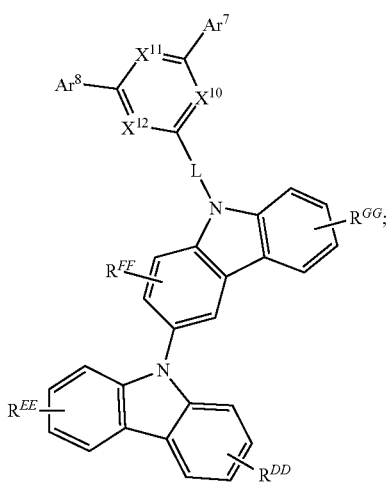

wherein,
R$^{DD}$, R$^{EE}$, R$^{FF}$, and R$^{GG}$ each independently represent mono to the maximum allowable substitutions, or no substitution;
each R$^{DD}$, R$^{EE}$, R$^{FF}$, and R$^{GG}$ is independently hydrogen, or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acid, ether, ester, nitrile, isonitrile, sulfanyl, sulfinyl, sulfonyl, phosphino, and combinations thereof;
Ar$^7$ and Ar$^8$ are each independently a substituted or unsubstituted aryl ring;
X$^{10}$, X$^{11}$, and X$^{12}$ are each independently N or CH;
at least two of X$^{10}$, X$^{11}$, and X$^{12}$ are N;
any two substituents may be joined or fused together to form a ring; and
L is either an aromatic linker or a direct bond.

\* \* \* \* \*

UNITED STATES PATENT AND TRADEMARK OFFICE
CERTIFICATE OF CORRECTION

PATENT NO. : 12,319,653 B2  Page 1 of 5
APPLICATION NO. : 18/430974
DATED : June 3, 2025
INVENTOR(S) : Bin Ma, Ting-Chih Wang and Vadim Adamovich It is certified that error appears in the above-identified patent and that said Letters Patent is hereby corrected as shown below:

In the Specification

Column 217, Lines 1-12, please delete the second compound

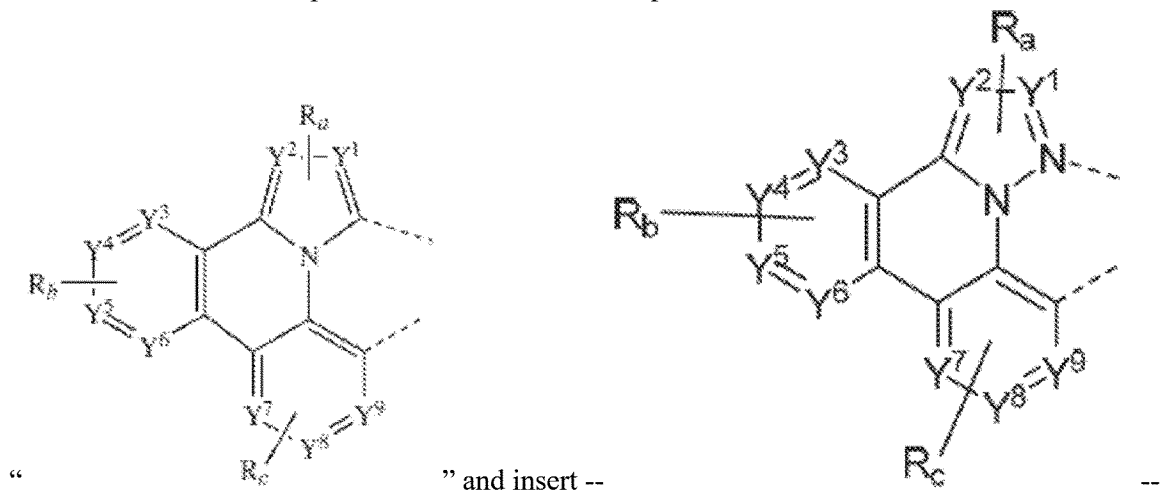

" and insert --                                                                 --

Columns 279 and 280, Lines 45-55, please delete both compounds

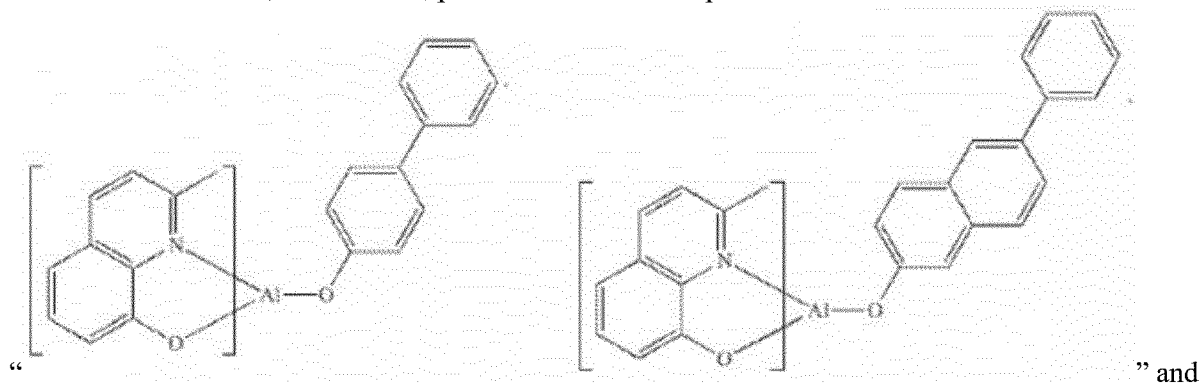

" and

Signed and Sealed this
Sixteenth Day of September, 2025

Coke Morgan Stewart
*Acting Director of the United States Patent and Trademark Office* insert -- 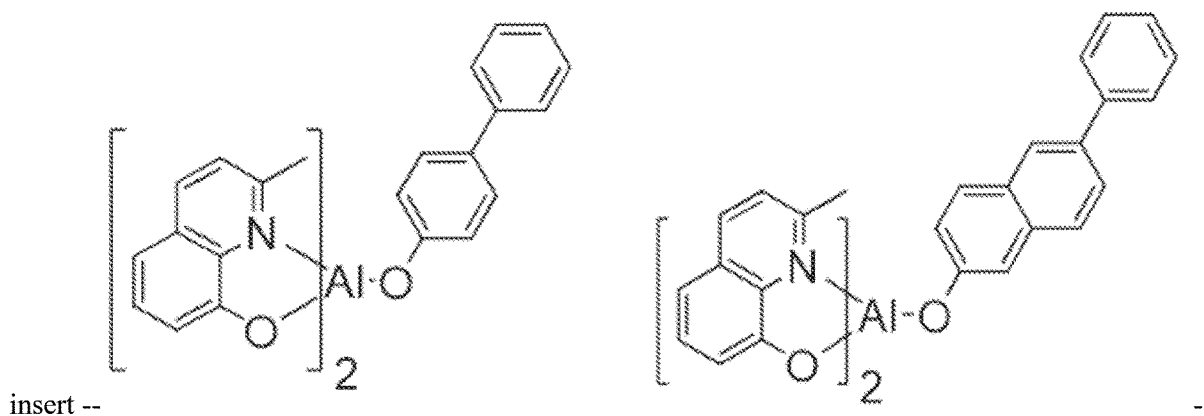 --
Column 287, Lines 1-15, please delete the compound
" 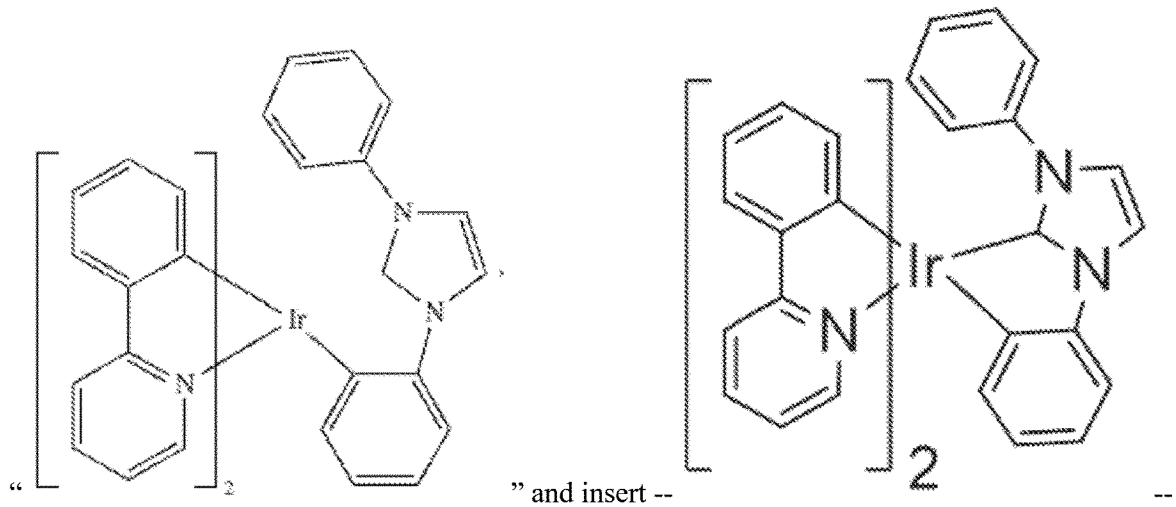 " and insert -- --
In the Claims
In Claim 7, Column 347, Lines 33-45, please delete the compound
" 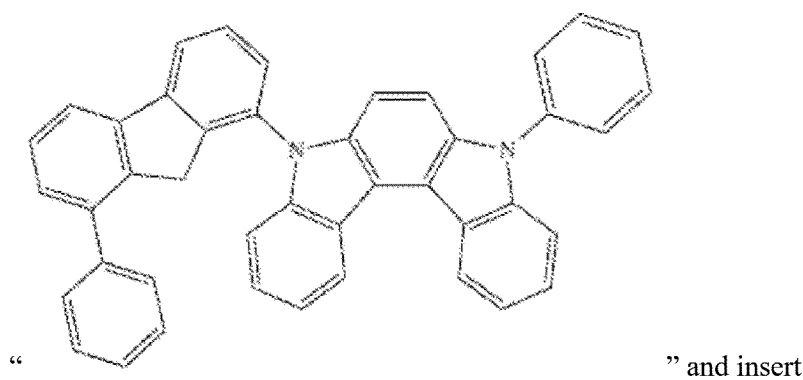 " and insert

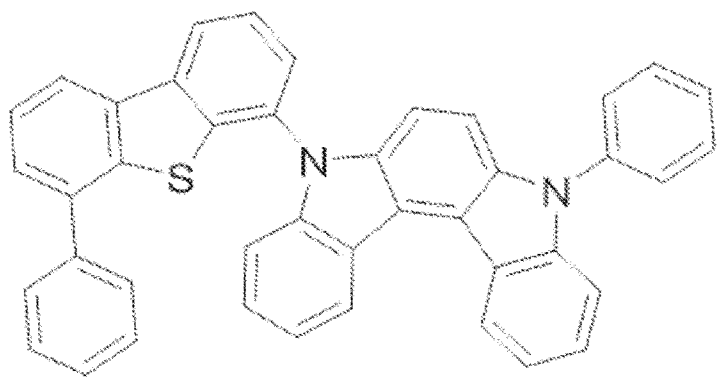
In Claim 7, Column 377, Lines 19-42, please delete the compound
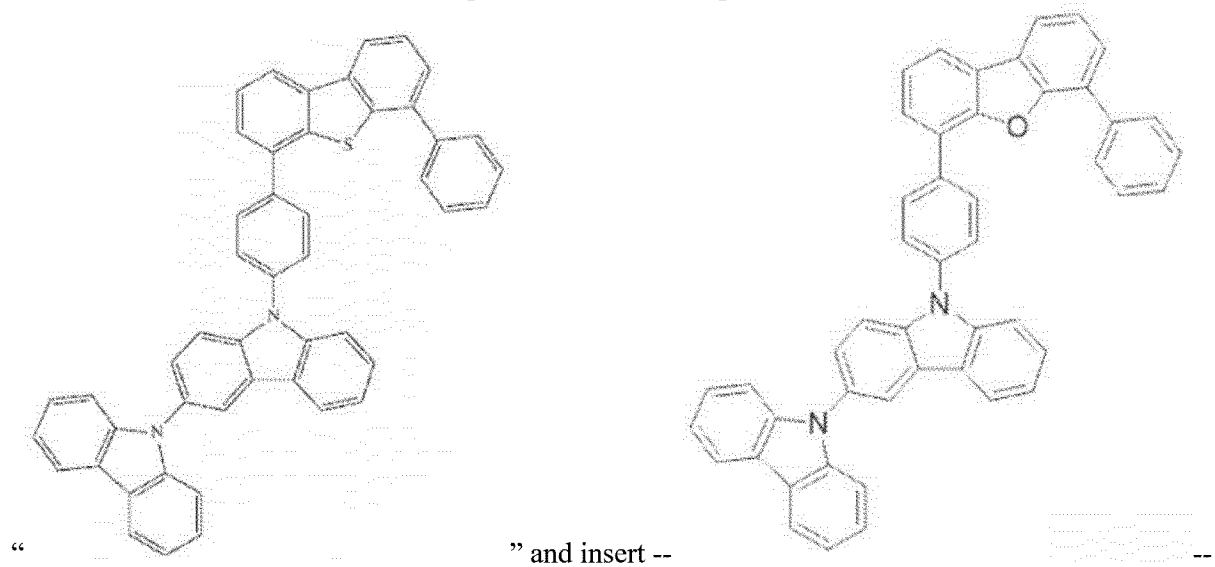
" and insert --
In Claim 15, Column 399, Lines 40-52, please delete the compound
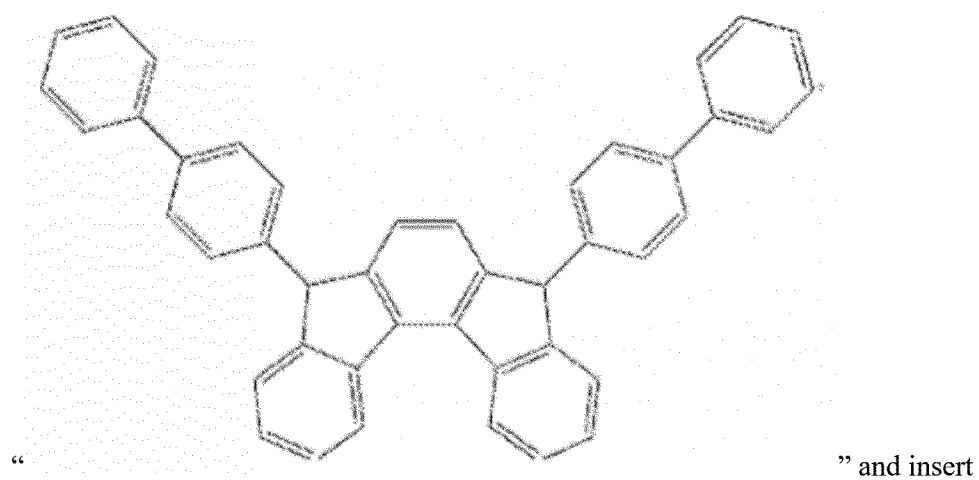
" and insert

CERTIFICATE OF CORRECTION (continued)

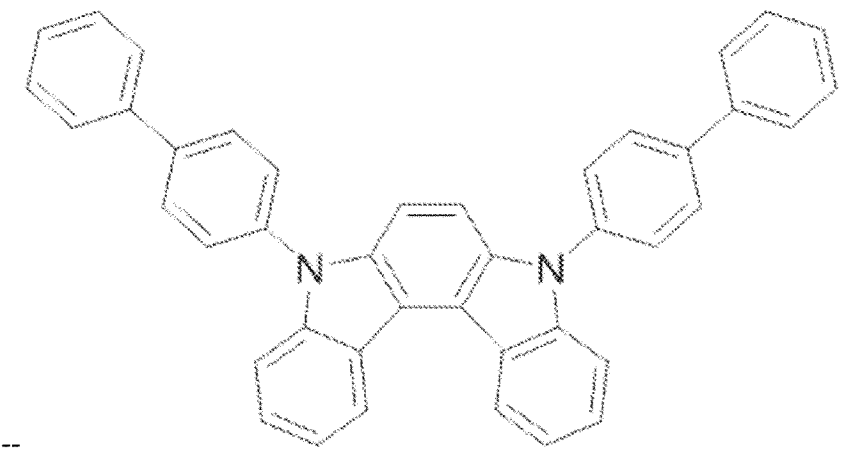

-- --

In Claim 18, Column 433, Lines 55-67, please delete the second compound

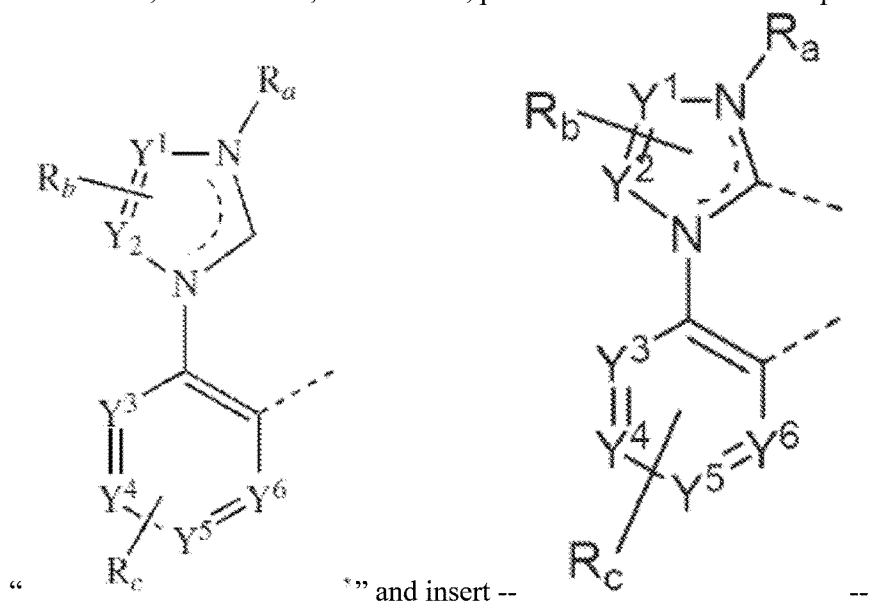

" " and insert -- --

In Claim 18, Column 434, Lines 1-12, please delete both compounds

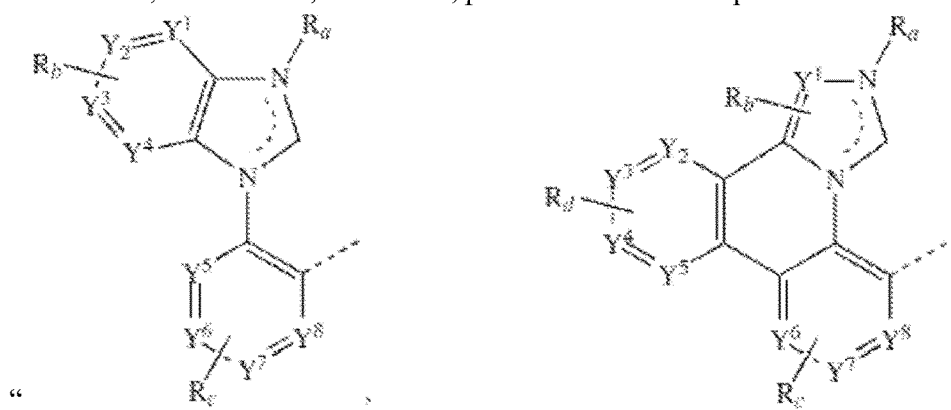

" " and insert

CERTIFICATE OF CORRECTION (continued)
U.S. Pat. No. 12,319,653 B2